(12) United States Patent
Aktoudianakis et al.

(10) Patent No.: US 12,269,812 B2
(45) Date of Patent: Apr. 8, 2025

(54) PD-1/PD-L1 INHIBITORS

(71) Applicant: Gilead Sciences, Inc., Foster City, CA (US)

(72) Inventors: Evangelos Aktoudianakis, Redwood City, CA (US); Aesop Cho, Mountain View, CA (US); Michael Graupe, Pacifica, CA (US); Lateshkumar Thakorlal Lad, Belmont, CA (US); Paulo A. Machicao Tello, Oakland, CA (US); Jonathan William Medley, San Mateo, CA (US); Samuel E. Metobo, Newark, CA (US); Devan Naduthambi, San Bruno, CA (US); Barton W. Phillips, San Mateo, CA (US); Scott Preston Simonovich, San Francisco, CA (US); Peiyuan Wang, San Mateo, CA (US); William J. Watkins, Saratoga, CA (US); Jie Xu, Foster City, CA (US); Kin Shing Yang, San Mateo, CA (US); Christopher Allen Ziebenhaus, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/923,750

(22) Filed: Jul. 8, 2020

(65) Prior Publication Data

US 2021/0024494 A1    Jan. 28, 2021

Related U.S. Application Data

(63) Continuation of application No. 16/510,647, filed on Jul. 12, 2019, now Pat. No. 10,774,071.

(60) Provisional application No. 62/808,763, filed on Feb. 21, 2019, provisional application No. 62/747,033, filed on Oct. 17, 2018, provisional application No. 62/697,932, filed on Jul. 13, 2018.

(51) Int. Cl.
| | | |
|---|---|---|
| C07D 401/14 | (2006.01) | |
| A61K 31/444 | (2006.01) | |
| A61K 31/497 | (2006.01) | |
| A61K 31/704 | (2006.01) | |
| A61K 31/7068 | (2006.01) | |
| A61K 39/395 | (2006.01) | |
| C07D 471/08 | (2006.01) | |

(52) U.S. Cl.
CPC .......... *C07D 401/14* (2013.01); *A61K 31/444* (2013.01); *A61K 31/497* (2013.01); *A61K 31/704* (2013.01); *A61K 31/7068* (2013.01); *A61K 39/3955* (2013.01); *C07D 471/08* (2013.01)

(58) Field of Classification Search
CPC .. C07D 401/14; C07D 471/08; A61K 31/497; A61K 31/444; A61K 31/704; A61K 31/7068; A61K 39/3955
See application file for complete search history.

(56) References Cited

U.S. PATENT DOCUMENTS

| | | | |
|---|---|---|---|
| 4,943,593 A | 7/1990 | Palfreyman et al. | |
| 4,965,288 A | 10/1990 | Palfreyman et al. | |
| 4,997,854 A | 3/1991 | Kagan et al. | |
| 5,021,456 A | 6/1991 | Palfreyman et al. | |
| 5,059,714 A | 10/1991 | Palfreyman et al. | |
| 5,120,764 A | 6/1992 | Mccarthy et al. | |
| 5,182,297 A | 1/1993 | Palfreyman et al. | |
| 5,252,608 A | 10/1993 | Palfreyman et al. | |
| 6,319,494 B1 | 11/2001 | Capon et al. | |
| 7,405,295 B2 | 7/2008 | Currie et al. | |
| 7,446,190 B2 | 11/2008 | Sadelain et al. | |
| 7,687,522 B2 | 3/2010 | Bellon et al. | |
| 7,741,465 B1 | 6/2010 | Eshhar et al. | |
| 7,750,048 B2 | 7/2010 | Kuo et al. | |
| 7,943,743 B2 | 5/2011 | Korman et al. | |
| 8,008,449 B2 | 8/2011 | Korman et al. | |
| 8,273,341 B2 | 9/2012 | Guo et al. | |
| 8,450,321 B2 | 5/2013 | Mitchell et al. | |
| 8,450,460 B2 | 5/2013 | Hill et al. | |
| 8,513,184 B2 | 8/2013 | Appleby et al. | |
| 8,541,424 B2 | 9/2013 | Degoey et al. | |
| 8,575,353 B2 | 11/2013 | Cannizzaro et al. | |
| 8,722,054 B2 | 5/2014 | Apelian et al. | |
| 8,835,451 B2 | 9/2014 | Serrano-Wu et al. | |
| 9,089,520 B2 | 7/2015 | Brenner | |
| 9,181,288 B2 | 11/2015 | Hartman et al. | |
| 9,186,337 B2 | 11/2015 | Baker et al. | |
| 10,710,986 B2 | 7/2020 | Aktoudianakis et al. | |
| 10,774,071 B2 | 9/2020 | Aktoudianakis et al. | |

(Continued)

FOREIGN PATENT DOCUMENTS

| | | |
|---|---|---|
| CN | 103848820 | 6/2014 |
| CN | 104341407 | 2/2015 |

(Continued)

OTHER PUBLICATIONS

Cannon, J. G., Chapter Nineteen in Burger's Medicinal Chemistry and Drug Discovery, Fifth Edition, vol. I: Principles and Practice, Wiley-Interscience 1995, pp. 783-802. (Year: 1995).

(Continued)

*Primary Examiner* — Rayna Rodriguez

(74) *Attorney, Agent, or Firm* — Schwegman Lundberg & Woessner, P.A.

(57) ABSTRACT

Compounds and methods of using said compounds singly or in combination with additional agents and compositions of said compounds for the treatment of cancer are disclosed.

11 Claims, No Drawings

(56) References Cited

U.S. PATENT DOCUMENTS

| | | |
|---|---|---|
| 2002/0091116 A1 | 7/2002 | Zhu et al. |
| 2003/0013028 A1 | 1/2003 | Kaoru et al. |
| 2003/0119844 A1 | 6/2003 | Huang et al. |
| 2004/0209936 A1 | 10/2004 | Bratton et al. |
| 2004/0235877 A1 | 11/2004 | Natsuki et al. |
| 2004/0248871 A1 | 12/2004 | Farjanel et al. |
| 2005/0224524 A1 | 10/2005 | Khan et al. |
| 2006/0019967 A1 | 1/2006 | Wu et al. |
| 2007/0155726 A1 | 7/2007 | Arnaiz et al. |
| 2008/0234251 A1 | 9/2008 | Doherty et al. |
| 2008/0306050 A1 | 12/2008 | Doherty et al. |
| 2009/0047249 A1 | 2/2009 | Graupe et al. |
| 2009/0142345 A1 | 6/2009 | Satou et al. |
| 2010/0015178 A1 | 1/2010 | Combs et al. |
| 2010/0029585 A1 | 2/2010 | Howbert et al. |
| 2010/0143301 A1 | 6/2010 | Desal et al. |
| 2010/0249175 A1 | 9/2010 | Wilson et al. |
| 2011/0092485 A1 | 4/2011 | Howbert et al. |
| 2011/0098248 A1 | 4/2011 | Halcomb et al. |
| 2011/0118235 A1 | 5/2011 | Howbert et al. |
| 2011/0287011 A1 | 11/2011 | Gurney et al. |
| 2012/0082658 A1 | 4/2012 | Hershberg |
| 2012/0225851 A1 | 6/2012 | Cardone et al. |
| 2012/0189539 A1 | 7/2012 | Wang et al. |
| 2012/0219615 A1 | 8/2012 | Hershberg et al. |
| 2012/0289558 A1 | 11/2012 | Kounnas et al. |
| 2012/0309701 A1 | 12/2012 | Janetka et al. |
| 2013/0022629 A1 | 1/2013 | Sharpe et al. |
| 2013/0023495 A1 | 1/2013 | Meyers et al. |
| 2013/0079327 A1 | 3/2013 | Yamamoto et al. |
| 2013/0217880 A1 | 8/2013 | Yamamoto et al. |
| 2013/0225552 A1 | 8/2013 | Allen et al. |
| 2013/0251673 A1 | 9/2013 | Hartman et al. |
| 2013/0267517 A1 | 10/2013 | Guo et al. |
| 2013/0310379 A1 | 11/2013 | Albrecht et al. |
| 2013/0324514 A1 | 12/2013 | Hamprecht et al. |
| 2013/0344029 A1 | 12/2013 | Aciro et al. |
| 2013/0344030 A1 | 12/2013 | Steadman et al. |
| 2014/0030221 A1 | 1/2014 | Aciro et al. |
| 2014/0045849 A1 | 2/2014 | McGowan et al. |
| 2014/0064053 A1 | 3/2014 | Tsuyama et al. |
| 2014/0066432 A1 | 3/2014 | Howbert et al. |
| 2014/0073631 A1 | 3/2014 | Shetty |
| 2014/0073642 A1 | 3/2014 | McGowan et al. |
| 2014/0088085 A1 | 3/2014 | Burgess et al. |
| 2014/0171432 A1 | 6/2014 | Kanouni et al. |
| 2014/0178337 A1 | 6/2014 | Hartman et al. |
| 2014/0194469 A1 | 7/2014 | Nie et al. |
| 2014/0213591 A1 | 7/2014 | Chen et al. |
| 2014/0275084 A1 | 9/2014 | Kanouni et al. |
| 2014/0275092 A1 | 9/2014 | Albrecht et al. |
| 2014/0275167 A1 | 9/2014 | Hartman |
| 2014/0330015 A1 | 11/2014 | Yamamoto et al. |
| 2014/0343032 A1 | 11/2014 | Guo et al. |
| 2014/0350031 A1 | 11/2014 | Mc et al. |
| 2014/0371195 A1 | 12/2014 | Labelle et al. |
| 2014/0371214 A1 | 12/2014 | Labelle et al. |
| 2015/0031687 A1 | 1/2015 | Guo et al. |
| 2015/0132258 A1 | 5/2015 | Hartman |
| 2015/0175616 A1 | 6/2015 | Blomgren et al. |
| 2015/0197533 A1 | 7/2015 | Hartman et al. |
| 2015/0197538 A1 | 7/2015 | Janetka et al. |
| 2015/0210682 A1 | 7/2015 | Han et al. |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0274652 A1 | 10/2015 | Hartman |
| 2015/0315159 A1 | 11/2015 | Hartman |
| 2015/0352206 A1 | 12/2015 | Gajewski et al. |
| 2016/0039808 A1 | 2/2016 | Kanouni et al. |
| 2016/0102096 A1 | 4/2016 | Boesen et al. |
| 2016/0122344 A1 | 5/2016 | Han et al. |
| 2016/0137652 A1 | 5/2016 | Beck et al. |
| 2016/0145304 A1 | 5/2016 | Baumann et al. |
| 2016/0333009 A1 | 5/2016 | Bartlett et al. |
| 2016/0166592 A1 | 6/2016 | Bae et al. |
| 2016/0176899 A1 | 6/2016 | Schwitter et al. |
| 2016/0194307 A1 | 7/2016 | Chupak et al. |
| 2016/0207923 A1 | 7/2016 | Youngman et al. |
| 2016/0220586 A1 | 8/2016 | Andre et al. |
| 2016/0237090 A1 | 8/2016 | Hu et al. |
| 2016/0333013 A1 | 11/2016 | Norris et al. |
| 2017/0037040 A1 | 2/2017 | Eckhardt et al. |
| 2017/0088532 A1 | 3/2017 | Cohen et al. |
| 2017/0100414 A1 | 4/2017 | Dunman et al. |
| 2017/0107202 A1 | 4/2017 | Yeung et al. |
| 2017/0107216 A1 | 4/2017 | Wu et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0210715 A1 | 7/2017 | Shao et al. |
| 2017/0239351 A1 | 8/2017 | Hamdy et al. |
| 2017/0252432 A1 | 9/2017 | Allen et al. |
| 2017/0262253 A1 | 9/2017 | Silva et al. |
| 2017/0266211 A1 | 9/2017 | David et al. |
| 2017/0283462 A1 | 10/2017 | Miller et al. |
| 2017/0283463 A1 | 10/2017 | Miller et al. |
| 2017/0320875 A1 | 11/2017 | Li et al. |
| 2017/0331067 A1 | 11/2017 | Park et al. |
| 2017/0362253 A1 | 12/2017 | Xiao et al. |
| 2018/0008554 A1 | 1/2018 | Lange et al. |
| 2018/0044303 A1 | 2/2018 | Sasikumar et al. |
| 2018/0044304 A1 | 2/2018 | Sasikumar et al. |
| 2018/0044305 A1 | 2/2018 | Sasikumar et al. |
| 2018/0044329 A1 | 2/2018 | Sasikumar et al. |
| 2018/0044350 A1 | 2/2018 | Sasikumar et al. |
| 2018/0045142 A1 | 2/2018 | Dierksmeier et al. |
| 2018/0057455 A1 | 3/2018 | Yeung et al. |
| 2018/0057486 A1 | 3/2018 | Wu et al. |
| 2018/0065917 A1 | 3/2018 | Webber et al. |
| 2018/0086793 A1 | 3/2018 | Gillman et al. |
| 2018/0273519 A1 | 9/2018 | Wu et al. |
| 2018/0305315 A1 | 10/2018 | Aktoudianakis et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0135745 A1 | 5/2019 | Lange et al. |
| 2019/0144402 A1 | 5/2019 | Sasikumar et al. |
| 2019/0144439 A1 | 5/2019 | Wu et al. |
| 2019/0202824 A1 | 7/2019 | Wu et al. |
| 2019/0270727 A1 | 9/2019 | Aktoudianakis et al. |
| 2019/0276435 A1 | 9/2019 | Shepard et al. |
| 2019/0282555 A1 | 9/2019 | Lange et al. |
| 2019/0345131 A1 | 11/2019 | Aktoudianakis et al. |
| 2020/0017471 A1 | 1/2020 | Aktoudianakis et al. |
| 2020/0157094 A1 | 5/2020 | Du et al. |
| 2021/0053946 A1 | 2/2021 | Aktoudianakis et al. |
| 2021/0323922 A1 | 10/2021 | Aktoudianakis et al. |
| 2023/0212155 A1 | 7/2023 | Aktoudianakis et al. |

FOREIGN PATENT DOCUMENTS

| | | |
|---|---|---|
| CN | 104876912 | 9/2015 |
| DE | 10104279 | 8/2002 |
| EP | 2002838 | 12/2008 |
| EP | 3363790 | 8/2018 |
| IN | 202418035767 A | 12/2024 |
| JP | 2001002661 | 1/2001 |
| JP | 2001335476 | 12/2001 |
| JP | 2012036168 | 2/2012 |
| JP | 2013147443 | 8/2013 |
| JP | 2016053633 | 4/2016 |
| UY | 35733 A | 4/2016 |
| WO | WO 1997/31910 | 9/1997 |
| WO | WO-9917777 | 4/1999 |
| WO | WO 2001/019798 | 3/2001 |
| WO | WO 2001/056989 | 8/2001 |
| WO | WO 2002/000647 | 1/2002 |
| WO | WO 2002/020436 | 3/2002 |
| WO | WO 2002/051775 | 7/2002 |
| WO | WO 2004/052848 | 6/2004 |
| WO | WO 2004/054582 | 7/2004 |
| WO | WO 2004/084824 | 10/2004 |
| WO | WO 2005/044797 | 5/2005 |

(56) References Cited

FOREIGN PATENT DOCUMENTS

| | | |
|---|---|---|
| WO | WO 2005/051890 | 6/2005 |
| WO | WO 2005/086808 | 9/2005 |
| WO | WO 2005/095338 | 10/2005 |
| WO | WO 2006/011615 | 2/2006 |
| WO | WO 2006/038738 | 4/2006 |
| WO | WO-2006040646 | 4/2006 |
| WO | WO 2006/052566 | 5/2006 |
| WO | WO 2006/083612 | 8/2006 |
| WO | WO 2006/083781 | 8/2006 |
| WO | WO 2006/091394 | 8/2006 |
| WO | WO 2006/123257 | 11/2006 |
| WO | WO 2006/127503 | 11/2006 |
| WO | WO 2007/013689 | 2/2007 |
| WO | WO 2007/033002 | 3/2007 |
| WO | WO 2007/047591 | 4/2007 |
| WO | WO 2007/049050 | 5/2007 |
| WO | WO 2007/052466 | 5/2007 |
| WO | WO 2007/096142 | 8/2007 |
| WO | WO 2007/104560 | 9/2007 |
| WO | WO 2007/106469 | 9/2007 |
| WO | WO 2007/109376 | 9/2007 |
| WO | WO 2007/123225 | 11/2007 |
| WO | WO 2007/128460 | 11/2007 |
| WO | WO 2007/131619 | 11/2007 |
| WO | WO 2007/131620 | 11/2007 |
| WO | WO 2007/131621 | 11/2007 |
| WO | WO 2007/131622 | 11/2007 |
| WO | WO 2007/132307 | 11/2007 |
| WO | WO 2007/136572 | 11/2007 |
| WO | WO 2008/001931 | 1/2008 |
| WO | WO 2008/014236 | 1/2008 |
| WO | WO 2008/021936 | 2/2008 |
| WO | WO 2008/030520 | 3/2008 |
| WO | WO 2008/037266 | 4/2008 |
| WO | WO 2008/054674 | 5/2008 |
| WO | WO 2008/054675 | 5/2008 |
| WO | WO 2008/063768 | 5/2008 |
| WO | WO 2008/065409 | 6/2008 |
| WO | WO 2008/066097 | 6/2008 |
| WO | WO 2008/067644 | 6/2008 |
| WO | WO 2008/073865 | 6/2008 |
| WO | WO 2008/079965 | 7/2008 |
| WO | WO 2008/083027 | 7/2008 |
| WO | WO 2008/090327 | 7/2008 |
| WO | WO 2008/090356 | 7/2008 |
| WO | WO 2008/106202 | 9/2008 |
| WO | WO 2008/130514 | 10/2008 |
| WO | WO 2008/139987 | 11/2008 |
| WO | WO 2008/144925 | 12/2008 |
| WO | WO 2008/147852 | 12/2008 |
| WO | WO 2008/156656 | 12/2008 |
| WO | WO 2009/017822 | 2/2009 |
| WO | WO 2009/025983 | 2/2009 |
| WO | WO 2009/038204 | 3/2009 |
| WO | WO 2009/039942 | 4/2009 |
| WO | WO 2009/039943 | 4/2009 |
| WO | WO 2009/047798 | 4/2009 |
| WO | WO 2009/048527 | 4/2009 |
| WO | WO 2009/054390 | 4/2009 |
| WO | WO 2009/054468 | 4/2009 |
| WO | WO 2009/054479 | 4/2009 |
| WO | WO 2009/058237 | 5/2009 |
| WO | WO 2009/102568 | 8/2009 |
| WO | WO 2009/102633 | 8/2009 |
| WO | WO 2009/111056 | 9/2009 |
| WO | WO 2009/112445 | 9/2009 |
| WO | WO 2010/012650 | 2/2010 |
| WO | WO 2010/017870 | 2/2010 |
| WO | WO 2010/039238 | 4/2010 |
| WO | WO 2010/045258 | 4/2010 |
| WO | WO 2010/066682 | 6/2010 |
| WO | WO 2010/082563 | 7/2010 |
| WO | WO 2010/085522 | 7/2010 |
| WO | WO 2010/085525 | 7/2010 |
| WO | WO 2010/085528 | 7/2010 |
| WO | WO 2010/091176 | 8/2010 |
| WO | WO 2010/091413 | 8/2010 |
| WO | WO 2010/096462 | 8/2010 |
| WO | WO 2010/099527 | 9/2010 |
| WO | WO 2010/111534 | 9/2010 |
| WO | WO 2010/123016 | 10/2010 |
| WO | WO 2010/123017 | 10/2010 |
| WO | WO 2010/132601 | 11/2010 |
| WO | WO 2010/143733 | 12/2010 |
| WO | WO 2010/144646 | 12/2010 |
| WO | WO 2011/008709 | 1/2011 |
| WO | WO 2011/024001 | 3/2011 |
| WO | WO 2011/031934 | 3/2011 |
| WO | WO 2011/031965 | 3/2011 |
| WO | WO 2011/044073 | 4/2011 |
| WO | WO 2011/046851 | 4/2011 |
| WO | WO 2011/049825 | 4/2011 |
| WO | WO 2011/052756 | 5/2011 |
| WO | WO 2011/066183 | 6/2011 |
| WO | WO 2011/066241 | 6/2011 |
| WO | WO 2011/073376 | 6/2011 |
| WO | WO 2011/076732 | 6/2011 |
| WO | WO 2011/076734 | 6/2011 |
| WO | WO 2011/078371 | 6/2011 |
| WO | WO 2011/080755 | 7/2011 |
| WO | WO 2011/082400 | 7/2011 |
| WO | WO 2011/092284 | 8/2011 |
| WO | WO 2011/119858 | 9/2011 |
| WO | WO 2011/119870 | 9/2011 |
| WO | WO 2011/138665 | 11/2011 |
| WO | WO 2011/143208 | 11/2011 |
| WO | WO 2011/143466 | 11/2011 |
| WO | WO 2011/151436 | 12/2011 |
| WO | WO 2011/161030 | 12/2011 |
| WO | WO 2012/004269 | 1/2012 |
| WO | WO 2012/004270 | 1/2012 |
| WO | WO 2012/010413 | 1/2012 |
| WO | WO 2012/011124 | 1/2012 |
| WO | WO 2012/012627 | 1/2012 |
| WO | WO 2012/036168 | 3/2012 |
| WO | WO 2012/046869 | 4/2012 |
| WO | WO 2012/050918 | 4/2012 |
| WO | WO 2012/065904 | 5/2012 |
| WO | WO 2012/068234 | 5/2012 |
| WO | WO 2012/072691 | 6/2012 |
| WO | WO 2012/078802 | 6/2012 |
| WO | WO 2012/083043 | 6/2012 |
| WO | WO 2012/083048 | 6/2012 |
| WO | WO 2012/083053 | 6/2012 |
| WO | WO 2012/083059 | 6/2012 |
| WO | WO 2012/083061 | 6/2012 |
| WO | WO 2012/098033 | 7/2012 |
| WO | WO 2012/111849 | 8/2012 |
| WO | WO 2012/129562 | 9/2012 |
| WO | WO 2012/136221 | 10/2012 |
| WO | WO 2012/147518 | 11/2012 |
| WO | WO 2012/154608 | 11/2012 |
| WO | WO 2013/009259 | 1/2013 |
| WO | WO 2013/025424 | 2/2013 |
| WO | WO 2013/057743 | 4/2013 |
| WO | WO 2013/102626 | 7/2013 |
| WO | WO 2013/104257 | 7/2013 |
| WO | WO 2013/106520 | 7/2013 |
| WO | WO 2013/109521 | 7/2013 |
| WO | WO 2013/122028 | 8/2013 |
| WO | WO 2013/122029 | 8/2013 |
| WO | WO 2013/128378 | 9/2013 |
| WO | WO 2013/144097 | 10/2013 |
| WO | WO 2013/154163 | 10/2013 |
| WO | WO 2013/164292 | 11/2013 |
| WO | WO 2013/170113 | 11/2013 |
| WO | WO 2013/170115 | 11/2013 |
| WO | WO 2013/178575 | 12/2013 |
| WO | WO 2014/014129 | 1/2014 |
| WO | WO 2014/014530 | 1/2014 |
| WO | WO 2014/019186 | 2/2014 |
| WO | WO 2014/035827 | 3/2014 |
| WO | WO 2014/073904 | 5/2014 |
| WO | WO 2014/078608 | 5/2014 |

(56) References Cited

FOREIGN PATENT DOCUMENTS

| | | |
|---|---|---|
| WO | WO 2014/078609 | 5/2014 |
| WO | WO 2014/078610 | 5/2014 |
| WO | WO 2014/081689 | 5/2014 |
| WO | WO 2014/082918 | 6/2014 |
| WO | WO 2014/086712 | 6/2014 |
| WO | WO 2014/122067 | 8/2014 |
| WO | WO 2014/130608 | 8/2014 |
| WO | WO 2014/133361 | 9/2014 |
| WO | WO 2014/134243 | 9/2014 |
| WO | WO 2014/145817 | 9/2014 |
| WO | WO 2014/146604 | 9/2014 |
| WO | WO 2014/169817 | 10/2014 |
| WO | WO 2014/170842 | 10/2014 |
| WO | WO 2014/171762 | 10/2014 |
| WO | WO 2014/187343 | 11/2014 |
| WO | WO 2015/000412 | 1/2015 |
| WO | WO 2015/010655 | 1/2015 |
| WO | WO 2015/020184 | 2/2015 |
| WO | WO 2015/024448 | 2/2015 |
| WO | WO 2015/024526 | 2/2015 |
| WO | WO 2015/028960 | 3/2015 |
| WO | WO 2015/032328 | 3/2015 |
| WO | WO 2015/034820 | 3/2015 |
| WO | WO 2015/044073 | 4/2015 |
| WO | WO 2015/051496 | 4/2015 |
| WO | WO 2015/062486 | 5/2015 |
| WO | WO 2015/065621 | 5/2015 |
| WO | WO 2015/073342 | 5/2015 |
| WO | WO 2015/076800 | 5/2015 |
| WO | WO 2015/078802 | 6/2015 |
| WO | WO 2015/078949 | 6/2015 |
| WO | WO 2015/084692 | 6/2015 |
| WO | WO 2015/088868 | 6/2015 |
| WO | WO 2015/089809 | 6/2015 |
| WO | WO 2015/097713 | 7/2015 |
| WO | WO 2015/105779 | 7/2015 |
| WO | WO 2015/105786 | 7/2015 |
| WO | WO 2018/121560 | 7/2015 |
| WO | WO-2015108861 | 7/2015 |
| WO | WO 2015/119899 | 8/2015 |
| WO | WO 2015/140717 | 9/2015 |
| WO | WO 2015/150097 | 10/2015 |
| WO | WO 2015/160641 | 10/2015 |
| WO | WO 2015/171722 | 11/2015 |
| WO | WO 2015/171733 | 11/2015 |
| WO | WO 2015/171757 | 11/2015 |
| WO | WO 2015/176267 | 11/2015 |
| WO | WO 2015/198045 | 12/2015 |
| WO | WO 2015/198046 | 12/2015 |
| WO | WO-2015191745 | 12/2015 |
| WO | WO 2016/007714 | 1/2016 |
| WO | WO 2016/019587 | 2/2016 |
| WO | WO 2016/022446 | 2/2016 |
| WO | WO 2016/022448 | 2/2016 |
| WO | WO 2016/022742 | 2/2016 |
| WO | WO 2016/026772 | 2/2016 |
| WO | WO 2016/032120 | 3/2016 |
| WO | WO 2016/039749 | 3/2016 |
| WO | WO 2016/041511 | 3/2016 |
| WO | WO 2016/060517 | 4/2016 |
| WO | WO 2016/060963 | 4/2016 |
| WO | WO-2016065226 | 4/2016 |
| WO | WO 2016/071283 | 5/2016 |
| WO | WO 2016/071293 | 5/2016 |
| WO | WO 2016/073774 | 5/2016 |
| WO | WO-2016068451 | 5/2016 |
| WO | WO 2016/110821 | 7/2016 |
| WO | WO 2016/128908 | 8/2016 |
| WO | WO 2016/142833 | 9/2016 |
| WO | WO 2016/142835 | 9/2016 |
| WO | WO 2016/142852 | 9/2016 |
| WO | WO 2016/142886 | 9/2016 |
| WO | WO 2016/142894 | 9/2016 |
| WO | WO-2016141092 | 9/2016 |
| WO | WO-2016165613 | 10/2016 |
| WO | WO 2016/195776 | 12/2016 |
| WO | WO 2016/197987 | 12/2016 |
| WO | WO-2016196381 | 12/2016 |
| WO | WO 2017/011279 | 1/2017 |
| WO | WO 2017/025368 | 2/2017 |
| WO | WO 2017/027309 | 2/2017 |
| WO | WO 2017/027310 | 2/2017 |
| WO | WO 2017/027312 | 2/2017 |
| WO | WO 2017/031392 | 2/2017 |
| WO | WO 2017/042121 | 3/2017 |
| WO | WO 2017/066227 | 4/2017 |
| WO | WO 2017/070089 | 4/2017 |
| WO | WO 2017/079669 | 5/2017 |
| WO | WO 2017/087777 | 5/2017 |
| WO | WO 2017/099034 | 6/2017 |
| WO | WO 2017/106634 | 6/2017 |
| WO | WO 2017/107979 | 6/2017 |
| WO | WO 2017/112730 | 6/2017 |
| WO | WO 2017/118762 | 7/2017 |
| WO | WO 2017/143220 | 8/2017 |
| WO | WO 2017/151830 | 9/2017 |
| WO | WO 2017/162284 | 9/2017 |
| WO | WO 2017/172505 | 10/2017 |
| WO | WO 2017/176608 | 10/2017 |
| WO | WO 2017/180457 | 10/2017 |
| WO | WO 2017/180571 | 10/2017 |
| WO | WO 2017/180769 | 10/2017 |
| WO | WO 2017/192961 | 11/2017 |
| WO | WO 2017/201683 | 11/2017 |
| WO | WO 2017/202273 | 11/2017 |
| WO | WO 2017/202274 | 11/2017 |
| WO | WO 2017/202275 | 11/2017 |
| WO | WO 2017/202276 | 11/2017 |
| WO | WO 2017/202744 | 11/2017 |
| WO | WO 2017/205464 | 11/2017 |
| WO | WO 2017/222976 | 12/2017 |
| WO | WO 2018/005374 | 1/2018 |
| WO | WO 2018/009505 | 1/2018 |
| WO | WO-2018013597 | 1/2018 |
| WO | WO 2018/026971 | 2/2018 |
| WO | WO 2018/029150 | 2/2018 |
| WO | WO-2018026871 | 2/2018 |
| WO | WO 2018/044783 | 3/2018 |
| WO | WO 2018/044963 | 3/2018 |
| WO | WO 2018/045142 | 3/2018 |
| WO | WO 2018/051254 | 3/2018 |
| WO | WO 2018/051255 | 3/2018 |
| WO | WO 2018/053302 | 3/2018 |
| WO | WO 2018/077699 | 5/2018 |
| WO | WO 2018/081047 | 5/2018 |
| WO | WO 2018/095877 | 5/2018 |
| WO | WO 2018/106518 | 6/2018 |
| WO | WO 2018/111012 | 6/2018 |
| WO | WO 2018/118664 | 6/2018 |
| WO | WO 2018/118670 | 6/2018 |
| WO | WO 2018/118848 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/138026 | 8/2018 |
| WO | WO 2018/138027 | 8/2018 |
| WO | WO 2018/138028 | 8/2018 |
| WO | WO 2018/138029 | 8/2018 |
| WO | WO 2018/138030 | 8/2018 |
| WO | WO 2018/146008 | 8/2018 |
| WO | WO 2018/172727 | 9/2018 |
| WO | WO 2018/181847 | 10/2018 |
| WO | WO 2018/182050 | 10/2018 |
| WO | WO 2018/183171 | 10/2018 |
| WO | WO 2018/195321 | 10/2018 |
| WO | WO 2018/196768 | 11/2018 |
| WO | WO 2019/008156 | 1/2019 |
| WO | WO 2019/023575 | 1/2019 |
| WO | WO 2019/032547 | 2/2019 |
| WO | WO 2019/034172 | 2/2019 |
| WO | WO 2019/059411 | 3/2019 |

(56) References Cited

FOREIGN PATENT DOCUMENTS

| WO | WO 2019/070643 | 4/2019 |
|---|---|---|
| WO | WO 2019/074241 | 4/2019 |
| WO | WO 2019/076343 | 4/2019 |
| WO | WO 2019/128918 | 7/2019 |
| WO | WO 2019/160882 | 8/2019 |
| WO | WO 2019/165043 | 8/2019 |
| WO | WO 2019/174533 | 9/2019 |
| WO | WO 2019/175897 | 9/2019 |
| WO | WO-2019170745 | 9/2019 |
| WO | WO-2019173665 | 9/2019 |
| WO | WO 2019/191624 | 10/2019 |
| WO | WO 2019/191707 | 10/2019 |
| WO | WO 2019/192506 | 10/2019 |
| WO | WO 2019/204609 | 10/2019 |
| WO | WO 2019/217821 | 11/2019 |
| WO | WO 2020/011246 | 1/2020 |
| WO | WO 2020/014643 | 1/2020 |
| WO | WO-2020086556 | 4/2020 |

OTHER PUBLICATIONS

Examination Report for Australian Patent Application No. 2019301811 dated Jun. 28, 2021. 2 pages.
Office Action for Israeli Patent Application No. 279991 dated Aug. 18, 2021. 5 pages.
Office Action for Ukraine Patent Application No. a202008123 dated Dec. 15, 2021. 7 pages.
Official Action for Panamanian Patent Application No. 93366-01 dated Feb. 22, 2021. 2 pages.
Official Notification for Uzbek Patent Application No. IAP 20210065 dated Apr. 23, 2021. 3 pages.
Opposition filed by Laboratorios Legrand S.A. for Colombian Patent Application No. NC2021/0000151 dated Apr. 15, 2021. 21 pages.
Opposition filed by Procaps S.A. for Colombian Patent Application No. NC2020/0009861 dated Nov. 27, 2020. 15 pages.
U.S. Appl. No. 16/551,550, filed Aug. 26, 2019, Aktoudianakis et al.
U.S. Appl. No. 16/840,217, filed Apr. 3, 2020, Aktoudianakis et al.
U.S. Appl. No. 16/891,880, filed Jun. 3, 2020, Aktoudianakis et al.
Gura, et al. Systems for Identifying New Drugs Are Often Faulty. Science. 1997; 278:1041-1042.
International Search Report and Written Opinion for International Application No. PCT/US2018/028382 dated Sep. 11, 2018. (17 pages).
International Search Report and Written Opinion for International Application No. PCT/US2019/017721 dated Apr. 8, 2019. (15 pages).
International Search Report and Written Opinion for International Application No. PCT/US2019/028129 dated Jul. 22, 2019. (13 pages).
International Search Report and Written Opinion for International Application No. PCT/US2019/041657 dated Sep. 12, 2019. (12 pages).
International Search Report and Written Opinion for International Application No. PCT/US2019/057407 dated Feb. 18, 2020. (11 pages).
Johnson, et al. Relationships between drug activity in NCI preclinical in vitro and in vivo models and early clinical trials. British Journal of Cancer. 2001; 84:1424-1431.
Office Action dated Jul. 16, 2020, for GCC Application 37906, 4 pages.
Search Report, Taiwan Application 108124749, dated Jul. 7, 2020, 12 pages.
Sham, K-C. et al.: Acid-induced formation of hydrogen-bonded double helix based on chiral polyphenyl-bridged bis(2,2'-bipyridine) ligands. RSC Advances, vol. 4, pp. 14513-14526, 2014.
Zarganes-Tzitzikes et al., "Inhibitors of programmed cell death 1 (PD-1): a patent review (2010-2015)", Expert Opinion on Therapeutic Patents, 2016, vol. 26, No. 9, pp. 973-977.
Partial European Search Report for European Patent Application No. 21204444.0 dated May 24, 2022. 13 pages.
Official Action for European Patent Application No. 19746317.7 dated Jan. 26, 2022. 5 pages.
Examination and Search Report for ARIPO AP/P/2021/012914 dated Feb. 2, 2022. 5 pages.
Examination Report for Canada Patent Application No. 3,103,286 dated Mar. 1, 2022. 3 pages.
Official Action for Japanese Patent Application No. 2021-500896 dated Mar. 11, 2022. 9 pages.
Office Action for Eurasian Patent Application No. 202092733 dated Apr. 22, 2022. 8 pages.
Official Action for Chilean Patent Application No. 202100084 dated May 10, 2022. 24 pages.
Examination Report for Indian Application No. 202117005496 dated Aug. 30, 2022. 7 pages.
Extended European Search Report for European Application No. 21204444.0 dated Aug. 24, 2022. 10 pages.
Garcia et al., Allosteric Inhibition of SHP2: Identification of a Potent, Selective, and Orally Efficacious Phosphatase Inhibitor, Journal of Medicinal Chemistry 2016, 59(17), pp. 7773-7782.
Office Action for Eurasian Application No. 202092733 dated Oct. 28, 2022. 8 pages.
Office Action for Uzbekistan Application No. IAP 20210065 dated Nov. 8, 2022. 4 pages.
Official Action for Panamanian Application No. 93366-01 dated Jul. 18, 2022. 8 pages.
Skalniak et al., Small-molecule inhibitors of PD-1/PD-L1 immune checkpoint alleviate the PD-L1- induced exhaustion of T-cells. Oncotarget, 2017, 8(42), pp. 72167-72181.
Sunshine et al., PD-1/PD-L1 inhibitors, Current Opinion in Pharmacology 2015, 23:32-38.
Office Action and Search Report for Chinese Application No. 201980046762.6 dated Dec. 27, 2022. 21 pages.
Office Action and Search Report for Taiwan Application No. 110122396 dated Jan. 4, 2023. 9 pages.
Official Action for Guatemala Application No. A2021-000006 dated Nov. 11, 2022. 4 pages.
Examination report for Australian Application No. 2022221403 dated May 8, 2023. 3 pages.
Extended European Search Report for European Application No. 23162059.2 dated Jul. 18, 2023. 8 pages.
Notice of Preliminary Rejection for Korean Application No. 10-2021-7003886 dated Apr. 24, 2023. 8 pages.
Office Action for Indonesian Application No. P00202100814 dated Jan. 11, 2023. 6 pages.
Office Action for Israeli Application No. 279991 dated Feb. 6, 2023. 3 pages.
Office Action for Uzbekistan Application No. IAP 20210065 dated Apr. 7, 2023. 4 pages.
Official Action for Colombian Application No. NC2021/0000151 dated Mar. 16, 2023. 12 pages.
Official Action for Japanese Application No. 2022-111092 dated Apr. 28, 2023. 2 pages.
Office Action for Gulf Co-Operation Council Application No. 37906 dated Mar. 19, 2023. 2 pages.
Zak et al., Structural basis for small molecule targeting of the programmed death ligand 1 (PD-L1), Oncotarget 2016, vol. 7, No. 21, pp. 30323-30335.
Extended European Search Report for European Application No. 23162699.5 dated Sep. 15, 2023. 12 pages.
Notice of Final Rejection for Korean Application No. 10-2021-7003886 dated Aug. 23, 2023. 8 pages.
Office Action for Chinese Application No. 201980046762.6 dated Aug. 12, 2023. 13 pages.
Office Action for Mexican Application No. MX/a/2021/000100 dated Jun. 7, 2023. 9 pages.
Office Action for Vietnamese Application No. 1-2021-00594 dated Jun. 28, 2023. 4 pages.
European Application Serial No. 23162699.5, Communication Pursuant to Article 94(3) EPC mailed Oct. 31, 2024, 4 pgs.
European Application Serial No. 23162699.5, Response filed Feb. 11, 2025 to Communication Pursuant to Article 94(3) EPC mailed Oct. 31, 2024, 254 pgs.

PD-1/PD-L1 INHIBITORS

CROSS-REFERENCE TO RELATED APPLICATIONS

This application is a continuation of U.S. application Ser. No. 16/510,647, filed on Jul. 12, 2019, now U.S. Pat. No. 10,774,071, which claims the benefit under 35 U.S.C. § 119(e) of U.S. Provisional Application Nos. 62/697,932, filed Jul. 13, 2018, 62/747,033, filed Oct. 17, 2018, and 62/808,763, filed Feb. 21, 2019, all of which are hereby incorporated by reference in their entireties.

FIELD

The present disclosure generally relates to compounds useful as inhibitors of PD-1, PD-L1 or the PD-1/PD-L1 interaction. Provided herein are compounds, compositions comprising such compounds, and methods for their use.

BACKGROUND

Programmed death-1 (CD279) is a receptor on T cells that has been shown to suppress activating signals from the T cell receptor when bound by either of its ligands, Programmed death-ligand 1 (PD-L1, CD274, B7-H1) or Programmed death-ligand 2 (PD-L2) (CD273, B7-DC). When Programmed death-1 (PD-1) expressing T cells contact cells expressing its ligands, functional activities in response to antigenic stimuli, including proliferation, cytokine secretion, and cytotoxicity are reduced. PD-1/PD-Ligand interactions down regulate immune responses during resolution of an infection or tumor, or during the development of self-tolerance. Chronic antigen stimulation, such as that which occurs during tumor disease or chronic infections, results in T cells that express elevated levels of PD-1 and are dysfunctional with respect to activity towards the chronic antigen. This is termed "T cell exhaustion." B cells also display PD-1/PD-ligand suppression and "exhaustion."

Blockade of the PD-1/PD-L1 ligation using antibodies to PD-L1 has been shown to restore and augment T cell activation in many systems. Patients with advanced cancer benefit from therapy with a monoclonal antibody to PD-L1. Preclinical animal models of tumors and chronic infections have shown that blockade of the PD-1/PD-L1 pathway by monoclonal antibodies can enhance the immune response and result in tumor rejection or control of infection. Antitumor immunotherapy via PD-1/PD-L1 blockade may augment therapeutic immune response to a number of histologically distinct tumors.

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1. Humanized mice infected with HIV-1 show enhanced protection against viremia and viral depletion of CD4+ T cells. Blockade of PD-1/PD-L1 through monoclonal antibodies to PD-L1 can restore in vitro antigen-specific functionality to T cells from HIV patients, HCV patients or HBV patients.

Accordingly, agents that block PD-1, PD-L1 and/or the PD-1/PD-L1 interaction are desired. Small molecule agents that block or inhibit PD-1, PD-L1 and/or the PD-1/PD-L1 interaction are particularly desired. Applicants have discovered small molecule compounds that have activity as inhibitors of PD-1, PD-L1 or inhibitors of the interaction of PD-1 with PD-L1, and thus may be useful for treating patients having cancer.

SUMMARY

The present disclosure provides a compound of Formula (I):

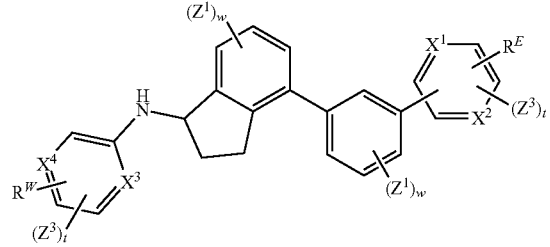

(I)

or a pharmaceutically acceptable salt, stereoisomer, mixture of stereoisomers, solvate, or tautomer thereof, wherein:
each of $X^1$, $X^2$, $X^3$ and $X^4$ are independently N, CH or $CZ^3$;
each $Z^1$ is independently is halo, $-OR^a$, $-NO_2$, cyano, $-NR^aR^b$, $-N_3$, $-S(O)_2R^a$, $-C_{1-6}$ alkyl, $-C_{1-6}$ haloalkyl, $-C_{2-6}$alkenyl, $-C_{2-6}$ alkynyl, $-O-C_{1-6}$ alkyl, $-O-C_{1-6}$ haloalkyl, $-C_{3-8}$ cycloalkyl, or $-C_{1-6}$ alkyl$C_{3-8}$ cycloalkyl; and wherein each alkyl, alkenyl, alkynyl, and cycloalkyl is optionally substituted with 1 to 4 groups independently selected from oxo, $-NO_2$, $-N_3$, $-OR^a$, halo, and cyano;

each w is independently 0, 1 or 2;
each $Z^3$ is independently halo, $-OR^a$, $-N_3$, $-NO_2$, cyano, $-NR^1R^2$, $-S(O)_2R^a$, $-S(O)_2NR^aR^b$, $-NR^aS(O)_2R^a$, $-NR^aC(O)R^a$, $-C(O)R^a$, $-C(O)OR^a$, $-C(O)NR^aR^b$, $-NR^aC(O)OR^a$, $-NR^aC(O)NR^1R^2$, $-OC(O)NR^aR^b$, $-NR^aS(O)_2NR^aR^b$, $-C(O)NR^aS(O)_2NR^aR^b$, $-C_{1-6}$ alkyl, $-C_{2-6}$ alkenyl, $-C_{2-6}$ alkynyl, $-O-C_{1-6}$ alkyl, $-C_{1-6}$ cyanoalkyl, $-C_{1-6}$ haloalkyl, $-O-C_{1-6}$ cyanoalkyl, $-O-C_{1-6}$ haloalkyl, $-C_{3-8}$cycloalkyl, $-C_{1-6}$ alkyl$C_{3-8}$ cycloalkyl, aryl, heteroaryl, heterocyclyl, and $R^N$; and wherein the alkyl, alkenyl, alkynyl, $C_{3-8}$ cycloalkyl, aryl, heteroaryl, or heterocyclyl group is optionally substituted with 1 to 4 groups independently selected from oxo, $-NO_2$, $-N_3$, $-OR^a$, halo, cyano, $-NR^aR^b$, $-C(O)R^a$, $-C(O)OR^a$, $-O-C_{1-6}$cyanoalkyl, $-C(O)NR^aR^b$, $-NR^aC(O)R^a$, $-NR^aC(O)OR^a$, $-S(O)_2R^a$, $-NR^aS(O)_2R^b$, $-SO_2NR^aR^b$, $-NR^aS(O)_2NR^aR^b$, $-C(O)NR^aS(O)_2NR^aR^b$ and $-C_{3-8}$ cycloalkyl;

$R^N$ is independently $-C_{1-6}$alkyl$NR^1R^2$, $-OC_{1-6}$ alkyl$NR^1R^2$, $-C_{1-6}$ alkyl-$O-C_{1-6}$ alkyl$NR^1R^2$, $-NR^aC_{1-6}$ alkyl$NR^1R^2$, $-C_{1-6}$ alkyl$C(O)NR^1R^2$, $-O-C_{1-6}$ alkyl$C(O)NR^1R^2$, $-O-C_{1-6}$ alkyl$C(O)OR^1$, $-SC_{1-6}$alkyl$NR^1R^2$, $-C_{1-6}$alkyl$OR^a$, or

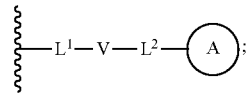

$L^1$ is independently a bond, —O—, —NR$^a$—, —S—, —S(O)—, or —S(O)$_2$—;

V is independently selected from a bond, $C_{1-6}$ alkyl, $C_{2-6}$ alkenyl, and $C_{2-6}$ alkynyl;
  wherein each alkyl, alkenyl, or alkynyl is optionally independently substituted with —OR$^a$, halo, cyano, —NR$^a$R$^b$ or —C$_{3-8}$ cycloalkyl;

$L^2$ is independently a bond, —O—, —NR$^a$—, —S—, —S(O)—, or —S(O)$_2$—;

ring A is independently cycloalkyl, aryl, heteroaryl, or heterocyclyl;
  wherein each cycloalkyl, aryl, heteroaryl, or heterocyclyl is optionally substituted with 1 to 4 groups independently selected from oxo, —NO$_2$, —N$_3$, —OR$^a$, halo, cyano, —C$_{1-6}$ alkyl, —C$_{1-6}$ haloalkyl, —C$_{2-6}$ alkenyl, —C$_{2-6}$ alkynyl, —O—C$_{1-6}$ haloalkyl, —NR$^a$R$^b$, —C(O)R$^a$, —C(O)OR$^a$, —O—C$_{1-6}$ cyanoalkyl, —C(O)NR$^a$R$^b$, —NR$^a$C(O)R$^a$, —NR$^a$C(O)OR$^a$, —NR$^a$C(O)OR$^a$, —C(O)N(R$^a$)OR$^b$, —S(O)$_2$R$^a$, —S(O)$_2$NR$^a$R$^b$, —NR$^a$S(O)$_2$R$^b$, —NR$^a$S(O)$_2$NR$^a$R$^b$, —C(O)NR$^a$S(O)$_2$NR$^a$R$^b$, C$_{3-8}$ cycloalkyl, and —C$_{1-6}$ alkylC$_{3-8}$ cycloalkyl; and
  wherein the alkyl, alkenyl, or alkynyl group is optionally independently substituted with —OR$^a$, halo, cyano, —NR$^a$R$^b$ or —C$_{3-8}$ cycloalkyl;

each t is independently 0, 1 or 2;

$R^E$ and $R^W$ are each independently —NR$^1$R$^2$, —C$_{1-6}$ alkylNR$^1$R$^2$, —O—C$_{1-6}$ alkylNR$^1$R$^2$, —C$_{1-6}$ alkyl-O—C$_{1-6}$alkylNR$^1$R$^2$, —NR$^a$—C$_{1-6}$ alkylNR$^1$R$^2$, —C$_{1-6}$ alkylN$^+$R$^1$R$^2$R$^3$, —S—C$_{1-6}$ alkylNR$^1$R$^2$, —C(O)NR$^1$R$^2$, —S(O)$_2$R$^a$, —(CH$_2$)$_u$S(O)$_2$NR$^1$R$^2$, —(CH$_2$)$_u$NR$^a$S(O)$_2$NR$^a$R$^b$, —S(O)$_2$NR$^a$C$_{1-6}$alkylNR$^1$R$^2$, —NR$^a$S(O)$_2$C$_{1-6}$alkylNR$^1$R$^2$, —(CH$_2$)$_u$C(O)NR$^a$S(O)$_2$NR$^a$R$^b$, —(CH$_2$)$_u$N$^+$R$^1$R$^2$O$^-$, —(CH$_2$)$_u$P$^+$R$^b$R$^c$R$^d$, —(CH$_2$)$_u$P$^+$R$^c$R$^d$O$^-$, —(CH$_2$)$_u$P$^+$O[NR$^a$R$^b$][NR$^c$R$^d$], —(CH$_2$)$_u$NR$^c$P(O)(OR$^c$)$_2$, —(CH$_2$)$_u$CH$_2$OP(O)(OR$^c$)(OR$^d$), —(CH$_2$)$_u$OP(O)(OR$^c$)(OR$^d$), —(CH$_2$)$_u$OP(O)NR$^a$R$^b$)(OR$^a$), or

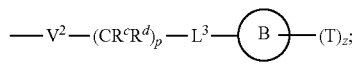

wherein:

$V^2$ is independently a bond, —O—, —NR$^a$—, —S—, —SO—, —SO$_2$—, —C(O)NR$^a$—, —NR$^a$C(O)—, —S(O)$_2$NR$^1$—, or —NR$^a$S(O)$_2$—;

$L^3$ is independently a bond, —O—, —NR$^a$—, —S—, —SO—, —SO$_2$—, —C(O)NR$^a$—, —NR$^a$C(O)—, —S(O)$_2$NR$^1$—, or —NR$^a$S(O)$_2$—;

ring B is independently cycloalkyl, aryl, heteroaryl, or heterocyclyl;

T is independently hydrogen, —OR$^a$, —(CH$_2$)$_q$NR$^1$R$^2$, —(CH$_2$)$_q$NR$^a$C(O)R, or —(CH$_2$)C(O)R$^e$;

p is independently 0, 1, 2, 3, 4, or 5;
q is independently 0, 1, 2, 3, 4, or 5;
u is 0, 1, 2, 3, or 4;
z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of —NR$^a$R$^b$, halo, cyano, oxo, —OR$^a$, —C$_{1-6}$alkyl, —C$_{1-6}$ haloalkyl, —C$_{1-6}$ cyanoalkyl, —C$_{1-6}$alkylNR$^a$R$^b$, —C$_{1-6}$ hydroxyalkyl, —C$_{3-8}$ cycloalkyl, and —C$_{1-3}$ alkylC$_{3-8}$cycloalkyl;

provided that at least one of $V^2$, $L^3$, ring B and T contains a nitrogen atom;

each $R^1$ is independently selected from hydrogen, —C$_{1-8}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{1-6}$ alkylC(O)OR$^a$, —C$_{2-6}$ alkenylC(O)OR$^a$, —S(O)$_2$R$^a$, —S(O)$_2$NR$^a$R$^b$, —C(O)NR$^a$S(O)$_2$R$^a$, and —C$_{1-6}$ alkylC$_{3-8}$cycloalkyl;
  wherein each alkyl, alkenyl, cycloalkyl, aryl, heteroaryl, or heterocyclyl is optionally substituted with 1 to 4 groups independently selected from —OR$^a$, cyano, halo, C$_{1-6}$ alkyl, —C$_{1-6}$ alkylOR$^a$, —C$_{1-6}$ cyanoalkyl, —C$_{1-6}$haloalkyl, C$_{3-8}$ cycloalkyl, —C$_{1-3}$alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —OC(O)NR$^a$R$^b$, NR$^a$C(O)OR$^b$, —C$_{1-6}$ alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$, —C$_{1-6}$alkylC(O)NR$^a$S(O)$_2$R$^b$, —NR$^a$C(O)R$^b$, and —C$_{1-6}$alkylNR$^a$C(O)R$^b$;

each $R^2$ is independently selected from hydrogen, —C$_{1-6}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, and —C$_{2-6}$ alkenylC(O)OR$^a$;
  wherein each alkyl, alkenyl, alkynyl, cycloalkyl, aryl, heteroaryl, or heterocyclyl is optionally substituted with 1 to 4 groups independently selected from —OR$^a$, cyano, halo, C$_{1-6}$alkyl, —C$_{1-6}$alkylOR$^a$, —C$_{1-6}$ cyanoalkyl, —C$_{1-6}$ haloalkyl, —C$_{3-8}$ cycloalkyl, —C$_{1-3}$alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$ and —NR$^a$C(O)R$^b$;

or $R^1$ and $R^2$ combine to form a heterocyclyl optionally substituted with 1 to 3 groups independently selected from oxo, —C$_{1-6}$ alkyl, —C$_{3-8}$ cycloalkyl, —C$_{2-6}$ alkenyl, —C$_{2-6}$ alkynyl, —OR$^a$, —C(O)OR$^a$, —C$_{1-6}$ cyanoalkyl, —C$_{1-6}$ alkylOR$^a$, —C$_{1-6}$ haloalkyl, —C$_{1-3}$ alkylC$_{3-8}$cycloalkyl, —C(O)R$^a$, C$_{1-6}$ alkylC(O)R$^a$, —C$_{1-6}$ alkylC(O)OR$^a$, —NR$^a$R$^b$, —C$_{1-6}$alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$NR$^a$C(O)R$^b$, and —C$_{1-6}$ alkylS(O)$_2$NR$^a$R$^b$;

each $R^3$ is independently hydrogen, —C$_{1-6}$ alkyl, —C$_{2-6}$ alkenyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, or —C$_{2-6}$ alkenylC(O)OR$^a$;

each $R^a$ is independently selected from hydrogen, —C$_{1-6}$ alkyl, —C$_{1-6}$ cyanoalkyl, —C$_{1-6}$haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each $R^b$ is independently selected from hydrogen, —C$_{1-6}$ alkyl, —C$_{1-6}$ cyanoalkyl, —C$_{1-6}$haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

or $R^a$ and $R^b$ may combine together to form a heterocyclyl optionally substituted with 1 to 4 groups independently selected from —OR$^1$, cyano, halo, —C$_{1-6}$ alkylOR$^f$, —C$_{1-6}$ cyanoalkyl, —C$_{1-6}$haloalkyl, —C$_{3-8}$ cycloalkyl, —C$_{1-3}$ alkylC$_{3-8}$cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, —C$_{1-6}$ alkylC(O)NR$^f$R$^g$, —S(O)$_2$R$^f$, —C$_{1-6}$ alkylS(O)$_2$R$^f$, —S(O)$_2$NR$^f$R$^g$, —C$_{1-6}$ alkylS(O)$_2$NR$^f$R$^g$, —C(O)NR$^f$S(O)$_2$R$^g$ and —NR$^f$C(O)R$^g$;

each R$^c$ is independently selected from hydrogen, —OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

each R$^d$ is independently selected from hydrogen, —C$_{1-6}$ alkyl, —C$_3$-C$_8$cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each R$^e$ is independently selected from hydrogen, —C$_{1-6}$ alkyl, —O—C$_{1-6}$alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —C$_{1-3}$ alkylC$_{3-8}$cycloalkyl, —C$_{1-6}$ alkylaryl, —C$_{1-6}$alkylheteroaryl, —NR$^f$R$^g$, —C$_{1-6}$ alkylNR$^f$R$^g$, —C(O)NR$^f$R$^g$, —C$_{1-6}$ alkylC(O)NR$^f$R$^g$, —NHS(O)$_2$R$^f$, —C$_{1-6}$ alkylS(O)$_2$R$^f$, and —C$_{1-6}$ alkylS(O)$_2$NR$^f$R$^g$;

each R$^f$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl; and each R$^g$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl.

Also provided herein are compounds of Table 1A or a pharmaceutically acceptable salt, stereoisomer, mixture of stereoisomers, solvate, or tautomer thereof.

Also provided herein are compounds of Table 1B or a pharmaceutically acceptable salt, stereoisomer, mixture of stereoisomers, solvate, or tautomer thereof.

The present disclosure provides a method of inhibiting PD-1, PD-L1 and/or the PD-1/PD-L1 interaction comprising administering a compound of formula (I), or any formula described herein (e.g., Formula (I), (IA), (IB), (IC), (ID), (II), (IIA), (IIB), (IIC), (IID), (III), (IIIA), (IIIB), (IIIC), (IIID), (IV), (IVA), (IVB), (IVC), (IVD), (V), (VA), (VB), (VC), (VD), (VIA), (VIB), (VIC), or (VID)), or a pharmaceutically acceptable salt, stereoisomer, mixture of stereoisomers, solvate, or tautomer thereof, to a patient in need thereof.

The present disclosure provides a method of treating cancer comprising administering a therapeutically effective amount of a compound formula (I), or any formula described herein, or a pharmaceutically acceptable salt, stereoisomer, mixture of stereoisomers, solvate, or tautomer thereof, to a patient in need thereof.

One embodiment provides the use of a compound as disclosed herein (e.g., a compound of formula (I), or any formula described herein), or a pharmaceutically acceptable salt, stereoisomer, mixture of stereoisomers, solvate, or tautomer thereof, for the treatment of a condition in a patient that is amenable to treatment by inhibiting PD-1, PD-L1 or the PD-1/PD-L1 interaction, e.g., cancer.

One embodiment provides the use of a compound of formula (I), or any formula described herein, or a pharmaceutically acceptable salt, stereoisomer, mixture of stereoisomers, solvate, or tautomer thereof, for the treatment of cancer or a condition in a patient that is amenable to treatment by inhibiting PD-1, PD-L1 or the PD-1/PD-L1 interaction comprising administering said compound of formula (I), or any formula described herein, or a pharmaceutically acceptable salt, stereoisomer, mixture of stereoisomers, solvate, or tautomer thereof, to said patient in need thereof.

In one embodiment, provided is a method for treating a cancer wherein the cancer is pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer or colon cancer, comprising administering a therapeutically effective amount of formula (I), or any formula described herein, or a pharmaceutically acceptable salt, stereoisomer, mixture of stereoisomers, solvate, or tautomer thereof, to a patient in need thereof.

In one embodiment, provided is a method for treating a cancer or a condition in a patient that is amenable to treatment by inhibiting PD-1, PD-L1 or the PD-1/PD-L1 interaction selected from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer comprising administering a therapeutically effective amount of a compound of formula (I), or any formula described herein, or a pharmaceutically acceptable salt, stereoisomer, mixture of stereoisomers, solvate, or tautomer thereof, to a patient in need thereof, further comprising administering at least one additional anticancer agent or therapy to a patient in need thereof. In certain embodiments, the additional anticancer agent or therapy is selected from nivolumab, pembrolizumab, atezolizumab, ipilimumab, chemotherapy, radiation therapy, and resection therapy, to a patient in need thereof.

In one embodiment, provided is a method for treating hepatitis B virus (HBV), comprising administering a therapeutically effective amount of formula (I), or any formula described herein, or a pharmaceutically acceptable salt, stereoisomer, mixture of stereoisomers, solvate, or tautomer thereof, to a patient in need thereof.

In one embodiment, provided is a compound of formula (I), or any formula described herein, or a pharmaceutically acceptable salt, stereoisomer, mixture of stereoisomers, solvate, or tautomer thereof, for the treatment of cancer or a condition in a patient selected from lymphoma, multiple myeloma, and leukemia. Additional diseases or conditions that may be treated include, but are not limited to acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma and diffuse large B-cell lymphoma (DLBCL).

In one embodiment, the present disclosure provides a compound of formula (I), or any formula described herein, or a pharmaceutically acceptable salt, stereoisomer, mixture of stereoisomers, solvate, or tautomer thereof, in combination with at least one additional anti-cancer agent selected from rituxan, doxorubicin, gemcitabine, nivolumab, pembrolizumab, and ipilimumab.

In one embodiment, the present disclosure provides a compound of formula (I), or any formula described herein, or a pharmaceutically acceptable salt, stereoisomer, mixture of stereoisomers, solvate, or tautomer thereof, in combination with at least one additional check-point inhibitor selected from nivolumab, pembrolizumab, atezolizumab, and ipilimumab.

In one embodiment, the present disclosure provides a pharmaceutical composition comprising a compound of formula (I), or any formula described herein, or a pharmaceutically acceptable salt, stereoisomer, mixture of stereoisomers, solvate, or tautomer thereof, and a pharmaceutically acceptable carrier or excipient.

In one embodiment, the present disclosure provides a pharmaceutical composition comprising a compound of formula (I), or any formula described herein, or a pharmaceutically acceptable salt, stereoisomer, mixture of stereoisomers, solvate, or tautomer thereof, and at least one additional anticancer agent and at least one pharmaceutically acceptable carrier or excipient.

In one embodiment, the present disclosure provides a pharmaceutical composition comprising a compound of formula (I), or any formula described herein, or a pharmaceutically acceptable salt, stereoisomer, mixture of stereoisomers, solvate, or tautomer thereof, at least one additional therapeutic agent suitable for treating an hepatitis B virus (HBV) infection, and at least one pharmaceutically acceptable carrier or excipient.

In one embodiment, the present disclosure provides a kit that includes a compound of formula (I), or any formula described herein, or a pharmaceutically acceptable salt, stereoisomer, mixture of stereoisomers, solvate, or tautomer thereof, a label and/or instructions for use of the compound in the treatment of cancer or a disease or condition mediated by PD-1, PD-L1 activity or the PD-1/PD-L1 interaction.

In one embodiment, the present disclosure provides a kit that includes a compound of formula (I), or any formula described herein, or a pharmaceutically acceptable salt, stereoisomer, mixture of stereoisomers, solvate, or tautomer thereof, at least one additional anticancer agent, a label(s) and/or instructions for use of the compound(s) in the treatment of a disease or condition mediated by PD-1, PD-L1 activity or PD-1/PD-L1 interaction.

In one embodiment, the present disclosure provides articles of manufacture that include a compound of formula (I), or any formula described herein, or a pharmaceutically acceptable salt, stereoisomer, mixture of stereoisomers, solvate, or tautomer thereof, and a container. In one embodiment, the container may be a vial, jar, ampoule, preloaded syringe, or an intravenous bag.

In one embodiment, the present disclosure provides a compound of formula (I), or any formula described herein, or a pharmaceutically acceptable salt, stereoisomer, mixture of stereoisomers, solvate, or tautomer thereof, for use in therapy.

In another embodiment, the present disclosure provides a compound of formula (I), or any formula described herein, or a pharmaceutically acceptable salt, stereoisomer, mixture of stereoisomers, solvate, or tautomer thereof, for use in the manufacture of a medicament for treating cancer.

DETAILED DESCRIPTION

Definitions

As used in the present disclosure, the following words and phrases are generally intended to have the meanings as set forth below unless expressly indicated otherwise or the context in which they are used indicates otherwise.

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount 5%. In certain other embodiments, the term "about" includes the indicated amount 1%. Also, to the term "about X" includes description of "X". Also, the singular forms "a" and "the "include plural references unless the context clearly dictates otherwise. Thus, e.g., reference to "the compound" includes a plurality of such compounds and reference to "the assay" includes reference to one or more assays and equivalents thereof known to those skilled in the art.

The term "substituted" means that any one or more (e.g., one to three, or one to five) hydrogen atoms on the designated atom or group is replaced with one or more (e.g., one to three, or one to five) substituents other than hydrogen, provided that the designated atom's normal valence is not exceeded. The one or more (e.g., one to three, or one to five) substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein, whether the substituents are the same or different. Unless otherwise noted, the maximum number of serial substitutions in compounds described herein is three. For example, serial substitutions of substituted aryl groups with two other substituted aryl groups are limited to ((substituted aryl)

substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

A "substituted" group also includes embodiments in which a monoradical substituent is bound to a single atom of the substituted group (e.g., forming a branch), and also includes embodiments in which the substituent may be a diradical bridging group bound to two adjacent atoms of the substituted group, thereby forming a fused ring on the substituted group.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl, and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—" or "—O-alkyl". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more (e.g., one to three, or one to five) hydrogen atoms are replaced by a halogen.

"Amino" refers to the group —$NR^yR^z$ wherein $R^y$ and $R^z$ are independently selected from hydrogen, alkyl, haloalkyl, cycloalkyl, aryl, heterocyclyl, or heteroaryl; each of which may be optionally substituted.

"Aryl" refers to a monoradical or diradical aromatic carbocyclic group having a single ring (e.g., monocyclic) or multiple rings (e.g., bicyclic or tricyclic) including fused ring systems wherein one or more (e.g., one, two, or three) fused rings is/are fully or partially unsaturated. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Non-limiting examples of aryl groups as used herein include phenyl, naphthyl, fluorenyl, indanyl, tetrahydroindanuyl, and anthryl. Aryl, however, does not encompass or overlap in any way with heteroaryl defined below. If one or more aryl groups are fused with a heteroaryl ring, the resulting ring system is heteroaryl. The classification of mono or diradical indicates whether the aryl group terminates the chain (monoradical) or is within a chain (diradical). The above definition does not preclude additional substituents on the aryl group. For example, as used herein, the aryl group in "A-aryl-B" is a diradical whereas the aryl group in "A-B-aryl" is monoradical, though additional substituents may be present on each aryl group.

The term "alkylsulfinyl" refers to the group —S(O)-alkyl, where alkyl is as defined above, and includes optionally substituted alkyl groups as also defined above.

The term "alkylsulfonyl" refers to the group —$S(O)_2$-alkyl, where alkyl is as defined above, and includes optionally substituted alkyl groups as also defined above.

"Cycloalkyl" refers to a saturated or partially saturated cyclic alkyl group having a single ring or multiple rings including fused, bridged, and spiro ring systems. As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl. As used herein the term "cycloalkenyl" refers to the non-aromatic carbocyclic (partially saturated cyclic alkyl) group having at least one double bond.

"Cyanoalkyl" refers to an alkyl group substituted with cyano (CN).

"Halogen" or "halo" includes fluoro, chloro, bromo, and iodo.

The term "haloalkyl" refers to a monoradical or diradical having the indicated carbon atoms of the alkyl group wherein one or more (e.g., one to three, or one to five) hydrogen hydrogen atoms have been substituted by a halogen. Examples of haloalkyl groups include —$CH_2F$, —$CHF_2$, —$CF_3$, —$CH_2CF_3$, —$CHFCH_2F$, —$CF_2$—, —CHF—, and the like. Similarly, the term "haloalkoxy", e.g., —O—$C_{1-3}$haloalkyl, refers to an alkoxy group wherein one or more (e.g., one to three, or one to five) hydrogen atoms of the alkyl group have been substituted by a halogen. Examples of haloalkoxy groups include —$OCH_2F$, —$OCHF_2$, —$OCF_3$, —$OCH_2CF_3$, —$OCHFCH_2F$, and the like. One of skill in the art is aware that similar definitions apply for the alkenyl and alkynyl analogs (e.g., $C_{2-4}$haloalkenyl, —O—$C_{2-4}$haloalkynyl).

"Heteroalkyl" refers to an alkyl group in which one or more (e.g., one to three, or one to five) hydrogen of the carbon atoms (and any associated hydrogen atoms) are each independently replaced with the same or different heteroatomic groups. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —$S(O)_2$—, and the like, where R is H, alkyl, aryl, cycloalkyl, heteroalkyl, heteroaryl, or heterocycloalkyl, each of which may be optionally substituted. Examples of heteroalkyl groups include —$OCH_3$, —$CH_2OCH_3$, —$SCH_3$, —$CH_2SCH_3$, —$NRCH_3$, and —$CH_2NRCH_3$, where R is hydrogen, alkyl, cycloalkyl, aryl, arylalkyl, heteroalkyl, or heteroaryl, each of which may be optionally substituted. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a monoradical or diradical aromatic group having a single ring, multiple rings, or multiple fused rings, with one or more ring heteroatoms independently selected from nitrogen, oxygen, and sulfur. The term includes fused ring systems wherein one or more (e.g., one, two, or three) fused rings is/are fully or partially unsaturated. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Non-limiting examples of heteroaryl groups include pyrimidinyl, purinyl, pyridyl, pyridazinyl, benzothiazolyl, benzodioxanyl, indolinyl, and pyrazolyl. The classification of mono or diradical indicates whether the heteroaryl group terminates the chain (monoradical) or is within a chain (diradical). The above definition does not preclude additional substituents on the heteroaryl group. For example, the heteroaryl group in "A-heteroaryl-B" is a diradical whereas the heteroaryl group in "A-B-heteroaryl" is monoradical, though additional substituents may be present on each heteroaryl group. Heteroaryl does not encompass or overlap with aryl as defined above.

"Heterocyclyl," "heterocycle," or "heterocyclic" refer to a saturated or unsaturated cyclic alkyl group, with one or more ring heteroatoms independently selected from nitrogen, oxygen and sulfur. A heterocycloalkyl may be a single ring or multiple rings wherein the multiple rings may be fused, bridged, or spiro. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, bridged-heterocycloalkyl includes bicyclic and tricyclic ring systems. Also used herein, the term "spiro-heterocyclyl" refers to a ring system in which a three- to ten-membered heterocycloalkyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of spiro-heterocyclyl include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl.

The term "heterocyclyl," "heterocycle," or "heterocyclic" includes monoradical or diradical saturated or unsaturated groups having a single ring or multiple condensed rings, having from 3 to 12 carbon atoms, from 1 to 6 heteroatoms, or from 1 to 4 heteroatoms, selected from nitrogen, sulfur, phosphorus, and/or oxygen within the ring. Where the group does not terminate the molecule, it is a diradical and is construed as such i.e., also referred to as heterocyclylene or heterocyclene.

The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. A heterocyclyl may contain one or more (e.g., one or two) oxo (=O or —O$^-$) and/or thioxo (=S) groups.

"Acyl" refers to a group —C(=O)R, wherein R is hydrogen, alkyl, cycloalkyl, heterocycloalkyl, aryl, heteroalkyl, or heteroaryl; each of which may be optionally substituted, as defined herein. Examples of acyl include formyl, acetyl, cyclohexylcarbonyl, cyclohexylmethyl-carbonyl, and benzoyl.

The term "N-alkylated" means an alkyl group is substituted for one of the hydrogen atoms of a mono substituted amine, or a di-substituted amine group or a tri substituted amine group. When the alkylation is on a tri-substituted amine group an alkonium salt is generated i.e., a positive charge is generated on the nitrogen atom. N-alkylation is commonly associated with alkyl substitution on a ring nitrogen atom.

The term "cyano" refers to the group —CN.

The term "oxo" refers to a group =O.

The term "carboxy" refers to a group —C(O)—OH.

The term "ester" or "carboxyl ester" refers to the group —C(O)OR, where R is alkyl, cycloalkyl, aryl, heteroaryl, or heterocyclyl, which may be optionally further substituted, for example, by alkyl, alkoxy, halogen, $CF_3$, amino, substituted amino, cyano or —S(O)$_y$R$^z$, in which R$^z$ is alkyl, aryl, or heteroaryl, and y is 0, 1 or 2.

The term "substituted amino" refers to the group —NRR, where each R is independently hydrogen, alkyl, cycloalkyl, aryl, heteroaryl, or heterocyclyl, each of which may be optionally substituted, or a group as described or exemplified herein, or where both R groups are joined to form a heterocyclic group (e.g., morpholino) as described or exemplified herein, which also may be optionally substituted.

The term "amido" refers to the group —C(O)NRR where each R is independently hydrogen, alkyl, cycloalkyl, aryl, heteroaryl, or heterocyclyl, each of which may be optionally substituted, or a group as described or exemplified herein, or where both R groups are joined to form a heterocyclic group (e.g., morpholino) as described or exemplified herein, which also may be optionally substituted.

The term "sulfoxide" refers to a group —S(O)R, in which R is alkyl, cycloalkyl, heterocyclyl, aryl, or heteroaryl, each of which may be optionally substituted.

The term "sulfone" refers to a group —S(O)$_2$R, in which R is alkyl, cycloalkyl, heterocyclyl, aryl, or heteroaryl, each of which may be optionally substituted.

As used herein, the terms "alkylcycloalkyl," "alkylaryl," "alkylheteroaryl" and "alkylheterocyclyl" are intended to refer to a cycloalkyl, aryl, heteroaryl or heterocyclyl group which is bound to the remainder of the molecule via an alkyl moiety, where the terms "alkyl," "cycloalkyl," "aryl," "heteroaryl" and "heterocyclyl" are as defined herein. Exemplary alkylaryl groups include benzyl, phenethyl, and the like.

"Optional" or "optionally" means that the subsequently described event or circumstance may or may not occur, and that the description includes instances where said event or circumstance occurs and instances in which it does not.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl, the last mentioned group contains the atom by which the moiety is attached to the rest of the molecule.

Where a group is represented by a bond, multiple adjacent groups whether the same or different, when represented by bonds, constitute a single bond. For example the group "-$L^1$-$V^1$-$L^2$-" constitutes a single bond if each of $L^1$, $V^1$ and $L^2$ is a bond.

Where a given group (moiety) is described herein as being attached to a second group and the site of attachment is not explicit, the given group may be attached at any available site of the given group or to any available site of the second group. For example, an "alkyl-substituted phenyl," where the attachment sites are not explicit, may have any available site of the alkyl group attached to any available site of the phenyl group. In this regard, an "available site" is a site of the group at which hydrogen of the group may be replaced with a substituent.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The compounds of the disclosure may possess one or more asymmetric centers and may be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixture of stereoisomers are encompassed within the scope of the present disclosure, all of which are intended to be depicted by the structures of this specification unless otherwise specifically indicated.

The absolute stereochemistry is specified according to the Cahn Ingold Prelog R S system. When the compound is a pure enantiomer the stereochemistry at each chiral carbon may be specified by either R or S. A resolved compound whose absolute configuration is unknown may be designated (+) or (−) depending on the direction (dextro- or laevorotary) that it rotates the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "solvate" refers to a complex formed by combining a compound of formula (I), or any other formula as disclosed herein, or a pharmaceutically acceptable salt, stereoisomer, mixture of stereoisomers, solvate, or tautomer thereof, and a solvent.

The term "hydrate" refers to the complex formed by the combining of a compound of formula (I), or any formula disclosed herein, or a pharmaceutically acceptable salt, stereoisomer, mixture of stereoisomers, solvate, or tautomer thereof, and water.

The term "prodrug" refers to compounds of formula (I), or derivatives of formula (I) disclosed herein, that include chemical groups which, in vivo, can be converted and/or can be split off from the remainder of the molecule to provide for the active drug. Pharmaceutically acceptable salts or biologically active metabolites thereof of the prodrug of a compound of formula (I), or any formula described herein, or a pharmaceutically acceptable salt, stereoisomer, mixture of stereoisomers, solvate, or tautomer thereof, are also within the ambit of the present disclosure.

Any formula or structure given herein, including formula (I), or any formula disclosed herein, is intended to represent unlabeled forms as well as isotopically labeled forms of the compounds. Isotopically labeled compounds have structures depicted by the formulas given herein except that one or more (e.g., one to three, or one to five) atoms are replaced by an isotope having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds of the present disclosure, for example those into which radioactive isotopes such as $^3H$, $^{13}C$ and $^{14}C$ are incorporated, are within the ambit of the present disclosure. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in treatment of patients. Such isotopically labeled analogs of compounds of the present disclosure may also be useful for treatment of diseases disclosed herein because they may provide improved pharmacokinetic and/or pharmacodynamic properties over the unlabeled forms of the same compounds. Such isotopically leveled forms of or analogs of compounds herein are within the ambit of the present disclosure. One of skill in the art is able to prepare and use such isotopically labeled forms following procedures for isotopically labeling compounds or aspects of compounds to arrive at isotopic or radiolabeled analogs of compounds disclosed herein.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, di-substituted cycloalkyl amine, tri-substituted cycloalkyl amines, cycloalkenyl amines, di(cycloalkenyl) amines, tri(cycloalkenyl) amines, substituted cycloalkenyl amines, di-substituted cycloalkenyl amine, tri-substituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have two of the three substituents on nitrogen ($R^{30}$, $R^{31}$, and $R^{32}$) as hydrogen, di-substituted amines have one of the three substituents on nitrogen ($R^{30}$, $R^{31}$, and $R^{32}$) as hydrogen, whereas tri-substituted amines have none of the three substituents on nitrogen ($R^{30}$, $R^{31}$, and $R^{32}$) as hydrogen. $R^{30}$, $R^{31}$, and $R^{32}$ are selected from a variety of substituents such as hydrogen, optionally substituted alkyl, aryl, heteroaryl, cycloalkyl, cycloalkenyl, heterocyclyl, and the like.

Specific examples of suitable amines include, by way of example only, isopropyl amine, trimethyl amine, diethyl amine, tri(iso-propyl) amine, tri(n-propyl) amine, ethanolamine, diethanolamine, 2-dimethylamino ethanol, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial, and antifungal agents, isotonic and absorption delaying agents and the like. The use of such media and agents for pharmaceutically active substances is well known in the art. Except insofar as any conventional media or agent is incompatible with the active ingredient, or unless otherwise indicated herein, its use in the therapeutic compositions is contemplated. Supplementary active ingredients can also be incorporated into the compositions.

The term "anticancer agent" is any drug that is effective in the treatment of a malignant, or cancerous disease. Effectiveness may mean inhibition, partial, or full remission, prolongation of life, improvement in quality of life, or cure. There are several major classes of anticancer drugs including chemical compositions as disclosed herein or known to one of skill in the art e.g., PD-1, PD-L1, PD-1/PD-L1 interaction inhibitors, alkylating agents, antimetabolites, natural products, and hormones.

The term "additional anticancer agent" as used herein means the use or combination of a second, third, fourth, fifth, etc., anticancer agent(s) in addition to a compound according to formula (I) disclosed herein.

The term "anticancer therapy" means any currently known therapeutic methods for the treatment of cancer.

The term "blockade agent" or "check point inhibitors" are classes of immune oncology agents that inhibit PD-1, PD-L1, or the PD-1/PD-L1 interaction.

The term "treatment" or "treating" means any administration of a compound or compounds according to the present disclosure to a subject (e.g., a human) having or susceptible to a condition or disease disclosed herein for the purpose of: 1) preventing or protecting against the disease or condition, that is, causing the clinical symptoms not to develop; 2) inhibiting the disease or condition, that is, arresting or suppressing the development of clinical symptoms; or 3) relieving the disease or condition that is causing the regression of clinical symptoms. In some embodiments, the term "treatment" or "treating" refers to relieving the disease or condition or causing the regression of clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment. The presence of a genetic mutation or the predisposition to having a mutation may not be alterable. However, prophylactic treatment (prevention) as used herein has the potential to avoid/ameliorate the symptoms or clinical consequences of having the disease engendered by such genetic mutation or predisposition.

It will be understood by those of ordinary skill in the art that in human medicine, it is not always possible to distinguish between "preventing" and "suppressing" since the ultimate inductive event or events may be unknown, latent, or the patient is not ascertained until well after the occurrence of the event or events. Therefore, as used herein, the term "prophylaxis" is intended as an element of "treatment" to encompass both "preventing" and "suppressing" as defined herein. The term "protection," as used herein, is meant to include "prophylaxis."

The term "patient" typically refers to a "mammal" which includes, without limitation, human, monkeys, rabbits, mice, domestic animals, such as dogs and cats, farm animals, such as cows, horses, or pigs, and laboratory animals. In some embodiments, the term patient refers to a human in need of treatment as defined herein.

Compounds

Provided herein are compounds that function as PD-1 inhibitors, PD-L1 inhibitors, and/or PD-1/PD-L1 interaction inhibitors, methods of using such compounds and compositions comprising such compounds optionally in combination with one or more additional anticancer agents or therapies. In all embodiments discussed herein where there is more than one occurrence of a group or variable, it is intended that the group or variable is independently selected the list that follows. It is further contemplated that all embodiments directed to compounds include any pharmaceutically acceptable salt, stereoisomer, mixture of stereoisomers, solvate, prodrug or tautomer thereof.

In one embodiment, provided is a compound of formula (I):

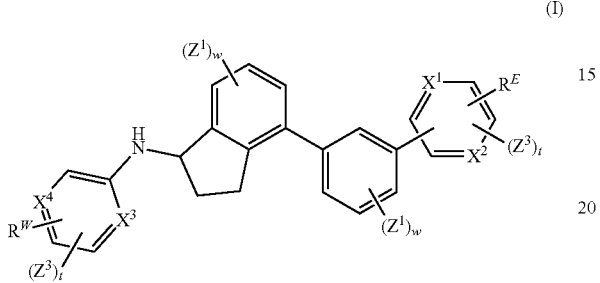

(I)

or a pharmaceutically acceptable salt, stereoisomer, mixture of stereoisomers, solvate, or tautomer thereof, wherein:
each of $X^1$, $X^2$, $X^3$ and $X^4$ are independently N, CH or $CZ^3$;
each $Z^1$ is independently is halo, —$OR^a$, —$NO_2$, cyano, —$NR^aR^b$, —$N_3$, —$S(O)_2R^a$, —$C_{1-6}$ alkyl, —$C_{1-6}$ haloalkyl, —$C_{2-6}$ alkenyl, —$C_{2-6}$ alkynyl, —O—$C_{1-6}$ alkyl, —O—$C_{1-6}$ haloalkyl, —$C_{3-8}$ cycloalkyl, or —$C_{1-6}$ alkyl$C_{3-8}$ cycloalkyl; and
wherein each alkyl, alkenyl, alkynyl, and cycloalkyl is optionally substituted with 1 to 4 groups independently selected from oxo, —$NO_2$, —$N_3$, —$OR^a$, halo, and cyano;
each w is independently 0, 1 or 2;
each $Z^3$ is independently halo, —$OR^a$, —$N_3$, —$NO_2$, cyano, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{1-6}$ cyanoalkyl, —$C_{1-6}$ haloalkyl, —O—$C_{1-6}$cyanoalkyl, —O—$C_{1-6}$ haloalkyl, —$C_{3-8}$cycloalkyl, —$C_{1-6}$alkyl$C_{3-8}$ cycloalkyl, aryl, heteroaryl, heterocyclyl, and $R^N$; and
wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$cyanoalkyl, —$C(O)NR^aR^b$, —$NR^aC(O)R^a$, —$NR^aC(O)OR^a$, —$S(O)_2R^a$, —$NR^aS(O)_2R^b$, —$SO_2NR^aR^b$, —$NR^aS(O)_2NR^aR^b$, —$C(O)NR^aS(O)_2NR^aR^b$ and —$C_{3-8}$ cycloalkyl;
$R^N$ is independently-$C_{1-6}$alkyl$NR^1R^2$, —$OC_{1-6}$ alkyl$NR^1R^2$, —$C_{1-6}$ alkyl-O—$C_{1-6}$ alkyl$NR^1R^2$, —$NR^aC_{1-6}$ alkyl$NR^1R^2$, —$C_{1-6}$ alkylC(O)$NR^1R^2$, —O—$C_{1-6}$ alkylC(O)$NR^1R^2$, —O—$C_{1-6}$ alkylC(O)$OR^1$, —$SC_{1-6}$alkyl$NR^1R^2$, —$C_{1-6}$alkyl$OR^a$, or

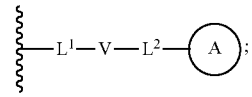

wherein:
$L^1$ is independently a bond, —O—, —$NR^a$—, —S—, —S(O)—, or —$S(O)_2$—;
V is independently selected from a bond, $C_{1-6}$ alkyl, $C_{2-6}$ alkenyl, and $C_{2-6}$ alkynyl; wherein each alkyl, alkenyl, or alkynyl is optionally independently substituted with —$OR^a$, halo, cyano, —$NR^aR^b$ or —$C_{3-8}$ cycloalkyl;
$L^2$ is independently a bond, —O—, —$NR^a$—, —S—, —S(O)—, or —$S(O)_2$—;
ring A is independently cycloalkyl, aryl, heteroaryl, or heterocyclyl;
wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$ alkenyl, —$C_{2-6}$ alkynyl, —O—$C_{1-6}$ haloalkyl, —$NR^aR^b$, —$C(O)R^a$, —$C(O)OR^a$, —O—$C_{1-6}$ cyanoalkyl, —$C(O)NR^aR^b$, —$NR^aC(O)R^a$, —$NR^aC(O)OR^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, $C_{3-8}$ cycloalkyl, and —$C_{1-6}$ alkyl$C_{3-8}$ cycloalkyl; and
wherein the alkyl, alkenyl, or alkynyl group is optionally independently substituted with —$OR^a$, halo, cyano, —$NR^aR^b$ or —$C_{3-8}$ cycloalkyl;
each t is independently 0, 1 or 2;
$R^E$ and $R^W$ are each independently —$NR^1R^2$, —$C_{1-6}$ alkyl$NR^1R^2$, —O—$C_{1-6}$ alkyl$NR^1R^2$, —$C_{1-6}$ alkyl-O—$C_{1-6}$ alkyl$NR^1R^2$, —$NR^a$—$C_{1-6}$ alkyl$NR^1R^2$, —$C_{1-6}$ alkyl$N^+R^1R^2R^3$, —S—$C_{1-6}$ alkyl$NR^1R^2$, —$C(O)NR^1R^2$, —$S(O)_2R^a$, —$(CH_2)_uS(O)_2NR^1R^2$, —$(CH_2)_uNR^aS(O)_2NR^aR^b$, —$S(O)_2NR^aC_{1-6}$ alkyl$NR^1R^2$, —$NR^aS(O)_2C_{1-6}$ alkyl$NR^1R^2$, —$(CH_2)_uC(O)NR^aS(O)_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR)(OR^c)(OR^d)$, —$(CH_2)_uOP(O)(OR^c)(OR^d)$, —$(CH_2)_uOP(O)NR^aR^b)(OR^a)$, or

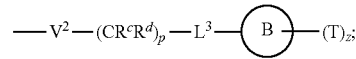

wherein:
$V^2$ is independently a bond, —O—, —$NR^a$—, —S—, —SO—, —$SO_2$—, —$C(O)NR^a$—, —$NR^aC(O)$—, —$S(O)_2NR^1$—, or —$NR^aS(O)_2$—;
$L^3$ is independently a bond, —O—, —$NR^a$—, —S—, —SO—, —$SO_2$—, —$C(O)NR^a$—, —$NR^aC(O)$—, —$S(O)_2NR^1$—, or —$NR^aS(O)_2$—;
ring B is independently cycloalkyl, aryl, heteroaryl, or heterocyclyl;
T is independently hydrogen, —$OR^a$, —$(CH_2)_qNR^1R^2$, —$(CH_2)_qNR^aC(O)R$, or —$(CH_2)C(O)R^e$;
p is independently 0, 1, 2, 3, 4, or 5;
q is independently 0, 1, 2, 3, 4, or 5;
u is 0, 1, 2, 3, or 4;
z is 0, 1, 2, or 3; and
wherein the alkyl, cycloalkyl, aryl, heteroaryl, or heterocyclyl of $R^E$ or $R^W$ is optionally substituted with 1 to 3 substituents independently selected from the group consisting of —$NR^aR^b$, halo, cyano, oxo, —$OR^a$, —$C_{1-6}$alkyl, —$C_{1-6}$ haloalkyl, —$C_{1-6}$ cyanoalkyl, —C$_{1-6}$alkylNR$^a$R$^b$, —C$_{1-6}$ hydroxyalkyl, —C$_{3-8}$ cycloalkyl, and —C$_{1-3}$ alkylC$_{3-8}$cycloalkyl;
provided that at least one of V$^2$, L$^3$, ring B and T contains a nitrogen atom;
each R$^1$ is independently selected from hydrogen, —C$_{1-8}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{1-6}$ alkylC(O)OR$^a$, —C$_{2-6}$ alkenylC(O)OR$^a$, —S(O)$_2$R$^a$, —S(O)$_2$NR$^a$R$^b$, —C(O)NR$^a$S(O)$_2$R$^a$, and —C$_{1-6}$ alkylC$_{3-8}$cycloalkyl;
 wherein each alkyl, alkenyl, cycloalkyl, aryl, heteroaryl, or heterocyclyl is optionally substituted with 1 to 4 groups independently selected from —OR$^a$, cyano, halo, C$_{1-6}$ alkyl, —C$_{1-6}$ alkylOR$^a$, —C$_{1-6}$ cyanoalkyl, —C$_{1-6}$haloalkyl, C$_{3-8}$ cycloalkyl, —C$_{1-3}$alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —OC(O)NR$^a$R$^b$, NR$^a$C(O)OR$^b$, —C$_{1-6}$ alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$ R$^a$, —S(O)$_2$NR$^a$R$^b$, —C$_{1-6}$ alkylS(O)$_2$NR$^a$R$^b$, —C(O)NR$^a$S(O)$_2$R$^b$, —C$_{1-6}$alkylC(O)NR$^a$S(O)$_2$R$^b$, —NR$^a$C(O)R$^b$, and —C$_{1-6}$alkylNR$^a$C(O)R$^b$;
each R$^2$ is independently selected from hydrogen, —C$_{1-6}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, and —C$_{2-6}$ alkenylC(O)OR$^a$;
 wherein each alkyl, alkenyl, alkynyl, cycloalkyl, aryl, heteroaryl, or heterocyclyl is optionally substituted with 1 to 4 groups independently selected from —OR$^a$, cyano, halo, C$_{1-6}$alkyl, —C$_{1-6}$alkylOR$^a$, —C$_{1-6}$ cyanoalkyl, —C$_{1-6}$ haloalkyl, —C$_{3-8}$cycloalkyl, —C$_{1-3}$alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)NR$^a$R$^b$, —S(O)$_2$R$^a$, —C$_{1-6}$ alkylS(O)$_2$NR$^a$R$^b$, —C(O)NR$^a$S(O)$_2$R$^b$ and —NR$^a$C(O)R$^b$;
or R$^1$ and R$^2$ combine to form a heterocyclyl optionally substituted with 1 to 3 groups independently selected from oxo, —C$_{1-6}$ alkyl, —C$_{3-8}$ cycloalkyl, —C$_{2-6}$ alkenyl, —C$_{2-6}$ alkynyl, —OR$^a$, —C(O)OR$^a$, —C$_{1-6}$ cyanoalkyl, —C$_{1-6}$ alkylOR$^a$, —C$_{1-6}$ haloalkyl, —C$_{1-3}$ alkylC$_{3-8}$cycloalkyl, —C(O)R$^a$, C$_{1-6}$ alkylC(O)R$^a$, —C$_{1-6}$ alkylC(O)OR$^a$, —NR$^a$R$^b$, —C$_{1-6}$alkylNR$^a$R$^b$, —C(O)NR$^a$R$^b$, —C$_{1-6}$ alkyl-C(O)NR$^a$R$^b$, —S(O)$_2$R$^a$, —C$_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$NR$^a$C(O)R$^b$, and —C$_{1-6}$ alkylS(O)$_2$NR$^a$R$^b$;
each R$^3$ is independently hydrogen, —C$_{1-6}$ alkyl, —C$_{2-6}$ alkenyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, or —C$_{2-6}$ alkenylC(O)OR$^a$;
each R$^a$ is independently selected from hydrogen, —C$_{1-6}$ alkyl, —C$_{1-6}$ cyanoalkyl, —C$_{1-6}$haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;
each R$^b$ is independently selected from hydrogen, —C$_{1-6}$ alkyl, —C$_{1-6}$ cyanoalkyl, —C$_{1-6}$haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;
or R$^a$ and R$^b$ may combine together to form a heterocyclyl optionally substituted with 1 to 4 groups independently selected from —OR$^1$, cyano, halo, —C$_{1-6}$ alkylOR$^f$, —C$_{1-6}$ cyanoalkyl, —C$_{1-6}$haloalkyl, —C$_{3-8}$ cycloalkyl, —C$_{1-3}$ alkylC$_{3-8}$cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$alkylNR$^f$R$^g$, —C(O)NR$^f$R$^g$, —C$_{1-6}$alkylC(O)NR$^f$R$^g$, —S(O)$_2$R$^f$, —C$_{1-6}$alkylS(O)$_2$R$^f$, —S(O)$_2$NR$^f$R$^g$, —C$_{1-6}$ alkylS(O)$_2$NR$^f$R$^g$, —C(O)NR$^f$S(O)$_2$R$^g$ and —NR$^f$C(O)R$^g$;
each R$^c$ is independently selected from hydrogen, —OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;
each R$^d$ is independently selected from hydrogen, —C$_{1-6}$ alkyl, —C$_3$-C$_8$cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;
each R$^e$ is independently selected from hydrogen, —C$_{1-6}$ alkyl, —O—C$_{1-6}$alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —C$_{1-3}$ alkylC$_{3-8}$cycloalkyl, —C$_{1-6}$ alkylaryl, —C$_{1-6}$alkylheteroaryl, —NR$^f$R$^g$, —C$_{1-6}$ alkylNR$^f$R$^g$, —C(O)NR$^f$R$^g$, —C$_{1-6}$ alkylC(O)NR$^f$R$^g$, —NHS(O)$_2$R$^f$, —C$_{1-6}$ alkylS(O)$_2$R$^f$, and —C$_{1-6}$ alkylS(O)$_2$NR$^f$R$^g$;
each R$^f$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl; and
each R$^g$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl.

Also provided are compounds of Formula (IA):

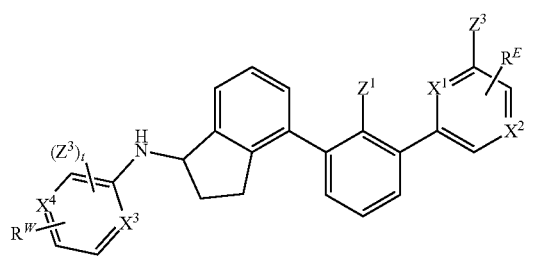

(IA)

or a pharmaceutically acceptable salt, stereoisomer, mixture of stereoisomers, solvate, or tautomer thereof, wherein X$^1$, X$^2$, X$^3$, X$^4$, Z$^1$, Z$^3$, t, R$^W$ and R$^E$ are as defined herein.

Also provided are compounds of Formula (IB):

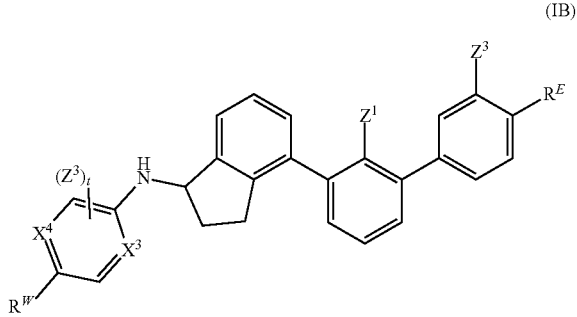

(IB)

or a pharmaceutically acceptable salt, stereoisomer, mixture of stereoisomers, solvate, or tautomer thereof, wherein X$^3$, X$^4$, Z$^1$, Z$^3$, t, R$^W$ and R$^E$ are as defined herein.

Also provided are compounds of Formula (IC):

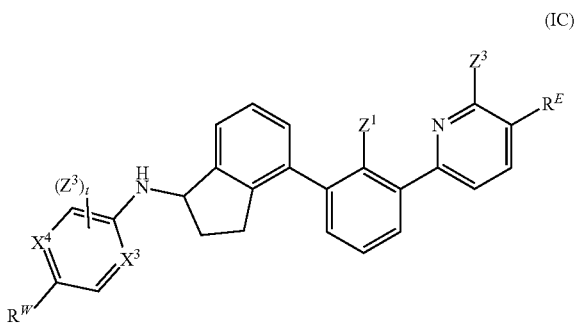

or a pharmaceutically acceptable salt, stereoisomer, mixture of stereoisomers, solvate, or tautomer thereof, wherein $X^3$, $X^4$, $Z^1$, $Z^3$, t, $R^W$ and $R^E$ are as defined herein.

Also provided are compounds of Formula (ID):

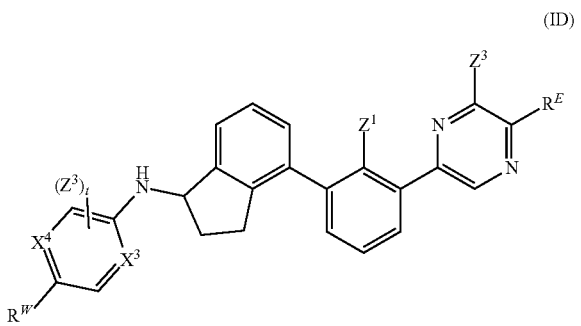

or a pharmaceutically acceptable salt, stereoisomer, mixture of stereoisomers, solvate, or tautomer thereof, wherein $X^3$, $X^4$, $Z^1$, $Z^3$, t, $R^W$ and $R^E$ are as defined herein.

Also provided are compounds of Formula (II):

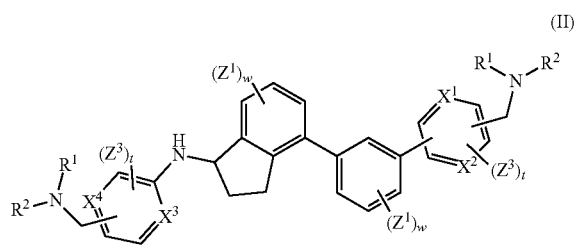

or a pharmaceutically acceptable salt, stereoisomer, mixture of stereoisomers, solvate, or tautomer thereof, wherein:
each of $X^1$, $X^2$, $X^3$ and $X^4$ are independently N, CH or $CZ^3$;
each $Z^1$ is independently halo, —$OR^a$, cyano, or —$C_{1-6}$ alkyl;
each w is independently 0, 1 or 2;
each $Z^3$ is independently halo, —$OR^a$, —$N_3$, —$NO_2$, cyano, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —$O$—$C_{1-6}$ alkyl, —$C_{1-6}$ cyanoalkyl, —$C_{1-6}$ haloalkyl, —$O$—$C_{1-6}$cyanoalkyl, —$O$—$C_{1-6}$ haloalkyl, —$C_{3-8}$cycloalkyl, —$C_{1-6}$alkyl$C_{3-8}$ cycloalkyl, aryl, heteroaryl, heterocyclyl, and $R^N$; and wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$O$—$C_{1-6}$cyanoalkyl, —$C(O)NR^aR^b$, —$NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$ and —$C_{3-8}$ cycloalkyl;

$R^N$ is independently -$C_{1-6}$alkyl$NR^1R^2$, —$OC_{1-6}$alkyl$NR^1R^2$, —$C_{1-6}$ alkyl$OC_{1-6}$alkyl$NR^1R^2$, —$NR^a$—$C_{1-6}$ alkyl$NR^1R^2$, —$C_{1-6}$ alkyl$C(O)NR^1R^2$, —$O$—$C_{1-6}$ alkyl$C(O)NR^1R^2$, —$O$—$C_{1-6}$ alkyl$C(O)OR^1$, —$S$—$C_{1-6}$alkyl$NR^1R^2$, —$C_{1-6}$ alkyl$OR^a$, or

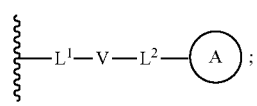

wherein: $L^1$ is independently a bond, —$O$—, —$NR^a$—, —$S$—, —$S(O)$—, or —$S(O)_2$—;
V is independently selected from a bond, $C_{1-6}$ alkyl, $C_{2-6}$ alkenyl, and $C_{2-6}$ alkynyl;
   wherein each alkyl, alkenyl, or alkynyl is optionally independently substituted with —$OR^a$, halo, cyano, —$NR^aR^b$ or —$C_{3-8}$ cycloalkyl;
$L^2$ is independently a bond, —$O$—, —$NR^a$—, —$S$—, —$S(O)$—, or —$S(O)_2$—;
ring A is independently cycloalkyl, aryl, heteroaryl, or heterocyclyl;
   wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$O$—$C_{1-6}$ haloalkyl, $NR^aR^b$, —$C(O)R^a$, —$C(O)OR^a$, —$OC_{1-6}$alkylCN, —$C(O)NR^aR^b$, —$NR^aC(O)R^a$, —$NR^aC(O)OR^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, —$C_{3-8}$cycloalkyl, heteroaryl, and —$C_{1-6}$ alkyl$C_{3-8}$ cycloalkyl; and
   wherein the alkyl, alkenyl, or alkynyl group is optionally independently substituted with —$OR^a$, halo, cyano, —$NR^aR^b$ or —$C_{3-8}$ cycloalkyl;

each t is independently 0, 1 or 2;
each $R^1$ is independently selected from hydrogen, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkyl$C(O)OR^a$, —$C_{2-6}$ alkenyl$C(O)OR^a$, —$S(O)_2R^a$, —$S(O)_2NR^aR^b$, —$C(O)NR^aS(O)_2R^a$, and —$C_{1-6}$ alkyl$C_{3-8}$cycloalkyl;
   wherein each alkyl, alkenyl, cycloalkyl, aryl, heteroaryl, or heterocyclyl is optionally substituted with 1 to 4 groups independently selected from —$OR^a$, cyano, halo, $C_{1-6}$alkyl, —$C_{1-6}$ alkyl$OR^a$, —$C_{1-6}$ cyanoalkyl, —$C_{1-6}$haloalkyl, $C_{3-8}$ cycloalkyl, —$C_{1-3}$alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$OC(O)NR^aR^b$, —$NR^aC(O)OR^b$, —$C_{1-6}$alkyl$NR^aR^b$, —$C(O)NR^aR^b$, —$C_{1-6}$alkyl$C(O)NR^aR^b$, —$SO_2R^a$, —$C_{1-6}$alkyl$SO_2R^a$, —$SO_2NR^aR^b$, —$C_{1-6}$ alkyl$SO_2NR^aR^b$, —$C(O)NR^aSO_2R^b$, —$C_{1-6}$ alkyl$C(O)NR^aSO_2R^b$, —$NR^aC(O)R^b$, and —$C_{1-6}$alkyl$NR^aC(O)R^b$;

each $R^2$ is independently selected from hydrogen, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-OR$^a$, —$C_{1-6}$ alkylC(O)OR$^a$, and —$C_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, cyano, halo, $C_{1-6}$ alkyl, —$C_{1-6}$alkylOR$^a$, —$C_{1-6}$ cyanoalkyl, —$C_{1-6}$ haloalkyl, —$C_{3-8}$cycloalkyl, —$C_{1-3}$alkylC$_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —$C_{1-6}$ alkylNR$^a$R$^b$, —C(O)NR$^a$R$^b$, $C_{1-6}$ alkylC(O)NR$^a$R$^b$, —S(O)$_2$R$^a$, —$C_{1-6}$ alkylS(O)$_2$R$^a$, —S(O)$_2$NR$^a$R$^b$, —$C_{1-6}$ alkylS(O)$_2$NR$^a$R$^b$, —C(O)NR$^a$S(O)$_2$R$^b$ and —NR$^a$C(O)R$^b$;

or $R^1$ and $R^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —OR$^a$, —C(O)OR$^a$, —$C_{1-6}$ cyanoalkyl, —$C_{1-6}$ alkylOR$^a$, —$C_{1-6}$ haloalkyl, —$C_{1-3}$ alkylC$_{3-8}$cycloalkyl, —C(O)R$^a$, —$C_{1-6}$ alkylC(O)R$^a$, —$C_{1-6}$ alkylC(O)OR$^a$, —NR$^a$R$^b$, —$C_{1-6}$alkylNR$^a$R$^b$, —C(O)NR$^a$R$^b$, —$C_{1-6}$ alkyl-C(O)NR$^a$R$^b$, —S(O)$_2$R$^a$, —$C_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$NR$^a$C(O)R$^b$, and —$C_{1-6}$ alkylS(O)$_2$NR$^a$R$^b$;

each $R^3$ is independently hydrogen, —$C_{1-6}$ alkyl, —$C_{2-6}$ alkenyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$alkyl-OR$^a$, —$C_{1-6}$ alkylC(O)OR$^a$, or —$C_{2-6}$ alkenylC(O)OR$^a$;

each $R^a$ is independently selected from hydrogen, —$C_{1-6}$ alkyl, —$C_{1-6}$ cyanoalkyl, —$C_{1-6}$haloalkyl, —$C_{3-8}$ cycloalkyl, aryl, heteroaryl, heterocyclyl, —$C_{1-3}$ alkylC$_{3-8}$cycloalkyl, —$C_{1-6}$ alkylaryl, —$C_{1-6}$ alkylheteroaryl, and —$C_{1-6}$ alkylheterocyclyl;

each $R^b$ is independently selected from hydrogen, —$C_{1-6}$ alkyl, —$C_{1-6}$ cyanoalkyl, —$C_{1-6}$haloalkyl, —$C_{3-8}$ cycloalkyl, aryl, heteroaryl, heterocyclyl, —$C_{1-3}$ alkylC$_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a heterocyclyl optionally substituted with 1 to 4 groups independently selected from —OR$^1$, cyano, halo, —$C_{1-6}$ alkylOR$^f$, —$C_{1-6}$ cyanoalkyl, —$C_{1-6}$haloalkyl, —$C_{3-8}$ cycloalkyl, —$C_{1-3}$ alkylC$_{3-8}$cycloalkyl, —C(O)R$^f$, —$C_{1-6}$ alkylC(O)R$^f$, —C(O)OR$^f$, —$C_{1-6}$ alkylC(O)OR$^f$, —NR$^f$R$^g$, —$C_{1-6}$ alkylNR$^f$R$^g$, —C(O)NR$^f$R$^g$, —$C_{1-6}$ alkylC(O)NR$^f$R$^g$, —S(O)$_2$R$^f$, —$C_{1-6}$ alkylS(O)$_2$R$^f$, —S(O)$_2$NR$^f$R$^g$, —$C_{1-6}$ alkylS(O)$_2$NR$^f$R$^g$, —C(O)NR$^f$S(O)$_2$R$^g$ and —NR$^f$C(O)R$^g$;

each $R^e$ is independently selected from hydrogen, —OH, —$C_{1-6}$ alkyl, —$C_{3-8}$ cycloalkyl, aryl, heteroaryl, heterocyclyl, —$C_{1-3}$ alkylC$_{3-8}$ cycloalkyl, —$C_{1-6}$ alkylaryl, —$C_{1-6}$ alkylheteroaryl, and —$C_{1-6}$ alkylheterocyclyl;

$R^d$ is independently selected from hydrogen, —$C_{1-6}$ alkyl, —$C_3$-$C_8$cycloalkyl, aryl, heteroaryl, heterocyclyl, —$C_{1-3}$ alkylC$_{3-8}$cycloalkyl, —$C_{1-6}$ alkylaryl, —$C_{1-6}$ alkylheteroaryl, and —$C_{1-6}$ alkylheterocyclyl;

each $R^f$ is independently selected from hydrogen, —$C_{1-6}$ alkyl, —$C_{3-8}$ cycloalkyl, aryl, heteroaryl, heterocyclyl, —$C_{1-3}$ alkylC$_{3-8}$ cycloalkyl, —$C_{1-6}$ alkylaryl, —$C_{1-6}$ alkylheteroaryl, and —$C_{1-6}$ alkylheterocyclyl; and each $R^g$ is independently selected from hydrogen, —$C_{1-6}$ alkyl, —$C_{3-8}$ cycloalkyl, aryl, heteroaryl, heterocyclyl, —$C_{1-3}$ alkylC$_{3-8}$ cycloalkyl, —$C_{1-6}$ alkylaryl, —$C_{1-6}$ alkylheteroaryl, and —$C_{1-6}$ alkylheterocyclyl.

Also provided are compounds of Formula (IIA):

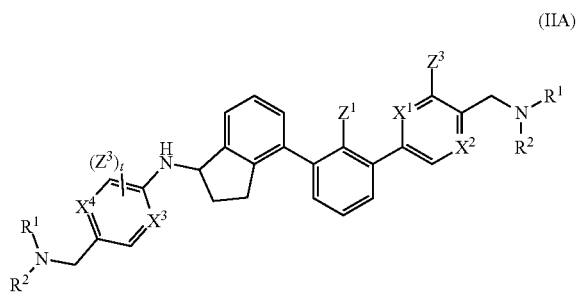

(IIA)

or a pharmaceutically acceptable salt, stereoisomer, mixture of stereoisomers, solvate, or tautomer thereof, wherein $X^1$, $X^2$, $X^3$, $X^4$, $Z^1$, $Z^3$, t, $R^1$ and $R^2$ are as defined herein.

Also provided are compounds of Formula (IIB):

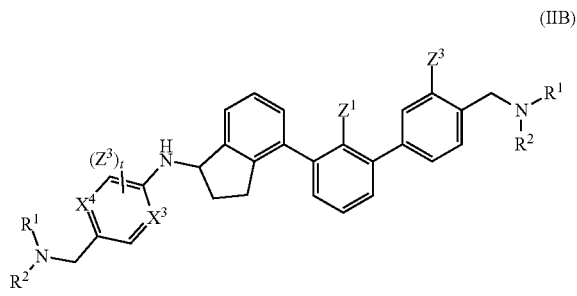

(IIB)

or a pharmaceutically acceptable salt, stereoisomer, mixture of stereoisomers, solvate, or tautomer thereof, wherein $X^3$, $X^4$, $Z^1$, $Z^3$, t, $R^1$ and $R^2$ are as defined herein.

Also provided are compounds of Formula (IIC):

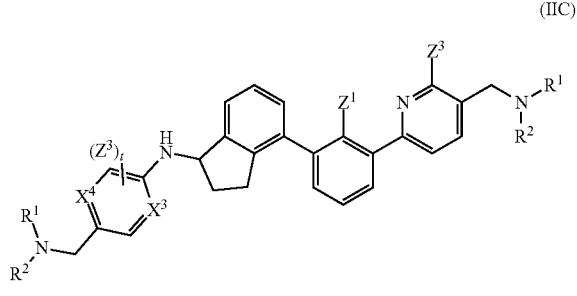

(IIC)

or a pharmaceutically acceptable salt, stereoisomer, mixture of stereoisomers, solvate, or tautomer thereof, wherein $X^3$, $X^4$, $Z^1$, $Z^3$, t, $R^1$ and $R^2$ are as defined herein.

Also provided are compounds of Formula (IID):

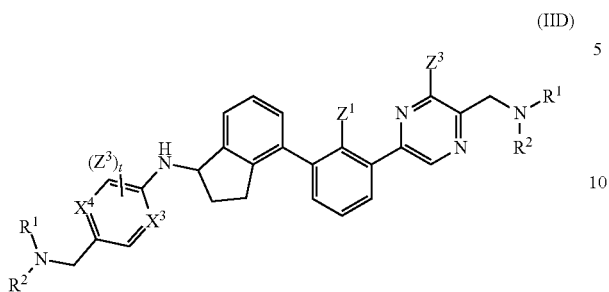

(IID)

or a pharmaceutically acceptable salt, stereoisomer, mixture of stereoisomers, solvate, or tautomer thereof, wherein $X^3$, $X^4$, $Z^1$, $Z^3$, t, $R^1$ and $R^2$ are as defined herein.

Also provided are compounds of Formula (III):

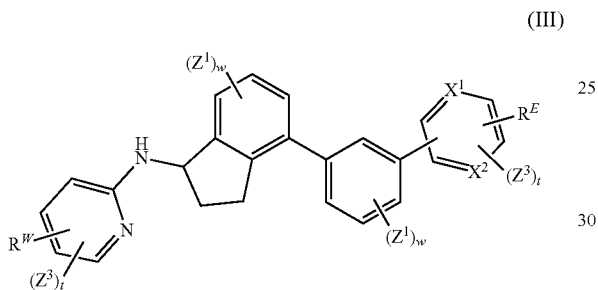

(III)

or a pharmaceutically acceptable salt, stereoisomer, mixture of stereoisomers, solvate, or tautomer thereof, wherein:
each of $X^1$, $X^2$, $X^3$ and $X^4$ are independently N, CH or $CZ^3$;
each $Z^1$ is independently is halo, —$OR^a$, —$NO_2$, cyano, —$NR^aR^b$, —$N_3$, —$S(O)_2R^a$, —$C_{1-6}$ alkyl, —$C_{1-6}$ haloalkyl, —$C_{2-6}$alkenyl, —$C_{2-6}$ alkynyl, —O—$C_{1-6}$ alkyl, —O—$C_{1-6}$ haloalkyl, —$C_{3-8}$ cycloalkyl, or —$C_{1-6}$ alkyl$C_{3-8}$ cycloalkyl; and
wherein each alkyl, alkenyl, alkynyl, and cycloalkyl is optionally substituted with 1 to 4 groups independently selected from oxo, —$NO_2$, —$N_3$, —$OR^a$, halo, and cyano;
each w is independently 0, 1 or 2;
each $Z^3$ is independently halo, —$OR^a$, —$N_3$, —$NO_2$, cyano, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{1-6}$ cyanoalkyl, —$C_{1-6}$ haloalkyl, —O—$C_{1-6}$cyanoalkyl, —O—$C_{1-6}$ haloalkyl, —$C_{3-8}$cycloalkyl, —$C_{1-6}$ alkyl$C_{3-8}$ cycloalkyl, aryl, heteroaryl, heterocyclyl, and $R^N$; and
wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$cyanoalkyl, —$C(O)NR^aR^b$, —$NR^aC(O)R^a$, —$NR^aC(O)OR^a$, —$S(O)_2R^a$, —$NR^aS(O)_2R^b$, —$SO_2NR^aR^b$, —$NR^aS(O)_2NR^aR^b$, —$C(O)NR^aS(O)_2NR^aR^b$ and —$C_{3-8}$ cycloalkyl;
$R^N$ is independently-$C_{1-6}$alkyl$NR^1R^2$, —$OC_{1-6}$ alkyl$NR^1R^2$, —$C_{1-6}$ alkyl-O—$C_{1-6}$ alkyl$NR^1R^2$, —$NR^aC_{1-6}$ alkyl$NR^1R^2$, —$C_{1-6}$ alkylC(O)$NR^1R^2$, —O—$C_{1-6}$ alkylC(O)$NR^1R^2$, —O—$C_{1-6}$ alkylC(O)$OR^1$, —$SC_{1-6}$alkyl$NR^1R^2$, —$C_{1-6}$alkyl$OR^a$, or

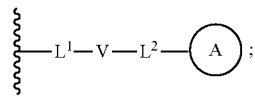

wherein:
$L^1$ is independently a bond, —O—, —$NR^a$—, —S—, —S(O)—, or —$S(O)_2$—;
V is independently selected from a bond, $C_{1-6}$ alkyl, $C_{2-6}$ alkenyl, and $C_{2-6}$ alkynyl;
  wherein each alkyl, alkenyl, or alkynyl is optionally independently substituted with —$OR^a$, halo, cyano, —$NR^aR^b$ or —$C_{3-8}$ cycloalkyl;
$L^2$ is independently a bond, —O—, —$NR^a$—, —S—, —S(O)—, or —$S(O)_2$—;
ring A is independently cycloalkyl, aryl, heteroaryl, or heterocyclyl;
  wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$ alkenyl, —$C_{2-6}$ alkynyl, —O—$C_{1-6}$ haloalkyl, —$NR^aR^b$, —$C(O)R^a$, —$C(O)OR^a$, —O—$C_{1-6}$ cyanoalkyl, —$C(O)NR^aR^b$, —$NR^aC(O)R^a$, —$NR^aC(O)OR^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, $C_{3-8}$ cycloalkyl, and —$C_{1-6}$ alkyl$C_{3-8}$ cycloalkyl; and
  wherein the alkyl, alkenyl, or alkynyl group is optionally independently substituted with —$OR^a$, halo, cyano, —$NR^aR^b$ or —$C_{3-8}$ cycloalkyl;
each t is independently 0, 1 or 2;
$R^E$ and $R^W$ are each independently —$NR^1R^2$, —$C_{1-6}$ alkyl$NR^1R^2$, —O—$C_{1-6}$ alkyl$NR^1R^2$, —$C_{1-6}$ alkyl-O—$C_{1-6}$ alkyl$NR^1R^2$, —$NR^a$—$C_{1-6}$ alkyl$NR^1R^2$, —$C_{1-6}$ alkyl$N^+R^1R^2R^3$, —S—$C_{1-6}$ alkyl$NR^1R^2$, —$C(O)NR^1R^2$, —$S(O)_2R^a$, —$(CH_2)_uS(O)_2NR^1R^2$, —$(CH_2)_uNR^aS(O)_2NR^aR^b$, —$S(O)_2NR^aC_{1-6}$alkyl$NR^1R^2$, —$NR^aS(O)_2C_{1-6}$ alkyl$NR^1R^2$, —$(CH_2)_uC(O)NR^aS(O)_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR)(OR^c)(OR^d)$, —$(CH_2)_uOP(O)(OR^c)(OR^d)$, —$(CH_2)_uOP(O)NR^aR^b)(OR^a)$, or

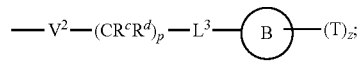

wherein:
$V^2$ is independently a bond, —O—, —$NR^a$—, —S—, —SO—, —$SO_2$—, —$C(O)NR^a$—, —$NR^aC(O)$—, —$S(O)_2NR^1$—, or —$NR^aS(O)_2$—;
$L^3$ is independently a bond, —O—, —$NR^a$—, —S—, —SO—, —$SO_2$—, —$C(O)NR^a$—, —$NR^aC(O)$—, —$S(O)_2NR^1$—, or —$NR^aS(O)_2$—;
ring B is independently cycloalkyl, aryl, heteroaryl, or heterocyclyl;
T is independently hydrogen, —$OR^a$, —$(CH_2)_qNR^1R^2$, —$(CH_2)_qNR^aC(O)R$, or —$(CH_2)C(O)R^e$;

p is independently 0, 1, 2, 3, 4, or 5;
q is independently 0, 1, 2, 3, 4, or 5;
u is 0, 1, 2, 3, or 4;
z is 0, 1, 2, or 3; and
wherein the alkyl, cycloalkyl, aryl, heteroaryl, or heterocyclyl of $R^E$ or $R^W$ is optionally substituted with 1 to 3 substituents independently selected from the group consisting of —$NR^aR^b$, halo, cyano, oxo, —$OR^a$, —$C_{1-6}$alkyl, —$C_{1-6}$ haloalkyl, —$C_{1-6}$ cyanoalkyl, —$C_{1-6}$alkyl$NR^aR^b$, —$C_{1-6}$ hydroxyalkyl, —$C_{3-8}$ cycloalkyl, and —$C_{1-3}$ alkyl$C_{3-8}$cycloalkyl;

provided that at least one of $V^2$, $L^3$, ring B and T contains a nitrogen atom;

each $R^1$ is independently selected from hydrogen, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkylC(O)$OR^a$, —$C_{2-6}$ alkenylC(O)$OR^a$, —S(O)$_2R^a$, —S(O)$_2NR^aR^b$, —C(O)$NR^aS(O)_2R^a$, and —$C_{1-6}$ alkyl$C_{3-8}$cycloalkyl;
wherein each alkyl, alkenyl, cycloalkyl, aryl, heteroaryl, or heterocyclyl is optionally substituted with 1 to 4 groups independently selected from —$OR^a$, cyano, halo, $C_{1-6}$ alkyl, —$C_{1-6}$ alkyl$OR^a$, —$C_{1-6}$ cyanoalkyl, —$C_{1-6}$haloalkyl, $C_{3-8}$ cycloalkyl, —$C_{1-3}$alkyl$C_{3-8}$cycloalkyl, —C(O)$R^a$, —$C_{1-6}$ alkylC(O)$R^a$, —C(O)$OR^a$, —$C_{1-6}$ alkylC(O)$OR^a$, —$NR^aR^b$, —OC(O)$NR^aR^b$, $NR^aC(O)OR^b$, —$C_{1-6}$ alkyl$NR^aR^b$, —C(O)$NR^aR^b$, —$C_{1-6}$ alkylC(O)$NR^aR^b$, —S(O)$_2R^a$, —$C_{1-6}$ alkylS(O)$_2$ $R^a$, —S(O)$_2NR^aR^b$, —$C_{1-6}$ alkylS(O)$_2NR^aR^b$, —C(O)$NR^aS(O)_2R^b$, —$C_{1-6}$alkylC(O)$NR^aS(O)_2R^b$, —$NR^aC(O)R^b$, and —$C_{1-6}$alkyl$NR^aC(O)R^b$;

each $R^2$ is independently selected from hydrogen, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-$OR^a$, —$C_{1-6}$ alkylC(O)$OR^a$, and —$C_{2-6}$ alkenylC(O)$OR^a$;
wherein each alkyl, alkenyl, alkynyl, cycloalkyl, aryl, heteroaryl, or heterocyclyl is optionally substituted with 1 to 4 groups independently selected from —$OR^a$, cyano, halo, $C_{1-6}$alkyl, —$C_{1-6}$alkyl$OR^a$, —$C_{1-6}$ cyanoalkyl, —$C_{1-6}$ haloalkyl, —$C_{3-8}$ cycloalkyl, —$C_{1-3}$alkyl$C_{3-8}$cycloalkyl, —C(O)$R^a$, —$C_{1-6}$ alkylC(O)$R^a$, —C(O)$OR^a$, —$C_{1-6}$ alkylC(O)$OR^a$, —$NR^aR^b$, —$C_{1-6}$alkyl$NR^aR^b$, —C(O)$NR^aR^b$, $C_{1-6}$ alkylC(O)$NR^aR^b$, —S(O)$_2R^a$, —$C_{1-6}$ alkylS(O)$_2R^a$, —S(O)$_2NR^aR^b$, —$C_{1-6}$ alkylS(O)$_2NR^aR^b$, —C(O)$NR^aS(O)_2R^b$ and —$NR^aC(O)R^b$;

or $R^1$ and $R^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —C(O)$OR^a$, —$C_{1-6}$ cyanoalkyl, —$C_{1-6}$ alkyl$OR^a$, —$C_{1-6}$ haloalkyl, —$C_{1-3}$ alkyl$C_{3-8}$cycloalkyl, —C(O)$R^a$, $C_{1-6}$ alkylC(O)$R^a$, —$C_{1-6}$ alkylC(O)$OR^a$, —$NR^aR^b$, —$C_{1-6}$alkyl$NR^aR^b$, —C(O)$NR^aR^b$, —$C_{1-6}$ alkyl-C(O)$NR^aR^b$, —S(O)$_2R^a$, —$C_{1-6}$ alkylS(O)$_2R^a$, —S(O)$_2NR^aR^b$, —C(O)N=S(O)$R^aNR^aR^b$, —C(O)N=S(O)$R^aNR^aC(O)R^b$, and —$C_{1-6}$alkylS(O)$_2NR^aR^b$;

each $R^3$ is independently hydrogen, —$C_{1-6}$ alkyl, —$C_{2-6}$ alkenyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-$OR^a$, —$C_{1-6}$ alkylC(O)$OR^a$, or —$C_{2-6}$ alkenylC(O)$OR^a$;

each $R^a$ is independently selected from hydrogen, —$C_{1-6}$ alkyl, —$C_{1-6}$ cyanoalkyl, —$C_{1-6}$haloalkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

each $R^b$ is independently selected from hydrogen, —$C_{1-6}$ alkyl, —$C_{1-6}$ cyanoalkyl, —$C_{1-6}$haloalkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a heterocyclyl optionally substituted with 1 to 4 groups independently selected from —$OR^1$, cyano, halo, —$C_{1-6}$ alkyl$OR^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)$R^1$, —$C_{1-6}$ alkylC(O)$R^f$, —C(O)$OR^f$, —$C_{1-6}$ alkylC(O)$OR^f$, —$NR^fR^g$, —$C_{1-6}$ alkyl$NR^fR^g$, —C(O)$NR^fR^g$, —$C_{1-6}$ alkylC(O)$NR^fR^g$, —S(O)$_2R^f$, —$C_{1-6}$ alkylS(O)$_2R^f$, —S(O)$_2NR^fR^g$, —$C_{1-6}$ alkylS(O)$_2NR^fR^g$, —C(O)$NR^fS(O)_2R^g$ and —$NR^fC(O)R^g$;

each $R^c$ is independently selected from hydrogen, —OH, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

each $R^d$ is independently selected from hydrogen, —$C_{1-6}$ alkyl, —$C_3$-$C_8$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

each $R^e$ is independently selected from hydrogen, —$C_{1-6}$ alkyl, —O—$C_{1-6}$alkyl, —$C_{3-8}$ cycloalkyl, aryl, heteroaryl, heterocyclyl, —O—$C_{3-8}$ cycloalkyl, —O-aryl, —O-heteroaryl, —O-heterocyclyl, —$C_{1-3}$ alkyl$C_{3-8}$cycloalkyl, —$C_{1-6}$ alkylaryl, —$C_{1-6}$alkylheteroaryl, —$NR^fR^g$, —$C_{1-6}$ alkyl$NR^fR^g$, —C(O)$NR^fR^g$, —$C_{1-6}$ alkylC(O)$NR^fR^g$, —NHS(O)$_2R^f$, —$C_{1-6}$ alkylS(O)$_2R^f$, and —$C_{1-6}$ alkylS(O)$_2NR^fR^g$;

each $R^f$ is independently selected from hydrogen, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl; and each $R^g$ is independently selected from hydrogen, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl.

Also provided are compounds of Formula (IIIA):

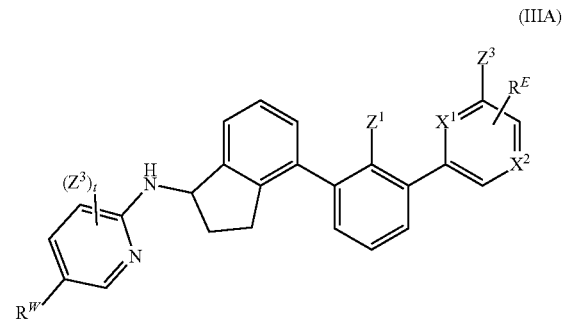

(IIIA)

or a pharmaceutically acceptable salt, stereoisomer, mixture of stereoisomers, solvate, or tautomer thereof, wherein $X^1$, $X^2$, $Z^1$, $Z^3$, t, $R^W$ and $R^E$ are as disclosed herein.

Also provided are compounds of Formula (IIIB):

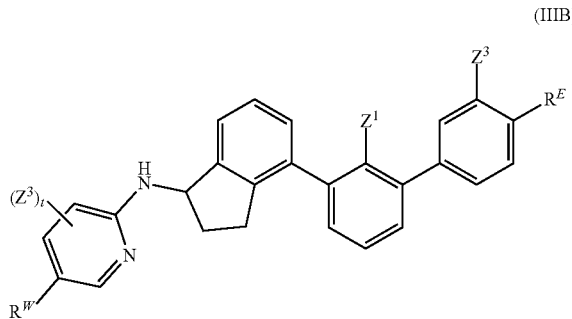

or a pharmaceutically acceptable salt, stereoisomer, mixture of stereoisomers, solvate, or tautomer thereof, wherein $Z^1$, $Z^3$, t, $R^W$ and $R^E$ are as disclosed herein.

Also provided are compounds of Formula (IIIC):

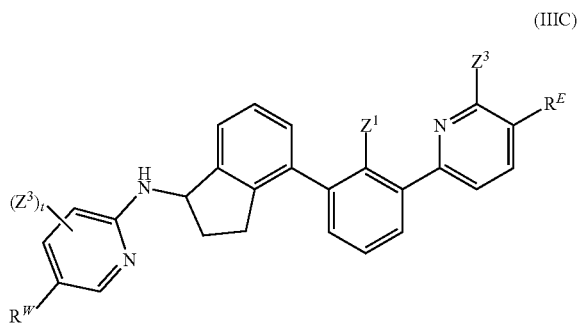

or a pharmaceutically acceptable salt, stereoisomer, mixture of stereoisomers, solvate, or tautomer thereof, wherein $Z^1$, $Z^3$, t, $R^W$ and $R^E$ are as disclosed herein.

Also provided are compounds of Formula (IIID):

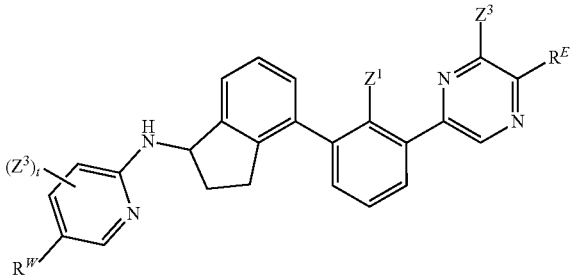

or a pharmaceutically acceptable salt, stereoisomer, mixture of stereoisomers, solvate, or tautomer thereof, wherein $Z^1$, $Z^3$, t, $R^W$ and $R^E$ are as disclosed herein.

Also provided are compounds of Formula (IV):

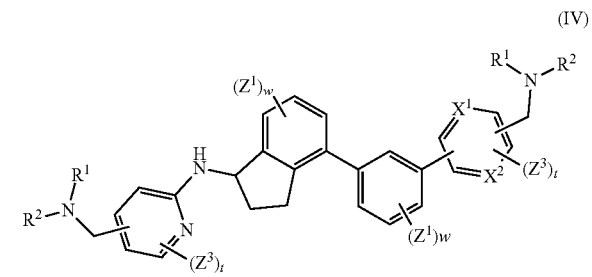

or a pharmaceutically acceptable salt, stereoisomer, mixture of stereoisomers, solvate, or tautomer thereof, wherein:
each of $X^1$ and $X^2$ are independently N, CH or $CZ^3$;
each $Z^1$ is independently halo, —$OR^a$, cyano, or —$C_{1-6}$ alkyl;
each w is independently 0, 1 or 2;
each $Z^3$ is independently halo, —$OR^a$, —$N_3$, —$NO_2$, cyano, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{1-6}$ cyanoalkyl, —$C_{1-6}$ haloalkyl, —O—$C_{1-6}$cyanoalkyl, —O—$C_{1-6}$ haloalkyl, —$C_{3-8}$cycloalkyl, —$C_{1-6}$alkyl$C_{3-8}$ cycloalkyl, aryl, heteroaryl, heterocyclyl, and $R^N$; and
wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$cyanoalkyl, —$C(O)NR^aR^b$, $NR^aC(O)R^a$, —$NR^aC(O)OR^a$, —$S(O)_2 R^a$, —$NR^aS(O)_2R^a$, —$S(O)_2NR^aR^b$, —$NR^aS(O)_2 NR^aR^b$, —$C(O)NR^aS(O)_2NR^aR^b$ and —$C_{3-8}$ cycloalkyl;
$R^N$ is independently -$C_{1-6}$ alkylNR$^1$R$^2$, —$OC_{1-6}$ alkylNR$^1$R$^2$, —$C_{1-6}$ alkylOC$_{1-6}$ alkylNR$^1$R$^2$, —$NR^a$—$C_{1-6}$ alkylNR$^1$R$^2$, —$C_{1-6}$ alkylC(O)NR$^1$R$^2$, —O—$C_{1-6}$ alkylC(O)NR$^1$R$^2$, —O—$C_{1-6}$ alkylC(O)OR$^1$, —S—$C_{1-6}$alkylNR$^1$R$^2$, —$C_{1-6}$alkylOR$^a$, or

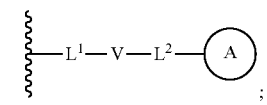

wherein: $L^1$ is independently a bond, —O—, —$NR^a$—, —S—, —S(O)—, or —$S(O)_2$—;
V is independently selected from a bond, $C_{1-6}$ alkyl, $C_{2-6}$ alkenyl, and $C_{2-6}$ alkynyl;
wherein each alkyl, alkenyl, or alkynyl is optionally independently substituted with —$OR^a$, halo, cyano, —$NR^aR^b$ or —$C_{3-8}$ cycloalkyl;
$L^2$ is independently a bond, —O—, —$NR^a$—, —S—, —S(O)—, or —$S(O)_2$—;
ring A is independently cycloalkyl, aryl, heteroaryl, or heterocyclyl;
wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —O—$C_{1-6}$ haloalkyl, $NR^aR^b$, —$C(O)R^a$, —$C(O)OR^a$, —$OC_{1-6}$alkylCN, —$C(O)NR^aR^b$, —$NR^aC(O)R^a$, —NR$^a$C(O)OR$^a$, —NR$^a$C(O)OR$^a$, —C(O)N(R$^a$)OR$^b$, —S(O)$_2$R$^a$, —S(O)$_2$NR$^a$R$^b$, —NR$^a$S(O)$_2$R$^b$, —NR$^a$S(O)$_2$NR$^a$R$^b$, —C(O)NR$^a$S(O)$_2$NR$^a$R$^b$, —C$_{3-8}$cycloalkyl, heteroaryl, and —C$_{1-6}$alkylC$_{3-8}$ cycloalkyl; and wherein the alkyl, alkenyl, or alkynyl group is optionally independently substituted with —OR$^a$, halo, cyano, —NR$^a$R$^b$ or —C$_{3-8}$ cycloalkyl;

each t is independently 0, 1 or 2;

each R$^1$ is independently selected from hydrogen, —C$_{1-8}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{1-6}$ alkylC(O)OR$^a$, —C$_{2-6}$ alkenylC(O)OR$^a$, —S(O)$_2$R$^a$, —S(O)$_2$NR$^a$R$^b$, —C(O)NR$^a$S(O)$_2$R$^a$, and —C$_{1-6}$ alkylC$_{3-8}$cycloalkyl;

wherein each alkyl, alkenyl, cycloalkyl, aryl, heteroaryl, or heterocyclyl is optionally substituted with 1 to 4 groups independently selected from —OR$^a$, cyano, halo, C$_{1-6}$alkyl, —C$_{1-6}$ alkylOR$^a$, —C$_{1-6}$ cyanoalkyl, —C$_{1-6}$haloalkyl, C$_{3-8}$ cycloalkyl, —C$_{1-3}$alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —OC(O)NR$^a$R$^b$, —NR$^a$C(O)OR$^b$, —C$_{1-6}$alkylNR$^a$R$^b$, —C(O)NR$^a$R$^b$, —C$_{1-6}$alkylC(O)NR$^a$R$^b$, —SO$_2$R$^a$, —C$_{1-6}$alkylSO$_2$R$^a$, —SO$_2$NR$^a$R$^b$, —C$_{1-6}$ alkylSO$_2$NR$^a$R$^b$, —C(O)NR$^a$SO$_2$R$^b$, —C$_{1-6}$ alkylC(O)NR$^a$SO$_2$R$^b$, —NR$^a$C(O)R$^b$, and —C$_{1-6}$alkylNR$^a$C(O)R$^b$;

each R$^2$ is independently selected from hydrogen, —C$_{1-6}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, and —C$_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, cyano, halo, C$_{1-6}$ alkyl, —C$_{1-6}$alkylOR$^a$, —C$_{1-6}$ cyanoalkyl, —C$_{1-6}$ haloalkyl, —C$_{3-8}$ cycloalkyl, —C$_{1-3}$ alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$ and —NR$^a$C(O)R$^b$;

or R$^1$ and R$^2$ combine to form a heterocyclyl optionally substituted with 1 to 3 groups independently selected from oxo, —C$_{1-6}$ alkyl, —C$_{3-8}$ cycloalkyl, —C$_{2-6}$ alkenyl, —C$_{2-6}$ alkynyl, —OR$^a$, —C(O)OR$^a$, —C$_{1-6}$ cyanoalkyl, —C$_{1-6}$ alkylOR$^a$, —C$_{1-6}$ haloalkyl, —C$_{1-3}$ alkylC$_{3-8}$cycloalkyl, —C(O)R$^a$, —C$_{1-6}$ alkylC(O)R$^a$, —C$_{1-6}$ alkylC(O)OR$^a$, —NR$^a$R$^b$, —C$_{1-6}$alkylNR$^a$R$^b$, —C(O)NR$^a$R$^b$, —C$_{1-6}$ alkyl-C(O)NR$^a$R$^b$, —S(O)$_2$R$^a$, —C$_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$NR$^a$C(O)R$^b$, and —C$_{1-6}$ alkylS(O)$_2$NR$^a$R$^b$;

each R$^3$ is independently hydrogen, —C$_{1-6}$ alkyl, —C$_{2-6}$ alkenyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, or —C$_{2-6}$ alkenylC(O)OR$^a$;

each R$^a$ is independently selected from hydrogen, —C$_{1-6}$ alkyl, —C$_{1-6}$ cyanoalkyl, —C$_{1-6}$haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each R$^b$ is independently selected from hydrogen, —C$_{1-6}$ alkyl, —C$_{1-6}$ cyanoalkyl, —C$_{1-6}$haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

or R$^a$ and R$^b$ may combine together to form a heterocyclyl optionally substituted with 1 to 4 groups independently selected from —OR$^1$, cyano, halo, —C$_{1-6}$ alkylOR$^f$, —C$_{1-6}$ cyanoalkyl, —C$_{1-6}$haloalkyl, —C$_{3-8}$ cycloalkyl, —C$_{1-3}$ alkylC$_{3-8}$cycloalkyl, —C(O)R$^1$, —C$_{1-6}$ alkylC(O)R$^f$, —C(O)OR$^f$, —C$_{1-6}$ alkylC(O)OR$^f$, —NR$^f$R$^g$, —C$_{1-6}$alkylNR$^f$R$^g$, —C(O)NR$^f$R$^g$, —C$_{1-6}$alkylC(O)NR$^f$R$^g$, —S(O)$_2$R$^f$, —C$_{1-6}$alkylS(O)$_2$R$^f$, —S(O)$_2$NR$^f$R$^g$, —C$_{1-6}$alkylS(O)$_2$NR$^f$R$^g$, —C(O)NR$^f$S(O)$_2$R$^g$ and —NR$^f$C(O)R$^g$;

each R$^c$ is independently selected from hydrogen, —OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

R$^d$ is independently selected from hydrogen, —C$_{1-6}$ alkyl, —C$_3$-C$_8$cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each R$^f$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl; and each R$^g$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl.

Also provided are compounds of Formula (IVA):

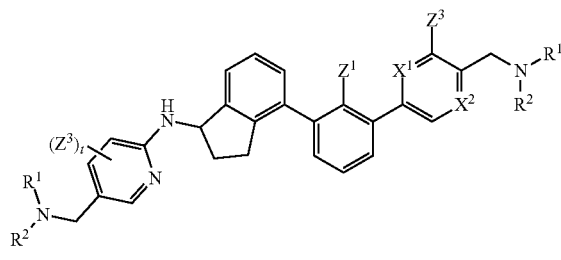

(IVA)

or a pharmaceutically acceptable salt, stereoisomer, mixture of stereoisomers, solvate, or tautomer thereof, wherein X$^1$, X$^2$, Z$^1$, Z$^3$, t, R$^1$ and R$^2$ are as disclosed herein.

Also provided are compounds of Formula (IVB):

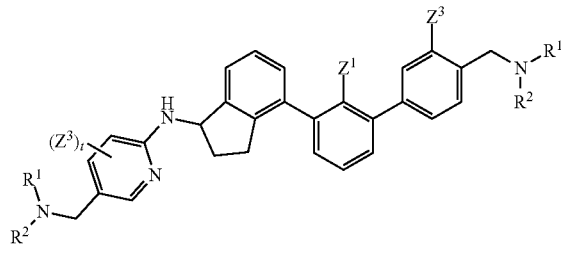

(IVB)

or a pharmaceutically acceptable salt, stereoisomer, mixture of stereoisomers, solvate, or tautomer thereof, wherein Z$^1$, Z$^3$, t, R$^1$ and R$^2$ are as disclosed herein.

Also provided are compounds of Formula (IVC):

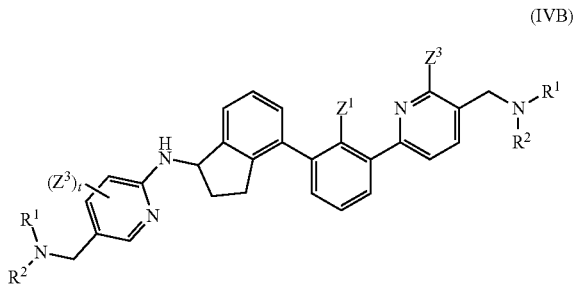
(IVB)

or a pharmaceutically acceptable salt, stereoisomer, mixture of stereoisomers, solvate, or tautomer thereof, wherein $Z^1$, $Z^3$, t, $R^1$ and $R^2$ are as disclosed herein.

Also provided are compounds of Formula (IVD):

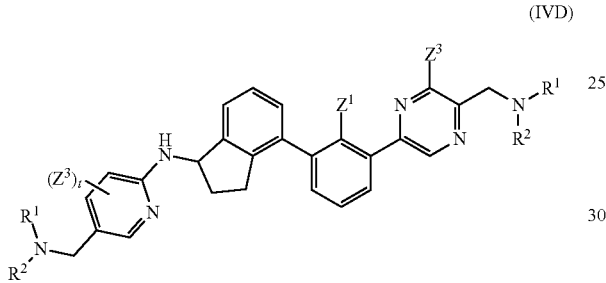
(IVD)

or a pharmaceutically acceptable salt, stereoisomer, mixture of stereoisomers, solvate, or tautomer thereof, wherein $Z^1$, $Z^3$, t, $R^1$ and $R^2$ are as disclosed herein.

Also provided are compounds of Formula (V):

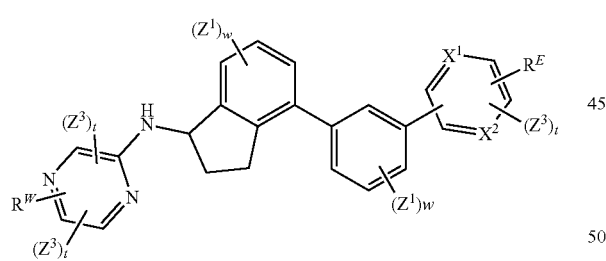
(V)

or a pharmaceutically acceptable salt, stereoisomer, mixture of stereoisomers, solvate, or tautomer thereof, wherein:
each of $X^1$, $X^2$, $X^3$ and $X^4$ are independently N, CH or $CZ^3$;
each $Z^1$ is independently is halo, —$OR^a$, —$NO_2$, cyano, —$NR^aR^b$, —$N_3$, —$S(O)_2R^a$, —$C_{1-6}$ alkyl, —$C_{1-6}$ haloalkyl, —$C_{2-6}$alkenyl, —$C_{2-6}$ alkynyl, —O—$C_{1-6}$ alkyl, —O—$C_{1-6}$ haloalkyl, —$C_{3-8}$ cycloalkyl, or —$C_{1-6}$ alkyl$C_{3-8}$ cycloalkyl; and
wherein each alkyl, alkenyl, alkynyl, and cycloalkyl is optionally substituted with 1 to 4 groups independently selected from oxo, —$NO_2$, —$N_3$, —$OR^a$, halo, and cyano;
each w is independently 0, 1 or 2;
each $Z^3$ is independently halo, —$OR^a$, —$N_3$, —$NO_2$, cyano, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{1-6}$ cyanoalkyl, —$C_{1-6}$ haloalkyl, —O—$C_{1-6}$cyanoalkyl, —O—$C_{1-6}$ haloalkyl, —$C_{3-8}$cycloalkyl, —$C_{1-6}$ alkyl$C_{3-8}$ cycloalkyl, aryl, heteroaryl, heterocyclyl, and $R^N$; and
wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$cyanoalkyl, —$C(O)NR^aR^b$, —$NR^aC(O)R^a$, —$NR^aC(O)OR^a$, —$S(O)_2R^a$, —$NR^aS(O)_2R^b$, —$SO_2NR^aR^b$, —$NR^aS(O)_2NR^aR^b$, —$C(O)NR^aS(O)_2NR^aR^b$ and —$C_{3-8}$ cycloalkyl;
$R^N$ is independently —$C_{1-6}$ alkyl$NR^1R^2$, —$OC_{1-6}$ alkyl$NR^1R^2$, —$C_{1-6}$ alkyl-O—$C_{1-6}$ alkyl$NR^1R^2$, —$NR^aC_{1-6}$ alkyl$NR^1R^2$, —$C_{1-6}$ alkyl$C(O)NR^1R^2$, —O—$C_{1-6}$ alkyl$C(O)NR^1R^2$, —O—$C_{1-6}$ alkyl$C(O)OR^1$, —$SC_{1-6}$ alkyl$NR^1R^2$, —$C_{1-6}$ alkyl$OR^a$, or

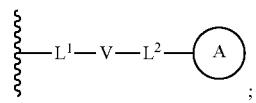
;

wherein:
$L^1$ is independently a bond, —O—, —$NR^a$—, —S—, —S(O)—, or —$S(O)_2$—;
V is independently selected from a bond, $C_{1-6}$ alkyl, $C_{2-6}$ alkenyl, and $C_{2-6}$ alkynyl;
wherein each alkyl, alkenyl, or alkynyl is optionally independently substituted with —$OR^a$, halo, cyano, —$NR^aR^b$ or —$C_{3-8}$ cycloalkyl;
$L^2$ is independently a bond, —O—, —$NR^a$—, —S—, —S(O)—, or —$S(O)_2$—;
ring A is independently cycloalkyl, aryl, heteroaryl, or heterocyclyl;
wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$ alkenyl, —$C_{2-6}$ alkynyl, —O—$C_{1-6}$ haloalkyl, —$NR^aR^b$, —$C(O)R^a$, —$C(O)OR^a$, —O—$C_{1-6}$ cyanoalkyl, —$C(O)NR^aR^b$, —$NR^aC(O)R^a$, —$NR^aC(O)OR^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, $C_{3-8}$ cycloalkyl, and —$C_{1-6}$ alkyl$C_{3-8}$ cycloalkyl; and
wherein the alkyl, alkenyl, or alkynyl group is optionally independently substituted with —$OR^a$, halo, cyano, —$NR^aR^b$ or —$C_{3-8}$ cycloalkyl;
each t is independently 0, 1 or 2;
$R^E$ and $R^W$ are each independently —$NR^1R^2$, —$C_{1-6}$ alkyl$NR^1R^2$, —O—$C_{1-6}$ alkyl$NR^1R^2$, —$C_{1-6}$ alkyl-O—$C_{1-6}$ alkyl$NR^1R^2$, —$NR^a$—$C_{1-6}$ alkyl$NR^1R^2$, —$C_{1-6}$ alkyl$N^+R^1R^2R^3$, —S—$C_{1-6}$ alkyl$NR^1R^2$, —$C(O)NR^1R^2$, —$S(O)_2R^a$, —$(CH_2)_uS(O)_2NR^1R^2$, —$(CH_2)_uNR^aS(O)_2NR^aR^b$, —$S(O)_2NR^aC_{1-6}$alkyl$NR^1R^2$, —$NR^aS(O)_2C_{1-6}$ alkyl$NR^1R^2$, —$(CH_2)_uC(O)NR^aS(O)_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —(CH$_2$)$_u$CH$_2$OP(O)(OR)(OR$^c$)(OR$^d$), —(CH$_2$)$_u$OP(O)(OR$^c$)(OR$^d$), —(CH$_2$)$_u$OP(O)NR$^a$R$^b$)(OR$^a$), or

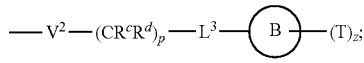

wherein:

V$^2$ is independently a bond, —O—, —NR$^a$—, —S—, —SO—, —SO$_2$—, —C(O)NR$^a$—, —NR$^a$C(O)—, —S(O)$_2$NR$^1$—, or —NR$^a$S(O)$_2$—;

L$^3$ is independently a bond, —O—, —NR$^a$—, —S—, —SO—, —SO$_2$—, —C(O)NR$^a$—, —NR$^a$C(O)—, —S(O)$_2$NR$^1$—, or —NR$^a$S(O)$_2$—;

ring B is independently cycloalkyl, aryl, heteroaryl, or heterocyclyl;

T is independently hydrogen, —OR$^a$, —(CH$_2$)$_q$NR$^1$R$^2$, —(CH$_2$)$_q$NR$^a$C(O)R$^e$, or —(CH$_2$)C(O)R$^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of R$^E$ or R$^W$ is optionally substituted with 1 to 3 substituents independently selected from the group consisting of —NR$^a$R$^b$, halo, cyano, oxo, —OR$^a$, —C$_{1-6}$alkyl, —C$_{1-6}$ haloalkyl, —C$_{1-6}$ cyanoalkyl, —C$_{1-6}$alkylNR$^a$R$^b$, —C$_{1-6}$ hydroxyalkyl, —C$_{3-8}$ cycloalkyl, and —C$_{1-3}$ alkylC$_{3-8}$cycloalkyl;

provided that at least one of V$^2$, L$^3$, ring B and T contains a nitrogen atom;

each R$^1$ is independently selected from hydrogen, —C$_{1-8}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{1-6}$ alkylC(O)OR$^a$, —C$_{2-6}$ alkenylC(O)OR$^a$, —S(O)$_2$R$^a$, —S(O)$_2$NR$^a$R$^b$, —C(O)NR$^a$S(O)$_2$R$^a$, and —C$_{1-6}$ alkylC$_{3-8}$cycloalkyl;

wherein each alkyl, alkenyl, cycloalkyl, aryl, heteroaryl, or heterocyclyl is optionally substituted with 1 to 4 groups independently selected from —OR$^a$, cyano, halo, C$_{1-6}$ alkyl, —C$_{1-6}$ alkylOR$^a$, —C$_{1-6}$ cyanoalkyl, —C$_{1-6}$haloalkyl, C$_{3-8}$ cycloalkyl, —C$_{1-3}$alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —OC(O)NR$^a$R$^b$, NR$^a$C(O)OR$^b$, —C$_{1-6}$ alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$ R$^a$, —S(O)$_2$NR$^a$R$^b$, —C$_{1-6}$ alkylS(O)$_2$NR$^a$R$^b$, —C(O)NR$^a$S(O)$_2$R$^b$, —C$_{1-6}$alkylC(O)NR$^a$S(O)$_2$R$^b$, —NR$^a$C(O)R$^b$, and —C$_{1-6}$alkylNR$^a$C(O)R$^b$;

each R$^2$ is independently selected from hydrogen, —C$_{1-6}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, and —C$_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, cyano, halo, C$_{1-6}$alkyl, —C$_{1-6}$alkylOR$^a$, —C$_{1-6}$ cyanoalkyl, —C$_{1-6}$ haloalkyl, —C$_{3-8}$ cycloalkyl, —C$_{1-3}$alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$ and —NR$^a$C(O)R$^b$;

or R$^1$ and R$^2$ combine to form a heterocyclyl optionally substituted with 1 to 3 groups independently selected from oxo, —C$_{1-6}$ alkyl, —C$_{3-8}$ cycloalkyl, —C$_{2-6}$ alkenyl, —C$_{2-6}$ alkynyl, —OR$^a$, —C(O)OR$^a$, —C$_{1-6}$ cyanoalkyl, —C$_{1-6}$ alkylOR$^a$, —C$_{1-6}$ haloalkyl, —C$_{1-3}$ alkylC$_{3-8}$cycloalkyl, —C(O)R$^a$, C$_{1-6}$ alkylC(O)R$^a$, —C$_{1-6}$ alkylC(O)OR$^a$, —NR$^a$R$^b$, —C$_{1-6}$alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$NR$^a$C(O)R$^b$, and —C$_{1-6}$ alkylS(O)$_2$NR$^a$R$^b$;

each R$^3$ is independently hydrogen, —C$_{1-6}$ alkyl, —C$_{2-6}$ alkenyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, or —C$_{2-6}$ alkenylC(O)OR$^a$;

each R$^a$ is independently selected from hydrogen, —C$_{1-6}$ alkyl, —C$_{1-6}$ cyanoalkyl, —C$_{1-6}$haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each R$^b$ is independently selected from hydrogen, —C$_{1-6}$ alkyl, —C$_{1-6}$ cyanoalkyl, —C$_{1-6}$haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

or R$^a$ and R$^b$ may combine together to form a heterocyclyl optionally substituted with 1 to 4 groups independently selected from —OR$^1$, cyano, halo, —C$_{1-6}$ alkylOR$^f$, —C$_{1-6}$ cyanoalkyl, —C$_{1-6}$haloalkyl, —C$_{3-8}$ cycloalkyl, —C$_{1-3}$ alkylC$_{3-8}$cycloalkyl, —C(O)R$^1$, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, —C$_{1-6}$ alkylC(O)NR$^f$R$^g$, —S(O)$_2$R$^f$, —C$_{1-6}$ alkylS(O)$_2$R$^f$, —S(O)$_2$NR$^f$R$^g$, —C$_{1-6}$ alkylS(O)$_2$NR$^f$R$^g$, —C(O)NR$^f$S(O)$_2$R$^g$ and —NR$^f$C(O)R$^g$;

each R$^c$ is independently selected from hydrogen, —OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

each R$^d$ is independently selected from hydrogen, —C$_{1-6}$ alkyl, —C$_3$-C$_8$cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl; each R$^e$ is independently selected from hydrogen, —C$_{1-6}$ alkyl, —O—C$_{1-6}$ alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —C$_{1-3}$ alkylC$_{3-8}$cycloalkyl, —C$_{1-6}$ alkylaryl, —C$_{1-6}$alkylheteroaryl, —NR$^f$R$^g$, —C$_{1-6}$ alkyINR$^f$R$^g$, —C(O)NR$^f$R$^g$, —C$_{1-6}$ alkylC(O)NR$^f$R$^g$, —NHS(O)$_2$R$^f$, —C$_{1-6}$ alkylS(O)$_2$R$^f$, and —C$_{1-6}$ alkylS(O)$_2$NR$^f$R$^g$;

each R$^f$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl; and each R$^g$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl.

Also provided are compounds of Formula (VA):

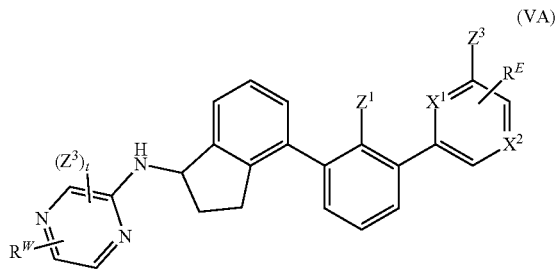

or a pharmaceutically acceptable salt, stereoisomer, mixture of stereoisomers, solvate, or tautomer thereof, wherein $X^1$, $X^2$, $Z^1$, $Z^3$, t, $R^W$ and $R^E$ are as disclosed herein.

Also provided are compounds of Formula (VB):

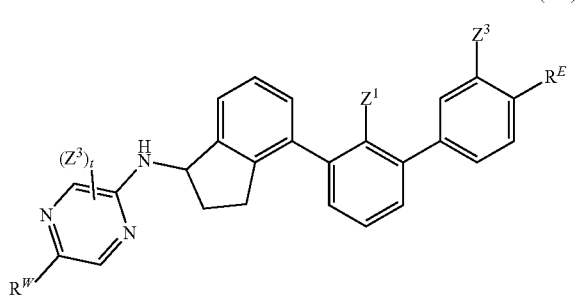

or a pharmaceutically acceptable salt, stereoisomer, mixture of stereoisomers, solvate, or tautomer thereof, wherein $Z^1$, $Z^3$, t, $R^W$ and $R^E$ are as disclosed herein.

Also provided are compounds of Formula (VC):

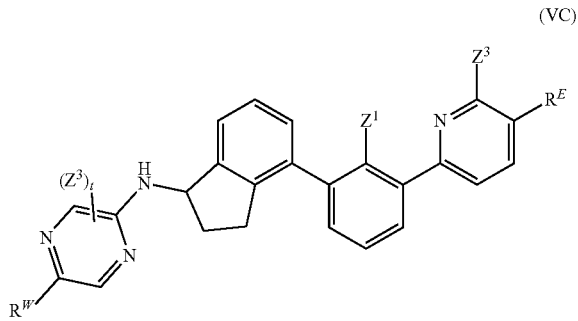

or a pharmaceutically acceptable salt, stereoisomer, mixture of stereoisomers, solvate, or tautomer thereof, wherein $Z^1$, $Z^3$, t, $R^W$ and $R^E$ are as disclosed herein.

Also provided are compounds of Formula (VD):

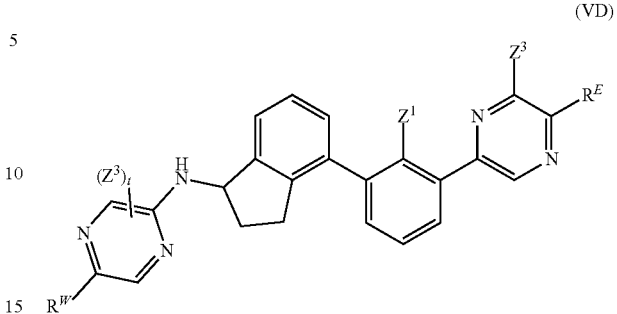

or a pharmaceutically acceptable salt, stereoisomer, mixture of stereoisomers, solvate, or tautomer thereof, wherein $Z^1$, $Z^3$, t, $R^W$ and $R^E$ are as disclosed herein.

Also provided are compounds of Formula (VI):

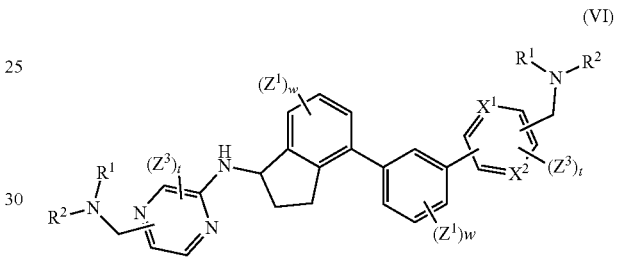

or a pharmaceutically acceptable salt, stereoisomer, mixture of stereoisomers, solvate, or tautomer thereof, wherein:
each of $X^1$ and $X^2$ are independently N, CH or $CZ^3$;
each $Z^1$ is independently halo, —$OR^a$, cyano, or —$C_{1-6}$ alkyl;
each w is independently 0, 1 or 2;
each $Z^3$ is independently halo, —$OR^a$, —$N_3$, —$NO_2$, cyano, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{1-6}$ cyanoalkyl, —$C_{1-6}$ haloalkyl, —O—$C_{1-6}$cyanoalkyl, —O—$C_{1-6}$ haloalkyl, —$C_{3-8}$cycloalkyl, —$C_{1-6}$alkyl$C_{3-8}$ cycloalkyl, aryl, heteroaryl, heterocyclyl, and $R^N$; and
wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$cyanoalkyl, —$C(O)NR^aR^b$, $NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$ and —$C_{3-8}$ cycloalkyl;
$R^N$ is independently-$C_{1-6}$ alkyl$NR^1R^2$, —$OC_{1-6}$alkyl$NR^1R^2$, —$C_{1-6}$ alkyl$OC_{1-6}$ alkyl$NR^1R^2$, —$NR^a$—$C_{1-6}$ alkyl$NR^1R^2$, —$C_{1-6}$ alkyl$C(O)NR^1R^2$, —O—$C_{1-6}$ alkyl$C(O)NR^1R^2$, —O—$C_{1-6}$ alkyl$C(O)OR^1$, —S—$C_{1-6}$alkyl$NR^1R^2$, —$C_{1-6}$ alkyl$OR^a$, or

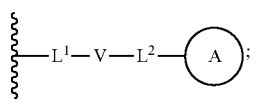

wherein: $L^1$ is independently a bond, —O—, —NR$^a$—, —S—, —S(O)—, or —S(O)$_2$—;

V is independently selected from a bond, $C_{1-6}$ alkyl, $C_{2-6}$ alkenyl, and $C_{2-6}$ alkynyl;

wherein each alkyl, alkenyl, or alkynyl is optionally independently substituted with —OR$^a$, halo, cyano, —NR$^a$R$^b$ or —C$_{3-8}$ cycloalkyl;

$L^2$ is independently a bond, —O—, —NR$^a$—, —S—, —S(O)—, or —S(O)$_2$—;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —NO$_2$, —N$_3$, —OR$^a$, halo, cyano, —C$_{1-6}$ alkyl, —C$_{1-6}$ haloalkyl, —C$_{2-6}$alkenyl, —C$_{2-6}$ alkynyl, —O—C$_{1-6}$ haloalkyl, NR$^a$R$^b$, —C(O)R$^a$, —C(O)OR$^a$, —OC$_{1-6}$ alkylCN, —C(O)NR$^a$R$^b$, —NR$^a$C(O)R$^a$, —NR$^a$C(O)OR$^a$, —NR$^a$C(O)OR$^a$, —C(O)N(R$^a$)OR$^b$, —S(O)$_2$R$^a$, —S(O)$_2$NR$^a$R$^b$, —NR$^a$S(O)$_2$R$^b$, —NR$^a$S(O)$_2$NR$^a$R$^b$, —C(O)NR$^a$S(O)$_2$NR$^a$R$^b$, —C$_{3-8}$cycloalkyl, heteroaryl, and —C$_{1-6}$alkylC$_{3-8}$ cycloalkyl; and wherein the alkyl, alkenyl, or alkynyl group is optionally independently substituted with —OR$^a$, halo, cyano, —NR$^a$R$^b$ or —C$_{3-8}$ cycloalkyl;

each t is independently 0, 1 or 2;

each $R^1$ is independently selected from hydrogen, —C$_{1-8}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{1-6}$ alkylC(O)OR$^a$, —C$_{2-6}$ alkenylC(O)OR$^a$, —S(O)$_2$R$^a$, —S(O)$_2$NR$^a$R$^b$, —C(O)NR$^a$S(O)$_2$R$^a$, and —C$_{1-6}$ alkylC$_{3-8}$cycloalkyl;

wherein each alkyl, alkenyl, cycloalkyl, aryl, heteroaryl, or heterocyclyl is optionally substituted with 1 to 4 groups independently selected from —OR$^a$, cyano, halo, C$_{1-6}$alkyl, —C$_{1-6}$ alkylOR$^a$, —C$_{1-6}$ cyanoalkyl, —C$_{1-6}$haloalkyl, C$_{3-8}$ cycloalkyl, —C$_{1-3}$alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —OC(O)NR$^a$R$^b$, —NR$^a$C(O)OR$^b$, —C$_{1-6}$alkylNR$^a$R$^b$, —C(O)NR$^a$R$^b$, —C$_{1-6}$alkylC(O)NR$^a$R$^b$, —SO$_2$R$^a$, —C$_{1-6}$alkylSO$_2$R$^a$, —SO$_2$NR$^a$R$^b$, —C$_{1-6}$ alkylSO$_2$NR$^a$R$^b$, —C(O)NR$^a$SO$_2$R$^b$, —C$_{1-6}$alkylC(O)NR$^a$SO$_2$R$^b$, —NR$^a$C(O)R$^b$, and —C$_{1-6}$alkylNR$^a$C(O)R$^b$;

each $R^2$ is independently selected from hydrogen, —C$_{1-6}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, and —C$_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, cyano, halo, C$_{1-6}$ alkyl, —C$_{1-6}$alkylOR$^a$, —C$_{1-6}$ cyanoalkyl, —C$_{1-6}$ haloalkyl, —C$_{3-8}$ cycloalkyl, —C$_{1-3}$ alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$ and —NR$^a$C(O)R$^b$;

or $R^1$ and $R^2$ combine to form a heterocyclyl optionally substituted with 1 to 3 groups independently selected from oxo, —C$_{1-6}$ alkyl, —C$_{3-8}$ cycloalkyl, —C$_{2-6}$ alkenyl, —C$_{2-6}$ alkynyl, —OR$^a$, —C(O)OR$^a$, —C$_{1-6}$ cyanoalkyl, —C$_{1-6}$ alkylOR$^a$, —C$_{1-6}$ haloalkyl, —C$_{1-3}$ alkylC$_{3-8}$cycloalkyl, —C(O)R$^a$, —C$_{1-6}$ alkylC(O)R$^a$, —C$_{1-6}$ alkylC(O)OR$^a$, —NR$^a$R$^b$, —C$_{1-6}$alkylNR$^a$R$^b$, —C(O)NR$^a$R$^b$, —C$_{1-6}$ alkyl-C(O)NR$^a$R$^b$, —S(O)$_2$R$^a$, —C$_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$NR$^a$C(O)R$^b$, and —C$_{1-6}$ alkylS(O)$_2$NR$^a$R$^b$;

each $R^3$ is independently hydrogen, —C$_{1-6}$ alkyl, —C$_{2-6}$ alkenyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, or —C$_{2-6}$ alkenylC(O)OR$^a$;

each $R^a$ is independently selected from hydrogen, —C$_{1-6}$ alkyl, —C$_{1-6}$ cyanoalkyl, —C$_{1-6}$haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$alkylheterocyclyl;

each $R^b$ is independently selected from hydrogen, —C$_{1-6}$ alkyl, —C$_{1-6}$ cyanoalkyl, —C$_{1-6}$haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

or $R^a$ and $R^b$ may combine together to form a heterocyclyl optionally substituted with 1 to 4 groups independently selected from —OR$^f$, cyano, halo, —C$_{1-6}$ alkylOR$^f$, —C$_{1-6}$ cyanoalkyl, —C$_{1-6}$haloalkyl, —C$_{3-8}$ cycloalkyl, —C$_{1-3}$alkylC$_{3-8}$cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$alkylNR$^f$R$^g$, —C(O)NR$^f$R$^g$, —C$_{1-6}$ alkylC(O)NR$^f$R$^g$, —S(O)$_2$R$^f$, —C$_{1-6}$ alkylS(O)$_2$R$^f$, —S(O)$_2$NR$^f$R$^g$, —C$_{1-6}$alkylS(O)$_2$NR$^f$R$^g$, —C(O)NR$^f$S(O)$_2$R$^g$ and —NR$^f$C(O)R$^g$;

each $R^c$ is independently selected from hydrogen, —OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

$R^d$ is independently selected from hydrogen, —C$_{1-6}$ alkyl, —C$_3$-C$_8$cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each $R^f$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl; and each $R^g$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl.

Also provided are compounds of Formula (VIA):

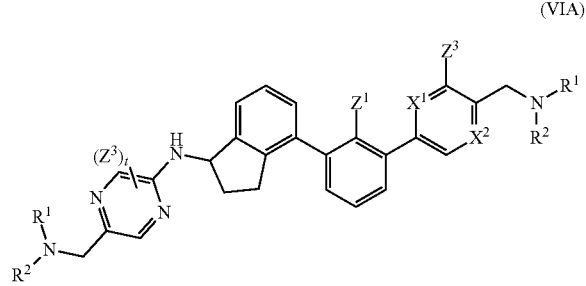

(VIA)

or a pharmaceutically acceptable salt, stereoisomer, mixture of stereoisomers, solvate, or tautomer thereof, wherein $X^1$, $X^2$, $Z^1$, $Z^3$, t, $R^1$ and $R^2$ are as disclosed herein.

Also provided are compounds of Formula (VIB):

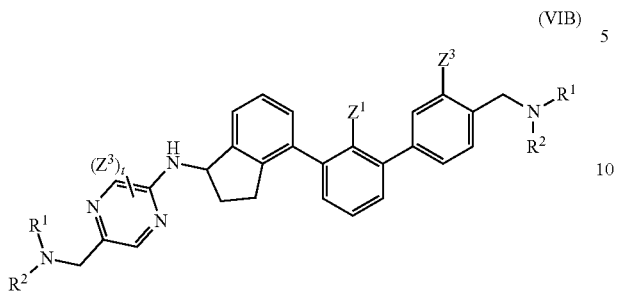

(VIB)

or a pharmaceutically acceptable salt, stereoisomer, mixture of stereoisomers, solvate, or tautomer thereof, wherein $Z^1$, $Z^3$, t, $R^1$ and $R^2$ are as disclosed herein.

Also provided are compounds of Formula (VIC):

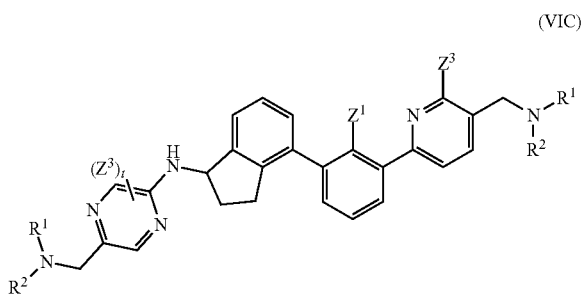

(VIC)

or a pharmaceutically acceptable salt, stereoisomer, mixture of stereoisomers, solvate, or tautomer thereof, wherein $Z^1$, $Z^3$, t, $R^1$ and $R^2$ are as disclosed herein.

Also provided are compounds of Formula (VID):

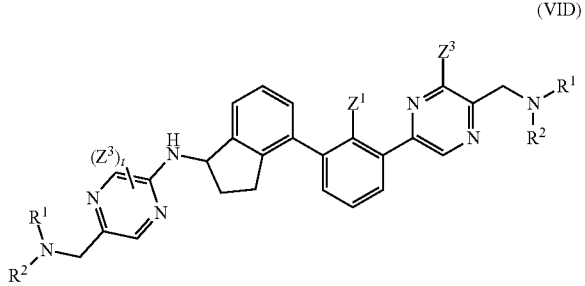

(VID)

or a pharmaceutically acceptable salt, stereoisomer, mixture of stereoisomers, solvate, or tautomer thereof, wherein $Z^1$, $Z^3$, t, $R^1$ and $R^2$ are as disclosed herein.

In some embodiments, each $Z^1$ is independently halo. In some embodiments, each $Z^1$ is halo. In some embodiments, each $Z^1$ is chloro.

In some embodiments, at least one $Z^3$ is halo, —$C_{1-6}$ alkyl, $C_{1-6}$ haloalkyl, —O-cyanoalkyl, —O—$C_{1-6}$ haloalkyl, or $C_{1-6}$alkoxy.

In some embodiments, at least one $Z^3$ is of the formula:

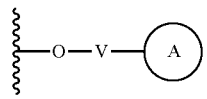

V is independently selected from a bond, $C_{1-6}$ alkyl, $C_{2-6}$ alkenyl, and $C_{2-6}$ alkynyl; wherein each alkyl, alkenyl, or alkynyl is optionally independently substituted with —$OR^a$, halo, cyano, —$NR^aR^b$ or —$C_{3-8}$ cycloalkyl;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —O—$C_{1-6}$haloalkyl, $NR^aR^b$, —$C(O)R^a$, —$C(O)OR^a$, —$OC_{1-6}$alkylCN, —$C(O)NR^aR^b$, —$NR^aC(O)R^a$, —$NR^aC(O)OR^a$, —$NR^aC(O)OR^a$, —$C(O)N(R^a)OR$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, —$C_{3-8}$ cycloalkyl, heteroaryl, and —$C_{1-6}$alkyl$C_{3-8}$ cycloalkyl.

In some embodiments, each $Z^3$ is independently halo, —$C_{1-6}$ alkyl, $C_{1-6}$ haloalkyl, —O-cyanoalkyl, —O—$C_{1-6}$ haloalkyl, or $C_{1-6}$alkoxy.

In some embodiments, each $Z^3$ is independently halo, —$C_{1-6}$alkoxy, —$C_{1-6}$ haloalkyl, or —O— cyanoalkyl.

In some embodiments, each $Z^3$ is independently fluoro, chloro, —$CF_3$, methoxy, or —$OCH_2CN$. In some embodiments, each $Z^3$ is independently —$CF_3$, methoxy, or —$OCH_2CN$.

In some embodiments, at least one of $R^E$ and $R^W$ is —$C_{1-6}$ alkyl$NR^1R^2$.

In some embodiments, both of $R^E$ and $R^W$ are each independently —$C_{1-6}$ alkyl$NR^1R^2$.

In some embodiments, $R^1$ and $R^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —OR, —$C(O)OR^a$, —$C_{1-6}$ cyanoalkyl, —$C_{1-6}$ alkyl$OR^a$, —$C_{1-6}$ haloalkyl, —$C_{1-3}$ alkyl$C_{3-8}$cycloalkyl, —$C(O)R^a$, —$C_{1-6}$ alkyl$C(O)R^a$, —$C_{1-6}$ alkyl$C(O)OR^a$, —$NR^aR^b$, —$C_{1-6}$alkyl$NR^aR^b$, —$C(O)NR^aR^b$, —$C_{1-6}$ alkyl$C(O)NR^aR^b$, —$S(O)_2R^a$, —$C_{1-6}$ alkyl$S(O)_2R^a$, —$S(O)_2NR^aR^b$, —$C(O)N=S(O)R^aNR^aR^b$, —$C(O)N=S(O)R^aNR^aC(O)R^b$, and —$C_{1-6}$ alkyl$S(O)_2NR^aR^b$.

In some embodiments, at least one of R and $R^2$ is —$C_{1-6}$ alkylheteroaryl.

In some embodiments, at least one of R and $R^2$ is —$C_{1-6}$ alkylheterocyclyl.

In some embodiments, one of $R^E$ and $R^W$ is —$C_{1-6}$ alkyl$NR^1R^2$, where $R^1$ and $R^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$ alkyl$OR^a$, —$C_{1-6}$ haloalkyl, —$C_{1-3}$ alkyl$C_{3-8}$ cycloalkyl, —$C(O)R^a$, —$C_{1-6}$ alkyl$C(O)R^a$, —$C_{1-6}$ alkyl$C(O)OR^a$, —$NR^aR^b$, —$C_{1-6}$alkyl$NR^aR^b$, —$C(O)NR^aR^b$, —$C_{1-6}$ alkyl$C(O)NR^aR^b$, —$S(O)_2R^a$, —$C_{1-6}$ alkyl$S(O)_2R^a$, —$S(O)_2NR^aR^b$, —$C(O)N=S(O)R^aNR^aR^b$, —$C(O)N=S(O)R^aNR^aC(O)R^b$, and —$C_{1-6}$ alkyl$S(O)_2NR^aR^b$; and the other of $R^E$ and $R^W$ is —$C_{1-6}$ alkyl$NR^1R^2$, where R is hydrogen and $R^2$ is —$C_{1-6}$ alkylheteroaryl.

In some embodiments, one of $R^E$ and $R^W$ is —$C_{1-6}$ alkyl$NR^1R^2$, where $R^1$ and $R^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$ alkyl$OR^a$, —$C_{1-6}$ haloalkyl, —$C_{1-3}$alkyl$C_{3-8}$cycloalkyl, —$C(O)R^a$, —$C_{1-6}$alkylC(O)$R^a$, —$C_{1-6}$alkylC(O)$OR^a$, —$NR^aR^b$, —$C_{1-6}$alkyl$NR^aR^b$, —$C(O)NR^aR^b$, —$C_{1-6}$alkylC(O)$NR^aR^b$, —$S(O)_2R^a$, —$C_{1-6}$alkylS(O)$_2R^a$, —$S(O)_2NR^aR^b$, —C(O)N=S(O)$R^aNR^aR^b$, —C(O)N=S(O)$R^aNR^aC(O)R^b$, and —$C_{1-6}$ alkylS(O)$_2NR^aR^b$; and the other of $R^E$ and $R^W$ is —$C_{1-6}$ alkyl$NR^1R^2$, where $R^1$ is hydrogen and $R^2$ is —$C_{1-6}$ alkylheterocyclyl.

In some embodiments, one of $R^E$ and $R^W$ is —$C_{1-6}$ alkyl$NR^1R^2$, where $R^1$ and $R^2$ combine to form a heterocyclyl optionally substituted with 1 to 3 groups independently selected from oxo, —$C_{1-6}$ alkyl, —OH, and —C(O)OH; and the other of $R^E$ and $R^W$ is —$C_{1-6}$ alkyl$NR^1R^2$, where $R^1$ is hydrogen or —$C_{1-6}$ alkyl, and $R^2$ is —$C_{1-6}$ alkylheterocyclyl.

In some embodiments, each of $R^E$ and $R^W$ is independently —$C_{1-6}$ alkyl$NR^1R^2$, where each $R^1$ is independently hydrogen or —$C_{1-6}$ alkyl, and each $R^2$ is independently —$C_{1-6}$ alkylheterocyclyl or —$C_{3-6}$ cycloalkyl, wherein each heterocyclyl or cycloalkyl is independently optionally substituted with 1 to 4 groups independently selected from —$OR^a$, cyano, halo, $C_{1-6}$alkyl, —$C_{1-6}$ alkyl$OR^a$, —$C_{1-6}$ cyanoalkyl, —$C_{1-6}$ haloalkyl, $C_{3-8}$cycloalkyl, —$C_{1-3}$alkyl$C_{3-8}$cycloalkyl, —$C(O)R^a$, —$C_{1-6}$alkylC(O)$R^a$, —$C(O)OR^a$, —$C_{1-6}$alkylC(O)$OR^a$, —$NR^aR^b$, —OC(O)$NR^aR^b$, —$NR^aC(O)OR^b$, —$C_{1-6}$alkyl$NR^aR^b$, —C(O)$NR^aR^b$, —$C_{1-6}$ alkylC(O)$NR^aR^b$, —$SO_2R$, —$C_{1-6}$ alkylSO$_2R^a$, —SO$_2NR^aR^b$, —$C_{1-6}$ alkylSO$_2NR^aR^b$, —C(O)$NR^aSO_2R^b$, —$C_{1-6}$alkylC(O)$NR^aSO_2R^b$, —$NR^aC(O)R^b$, and —$C_{1-6}$alkyl$NR^aC(O)R^b$.

In some embodiments, each $R^a$ and $R^b$ are independently selected from hydrogen and methyl.

In some embodiments, each of $R^E$ and $R^W$ is independently —$C_{1-6}$ alkyl$NR^1R^2$, where each R is independently hydrogen or —$C_{1-6}$ alkyl, and each $R^2$ is independently —$C_{1-8}$ alkyl, —$C_{1-6}$ alkylheterocyclyl or —$C_{3-6}$ cycloalkyl, wherein each alkyl, heterocyclyl or cycloalkyl is independently optionally substituted with 1 to 3 groups independently selected from oxo, —$C_{1-6}$ alkyl, —OH, and —C(O)OH.

In some embodiments, $R^E$ and $R^W$ are each independently —$CH_2$—$NR^1R^2$; where each $R^1$ and $R^2$ is independently hydrogen, —$C_{1-6}$ alkyl substituted with 1 to 4 substituents independently selected from —$OCH_3$, —C(O)OH, —C(O)$OCH_3$, —C(O)$NH_2$, —C(O)NH($CH_3$), —C(O)N($CH_3$)$_2$, cyclopropyl, 5-oxopyrrolidin-2-yl optionally substituted with —OH, and cyclobutyl substituted with 1 to 2 substituents independently selected from —OH and methyl, or $C_{3-6}$ cycloalkyl substituted with 1 to 2 substituents independently selected from methyl, fluoromethyl, —OH, and —C(O)OH; or $R^1$ and $R^2$ combine to form a heterocyclyl optionally substituted with 1 to 3 groups independently selected from methyl, ethyl, —OH, —C(O)H, or —C(O)$OCH_3$.

Also provided is a compound of formula (I), (IA), (IB), (IC), (ID), (II), (IIA), (IIB), (IIC), (IID), (III), (IIIA), (IIIB), (IIC), (IIID), (IV), (IVA), (IVB), (IVC), (IVD), (V), (VA), (VB), (VC), (VD), (VIA), (VIB), (VIC), or (VID), or a pharmaceutically acceptable salt, stereoisomer, mixture of stereoisomers, solvate, or tautomer thereof, wherein:

each $Z^1$ is independently halo;

each $Z^3$ is independently halo, —$C_{1-6}$ alkyl, $C_{1-6}$haloalkyl, —O-cyanoalkyl, —O—$C_{1-6}$ haloalkyl, or $C_{1-6}$ alkoxy;

$R^E$ and $R^W$ are each independently —$C_{1-6}$ alkyl$NR^1R^2$;

$R^1$ and $R^2$ are each independently hydrogen or —$C_{1-6}$ alkylheteroaryl, or $R^1$ and $R^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$ alkyl$OR^a$, —$C_{1-6}$ haloalkyl, —$C_{1-3}$alkyl$C_{3-8}$ cycloalkyl, —$C(O)R^a$, —$C_{1-6}$ alkylC(O)$R^a$, —$C_{1-6}$ alkylC(O)$OR^a$, —$NR^aR^b$, —$C_{1-6}$alkyl$NR^aR^b$, —C(O)$NR^aR^b$, —$C_{1-6}$ alkylC(O)$NR^aR^b$, —$S(O)_2R^a$, —$C_{1-6}$ alkylS(O)$_2R^a$, —$S(O)_2NR^aR^b$, —C(O)N=S(O)$R^aNR^aR^b$, —C(O)N=S(O)$R^aNR^aC(O)R^b$, and —$C_{1-6}$ alkylS(O)$_2NR^aR^b$;

each $R^a$ is independently selected from hydrogen, —$C_{1-6}$ alkyl, —$C_{1-6}$ cyanoalkyl, —$C_{1-6}$haloalkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl; and each $R^b$ is independently selected from hydrogen, —$C_{1-6}$ alkyl, —$C_{1-6}$ cyanoalkyl, —$C_{1-6}$haloalkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl.

Also provided is a compound of formula (I), (IA), (IB), (IC), (ID), (II), (IIA), (IIB), (IIC), (IID), (III), (IIIA), (IIIB), (IIIC), (IIID), (IV), (IVA), (IVB), (IVC), (IVD), (V), (VA), (VB), (VC), (VD), (VIA), (VIB), (VIC), or (VID), or a pharmaceutically acceptable salt, stereoisomer, mixture of stereoisomers, solvate, or tautomer thereof, wherein:

each $Z^1$ is independently halo;

each $Z^3$ is independently halo, —$C_{1-6}$ alkyl, $C_{1-6}$ haloalkyl, —O-cyanoalkyl, —O—$C_{1-6}$ haloalkyl, or $C_{1-6}$ alkoxy;

$R^E$ and $R^W$ are each independently —$C_{1-6}$ alkyl$NR^1R^2$;

$R^1$ and $R^2$ are each independently hydrogen or —$C_{1-6}$ alkylheteroaryl, or $R^1$ and $R^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$ alkyl$OR^a$, —$C_{1-6}$ haloalkyl, —$C_{1-3}$ alkyl$C_{3-8}$ cycloalkyl, —$C(O)R^a$, —$C_{1-6}$ alkylC(O)$R^a$, —$C_{1-6}$ alkylC(O)$OR^a$, —$NR^aR^b$, —$C_{1-6}$alkyl$NR^aR^b$, —C(O)$NR^aR^b$, —$C_{1-6}$ alkylC(O)$NR^aR^b$, —$S(O)_2R^a$, —$C_{1-6}$ alkylS(O)$_2R^a$, —$S(O)_2NR^aR^b$, —C(O)N=S(O)$R^aNR^aR^b$, —C(O)N=S(O)$R^aNR^aC(O)R^b$, and —$C_{1-6}$ alkylS(O)$_2NR^aR^b$, wherein each alkyl, heterocyclyl or cycloalkyl is independently optionally substituted with 1 to 3 groups independently selected from oxo, —$C_{1-6}$ alkyl, —OH, and —C(O)OH;

each $R^a$ is independently selected from hydrogen, —$C_{1-6}$ alkyl, —$C_{1-6}$ cyanoalkyl, —$C_{1-6}$haloalkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl; and each $R^b$ is independently selected from hydrogen, —$C_{1-6}$ alkyl, —$C_{1-6}$ cyanoalkyl, —$C_{1-6}$haloalkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl.

Also provided is a compound of formula (I), (IA), (IB), (IC), (ID), (II), (IIA), (IIB), (IIC), (IID), (III), (IIIA), (IIIB), (IIIC), (IIID), (IV), (IVA), (IVB), (IVC), (IVD), (V), (VA), (VB), (VC), (VD), (VIA), (VIB), (VIC), or (VID), or a pharmaceutically acceptable salt, stereoisomer, mixture of stereoisomers, solvate, or tautomer thereof, wherein:

each $Z^1$ is chloro;

each $Z^3$ is independently fluoro, chloro, —$CF_3$, methoxy, or —$OCH_2CN$. In some embodiments, each $Z^3$ is independently —$CF_3$, methoxy, or —$OCH_2CN$;

$R^E$ and $R^W$ are each independently —$CH_2$—$NR^1R^2$; where each $R^1$ and $R^2$ is independently hydrogen, —$C_{1-6}$ alkyl substituted with 1 to 4 substituents independently selected from —OCH₃, —C(O)OH, —C(O)OCH₃, —C(O)NH₂, —C(O)NH(CH₃), —C(O)N(CH₃)₂, cyclopropyl, 5-oxopyrrolidin-2-yl optionally substituted with —OH, and cyclobutyl substituted with 1 to 2 substituents independently selected from —OH and methyl, or $C_{3-6}$ cycloalkyl substituted with 1 to 2 substituents independently selected from methyl, fluoromethyl, —OH, and —C(O)OH;

or $R^1$ and $R^2$ combine to form a heterocyclyl optionally substituted with 1 to 3 groups independently selected from methyl, ethyl, —OH, —C(O)H, or —C(O)OCH₃.

In certain embodiments, each of $R^E$ and $R^W$ is independently selected from

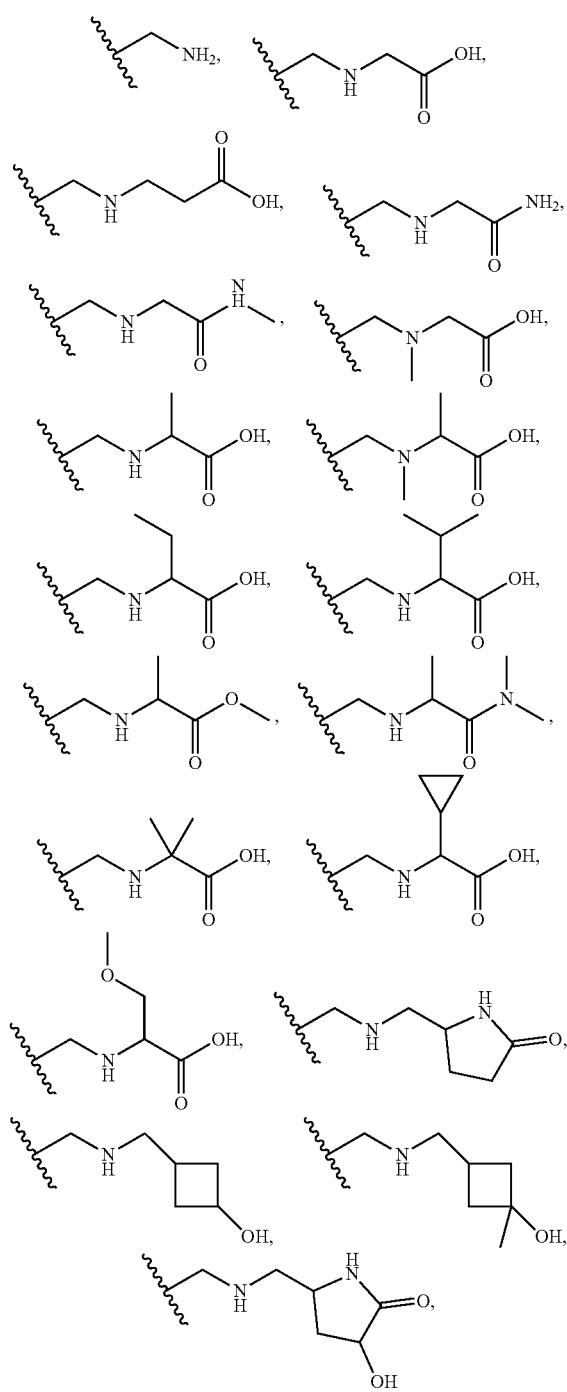

-continued

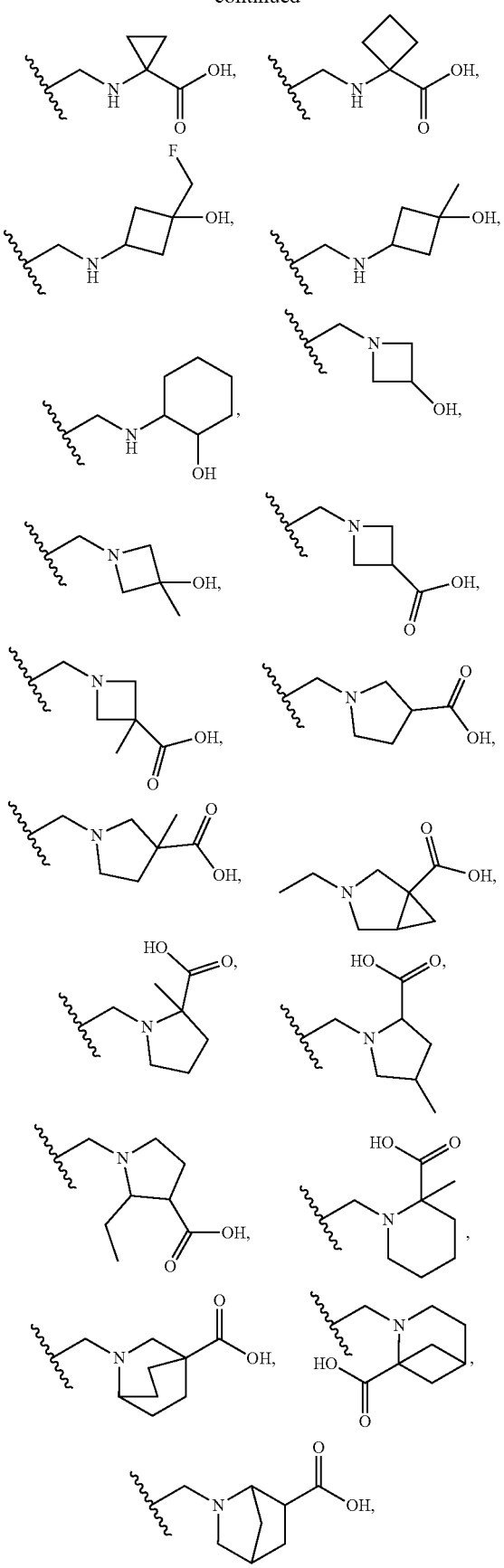

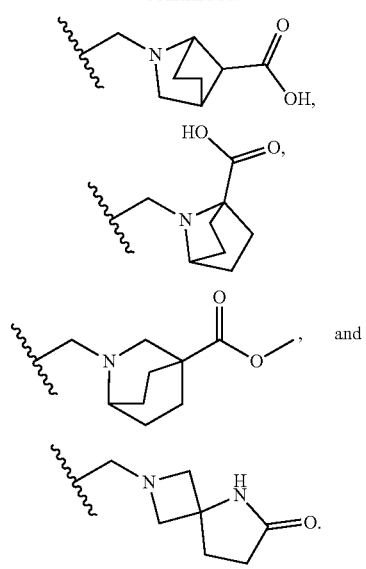
In certain embodiments, one of $R^E$ and $R^W$ is
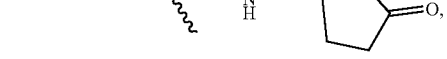
and the other of $R^E$ and $R^W$ is
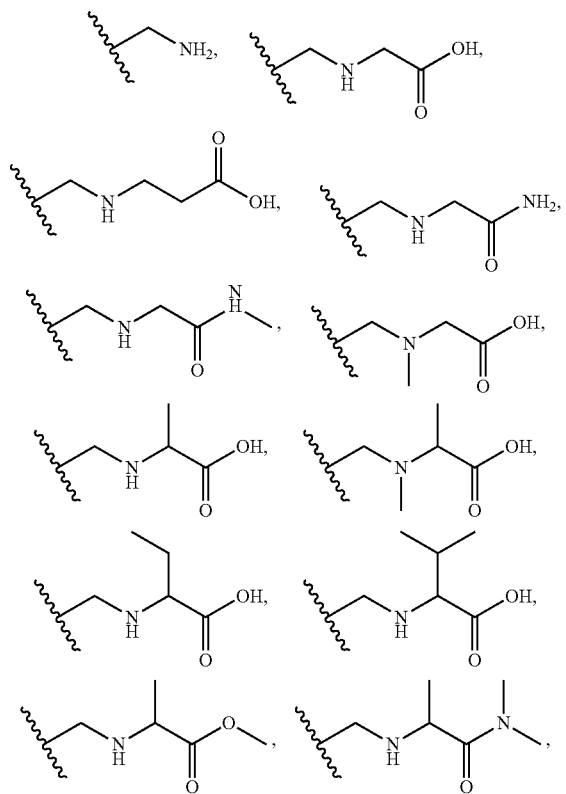
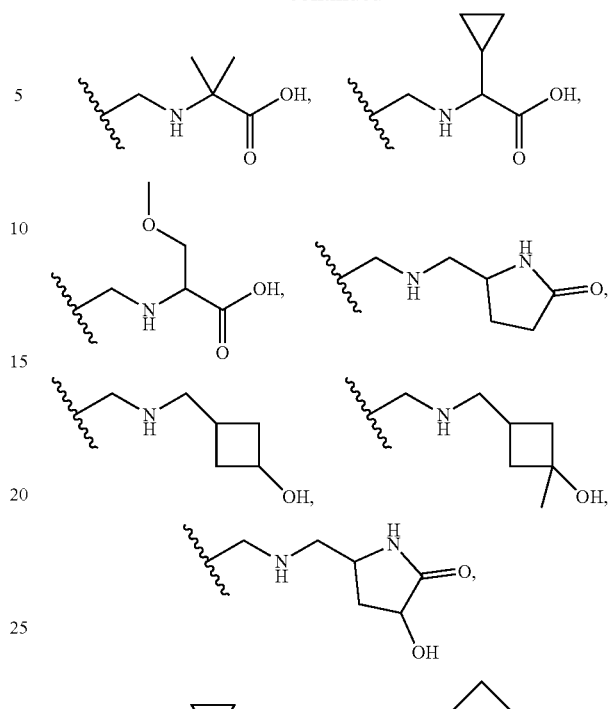

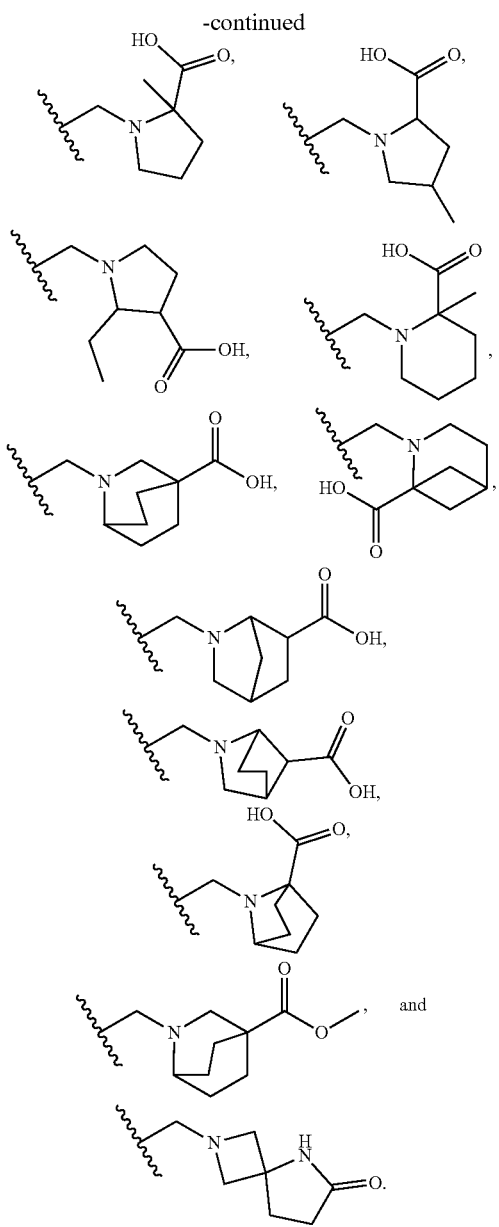

In certain embodiments, provided is a compound as shown in Table 1A, or a pharmaceutically acceptable salt, stereoisomer, mixture of stereoisomers, solvate, or tautomer thereof.

In certain embodiments, provided is a compound as shown in Table 1B, or a pharmaceutically acceptable salt, stereoisomer, mixture of stereoisomers, solvate, or tautomer thereof.

In certain embodiments, the compound as provided herein has a molecular weight of less than about 850 g/mol, or less than about 800 g/mol, or less than about 750 g/mol, or less than about 700 g/mol, or between about 500 to about 850 g/mol, or between about 500 to about 600 g/mol, or between about 550 to about 650 g/mol, or between about 600 to about 700 g/mol, or between about 650 to about 750 g/mol, or between about 700 to about 800 g/mol, or between about 750 to about 850 g/mol.

One of skill in the art is aware that each and every embodiment of a group (e.g., $R^E$) disclosed herein may be combined with any other embodiment of each of the remaining groups (e.g., R, $Z^1$, $Z^3$, etc.) to generate a complete compound of formula (I), or any formula described herein or a pharmaceutically acceptable salt, stereoisomer, mixture of stereoisomers, solvate, or tautomer thereof, each of which is deemed within the ambit of the present disclosure.

Formulations and Methods

PD-1 and its ligand, PD-L1, are monomeric type I transmembrane proteins that play critical roles in T cell inhibition and exhaustion. PD-L1 is composed of two extracellular immunoglobulin (Ig)-like domains whereas PD-1 is composed of a single extracellular Ig like domain and an intracellular tail. The crystal structure of the PD-1/PD-L1 complex reveals that PD-1 binds to PD-L1 with a 1:1 stoichiometry to form a monomeric complex (see, e.g., Cheng et al. *J Biol Chem*, 2013; 288(17); 11771-85, Lin et al. *Proc Natl Acad Sci USA*, 2008; 105(8); 3011-6, Zak et al. *Structure*, 2015; 23(12); 2341-8). This arrangement represents a distinct ligand-binding mode and signaling mechanism that differs from other co-inhibitory receptor/ligand interactions such as CTLA-4/B7, where oligomerization plays an important role in signaling (see, e.g., Schwartz et al. *Nature*, 2001; 410(6828); 604-8). Engagement of PD-1 to PD-L1, along with TCR signaling, leads to phosphorylation of the cytoplasmic domain tyrosines on PD-1 and recruitment of Src-homology 2-containing tyrosine phosphatases (SHP-1 and SHP-2). These phosphatases dephosphorylate TCR-associated proteins, resulting in alteration of downstream signaling including blocking phosphoinositide 3 kinase (PI3K) and Akt kinase activation, disrupting glucose metabolism, and inhibiting IL-2 and IFN-γ secretion (see, e.g., Hofmeyer et al. *J Biomed Biotechnol*, 2011; 2011; 451694, Latchman et al. *Nature immunology*, 2001; 2(3); 261-8).

Monoclonal antibodies developed for cancer immunotherapy binding to either PD-1 or PD-L1 have demonstrated significant response rates in patients, particularly for melanoma, non-small cell lung cancer (NSCLC), renal cell carcinoma (RCC) and bladder cancer. Many of these studies have shown that blockade of the PD-1/PD-L1 axis leads to an enhancement in T cell cytotoxic activity at the tumor site (see, e.g., Wherry E J. *Nat Immunol*, 2011; 12(6); 492-9). In addition to cancer, inhibition of this pathway has also shown promise for the control or elimination of chronic viral infections, such as HBV (see, e.g., Bengsch et al. *J Hepatol*, 2014; 61(6); 1212-9, Fisicaro et al. *Gastroenterology*, 2010; 138(2), 682-93, 93 e1-4, Fisicaro et al. *Gastroenterology*, 2012; 143(6), 1576-85 e4).

Methods

In one embodiment, the present disclosure provides a compound of formula (I), or any formula described herein, or a pharmaceutically acceptable salt, stereoisomer, mixture of stereoisomers, solvate, or tautomer thereof, useful as an inhibitor of PD-1, PD-L1 and/or the PD-1/PD-L1 interaction. In some embodiments, compounds disclosed herein inhibit the PD-1/PD-L1 interaction by dimerizing PD-L1, or by inducing or stabilizing PD-L1 dimer formation.

In one embodiment, the present disclosure provides a pharmaceutical composition comprising a compound of formula (I) or a pharmaceutically acceptable salt, stereoisomer, mixture of stereoisomers or tautomer thereof, at least one additional therapeutic agent suitable for treating an HBV infection, and at least one pharmaceutically acceptable carrier or excipient.

In one embodiment, provided is a compound of formula (I) or a pharmaceutically acceptable salt, stereoisomer, mixture of stereoisomers or tautomer thereof, useful for treating an HBV infection or a condition in a patient that is amenable to treatment by inhibiting PD-1, PD-L1 or the PD-1/PD-L1 interaction.

In another embodiment, the present disclosure provides a compound of formula (I) for use in the manufacture of a medicament for treating or eliminating HBV. Elimination of HBV during acute infection is associated with the emergence of functional HBV-specific $CD8^+$ T cells. In contrast, chronic infection is marked by the presence of dysfunctional HBV-specific $CD8^+$ T cells that are unable to control viral infection (see, e.g., Boni et al. *J Virol,* 2007; 81(8); 4215-4225, Ferrari, *Liver Int,* 2015; 35; Suppl 1:121-8, Fisicaro et al., *Gastroenterology,* 2010; 138(2); 682-693, 93 e1-4, Guidotti et al. *Cell,* 2015; 161(3); 486-500). Mechanisms that may contribute to the dysfunction of HBV-specific T cells in CHB include upregulation of inhibitory T cell receptors (e.g. PD-1, CTLA-4 and TIM-3), due to persistent high viral load and antigen levels (see, e.g., Boni et al. *J Virol,* 2007; 81(8); 4215-4225, Franzese et al. *J Virol,* 2005; 79(6); 3322-3328, Peppa et al. *J Exp Med,* 2013; 210(1); 99-114, Wherry E J. *Nature immunology* 2011; 12(6); 492-499). Among all inhibitory immune receptors, PD-1 is most frequently upregulated on HBV-specific T cells. Furthermore, multiple studies have confirmed that the majority of circulating and intrahepatic HBV-specific $CD8^+$ T cells in CHB patients are exhausted and express high levels of PD-1 (see, e.g., Bengsch et al. *J Hepatol,* 2014; 61(6); 1212-1219, Fisicaro et al., *Gastroenterology,* 2010; 138(2); 682-693, 93 e1-4). Notably, the defects in effector cytokine production by HBV-specific $CD4^+$ and $CD8^+$ T cells were partially reversed by blocking the PD-1/PD-L1 interaction with an anti-PD-L1 antibody in PBMCs isolated from CHB patients (see, e.g., Bengsch et al. *J Hepatol,* 2014; 61(6); 1212-1219, Fisicaro et al., *Gastroenterology,* 2010; 138(2); 682-693, 93 e1-4, Fisicaro et al. *Gastroenterology,* 2012; 143(6); 1576-1585 e4). Consistent with these pre-clinical data, a clinical study evaluating α-PD-1 therapy in CHB subjects showed significant reductions in HBsAg levels in the majority of subjects which includes three out of twenty patients with reduction in HBsAg levels of over 0.5 $\log_{10}$ and one subject that experienced a functional cure (sustained HBsAg loss and appearance of anti-HBsAb) (see, e.g., Gane et al. "A phase 1 study evaluating anti-PD-1 treatment with or without GS-4774 in HBeAg negative chronic hepatitis B patients", Abstract PS-044, European Association for the Study of the Liver (EASL); 2017; April 19-23; Amsterdam, The Netherlands). Taken together, these findings demonstrate that inhibiting the PD-1/PD-L1 axis may improve T cell function in CHB patients and increase the rates of functional cure. Disclosed herein are selective and potent PD-L1 small molecule inhibitors that bind specifically to PD-L1 and inhibit the PD-1/PD-L1 interaction by inducing PD-L1 dimerization.

In one embodiment, the present disclosure provides a method of treating cancer in a patient in need thereof, comprising administering a compound of formula (I), or any formula described herein, or a pharmaceutically acceptable salt, stereoisomer, mixture of stereoisomers, solvate, or tautomer thereof, in combination with one or more checkpoint inhibitors selected from nivolumab, pembrolizumab, and artezolizumab.

In one embodiment, the present disclosure provides a method of treating an infectious disease in a patient, comprising administering an effective amount of a compound as disclosed herein (e.g., a compound of formula (I), or any formula described herein), or a pharmaceutically acceptable salt, stereoisomer, mixture of stereoisomers, solvate, or tautomer thereof, to a patient in need thereof. Exemplary infectious diseases include, but are not limited to, diseases such as hepatitis A, hepatitis B (HBV), hepatitis C (HCV), hepatitis D (HDV), HIV, human papillomavirus (HPV), respiratory syncytial virus (RSV), severe acute respiratory syndrome (SARS), influenza, parainfluenza, cytomegalovirus, dengue, herpes simplex virus-1, herpes simplex virus-2, leishmania infection, and respiratory syncytial virus as well as coinfections thereof, including HDV/HBV coinfection. In certain embodiments, infectious diseases include, but are not limited to, diseases such as hepatitis A, hepatitis B (HBV), hepatitis D (HDV), HIV, human papillomavirus (HPV), respiratory syncytial virus (RSV), severe acute respiratory syndrome (SARS), influenza, parainfluenza, cytomegalovirus, dengue, herpes simplex virus-1, herpes simplex virus-2, leishmania infection, and respiratory syncytial virus.

In one embodiment, the present disclosure provides a pharmaceutical composition comprising a compound of formula (I), or any formula described herein, or a pharmaceutically acceptable salt, stereoisomer, mixture of stereoisomers, solvate, or tautomer thereof, and a pharmaceutically acceptable carrier.

In one embodiment, the present disclosure provides a pharmaceutical composition comprising a compound of formula (I), or any formula described herein, or a pharmaceutically acceptable salt, stereoisomer, mixture of stereoisomers, solvate, or tautomer thereof, and at least one additional anticancer agent and at least one pharmaceutically acceptable excipient.

The present disclosure provides a compound of formula (I), or any formula described herein, or a pharmaceutically acceptable salt, stereoisomer, mixture of stereoisomers, solvate, or tautomer thereof, for use in therapy. In another embodiment, the present disclosure provides a compound of formula (I), or any formula described herein, or a pharmaceutically acceptable salt, stereoisomer, mixture of stereoisomers, solvate, or tautomer thereof, for use in the manufacture of a medicament for treating cancer.

In one embodiment, provided is a compound of formula (I), or any formula described herein, or a pharmaceutically acceptable salt, stereoisomer, mixture of stereoisomers, solvate, or tautomer thereof, useful for the treatment of cancer or a condition in a patient that is amenable to treatment by inhibiting PD-1, PD-L1 or the PD-1/PD-L1 interaction. Cancers that may be treated with the compounds of formula (I) disclosed herein include pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer.

In one embodiment, provided is a compound of formula (I), or any formula described herein, or a pharmaceutically acceptable salt, stereoisomer, mixture of stereoisomers, solvate, or tautomer thereof, useful for the treatment of cancer or a condition in a patient that is amenable to treatment by inhibiting PD-1, PD-L1 or the PD-1/PD-L1 interaction including, but not limited to, lymphoma, multiple myeloma, and leukemia. Additional diseases or conditions that may be treated include, but are not limited to acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma and diffuse large B-cell lymphoma (DLBCL).

"Administering" or "administration" refers to the delivery of one or more therapeutic agents to a patient. In one embodiment, the administration is a monotherapy wherein a compound of formula (I), or any formula described herein, or a pharmaceutically acceptable salt, stereoisomer, mixture of stereoisomers, solvate, or tautomer thereof, is the only active ingredient administered to the patient in need of therapy. In another embodiment, the administration is co-administration such that two or more therapeutic agents are delivered together during the course of the treatment. In one embodiment, two or more therapeutic agents may be co-formulated into a single dosage form or "combined dosage unit", or formulated separately and subsequently combined into a combined dosage unit, as is typically for intravenous administration or oral administration as a mono or bilayer tablet or capsule.

In one embodiment, the compound of formula (I), or any formula described herein, or a pharmaceutically acceptable salt, stereoisomer, mixture of stereoisomers, solvate, or tautomer thereof, in an effective amount, such as, from about 0.1 mg to about 5 g per day, or from about 0.1 mg to about 1 g per day of said compound. In one embodiment, the effective amount is from about 0.1 mg to about 200 mg per day. In one embodiment, the effective amount is from about 1 mg to about 100 mg per day. In other embodiments, the effective amount is about 10 mg, about 9 mg, about 8 mg, about 7 mg, about 6 mg, about 5 mg, about 4 mg, about 3 mg, about 2 mg, about 1 mg, about 3 mg, about 5 mg, about 10 mg, about 15 mg, about 18 mg, about 20 mg, about 30 mg, about 40 mg, about 60 mg, about 80 mg, or about 100 mg per day.

In one embodiment, the compound of formula (I), or any formula described herein, or a pharmaceutically acceptable salt, stereoisomer, mixture of stereoisomers, solvate, or tautomer thereof, and at least one additional anticancer agent is administered to a human patient in need thereof in an effective amount of each agent, independently from about 0.1 mg to about 1000 mg per compound or formulation per day per compounds. In one embodiment, the effective amount of the combination treatment of a compound of formula (I), or any formula described herein, or a pharmaceutically acceptable salt, stereoisomer, mixture of stereoisomers, solvate, or tautomer thereof, and an additional compound is independently from about 0.1 mg to about 200 mg per compound per day. In one embodiment, the effective amount of the combination treatment of a compound of formula (I), or any formula described herein, or a pharmaceutically acceptable salt, stereoisomer, mixture of stereoisomers, solvate, or tautomer thereof, and an additional compound is independently from about 1 mg to about 100 mg per compound per day. In other embodiments, the effective amount of the combination treatment of a compound of formula (I), or any formula described herein, or a pharmaceutically acceptable salt, stereoisomer, mixture of stereoisomers, solvate, or tautomer thereof, and an additional compound is for each component, about 1 mg, about 3 mg, about 5 mg, about 10 mg, about 15 mg, about 18 mg, about 20 mg, about 30 mg, about 40 mg, about 60 mg, about 80 mg, about 100 mg, about 200 mg, or about 500 mg each per day.

In one embodiment, the compound of formula (I), or any formula described herein, or a pharmaceutically acceptable salt, stereoisomer, mixture of stereoisomers, solvate, or tautomer thereof, and/or a combination of the compound of formula (I), or any formula described herein, or a pharmaceutically acceptable salt, stereoisomer, mixture of stereoisomers, solvate, or tautomer thereof, and an additional anticancer agent or a pharmaceutically acceptable salt thereof is administered once a day. In yet another embodiment, the compound of formula (I), or any formula described herein, or a pharmaceutically acceptable salt, stereoisomer, mixture of stereoisomers, solvate, or tautomer thereof, and/or an additional anticancer agent or a pharmaceutically acceptable salt thereof is administered as a loading dose of from about 10 mg to about 500 mg per compound on the first day and each day or on alternate days or weekly for up to a month followed by a regular regimen of a compound of formula (I), or any formula described herein, or a pharmaceutically acceptable salt, stereoisomer, mixture of stereoisomers, solvate, or tautomer thereof, and/or one or more additional anticancer agents or therapies. The maintenance dose may be 1-500 mg daily or weekly for each component of a multi component drug regimen. A qualified care giver or treating physician is aware of what dose regimen is best for a particular patient or particular presenting conditions and will make appropriate treating regimen decisions for that patient. Thus, in another embodiment, the qualified caregiver is able to tailor a dose regimen of the compound of formula (I), or any formula described herein, or a pharmaceutically acceptable salt, stereoisomer, mixture of stereoisomers, solvate, or tautomer thereof, and/or an additional agent(s) as disclosed herein to fit with the particular needs of the patient. Thus, it will be understood that the amount of the compound of formula (I), or any formula described herein, or a pharmaceutically acceptable salt, stereoisomer, mixture of stereoisomers, solvate, or tautomer thereof, and the amount of an additional agent actually administered will usually be determined by a physician, in light of the relevant circumstances, including the condition (s) to be treated, the chosen route of administration, the actual compound (e.g., salt or free base) administered and its relative activity, the age, weight, and response of the individual patient, the severity of the patient's symptoms, and the like.

Co-administration may also include administering component drugs e.g., one on more compounds of formula (I), or any formula described herein, and one or more additional (e.g., a second, third, fourth or fifth) anticancer or other therapeutic agent(s). Such combination of one on more compounds of formula (I), or any formula described herein, and one or more additional anticancer or other therapeutic agent(s) may be administered simultaneously or in sequence (one after the other) within a reasonable period of time of each administration (e.g., about 1 minute to 24 hours) depending on the pharmacokinetic and/or pharmacodynamics properties of each agent or the combination. Co-administration may also involve treatment with a fixed combination wherein agents of the treatment regimen are combinable in a fixed dosage or combined dosage medium e.g., solid, liquid or aerosol. In one embodiment, a kit may be used to administer the drug or drug components.

Thus, one embodiment of the present disclosure is a method of treating a disease amenable to treatment with a PD-1, PD-L1 inhibitor or a PD-1/PD-L1 interaction inhibitor e.g., cancer comprising administering therapeutically effective amounts of formulations of one on more compounds of formula (I), or any formula described herein, and one or more additional anticancer agents, including for example, via a kit to a patient in need thereof. It will be understood that a qualified care giver will administer or direct the administration of a therapeutically effective amount of any of the compound(s) or combinations of compounds of the present disclosure.

"Intravenous administration" is the administration of substances directly into a vein, or "intravenously." Compared with other routes of administration, the intravenous (IV) route is a faster way to deliver fluids and medications throughout the body. An infusion pump can allow precise control over the flow rate and total amount of medication delivered. However, in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, as a "flush", following the injection to push the medicine into the bloodstream more quickly. Thus in one embodiment, compound(s) or combination of compounds described herein may be administered by IV administration alone or in combination with administration of certain components of the treatment regimen by oral or parenteral routes.

"Oral administration" is a route of administration where a substance is taken through the mouth, and includes buccal, sub labial, and sublingual administration, as well as enteral administration and that through the respiratory tract, unless made through e.g., tubing so the medication is not in direct contact with any of the oral mucosa. Typical form for the oral administration of therapeutic agents includes the use of tablets or capsules. Thus in one embodiment, compound(s) or combination of compounds described herein may be administered by oral route alone or in combination with administration of certain components of the treatment regimen by IV or parenteral routes.

Pharmaceutical Formulations

The compound(s) of formula (I), or any formula described herein, or a pharmaceutically acceptable salt, stereoisomer, mixture of stereoisomers, solvate, or tautomer thereof, may be administered in a pharmaceutical formulation. Pharmaceutical formulations/compositions contemplated by the present disclosure comprise, in addition to a carrier, the compound of formula (I), or any formula described herein, or a pharmaceutically acceptable salt, stereoisomer, mixture of stereoisomers, solvate, or tautomer thereof, or a combination of compound of formula (I), or any formula described herein, or a pharmaceutically acceptable salt, stereoisomer, mixture of stereoisomers, solvate, or tautomer thereof, optionally in combination with an additional agent such as for example, ipilimumab, or a pharmaceutically acceptable salt thereof.

Pharmaceutical formulations/compositions contemplated by the present disclosure may also be intended for administration by injection and include aqueous solutions, oil suspensions, emulsions (with sesame oil, corn oil, cottonseed oil, or peanut oil) as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component compound(s) in the required amount in the appropriate solvent with various other ingredients as enumerated above or as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient(s) plus any additional desired ingredient from a previously sterile-filtered solution thereof.

In making pharmaceutical compositions that comprise compound of formula (I), or any formula described herein, or a pharmaceutically acceptable salt, stereoisomer, mixture of stereoisomers, solvate, or tautomer thereof, optionally in combination with an additional agent/therapy useful for the purpose or pharmaceutically acceptable salt thereof, the active ingredient is usually diluted by an excipient or carrier and/or enclosed or mixed with such a carrier that may be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 20% by weight of the active compounds, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the disclosure may be formulated so as to provide quick, sustained or delayed release of the active ingredient after administration to the patient by employing procedures known in the art. In one embodiment, sustained release formulations are used. Controlled release drug delivery systems for oral administration include osmotic pump systems and dissolutional systems containing polymer-coated reservoirs or drug-polymer matrix formulations.

Certain compositions are formulated in a unit dosage form. The term "unit dosage forms" or "combined dosage unit" refers to physically discrete units suitable as unitary dosages for human subjects and other mammals, each unit containing a predetermined quantity of one or more of the active materials (e.g., compound (I), optionally in combination with an additional agent calculated to produce the desired effect, in association with a suitable pharmaceutical excipient in for example, a tablet, capsule, ampoule or vial for injection. It will be understood, however, that the amount of each active agent actually administered will be determined by a physician, in the light of the relevant circumstances, including the condition to be treated, the chosen route of administration, the actual compounds administered and their relative activity, the age, weight, and response of the individual patient, the severity of the patient's symptoms, and the like.

For preparing solid compositions such as tablets, the principal active ingredient(s) is/are mixed with a pharmaceutical excipient to form a solid pre-formulation composition containing a homogeneous mixture of a compound of the present disclosure. When referring to these pre-formulation compositions as homogeneous, it is meant that the active ingredient(s) are dispersed evenly throughout the composition so that the composition may be readily subdivided into equally effective unit dosage forms such as tablets, pills and capsules.

The tablets or pills comprising compound of formula (I), or any formula described herein, or a pharmaceutically acceptable salt, stereoisomer, mixture of stereoisomers, solvate, or tautomer thereof, of the present disclosure optionally in combination with the second agent may be coated or otherwise compounded to provide a dosage form affording the advantage of prolonged action, or to protect from the acidic conditions of the stomach. For example, the tablet or pill can comprise an inner dosage and an outer dosage element, the latter being in the form of an envelope over the former. In one embodiment, the inner dosage element may comprise the compound and the outer dosage element may comprise the second or additional agent or vice versa. Alternatively, the combined dosage unit may be side by side configuration as in a capsule or tablet where one portion or half of the tablet or capsule is filled with a formulation of the compound of formula (I), or any formula described herein, or a pharmaceutically acceptable salt, stereoisomer, mixture of stereoisomers, solvate, or tautomer thereof, while the other portion or half of the table or capsule comprises the additional agent.

A variety of materials may be used for such enteric layers or coatings, such materials including a number of polymeric acids and mixtures of polymeric acids with such materials as shellac, cetyl alcohol, and cellulose acetate. One of ordinary skill in the art is aware of techniques and materials used in the manufacture of dosages of formulations disclosed herein.

A "sustained release formulation" or "extended release formulation" is a formulation which is designed to slowly release a therapeutic agent into the body over an extended period of time, whereas an "immediate release formulation" is a formulation which is designed to quickly release a therapeutic agent into the body over a shortened period of time. In some cases the immediate release formulation may be coated such that the therapeutic agent is only released once it reaches the desired target in the body (e.g., the stomach). One of ordinary skill in the art is able to develop sustained release formulations of the presently disclosed compounds without undue experimentation. Thus in one embodiment, compound(s) or combination of compounds described herein may be delivered via sustained released formulations alone or in combination with administration of certain components of the treatment regimen by oral, IV or parenteral routes.

A lyophilized formulation may also be used to administer a compound of formula (I), or any formula described herein, singly or in combination with an additional anticancer agent. One of skill in the art is aware of how to make and use lyophilized formulations of drug substances amenable to lyophilization.

Spray-dried formulation may also be used to administer a compound of formula (I), or any formula described herein, or a pharmaceutically acceptable salt, stereoisomer, mixture of stereoisomers, solvate, or tautomer thereof, singly or in combination with an additional anti-cancer agent. One of skill in the art is aware of how to make and use spray-dried formulations of drug substances amenable to spray-drying. Other known formulation techniques may also be employed to formulate a compound or combination of compounds disclosed herein.

In one embodiment, the instructions are directed to use of the pharmaceutical composition for the treatment of cancer, including for example, leukemia or lymphoma. In specific embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL).

In one embodiment, the instructions are directed to use of the pharmaceutical composition for the treatment of an autoimmune disease. Specific embodiments of an autoimmune disease include asthma, rheumatoid arthritis, multiple sclerosis, and lupus.

Articles of Manufacture

Articles of manufacture comprising a container in which a compound of formula (I), or any formula described herein, or a pharmaceutically acceptable salt, stereoisomer, mixture of stereoisomers, solvate, or tautomer thereof, and at least one pharmaceutically acceptable carrier are contained are provided. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions.

It should be understood that the active ingredient may be packaged in any material capable of providing reasonable chemical and physical stability, such as an aluminum foil bag.

Unit dosage forms of the pharmaceutical composition comprising a compound of formula (I), or any formula described herein, or a pharmaceutically acceptable salt, stereoisomer, mixture of stereoisomers, solvate, or tautomer thereof, and at least one pharmaceutically acceptable carrier are also provided.

Any pharmaceutical composition provided in the present disclosure may be used in the articles of manufacture, the same as if each and every composition were specifically and individually listed for use an article of manufacture.

Also provided is a kit that includes a compound of formula (I), or any formula described herein, or a pharmaceutically acceptable salt, stereoisomer, mixture of stereoisomers, solvate, or tautomer thereof, a label, and/or instructions for use of the compound in the treatment of a disease or condition mediated by PD-1, PD-L1 activity or PD-1/PD-L1 interaction.

Also provided is an article of manufacture which includes a compound of formula (I), or any formula described herein, or a pharmaceutically acceptable salt, stereoisomer, mixture of stereoisomers, solvate, or tautomer thereof, and a container. In one embodiment, the container may be a vial, jar, ampoule, preloaded syringe, or an intravenous bag.

Formulations of compound(s) of the present disclosure i.e., a compound of formula (I), or any formula described herein, or a pharmaceutically acceptable salt, stereoisomer, mixture of stereoisomers, solvate, or tautomer thereof, or the combination of a compound of formula (I), or any formula described herein, or a pharmaceutically acceptable salt, stereoisomer, mixture of stereoisomers, solvate, or tautomer thereof, and an additional agent may be accomplished by admixing said compounds or salt thereof with one or more non-toxic, pharmaceutically acceptable vehicles, carriers and/or diluents and/or adjuvants collectively referred to herein as excipients or carrier materials. The compounds of the disclosure may be administered by any suitable route, such as in the form of a pharmaceutical composition adapted to such route, and in a therapeutically effective dose. The compounds or the combination of compounds for the disclosure may be delivered orally, mucosally, parenterally, including intravascularly, intravenously, intraperitoneally, subcutaneously, intramuscularly, and intranasally in dosage formulations containing conventional pharmaceutical excipients.

In one embodiment, the combination of a compound formula (I), or any formula described herein, or a pharmaceutically acceptable salt, stereoisomer, mixture of stereoisomers, solvate, or tautomer thereof, and an additional agent useful for the treatment of cancer may be formulated in a fixed dose or combined dose formulation in a tablet, capsule or premixed IV solution. In another embodiment, the fixed dose combination comprises a compound formula (I), or any formula described herein, and an additional anticancer agent. Other fixed dose formulations may include premixed liquids, suspensions, elixirs, aerosolized sprays or patch presentations. As used herein fixed dose or combined dose formulations are synonymous with simultaneous co-administration of the active ingredients of the compound of formula (I), or any formula described herein, or a pharmaceutically acceptable salt, stereoisomer, mixture of stereoisomers, solvate, or tautomer thereof, and at least one additional agent.

Combination Therapy

Also provided are methods of treatment in which a compound of formula (I), or any formula described herein, or a pharmaceutically acceptable salt, stereoisomer, mixture of stereoisomers, solvate, or tautomer thereof, is given to a patient in combination with one or more additional active agents or therapy. The compound described herein may be used or combined with one or more of the additional therapeutic agents. The one or more therapeutic agents include, but are not limited to, an inhibitor, agonist, antagonist, ligand, modulator, stimulator, blocker, activator or suppressor of a gene, ligand, receptor, protein, factor such as Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C-C motif) receptor (such as CCR2, CCR4, CCR5, CCR8), chemokine (C-X-C motif) receptor (such as CXCR4, CXCR1 and CXCR2), Chemokine CC21 ligand, Cholecystokinin CCK2 receptor, Chorionic gonadotropin, c-Kit (tyrosine-protein kinase Kit or CD117), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COP9 signalosome subunit 5, CSF-1 (colony-stimulating factor 1 receptor), CSF2 gene, CTLA-4 (cytotoxic T-lymphocyte protein 4) receptor, Cyclin D1, Cyclin G1, cyclin-dependent kinases (CDK, such as CDK1, CDK1B, CDK2-9), cyclooxygenase (such as 1, 2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, Fms-related tyrosine kinase 3 (Flt3), FMS-like tyrosine kinase-3 ligand (FLT3L), focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releasing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heme oxygenase 1 (HO1), Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOTL), histone deacetylase (HDAC, such as 1, 2, 3, 6, 10, 11), Histone H1, Histone H3, HLA class I antigen (A-2 alpha), HLA class II antigen, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIF1α), Imprinted Maternally Expressed Transcript (H19) gene, mitogen-activated protein kinase kinase kinase kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyl-transferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly ADP ribose polymerase (PARP, such as PARP1, 2 and 3), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAFI gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, Rosi tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Semaphorin-4D, Serine protease, serine/threonine kinase (STK), serine/threonine-protein kinase (TBK, such as TBKI), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Sp) transcription factor, Sphingomyelin synthase, Sphingosine kinase (such as 1, 2), Sphingosine-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, TGF beta 2 ligand, Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, Transferrin, Transforming growth factor (TGF, such as beta) kinase, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E21 (UBE2I, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Yes, Wee-1 protein kinase, Wilms' tumor antigen 1, Wilms' tumor protein, X-linked inhibitor of apoptosis protein, Zinc finger protein transcription factor or any combination thereof.

In one embodiment, a method of treating cancer and/or diseases or symptoms that co-present or are exacerbated or triggered by the cancer e.g., an allergic disorder and/or an autoimmune and/or inflammatory disease, and/or an acute inflammatory reaction, comprises administering to a patient in need thereof an effective amount of a compound of formula (I), or any formula described herein, or a pharmaceutically acceptable salt, stereoisomer, mixture of stereoisomers, solvate, or tautomer thereof, optionally in combination with an additional agent (e.g., a second, third, fourth or fifth active agent) which can be useful for treating a cancer, an allergic disorder and/or an autoimmune and/or inflammatory disease, and/or an acute inflammatory reaction incident to or co-presenting with a cancer. Treatment with the second, third, fourth or fifth active agent may be prior to, concomitant with, or following treatment with a compound of formula (I), or any formula described herein, or a pharmaceutically acceptable salt, stereoisomer, mixture of stereoisomers, solvate, or tautomer thereof. In one embodiment, a compound of formula (I), or any formula described herein, or a pharmaceutically acceptable salt, stereoisomer, mixture of stereoisomers, solvate, or tautomer thereof, is combined with another active agent in a single dosage form. Suitable antitumor or anticancer therapeutics that may be used in combination with a compound of formula (I), or any formula described herein, or a pharmaceutically acceptable salt, stereoisomer, mixture of stereoisomers, solvate, or tautomer thereof, include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

A compound of formula (I), or any formula described herein, or a pharmaceutically acceptable salt, stereoisomer, mixture of stereoisomers, solvate, or tautomer thereof, an be useful as chemo-sensitizing agents, and thus, can be useful in combination with other chemotherapeutic drugs, in particular, drugs that induce apoptosis. Thus, in one embodiment, the present disclosure provides a method for increasing sensitivity of cancer cells to chemotherapy, comprising administering to a patient in need of or undergoing chemotherapy, a chemotherapeutic agent together with a compound of formula (I), or a pharmaceutically acceptable salt, stereoisomer, mixture of stereoisomers, solvate, or tautomer thereof, in an amount sufficient to increase the sensitivity of cancer cells to the chemotherapeutic agent.

Anti-Cancer Combination Therapy

The compounds described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, a gene modifier or editor (such as CRISPR/Cas9, zinc finger nucleases or synthetic nucleases, TALENs), a CAR (chimeric antigen receptor) T-cell immunotherapeutic agent, an engineered T cell receptor (TCR-T), or any combination thereof. These therapeutic agents may be in the forms of compounds, antibodies, polypeptides, or polynucleotides. In one embodiment, the application provides a product comprising a compound described herein and an additional therapeutic agent as a combined preparation for simultaneous, separate, or sequential use in therapy.

As used herein, the term "chemotherapeutic agent" or "chemotherapeutic" (or "chemotherapy" in the case of treatment with a chemotherapeutic agent) is meant to encompass any non-proteinaceous (i.e., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL), abraxane, docetaxel (TAXOTERE), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR©); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFIRI (fluorouracil, leucovorin, and irinotecan); and pharmaceutically acceptable salts, acids, or derivatives of any of the above.

The compound described herein may be used or combined with one or more of the additional therapeutic agents. Therapeutic agents may be categorized by their mechanism of action into, for example, the following groups: antimetabolites/anti-cancer agents, such as pyrimidine analogs floxuridine, capecitabine, cytarabine, CPX-351 (liposomal cytarabine, daunorubicin), and TAS-118; purine analogs, folate antagonists (such as pralatrexate), and related inhibitors; antiproliferative/antimitotic agents including natural products, such as *vinca* alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide); DNA damaging agents, such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide; DNA-hypomethylating agents, such as guadecitabine (SGI-110), ASTX727; antibiotics such as dactinomycin, daunorubicin, doxorubicin, idarubicin, anthracyclines, mitoxantrone, bleomycins, plicamycin (mithramycin); enzymes such as L-asparaginase which systemically metabolizes L-asparagine and deprives cells which do not have the capacity to synthesize their own asparagine; antiplatelet agents; DNAi oligonucleotides targeting Bcl-2, such as PNT2258; agents that activate or reactivate latent human immunodeficiency virus (HIV), such as panobinostat and romidepsin; asparaginase stimulators, such as crisantaspase (Erwinase®) and GRASPA (ERY-001, ERY-ASP), calaspargase pegol; pan-Trk, ROS1 and ALK inhibitors, such as entrectinib, TPX-0005; anaplastic lymphoma kinase (ALK) inhibitors, such as alectinib, ceritinib; antiproliferative/antimitotic alkylating agents, such as nitrogen mustard cyclophosphamide and analogs (melphalan, chlorambucil, hexamethylmelamine, thiotepa), alkyl nitrosoureas (carmustine) and analogs, streptozocin, and triazenes (dacarbazine); antiproliferative/antimitotic antimetabolites, such as folic acid analogs (methotrexate); platinum coordination complexes (cisplatin, oxiloplatinim, and carboplatin), procarbazine, hydroxyurea, mitotane, and aminoglutethimide; hormones, hormone analogs (estrogen, tamoxifen, goserelin, bicalutamide, and nilutamide), and aromatase inhibitors (letrozole and anastrozole); anticoagulants such as heparin, synthetic heparin salts, and other inhibitors of thrombin; fibrinolytic agents such as tissue plasminogen activator, streptokinase, urokinase, aspirin, dipyridamole, ticlopidine, and clopidogrel; antimigratory agents; antisecretory agents (breveldin); immunosuppressives, such as tacrolimus, sirolimus, azathioprine, and mycophenolate; growth factor inhibitors, and vascular endothelial growth factor inhibitors; fibroblast growth factor inhibitors, such as FPA14; anti-VEGFR antibodies, such as IMC-3C5, GNR-011, tanibirumab; anti-VEGF/DDL4 antibodies, such as ABT-165; anti-cadherins antibodies, such as HKT-288; anti-CD70 antibodies, such as AMG-172; anti-leucine-rich repeat containing 15 (LRRC15) antibodies, such as ABBV-085, and ARGX-110; angiotensin receptor blockers; nitric oxide donors; antisense oligonucleotides, such as AEG35156, IONIS-KRAS-2.5Rx, EZN-3042, RX-0201, IONIS-AR-2.5Rx, BP-100 (prexigebersen), IONIS-STAT3-2.5Rx; DNA interference oligonucleotides, such as PNT2258, AZD-9150; anti-ANG-2 antibodies, such as MEDI3617, and LY3127804; anti-ANG-1/ANG-2 antibodies, such as AMG-780; anti-MET/EGFR antibodies, such as LY3164530; anti-EGFR antibodies, such as ABT-414, AMG-595, necitumumab, ABBV-221, depatuxizumab mafodotin (ABT-414), tomuzotuximab, ABT-806, vectibix, modotuximab, RM-1929; anti-CSF1R antibodies, such as emactuzumab, LY3022855, AMG-820, FPA-008 (cabiralizumab); anti-CD40 antibodies, such as RG7876, SEA-CD40, APX-005M, ABBV-428; anti-endoglin antibodies, such as TRC105 (carotuximab); anti-CD45 antibodies, such as 131I-BC8 (lomab-B); anti-HER3 antibodies, such as LJM716, GSK2849330; anti-HER2 antibodies, such as margetuximab, MEDI4276, BAT-8001; anti-HLA-DR antibodies, such as IMMU-114; anti-IL-3 antibodies, such as JNJ-56022473; anti-OX40 antibodies, such as MEDI6469, MEDI6383, MEDI0562 (tavolixizumab), MOXR0916, PF-04518600, RG-7888, GSK-3174998, INCAGN1949, BMS-986178, GBR-8383, ABBV-368; anti-EphA3 antibodies, such as KB-004; anti-CD20 antibodies, such as obinutuzumab, IGN-002; anti-CD20/CD3 antibodies, such as RG7828; anti-CD37 antibodies, such as AGS67E, otlertuzumab (TRU-016); anti-ENPP3 antibodies, such as AGS-16C3F; anti-FGFR-3 antibodies, such as LY3076226, B-701; anti-FGFR-2 antibodies, such as GAL-F2; anti-C5 antibodies, such as ALXN-1210; anti-CD27 antibodies, such as varlilumab (CDX-1127); anti-TROP-2 antibodies, such as IMMU-132; anti-NKG2a antibodies, such as monalizumab; anti-VISTA antibodies, such as HMBD-002; anti-PVRIG antibodies, such as COM-701; anti-EpCAM antibodies, such as VB4-845; anti-BCMA antibodies, such as GSK-2857916; anti-CEA antibodies, such as RG-7813; anti-cluster of differentiation 3 (CD3) antibodies, such as MGD015; anti-folate receptor alpha antibodies, such as IMGN853; MCL-1 inhibitors, such as AMG-176, AMG-397, S-64315, and AZD-5991, 483-LM, A-1210477, UMI-77, JKY-5-037; epha2 inhibitors, such as MM-310; anti LAG-3 antibodies, such as relatlimab (ONO-4482), LAG-525, MK-4280, REGN-3767; raf kinase/VEGFR inhibitors, such as RAF-265; polycomb protein (EED) inhibitors, such as MAK683; anti-fibroblast activation protein (FAP)/IL-2R antibodies, such as RG7461; anti-fibroblast activation protein (FAP)/TRAIL-R$^2$ antibodies, such as RG7386; anti-fucosyl-GM1 antibodies, such as BMS-986012; p38 MAP kinase inhibitors, such as ralimetinib; PRMT1 inhibitors, such as MS203; Sphingosine kinase 2 (SK2) inhibitors, such as opaganib; FLT3-ITD inhibitors, such as BCI-332; Nuclear erythroid 2-related factor 2 stimulators, such as omaveloxolone (RTA-408); Tropomyosin receptor kinase (TRK) inhibitors, such as LOXO-195, ONO-7579; anti-ICOS antibodies, such as JTX-2011, GSK3359609; anti-DR5 (TRAIL2) antibodies, such as DS-8273; anti-GD2 antibodies, such as APN-301; anti-interleukin-17 (IL-17) antibodies, such as CJM-112; anti-carbonic anhydrase IX antibodies, such as TX-250; anti-CD38-attenukine, such as TAK573; anti-Mucin 1 antibodies, such as gatipotuzumab; Mucin 1 inhibitors, such as GO-203-2C; MARCKS protein inhibitors, such as BIO-11006; Folate antagonists, such as arfolitixorin; Galectin-3 inhibitors, such as GR-MD-02; Phosphorylated P68 inhibitors, such as RX-5902; CD95/TNF modulators, such as ofranergene obadenovec; PI3K/Akt/mTOR inhibitors, such as ABTL-0812; pan-PIM kinase inhibitors, such as INCB-053914; IL-12 gene stimulators, such as EGEN-001, tavokinogene telseplasmid; Heat shock protein HSP90 inhibitors, such as TAS-116, PEN-866; VEGF/HGF antagonists, such as MP-0250; SYK tyrosine kinase/FLT3 tyrosine kinase inhibitors, such as TAK-659; SYK tyrosine kinase/JAK tyrosine kinase inhibitors, such as ASN-002; FLT3 tyrosine kinase, such as FF-10101; FMS-like tyrosine kinase-3 ligand (FLT3L), such as CDX-301; FLT3/MEK1 inhibitors, such as E-6201; IL-24 antagonist, such as AD-IL24; RIG-I agonists, such as RGT-100; Aerolysin stimulators, such as topsalysin; P-Glycoprotein 1 inhibitors, such as HM-30181A; CSF-1 antagonists, such as ARRY-382, BLZ-945; CCR8 inhibitors, such as I-309, SB-649701, HG-1013, RAP-310; anti-Mesothelin antibodies, such as SEL-403; Thymidine kinase stimulators, such as aglatimagene besadenovec; Polo-like kinase 1 inhibitors, such as PCM-075; TLR-7 agonists, such as TMX-101 (imiquimod); NEDD8 inhibitors, such as pevonedistat (MLN-4924), TAS-4464; Pleiotropic pathway modulators, such as avadomide (CC-122); FoxM1 inhibitors, such as thiostrepton; Anti-MUC1 antibodies, such as Mab-AR-20.5; anti-CD38 antibodies, such as isatuximab, MOR-202; UBA1 inhibitors, such as TAK-243; Src tyrosine kinase inhibitors, such as VAL-201; VDAC/HK inhibitors, such as VDA-1102; BRAF/PI3K inhibitors, such as ASN-003; Elf4a inhibitors, such as rohinitib, eFT226; TP53 gene stimulators, such as ad-p53; PD-L1/EGFR inhibitors, such as GNS-1480; Retinoic acid receptor alpha (RARα) inhibitors, such as SY-1425; SIRT3 inhibitors, such as YC8-02; Stromal cell-derived factor 1 ligand inhibitors, such as olaptesed pegol (NOX-A12); IL-4 receptor modulators, such as MDNA-55; Arginase-I stimulators, such as pegzilarginase; Topoisomerase I inhibitor/hypoxia inducible factor-1 alpha inhibitors, such as PEG-SN38 (firtecan pegol); Hypoxia inducible factor-1 alpha inhibitors, such as PT-2977, PT-2385; CD122 agonists such as NKTR-214; p53 tumor suppressor protein stimulators such as kevetrin; Mdm4/Mdm2 p53-binding protein inhibitors, such as ALRN-6924; kinesin spindle protein (KSP) inhibitors, such as filanesib (ARRY-520); CD80-fc fusion protein inhibitors, such as FPT-155; Menin and mixed lineage leukemia (MLL) inhibitors such as KO-539; Liver x receptor agonists, such as RGX-104; IL-10 agonists, such as AM-0010; EGFR/ErbB-2 inhibitors, such as varlitinib; VEGFR/PDGFR inhibitors, such as vorolanib; IRAK4 inhibitors, such as CA-4948; anti-TLR-2 antibodies, such as OPN-305; Calmodulin modulators, such as CBP-501; Glucocorticoid receptor antagonists, such as relacorilant (CORT-125134); Second mitochondria-derived activator of caspases (SMAC) protein inhibitors, such as BI-891065; Lactoferrin modulators, such as LTX-315; Kit tyrosine kinase/PDGF receptor alpha antagonists such as DCC-2618; KIT inhibitors, such as PLX-9486; Exportin 1 inhibitors, such as eltanexor; EGFR/ErbB2/Ephb4 inhibitors, such as tesevatinib; anti-CD33 antibodies, such as IMGN-779; anti-KMA antibodies, such as MDX-1097; anti-TIM-3 antibodies, such as TSR-022, LY-3321367, MBG-453; anti-CD55 antibodies, such as PAT-SC1; anti-PSMA antibodies, such as ATL-101; anti-CD100 antibodies, such as VX-15; anti-EPHA3 antibodies, such as fibatuzumab; anti-Erbb antibodies, such as CDX-3379, HLX-02, seribantumab; anti-APRIL antibodies, such as BION-1301; Anti-Tigit antidbodies, such as BMS-986207, RG-6058; CHST15 gene inhibitors, such as STNM-01; RAS inhibitors, such as NEO-100; Somatostatin receptor antagonist, such as OPS-201; CEBPA gene stimulators, such as MTL-501; DKK3 gene modulators, such as MTG-201; p70s6k inhibitors, such as MSC2363318A; methionine aminopeptidase 2 (MetAP2) inhibitors, such as M8891, APL-1202; arginine N-methyltransferase 5 inhibitors, such as GSK-3326595; anti-programmed cell death protein 1 (anti-PD-1) antibodies, such as nivolumab (OPDIVO®, BMS-936558, MDX-1106), pembrolizumab (KEYTRUDA, MK-3477, SCH-900475, lambrolizumab, CAS Reg. No. 1374853-91-4), pidilizumab, PF-06801591, BGB-A317, GLS-010 (WBP-3055), AK-103 (HX-008), MGA-012, BI-754091, REGN-2810 (cemiplimab), AGEN-2034, JS-001, JNJ-63723283, genolimzumab (CBT-501), LZM-009, BCD-100, LY-3300054, SHR-1201, BAT-1306, and anti-programmed death-ligand 1 (anti-PD-L1) antibodies such as BMS-936559, atezolizumab (MPDL3280A), durvalumab (MEDI4736), avelumab, CK-301, (MSB0010718C), MEDI0680, CX-072, CBT-502, PDR-001 (spartalizumab), TSR-042 (dostarlimab), JTX-4014, BGB-A333, SHR-1316, CS-1001 (WBP-3155, KN-035, IBI-308, FAZ-053, and MDX1105-01; PD-L1/VISTA antagonists such as CA-170; anti-PD-L/TGFβ antibodies, such as M7824; anti-transferrin antibodies, such as CX-2029; anti-IL-8 (Interleukin-8) antibodies, such as HuMax-Inflam; ATM (ataxia telangiectasia) inhibitors, such as AZD0156; CHK1 inhibitors, such as GDC-0575, LY2606368 (prexasertib), SRA737, RG7741 (CHK1/2); CXCR4 antagonists, such as BL-8040, LY2510924, burixafor (TG-0054), X4P-002, X4P-001-IO; EXH2 inhibitors, such as GSK2816126; HER2 inhibitors, such as neratinib, tucatinib (ONT-380); KDM1 inhibitors, such as ORY-1001, IMG-7289, INCB-59872, GSK-2879552; CXCR2 antagonists, such as AZD-5069; GM-CSF antibodies, such as lenzilumab; DNA dependent protein kinase inhibitors, such as MSC2490484A (nedisertib), VX-984, AsiDNA (DT-01); protein kinase C (PKC) inhibitors, such as LXS-196, and sotrastaurin; Selective estrogen receptor downregulators (SERD), such as fulvestrant (Faslodex®), RG6046, RG6047, elacestrant (RAD-1901) and AZD9496; Selective estrogen receptor covalent antagonists (SERCAs), such as H3B-6545; selective androgen receptor modulator (SARM), such as GTX-024, and darolutamide; transforming growth factor-beta (TGF-beta) kinase antagonists, such as galunisertib; anti-transforming growth factor-beta (TGF-beta) antibodies, such as LY3022859, NIS793, and XOMA 089; bispecific antibodies, such as MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), and MGD-009 (CD3/B7H3); mutant selective EGFR inhibitors, such as PF-06747775, EGF816 (nazartinib), ASP8273, ACEA-0010, and BI-1482694; anti-GITR (glucocorticoid-induced tumor necrosis factor receptor-related protein) antibodies, such as MEDI1873, FPA-154, INCAGN-1876, TRX-518, BMS-986156, MK-1248, and GWN-323; anti-delta-like protein ligand 3 (DDL3) antibodies, such as rovalpituzumab tesirine; anti-clusterin antibodies, such as AB-16B5; anti-Ephrin-A4 (EFNA4) antibodies, such as PF-06647263; anti-RANKL antibodies, such as denosumab; anti-mesothelin antibodies, such as BMS-986148, and anti-MSLN-MMAE; anti-sodium phosphate cotransporter 2B (NaP2B) antibodies, such as lifastuzumab; anti-c-Met antibodies, such as ABBV-399; adenosine A2A receptor antagonists, such as CPI-444, AZD-4635, preladenant, and PBF-509; alpha-ketoglutarate dehydrogenase (KGDH) inhibitors, such as CPI-613; XPO1 inhibitors, such as selinexor (KPT-330); isocitrate dehydrogenase 2 (IDH2) inhibitors, such as enasidenib (AG-221); IDH1 inhibitors such as AG-120, and AG-881 (IDH1 and IDH2), IDH-305, and BAY-1436032; interleukin-3 receptor (IL-3R) modulators, such as SL-401; Arginine deiminase stimulators, such as pegargiminase (ADI-PEG-20); antibody-drug conjugates, such as MLN0264 (anti-GCC, guanylyl cyclase C), T-DM1 (trastuzumab emtansine, Kadcycla), milatuzumab-doxorubicin (hCD74-DOX), brentuximab vedotin, DCDT2980S, polatuzumab vedotin, SGN-CD70A, SGN-CD19A, inotuzumab ozogamicin, lorvotuzumab mertansine, SAR3419, isactuzumab govitecan, enfortumab vedotin (ASG-22ME), ASG-15ME, DS-8201 ((trastuzumab deruxtecan), 225Ac-lintuzumab, U3-1402, 177Lu-tetraxetan-tetuloma, tisotumab vedotin, anetumab ravtansine, CX-2009, SAR-566658, W-0101, polatuzumab vedotin, and ABBV-085; claudin-18 inhibitors, such as claudiximab; β-catenin inhibitors, such as CWP-291; anti-CD73 antibodies, such as MEDI-9447 (oleclumab), CPX-006, IPH-53, BMS-986179, and NZV-930; CD73 antagonists, such as AB-680, PSB-12379, PSB-12441, PSB-12425, and CB-708; CD39/CD73 antagonists, such as PBF-1662; chemokine receptor 2 (CCR) inhibitors, such as PF-04136309, CCX-872, and BMS-813160 (CCR2/CCR5); thymidylate synthase inhibitors, such as ONX-0801; ALK/ROS1 inhibitors, such as lorlatinib; tankyrase inhibitors, such as G007-LK; Mdm2 p53-binding protein inhibitors, such as CMG-097, and HDM-201; c-PIM inhibitors, such as PIM447; BRAF inhibitors, such as dabrafenib, vemurafenib, encorafenib (LGX818), and PLX8394; sphingosine kinase-2 (SK2) inhibitors, such as Yeliva® (ABC294640); cell cycle inhibitors, such as selumetinib (MEK/2), and sapacitabine; AKT inhibitors such as MK-2206, ipatasertib, afuresertib, AZD5363, and ARQ-092, capivasertib, and triciribine; anti-CTLA-4 (cytotoxic T-lymphocyte protein-4) inhibitors, such as tremelimumab, AGEN-1884, and BMS-986218; c-MET inhibitors, such as AMG-337, savolitinib, tivantinib (ARQ-197), capmatinib, and tepotinib, ABT-700, AG213, AMG-208, JNJ-38877618 (OMO-1), merestinib, and HQP-8361; c-Met/VEGFR inhibitors, such as BMS-817378, and TAS-115; c-Met/RON inhibitors, such as BMS-777607; BRAF/EGFR inhibitors, such as BGB-283; bcr/abl inhibitors, such as rebastinib, asciminib; MNK1/MNK2 inhibitors, such as eFT-508; mTOR inhibitor/cytochrome P450 3A4 stimulators, such as TYME-88; lysine-specific demethylase-1 (LSD1) inhibitors, such as CC-90011; Pan-RAF inhibitors, such as LY3009120, LXH254, and TAK-580; Raf/MEK inhibitors, such as RG7304; CSF1R/KIT and FLT3 inhibitors, such as pexidartinib (PLX3397); kinase inhibitors, such as vandetanib; E selectin antagonists, such as GMI-1271; differentiation inducers, such as tretinoin; epidermal growth factor receptor (EGFR) inhibitors, such as osimertinib (AZD-9291); topoisomerase inhibitors, such as doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), and irofulven (MGI-114); corticosteroids, such as cortisone, dexamethasone, hydrocortisone, methylprednisolone, prednisone, and prednisolone; growth factor signal transduction kinase inhibitors; nucleoside analogs, such as DFP-10917; Axl inhibitors, such as BGB-324 (bemcentinib), and SLC-0211; BET inhibitors, such as INCB-054329, INCB057643, TEN-010, AZD-5153, ABT-767, BMS-986158, CC-90010, GSK525762 (molibresib), NHWD-870, ODM-207, GSK-2820151, GSK-1210151A, ZBC246, ZBC260, ZEN3694, FT-1101, RG-6146, CC-90010, mivebresib, BI-894999, PLX-2853, PLX-51107, CPI-0610, and GS-5829; PARP inhibitors, such as olaparib, rucaparib, veliparib, talazoparib, ABT-767, and BGB-290; proteasome inhibitors, such as ixazomib, carfilzomib (Kyprolis®), marizomib; glutaminase inhibitors, such as CB-839; vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131; bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, stapuldencel-T, eltrapuldencel-T, SL-701, BSK01™, rocapuldencel-T (AGS-003), DCVAC, CVac™, stapuldencel-T, eltrapuldencel-T, SL-701, BSK01™, ADXS31-142; oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; and GI-4000; anti-DLL4 (delta like ligand 4) antibodies, such as demcizumab; STAT-3 inhibitors, such as napabucasin (BBI-608); ATPase p97 inhibitors, such as CB-5083; smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole; interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-Ib, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon); interferon gamma ligand modulators, such as interferon gamma (OH-6000, Ogamma 100); IL-6 receptor modulators, such as tocilizumab, siltuximab, and AS-101 (CB-06-02, IVX-Q-101); Telomerase modulators, such as, tertomotide (GV-1001, HR-2802, Riavax) and imetelstat (GRN-163, JNJ-63935937); DNA methyltransferases inhibitors, such as temozolomide (CCRG-81045), decitabine, guadecitabine (5-110, SGI-110), KRX-0402, RX-3117, RRx-001, and azacitidine; DNA gyrase inhibitors, such as pixantrone and sobuzoxane; Bcl-2 family protein inhibitors, such as ABT-263, venetoclax (ABT-199), ABT-737, and AT-101; Notch inhibitors, such as LY3039478 (crenigacestat), tarextumab (anti-Notch2/3), and BMS-906024; anti-myostatin inhibitors, such as landogrozumab; hyaluronidase stimulators, such as PEGPH-20; Wnt pathway inhibitors, such as SM-04755, PRI-724, and WNT-974; gamma-secretase inhibitors, such as PF-03084014, MK-0752, and RO-4929097; Grb-2 (growth factor receptor bound protein-2) inhibitors, such as BP1001; TRAIL pathway-inducing compounds, such as ONC201, and ABBV-621; Focal adhesion kinase inhibitors, such as VS-4718, defactinib, and GSK2256098; hedgehog inhibitors, such as saridegib, sonidegib (LDE225), glasdegib and vismodegib; Aurora kinase inhibitors, such as alisertib (MLN-8237), and AZD-2811, AMG-900, barasertib, and ENMD-2076;

HSPB1 modulators (heat shock protein 27, HSP27), such as brivudine, and apatorsen; ATR inhibitors, such as BAY-937, AZD6738, AZD6783, VX-803, VX-970 (berzosertib) and VX-970; mTOR inhibitors, such as sapanisertib and vistusertib (AZD2014), and ME-344; mTOR/PI3K inhibitors, such as gedatolisib, GSK2141795, omipalisib, and RG6114; Hsp90 inhibitors, such as AUY922, onalespib (AT13387), SNX-2112, SNX5422; murine double minute (mdm2) oncogene inhibitors, such as DS-3032b, RG7775, AMG-232, HDM201, and idasanutlin (RG7388); CD137 agonists, such as urelumab, utomilumab (PF-05082566); STING agonists, such as ADU-S100 (MIW-815), SB-11285, MK-1454, SR-8291, AdVCA0848, GSK-532, SYN-STING, MSA-1, SR-8291; FGFR inhibitors, such as FGF-401, INCB-054828, BAY-1163877, AZD4547, JNJ-42756493, LY2874455, and Debio-1347; fatty acid synthase (FASN) inhibitors, such as TVB-2640; anti-KIR monoclonal antibodies, such as lirilumab (IPH-2102), and IPH-4102; antigen CD19 inhibitors, such as MOR208, MEDI-551, AFM-11, and inebilizumab; CD44 binders, such as A6; protein phosphatase 2A (PP2A) inhibitors, such as LB-100; CYP17 inhibitors, such as seviteronel (VT-464), ASN-001, ODM-204, CFG920, and abiraterone acetate; RXR agonists, such as IRX4204; hedgehog/smoothened (hh/Smo) antagonists, such as taladegib, and patidegib; complement C3 modulators, such as Imprime PGG; IL-15 agonists, such as ALT-803, NKTR-255, and hetIL-15; EZH2 (enhancer of zeste homolog 2) inhibitors, such as tazemetostat, CPI-1205, GSK-2816126; oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, and OBP-301; DOT1L (histone methyltransferase) inhibitors, such as pinometostat (EPZ-5676); toxins such as Cholera toxin, ricin, *Pseudomonas* exotoxin, *Bordetella pertussis* adenylate cyclase toxin, diphtheria toxin, and caspase activators; DNA plasmids, such as BC-819; PLK inhibitors of PLK 1, 2, and 3, such as volasertib (PLK1); WEE1 inhibitors, such as AZD1775 (adavosertib); Rho kinase (ROCK) inhibitors, such as AT13148, and KD025; ERK inhibitors, such as GDC-0994, LY3214996, and MK-8353; IAP inhibitors, such as ASTX660, debio-1143, birinapant, APG-1387, and LCL-161; RNA polymerase inhibitors, such has lurbinectedin (PM-1183), and CX-5461; tubulin inhibitors, such as PM-184, BAL-101553 (lisavanbulin), OXI-4503, fluorapacin (AC-0001), and plinabulin; Toll-like receptor 4 (TL4) agonists, such as G100, GSK1795091, and PEPA-10; elongation factor 1 alpha 2 inhibitors, such as plitidepsin; CD95 inhibitors, such as APG-101, APO-010, and asunercept; WT1 inhibitors, such as DSP-7888; splicing factor 3B subunit1 (SF3B1) inhibitors, such as H3B-8800; PDGFR alpha/KIT mutant-specific inhibitors such as BLU-285; SHP-2 inhibitors, such as TNO155 (SHP-099), RMC-4550, JAB-3068, and RMC-4630; or retinoid Z receptor gamma (RORγ) agonists, such as LYC-55716.

Examples of other chemotherapeutic drugs that can be used in combination with compounds of formula (I), or any or a pharmaceutically acceptable salt, stereoisomer, mixture of stereoisomers, solvate, or tautomer thereof, include topoisomerase I inhibitors (camptothesin or topotecan), topoisomerase II inhibitors (e.g., daunomycin and etoposide), alkylating agents (e.g., cyclophosphamide, melphalan and BCNU), tubulin directed agents (e.g., taxol and vinblastine), and biological agents (e.g., antibodies such as anti CD20 antibody, IDEC 8, immunotoxins, and cytokines).

In some embodiments, the compound(s) of formula (I), or any formula described herein, or a pharmaceutically acceptable salt, stereoisomer, mixture of stereoisomers, solvate, or tautomer thereof, is used in combination with Rituxan® (Rituximab) and/or other agents that work by selectively depleting CD20+ B-cells.

Included herein are methods of treatment in which a compound of formula (I), or any formula described herein, or a pharmaceutically acceptable salt, stereoisomer, mixture of stereoisomers, solvate, or tautomer thereof, is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In one embodiment, the compound(s) of formula (I), or any formula described herein, or a pharmaceutically acceptable salt, stereoisomer, mixture of stereoisomers, solvate, or tautomer thereof, is used in combination with at least one anti-inflammatory compound that is an anti-C5 monoclonal antibody (such as eculizumab or pexelizumab), a TNF antagonist, such as entanercept, or infliximab, which is an anti-TNF alpha monoclonal antibody.

In one embodiment, the compound(s) of formula (I), or any formula described herein, or a pharmaceutically acceptable salt, stereoisomer, mixture of stereoisomers, solvate, or tautomer thereof, is used in combination with at least one active agent that is an immunosuppressant compound such as methotrexate, leflunomide, cyclosporine, tacrolimus, azathioprine, or mycophenolate mofetil.

In other embodiments, the compound(s) of formula (I), or any formula described herein, or a pharmaceutically acceptable salt, stereoisomer, mixture of stereoisomers, solvate, or tautomer thereof, is used in combination with one or more phosphatidylinositol 3-kinase (PI3K) inhibitors, including for example, Compounds A, B and C (whose structures are provided below), or a pharmaceutically acceptable salt thereof.

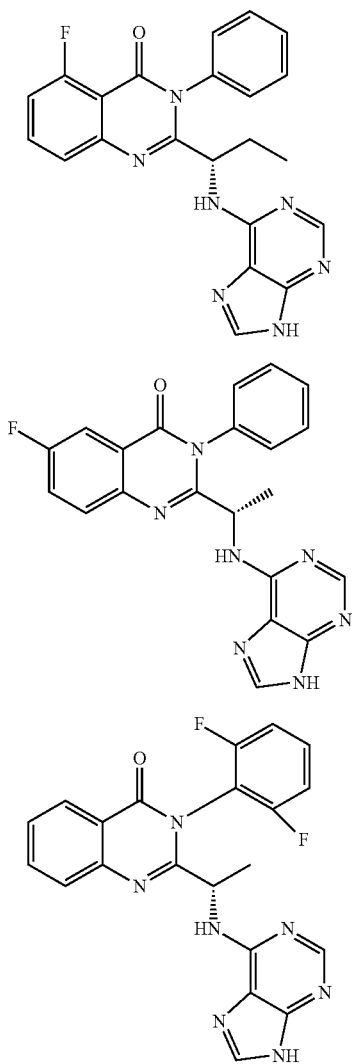

Compound A

Compound B

Compound C

Compounds A, B and C are disclosed in WO2015/017460 and WO2015/100217. PI3K inhibitors include inhibitors of PI3Kγ, PI3Kδ, PI3Kβ, PI3Kα, and/or pan-PI3K. Additional examples of PI3K inhibitors include, but are not limited to, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0941, GDC-0980, GSK2636771, GSK2269557, idelalisib (Zydelig®), IPI-145, IPI-443, IPI-549, KAR4141, LY294002, LY3023414, MLN1117, OXY111A, PA799, PX-866, RG7604, rigosertib, RP5090, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences). Further examples of PI3K inhibitors include, but are not limited to, GDC-0032, GDC-0077, INCB50465, RP6530, and SRX3177.

In yet another embodiment, the compound(s) of formula (I) may be used in combination with Spleen Tyrosine Kinase (SYK) Inhibitors. Examples of SYK inhibitors include, but are not limited to, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Connecticut) and those described in U.S. 2015/0175616.

In yet another embodiment, the compounds of formula (I) may be used in combination with Tyrosine-kinase Inhibitors (TKIs). TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087, asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, midostaurin, nintedanib, ODM-203, osimertinib (AZD-9291), ponatinib, poziotinib, quizartinib, radotinib, rociletinib, sulfatinib (HMPL-012), sunitinib, and TH-4000. In ceerrtain embodiments, TKIs include, but are not limited to, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, tivoanib, TH-4000, and MEDI-575 (anti-PDGFR antibody).

In yet other embodiments, the compound(s) of formula (I), or any formula described herein, or a pharmaceutically acceptable salt, stereoisomer, mixture of stereoisomers, solvate, or tautomer thereof, is used in combination with one or more inhibitors of lysyl oxidase-like 2 (LOXL) or a substance that binds to LOXL, including for example, a humanized monoclonal antibody (mAb) with an immunoglobulin IgG4 isotype directed against human LOXL2. LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics).

In yet another embodiment, the compounds of formula (I) may be used in combination with Toll-like receptor 8 (TLR8) inhibitors. Examples of TLR8 inhibitors include, but are not limited to, E-6887, IMO-4200, IMO-8400, IMO-9200, MCT-465, MEDI-9197, motolimod, resiquimod, VTX-1463, and VTX-763.

In yet another embodiment, the compounds of formula (I) may be used in combination with Toll-like receptor (TLR9) inhibitors. Examples of TLR9 inhibitors include, but are not limited to, AST-008, IMO-2055, IMO-2125, lefitolimod, litenimod, MGN-1601, and PUL-042.

In one embodiment, the compound of formula (I), or any formula described herein, or a pharmaceutically acceptable salt, stereoisomer, mixture of stereoisomers, solvate, or tautomer thereof, is useful for the treatment of cancer in combination with a BTK (Bruting's Tyrosine kinase) inhibitor. An example of such BTK inhibitor is a compound disclosed in U.S. Pat. No. 7,405,295. Additional examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, HM71224, ibrutinib, M-2951 (evobrutinib), tirabrutinib (ONO-4059), PRN-1008, spebrutinib (CC-292), and TAK-020. Further examples of BTK inhibitors include, but are not limited to, CB988, M7583, vecabrutinib, ARQ-531, SHR-1459, DTRMWXHS-12, and TAS-5315.

In one embodiment, the compound of formula (I), or any formula described herein, or a pharmaceutically acceptable salt, stereoisomer, mixture of stereoisomers, solvate, or tautomer thereof, is useful for the treatment of cancer in combination with a BET inhibitor. An example of such BET inhibitor is a compound disclosed in WO2014/182929, the entire contents of which are incorporated herein by reference.

In one embodiment, the compound of formula (I), or any formula described herein, or a pharmaceutically acceptable salt, stereoisomer, mixture of stereoisomers, solvate, or tautomer thereof, is useful for the treatment of cancer in combination with a TBK (Tank Binding kinase) inhibitor. An example of such TBK inhibitor is a compound disclosed in WO2016/049211.

In one embodiment, the compound of formula (I) is useful for the treatment of cancer in combination with a MMP inhibitor. Exemplary MMP inhibitors include inhibitors of MMP1 through 10. Additional examples of MMP9 inhibitors include, but are not limited to, marimastat (BB-2516), cipemastat (Ro 32-3555), GS-5745 (andecaliximab) and those described in WO 2012/027721 (Gilead Biologics).

In one embodiment, the compound of formula (I), or any formula described herein, or a pharmaceutically acceptable salt, stereoisomer, mixture of stereoisomers, solvate, or tautomer thereof, is useful for the treatment of cancer in combination with a OX40 inhibitor. An example of such OX40 inhibitor is a compound disclosed in U.S. Pat. No. 8,450,460, the entire contents of which are incorporated herein by reference.

In one embodiment, the compound of formula (I), or any formula described herein, or a pharmaceutically acceptable salt, stereoisomer, mixture of stereoisomers, solvate, or tautomer thereof, is useful for the treatment of cancer in combination with a JAK-1 inhibitor. An example of such JAK-1 inhibitor is a compound disclosed in WO2008/109943. Examples of other JAK inhibitors include, but are not limited to, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019.

In one embodiment, the compound of formula (I), or any formula described herein, or a pharmaceutically acceptable salt, stereoisomer, mixture of stereoisomers, solvate, or tautomer thereof, is useful for the treatment of cancer in combination with an Indoleamine-pyrrole-2,3-dioxygenase (IDO) inhibitors. An example of such IDO inhibitor is a compound disclosed in WO2016/186967. In one embodiment, the compounds of formula (I) are useful for the treatment of cancer in combination with IDO1 inhibitors including but not limited to BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST. Other examples of IDO1 inhibitors include, but are not limited to, BMS-986205, EOS-200271, KHK-2455, LY-3381916.

In one embodiment, the compound of formula (I), or any formula described herein, or a pharmaceutically acceptable salt, stereoisomer, mixture of stereoisomers, solvate, or tautomer thereof, is useful for the treatment of cancer in combination with a Mitogen-activated Protein Kinase (MEK) Inhibitors. MEK inhibitors useful for combination treatment with a compound(s) of formula (I) includes antroquinonol, binimetinib, cobimetinib (GDC-0973, XL-518), MT-144, selumetinib (AZD6244), sorafenib, trametinib (GSK1120212), uprosertib and trametinib. Other exemplary MEK inhibitors include PD-0325901, pimasertib, LTT462, AS703988, CC-90003, and refametinib.

In one embodiment, the compound of formula (I), or any formula described herein, or a pharmaceutically acceptable salt, stereoisomer, mixture of stereoisomers, solvate, or tautomer thereof, is useful for the treatment of cancer in combination with an Apoptosis Signal-Regulating Kinase (ASK) Inhibitors: ASK inhibitors include but are not limited to those described in WO 2011/008709 (Gilead Sciences) and WO 2013/112741 (Gilead Sciences) including, for example, selonsertib.

In one embodiment, the compounds of formula (I) may be combined with Cluster of Differentiation 47 (CD47) inhibitors. Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621.

In one embodiment, the compounds of formula (I) may be combined with Cyclin-dependent Kinase (CDK) Inhibitors. CDK inhibitors include inhibitors of CDK 1, 2, 3, 4, 6 and 9, such as abemaciclib, alvocidib (HMR-1275, flavopiridol), AT-7519, FLX-925, LEE001, palbociclib, ribociclib, rigosertib, selinexor, UCN-01, and TG-02. Other exemplary CDK inhibitors include dinaciclib, ibrance, SY1365, CT-7001, SY-1365, G1T38, milciclib, and trilaciclib.

In one embodiment, the compounds of formula (I) may be combined with Discoidin Domain Receptor (DDR) Inhibitors for the treatment of cancer. DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations).

In one embodiment, the compounds of formula (I) may be combined with Histone Deacetylase (HDAC) Inhibitors such as those disclosed in U.S. Pat. No. 8,575,353 and equivalents thereof. Additional examples of HDAC inhibitors include, but are not limited to, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat. Further examples of HDAC inhibitors include, but are not limited to, tinostamustine, remetinostat, entinostat.

In one embodiment, the compounds of formula (I) may be combined with a Hematopoietic Progenitor Kinase 1 (HPK1) inhibitor. Examples of Hematopoietic Progenitor Kinase 1 (HPK1) inhibitors include, but are not limited to, those described in WO18183956, WO18183964, WO18167147, and WO16090300.

Anti-hormonal Agents: Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, and ODM-204.

Examples of progesterone receptor antagonist include onapristone.

Anti-angiogenic Agents: Anti-angiogenic agents include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cishydroxyproline, d,l-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, such as monoclonal antibodies against these angiogenic growth factors: beta-FGF, alpha-FGF, FGF-5, VEGF isoforms, VEGF-C, HGF/SF, and Ang-1/Ang-2.

Anti-fibrotic Agents: Anti-fibrotic agents include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Immunotherapeutic Agents: The immunotherapeutic agents include and are not limited to therapeutic antibodies suitable for treating patients. Some examples of therapeutic antibodies include abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY™, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

Cancer Gene Therapy and Cell Therapy: Cancer Gene Therapy and *Cell* Therapy including the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Gene Editors: The genome editing system is selected from the group consisting of: a CRISPR/Cas9 system, a zinc finger nuclease system, a TALEN system, a homing endonucleases system, and a meganuclease system.

CAR-T cell therapy and TCR-T cell therapy: A population of immune effector cells engineered to express a chimeric antigen receptor (CAR), wherein the CAR comprises a tumor antigen-binding domain. The immune effector cell is a T cell or an NK cell. TCR-T cells are engineered to target tumor derived peptides present on the surface of tumor cells. Cells can be autologous or allogeneic.

In some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon R1b), CD79a, CD79b, Fcgamma RIIa, DAP10, and DAP12.

In some embodiments, the costimulatory domain comprises a functional domain of one or more proteins selected from the group consisting of CD27, CD28, 4-BB(CD137), OX40, CD30, CD40, PD-1, ICOS, lymphocyte function-associated antigen-1 (LFA-I), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD 1 ld, ITGAE, CD103, ITGAL, CD 1 la, LFA-1, ITGAM, CD1 lb, ITGAX, CD1 lc, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD00 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD1 la, CD18), ICOS (CD278), 4-BB (CD137), GITR, CD40, BAFFR, HVEM (LIGHTR), SLAMF7, NKp80 (KLRF), CD160, CD19, IL2R beta, IL2R gamma, IL7R u, ITGA1, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the antigen binding domain binds a tumor antigen. In some embodiments, the tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvIII); ganglioside G2 (GD2); ganglioside GD3 (aNeuSAc(2-8)aNeuSAc(2-3)bD-Gaip(1-4)bDGIcp(1-1)Cer); TNF receptor family member B cell maturation (BCMA); Tn antigen ((Tn Ag) or (GalNAcu-Ser/Thr)); prostate-specific membrane antigen (PSMA); Receptor tyrosine kinase-like orphan receptor 1 (RORI); Fms-Like, Tyrosine Kinase 3 (FLT3); Tumor-associated glycoprotein 72 (TAG72); CD38; CD44v6; Carcinoembryonic antigen (CEA); Epithelial cell adhesion molecule (EP-CAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; delta like 3 (DLL3); Folate receptor alpha; Receptor tyrosine-protein kinase, ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murineleukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeuSAc(2-3)bDGalp(1-4)bDGlcp(1-1)Cer); transglutaminase 5 (TGS5); high molecular weight-melanoma associated antigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-la); Melanomaassociated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the tumor antigen is selected from CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acethycholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microglobulin, and Fc Receptor-like 5 (FcRL5).

Non limiting examples of cell therapies include Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, and CSG-005.

Additional agents include those where the tumor targeting antigen is: Alpha-fetoprotein, such as ET-1402, and AFP-TCR; Anthrax toxin receptor 1, such as anti-TEM8 CAR T-cell therapy; B cell maturation antigens (BCMA), such as bb-2121, UCART-BCMA, ET-140, KITE-585, MCM-998, LCAR-B38M, CART-BCMA, SEA-BCMA, BB212, UCART-BCMA, ET-140, P-BCMA-101, and AUTO-2 (APRIL-CAR); Anti-CLL-1 antibodies, such as KITE-796; B7 homolog 6, such as CAR-NKp30 and CAR-B7H6; B-lymphocyte antigen CD19, such as TBI-1501, CTL-119 huCART-19 T cells, JCAR-015 U.S. Pat. No. 7,446,190, JCAR-014, JCAR-017, (WO2016196388, WO2016033570, WO2015157386), axicabtagene ciloleucel (KTE-C19), U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, and IM19 CAR-T; B-lymphocyte antigen CD20, such as ATTCK-20; B-lymphocyte cell adhesion, such as UCART-22, and JCAR-018 (WO2016090190); NY-ESO-1, such as GSK-3377794, and TBI-1301; Carbonic anhydrase, such as DC-Ad-GMCAIX; Caspase 9 suicide gene, such as CaspaCIDe DLI, and BPX-501; CCR5, such as SB-728; CDw123, such as MB-102, and UCART-123; CD20m such as CBM-C20.1; CD4, such as ICG-122; CD30, such as CART30 (CBM-C30.1; CD33, such as CIK-CAR.CD33; CD38, such as T-007, UCART-38; CD40 ligand, such as BPX-201; CEACAM protein 4 modulators, such as MG7-CART; Claudin 6, such as CSG-002; EBV targeted, such as CMD-003; EGFR, such as autologous 4H11-28z/fIL-12/EFGRt T cell; Endonuclease, such as PGN-514, PGN-201; Epstein-Barr virus specific T-lymphocytes, such as TT-10; Erbb2, such as CST-102, CIDeCAR; Ganglioside (GD2), such as 4SCAR-GD2; Glutamate carboxypeptidase II, such as CIK-CAR.PSMA, CART-PSMA-TGFßRDN, and P-PSMA-101; Glypican-3 (GPC3), such as TT-16, and GLYCAR; Hemoglobin, such as PGN-236; Hepatocyte growth factor receptor, such as anti-cMet RNA CAR T; Human papillomavirus E7 protein, such as KITE-439; Immunoglobulin gamma Fc receptor III, such as ACTR087; IL-12, such as DC-RTS-IL-12; IL-12 agonist/mucin 16, such as JCAR-020; IL-13 alpha 2, such as MB-101; IL-2, such as CST-101; K-Ras GTPase, such as anti-KRAS G12V mTCR cell therapy; Neural cell adhesion molecule L1 LICAM (CD171), such as JCAR-023; Latent membrane protein 1/Latent membrane protein 2, such as Ad5f35-LMPd1-2-transduced autologous dendritic cells; Melanoma associated antigen 10, such as MAGE-A10C796T MAGE-A10 TCR; Melanoma associated antigen 3/Melanoma associated antigen 6 (MAGE A3/A6) such as KITE-718; Mesothelin, such as CSG-MESO, and TC-210; NKG2D, such as NKR-2; Ntrkr1 tyrosine kinase receptor, such as JCAR-024; T cell receptors, such as BPX-701, and IMCgp100; T-lymphocyte, such as TT-12;

Tumor infiltrating lymphocytes, such as LN-144, and LN-145; or Wilms tumor protein, such as JTCR-016, and WT1-CTL.

Subjects

Any of the methods of treatment provided may be used to treat a subject (e.g., human) who has been diagnosed with or is suspected of having cancer. As used herein, a subject refers to a mammal, including, for example, a human.

In some embodiments, the subject may be a human who exhibits one or more symptoms associated with cancer or hyperproliferative disease. In some embodiments, the subject may be a human who exhibits one or more symptoms associated with cancer. In some embodiments, the subject is at an early stage of a cancer. In other embodiments, the subject is at an advanced stage of cancer.

In certain, the subject may be a human who is at risk, or genetically or otherwise predisposed (e.g., risk factor) to developing cancer or hyperproliferative disease who has or has not been diagnosed. As used herein, an "at risk" subject is a subject who is at risk of developing cancer. The subject may or may not have detectable disease, and may or may not have displayed detectable disease prior to the treatment methods described herein. An at risk subject may have one or more so-called risk factors, which are measurable parameters that correlate with development of cancer, which are described herein. A subject having one or more of these risk factors has a higher probability of developing cancer than an individual without these risk factor(s). These risk factors may include, for example, age, sex, race, diet, history of previous disease, presence of precursor disease, genetic (e.g., hereditary) considerations, and environmental exposure. In some embodiments, the subjects at risk for cancer include, for example, those having relatives who have experienced the disease, and those whose risk is determined by analysis of genetic or biochemical markers.

In addition, the subject may be a human who is undergoing one or more standard therapies, such as chemotherapy, radiotherapy, immunotherapy, surgery, or combination thereof. Accordingly, one or more kinase inhibitors may be administered before, during, or after administration of chemotherapy, radiotherapy, immunotherapy, surgery or combination thereof.

In certain embodiments, the subject may be a human who is (i) substantially refractory to at least one chemotherapy treatment, or (ii) is in relapse after treatment with chemotherapy, or both (i) and (ii). In some of embodiments, the subject is refractory to at least two, at least three, or at least four chemotherapy treatments (including standard or experimental chemotherapies).

As used herein, a "therapeutically effective amount" means an amount sufficient to modulate a specific pathway, and thereby treat a subject (such as a human) suffering an indication, or to alleviate the existing symptoms of the indication. Determination of a therapeutically effective amount is within the capability of those skilled in the art, especially in light of the detailed disclosure provided herein. In some embodiments, a therapeutically effective amount of a JAK inhibitor, such as Compound A or ruxolitinib or pharmaceutically acceptable salt thereof, and a therapeutically effective amount of PI3K inhibitor, such as Compound B, Compound C, Compound D, or Compound E and pharmaceutically acceptable salt thereof, may (i) reduce the number of diseased cells; (ii) reduce tumor size; (iii) inhibit, retard, slow to some extent, and preferably stop the diseased cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with cancer or myeloproliferative disease. In other embodiments, a therapeutically effective amount of Compound B or Compound C and a therapeutically effective amount of obinutuzumab may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

In some embodiments, the cancer is Burkitt's lymphoma, Hodgkin's lymphoma, non-Hodgkin's lymphoma (NHL), indolent non-Hodgkin's lymphoma (iNHL), refractory iNHL, multiple myeloma (MM), chronic myeloid leukemia (CML), acute lymphocytic leukemia (ALL), B-cell ALL, acute myeloid leukemia (AML), chronic lymphocytic leukemia (CLL), small lymphocytic lymphoma (SLL), myelodysplastic syndrome (MDS), myeloproliferative disease (MPD), mantle cell lymphoma (MCL), follicular lymphoma (FL), Waldestrom's macroglobulinemia (WM), T-cell lymphoma, B-cell lymphoma, diffuse large B-cell lymphoma (DLBCL), or marginal zone lymphoma (MZL). In one embodiment, the cancer is minimal residual disease (MRD). In additional embodiment, the cancer is selected from Hodgkin's lymphoma, non-Hodgkin's lymphoma (NHL), indolent non-Hodgkin's lymphoma (iNHL), and refractory iNHL. In certain embodiment, the cancer is indolent non-Hodgkin's lymphoma (iNHL). In some embodiment, the cancer is refractory iNHL. In one embodiment, the cancer is chronic lymphocytic leukemia (CLL). In other embodiment, the cancer is diffuse large B-cell lymphoma (DLBCL).

In certain embodiments, the cancer is a solid tumor is selected from the group consisting of pancreatic cancer; bladder cancer; colorectal cancer; breast cancer, including metastatic breast cancer; prostate cancer, including androgen-dependent and androgen-independent prostate cancer; kidney or renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma, hepatic carcinoma, rectal cancer, penile carcinoma, vulval cancer, thyroid cancer, salivary gland carcinoma, endometrial or uterine carcinoma, hepatoma, hepatocellular cancer, liver cancer, gastric or stomach cancer including gastrointestinal cancer, cancer of the peritoneum, squamous carcinoma of the lung, gastroesophagal cancer, biliary tract cancer, gall bladder cancer, colorectal/appendiceal cancer, squamous cell cancer (e.g., epithelial squamous cell cancer).

Any of the methods of treatment provided may be used to treat cancer at various stages. By way of example, the cancer stage includes but is not limited to early, advanced, locally advanced, remission, refractory, reoccurred after remission and progressive.

Lymphoma or Leukemia Combination Therapy: Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17-AAG), hyperC-VAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R-MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCl-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy: Treatment of non-Hodgkin's lymphomas (NHL), especially those of B cell origin, includes using monoclonal antibodies, standard chemotherapy approaches (e.g., CHOP, CVP, FCM, MCP, and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP, R-FCM, R-CVP, and R-MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy: Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CC-779), everolimus (RAD001), BMS-345541, curcumin, SAHA, thalidomide, lenalidomide (REVLIMID®, CC-5013), and geldanamycin (17-AAG).

Waldenstrom's Macroglobulinemia Combination Therapy: Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, antithymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA©), simvastatin, sirolimus, tacrolimus, tanespimycin, thalidomide, therapeutic allogeneic lymphocytes, thiotepa, tipifarnib, tositumomab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-cell Lymphoma Combination Therapy: Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and R-ICE.

Chronic Lymphocytic Leukemia Combination Therapy: Examples of therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy: Myelofibrosis inhibiting agents include, but are not limited to, hedgehog inhibitors, histone deacetylase (HDAC) inhibitors, and tyrosine kinase inhibitors. Non-limiting examples of hedgehog inhibitors are saridegib and vismodegib. Examples of HDAC inhibitors include, but are not limited to, pracinostat and panobinostat. Non-limiting examples of tyrosine kinase inhibitors are lestaurtinib, bosutinib, imatinib, gilteritinib, radotinib, and cabozantinib.

Hyperproliferative Disorder Combination Therapy: Gemcitabine, nab-paclitaxel, and gemcitabine/nab-paclitaxel may be used with a JAK inhibitor and/or PI3KS inhibitor to treat hyperproliferative disorders.

Bladder cancer combination therapy: Therapeutic agents used to treat bladder cancer include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combination thereof.

Breast cancer combination therapy: Therapeutic agents used to treat breast cancer include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple negative breast cancer combination therapy: Therapeutic agents used to treat triple negative breast cancer include cyclophosphamide, docetaxel, doxorubicin, epirubicin, fluorouracil, paclitaxel, and combinations thereof.

Colorectal cancer combination therapy: Therapeutic agents used to treat colorectal cancer include bevacizumab, capecitabine, cetuximab, fluorouracil, irinotecan, leucovorin, oxaliplatin, panitumumab, ziv-aflibercept, and any combinations thereof.

Castration-resistant prostate cancer combination therapy: Therapeutic agents used to treat castration-resistant prostate cancer include abiraterone, cabazitaxel, docetaxel, enzalutamide, prednisone, sipuleucel-T, and any combinations thereof.

Esophageal and esophagogastric junction cancer combination therapy: Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric cancer combination therapy: Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head & neck cancer combination therapy: Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary cancer combination therapy: Therapeutic agents used to treat hepatobiliary cancer include capecitabine, cisplatin, fluoropyrimidine, 5-fluorourcil, gemecitabine, oxaliplatin, sorafenib, and any combinations thereof.

Hepatocellular carcinoma combination therapy: Therapeutic agents used to treat hepatocellular carcinoma include capecitabine, doxorubicin, gemcitabine, sorafenib, and any combinations thereof.

Non-small cell lung cancer combination therapy: Therapeutic agents used to treat non-small cell lung cancer (NSCLC) include afatinib, albumin-bound paclitaxel, alectinib, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small cell lung cancer combination therapy: Therapeutic agents used to treat small cell lung cancer (SCLC) include bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof.

Melanoma combination therapy: Therapeutic agents used to treat melanoma cancer include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.

Ovarian cancer combination therapy: Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcibabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic cancer combination therapy: Therapeutic agents used to treat pancreatic cancer include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.

Renal cell carcinoma combination therapy: Therapeutic agents used to treat renal cell carcinoma include axitinib, bevacizumab, cabozantinib, erlotinib, everolimus, levantinib, nivolumab, pazopanib, sorafenib, sunitinib, temsirolimus, and any combinations thereof.

In one embodiment, the compound of formula (I), or any formula described herein, or a pharmaceutically acceptable salt, stereoisomer, mixture of stereoisomers, solvate, or tautomer thereof, is useful for the treatment of cancer in combination with a standard of care in the treatment of the respective cancer. One of skill in the art is aware of the standard of care as of a given date in the particular field of cancer therapy or with respect to a given cancer.

Certain embodiments of the present application include or use one or more additional therapeutic agent. The one or more additional therapeutic agent may be an agent useful for the treatment of cancer, inflammation, autoimmune disease and/or related conditions. The one or more additional therapeutic agent may be a chemotherapeutic agent, an anti-angiogenic agent, an antifibrotic agent, an anti-inflammatory agent, an immune modulating agent, an immunotherapeutic agent, a therapeutic antibody, a radiotherapeutic agent, an anti-neoplastic agent, an anti-cancer agent, an anti-proliferation agent, or any combination thereof. In some embodiments, the compound(s) described herein may be used or combined with a chemotherapeutic agent, an anti-angiogenic agent, an anti-fibrotic agent, an anti-inflammatory agent, an immune modulating agent, an immunotherapeutic agent, a therapeutic antibody, a radiotherapeutic agent, an antineoplastic agent or an anti-cancer agent, an anti-proliferation agent, or any combination thereof.

In one embodiment, a compound(s) of formula (I) optionally in combination with an additional anticancer agent described herein, may be used or combined with an anti-neoplastic agent or an anti-cancer agent, anti-fibrotic agent, an anti-anti-inflammatory agent, or an immune modulating agent.

In one embodiment, provided are kits comprising a pharmaceutical composition comprising a compound of formula (I), or any formula described herein, or a pharmaceutically acceptable salt, stereoisomer, mixture of stereoisomers, solvate, or tautomer thereof, or a compound of formula (I), or any formula described herein, or a pharmaceutically acceptable salt, stereoisomer, mixture of stereoisomers, solvate, or tautomer thereof, and at least one additional anticancer agent, or a pharmaceutically acceptable salt thereof, and at least one pharmaceutically acceptable carrier. In one embodiment, the kit comprises instructions for use in the treatment of cancer or inflammatory conditions. In one embodiment, the instructions in the kit are directed to use of the pharmaceutical composition for the treatment of cancer selected from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer.

The application also provides method for treating a subject who is undergoing one or more standard therapies, such as chemotherapy, radiotherapy, immunotherapy, surgery, or combination thereof comprising administering or co-administering a compound of formula (I), or any formula described herein, or a pharmaceutically acceptable salt, stereoisomer, mixture of stereoisomers, solvate, or tautomer thereof, said subject. Accordingly, one or more compound(s) of formula (I), or any formula described herein, or pharmaceutically acceptable salt thereof, may be administered before, during, or after administration of a chemotherapy, radiotherapy, immunotherapy, surgery or combination thereof.

In one embodiment, the subject may be a human who is (i) substantially refractory to at least one chemotherapy treatment, or (ii) in relapse after treatment with chemotherapy, or both (i) and (ii). In some of embodiments, the subject is refractory to at least two, at least three, or at least four chemotherapy treatments (including standard or experimental chemotherapies).

In one embodiment, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" The New England Journal of Medicine 2008, 359(6), p. 613-626; and Wierda, W. G., "Current and Investigational Therapies for Patients with CLL" Hematology 2006, p. 285-294. Lymphoma incidence patterns in the United States is profiled in Morton, L. M., et al. "Lymphoma Incidence Patterns by WHO Subtype in the United States, 1992-2001" Blood 2006, 107(1), p. 265-276.

Examples of immunotherapeutic agents treating lymphoma or leukemia include, but are not limited to, rituximab (such as Rituxan), alemtuzumab (such as Campath, MabCampath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CC-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (Rituximab-MCP).

In some embodiments, the cancer is melanoma. Suitable agents for use in combination with the compounds described herein include, without limitation, dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC, temozolomide or YERVOY™. Compounds disclosed herein may also be combined with immunotherapy drugs, including cytokines such as interferon alpha, interleukin 2, and tumor necrosis factor (TNF) in the treatment of melanoma.

Compounds described here may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds described herein, using for example, a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF) and optionally in combination with a compound of formula (I), or any formula described herein or a pharmaceutically acceptable salt, stereoisomer, mixture of stereoisomers, solvate, or tautomer thereof.

The therapeutic treatments can be supplemented or combined with any of the aforementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures useful in combination with treatment with a compound of formula (I), or any formula described herein, or a pharmaceutically acceptable salt, stereoisomer, mixture of stereoisomers, solvate, or tautomer thereof, include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

In some embodiments, the application provides pharmaceutical compositions comprising a compound of formula (I), or any formula described herein, or a pharmaceutically acceptable salt, stereoisomer, mixture of stereoisomers, solvate, or tautomer thereof, in combination with an MMP9 binding protein and/or one or more additional therapeutic agent, and a pharmaceutically acceptable diluent, carrier or excipient. In one embodiment, the pharmaceutical compositions comprise an MMP9 binding protein, one or more additional therapeutic agent, and a pharmaceutically acceptable excipient, carrier or diluent. In some embodiments, the pharmaceutical compositions comprise the compound of formula (I), or any formula described herein, or a pharmaceutically acceptable salt, stereoisomer, mixture of stereoisomers, solvate, or tautomer thereof, and anti-MMP9 antibody AB0045.

In one embodiment, the pharmaceutical compositions comprise the compound of formula (I), or any formula described herein, or a pharmaceutically acceptable salt, stereoisomer, mixture of stereoisomers, solvate, or tautomer thereof, anti-MMP9 antibody AB0045, at least one additional therapeutic agent that is an immunomodulating agent, and a pharmaceutically acceptable diluent, carrier or excipient. In certain other embodiments, the pharmaceutical compositions comprise the anti-MMP9 antibody AB0045, at least one additional therapeutic agent that is an anti-inflammatory agent, and a pharmaceutically acceptable diluent, carrier or excipient. In certain other embodiments, the pharmaceutical compositions comprise compound of formula (I), or any formula described herein, or a pharmaceutically acceptable salt, stereoisomer, mixture of stereoisomers, solvate, or tautomer thereof, the anti-MMP9 antibody AB0045, at least one additional therapeutic agent that is an antineoplastic agent or anti-cancer agent, and a pharmaceutically acceptable diluent, carrier or excipient. In one embodiment, MMP9 compounds useful for combination treatment with a compound of formula (I), or any formula described herein, or a pharmaceutically acceptable salt, stereoisomer, mixture of stereoisomers, solvate, or tautomer thereof, include but are not limited to marimastat (BB-2516), cipemastat (Ro 32-3555) and those described in WO 2012/027721 (Gilead Biologics).

In one embodiment, the one or more additional therapeutic agent is an immune modulating agent, e.g., an immunostimulant or an immunosuppressant. In certain other embodiments, an immune modulating agent is an agent capable of altering the function of immune checkpoints, including the CTLA-4, LAG-3, B7-H3, B7-H4, Tim3, BTLA, KIR, A2aR, CD200 and/or PD-1 pathways. In other embodiments, the immune modulating agent is immune checkpoint modulating agents. Exemplary immune checkpoint modulating agents include anti-CTLA-4 antibody (e.g., ipilimumab), anti-LAG-3 antibody, anti-B7-H3 antibody, anti-B7-H4 antibody, anti-Tim3 antibody, anti-BTLA antibody, anti-KIR antibody, anti-A2aR antibody, anti CD200 antibody, anti-PD-1 antibody, anti-PD-L1 antibody, anti-CD28 antibody, anti-CD80 or -CD86 antibody, anti-B7RP1 antibody, anti-B7-H3 antibody, anti-HVEM antibody, anti-CD137 or -CD137L antibody, anti-OX40 or -OX40L antibody, anti-CD40 or -CD40L antibody, anti-GAL9 antibody, anti-IL-10 antibody and A2aR drug. For certain such immune pathway gene products, the use of either antagonists or agonists of such gene products is contemplated, as are small molecule modulators of such gene products. In one embodiment, the immune modulatory agent is an anti-PD-1 or anti-PD-L1 antibody. In some embodiments, immune modulating agents include those agents capable of altering the function of mediators in cytokine mediated signaling pathways.

In some embodiments, the one or more additional therapy or anti-cancer agent is cancer gene therapy or cell therapy. Cancer gene therapy and cell therapy include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer. Non limiting examples are Algenpantucel-L (2 pancreatic cell lines), Sipuleucel-T, SGT-53 liposomal nanodelivery (scL) of gene p53; T-cell therapy, such as CD19 CAR-T tisagenlecleucel-T (CTL019) WO2012079000, WO2017049166, axicabtagene ciloleucel (KTE-C19) U.S. Pat. Nos. 7,741,465, 6,319,494, JCAR-015 U.S. Pat. No. 7,446,190, JCAR-014, JCAR-020, JCAR-024, JCAR-023, JTCR-016, JCAR-018 WO2016090190, JCAR-017, (WO2016196388, WO2016033570, WO2015157386), BPX-501 U.S. Pat. No. 9,089,520, WO2016100236, AU-105, UCART-22, ACTR-087, P-BCMA-101; activated allogeneic natural killer cells CNDO-109-AANK, FATE-NK100, LFU-835 hematopoietic stem cells.

In one embodiment, the one or more additional therapeutic agent is an immune checkpoint inhibitor. Tumors subvert the immune system by taking advantage of a mechanism known as T-cell exhaustion, which results from chronic exposure to antigens and is characterized by the up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular determinants to influence whether cell cycle progression and other intracellular signaling processes should proceed based upon extracellular information.

In addition to specific antigen recognition through the T-cell receptor (TCR), T-cell activation is regulated through a balance of positive and negative signals provided by costimulatory receptors. These surface proteins are typically members of either the TNF receptor or B7 superfamilies. Agonistic antibodies directed against activating co-stimulatory molecules and blocking antibodies against negative co-stimulatory molecules may enhance T-cell stimulation to promote tumor destruction.

Programmed Cell Death Protein 1, (PD-1 or CD279), a 55-kD type 1 transmembrane protein, is a member of the CD28 family of T cell co-stimulatory receptors that include immunoglobulin superfamily member CD28, CTLA-4, inducible co-stimulator (ICOS), and BTLA. PD-1 is highly expressed on activated T cells and B cells. PD-1 expression can also be detected on memory T-cell subsets with variable levels of expression. Two ligands specific for PD-1 have been identified: programmed death-ligand 1 (PD-L1, also known as B7-H1 or CD274) and PD-L2 (also known as B7-DC or CD273). PD-L1 and PD-L2 have been shown to down-regulate T cell activation upon binding to PD-1 in both mouse and human systems (Okazaki et al., Int. Immunol., 2007; 19: 813-824). The interaction of PD-1 with its ligands, PD-L1 and PD-L2, which are expressed on antigen-presenting, cells (APCs) and dendritic cells (DCs), transmits negative regulatory stimuli to down-modulate the activated T cell immune response. Blockade of PD-1 suppresses this negative signal and amplifies T cell responses. Numerous studies indicate that the cancer microenvironment manipulates the PD-L1/PD-1 signaling pathway and that induction of PD-L1 expression is associated with inhibition of immune responses against cancer, thus permitting cancer progression and metastasis. The PD-L1/PD-1 signaling pathway is a primary mechanism of cancer immune evasion for several reasons. This pathway is involved in negative regulation of immune responses of activated T effector cells found in the periphery. PD-L1 is up-regulated in cancer microenvironments, while PD-1 is also up-regulated on activated tumor infiltrating T cells, thus possibly potentiating a vicious cycle of inhibition. This pathway is also intricately involved in both innate and adaptive immune regulation through bi-directional signaling. These factors make the PD-1/PD-L1 complex a central point through which cancer can manipulate immune responses and promote its own progression.

The first immune-checkpoint inhibitor to be tested in a clinical trial was ipilimumab (Yervoy, Bristol-Myers Squibb), a CTLA-4 mAb. CTLA-4 belongs to the immunoglobulin superfamily of receptors, which also includes PD-1, BTLA, TIM-3, and V-domain immunoglobulin suppressor of T cell activation (VISTA). Anti-CTLA-4 mAb is a powerful checkpoint inhibitor which removes "the break" from both naive and antigen-experienced cells.

Therapy enhances the antitumor function of CD8+ T cells, increases the ratio of CD8+ T cells to Foxp3+ T regulatory cells, and inhibits the suppressive function of T regulatory cells. TIM-3 has been identified as another important inhibitory receptor expressed by exhausted CD8+ T cells. In mouse models of cancer, it has been shown that the most dysfunctional tumor-infiltrating CD8+ T cells actually co-express PD-1 and LAG-3. LAG-3 is another recently identified inhibitory receptor that acts to limit effector T-cell function and augment the suppressive activity of T regulatory cells. It has recently been revealed that PD-1 and LAG-3 are extensively co-expressed by tumor-infiltrating T cells in mice, and that combined blockade of PD-1 and LAG-3 provokes potent synergistic antitumor immune responses in mouse models of cancer.

Thus in one embodiment, the present disclosure provides the use of immune checkpoint inhibitors of formula (I) disclosed herein in combination with one or more additional immune checkpoint inhibitors. In one embodiment, the present disclosure provides the use of immune checkpoint inhibitors of formula (I) disclosed herein in combination with one or more additional immune checkpoint inhibitors and an anti-MMP9 antibody or antigen binding fragment thereof to treat or prevent cancer. In some embodiments, the immune checkpoint inhibitors may be an anti-PD-1 and/or an anti-PD-L1 antibody or an anti PD-1/PD-L1 interaction inhibitor. In some embodiments, the anti-PD-L1 antibody may be B7-H1 antibody, BMS 936559 antibody, MPDL3280A (atezolizumab) antibody, MEDI-4736 antibody, MSB0010718C antibody or combinations thereof. According to another embodiment, the anti-PD-1 antibody may be nivolumab antibody, pembrolizumab antibody, pidilizumab antibody or combinations thereof.

In addition, PD-1 may also be targeted with AMP-224, which is a PD-L2-IgG recombinant fusion protein. Additional antagonists of inhibitory pathways in the immune response include IMP321, a soluble LAG-3 Ig fusion protein and MHC class II agonist, which is used to increase an immune response to tumors. Lirilumab is an antagonist to the KIR receptor and BMS 986016 is an antagonist of LAG3. The TIM-3-Galectin-9 pathway is another inhibitory checkpoint pathway that is also a promising target for checkpoint inhibition. RX518 targets and activates the glucocorticoid-induced tumor necrosis factor receptor (GITR), a member of the TNF receptor superfamily that is expressed on the surface of multiple types of immune cells, including regulatory T cells, effector T cells, B cells, natural killer (NK) cells, and activated dendritic cells. Thus, in one embodiment, the compound(s) of formula (I) may be used in combination with IMP321, Lirilumab and/or BMS 986016.

Anti-PD-1 antibodies that may be used in the compositions and methods described herein include but are not limited to: Nivolumab/MDX-1106/BMS-936558/ONO1152, a fully human IgG4 anti-PD-1 monoclonal antibody; pidilizumab (MDV9300/CT-011), a humanized IgG1 monoclonal antibody; pembrolizumab (MK-3475/pembrolizumab/lambrolizumab), a humanized monoclonal IgG4 antibody; durvalumab (MEDI-4736) and atezolizumab. Anti-PD-L1 antibodies that may be used in compositions and methods described herein include but are not limited to: avelumab; BMS-936559, a fully human IgG4 antibody; atezolizumab (MPDL3280A/RG-7446), a human monoclonal antibody; MEDI4736; MSB0010718C, and MDX1105-01.

In one embodiment, the compound of formula (I), or any formula described herein, or a pharmaceutically acceptable salt, stereoisomer, mixture of stereoisomers, solvate, or tautomer thereof, is administered in combination with the anti-PD-1 antibody nivolumab, pembrolizumab, and/or pidilizumab to a patient in need thereof. In one embodiment, the anti-PD-L1 antibody useful for combination treatment with a compound of formula (I), or any formula described herein, or a pharmaceutically acceptable salt, stereoisomer, mixture of stereoisomers, solvate, or tautomer thereof, is BMS-936559, atezolizumab, or avelumab. In one embodiment, the immune modulating agent inhibits an immune checkpoint pathway. In another embodiment, the immune checkpoint pathway is selected from CTLA-4, LAG-3, B7-H3, B7-H4, Tim3, BTLA, KIR, A2aR, CD200 and PD-1. Additional antibodies that may be used in combination with a compound of formula (I), or any formula described herein, or a pharmaceutically acceptable salt, stereoisomer, mixture of stereoisomers, solvate, or tautomer thereof, in compositions and methods described herein include the anti-PD-1 and anti-PD-L1 antibodies disclosed in U.S. Pat. Nos. 8,008,449 and 7,943,743, respectively.

In one embodiment, the one or more additional therapeutic agent is an anti-inflammatory agent. In certain other embodiments, the anti-inflammatory agent is a tumor necrosis factor alpha (TNF-α) inhibitor. As used herein, the terms "TNF alpha," "TNF-α," and "TNFα," are interchangeable. TNF-α is a pro-inflammatory cytokine secreted primarily by macrophages but also by a variety of other cell types including lymphoid cells, mast cells, endothelial cells, cardiac myocytes, adipose tissue, fibroblasts, and neuronal tissue. TNF-α is also known as endotoxin-induced factor in serum, cachectin, and differentiation inducing factor. The tumor necrosis factor (TNF) family includes TNF alpha, TNF beta, CD40 ligand (CD40L), Fas ligand (FasL), TNF-related apoptosis inducing ligand (TRAIL), and LIGHT (homologous to lymphotoxins, exhibits inducible expression, and competes with HSV glycoprotein D for HVEM, a receptor expressed by T lymphocytes), some of the most important cytokines involved in, among other physiological processes, systematic inflammation, tumor lysis, apoptosis and initiation of the acute phase reaction.

The above therapeutic agents when employed in combination with a compound(s) disclosed herein, may be used, for example, in those amounts indicated in the referenced manuals e.g., Physicians Desk Reference or in amounts generally known to a qualified care giver, i.e., one of ordinary skill in the art. In the methods of the present disclosure, such other therapeutic agent(s) may be administered prior to, simultaneously with, or following the administration of the compound(s) of formula (I). Certain other therapeutic agents may be combined into a single formulation or kit when amenable to such. For example, tablet, capsule or liquid formulations may be combined with other tablet, capsule or liquid formulations into one fixed or combined dose formulation or regimen. Other combinations may be given separately, contemporaneously or otherwise.

Combination Therapy for HBV

In certain embodiments, a method for treating or preventing an HBV infection in a human having or at risk of having the infection is provided, comprising administering to the human a therapeutically effective amount of a compound disclosed herein, or any formula described herein, or a pharmaceutically acceptable salt, stereoisomer, mixture of stereoisomers, solvate, or tautomer thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or any formula described herein, or a pharmaceutically acceptable salt, stereoisomer, mixture of stereoisomers, solvate, or tautomer thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or any formula described herein, or a pharmaceutically acceptable salt, stereoisomer, mixture of stereoisomers, solvate, or tautomer thereof, in combination with a therapeutically effective amount of one or more (e.g., one, two, three, four, one or two, one to three, or one to four) additional therapeutic agents which are suitable for treating an HBV infection.

In certain embodiments, a compound disclosed herein, or any formula described herein, or a pharmaceutically acceptable salt, stereoisomer, mixture of stereoisomers, solvate, or tautomer thereof, is combined with one, two, three, four, or more additional therapeutic agents. In certain embodiments, a compound disclosed herein, or any formula described herein, or a pharmaceutically acceptable salt, stereoisomer, mixture of stereoisomers, solvate, or tautomer thereof, is combined with two additional therapeutic agents. In other embodiments, a compound disclosed herein, or any formula described herein, or a pharmaceutically acceptable salt, stereoisomer, mixture of stereoisomers, solvate, or tautomer thereof, is combined with three additional therapeutic agents. In further embodiments, a compound disclosed herein, or any formula described herein, or a pharmaceutically acceptable salt, stereoisomer, mixture of stereoisomers, solvate, or tautomer thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when a compound disclosed herein is combined with one or more additional therapeutic agents as described above, the components of the composition are administered as a simultaneous or sequential regimen. When administered sequentially, the combination may be administered in two or more administrations.

Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Co-administration includes administration of unit dosages of the compounds disclosed herein before or after administration of unit dosages of one or more additional therapeutic agents. The compound disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments a compound of formula (I), or any formula described herein, or a pharmaceutically acceptable salt, stereoisomer, mixture of stereoisomers, solvate, or tautomer thereof, is formulated as a tablet, which may optionally contain one or more other compounds useful for treating hepatitis B virus (HBV). In certain embodiments, the tablet can contain another active ingredient for treating hepatitis B virus (HBV).

In certain embodiments, such tablets are suitable for once daily dosing.

The compounds described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof.

In the above embodiments, the additional therapeutic agent may be an anti-HBV agent. For example, the additional therapeutic agent may be selected from the group consisting of HBV combination drugs, other drugs for treating hepatitis B virus (HBV), 3-dioxygenase (IDO) inhibitors, antisense oligonucleotide targeting viral mRNA, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), covalently closed circular DNA (cccDNA) inhibitors, cyclophilin inhibitors, cytokines, cytotoxic T-lymphocyte-associated protein 4 (ipi4) inhibitors, DNA polymerase inhibitor, Endonuclease modulator, epigenetic modifiers, Farnesoid X receptor agonist, gene modifiers or editors, HBsAg inhibitors, HBsAg secretion or assembly inhibitors, HBV antibodies, HBV DNA polymerase inhibitors, HBV replication inhibitors, HBV RNAse inhibitors, HBV vaccines, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, Immunoglobulin agonist, Immunoglobulin G modulator, immunomodulators, indoleamine-2, inhibitors of ribonucleotide reductase, Interferon agonist, Interferon alpha 1 ligand, Interferon alpha 2 ligand, Interferon alpha 5 ligand modulator, Interferon alpha ligand, Interferon alpha ligand modulator, interferon alpha receptor ligands, Interferon beta ligand, Interferon ligand, Interferon receptor modulator, Interleukin-2 ligand, ipi4 inhibitors, lysine demethylase inhibitors, histone demethylase inhibitors, KDM5 inhibitors, KDM1 inhibitors, killer cell lectin-like receptor subfamily G member 1 inhibitors, lymphocyte-activation gene 3 inhibitors, lymphotoxin beta receptor activators, microRNA (miRNA) gene therapy agents, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, PEG-Interferon Lambda, Peptidylprolyl isomerase inhibitor, phosphatidylinositol-3 kinase (PI3K) inhibitors, recombinant scavenger receptor A (SRA) proteins, recombinant thymosin alpha-1, Retinoic acid-inducible gene 1 stimulator, Reverse transcriptase inhibitor, Ribonuclease inhibitor, RNA DNA polymerase inhibitor, short interfering RNAs (siRNA), short synthetic hairpin RNAs (sshRNAs), SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, zinc finger nucleases or synthetic nucleases (TALENs), and combinations thereof.

In some embodiments, provided herein is a method for treating hepatitis B virus (HBV) in a patient in need thereof, comprising administering an effective amount of a compound described herein in combination with an effective amount of one or more anti-HCV agents, such as a NS5A inhibitor, a NS5B inhibitor, a NS3 inhibitor, or a combination thereof.

In some embodiments, provided is a method of treating a hepatitis B virus (HBV) infection in a human in need thereof, comprising administering to the patient an effective amount of a compound described herein in combination with an effective amount of a NS5A inhibitor. In some embodiments, the NS5A inhibitor is ledipasvir or velpatasvir. In some embodiments, is provided a method of treating a hepatitis B virus (HBV) infection in a human in need thereof, comprising administering to the patient an effective amount of a compound described herein in combination with an effective amount of a NS5B inhibitor. In some embodiments, the NS5B inhibitor is sofosbuvir or mericitabine. In some embodiments, is provided a method of treating a hepatitis B virus (HBV) infection in a human in need thereof, comprising administering to the patient an effective amount of a compound described herein in combination with an effective amount of a NS3 inhibitor. In some embodiments, the NS3 inhibitor is voxilaprevir.

In some embodiments, the patient is administered an effective amount of a compound described herein in combination with an effective amount of both an effective amount of a NS5A inhibitor and an effective amount of a NS5B inhibitor. In some embodiments, the NS5A inhibitor is ledipasvir and the NS5B inhibitor is sofosbuvir. In some embodiments, the patient is administered an effective amount of a compound described herein in combination with an effective amount of a fixed dose combination of a NS5A inhibitor and a NS5B inhibitor. In some embodiments, the patient is administered an effective amount of a compound described herein in combination with an effective amount of a fixed dose combination of ledipasvir and sofosbuvir (e.g., ledipasvir 90 mg/sofosbuvir 400 mg). In some embodiments, the patient is administered an effective amount of a compound described herein in combination with an effective amount of HARVONI®. In some embodiments, the patient is administered an effective amount of a compound described herein in combination with an effective amount of a fixed dose combination of velpatasvir and sofosbuvir (e.g., velpatasvir 100 mg/sofosbuvir 400 mg). In some embodiments, the patient is administered an effective amount of a compound described herein in combination with an effective amount of EPCLUSA®.

In some embodiments, the patient is administered an effective amount of a compound of Table 1A or Table 1B in combination with an effective amount of both an effective amount of a NS5A inhibitor and an effective amount of a NS5B inhibitor. In some embodiments, the NS5A inhibitor is ledipasvir and the NS5B inhibitor is sofosbuvir. In some embodiments, the patient is administered an effective amount of a compound of Table 1A or Table 1B in combination with an effective amount of a fixed dose combination of a NS5A inhibitor and a NS5B inhibitor. In some embodiments, the patient is administered an effective amount of a compound of Table 1A or Table 1B in combination with an effective amount of a fixed dose combination of ledipasvir and sofosbuvir (e.g., ledipasvir 90 mg/sofosbuvir 400 mg). In some embodiments, the patient is administered an effective amount of a compound of Table 1A or Table 1B in combination with an effective amount of HARVONI®. In some embodiments, the patient is administered an effective amount of a compound of Table 1A or Table 1B in combination with an effective amount of a fixed dose combination of velpatasvir and sofosbuvir (e.g., velpatasvir 100 mg/sofosbuvir 400 mg). In some embodiments, the patient is administered an effective amount of a compound of Table 1A or Table 1B in combination with an effective amount of EPCLUSA®.

In some embodiments, the patient is administered an effective amount of a compound described herein in combination with an effective amount of both an effective amount of a NS5A inhibitor and an effective amount of a NS5B inhibitor, and optionally a NS3 inhibitor. In some embodiments, the patient is administered an effective amount of a compound described herein in combination with an effective amount of sofosbuvir, velpatasvir, and voxilaprevir (e.g., sofosbuvir 400 mg/velpatasvir 100 mg/voxilaprevir 100 mg). In some embodiments, the patient is administered an effective amount of a compound described herein (e.g., Table 1A or Table 1B) in combination with an effective amount of VOSEVI™.

In certain embodiments, a compound of formula (I), or any formula described herein, or a pharmaceutically acceptable salt, stereoisomer, mixture of stereoisomers, solvate, or tautomer thereof, is formulated as a tablet, which may optionally contain one or more other compounds useful for treating hepatitis B virus (HBV). In certain embodiments, the tablet can contain another active ingredient for treating hepatitis B virus (HBV), such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

In certain embodiments, a compound of the present disclosure, or any formula described herein, or a pharmaceutically acceptable salt, stereoisomer, mixture of stereoisomers, solvate, or tautomer thereof, is combined with one, two, three, four or more additional therapeutic agents selected from hepatitis B virus (HBV) combination drugs, HBV vaccines, HBV DNA polymerase inhibitors, immunomodulators toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucleotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2,3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203 adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPER-VAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/ antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA©), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, INO-9112, polymer polyethyleneimine (PEI), Gepon, VGV-1, MOR-22, BMS-936559, RO-7011785, RO-6871765, AIC-649, and IR-103.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, GS-9688 and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, RG-7854, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP- 9C, REP-9, REP-2139, REP-2139-Ca, REP-2165, REP-2055, REP-2163, REP-2165, REP-2053, REP-2031 and REP-006, and REP-9AC'.

Examples of HBsAg Secretion Inhibitors Include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GSK6-LRx, GSK-3389404, RG-6004.

Short Interfering RNAs (siRNA) and ddRNAi.

Examples of siRNA include TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucelotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Example of farnesoid x receptor agonist such as EYP-001.

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed). Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, Hepa-Gam B, igantibe, Niuliva, CT-P24, hepatitis B immunoglobulin (intravenous, pH4, HBV infection, Shanghai RAAS Blood Products), and Fovepta (BT-088). Fully human monoclonal antibodies such as HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include AB-423, AT-130, GLS4, NVR-1221, NVR-3778, BAY 41-4109, morphothiadine mesilate, JNJ-379, RG-7907, ABI-H0731, ABI-H2158 and DVR-23.

Examples of capsid inhibitors include the compounds disclosed in US2014/0275167 (Novira Therapeutics), US2013/0251673 (Novira Therapeutics), US2014/0343032 (Roche), WO2014037480 (Roche), US2013/0267517 (Roche), WO2014131847 (Janssen), WO2014033176 (Janssen), WO2014033170 (Janssen), WO2014033167 (Janssen), WO2015059212 (Janssen), WO2015118057 (Janssen), WO2015011281 (Janssen), WO2014184365 (Janssen), WO2014184350 (Janssen), WO2014161888 (Janssen), WO2013096744 (Novira), US2015/0225355 (Novira), US2014/0178337 (Novira), US2015/0315159 (Novira), US2015/0197533 (Novira), US2015/0274652 (Novira), US2015/0259324, (Novira), US2015/0132258 (Novira), U.S. Pat. No. 9,181,288 (Novira), WO2014184350 (Janssen), WO2013144129 (Roche).

Retinoic Acid-Inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-Kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2,3-Dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US2010/0015178 (Incyte), US2016/137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include nivolumab, pembrolizumab, pidilizumab, BGB-108, SHR-1210, PDR-001, PF-06801591, IBI-308, GB-226, STI-1110, and mDX-400.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, CX-072, and BMS-936559.

In a particular embodiment, a compound disclosed herein, or any formula described herein, or a pharmaceutically acceptable salt, stereoisomer, mixture of stereoisomers, solvate, or tautomer thereof, is combined with compounds such as those disclosed in WO2018026971, US20180044329, US20180044305, US20180044304, US20180044303, US20180044350, US20180057455, US20180057486, US20180045142, WO20180044963, WO2018044783, WO2018009505, WO20180044329, WO2017066227, WO2017087777, US20170145025, WO2017079669, WO2017070089, US2017107216, WO2017222976, US20170262253, WO2017205464, US20170320875, WO2017192961, WO2017112730, US20170174679, WO2017106634, WO2017202744, WO2017202275, WO2017202273, WO2017202274, WO2017202276, WO2017180769, WO2017118762, WO2016041511, WO2016039749, WO2016142835, WO2016142852, WO2016142886, WO2016142894, and WO2016142833.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), and GSK-2879552, RG-6016, ORY-2001.

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Gene Editors

The genome editing system is selected from the group consisting of: a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X, PreS1, PreS2, S, P or SP gene refers to (1) reducing or eliminating PreC, C, X, PreS1, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knock-down of one or more of the PreC, C, X, PreS1, PreS2, S, P and/or SP gene(s) is performed by targeting the gene(s) within HBV cccDNA and/or integrated HBV DNA.

CAR-T Cell Therapy

A population of immune effector cells engineered to express a chimeric antigen receptor (CAR), wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

TCR-T Cell Therapy

T cells expressing HBV-specific T cell receptors. TCR-T cells are engineered to target HBV derived peptides presented on the surface of virus-infected cells.

T-Cells expressing HBV surface antigen (HBsAg)-specific TCR.

TCR-T therapy directed to treatment of HBV, such as LTCR-H2-1

HBV Combination Therapy

In a particular embodiment, a compound disclosed herein, or any formula described herein, or a pharmaceutically acceptable salt, stereoisomer, mixture of stereoisomers, solvate, or tautomer thereof, is combined with one, two, three, or four additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In one embodiment, pharmaceutical compositions comprising a compound disclosed herein, or any formula described herein, or a pharmaceutically acceptable salt, stereoisomer, mixture of stereoisomers, solvate, or tautomer thereof, in combination with one or more (e.g., one, two, three, four, one or two, or one to three, or one to four) additional therapeutic agents and a pharmaceutically acceptable carrier, diluent, or excipient are provided.

HBV DNA Polymerase Inhibitor Combination Therapy

In a specific embodiment, a compound disclosed herein, or any formula described herein, or a pharmaceutically acceptable salt, stereoisomer, mixture of stereoisomers, solvate, or tautomer thereof, is combined with an HBV DNA polymerase inhibitor. In another specific embodiment, a compound disclosed herein, or any formula described herein, or a pharmaceutically acceptable salt, stereoisomer, mixture of stereoisomers, solvate, or tautomer thereof, is combined with an HBV DNA polymerase inhibitor and at least one additional therapeutic agent selected from the group consisting of: immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshR-NAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, cytotoxic T-lymphocyte-associated protein 4 (ipi4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, epigenetic modifiers, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, IDO inhibitors, and hepatitis B virus replication inhibitors.

In another specific embodiment, a compound disclosed herein, or any formula described herein, or a pharmaceutically acceptable salt, stereoisomer, mixture of stereoisomers, solvate, or tautomer thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or any formula described herein, or a pharmaceutically acceptable salt, stereoisomer, mixture of stereoisomers, solvate, or tautomer thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound disclosed herein, or any formula described herein, or a pharmaceutically acceptable salt, stereoisomer, mixture of stereoisomers, solvate, or tautomer thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

HBV Drug Combination Therapy

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, and TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, IDO inhibitors, recombinant thymosin alpha-1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, ipi4 inhibitors, CD137 inhibitors, killer cell lectin-like receptor subfamily G member 1 inhibitors, TIM-3 inhibitors, B- and T-lymphocyte attenuator inhibitors, epigenetic modifiers, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, and hepatitis B virus replication inhibitors.

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®) or lamivudine (EPIVIR-HBV®) and at least a second additional therapeutic agent selected from the group consisting of peginterferon alfa-2b (PEG-INTRON®), MULTIFERON®, interferon alpha 1b (HAPGEN®), interferon alpha-2b (INTRON A®), pegylated interferon alpha-2a (PEGASYS®), interferon alfa-n1 (HUMOFERON®), ribavirin, interferon beta-1a (AVONEX®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon, and celmoleukin.

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, Arginase inhibitors, PI3K inhibitors, PD-1 inhibitors, PD-L1 inhibitors, IDO inhibitors, and stimulators of NOD2.

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of: adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one, two, or three additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); and and one, two, three, or four additional therapeutic agents selected from the group consisting of immunomodulators, TLR7 modulators, TLR8 modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, stimulators of NOD2 HBV viral entry inhibitors, NTCP inhibitors, HBx inhibitors, cccDNA inhibitors, siRNA, miRNA gene therapy agents, sshRNAs, KDM5 inhibitors, and nucleoprotein modulators (HBV core or capsid protein modulators).

In a particular embodiment, a compound disclosed herein, or any formula described herein, or a pharmaceutically acceptable salt, stereoisomer, mixture of stereoisomers, solvate, or tautomer thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (*Flexus* Biosciences, Inc.), WO2014073738 (*Flexus* Biosciences, Inc.), WO2015188085 (*Flexus* Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating hepatitis B virus (HBV), and combinations thereof.

In certain embodiments, a compound as disclosed herein (e.g., any compound of Formula I) may be combined with one or more (e.g., one, two, three, four, one or two, one to three, or one to four) additional therapeutic agents in any dosage amount of the compound of formula (I), or any formula described herein, or a pharmaceutically acceptable salt, stereoisomer, mixture of stereoisomers, solvate, or tautomer thereof, (e.g., from 10 mg to 1000 mg of compound).

In certain embodiments, a compound disclosed herein, or any formula described herein, or a pharmaceutically acceptable salt, stereoisomer, mixture of stereoisomers, solvate, or tautomer thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt, stereoisomer, mixture of stereoisomers, solvate, or tautomer thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt, stereoisomer, mixture of stereoisomers, solvate, or tautomer thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt, stereoisomer, mixture of stereoisomers, solvate, or tautomer thereof, is combined with 25 mg tenofovir alafenamide fumarate, tenofovir alafenamide hemifumarate, or tenofovir alafenamide. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt, stereoisomer, mixture of stereoisomers, solvate, or tautomer thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt, stereoisomer, mixture of stereoisomers, solvate, or tautomer thereof, is combined with 100 mg to 150 mg; 100 mg to 200 mg; 100 mg to 250 mg; 100 mg to 300 mg; 100 mg to 350 mg; 150 mg to 200 mg; 150 mg to 250 mg; 150 mg to 300 mg; 150 mg to 350 mg; 150 mg to 400 mg; 200 mg to 250 mg; 200 mg to 300 mg; 200 mg to 350 mg; 200 mg to 400 mg; 250 mg to 350 mg; 250 mg to 400 mg; 350 mg to 400 or 300 mg to 400 mg tenofovir disoproxil fumarate, tenofovir disoproxil hemifumarate, or tenofovir disoproxil. In certain embodiments, a compound disclosed herein, or a pharmaceutically acceptable salt, stereoisomer, mixture of stereoisomers, solvate, or tautomer thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt, stereoisomer, mixture of stereoisomers, solvate, or tautomer thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt, stereoisomer, mixture of stereoisomers, solvate, or tautomer thereof, is combined with 150 mg tenofovir disoproxil fumarate, tenofovir disoproxil hemifumarate, or tenofovir disoproxil. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In one embodiment, kits comprising a compound disclosed herein, or a pharmaceutically acceptable salt, stereoisomer, mixture of stereoisomers, solvate, or tautomer thereof, in combination with one or more (e.g., one, two, three, four, one or two, or one to three, or one to four) additional therapeutic agents are provided.

Any pharmaceutical composition provided in the present disclosure may be used in the kits, the same as if each and every composition were specifically and individually listed for use in a kit.

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of formula (I), e.g., compounds having structures described by one or more of formula (I), or other formulas or compounds disclosed herein, or a pharmaceutically acceptable salt, stereoisomer, mixture of stereoisomers, solvate, or tautomer thereof, may be accomplished as described in the following examples.

General Syntheses

Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein. Group labels (e.g., $R^1$, $R^a$, $R^b$) used in the reaction schemes herein are for illustrative purposes only and unless otherwise specified do not necessarily match by name or function the labels used elsewhere to describe compounds of formula (I), or any formula described herein, or aspects or fragments thereof.

Synthetic Reaction Parameters

The compounds of this disclosure can be prepared from readily available starting materials using, for example, the following general methods and procedures. It will be appreciated that where typical or preferred process conditions (e.g., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds as provided herein may be synthesized according to the general schemes provided below. In the Schemes below, it should be appreciated that each of the compounds shown therein may have protecting groups as required present at any step. Standard protecting groups are well within the pervue of one skilled in the art.

Scheme 1 shows an exemplary synthetic route for the synthesis of compounds provided herein (e.g., compounds of Formula I). In Scheme 1, $R^E$, $R^W$, $Z^1$, $Z^3$, t, w, $X^1$, $X^2$, $X^3$ and $X^4$ are as defined herein, Y is O or NH, each $R^{52}$ is independently $C_{1-6}$ alkyl or two $R^{52}$ together with the atom to which they are attached form a ring, each X is independently halo (e.g., bromo), $R^{50}$ is a functional group capable of forming a covalent bond with compound 108 (e.g., —C(O)H), $R^{55}$ is a leaving group (e.g., halo) and $R^{54}$ is hydrogen, a suitable protecting group and/or a leaving group with the oxygen atom to which it is bound.

In Scheme 1, suitably compound 100 is reacted with compound 101 under standard coupling conditions. In compound 100, $R^{54}$ is a suitable protecting group, such as a silane (e.g., TBS). Compound 102 is converted to compound 103 by converting —$OR^{54}$ to a leaving group (e.g., —OTf) and a suitable borate or borane reagent (e.g., 4,4,4',4',5,5, 5',5'-octamethyl-2,2'-bi(1,3,2-dioxaborolane).

In Scheme 1, compound 103 is coupled with compound 104 under standard metal-catalyzed coupling conditions (e.g., using a palladium catalyst) in a suitable solvent (e.g., dioxane, water, etc.), optionally under an inert atmosphere, to provide compound 105. Compound 105 is then coupled with compound 106 under standard metal-catalyzed cou-

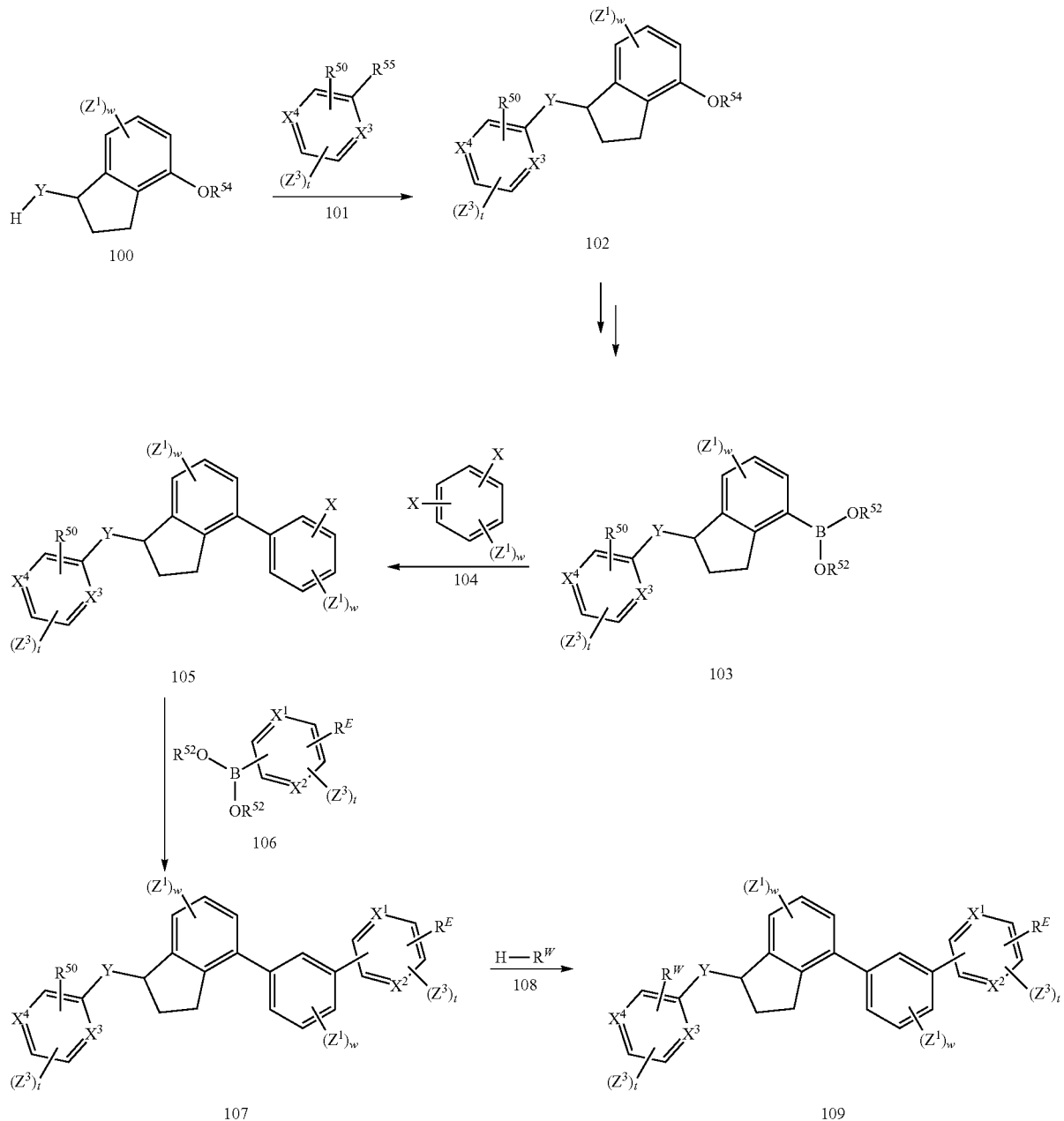

Scheme 1 pling conditions (e.g., using a palladium catalyst) in a suitable solvent (e.g., dioxane, water, etc.), optionally under an inert atmosphere, to provide compound 107. Compound 107 is then reacted with compound 108 under conditions suitable to provide compound 109. Exemplary conditions include, but are not limited to, reductive amination when $R^{50}$ is an aldehyde and compound 108 comprises a primary or secondary amine.

Suitably substituted compounds 100, 101, 104, 106 and 108 for use in the methods provided herein can be purchased from commercial sources or synthesized by known methods. Resolution of the isomers of Formula (I) can be performed as needed using standard chiral separation/resolution conditions (e.g., chromatography, crystallization, etc.).

EXAMPLES

The compounds were named using the IUPAC naming convention or using ChemBioDraw Ultra Version 14.0. Structures are drawn ChemBioDraw.

When production of starting materials is not particularly described, the compounds are known or may be prepared analogously to methods known in the art or as disclosed in the Examples. One of skill in the art will appreciate that synthetic methodologies described herein are only representative of methods for preparation of the compounds described herein, and that other known methods and variants of methods described herein may be used. The methods or features described in various Examples may be combined or adapted in various ways to provide additional ways of making the compounds described herein.

Intermediate I: (S)-5-(((((6-(2-chloro-3-(4,4,5,5-tetramethyl-1,3,2-dioxaborolan-2-yl)phenyl)-2-methoxypyridin-3-yl)methyl)amino)methyl)pyrrolidin-2-one

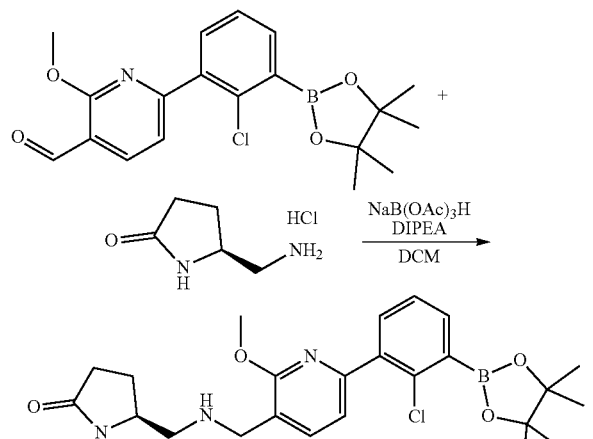

Intermediate I 6-(2-chloro-3-(4,4,5,5-tetramethyl-1,3,2-dioxaborolan-2-yl)phenyl)-2-methoxynicotinaldehyde (0.85 g, 2.28 mmol) and (S)-5-(aminomethyl)pyrrolidin-2-one hydrochloride (0.68 g, 4.56 mmol) were suspended in DCM. DIPEA (0.30 g, 2.28 mmol) was added and the mixture was stirred for 30 min at room temperature. Sodium triacetoxyborohydride (1.44 g, 6.8 mmol) was added and the reaction was stirred at ambient temperature for 4 h. The reaction was quenched with aq. NaHCO₃, and stirred vigorously at room temperature for 30 min. The reaction was diluted with brine, and extracted with DCM (50 mL, 2×). The combined organics were dried over anhydrous Na₂SO₄, concentrated, and purified by column chromatography. (10% MeOH in DCM), to provide (S)-5-((((6-(2-chloro-3-(4,4,5,5-tetramethyl-1,3,2-dioxaborolan-2-yl)phenyl)-2-methoxypyridin-3-yl)methyl)amino)methyl)pyrrolidin-2-one.

Intermediate II: 6-chloro-2-methoxynicotinaldehyde

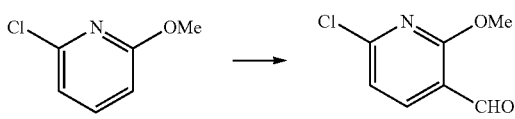 [SMILES: COc1cccc(Cl)n1 ; COc1nc(Cl)ccc1C=O]

To a stirred solution of 2-chloro-6-methoxypyridine (22.00 g, 143 mmol) in 500 mL THF at −78° C. was added t-BuLi in pentane (ca. 1.6 M, 1.1 equiv) via canula over 15 min. After stirring at the same temperature for 1 h, DMF (35.45 mL, 459 mmol, 3.0 equiv) was added dropwise (first 12 mL over 15 min, rest over 5 min). After being stirred at the same temperature for 30 min, the reaction mixture was warmed to room temperature over 30 min. The reaction was quenched with 1 M aqueous citric acid (326 mL), and the THF removed under vacuum. Aqueous layer was pH 4. The solid precipitate was filtered, washed well with water. The solid was dissolved in DCM, dried with MgSO₄ and filtered. Concentration provided a faintly yellow solid. Recrystallization from hexanes (36 mL) provided 6-chloro-2-methoxynicotinaldehyde. H NMR (400 MHz, DMSO-d₆) δ 10.16 (d, J=0.7 Hz, 1H), 8.11 (d, J=7.9 Hz, 1H), 7.26 (dd, J=7.9, 0.7 Hz, 1H), 4.00 (s, 3H).

Intermediate III: 6-(2-chloro-3-(4,4,5,5-tetramethyl-1,3,2-dioxaborolan-2-yl)phenyl)-2-methoxynicotinaldehyde

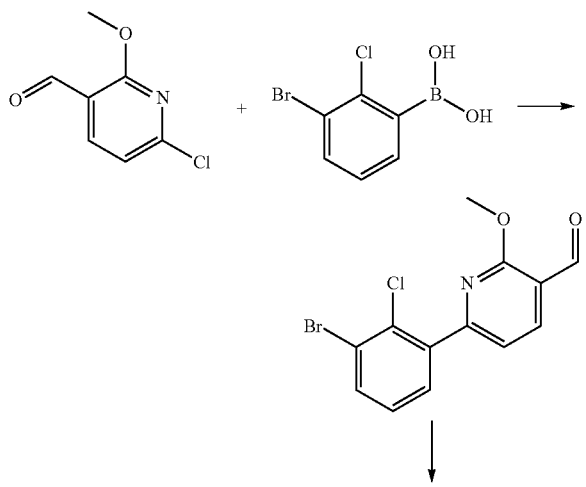

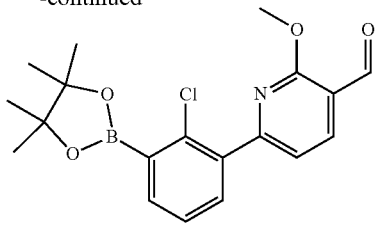

6-Chloro-2-methoxynicotinaldehyde (1.2 g, 7.01 mmol), (3-bromo-2-chlorophenyl)boronic acid (1.5 g, 6.38 mmol), potassium carbonate (1.76 g, 12.75 mmol), and tetrakis(triphenylphosphine)palladium(0) (0.37 g, 0.32 mmol), were suspended in 30 mL of a 10:1 mixture of dioxane and water. The mixture was sparged with argon gas for 10 minutes, and heated at 95 C for 3 h. The solution was cooled to room temperature, and diluted with dichloromethane (100 mL), water (50 mL), and brine (50 mL). The organic layer was separated, and aqueous layer extracted once with dichloromethane (50 mL). The combined organic layers were dried over $Na_2SO_4$, filtered, and concentrated to yield a crude yellow solid. The yellow solid was crushed, and diluted with diethylether, sonicated, and filtered. The solid was washed twice with diethylether and dried to give 6-(3-bromo-2-chlorophenyl)-2-methoxynicotinaldehyde. $^1$H NMR (400 MHz, DMSO-$d_6$) δ 10.30 (s, 1H), 8.22 (d, J=7.7 Hz, 1H), 7.93 (dd, J=8.1, 1.5 Hz, 1H), 7.65 (dd, J=7.7, 1.5 Hz, 1H), 7.53-7.31 (m, 2H), 4.04 (s, 3H).

6-(3-bromo-2-chlorophenyl)-2-methoxynicotinaldehyde (720 mg, 2.2 mmol), bis(pinacolato)diborane (615.85 mg, 2.43 mmol), potassium acetate (605.85 mg, 6.17 mmol), and 1,1'-Bis(diphenylphosphino)ferrocene-palladium(II)dichloride dichloromethane complex (182.27 mg, 0.22 mmol) were suspended in 20 mL of dioxane. The resulting suspension was sparged with argon for 5 min. The reaction was sealed and stirred at 95 C for 6 h. The reaction was diluted with ethyl acetate, and filtered through a plug of celite. The filtrate was concentrated and purified by silica gel chromatography, eluting with EtOAc (0-10%) in hexanes to provide 6-(2-chloro-3-(4,4,5,5-tetramethyl-1,3,2-dioxaborolan-2-yl)phenyl)-2-methoxynicotinaldehyde. $^1$H NMR (400 MHz, DMSO-$d_6$) δ 10.30 (s, 1H), 8.20 (d, J=7.7 Hz, 1H), 7.88-7.61 (m, 2H), 7.49 (t, J=7.5 Hz, 1H), 7.42 (d, J=7.7 Hz, 1H), 4.04 (s, 3H), 1.34 (s, 12H).

Intermediate IV: Methyl 2-azabicyclo[2.2.2]octane-4-carboxylate hydrochloride

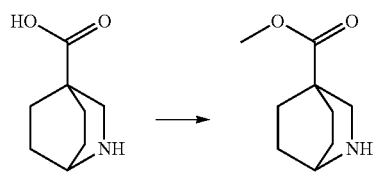

In a glass recovery flask 10.00 g (0.052 mol) of 2-azabicyclo[2.2.2]octane-4-carboxylic acid hydrochloride was dissolved in 104 ml of dry methanol and the solution was cooled in an ice bath for 5 min. The flask was capped using a rubber septum and attached to a line of nitrogen. Internal temperature was measured at 3° C. and at this point thionyl chloride 7.76 ml (0.104 mol) was added dropwise while keeping the solution in an ice bath. Once addition was complete the ice bath was removed and solution was stirred for 5 min at room temperature. The septum was removed and a water condenser was attached. The solution was stirred at 40° C. for 2 hours under a stream of nitrogen. After completion, volatiles were removed under reduced pressure to obtain methyl 2-azabicyclo[2.2.2]octane-4-carboxylate hydrochloride.

Intermediate V: Methyl(S)-2-((5-((4-bromo-2,3-dihydro-1H-inden-1-yl)amino)-3-methoxy-6-(trifluoromethyl)pyrazin-2-yl)methyl)-2-azabicyclo[2.2.2]octane-4-carboxylate

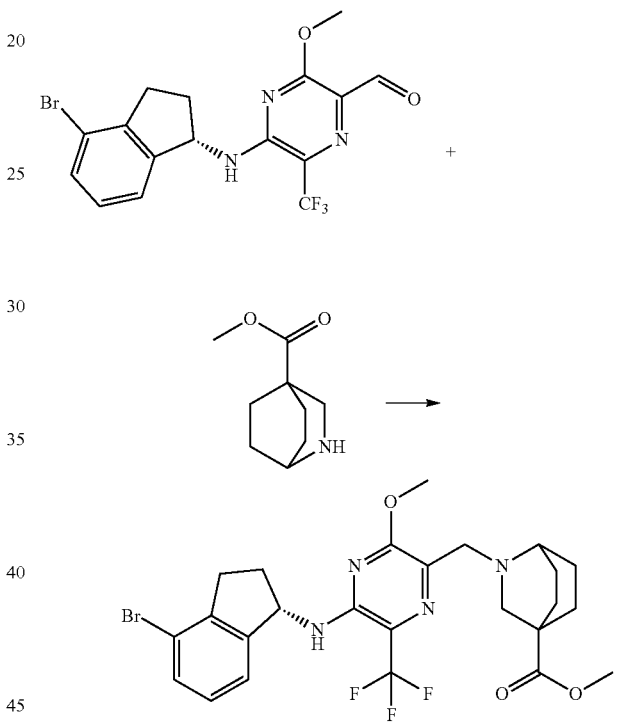

In a glass recovery flask 15.00 g of (S)-5-((4-bromo-2,3-dihydro-1H-inden-1-yl)amino)-3-methoxy-6-(trifluoromethyl)pyrazine-2-carbaldehyde (0.036 mol) and 9.00 g of 2-azabicyclo[2.2.2]octane-4-carboxylate hydrochloride (0.044 mol) were dissolved in 150 ml of dry MethylTHF. 18.8 ml of DIPEA was added in one portion and stirred vigorously at room temperature for 5 min. 16.80 g of sodium triacetoxyborohydride (0.079 mol) was added in small portions at room temperature and stirred for 1 hour under nitrogen. Upon completion by LCMS, the reaction was quenched with 300 ml of 5% $NaHCO_3$. An additional 20 ml MethylTHF was added and stirred vigorously for 10 min. The solution was then transferred to a separatory funnel and organics were extracted 3 times with 100 ml of MethylTHF. The organic layer was washed 3 times with brine dried over magnesium sulfate, filtered, and volatiles were removed under reduced pressure. The residue was loaded onto a silica gel column and eluted with 0-100% EtOAc/Hex to give the title compound.

Intermediate VI: (S)-5-((4-bromo-2,3-dihydro-1H-inden-1-yl)amino)-3-methoxy-6-(trifluoromethyl)pyrazine-2-carbaldehyde

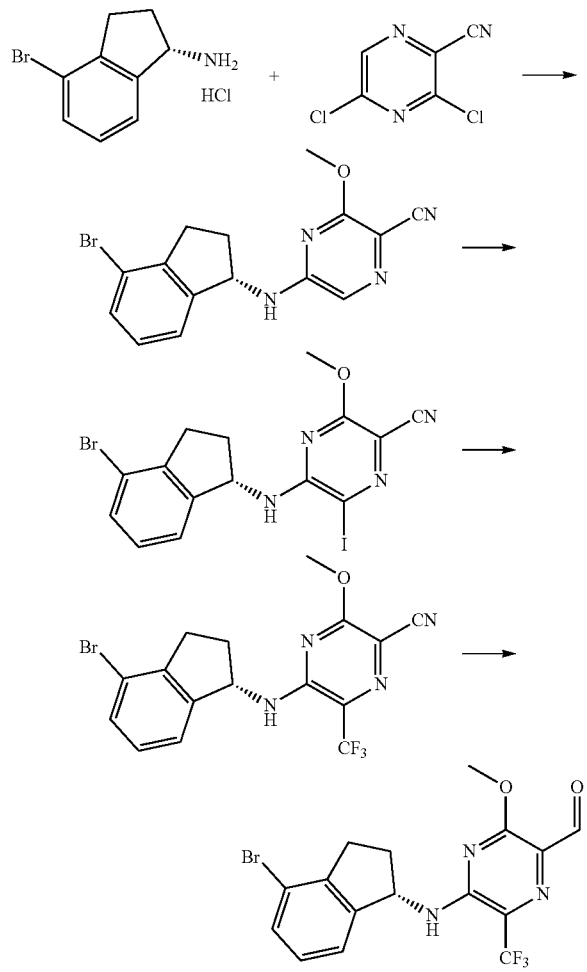

(S)-5-((4-bromo-2,3-dihydro-1H-inden-1-yl)amino)-3-methoxypyrazine-2-carbonitrile: (S)-4-bromo-2,3-dihydro-1H-inden-1-amine hydrochloride (100 g) was suspended in 500 mL DMF. Hunigs base (154 mL) was added in a single portion and the suspension was cooled in an ice bath for 10 min. When internal temp reached −10 C, 3,5-dichloropyrazine-2-carbonitrile (73.5 g, 1.05 eq) was added portionwise over 10 min. The internal temperature was −25 C at the end of the addition. The ice bath was removed and the reaction stirred for 15 min. 1 L of 25% sodium methoxide was added and the reaction was heated to 95 C external temp. Internal −80 C after 1 h. After 90 min total reaction time, the mixture was cooled to RT, and then cooled in an ice bath for 30 min. 1 L of water was added dropwise while cooling in an ice bath over 1 h. The reaction was filtered, rinsed twice with water, and the solid was dried overnight in a vacuum oven to give (S)-5-((4-bromo-2,3-dihydro-1H-inden-1-yl)amino)-3-methoxypyrazine-2-carbonitrile.

(S)-5-((4-bromo-2,3-dihydro-1H-inden-1-yl)amino)-6-iodo-3-methoxypyrazine-2-carbonitrile: (S)-5-((4-bromo-2,3-dihydro-1H-inden-1-yl)amino)-3-methoxypyrazine-2-carbonitrile (126 g) and potassium acetate (90 g) were suspended in 2 L of acetic acid. After stirring the suspension for 15 minutes, N-iodosuccinimide (88.7 g) was added in portions over 10 min. The reaction was heated to an internal temperature of 41° C. (50° C. external temperature) for 3 h. Water (1 L) was added in a controlled manner to facilitate precipitation of the product. The precipitate was filtered, washed with water, and dried overnight in a vacuum oven to provide (S)-5-((4-bromo-2,3-dihydro-1H-inden-1-yl)amino)-6-iodo-3-methoxypyrazine-2-carbonitrile.

(S)-5-((4-bromo-2,3-dihydro-1H-inden-1-yl)amino)-3-methoxy-6-(trifluoromethyl)pyrazine-2-carbonitrile: (S)-5-((4-bromo-2,3-dihydro-1H-inden-1-yl)amino)-6-iodo-3-methoxypyrazine-2-carbonitrile (165 g) and CuI (80.1 g) were suspended in DMF (700 mL). Methyl 2-(fluorosulfonyl)difluoroacetate (125 g) was added to the suspension and the mixture was sparged with argon gas for 5 minutes. The reaction mixture was heated for 2.5 h at 100° C. (internal temperature of 95° C. at 2 h reaction time). The reaction was filtered to remove insoluble copper salts, and rinsed with minimal DMF. The DMF filtrate was cooled with an ice bath, and water (750 mL) was added in a controlled manner over 45 min to facilitate precipitation of the product. The filtrate was washed with water, and dried overnight in vacuum oven to provide (S)-5-((4-bromo-2,3-dihydro-1H-inden-1-yl)amino)-3-methoxy-6-(trifluoromethyl)pyrazine-2-carbonitrile.

(S)-5-((4-bromo-2,3-dihydro-1H-inden-1-yl)amino)-3-methoxy-6-(trifluoromethyl) pyrazine-2-carbaldehyde: (S)-5-((4-bromo-2,3-dihydro-1H-inden-1-yl)amino)-3-methoxy-6-(trifluoromethyl) pyrazine-2-carbonitrile (139 g) was dissolved in 2.1 L DCM and cooled with an ice bath (internal temperature—3° C.) under stirring. Schwartz reagent (Cp$_2$ZrClH) (150 g, 1.75 equiv.) was added portion wise over 20 min to maintain an internal temperature of <3° C. After 45 min, LCMS showed complete conversion, and the reaction was quenched with acetonitrile 30 mL, and stirred for 15 min at rt. Silica gel 625 g, and water (12 mL) was added and stirred for 15 min. The mixture was divided into two equal portions and each was filtered over a plug of silica (300 g) and eluted with 4×1.5 L of DCM to provide four fractions. All fractions were combined and concentrated to dryness. Toluene (750 mL) was charged to the material and heated to reflux to yield a brown solution. The solution was placed in a 100° C. sand bath and stirred. The heating element was turned off and hexane (370 mL) was added dropwise over 1-2 h. The reaction cooled overnight gradually under stirring to allow for crystallization. The tan solid was filtered the next day to provide (S)-5-((4-bromo-2,3-dihydro-1H-inden-1-yl)amino)-3-methoxy-6-(trifluoromethyl) pyrazine-2-carbaldehyde.

Intermediate VII: (S)-5-(((((6-(2-chloro-3-(4,4,5,5-tetramethyl-1,3,2-dioxaborolan-2-yl)phenyl)-2-methoxypyridin-3-yl)methyl)amino)methyl)pyrrolidin-2-one

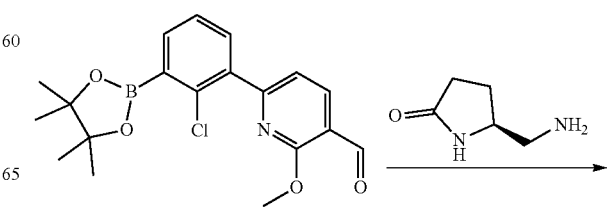

-continued

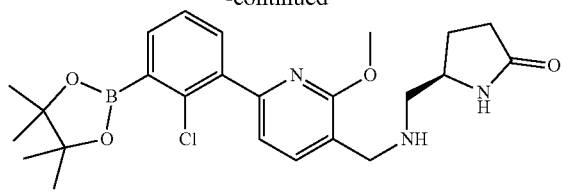

6-(2-chloro-3-(4,4,5,5-tetramethyl-1,3,2-dioxaborolan-2-yl)phenyl)-2-methoxynicotinaldehyde (50 g, 133.82 mmol), (S)-5-(aminomethyl)pyrrolidin-2-one hemioxalate (25.6 g, 160.6 mmol), N,N-Diisopropylethylamine (58 mL, 334.5 mmol) were suspended in 500 mL 1:1 DCM/EtOH and allowed to mix for 0.5 h. Sodium triacetoxyborohydride (85 g, 401.5 mmol) was then added portion wise over 5 min and allowed to mix for 1 h. A saturated solution of sodium bicarbonate (500 mL) and water (500 mL) was then gradually added. Upon cessation of gas formation the crude mixture was transferred to a 2 L separatory funnel and the organic layer was separated. The aqueous layer was then extracted twice more with 250 mL DCM. The organic layers were combined, dried over sodium sulfate and concentrated to dryness in vacuo. The crude material was then purified by flash chromatography using a 0 to 20% DCM/Methanol gradient to provide (S)-5-(((((6-(2-chloro-3-(4,4,5,5-tetramethyl-1,3,2-dioxaborolan-2-yl)phenyl)-2-methoxypyridin-3-yl)methyl)amino)methyl)pyrrolidin-2-one.

Procedure 1: (R)-1-((6-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-2-methoxy-5-(trifluoromethyl)pyridin-3-yl)methyl)-3-methylpyrrolidine-3-carboxylic Acid (A-2)

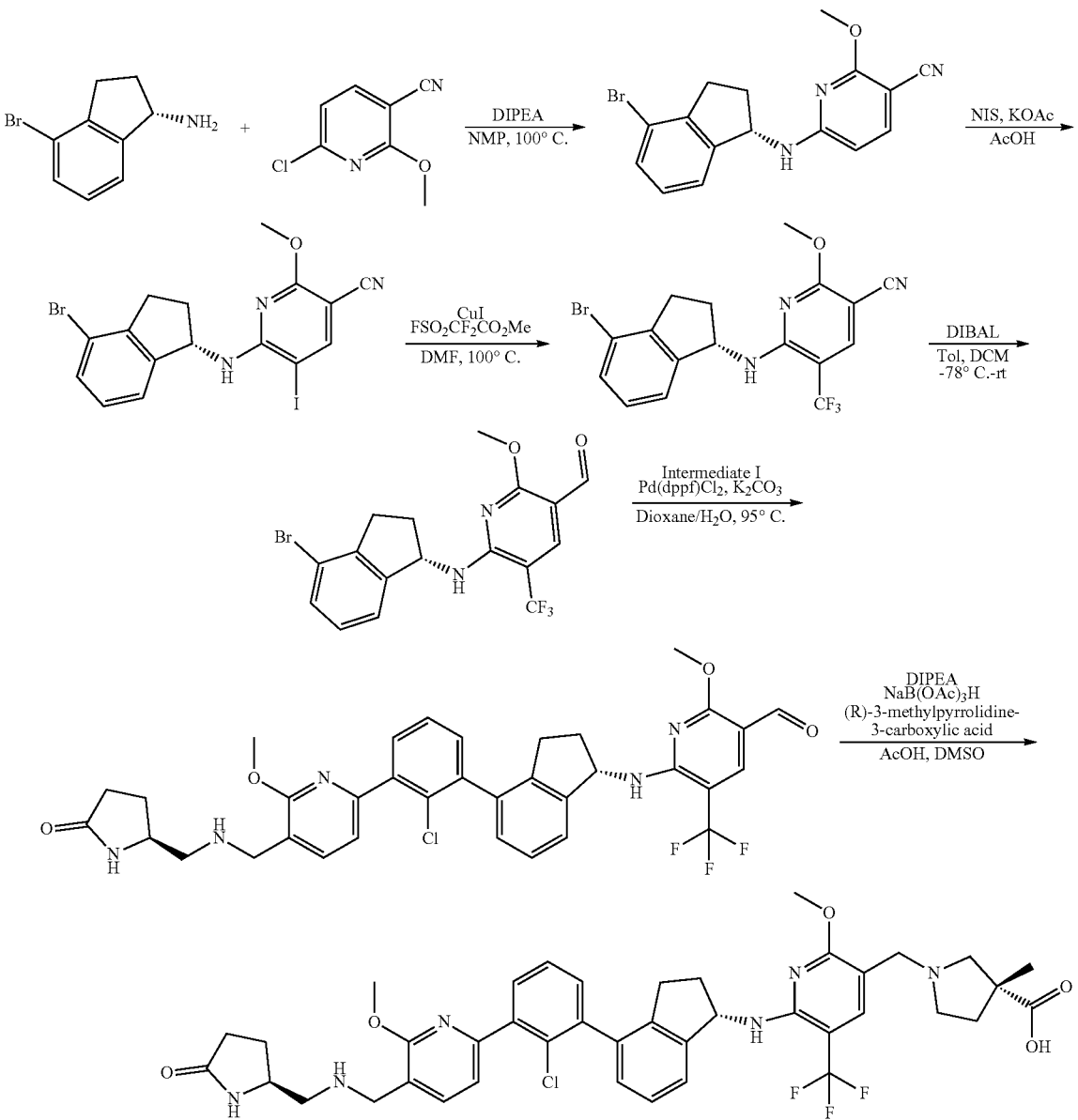

(S)-6-((4-bromo-2,3-dihydro-1H-inden-1-yl)amino)-2-methoxynicotinonitrile: (S)-4-bromo-2,3-dihydro-1H-inden-1-amine (1.5 g, 7.07 mmol), 6-chloro-2-methoxynicotinonitrile (1.50 g, 8.8 mmol), and N,N-diisopropylethylamine (1.83 g, 14.1 mmol), were suspended in N-Methyl-2-pyrrolidone (7 mL). The suspension was stirred and heated to 100° C. for 4 h. The reaction was cooled to room temperature, and diluted with ethyl acetate and diethyl ether. The mixture was washed with water and brine, dried over anhydrous sodium sulfate, and concentrated. The product was purified by column chromatography (ethyl acetate/hexanes) to provide (S)-6-((4-bromo-2,3-dihydro-1H-inden-1-yl)amino)-2-methoxynicotinonitrile.

(S)-6-((4-bromo-2,3-dihydro-1H-inden-1-yl)amino)-5-iodo-2-methoxynicotinonitrile: (S)-6-((4-bromo-2,3-dihydro-1H-inden-1-yl)amino)-2-methoxynicotinonitrile (600 mg, 1.74 mmol), potassium acetate (1.7 g mg, 17.4 mmol), and N-iodosuccinimide (430 mg, 1.9 mmol), were suspended in acetic acid (10 mL). The reaction was stirred at room temperature for 30 minutes and then diluted with ethyl acetate and water. The reaction was cooled with an ice bath and quenched carefully with 2M NaOH until pH>9. The organic layer was separated, and the aqueous extracted with ethyl acetate. The combined organics were dried over anhydrous sodium sulfate, and concentrated. The product was purified by column chromatography (ethyl acetate/hexanes) to provide (S)-6-((4-bromo-2,3-dihydro-1H-inden-1-yl)amino)-5-iodo-2-methoxynicotinonitrile.

(S)-6-((4-bromo-2,3-dihydro-1H-inden-1-yl)amino)-2-methoxy-5-(trifluoromethyl)nicotinonitrile: (S)-6-((4-bromo-2,3-dihydro-1H-inden-1-yl)amino)-5-iodo-2-methoxynicotinonitrile (465 mg, 1.0 mmol) and copper(I) iodide (283 mg, 1.48 mmol) were suspended in DMF (5 mL). Methyl 2-(fluorosulfonyl)difluoroacetate (380 mg, 1.98 mmol) was added to the suspension and the mixture was sparged with argon gas for 5 minutes. The reaction was transferred to a heating block and stirred for 2 h at 100° C. The reaction was cooled and diluted with ethyl acetate and diethyl ether. The reaction was filtered to remove insoluble copper salts, and rinsed with ethyl acetate.

The combined organics were washed with water and brine, dried over anhydrous sodium sulfate, and concentrated. The product was purified by column chromatography (ethyl acetate/hexanes) to provide (S)-6-((4-bromo-2,3-dihydro-1H-inden-1-yl)amino)-2-methoxy-5-(trifluoromethyl)nicotinonitrile.

(S)-6-((4-bromo-2,3-dihydro-1H-inden-1-yl)amino)-2-methoxy-5-(trifluoromethyl)nicotinaldehyde: (S)-6-((4-bromo-2,3-dihydro-1H-inden-1-yl)amino)-2-methoxy-5-(trifluoromethyl)nicotinonitrile (0.36 g, 0.88 mmol), was dissolved in toluene (9 mL). The solution was cooled to −78° C., and then a 1 M solution of diisobutylaluminum hydride in DCM (1.75 mL, 1.75 mmol) was added dropwise. The reaction was warmed to room temperature and stirred for 30 minutes, upon which the reaction was cooled to 0° C., and a mixture of 1 M HCl, and MeOH was added to quench the reaction. The reaction was warmed to room temperature and stirred vigorous for 1 h. The reaction was diluted with ethyl acetate, and basified with 2M NaOH. The aqueous layer was extracted 2× with ethyl acetate. The combined organics were washed with water and brine, dried over anhydrous sodium sulfate, and concentrated. The product was purified by column chromatography (ethyl acetate/hexanes) to provide (S)-6-((4-bromo-2,3-dihydro-1H-inden-1-yl)amino)-2-methoxy-5-(trifluoromethyl)nicotinaldehyde.

6-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-2-methoxy-5-(trifluoromethyl)nicotinaldehyde: (S)-6-((4-bromo-2,3-dihydro-1H-inden-1-yl)amino)-2-methoxy-5-(trifluoromethyl)nicotinaldehyde (280 mg, 0.67 mmol), (S)-5-((((6-(2-chloro-3-(4,4,5,5-tetramethyl-1,3,2-dioxaborolan-2-yl)phenyl)-2-methoxypyridin-3-yl)methyl)amino)methyl)pyrrolidin-2-one [Intermediate I] (318.15 mg, 0.67 mmol), (1,1'-Bis(diphenylphosphino)ferrocene)palladium(II) dichloride (73 mg, 0.09 mmol), and potassium carbonate (280 mg, 2.02 mmol) were suspended in a 9:1 mixture of dioxane to water (7 mL). The suspension was sparged with argon gas for 5 minutes and heated to 95° C. for 4 h. The reaction was diluted with EtOAc and dried over anhydrous sodium sulfate. The solution was filtered, concentrated, and purified by column chromatography (10% MeOH in DCM) to provide 6-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-2-methoxy-5-(trifluoromethyl)nicotinaldehyde.

(R)-1-((6-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-2-methoxy-5-(trifluoromethyl)pyridin-3-yl)methyl)-3-methylpyrrolidine-3-carboxylic acid: 6-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-2-methoxy-5-(trifluoromethyl)nicotinaldehyde (45 mg, 0.07 mmol), (R)-3-methylpyrrolidine-3-carboxylic acid (34 mg, 0.26 mmol), DIPEA (34 mg, 0.26 mmol), and AcOH (4 mg, 0.07 mmol) were suspended in DMSO (2 mL). The suspension was heated to 50° C. and stirred for 30 minutes. Sodium triacetoxyborohydride (112 mg, 0.53 mmol) was added in one portion and the reaction was stirred at to 50° C. for 2 h. The reaction was cooled to 0° C. and diluted with DMF (0.5 mL), water (1 mL) and trifluoroacetic acid (0.2 mL). The reaction was stirred vigorously for 30 minutes and purified by reverse phase HPLC (0.1% trifluoroacetic acid in acetonitrile/water) providing (R)-1-((6-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-2-methoxy-5-(trifluoromethyl)pyridin-3-yl)methyl)-3-methylpyrrolidine-3-carboxylic acid as the bis-TFA salt. [M+1]=792.874. $^1$H NMR (400 MHz, Methanol-$d_4$) δ 7.95-7.79 (m, 2H), 7.59 (d, J=8.1 Hz, 1H), 7.48 (t, J=7.6 Hz, 1H), 7.41-7.21 (m, 4H), 7.21-7.12 (m, 1H), 5.99-5.80 (m, 1H), 4.41-4.23 (m, 4H), 4.10 (s, 3H), 4.08-3.80 (m, 5H), 3.61 (s, 1H), 3.44-3.33 (m, 1H), 3.28-3.19 (m, 2H), 3.13-2.72 (m, 3H), 2.69-2.25 (m, 5H), 2.25-1.83 (m, 3H), 1.46 (d, J=15.8 Hz, 3H).

131

Procedure 2: (R)-1-(5-chloro-4-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-2-methoxybenzyl)-3-methylpyrrolidine-3-carboxylic Acid (A-14)

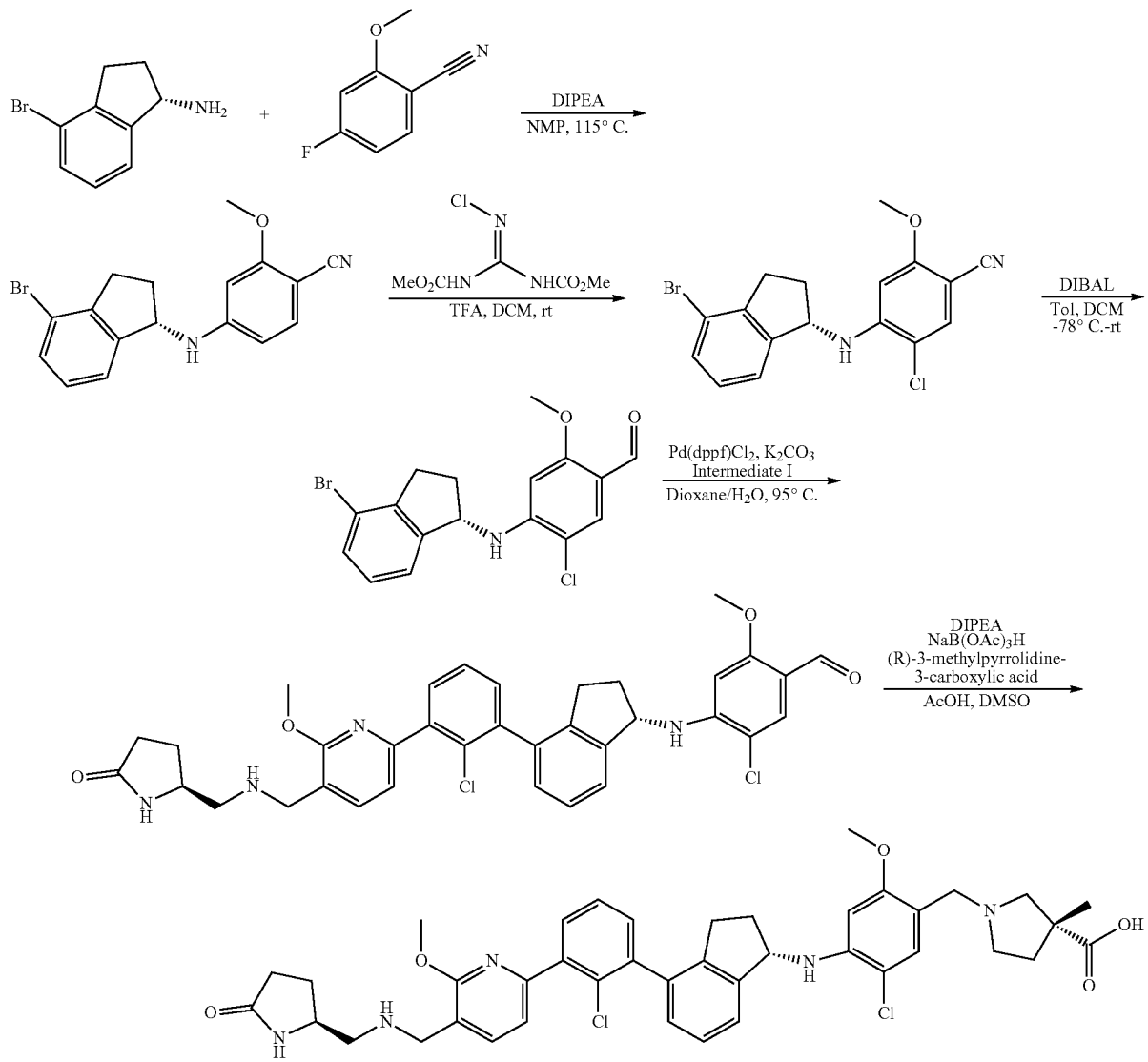

(S)-4-((4-bromo-2,3-dihydro-1H-inden-1-yl)amino)-2-methoxybenzonitrile: (S)-4-bromo-2,3-dihydro-1H-inden-1-amine (1.0 g, 4.7 mmol), 4-fluoro-2-methoxybenzonitrile (0.89 g, 5.89 mmol), and N,N-Diisopropylethylamine (0.90 g, 7.1 mmol), were suspended in N-Methyl-2-pyrrolidone (5 mL). The suspension was stirred and heated to 115° C. for 48 h. The reaction was cooled to room temperature, and diluted with ethyl acetate and diethyl ether. The mixture was washed with water and brine, dried over anhydrous sodium sulfate, and concentrated. The product was purified by column chromatography (ethyl acetate/hexanes) to provide (S)-4-((4-bromo-2,3-dihydro-1H-inden-1-yl)amino)-2-methoxybenzonitrile.

(S)-4-((4-bromo-2,3-dihydro-1H-inden-1-yl)amino)-5-chloro-2-methoxybenzonitrile: (S)-4-((4-bromo-2,3-di-hydro-1H-inden-1-yl)amino)-2-methoxybenzonitrile (150 mg, 0.44 mmol) and 2-Chloro-1,3-bis(methoxycarbonyl)guanidine (92 mg, 0.44 mmol) was suspended in chloroform (5 mL). Trifluoroacetic acid (5 mg 0.04 mmol), was added and the solution was stirred at room temperature for 1 h. The reaction was diluted with DCM, washed with sat. aqueous NaHCO$_3$, and brine. The organic layer was dried over anhydrous sodium sulfate, and concentrated. The product was purified by column chromatography (ethyl acetate/hexanes) to provide (S)-4-((4-bromo-2,3-dihydro-1H-inden-1-yl)amino)-5-chloro-2-methoxybenzonitrile.

(R)-1-(5-chloro-4-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-2-methoxybenzyl)-3-methylpyrrolidine-3-carboxylic acid: The title compound was synthesized and isolated as the bis-TFA salt following procedures from Procedure 1, in which (S)-4-((4-bromo-2,3-dihydro-1H-inden-1-yl)amino)-5-chloro-2-methoxybenzonitrile was used in the place of (S)-6-((4-bromo-2,3-dihydro-1H-inden-1-yl)amino)-2-methoxy-5-(trifluoromethyl)nicotinaldehyde. [M+1]

=757.896. ¹H NMR (400 MHz, Methanol-d₄) δ 7.99-7.84 (m, 1H), 7.72-7.54 (m, 1H), 7.54-7.45 (m, 1H), 7.44-7.28 (m, 5H), 7.20 (s, 1H), 6.65-6.49 (m, 1H), 5.39-5.23 (m, 1H), 4.41-4.22 (m, 4H), 4.15-4.00 (m, 4H), 4.00-3.81 (m, 4H), 3.65-3.51 (m, 1H), 3.44-3.35 (m, 1H), 3.29-3.20 (m, 2H), 3.08-2.95 (m, 1H), 2.92-2.70 (m, 2H), 2.68-2.62 (m, 1H), 2.57-2.22 (m, 4H), 2.20-1.82 (m, 3H), 1.45 (d, J=14.6 Hz, 3H).

Procedure 3: 2-((5-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-3-methoxy-6-(trifluoromethyl)pyrazin-2-yl)methyl)-2-azabicyclo[2.2.2]octane-4-carboxylic Acid (A-18)

(S)-5-((4-bromo-2,3-dihydro-1H-inden-1-yl)amino)-3-chloropyrazine-2-carbonitrile: A solution of (S)-4-bromo-2,3-dihydro-1H-inden-1-amine (1.0 g, 4.7 mmol) in DMF (2 mL) was added dropwise to a mixture of 3,5-dichloropyrazine-2-carbonitrile (1.0 g, 5.89 mmol) and N,N-Diisopropylethylamine (1.2 g, 9.4 mmol) in DMF (3 mL). After stirring for 15 minutes at room temperature, the reaction was diluted with ethyl acetate and diethyl ether. The mixture was washed with water and brine, dried over anhydrous sodium sulfate, and concentrated. The product was purified by column chromatography (ethyl acetate/hexanes) to provide (S)-5-((4-bromo-2,3-dihydro-1H-inden-1-yl)amino)-3-chloropyrazine-2-carbonitrile.

(S)-5-((4-bromo-2,3-dihydro-1H-inden-1-yl)amino)-3-methoxypyrazine-2-carbonitrile: (S)-5-((4-bromo-2,3-dihydro-1H-inden-1-yl)amino)-3-chloropyrazine-2-carboni-

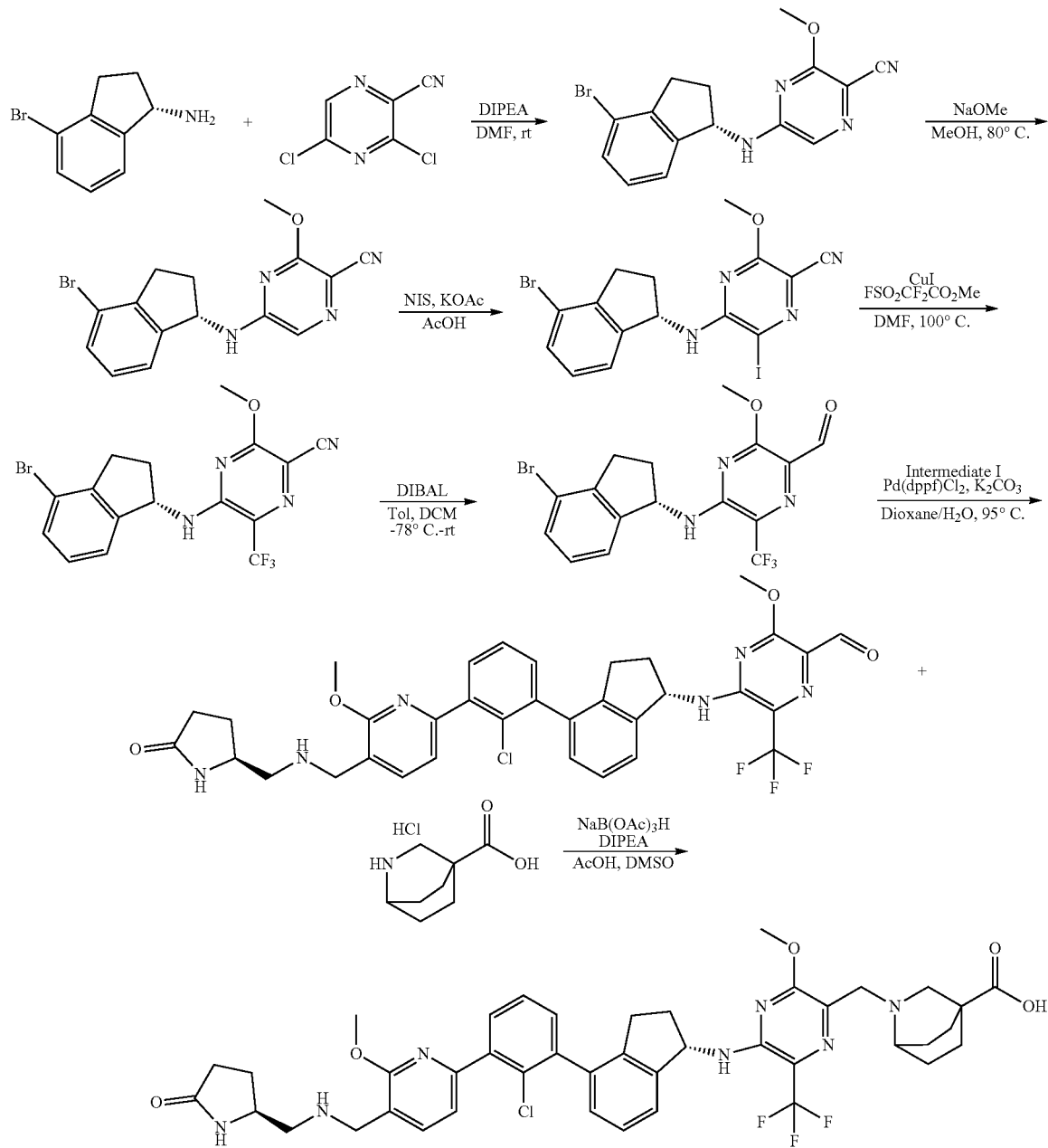

trile (1.6 g, 4.6 mmol) was dissolved in methanol (15 mL). A 25% solution of sodium methoxide in methanol (6 mL) was added and the solution was heated to 80° C. for 2 h. The reaction was cooled to room temperature, diluted with ethyl acetate, and washed with sat. aqueous NaHCO$_3$, and brine. The organic layer was dried over anhydrous sodium sulfate, and concentrated. The product was purified by column chromatography (ethyl acetate/hexanes) to provide (S)-5-((4-bromo-2,3-dihydro-1H-inden-1-yl)amino)-3-methoxypyrazine-2-carbonitrile.

5-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-3-methoxy-6-(trifluoromethyl)pyrazine-2-carbaldehyde: The title compound was synthesized and obtained following procedures from Procedure 1, in which (S)-5-((4-bromo-2,3-dihydro-1H-inden-1-yl)amino)-3-methoxypyrazine-2-carbonitrile was used in the place of (S)-6-((4-bromo-2,3-dihydro-1H-inden-1-yl)amino)-2-methoxynicotinonitrile.

2-((5-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-3-methoxy-6-(trifluoromethyl)pyrazin-2-yl)methyl)-2-azabicyclo[2.2.2]octane-4-carboxylic acid: 5-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-3-methoxy-6-(trifluoromethyl)pyrazine-2-carbaldehyde (70 mg, 0.1 mol), 2-azabicyclo[2.2.2]octane-4-carboxylic acid hydrochloride (59 mg, 0.31 mmol), DIPEA (53 mg, 0.41 mmol), and AcOH (4 mg, 0.07 mmol) was suspended in DMSO (2.5 mL). The suspension was heated to 50° C. and stirred for 30 minutes. Sodium triacetoxyborohydride (175 mg, 0.82 mmol) was added in one portion and the reaction was stirred at to 50° C. for 5 h. The reaction was cooled to 0° C. and diluted with DMF (1 mL), water (2 mL) and trifluoroacetic acid (0.3 mL). The reaction was stirred vigorously for 30 minutes and purified by reverse phase HPLC (0.1% trifluoroacetic acid in acetonitrile/water) providing 2-((5-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-3-methoxy-6-(trifluoromethyl)pyrazin-2-yl)methyl)-2-azabicyclo[2.2.2]octane-4-carboxylic acid as the bis-TFA salt. [M+1]=820.206. $^1$H NMR (400 MHz, Methanol-d$_4$) δ 8.00-7.87 (m, 1H), 7.70-7.56 (m, 1H), 7.56-7.47 (m, 1H), 7.46-7.26 (m, 4H), 7.24-7.13 (m, 1H), 6.00-5.79 (m, 1H), 4.60-4.29 (m, 4H), 4.16-4.02 (m, 4H), 3.99 (s, 3H), 3.77 (d, J=12.5 Hz, 1H), 3.61 (s, 1H), 3.30-3.27 (m, 2H), 2.92-2.71 (m, 2H), 2.63 (s, 1H), 2.50-2.35 (m, 4H), 2.24-1.77 (m, 9H).

Procedure 5: 2-((5-(((S)-4-(2-chloro-3-(6-methoxy-5-(((((S)-5-oxopyrrolidin-2-yl)methyl)amino) methyl)pyridin-2-yl)phenyl)-2,3-dihydro-1H-inden-1-yl)amino)-3-methoxy-6-(trifluoromethyl)pyrazin-2-yl)methyl)-2-azabicyclo[2.2.2]octane-4-carboxylic Acid (A-18)

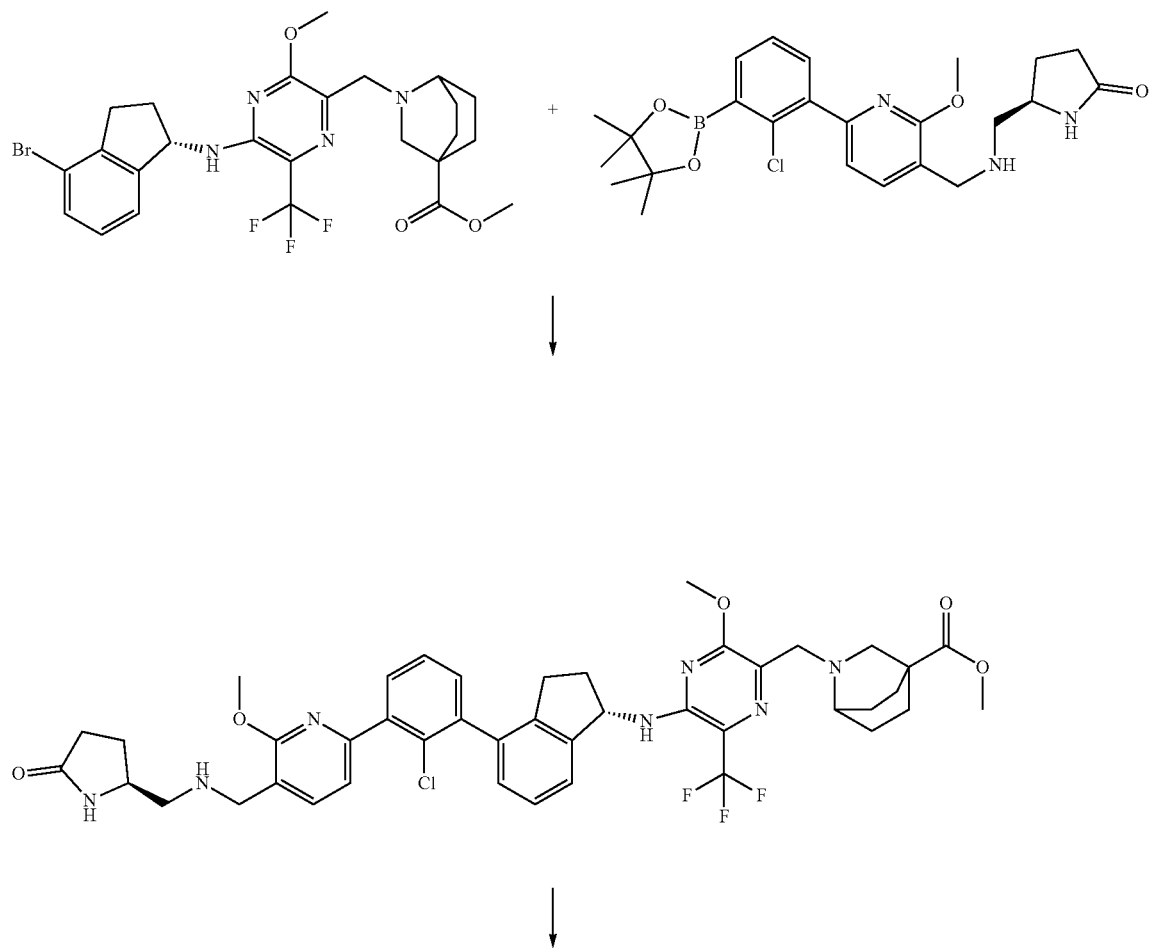

-continued

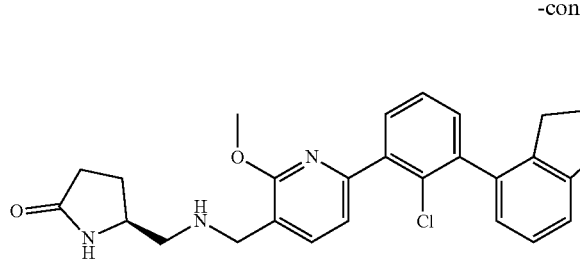 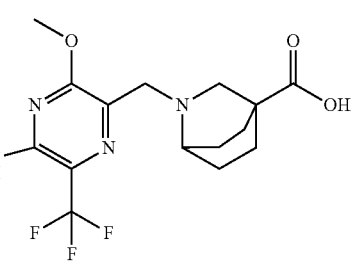

To a 250 mL flask was charged 5.395 g (9.475 mmol) methyl (S)-2-((5-((4-bromo-2,3-dihydro-1H-inden-1-yl)amino)-3-methoxy-6-(trifluoromethyl)pyrazin-2-yl)methyl)-2-azabicyclo[2.2.2]octane-4-carboxylate, 6.258 g (13.26 mmol) (S)-5-(((6-(2-chloro-3-(4,4,5,5-tetramethyl-1,3,2-dioxaborolan-2-yl)phenyl)-2-methoxypyridin-3-yl)methyl)amino)methyl)pyrrolidin-2-one, 2.619 g (18.95 mmol) of $K_2CO_3$, 10.79 mL water and 43.19 mL DME. The mixture was degassed with $N_2$. 0.6777 g (0.9475 mmol) $PdCl_2Bis(Amphos)$ was added and the mixture was heated at 80° C. for 1.5 h. The reaction was cooled to 20° C. and split between 80 mL iPrOAc and 80 mL water. The organic phase was washed a second time with 54 mL of water. The organic phase was stripped down to a foam which was dissolved in 65 mL DMF. 3.8 mL Ethane-1,2-diamine and 1.6 g Darco was added and with vigorous stirring, heated to 45° C. for 2 h. The dark solution was then cooled to 20° C. and filtered over celite. The flask and celite were washed with 270 mL of iPrOAc. The large organic phase was washed twice with 100 mL of water to remove the DMF and the resultant organic phase was evaporated. The residue was further purified by flash column using 0-20% methanol in DCM to yield methyl 2-((5-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-3-methoxy-6-(trifluoromethyl)pyrazin-2-yl)methyl)-2-azabicyclo[2.2.2]octane-4-carboxylate.

Methyl 2-((5-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-3-methoxy-6-(trifluoromethyl)pyrazin-2-yl)methyl)-2-azabicyclo[2.2.2]octane-4-carboxylate (1000 mg, 1.2 mmol) and isopropanol (5 mL) were combined. 1N NaOH solution (2.4 mL, 2 eq) was added. The mixture was stirred at rt overnight, then neutralized with 1N HCl to pH7. Aqueous $NaHCO_3$ (10 mL) and brine (10 mL) were added. The mixture was extracted with isopropyl acetate (15 mL). The aqueous phase was separated and extracted with DCM. The organic phases were combined, dried over $Na_2SO_4$, filtered and concentrated to give 2-((5-(((S)-4-(2-chloro-3-(6-methoxy-5-(((((S)-5-oxopyrrolidin-2-yl)methyl)amino)methyl)pyridin-2-yl)phenyl)-2,3-dihydro-1H-inden-1-yl)amino)-3-methoxy-6-(trifluoromethyl)pyrazin-2-yl)methyl)-2-azabicyclo[2.2.2]octane-4-carboxylic acid.

The following compounds of Table 1A and Table 1B were prepared according to the procedures described herein using the appropriate starting material(s) and appropriate protecting group chemistry as needed.

TABLE 1A

| No. | Structure | LC/MS |
|---|---|---|
| A-1 | 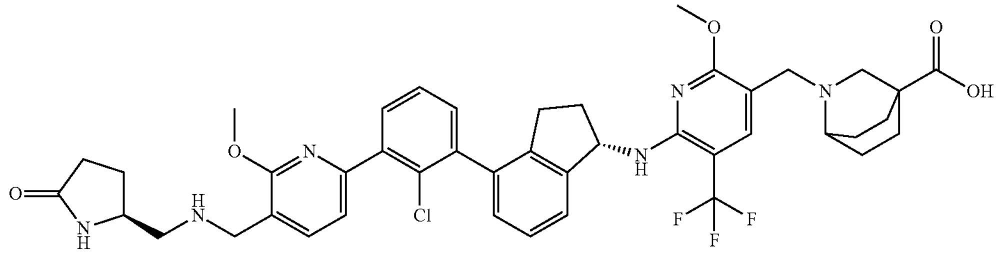 [SMILES: COc1nc(-c2cccc(-c3cccc4c3CC[C@@H]4Nc3nc(OC)c(CN4CC5(C(=O)O)CCC4CC5)cc3C(F)(F)F)c2Cl)ccc1CNC[C@@H]1CCC(=O)N1] | 818.853 |
| A-2 | 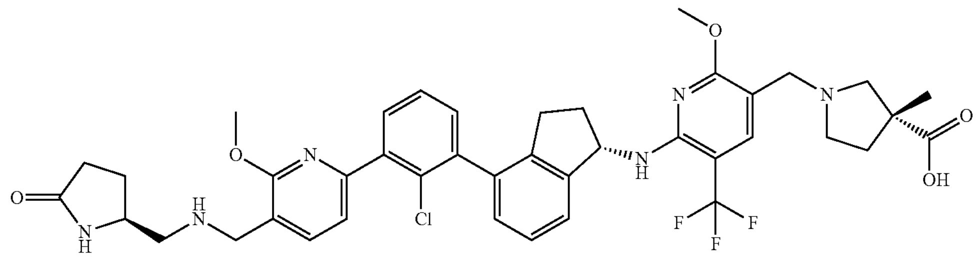 [SMILES: COc1nc(-c2cccc(-c3cccc4c3CC[C@@H]4Nc3nc(OC)c(CN4CC[C@@](C)(C(=O)O)C4)cc3C(F)(F)F)c2Cl)ccc1CNC[C@@H]1CCC(=O)N1] | 792.874 |

TABLE 1A-continued

| No. | Structure | LC/MS |
|---|---|---|
| A-3 | 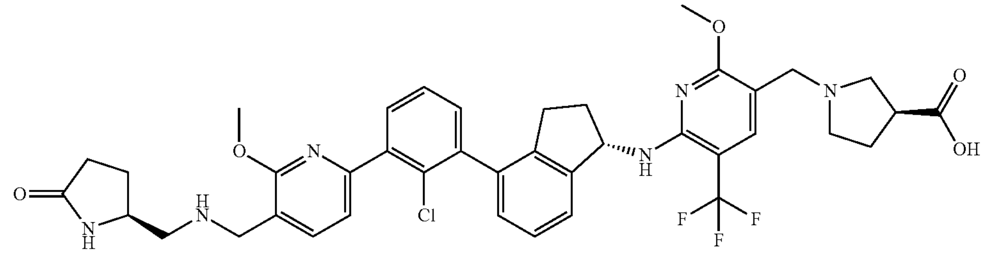 [SMILES: COc1nc(-c2cccc(-c3cccc4c3CC[C@@H]4Nc3nc(OC)c(CN4CC[C@H](C(=O)O)C4)cc3C(F)(F)F)c2Cl)ccc1CNC[C@@H]1CCC(=O)N1] | 778.839 |
| A-4 | 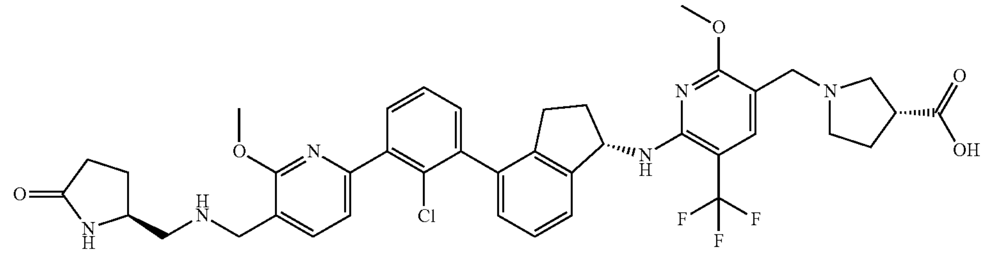 [SMILES: COc1nc(-c2cccc(-c3cccc4c3CC[C@@H]4Nc3nc(OC)c(CN4CC[C@@H](C(=O)O)C4)cc3C(F)(F)F)c2Cl)ccc1CNC[C@@H]1CCC(=O)N1] | 778.869 |
| A-5 | 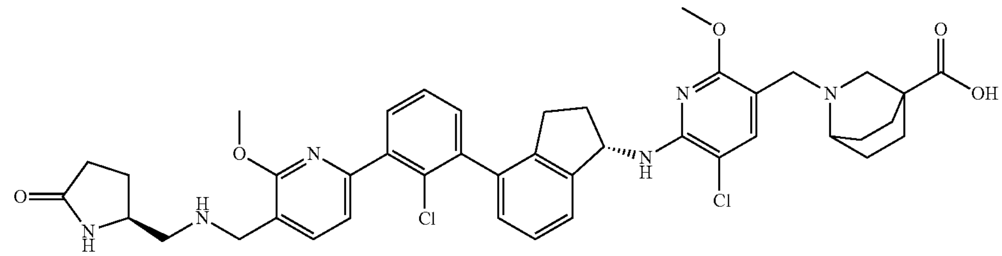 [SMILES: COc1nc(-c2cccc(-c3cccc4c3CC[C@@H]4Nc3nc(OC)c(CN4CC5(C(=O)O)CCC4CC5)cc3Cl)c2Cl)ccc1CNC[C@@H]1CCC(=O)N1] | 784.802 |
| A-6 | 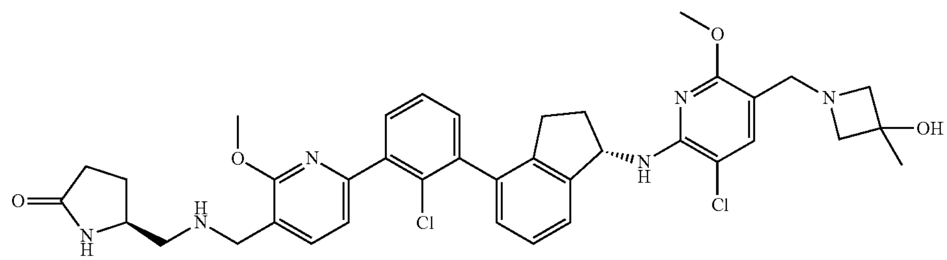 [SMILES: COc1nc(-c2cccc(-c3cccc4c3CC[C@@H]4Nc3nc(OC)c(CN4CC(C)(O)C4)cc3Cl)c2Cl)ccc1CNC[C@@H]1CCC(=O)N1] | 716.79 |
| A-7 | 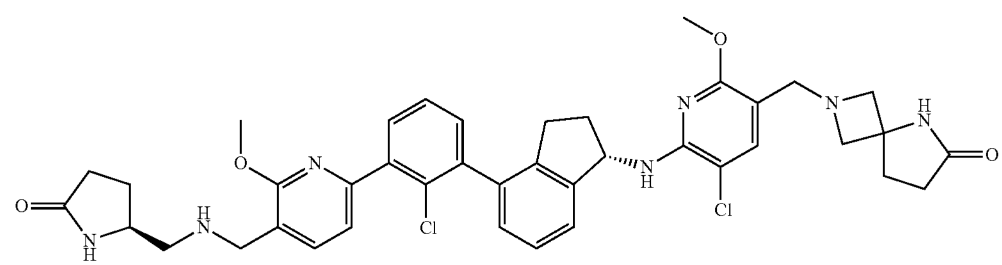 [SMILES: COc1nc(-c2cccc(-c3cccc4c3CC[C@@H]4Nc3nc(OC)c(CN4CC5(CCC(=O)N5)C4)cc3Cl)c2Cl)ccc1CNC[C@@H]1CCC(=O)N1] | 755.78 |
| A-8 | 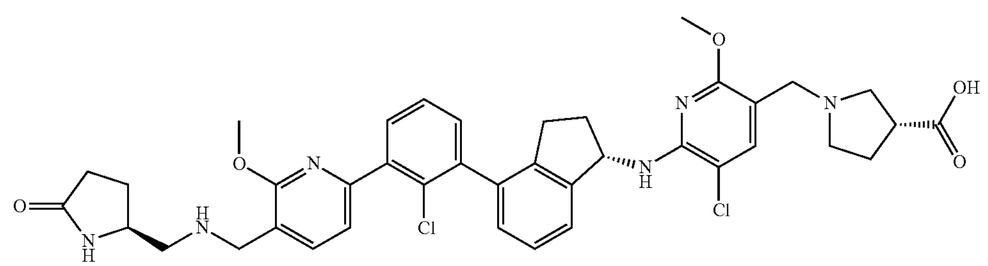 [SMILES: COc1nc(-c2cccc(-c3cccc4c3CC[C@@H]4Nc3nc(OC)c(CN4CC[C@@H](C(=O)O)C4)cc3Cl)c2Cl)ccc1CNC[C@@H]1CCC(=O)N1] | 744.706 |

TABLE 1A-continued
| No. | Structure | LC/MS |
|---|---|---|
| A-9 | 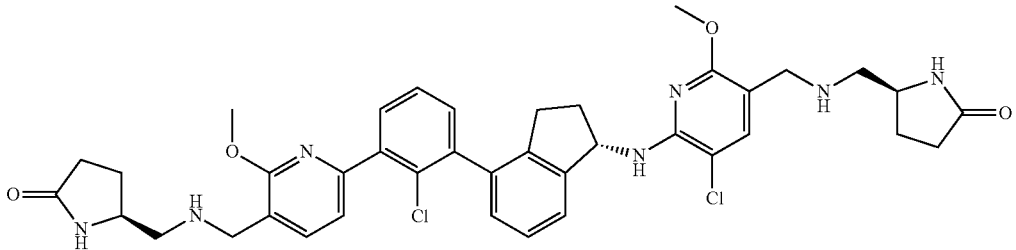 [SMILES: COc1nc(-c2cccc(-c3cccc4c3CC[C@@H]4Nc3nc(OC)c(CNC[C@@H]4CCC(=O)N4)cc3Cl)c2Cl)ccc1CNC[C@@H]1CCC(=O)N1] | 743.606 |
| A-10 | 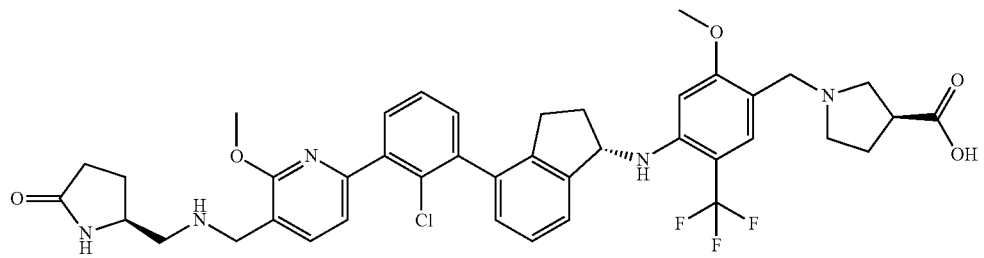 [SMILES: COc1cc(N[C@H]2CCc3c(-c4cccc(-c5ccc(CNC[C@@H]6CCC(=O)N6)c(OC)n5)c4Cl)cccc32)c(C(F)(F)F)cc1CN1CC[C@H](C(=O)O)C1] | 778.218 |
| A-11 | 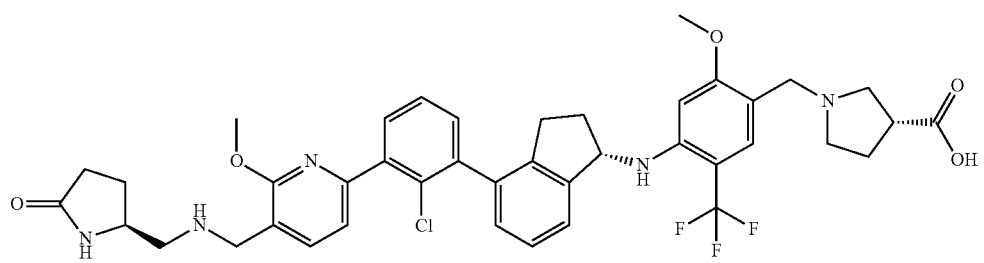 [SMILES: COc1cc(N[C@H]2CCc3c(-c4cccc(-c5ccc(CNC[C@@H]6CCC(=O)N6)c(OC)n5)c4Cl)cccc32)c(C(F)(F)F)cc1CN1CC[C@@H](C(=O)O)C1] | 778.206 |
| A-12 | 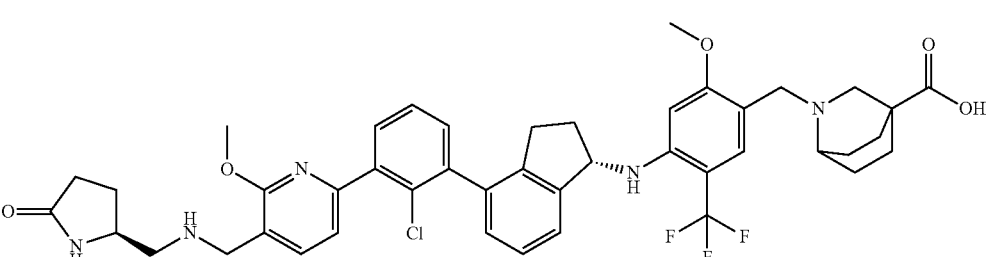 | 818.397 |
| A-13 | 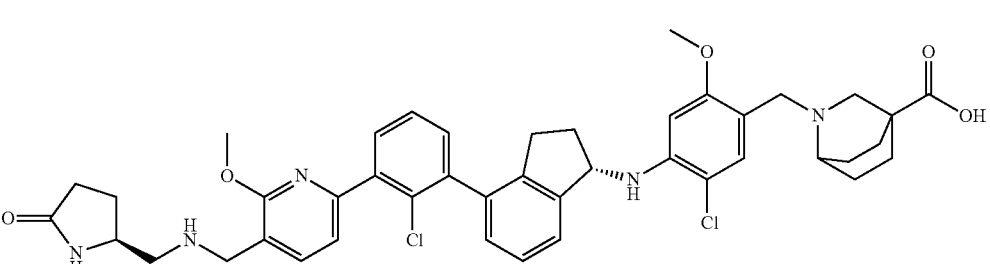 | 783.829 |
| A-14 | 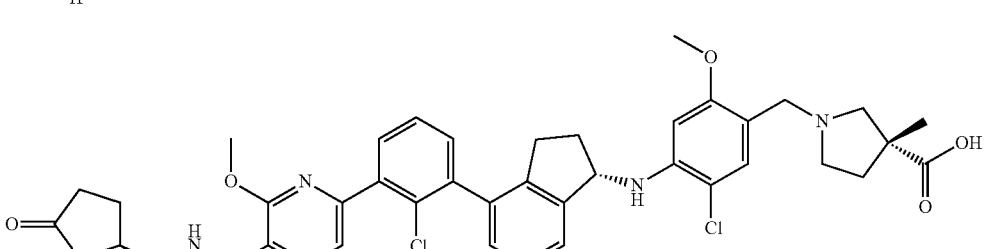 | 757.896 |

TABLE 1A-continued
| No. | Structure | LC/MS |
|---|---|---|
| A-15 | 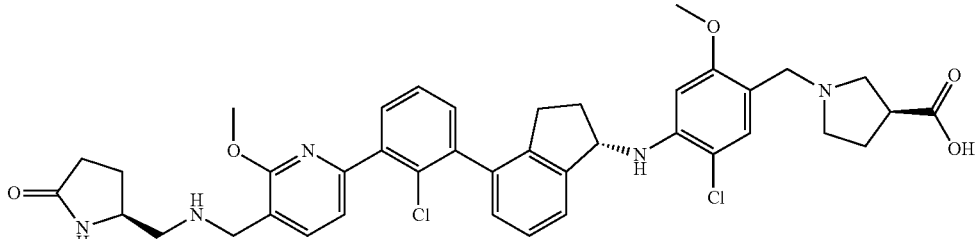 | 743.85 |
| A-16 | 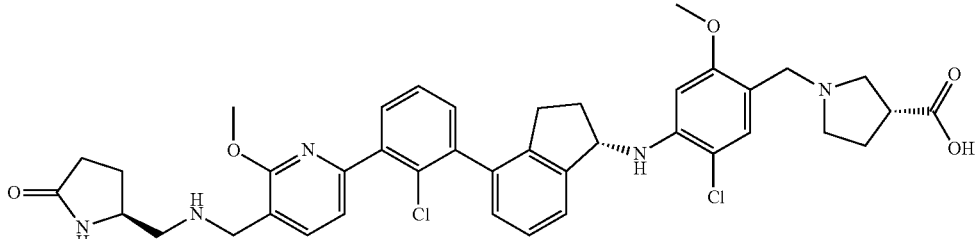 | 743.876 |
| A-17 | 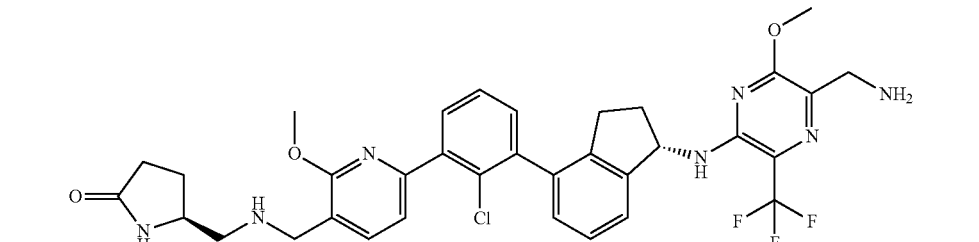 | 682.2 |
| A-18 | 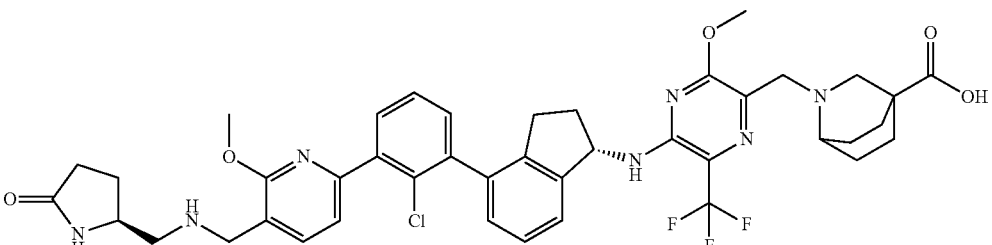 | 820.206 |
| A-19 | 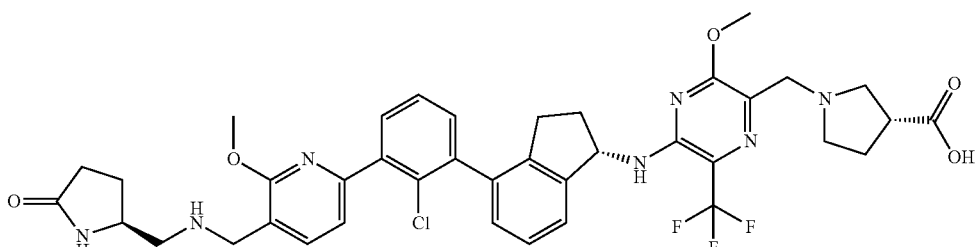 | 780.2 |
| A-20 | 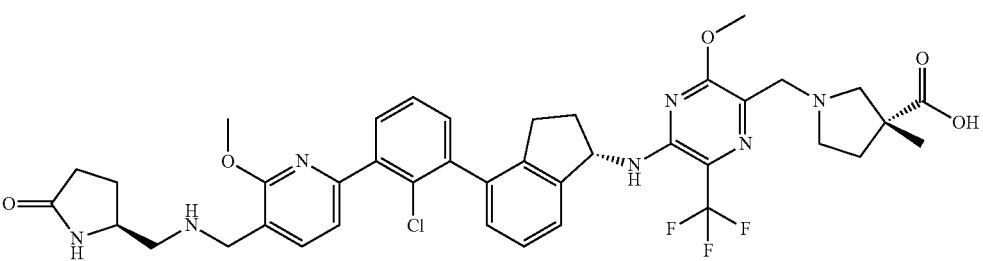 [SMILES: COc1nc(-c2cccc(-c3cccc4c3CC[C@@H]4Nc3nc(OC)c(CN4CC[C@@](C)(C(=O)O)C4)nc3C(F)(F)F)c2Cl)ccc1CNC[C@@H]1CCC(=O)N1] | 794.239 |

TABLE 1A-continued

| No. | Structure | LC/MS |
|---|---|---|
| A-21 | 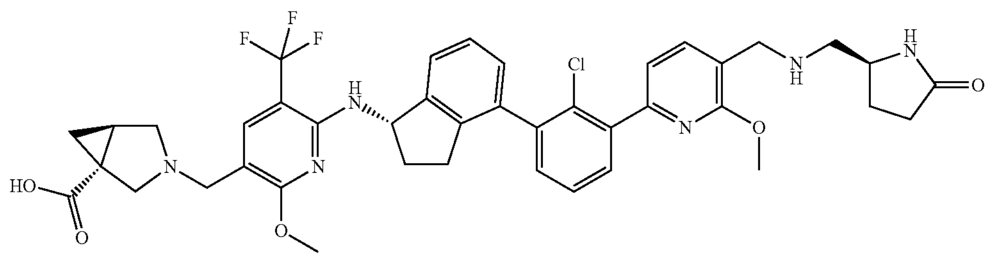 [SMILES: COc1nc(-c2cccc(-c3cccc4c3CC[C@@H]4Nc3nc(OC)c(CN4C[C@@H]5C[C@]5(C(=O)O)C4)cc3C(F)(F)F)c2Cl)ccc1CNC[C@@H]1CCC(=O)N1] | 777.2 |
| A-22 | 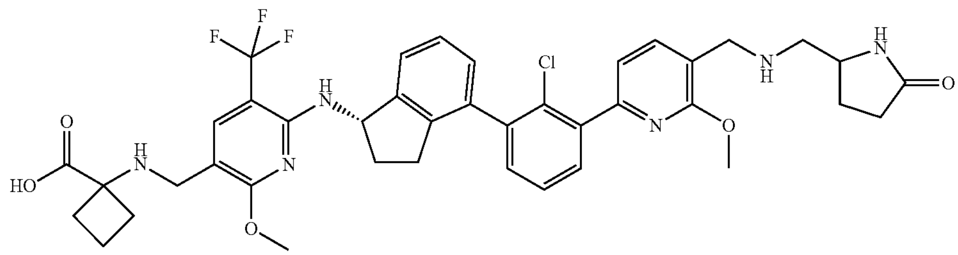 [SMILES: COc1nc(-c2cccc(-c3cccc4c3CC[C@@H]4Nc3nc(OC)c(CNC4(C(=O)O)CCC4)cc3C(F)(F)F)c2Cl)ccc1CNCC1CCC(=O)N1] | 779.2 |
| A-23 | 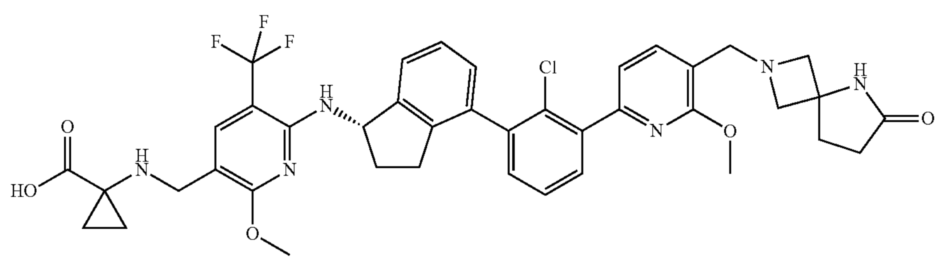 [SMILES: COc1nc(-c2cccc(-c3cccc4c3CC[C@@H]4Nc3nc(OC)c(CNC4(C(=O)O)CC4)cc3C(F)(F)F)c2Cl)ccc1CN1CC2(CCC(=O)N2)C1] | 777.2 |
| A-24 | 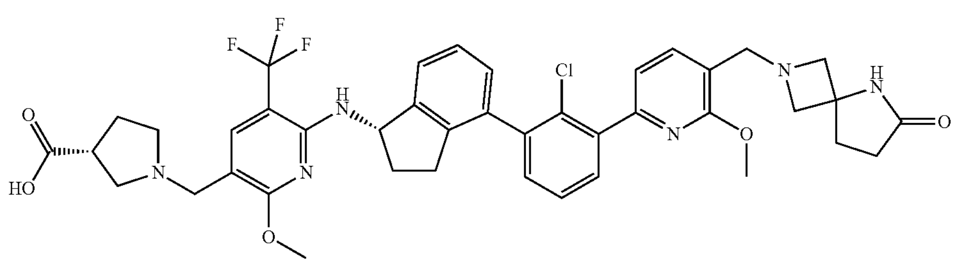 [SMILES: COc1nc(-c2cccc(-c3cccc4c3CC[C@@H]4Nc3nc(OC)c(CN4CC[C@@H](C(=O)O)C4)cc3C(F)(F)F)c2Cl)ccc1CN1CC2(CCC(=O)N2)C1] | 791.25 |
| A-25 | 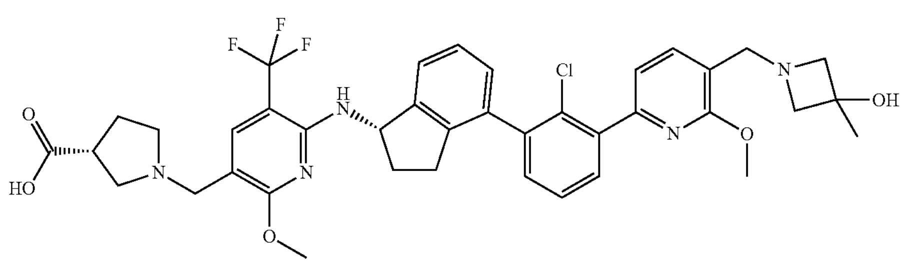 [SMILES: COc1nc(-c2cccc(-c3cccc4c3CC[C@@H]4Nc3nc(OC)c(CN4CC[C@@H](C(=O)O)C4)cc3C(F)(F)F)c2Cl)ccc1CN1CC(C)(O)C1] | 752.2 |

TABLE 1A-continued

| No. | Structure | LC/MS |
|---|---|---|
| A-26 | 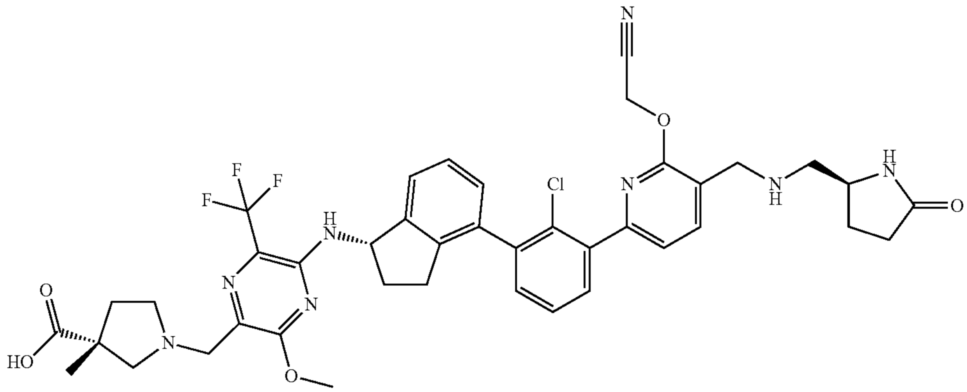 [SMILES: COc1nc(N[C@H]2CCc3c(-c4cccc(-c5ccc(CNC[C@@H]6CCC(=O)N6)c(OCC#N)n5)c4Cl)cccc32)c(C(F)(F)F)nc1CN1CC[C@@](C)(C(=O)O)C1] | 819.4 |
| A-27 | 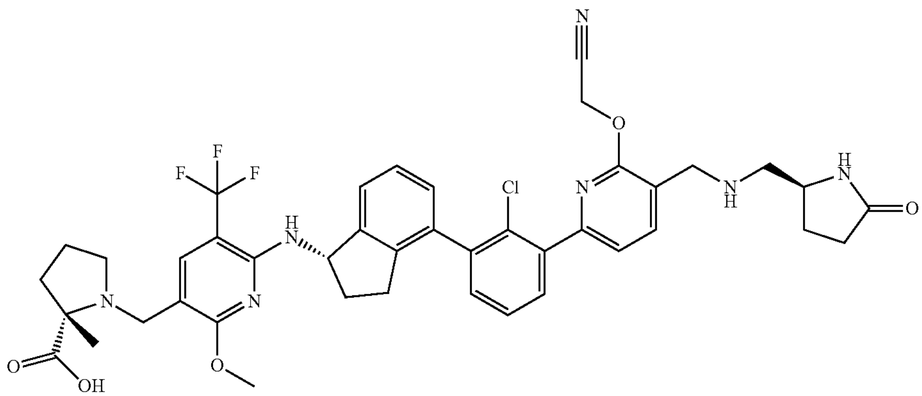 [SMILES: COc1nc(N[C@H]2CCc3c(-c4cccc(-c5ccc(CNC[C@@H]6CCC(=O)N6)c(OCC#N)n5)c4Cl)cccc32)c(C(F)(F)F)cc1CN1CCC[C@@]1(C)C(=O)O] | 818.2 |
| A-28 | 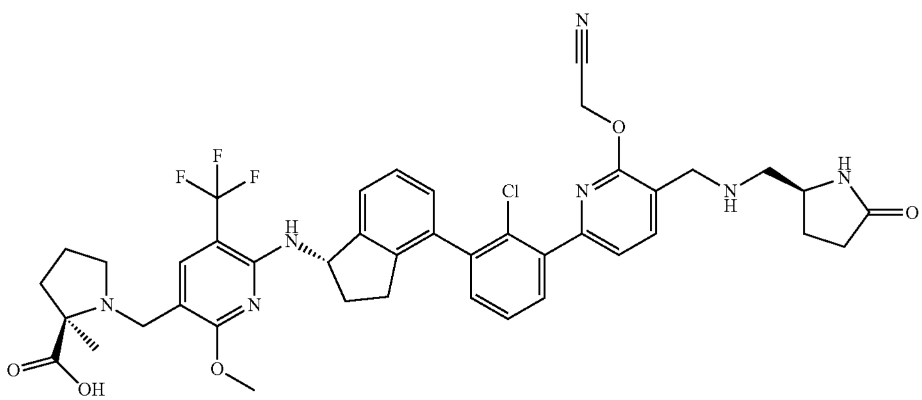 [SMILES: COc1nc(N[C@H]2CCc3c(-c4cccc(-c5ccc(CNC[C@@H]6CCC(=O)N6)c(OCC#N)n5)c4Cl)cccc32)c(C(F)(F)F)cc1CN1CCC[C@]1(C)C(=O)O] | 818.4 |
| A-29 | 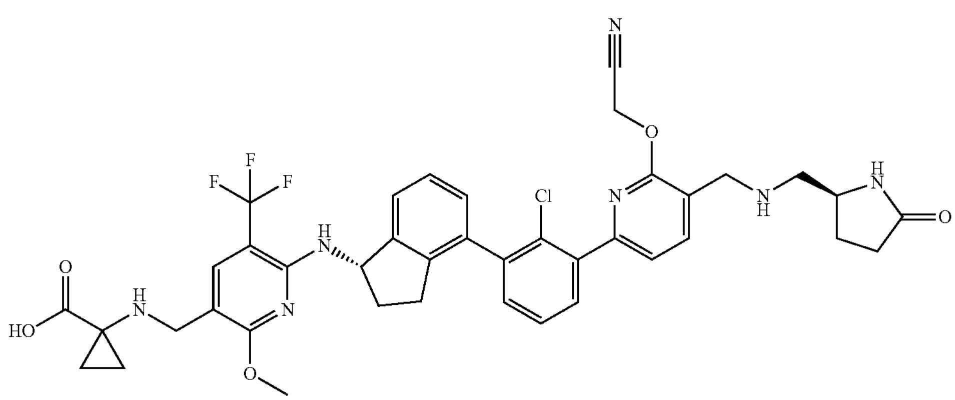 | 790.2 |

TABLE 1A-continued
| No. | Structure | LC/MS |
|---|---|---|
| A-30 | 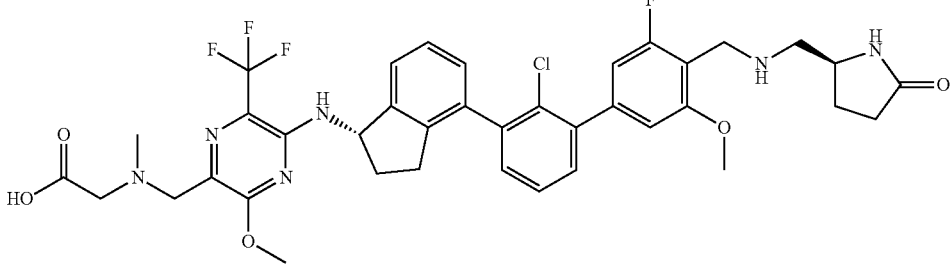 | 770.93 |
| A-31 | 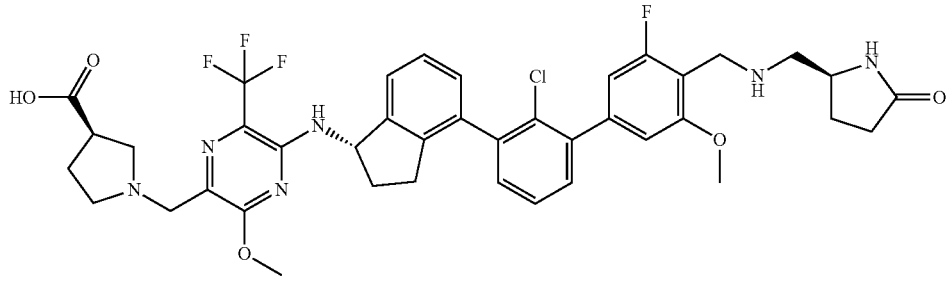 [SMILES: COc1cc(-c2cccc(-c3cccc4c3CC[C@@H]4Nc3nc(OC)c(CN4CC[C@@H](C(=O)O)C4)nc3C(F)(F)F)c2Cl)cc(F)c1CNC[C@@H]1CCC(=O)N1] | 797.0214 |
| A-32 | 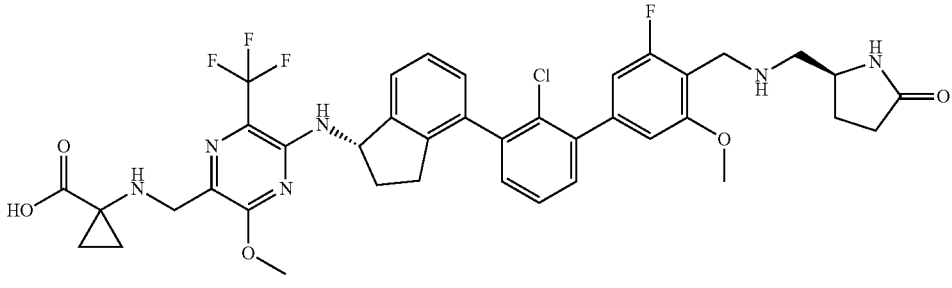 [SMILES: COc1cc(-c2cccc(-c3cccc4c3CC[C@@H]4Nc3nc(OC)c(CNC4(C(=O)O)CC4)nc3C(F)(F)F)c2Cl)cc(F)c1CNC[C@@H]1CCC(=O)N1] | 782.851 |
| A-33 | 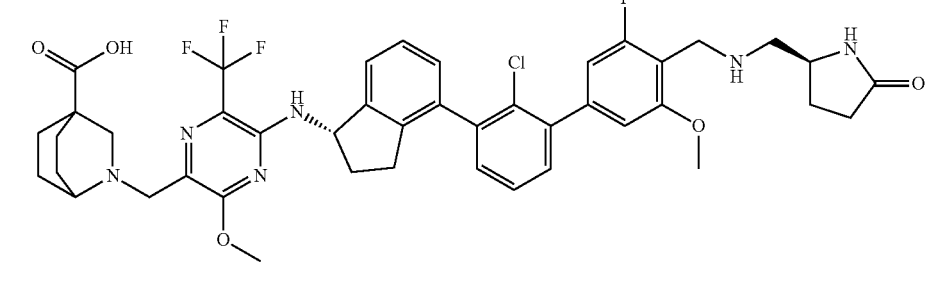 | 837.043 |
| A-34 | 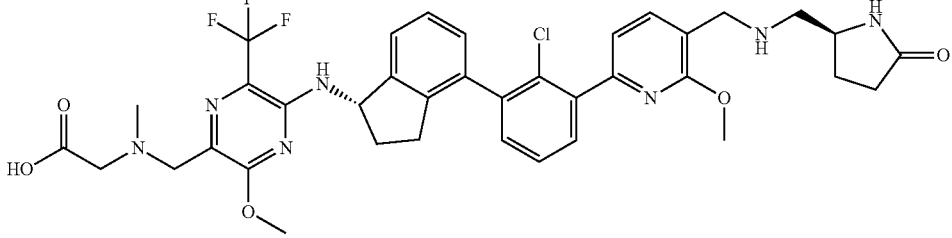 | 753.851 |

TABLE 1A-continued

| No. | Structure | LC/MS |
|---|---|---|
| A-35 | 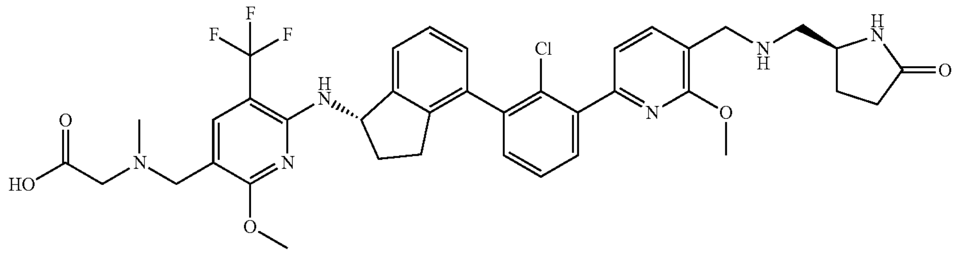 [SMILES: COc1nc(-c2cccc(-c3cccc4c3CC[C@@H]4Nc3nc(OC)c(CN(C)CC(=O)O)nc3C(F)(F)F)c2Cl)ccc1CNC[C@@H]1CCC(=O)N1] | 752.701 |
| A-36 | 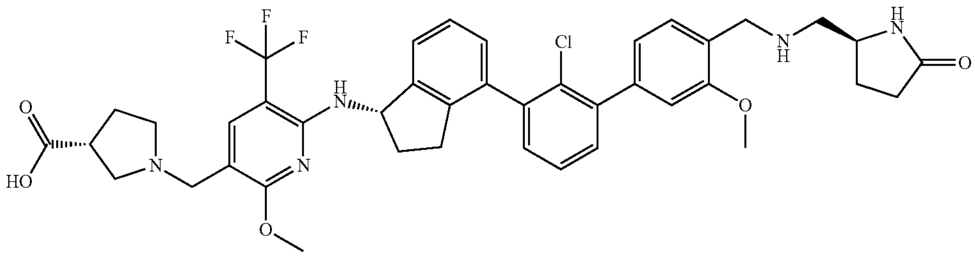 [SMILES: COc1cc(-c2cccc(-c3cccc4c3CC[C@@H]4Nc3nc(OC)c(CN4CC[C@@H](C(=O)O)C4)cc3C(F)(F)F)c2Cl)ccc1CNC[C@@H]1CCC(=O)N1] | 778.20 |
| A-37 | 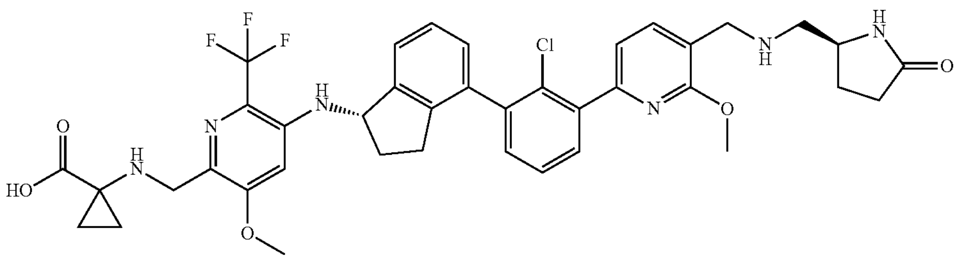 [SMILES: COc1cc(N[C@H]2CCc3c(-c4cccc(-c5ccc(CNC[C@@H]6CCC(=O)N6)c(OC)n5)c4Cl)cccc32)c(C(F)(F)F)nc1CNC1(C(=O)O)CC1] | 765.20 |
| A-38 | 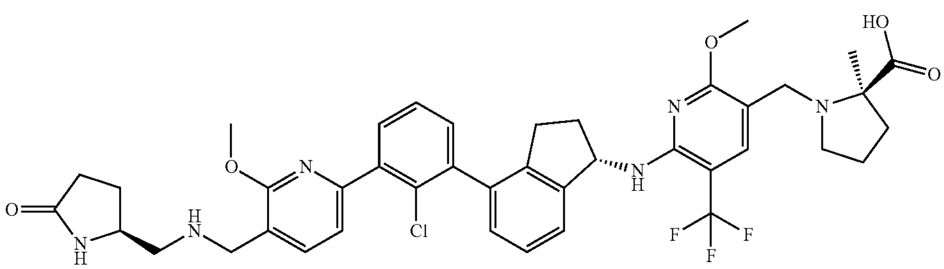 [SMILES: COc1nc(-c2cccc(-c3cccc4c3CC[C@@H]4Nc3nc(OC)c(CN4CCC[C@]4(C)C(=O)O)cc3C(F)(F)F)c2Cl)ccc1CNC[C@@H]1CCC(=O)N1] | 792.79 |
| A-39 | 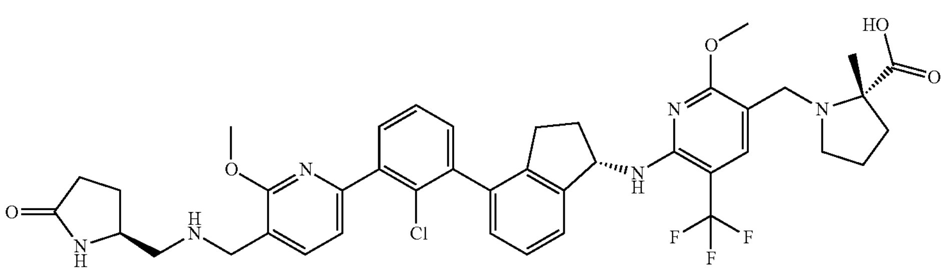 [SMILES: COc1nc(-c2cccc(-c3cccc4c3CC[C@@H]4Nc3nc(OC)c(CN4CCC[C@@]4(C)C(=O)O)cc3C(F)(F)F)c2Cl)ccc1CNC[C@@H]1CCC(=O)N1] | 792.786 |
| A-40 | 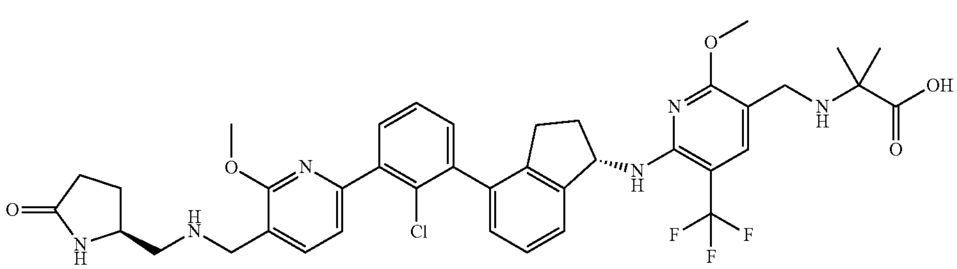 [SMILES: COc1nc(-c2cccc(-c3cccc4c3CC[C@@H]4Nc3nc(OC)c(CNC(C)(C)C(=O)O)cc3C(F)(F)F)c2Cl)ccc1CNC[C@@H]1CCC(=O)N1] | 767.335 |

TABLE 1A-continued

| No. | Structure | LC/MS |
|---|---|---|
| A-41 | 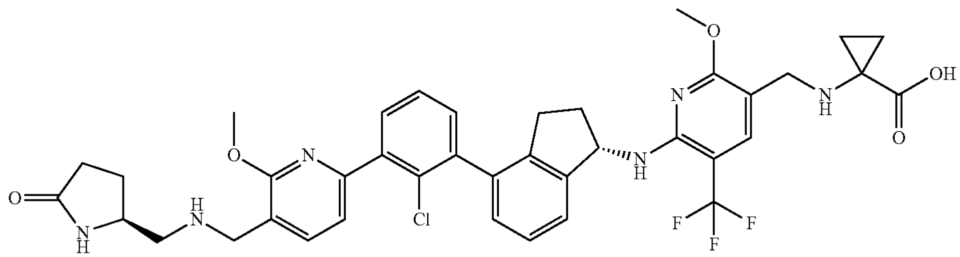 [SMILES: COc1nc(-c2cccc(-c3cccc4c3CC[C@@H]4Nc3nc(OC)c(CNC4(C(=O)O)CC4)cc3C(F)(F)F)c2Cl)ccc1CNC[C@@H]1CCC(=O)N1] | 765.2 |
| A-42 | 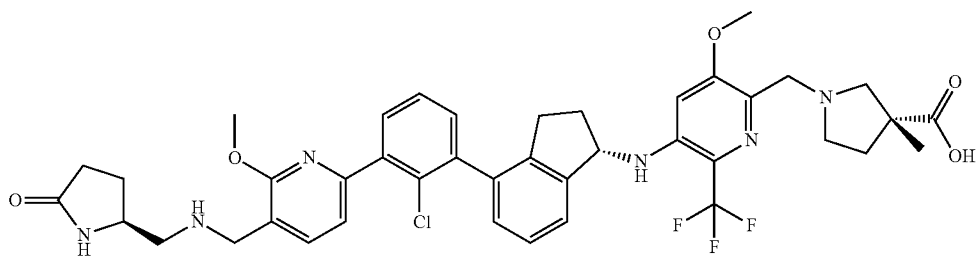 [SMILES: COc1cc(N[C@H]2CCc3c(-c4cccc(-c5ccc(CNC[C@@H]6CCC(=O)N6)c(OC)n5)c4Cl)cccc32)c(C(F)(F)F)nc1CN1CC[C@@](C)(C(=O)O)C1] | 793.214 |
| A-43 | 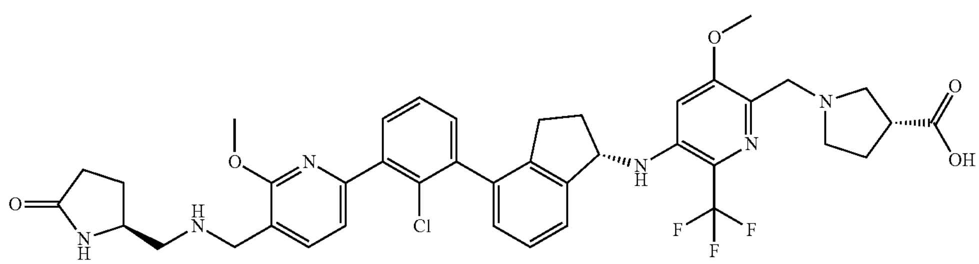 [SMILES: COc1cc(N[C@H]2CCc3c(-c4cccc(-c5ccc(CNC[C@@H]6CCC(=O)N6)c(OC)n5)c4Cl)cccc32)c(C(F)(F)F)nc1CN1CC[C@@H](C(=O)O)C1] | 779.2 |
| A-44 | 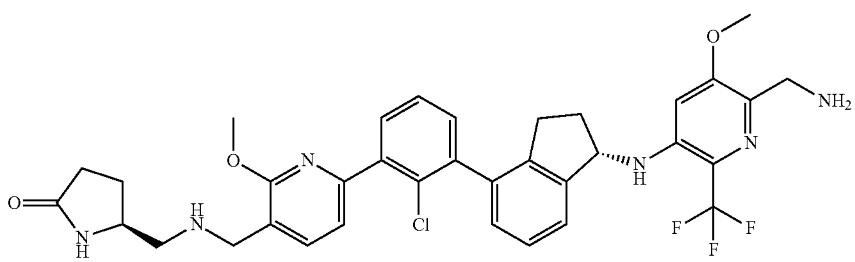 [SMILES: COc1cc(N[C@H]2CCc3c(-c4cccc(-c5ccc(CNC[C@@H]6CCC(=O)N6)c(OC)n5)c4Cl)cccc32)c(C(F)(F)F)nc1CN] | 681.2 |
| A-45 | 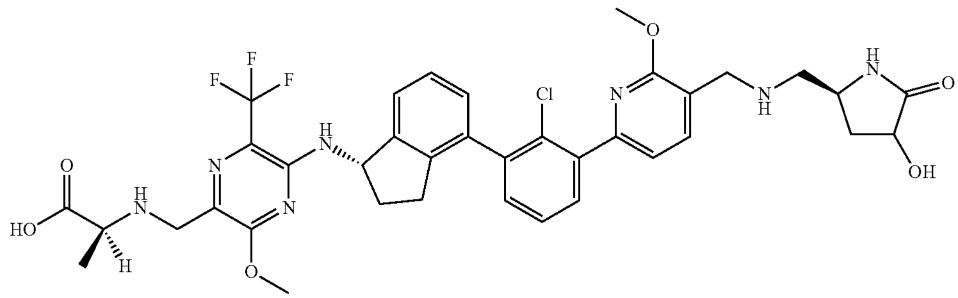 [SMILES: COc1nc(-c2cccc(-c3cccc4c3CC[C@@H]4Nc3nc(OC)c(CN[C@@H](C)C(=O)O)nc3C(F)(F)F)c2Cl)ccc1CNC[C@@H]1CC(O)C(=O)N1] | 770.06 |

TABLE 1A-continued

| No. | Structure | LC/MS |
|---|---|---|
| A-46 | 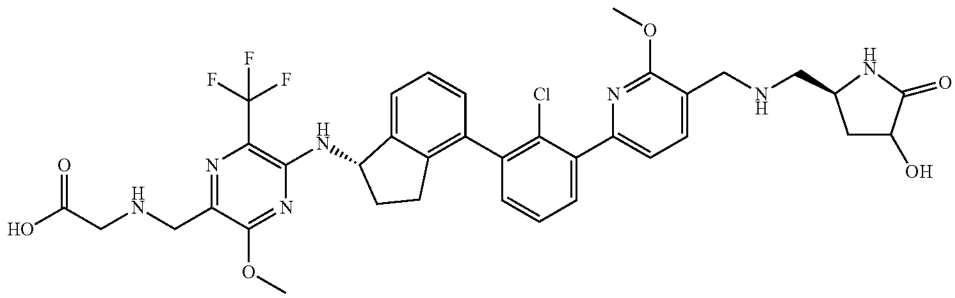 [SMILES: COc1nc(-c2cccc(-c3cccc4c3CC[C@@H]4Nc3nc(OC)c(CNCC(=O)O)nc3C(F)(F)F)c2Cl)ccc1CNC[C@@H]1CC(O)C(=O)N1] | 755.98 |
| A-47 | 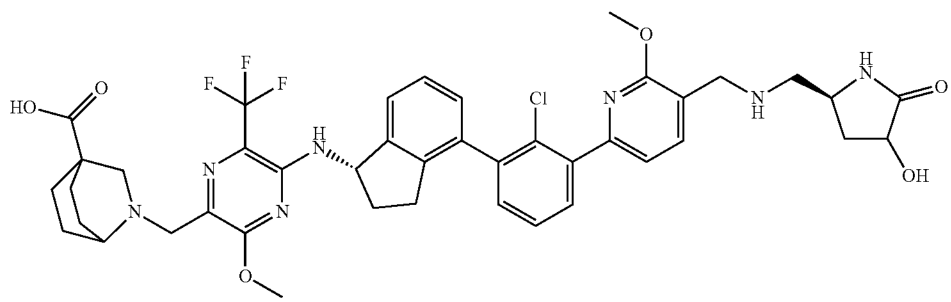 [SMILES: COc1nc(-c2cccc(-c3cccc4c3CC[C@@H]4Nc3nc(OC)c(CN4CC5(C(=O)O)CCC4CC5)nc3C(F)(F)F)c2Cl)ccc1CNC[C@@H]1CC(O)C(=O)N1] | 836.23 |
| A-48 | 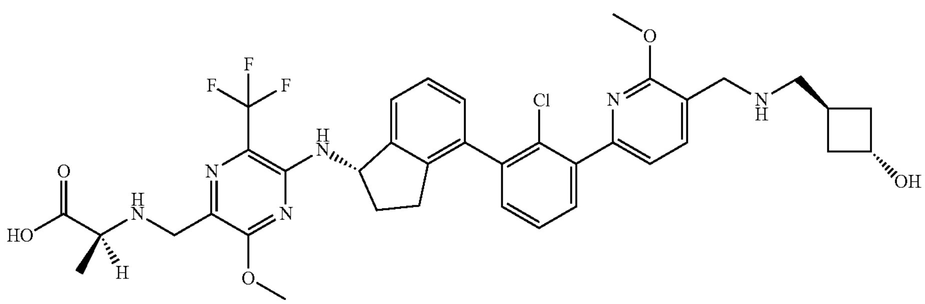 [SMILES: COc1nc(-c2cccc(-c3cccc4c3CC[C@@H]4Nc3nc(OC)c(CN[C@@H](C)C(=O)O)nc3C(F)(F)F)c2Cl)ccc1CNC[C@H]1C[C@H](O)C1] | 741 |
| A-49 | 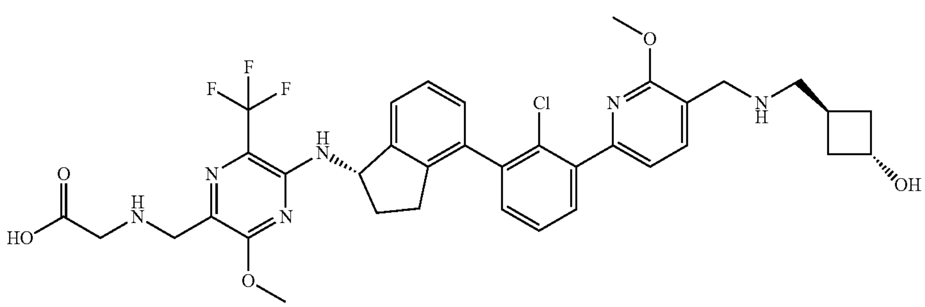 [SMILES: COc1nc(-c2cccc(-c3cccc4c3CC[C@@H]4Nc3nc(OC)c(CNCC(=O)O)nc3C(F)(F)F)c2Cl)ccc1CNC[C@H]1C[C@H](O)C1] | 726.96 |
| A-50 | 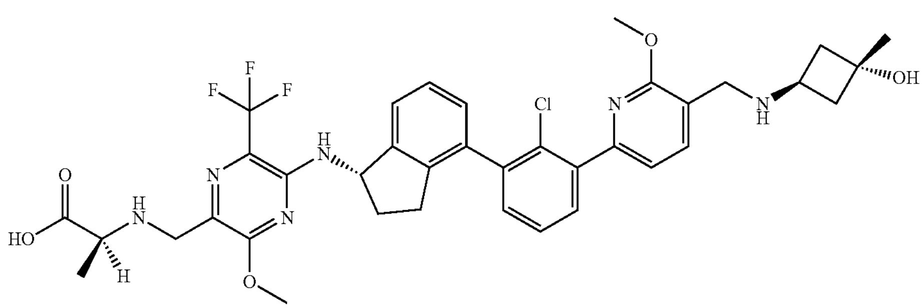 [SMILES: COc1nc(-c2cccc(-c3cccc4c3CC[C@@H]4Nc3nc(OC)c(CN[C@@H](C)C(=O)O)nc3C(F)(F)F)c2Cl)ccc1CN[C@H]1C[C@](C)(O)C1] | 741 |

TABLE 1A-continued

| No. | Structure | LC/MS |
|---|---|---|
| A-51 | 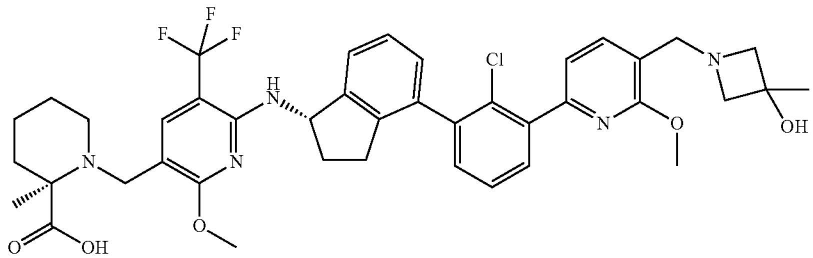 [SMILES: COc1nc(-c2cccc(-c3cccc4c3CC[C@@H]4Nc3nc(OC)c(CN4CCCC[C@]4(C)C(=O)O)cc3C(F)(F)F)c2Cl)ccc1CN1CC(C)(O)C1] | 780.4 |
| A-52 | 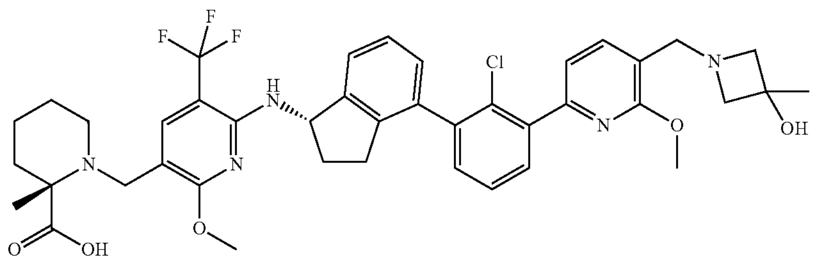 [SMILES: COc1nc(-c2cccc(-c3cccc4c3CC[C@@H]4Nc3nc(OC)c(CN4CCCC[C@@]4(C)C(=O)O)cc3C(F)(F)F)c2Cl)ccc1CN1CC(C)(O)C1] | 780.4 |
| A-53 | 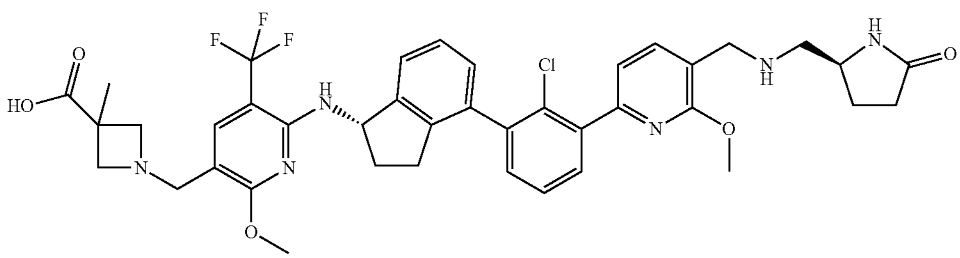 [SMILES: COc1nc(-c2cccc(-c3cccc4c3CC[C@@H]4Nc3nc(OC)c(CN4CC(C)(C(=O)O)C4)cc3C(F)(F)F)c2Cl)ccc1CNC[C@@H]1CCC(=O)N1] | 779.2 |
| A-54 | 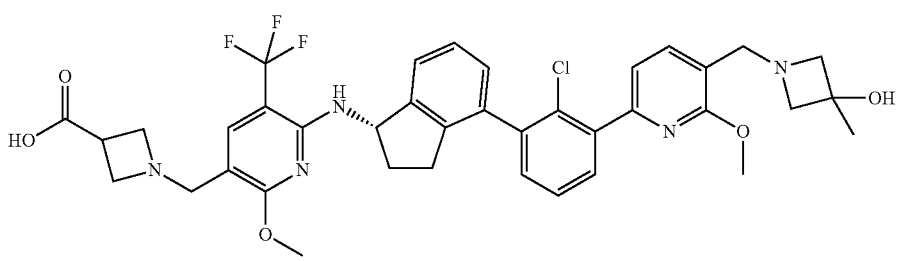 [SMILES: COc1nc(-c2cccc(-c3cccc4c3CC[C@@H]4Nc3nc(OC)c(CN4CC(C(=O)O)C4)cc3C(F)(F)F)c2Cl)ccc1CN1CC(C)(O)C1] | 738.2 |
| A-55 | 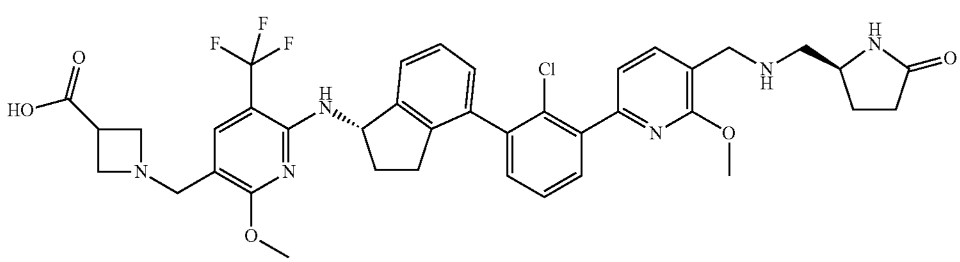 [SMILES: COc1nc(-c2cccc(-c3cccc4c3CC[C@@H]4Nc3nc(OC)c(CN4CC(C(=O)O)C4)cc3C(F)(F)F)c2Cl)ccc1CNC[C@@H]1CCC(=O)N1] | 765.204 |
| A-56 | 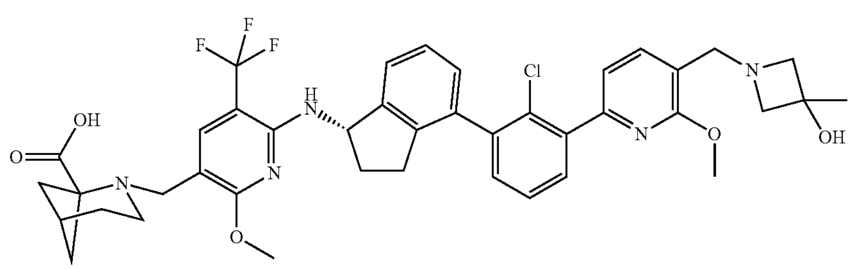 [SMILES: COc1nc(-c2cccc(-c3cccc4c3CC[C@@H]4Nc3nc(OC)c(CN4CCC5CC4(C(=O)O)C5)cc3C(F)(F)F)c2Cl)ccc1CN1CC(C)(O)C1] | 778.4 |

TABLE 1A-continued

| No. | Structure | LC/MS |
|---|---|---|
| A-57 | 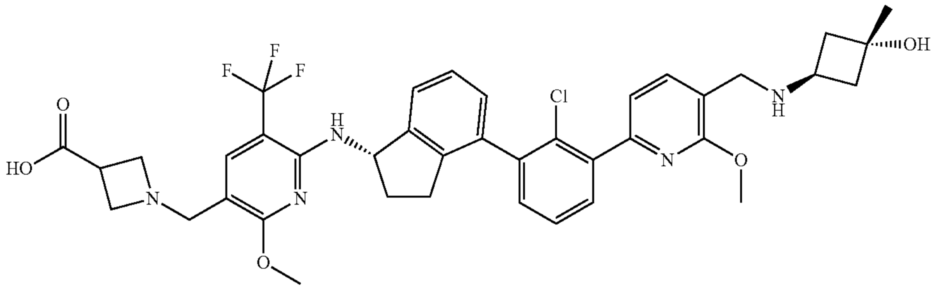 [SMILES: COc1nc(-c2cccc(-c3cccc4c3CC[C@@H]4Nc3nc(OC)c(CN4CC(C(=O)O)C4)cc3C(F)(F)F)c2Cl)ccc1CN[C@H]1C[C@](C)(O)C1] | 752.3 |
| A-58 | 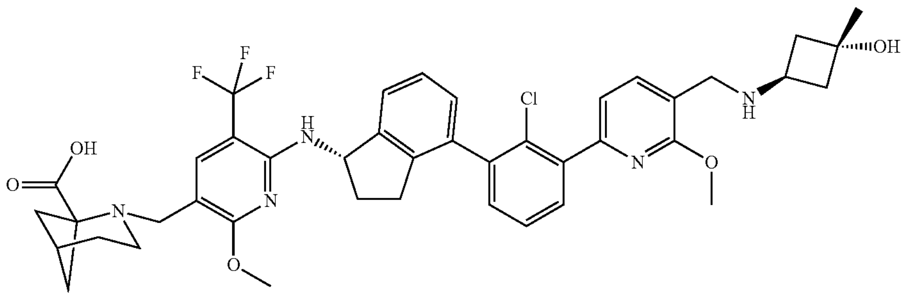 [SMILES: COc1nc(-c2cccc(-c3cccc4c3CC[C@@H]4Nc3nc(OC)c(CN4CCC5CC4(C(=O)O)C5)cc3C(F)(F)F)c2Cl)ccc1CN[C@H]1C[C@](C)(O)C1] | 792.4 |
| A-59 | 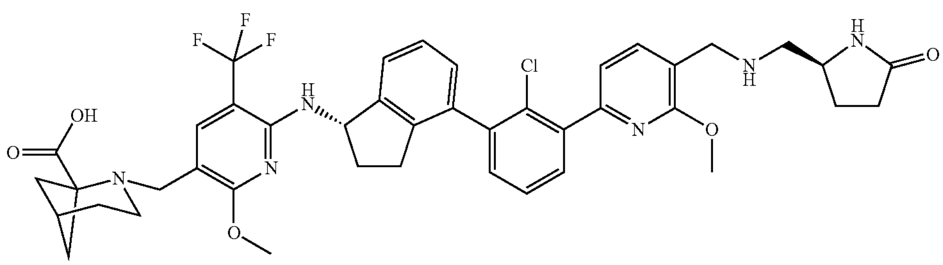 [SMILES: COc1nc(-c2cccc(-c3cccc4c3CC[C@@H]4Nc3nc(OC)c(CN4CCC5CC4(C(=O)O)C5)cc3C(F)(F)F)c2Cl)ccc1CNC[C@@H]1CCC(=O)N1] | 805.4 |
| A-60 | 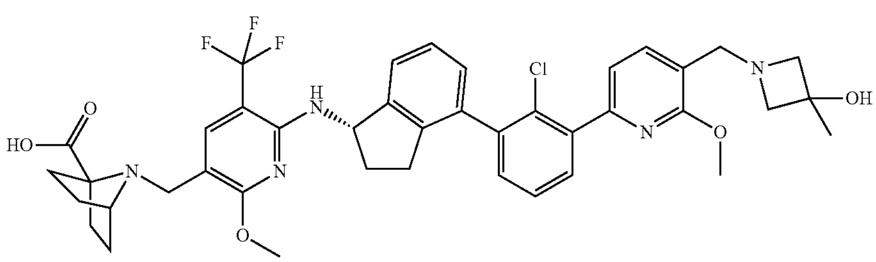 [SMILES: COc1nc(-c2cccc(-c3cccc4c3CC[C@@H]4Nc3nc(OC)c(CN4C5CCC4(C(=O)O)CC5)cc3C(F)(F)F)c2Cl)ccc1CN1CC(C)(O)C1] | 778.4 |
| A-61 | 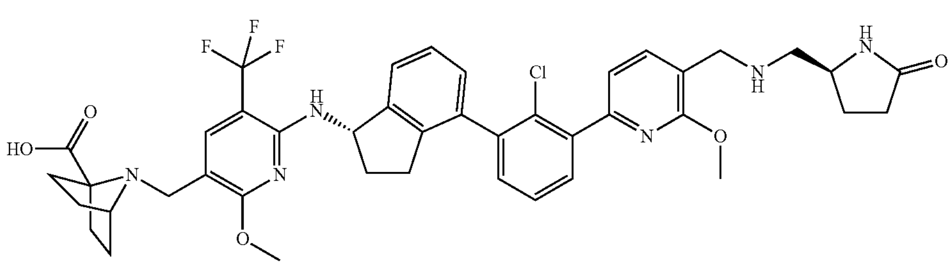 [SMILES: COc1nc(-c2cccc(-c3cccc4c3CC[C@@H]4Nc3nc(OC)c(CN4C5CCC4(C(=O)O)CC5)cc3C(F)(F)F)c2Cl)ccc1CNC[C@@H]1CCC(=O)N1] | 805.4 |

TABLE 1A-continued
| No. | Structure | LC/MS |
|---|---|---|
| A-62 | 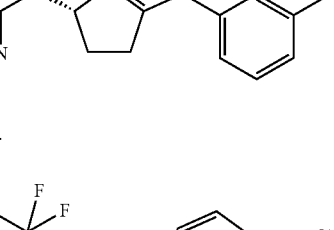 | 820.4 |
| A-63 | 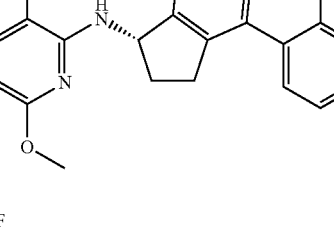 | 726.2 |
| A-64 | 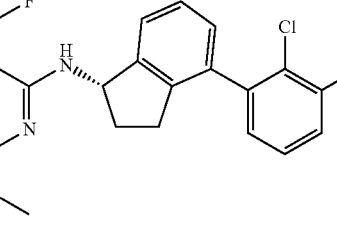 | 753.2 |
| A-65 | 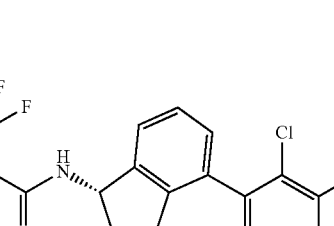 | 739.2 |
| A-66 | 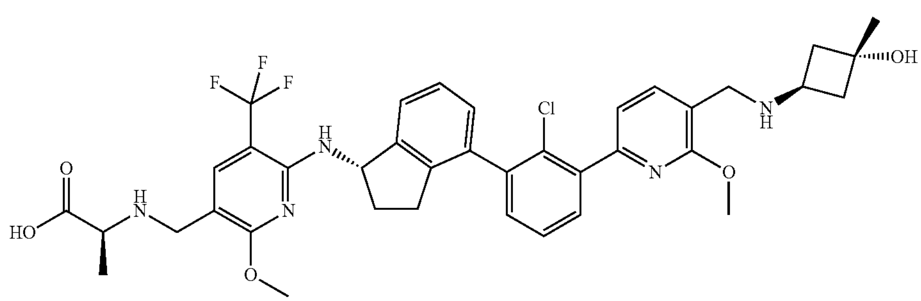 [SMILES: COc1nc(-c2cccc(-c3cccc4c3CC[C@@H]4Nc3nc(OC)c(CN[C@@H](C)C(=O)O)cc3C(F)(F)F)c2Cl)ccc1CN[C@H]1C[C@](C)(O)C1] | 740.3 |

TABLE 1A-continued

| No. | Structure | LC/MS |
|---|---|---|
| A-67 | 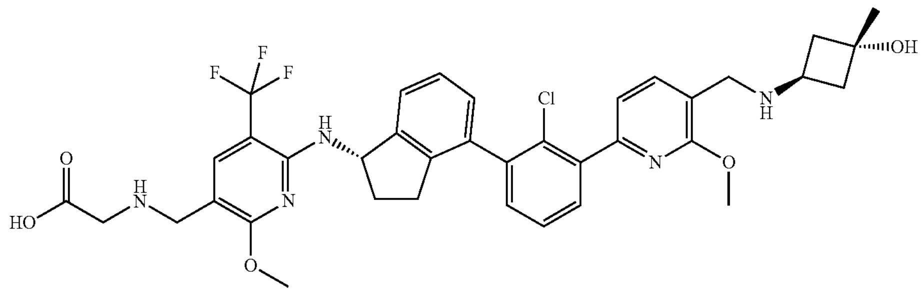 [SMILES: COc1nc(-c2cccc(-c3cccc4c3CC[C@@H]4Nc3nc(OC)c(CNCC(=O)O)cc3C(F)(F)F)c2Cl)ccc1CN[C@H]1C[C@](C)(O)C1] | 726.3 |
| A-68 | 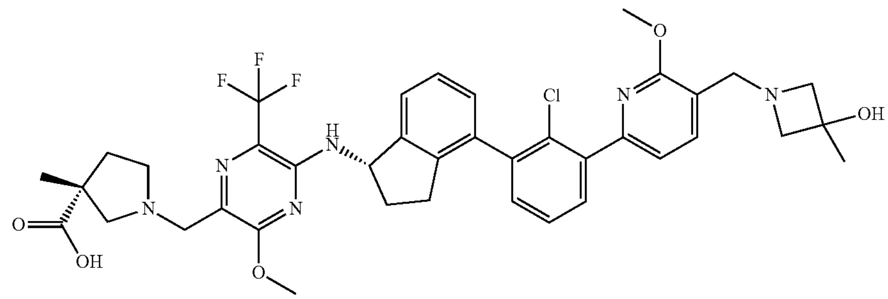 [SMILES: COc1nc(-c2cccc(-c3cccc4c3CC[C@@H]4Nc3nc(OC)c(CN4CC[C@@](C)(C(=O)O)C4)nc3C(F)(F)F)c2Cl)ccc1CN1CC(C)(O)C1] | 767.4 |
| A-69 | 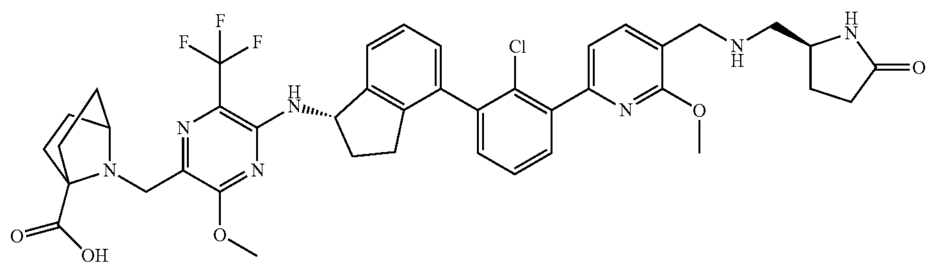 [SMILES: COc1nc(-c2cccc(-c3cccc4c3CC[C@@H]4Nc3nc(OC)c(CN4C5CCC4(C(=O)O)CC5)nc3C(F)(F)F)c2Cl)ccc1CNC[C@@H]1CCC(=O)N1] | 805.906 |
| A-70 | 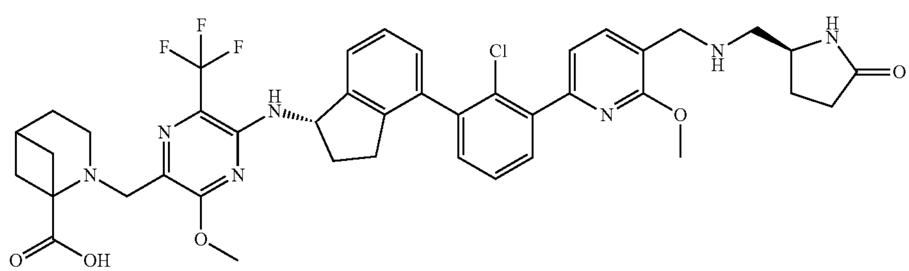 [SMILES: COc1nc(-c2cccc(-c3cccc4c3CC[C@@H]4Nc3nc(OC)c(CN4CCC5CC4(C(=O)O)C5)nc3C(F)(F)F)c2Cl)ccc1CNC[C@@H]1CCC(=O)N1] | 805.881 |
| A-71 | 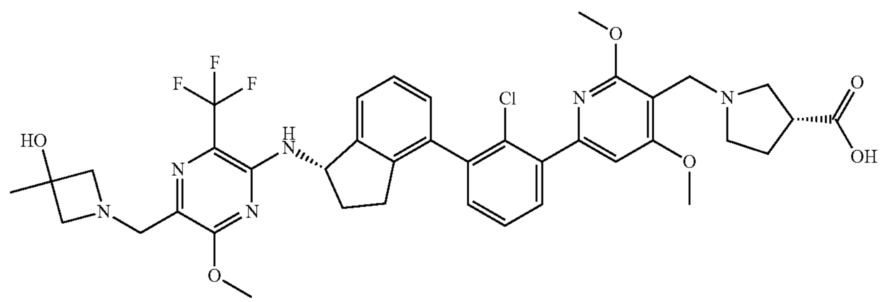 [SMILES: COc1cc(-c2cccc(-c3cccc4c3CC[C@@H]4Nc3nc(OC)c(CN4CC(C)(O)C4)nc3C(F)(F)F)c2Cl)nc(OC)c1CN1CC[C@@H](C(=O)O)C1] | 753.03 |

TABLE 1A-continued
| No. | Structure | LC/MS |
|---|---|---|
| A-72 | 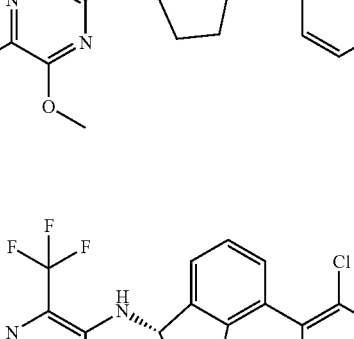 | 712.953 |
| A-73 | 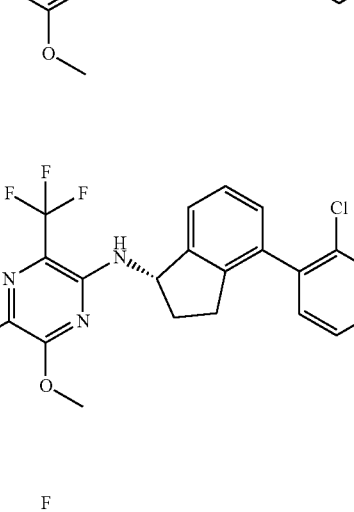 | 698.941 |
| A-74 | 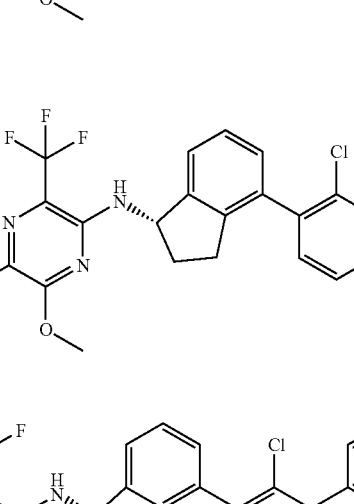 | 726.965 |
| A-75 | 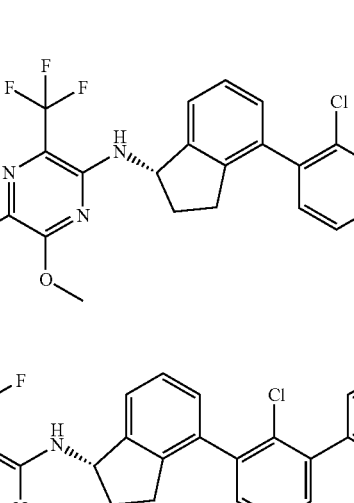 | 712.965 |
| A-76 | 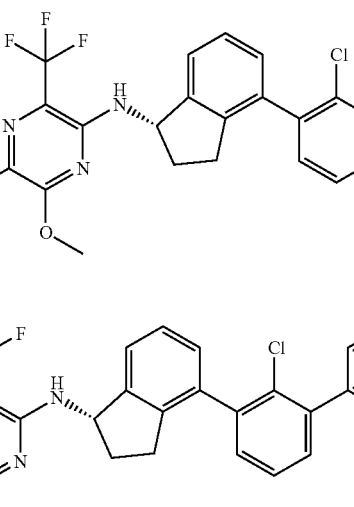 | 794.022 |

TABLE 1A-continued

| No. | Structure | LC/MS |
|---|---|---|
| A-77 | 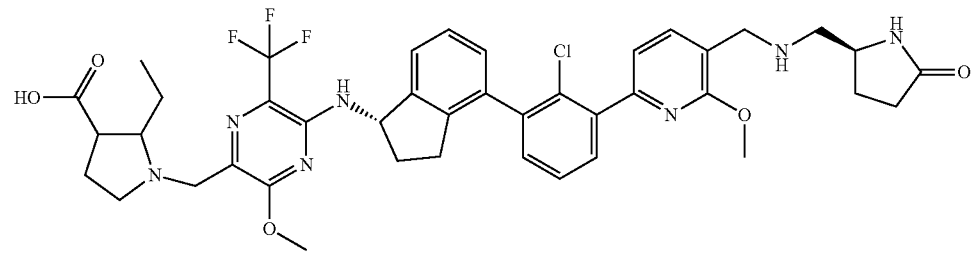 | 808.044 |
| A-78 | 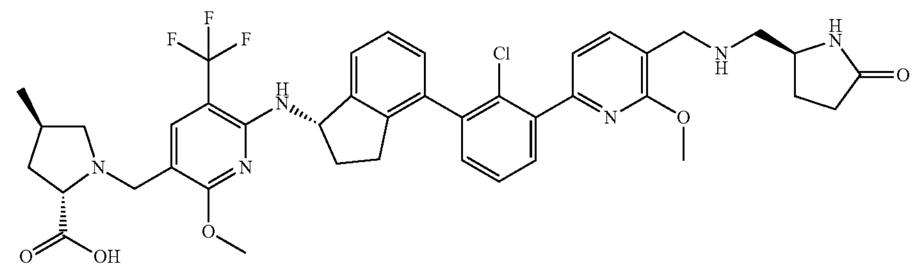 [SMILES: COc1nc(-c2cccc(-c3cccc4c3CC[C@@H]4Nc3nc(OC)c(CN4C[C@H](C)C[C@H]4C(=O)O)nc3C(F)(F)F)c2Cl)ccc1CNC[C@@H]1CCC(=O)N1] | 792.841 |
| A-79 | 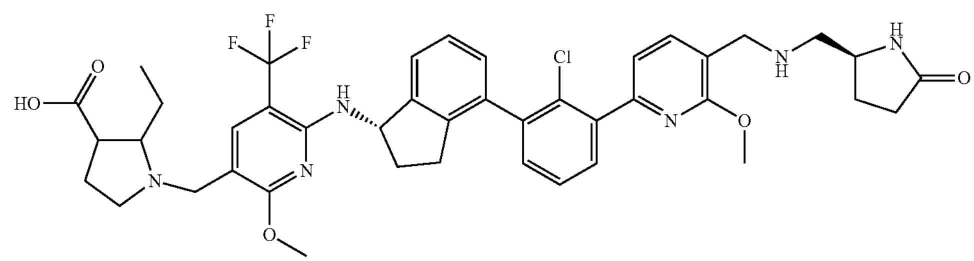 [SMILES: CCC1C(C(=O)O)CCN1Cc1nc(C(F)(F)F)c(N[C@H]2CCc3c(-c4cccc(-c5ccc(CNC[C@@H]6CCC(=O)N6)c(OC)n5)c4Cl)cccc32)nc1OC] | 806.887 |
| A-80 | 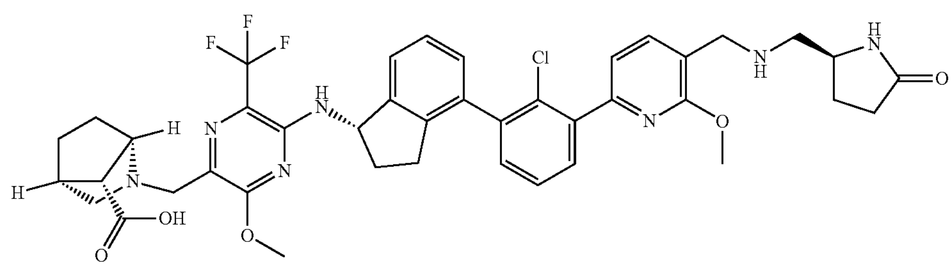 [SMILES: COc1nc(-c2cccc(-c3cccc4c3CC[C@@H]4Nc3nc(OC)c(CN4C[C@@H]5CC[C@H]4[C@@H]5C(=O)O)nc3C(F)(F)F)c2Cl)ccc1CNC[C@@H]1CCC(=O)N1] | 806.005 |
| A-81 | 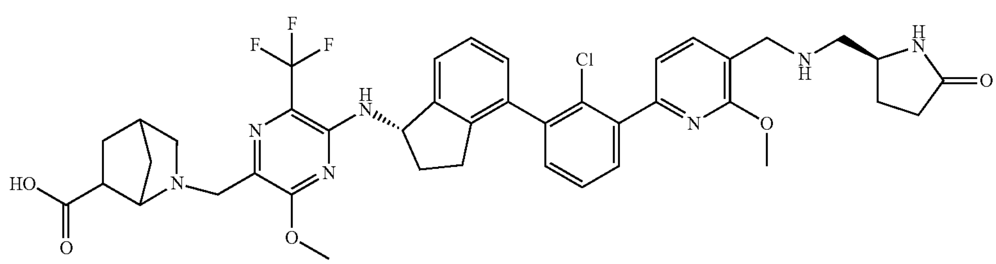 [SMILES: COc1nc(-c2cccc(-c3cccc4c3CC[C@@H]4Nc3nc(OC)c(CN4CC5CC(C(=O)O)C4C5)nc3C(F)(F)F)c2Cl)ccc1CNC[C@@H]1CCC(=O)N1] | 806.022 |
| A-82 | 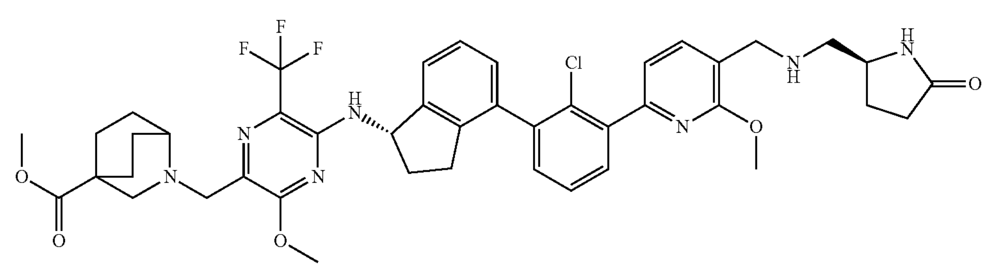 [SMILES: COC(=O)C12CCC(CC1)N(Cc1nc(C(F)(F)F)c(N[C@H]3CCc4c(-c5cccc(-c6ccc(CNC[C@@H]7CCC(=O)N7)c(OC)n6)c5Cl)cccc43)nc1OC)C2] | 834.34 |

TABLE 1A-continued
| No. | Structure | LC/MS |
|---|---|---|
| A-83 | 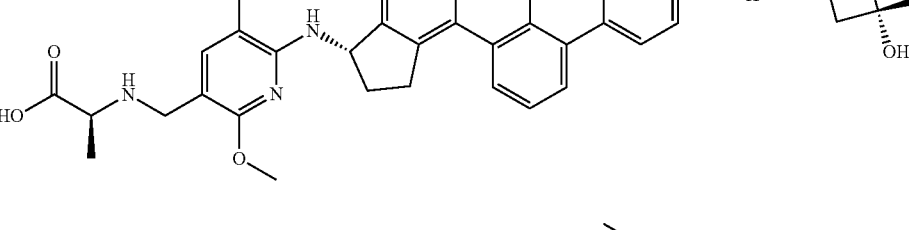 | 753.93 |
| A-84 | 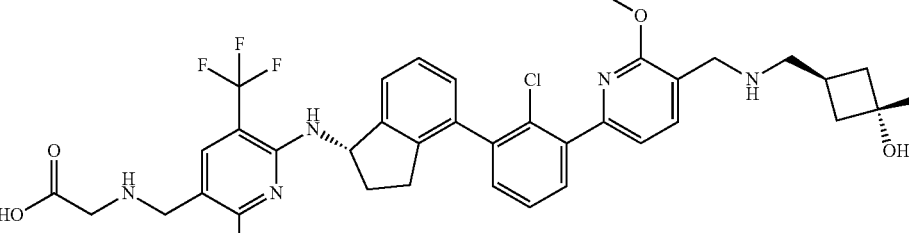 | 739.9 |
| A-85 | 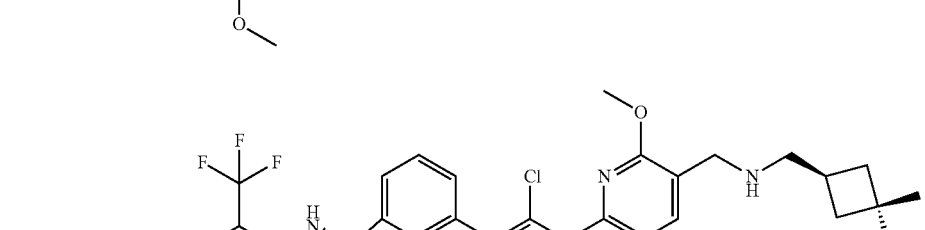 | 766.96 |
| A-86 | 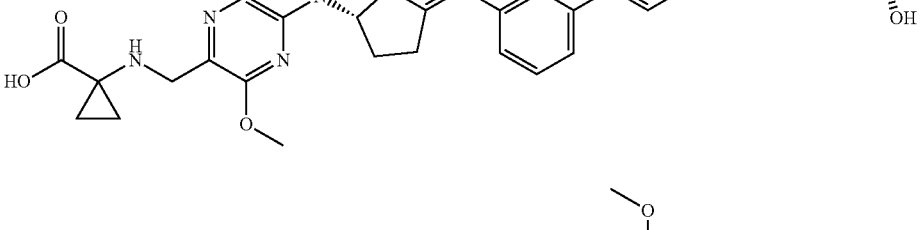 | 754.97 |
| A-87 | 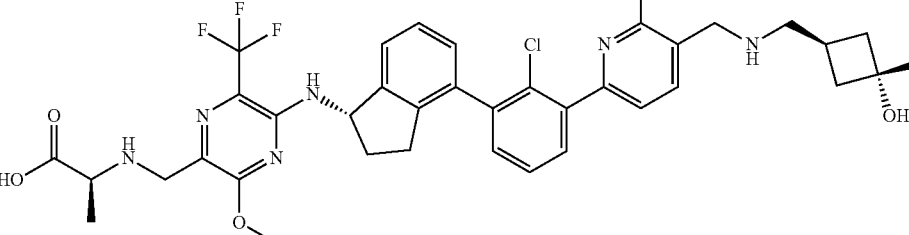 | 740.95 |

TABLE 1A-continued

| No. | Structure | LC/MS |
|---|---|---|
| A-88 | 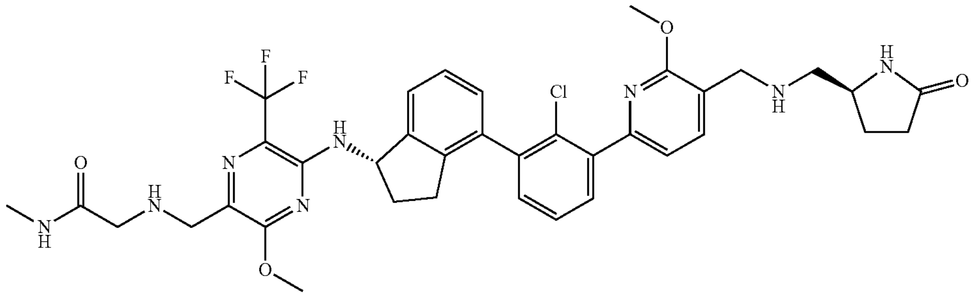 [SMILES: CNC(=O)CNCc1nc(C(F)(F)F)c(N[C@H]2CCc3c(-c4cccc(-c5ccc(CNC[C@@H]6CCC(=O)N6)c(OC)n5)c4Cl)cccc32)nc1OC] | 752.90 |
| A-89 | 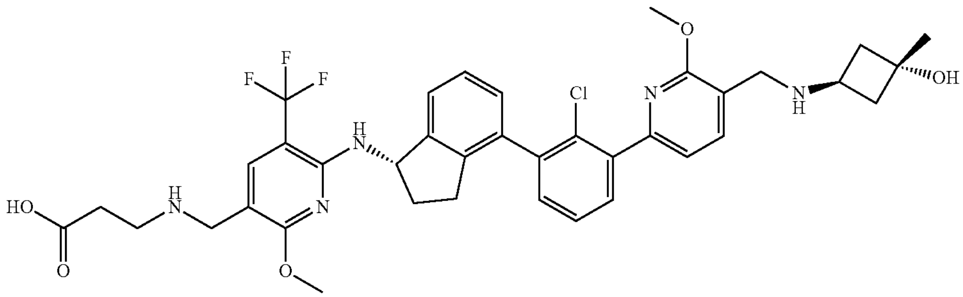 [SMILES: COc1nc(-c2cccc(-c3cccc4c3CC[C@@H]4Nc3nc(OC)c(CNCCC(=O)O)cc3C(F)(F)F)c2Cl)ccc1CN[C@H]1C[C@](C)(O)C1] | 739.79 |
| A-90 | 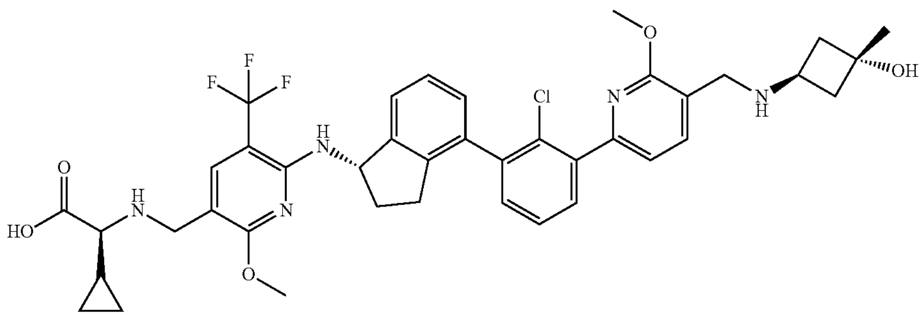 [SMILES: COc1nc(-c2cccc(-c3cccc4c3CC[C@@H]4Nc3nc(OC)c(CN[C@H](C(=O)O)C4CC4)cc3C(F)(F)F)c2Cl)ccc1CN[C@H]1C[C@](C)(O)C1] | 765.92 |
| A-91 | 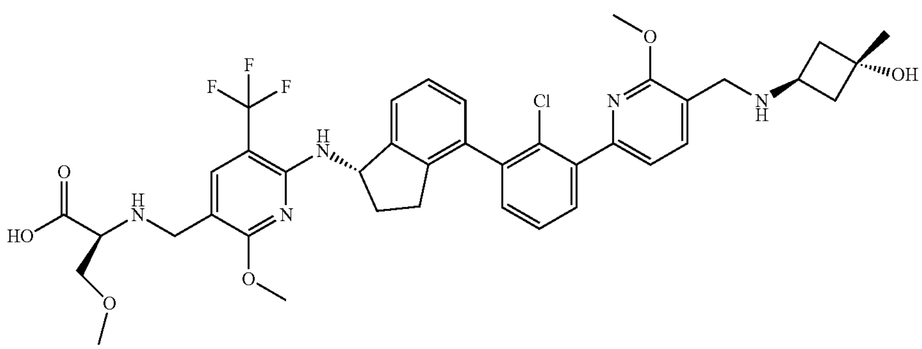 [SMILES: COC[C@H](NCc1cc(C(F)(F)F)c(N[C@H]2CCc3c(-c4cccc(-c5ccc(CN[C@H]6C[C@](C)(O)C6)c(OC)n5)c4Cl)cccc32)nc1OC)C(=O)O] | 769.81 |
| A-92 | 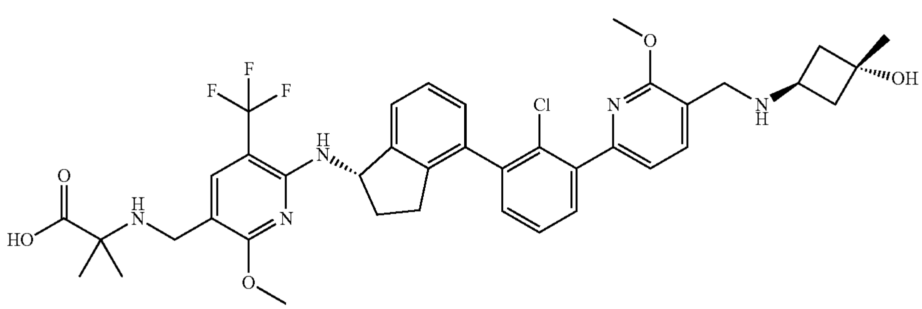 [SMILES: COc1nc(-c2cccc(-c3cccc4c3CC[C@@H]4Nc3nc(OC)c(CNC(C)(C)C(=O)O)cc3C(F)(F)F)c2Cl)ccc1CN[C@H]1C[C@](C)(O)C1] | 753.92 |

TABLE 1A-continued
| No. | Structure | LC/MS |
|---|---|---|
| A-93 | 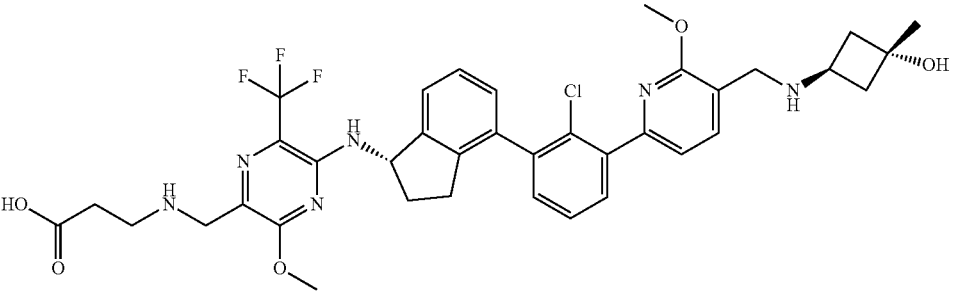 [SMILES: COc1nc(-c2cccc(-c3cccc4c3CC[C@@H]4Nc3nc(OC)c(CNCCC(=O)O)nc3C(F)(F)F)c2Cl)ccc1CN[C@H]1C[C@](C)(O)C1] | 740.94 |
| A-94 | 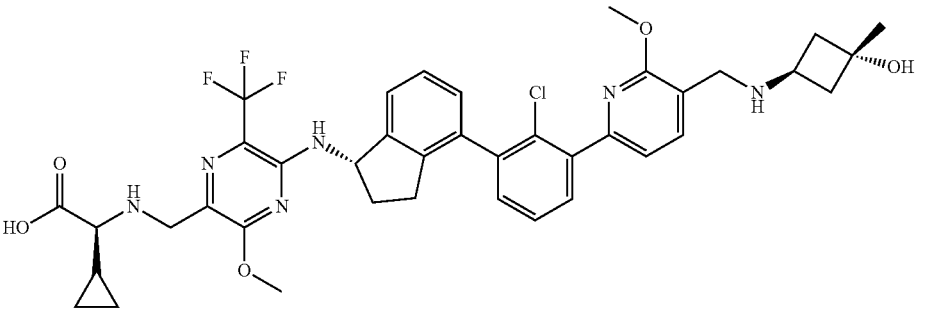 [SMILES: COc1nc(-c2cccc(-c3cccc4c3CC[C@@H]4Nc3nc(OC)c(CN[C@H](C(=O)O)C4CC4)nc3C(F)(F)F)c2Cl)ccc1CN[C@H]1C[C@](C)(O)C1] | 766.94 |
| A-95 | 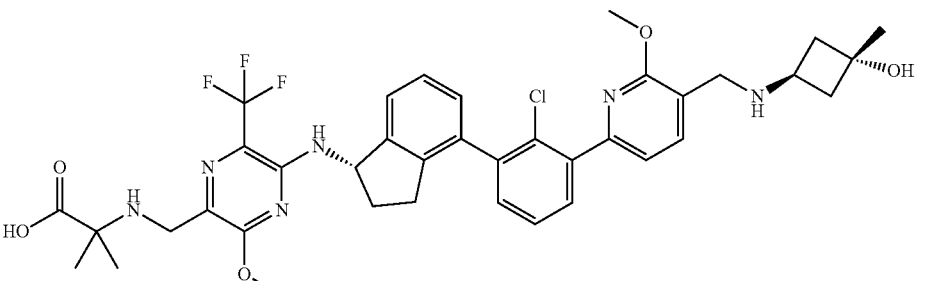 | 754.92 |
| A-96 | 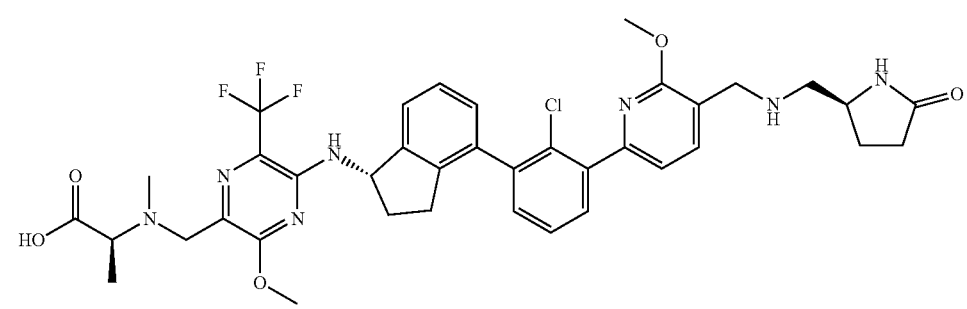 [SMILES: COc1nc(-c2cccc(-c3cccc4c3CC[C@@H]4Nc3nc(OC)c(CN(C)[C@@H](C)C(=O)O)nc3C(F)(F)F)c2Cl)ccc1CNC[C@@H]1CCC(=O)N1] | 767.98 |
| A-97 | 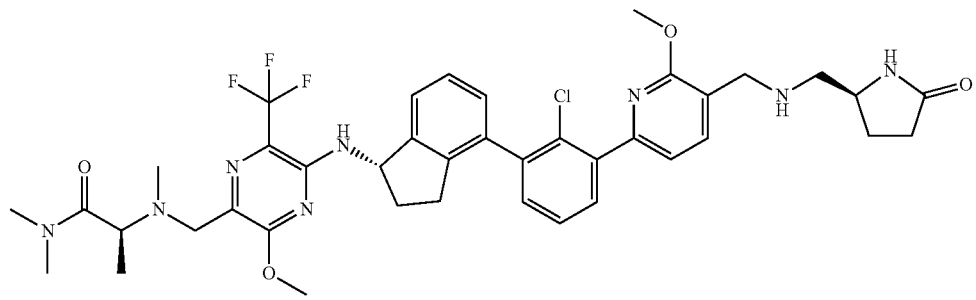 [SMILES: COc1nc(-c2cccc(-c3cccc4c3CC[C@@H]4Nc3nc(OC)c(CN(C)[C@@H](C)C(=O)N(C)C)nc3C(F)(F)F)c2Cl)ccc1CNC[C@@H]1CCC(=O)N1] | 781.03 |

TABLE 1A-continued

| No. | Structure | LC/MS |
|---|---|---|
| A-98 | 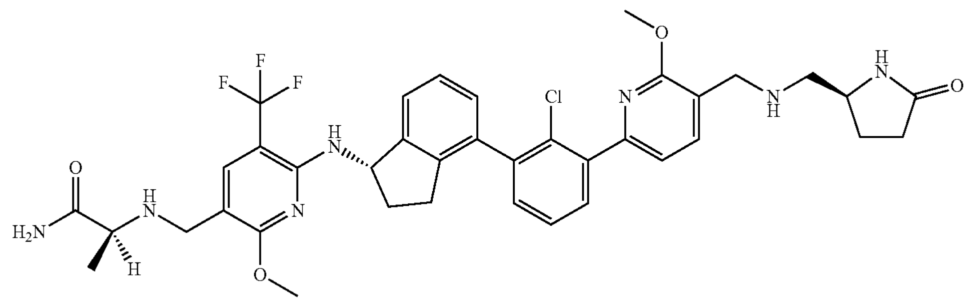 [SMILES: COc1nc(-c2cccc(-c3cccc4c3CC[C@@H]4Nc3nc(OC)c(CN[C@@H](C)C(N)=O)cc3C(F)(F)F)c2Cl)ccc1CNC[C@@H]1CCC(=O)N1] | 751.83 |
| A-99 | 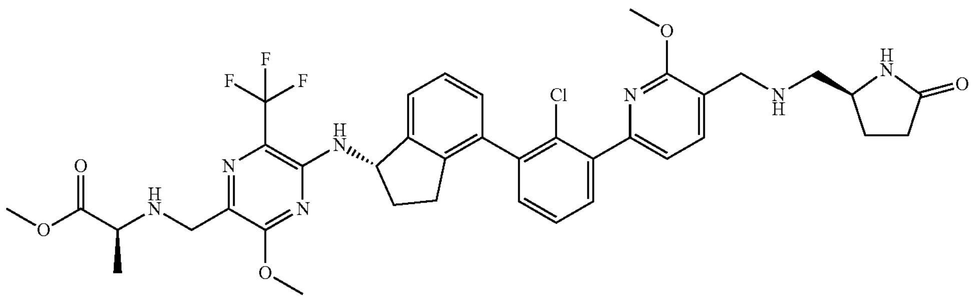 [SMILES: COC(=O)[C@H](C)NCc1nc(C(F)(F)F)c(N[C@H]2CCc3c(-c4cccc(-c5ccc(CNC[C@@H]6CCC(=O)N6)c(OC)n5)c4Cl)cccc32)nc1OC] | 767.8 |
| A-100 | 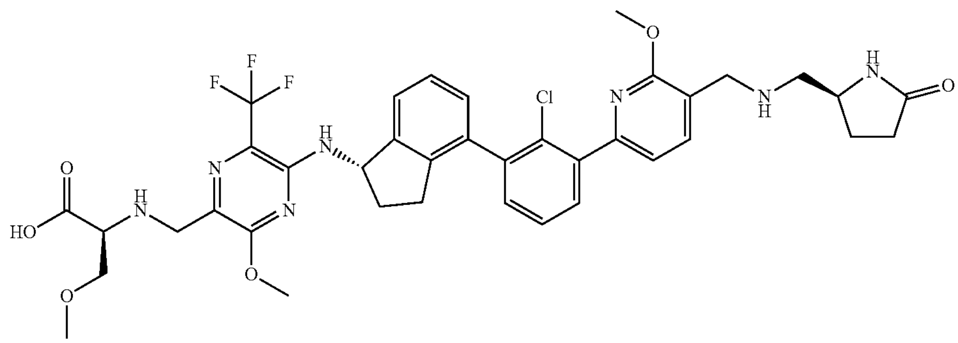 [SMILES: COC[C@H](NCc1nc(C(F)(F)F)c(N[C@H]2CCc3c(-c4cccc(-c5ccc(CNC[C@@H]6CCC(=O)N6)c(OC)n5)c4Cl)cccc32)nc1OC)C(=O)O] | 783.91 |
| A-101 | 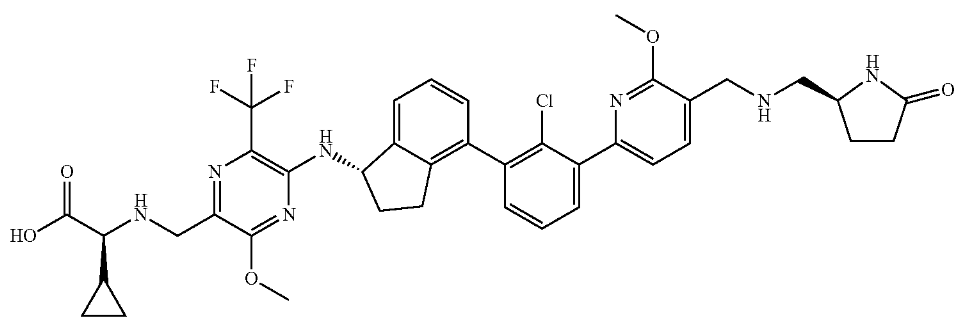 [SMILES: COc1nc(-c2cccc(-c3cccc4c3CC[C@@H]4Nc3nc(OC)c(CN[C@H](C(=O)O)C4CC4)nc3C(F)(F)F)c2Cl)ccc1CNC[C@@H]1CCC(=O)N1] | 780.04 |
| A-102 | 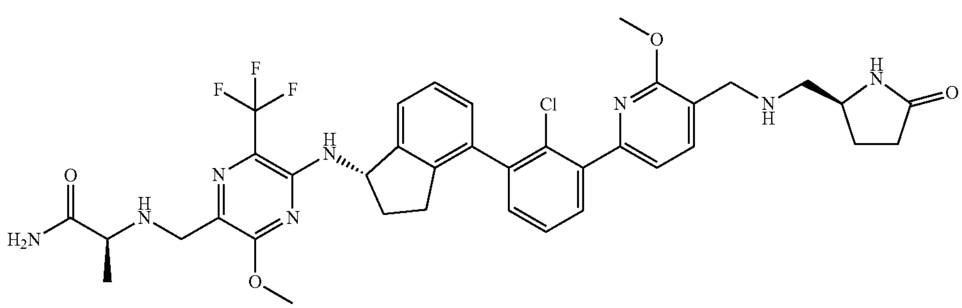 [SMILES: COc1nc(-c2cccc(-c3cccc4c3CC[C@@H]4Nc3nc(OC)c(CN[C@@H](C)C(N)=O)nc3C(F)(F)F)c2Cl)ccc1CNC[C@@H]1CCC(=O)N1] | 752.89 |

TABLE 1A-continued

| No. | Structure | LC/MS |
|---|---|---|
| A-103 | 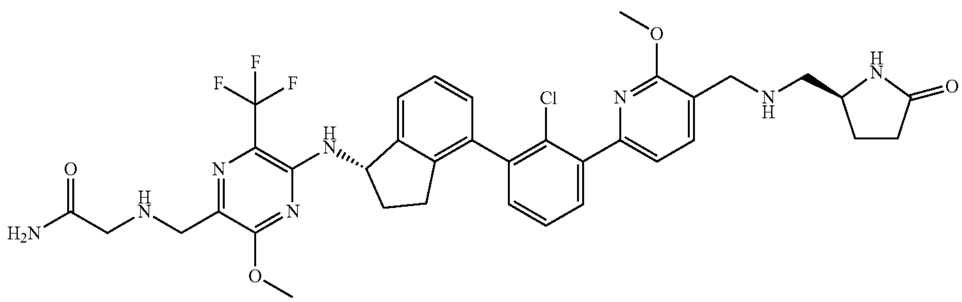 [SMILES: COc1nc(-c2cccc(-c3cccc4c3CC[C@@H]4Nc3nc(OC)c(CNCC(N)=O)nc3C(F)(F)F)c2Cl)ccc1CNC[C@@H]1CCC(=O)N1] | 738.85 |
| A-104 | 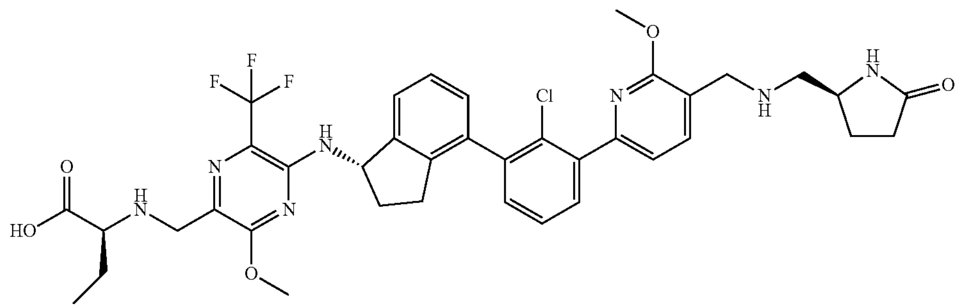 [SMILES: CC[C@H](NCc1nc(C(F)(F)F)c(N[C@H]2CCc3c(-c4cccc(-c5ccc(CNC[C@@H]6CCC(=O)N6)c(OC)n5)c4Cl)cccc32)nc1OC)C(=O)O] | 767.81 |
| A-105 | 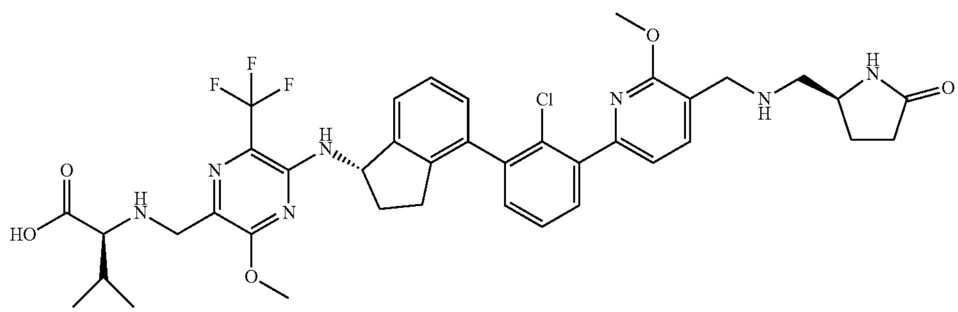 [SMILES: COc1nc(-c2cccc(-c3cccc4c3CC[C@@H]4Nc3nc(OC)c(CN[C@H](C(=O)O)C(C)C)nc3C(F)(F)F)c2Cl)ccc1CNC[C@@H]1CCC(=O)N1] | 781.83 |
| A-106 | 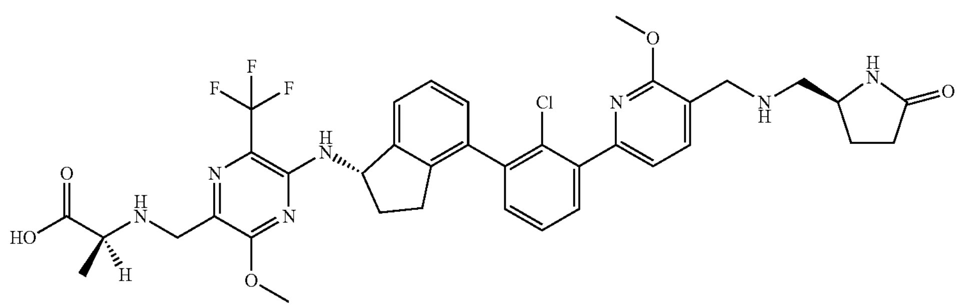 [SMILES: COc1nc(-c2cccc(-c3cccc4c3CC[C@@H]4Nc3nc(OC)c(CN[C@@H](C)C(=O)O)nc3C(F)(F)F)c2Cl)ccc1CNC[C@@H]1CCC(=O)N1] | 753.89 |
| A-107 | 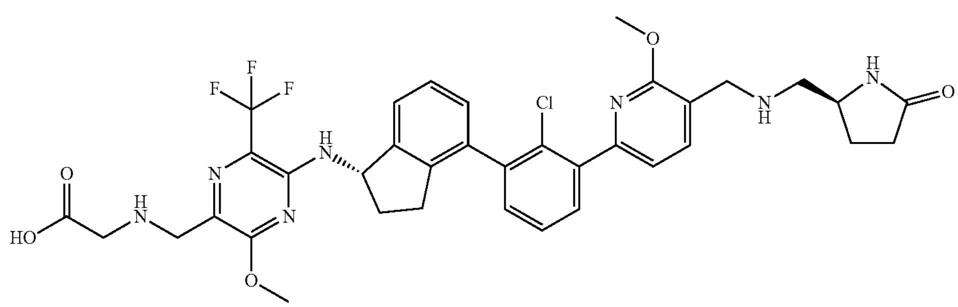 [SMILES: COc1nc(-c2cccc(-c3cccc4c3CC[C@@H]4Nc3nc(OC)c(CNCC(=O)O)nc3C(F)(F)F)c2Cl)ccc1CNC[C@@H]1CCC(=O)N1] | 739.93 |

TABLE 1A-continued

| No. | Structure | LC/MS |
|---|---|---|
| A-108 | 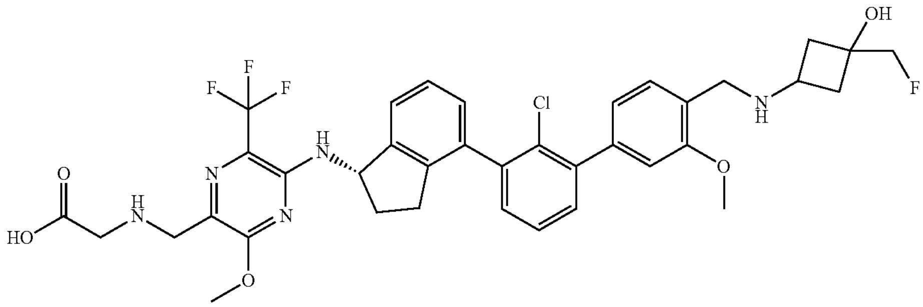 [SMILES: COc1cc(-c2cccc(-c3cccc4c3CC[C@@H]4Nc3nc(OC)c(CNCC(=O)O)nc3C(F)(F)F)c2Cl)ccc1CNC1CC(O)(CF)C1] | 744.0 |
| A-109 | 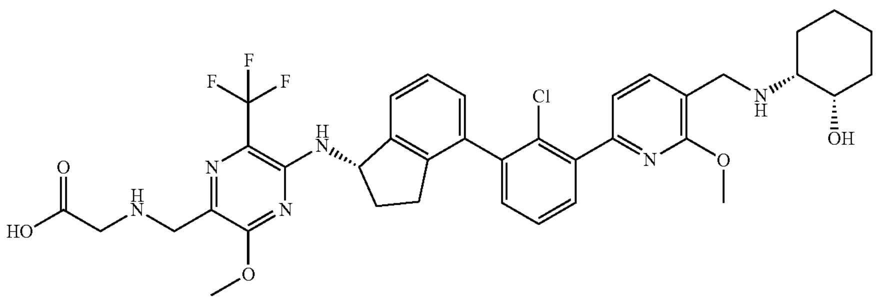 [SMILES: COc1nc(-c2cccc(-c3cccc4c3CC[C@@H]4Nc3nc(OC)c(CNCC(=O)O)nc3C(F)(F)F)c2Cl)ccc1CN[C@@H]1CCCC[C@@H]1O] | 741.0 |

TABLE 1B

| No. | Structure | LCMS |
|---|---|---|
| B-1 | 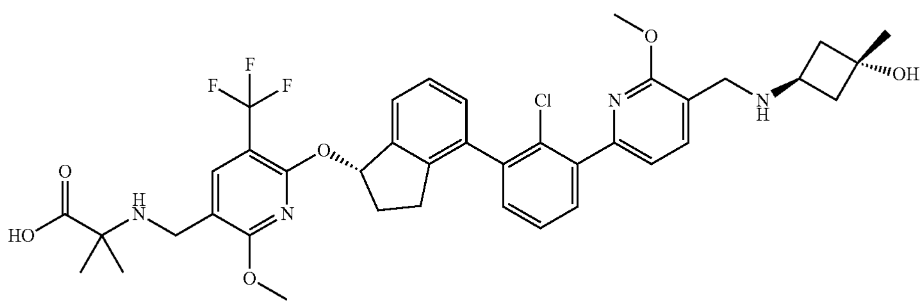 [SMILES: COc1nc(-c2cccc(-c3cccc4c3CC[C@@H]4Oc3nc(OC)c(CNC(C)(C)C(=O)O)cc3C(F)(F)F)c2Cl)ccc1CN[C@H]1C[C@](C)(O)C1] | 755.11 |
| B-2 | 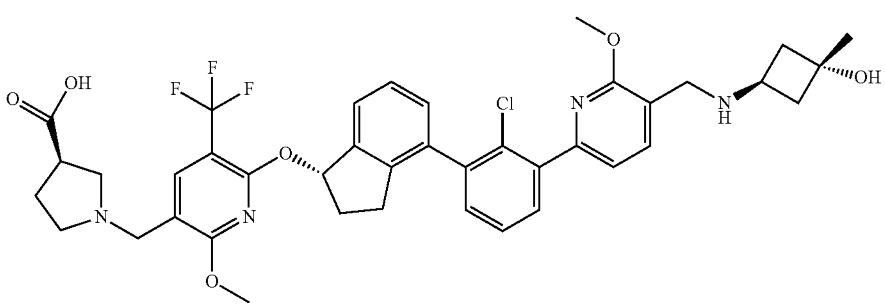 [SMILES: COc1nc(-c2cccc(-c3cccc4c3CC[C@@H]4Oc3nc(OC)c(CN4CC[C@@H](C(=O)O)C4)cc3C(F)(F)F)c2Cl)ccc1CN[C@H]1C[C@](C)(O)C1] | 767.09 |

TABLE 1B-continued

| No. | Structure | LCMS |
|---|---|---|
| B-3 | 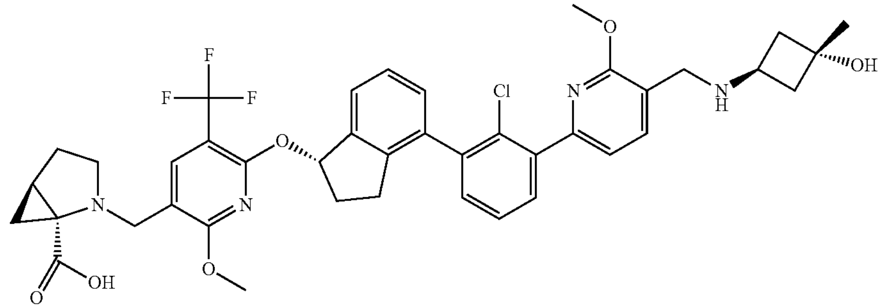 [SMILES: COc1nc(-c2cccc(-c3cccc4c3CC[C@@H]4Oc3nc(OC)c(CN4CC[C@@H]5C[C@@]54C(=O)O)cc3C(F)(F)F)c2Cl)ccc1CN[C@H]1C[C@](C)(O)C1] | 779.1 |
| B-4 | 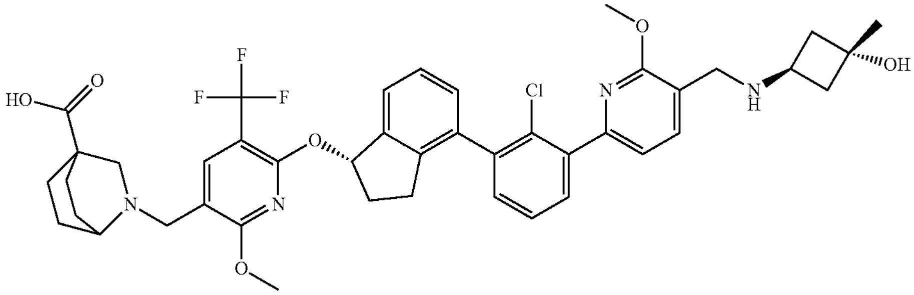 [SMILES: COc1nc(-c2cccc(-c3cccc4c3CC[C@@H]4Oc3nc(OC)c(CN4CC5(C(=O)O)CCC4CC5)cc3C(F)(F)F)c2Cl)ccc1CN[C@H]1C[C@](C)(O)C1] | 807.11 |
| B-5 | 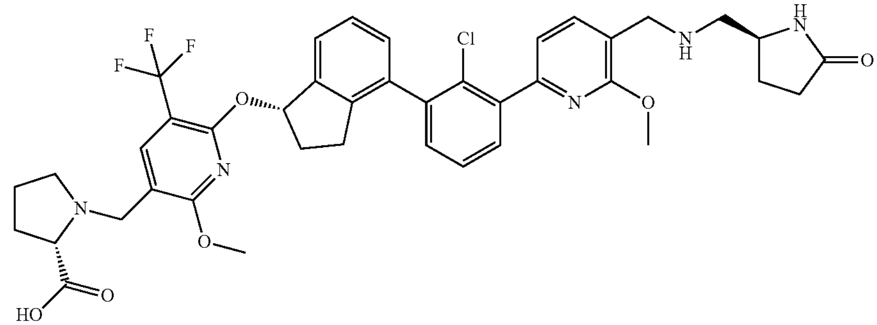 [SMILES: COc1nc(-c2cccc(-c3cccc4c3CC[C@@H]4Oc3nc(OC)c(CN4CCC[C@H]4C(=O)O)cc3C(F)(F)F)c2Cl)ccc1CNC[C@@H]1CCC(=O)N1] | 781.2 |
| B-6 | 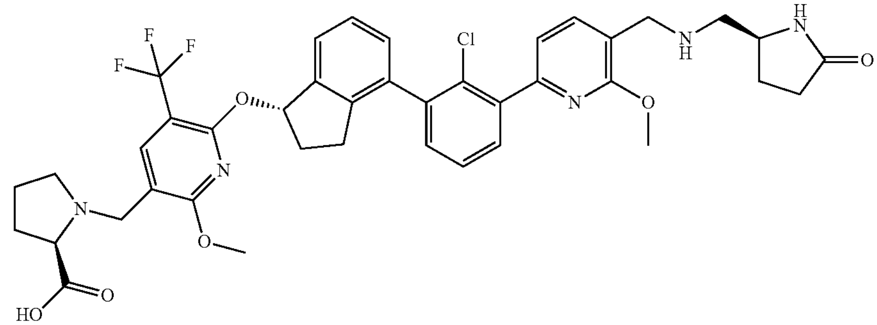 [SMILES: COc1nc(-c2cccc(-c3cccc4c3CC[C@@H]4Oc3nc(OC)c(CN4CCC[C@@H]4C(=O)O)cc3C(F)(F)F)c2Cl)ccc1CNC[C@@H]1CCC(=O)N1] | 781.2 |
| B-7 | 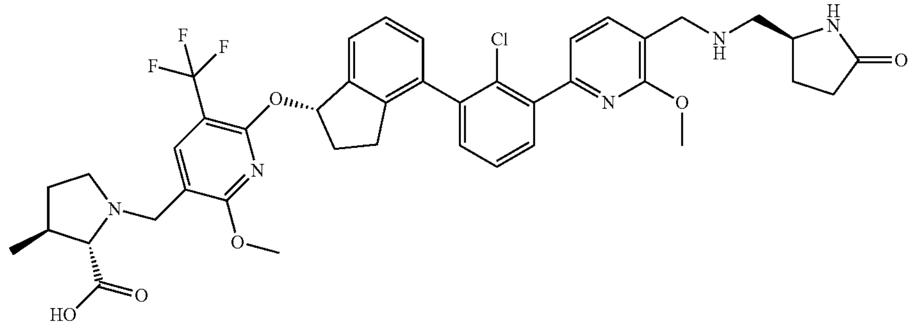 [SMILES: COc1nc(-c2cccc(-c3cccc4c3CC[C@@H]4Oc3nc(OC)c(CN4CC[C@H](C)[C@H]4C(=O)O)cc3C(F)(F)F)c2Cl)ccc1CNC[C@@H]1CCC(=O)N1] | 795.3 |

TABLE 1B-continued

| No. | Structure | LCMS |
|---|---|---|
| B-8 | 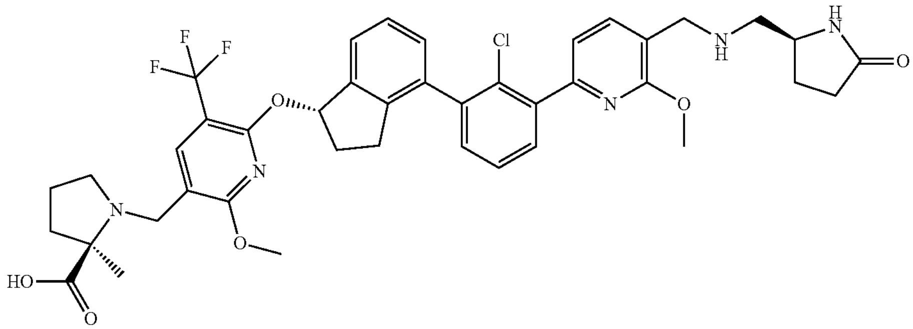 [SMILES: COc1nc(-c2cccc(-c3cccc4c3CC[C@@H]4Oc3nc(OC)c(CN4CCC[C@]4(C)C(=O)O)cc3C(F)(F)F)c2Cl)ccc1CNC[C@@H]1CCC(=O)N1] | 795.3 |
| B-9 | 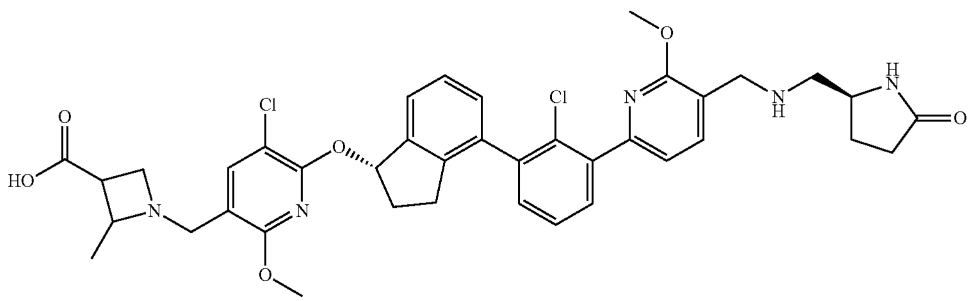 [SMILES: COc1nc(-c2cccc(-c3cccc4c3CC[C@@H]4Oc3nc(OC)c(CN4CC(C(=O)O)C4C)cc3Cl)c2Cl)ccc1CNC[C@@H]1CCC(=O)N1] | 746.25 |
| B-10 | 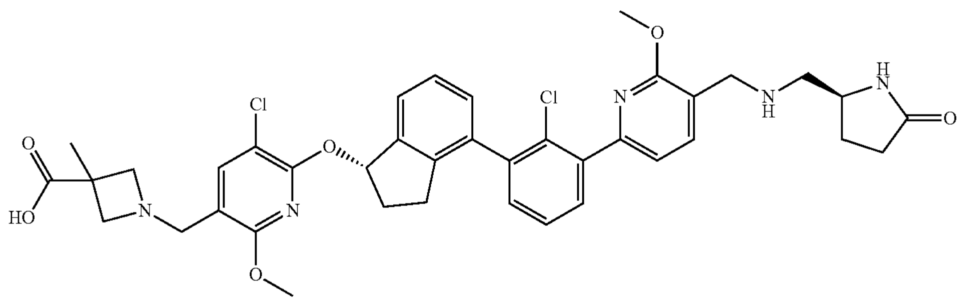 [SMILES: COc1nc(-c2cccc(-c3cccc4c3CC[C@@H]4Oc3nc(OC)c(CN4CC(C)(C(=O)O)C4)cc3Cl)c2Cl)ccc1CNC[C@@H]1CCC(=O)N1] | 746.25 |
| B-11 | 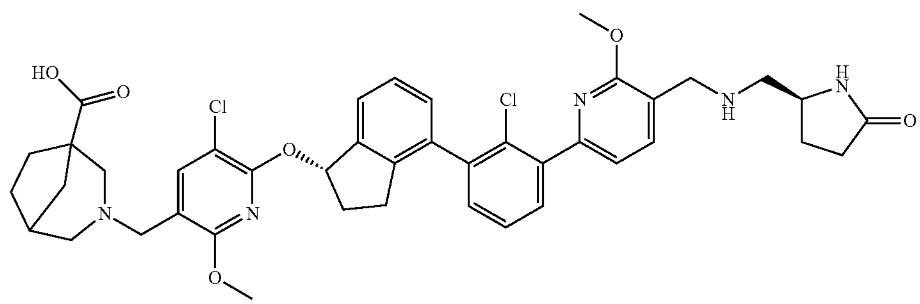 [SMILES: COc1nc(-c2cccc(-c3cccc4c3CC[C@@H]4Oc3nc(OC)c(CN4CC5CCC(C(=O)O)(C5)C4)cc3Cl)c2Cl)ccc1CNC[C@@H]1CCC(=O)N1] | 786.28 |
| B-12 | 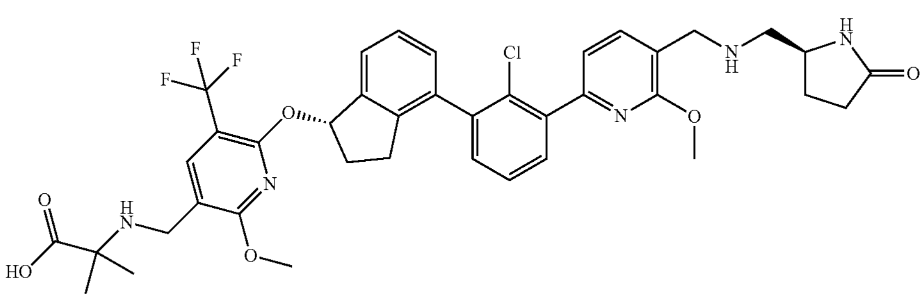 [SMILES: COc1nc(-c2cccc(-c3cccc4c3CC[C@@H]4Oc3nc(OC)c(CNC(C)(C)C(=O)O)cc3C(F)(F)F)c2Cl)ccc1CNC[C@@H]1CCC(=O)N1] | 769.2 |

TABLE 1B-continued

| No. | Structure | LCMS |
|---|---|---|
| B-13 | 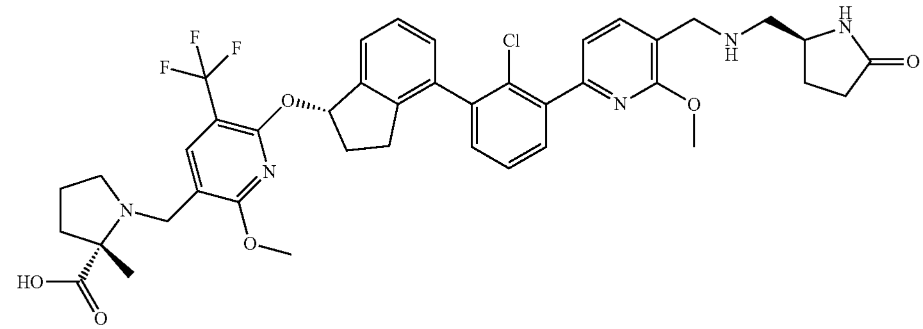 [SMILES: COc1nc(-c2cccc(-c3cccc4c3CC[C@@H]4Oc3nc(OC)c(CN4CCC[C@@]4(C)C(=O)O)cc3C(F)(F)F)c2Cl)ccc1CNC[C@@H]1CCC(=O)N1] | 795.3 |
| B-14 | 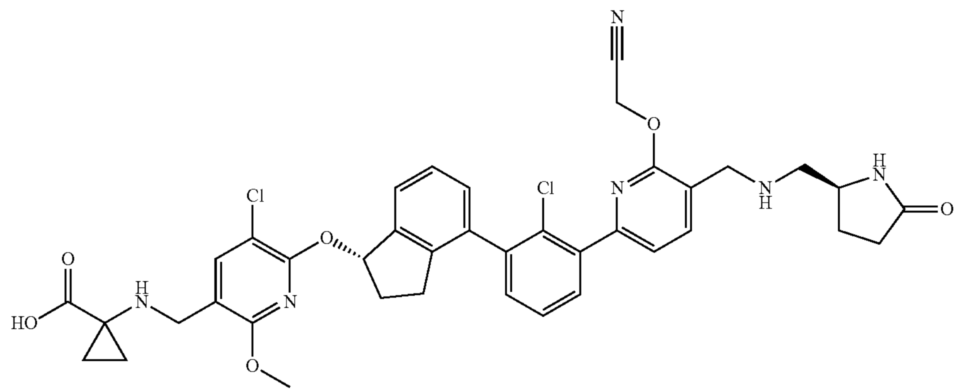 [SMILES: COc1nc(O[C@H]2CCc3c(-c4cccc(-c5ccc(CNC[C@@H]6CCC(=O)N6)c(OCC#N)n5)c4Cl)cccc32)c(Cl)cc1CNC1(C(=O)O)CC1] | 757.2 |
| B-15 | 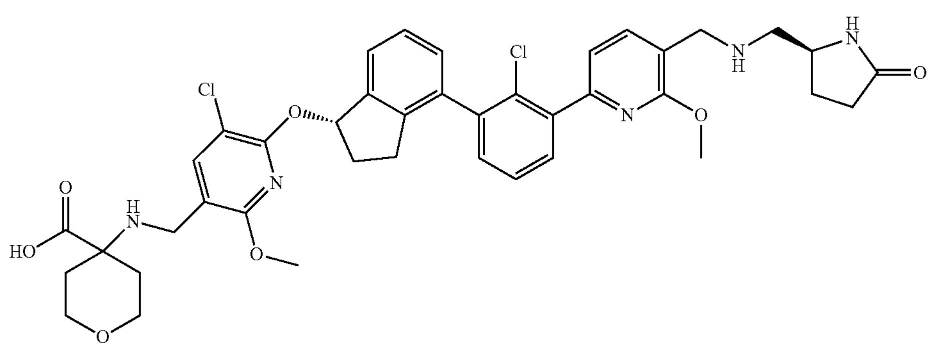 [SMILES: COc1nc(-c2cccc(-c3cccc4c3CC[C@@H]4Oc3nc(OC)c(CNC4(C(=O)O)CCOCC4)cc3Cl)c2Cl)ccc1CNC[C@@H]1CCC(=O)N1] | 777.7 |
| B-16 | 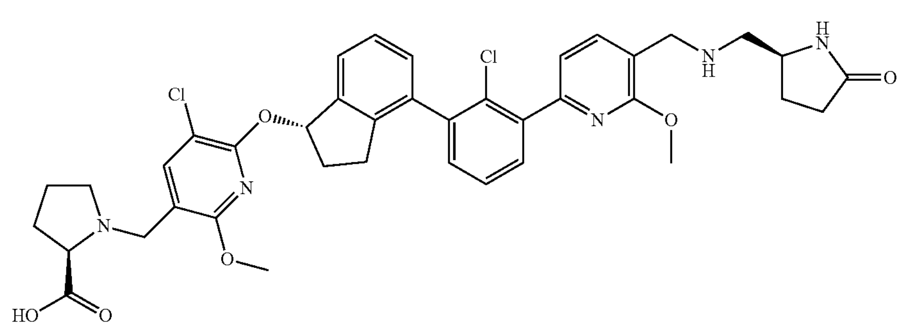 [SMILES: COc1nc(-c2cccc(-c3cccc4c3CC[C@@H]4Oc3nc(OC)c(CN4CCC[C@@H]4C(=O)O)cc3Cl)c2Cl)ccc1CNC[C@@H]1CCC(=O)N1] | 747.7 |

TABLE 1B-continued

| No. | Structure | LCMS |
|---|---|---|
| B-17 | 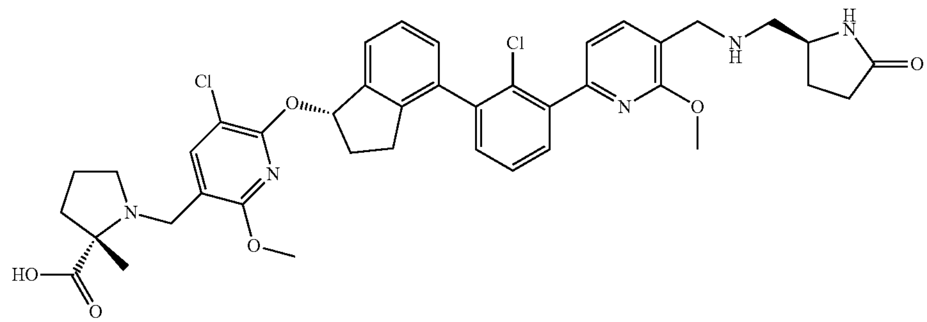 [SMILES: COc1nc(-c2cccc(-c3cccc4c3CC[C@@H]4Oc3nc(OC)c(CN4CCC[C@@]4(C)C(=O)O)cc3Cl)c2Cl)ccc1CNC[C@@H]1CCC(=O)N1] | 761.7 |
| B-18 | 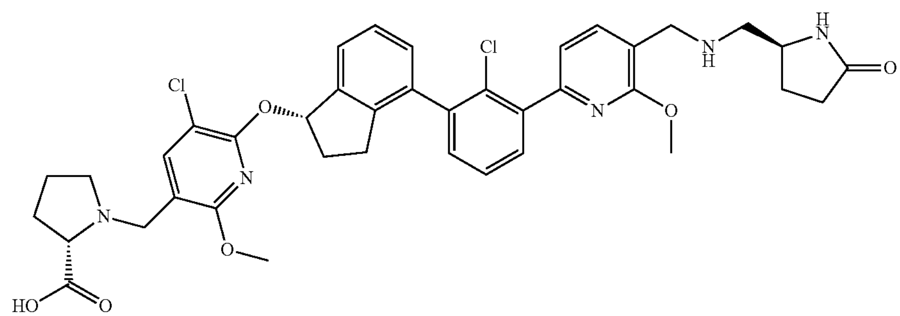 [SMILES: COc1nc(-c2cccc(-c3cccc4c3CC[C@@H]4Oc3nc(OC)c(CN4CCC[C@H]4C(=O)O)cc3Cl)c2Cl)ccc1CNC[C@@H]1CCC(=O)N1] | 747.7 |
| B-19 | 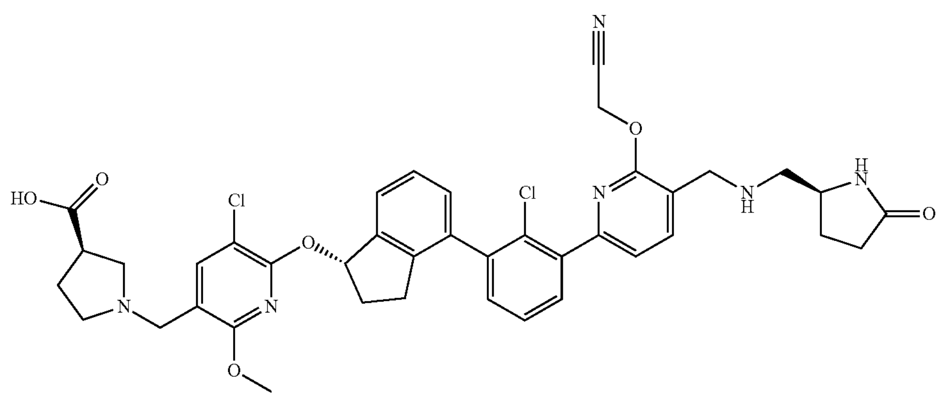 [SMILES: COc1nc(O[C@H]2CCc3c(-c4cccc(-c5ccc(CNC[C@@H]6CCC(=O)N6)c(OCC#N)n5)c4Cl)cccc32)c(Cl)cc1CN1CC[C@@H](C(=O)O)C1] | 771.2 |
| B-20 | 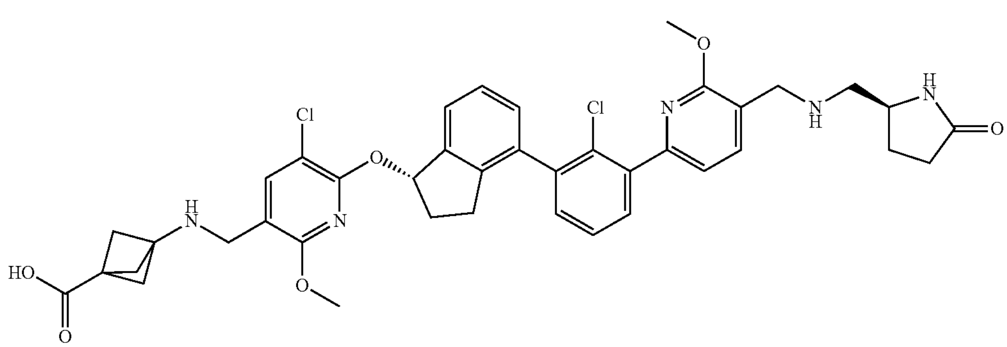 [SMILES: COc1nc(-c2cccc(-c3cccc4c3CC[C@@H]4Oc3nc(OC)c(CNC45CC(C(=O)O)(C4)C5)cc3Cl)c2Cl)ccc1CNC[C@@H]1CCC(=O)N1] | 757.8 |

TABLE 1B-continued

| No. | Structure | LCMS |
|---|---|---|
| B-21 | 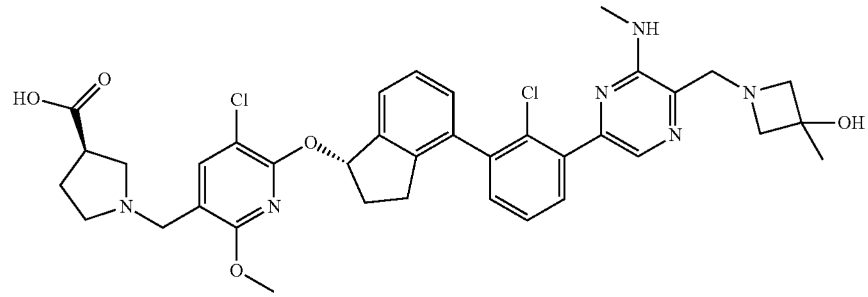 [SMILES: CNc1nc(-c2cccc(-c3cccc4c3CC[C@@H]4Oc3nc(OC)c(CN4CC[C@@H](C(=O)O)C4)cc3Cl)c2Cl)cnc1CN1CC(C)(O)C1] | 719 |
| B-22 | 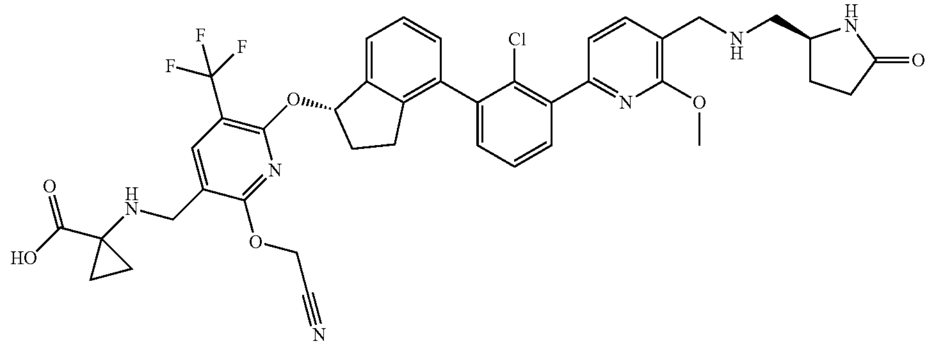 [SMILES: COc1nc(-c2cccc(-c3cccc4c3CC[C@@H]4Oc3nc(OCC#N)c(CNC4(C(=O)O)CC4)cc3C(F)(F)F)c2Cl)ccc1CNC[C@@H]1CCC(=O)N1] | 792.2 |
| B-23 | 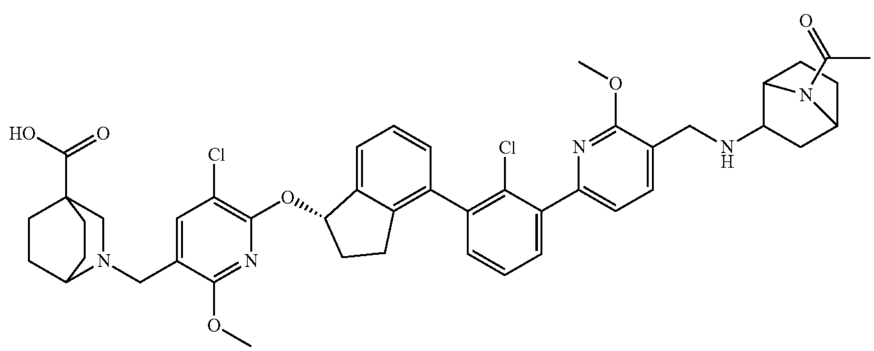 [SMILES: COc1nc(-c2cccc(-c3cccc4c3CC[C@@H]4Oc3nc(OC)c(CN4CC5(C(=O)O)CCC4CC5)cc3Cl)c2Cl)ccc1CNC1CC2CCC1N2C(C)=O] | 826.31 |
| B-24 | 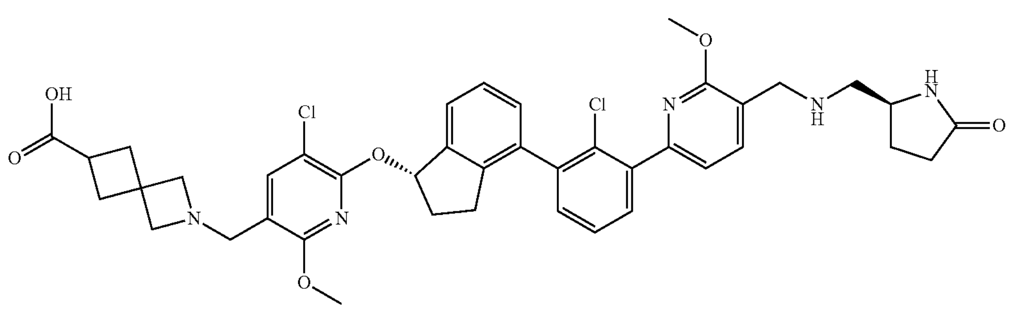 [SMILES: COc1nc(-c2cccc(-c3cccc4c3CC[C@@H]4Oc3nc(OC)c(CN4CC5(CC(C(=O)O)C5)C4)cc3Cl)c2Cl)ccc1CNC[C@@H]1CCC(=O)N1] | 771.9 |
| B-25 | 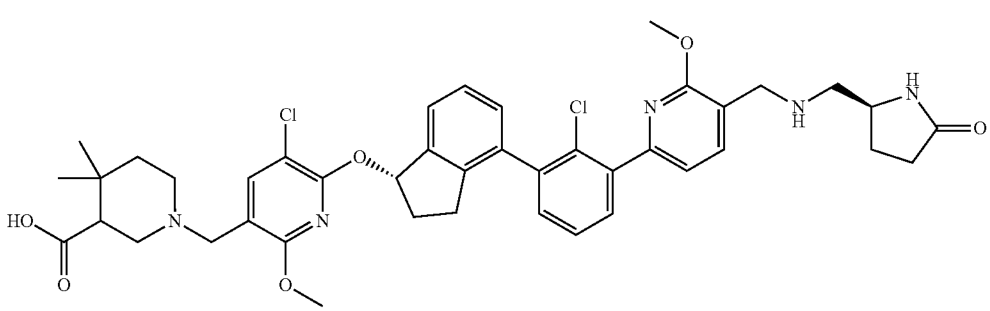 [SMILES: COc1nc(-c2cccc(-c3cccc4c3CC[C@@H]4Oc3nc(OC)c(CN4CCC(C)(C)C(C(=O)O)C4)cc3Cl)c2Cl)ccc1CNC[C@@H]1CCC(=O)N1] | 788 |

TABLE 1B-continued

| No. | Structure | LCMS |
|---|---|---|
| B-26 | 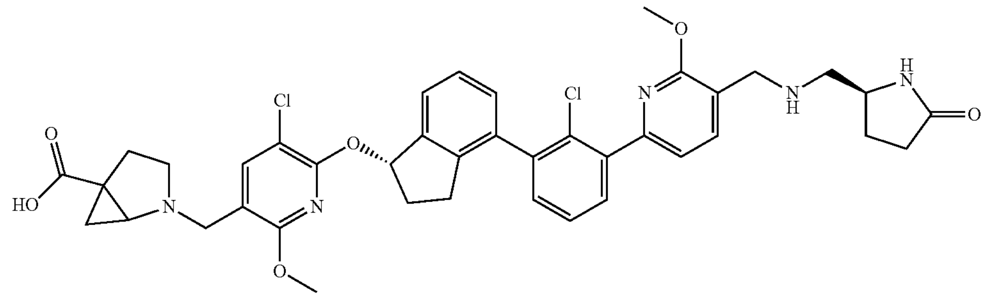 [SMILES: COc1nc(-c2cccc(-c3cccc4c3CC[C@@H]4Oc3nc(OC)c(CN4CCC5(C(=O)O)CC45)cc3Cl)c2Cl)ccc1CNC[C@@H]1CCC(=O)N1] | 757.8 |
| B-27 | 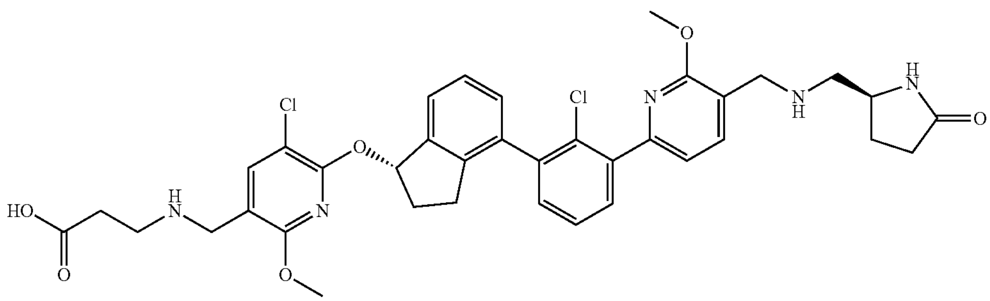 [SMILES: COc1nc(-c2cccc(-c3cccc4c3CC[C@@H]4Oc3nc(OC)c(CNCCC(=O)O)cc3Cl)c2Cl)ccc1CNC[C@@H]1CCC(=O)N1] | 719.9 |
| B-28 | 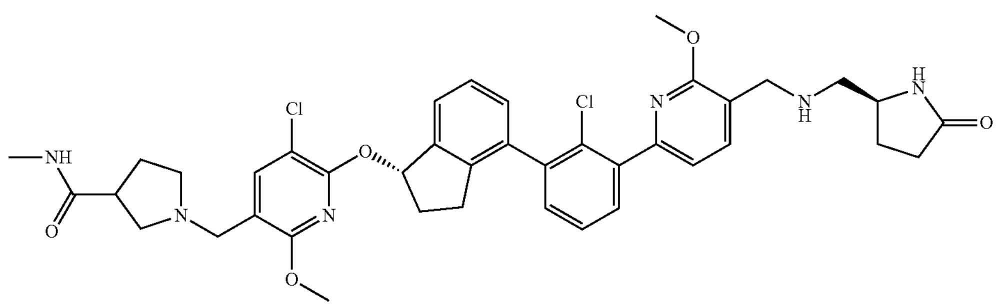 [SMILES: CNC(=O)C1CCN(Cc2cc(Cl)c(O[C@H]3CCc4c(-c5cccc(-c6ccc(CNC[C@@H]7CCC(=O)N7)c(OC)n6)c5Cl)cccc43)nc2OC)C1] | 759.9 |
| B-29 | 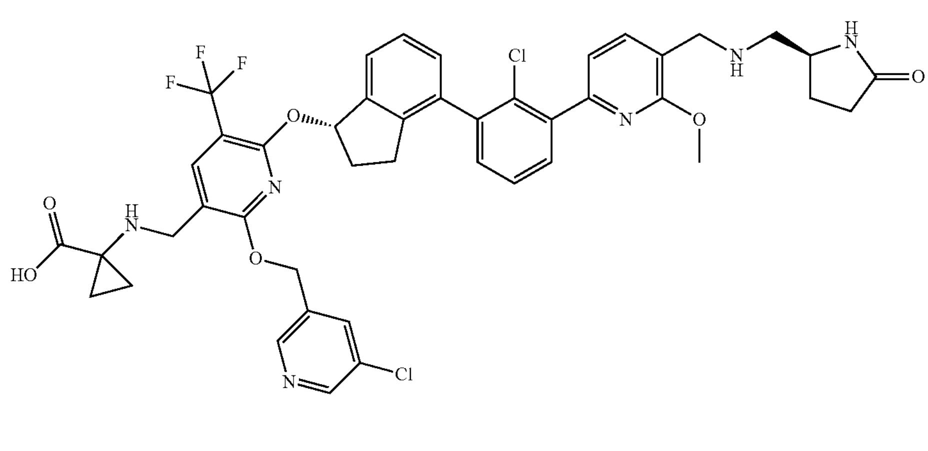 [SMILES: COc1nc(-c2cccc(-c3cccc4c3CC[C@@H]4Oc3nc(OCc4cncc(Cl)c4)c(CNC4(C(=O)O)CC4)cc3C(F)(F)F)c2Cl)ccc1CNC[C@@H]1CCC(=O)N1] | 878.7 |

TABLE 1B-continued

| No. | Structure | LCMS |
|---|---|---|
| B-30 | 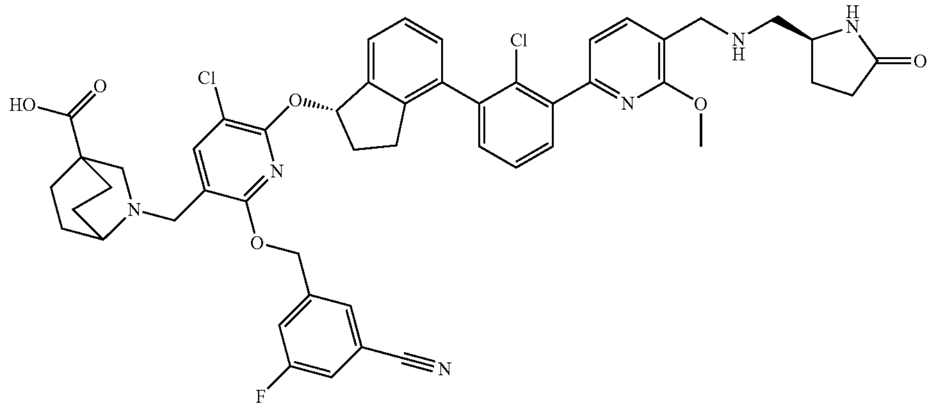 | 906.8 |
| B-31 | 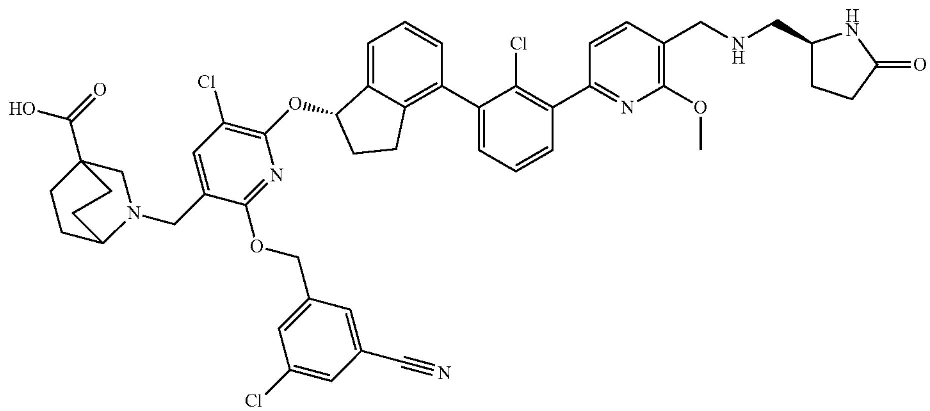 [SMILES: COc1nc(-c2cccc(-c3cccc4c3CC[C@@H]4Oc3nc(OCc4cc(F)cc(C#N)c4)c(CN4CC5(C(=O)O)CCC4CC5)cc3Cl)c2Cl)ccc1CNC[C@@H]1CCC(=O)N1] | 923.3 |
| B-32 | 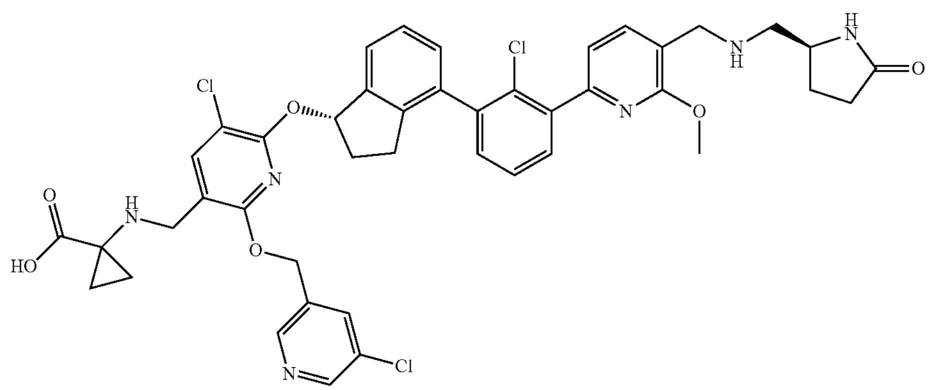 [SMILES: COc1nc(-c2cccc(-c3cccc4c3CC[C@@H]4Oc3nc(OCc4cncc(Cl)c4)c(CNC4(C(=O)O)CC4)cc3Cl)c2Cl)ccc1CNC[C@@H]1CCC(=O)N1] | 845.2 |
| B-33 | 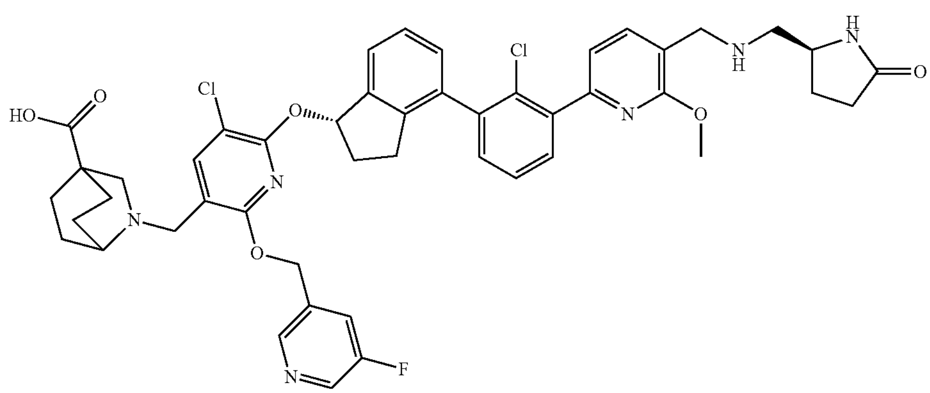 | 882.8 |

TABLE 1B-continued

| No. | Structure | LCMS |
|---|---|---|
| B-34 | 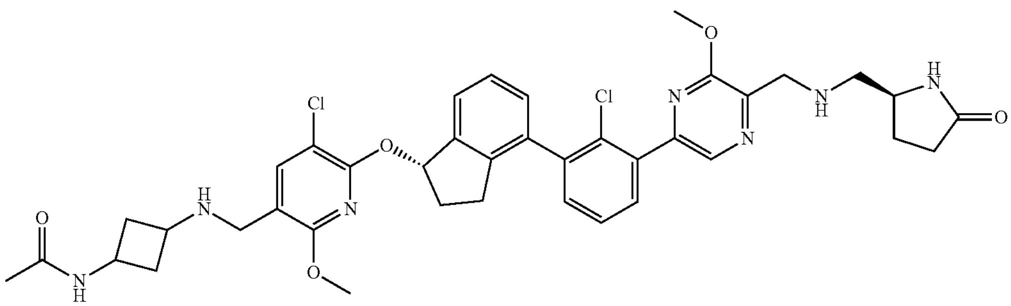 [SMILES: COc1nc(O[C@H]2CCc3c(-c4cccc(-c5cnc(CNC[C@@H]6CCC(=O)N6)c(OC)n5)c4Cl)cccc32)c(Cl)cc1CNC1CC(NC(C)=O)C1] | 759.9 |
| B-35 | 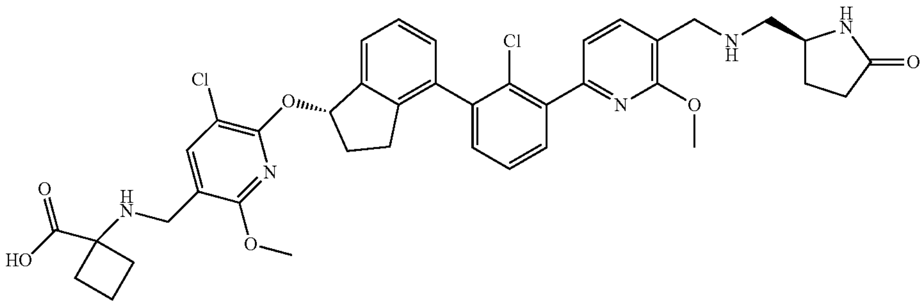 [SMILES: COc1nc(-c2cccc(-c3cccc4c3CC[C@@H]4Oc3nc(OC)c(CNC4(C(=O)O)CCC4)cc3Cl)c2Cl)ccc1CNC[C@@H]1CCC(=O)N1] | 747.7 |
| B-36 | 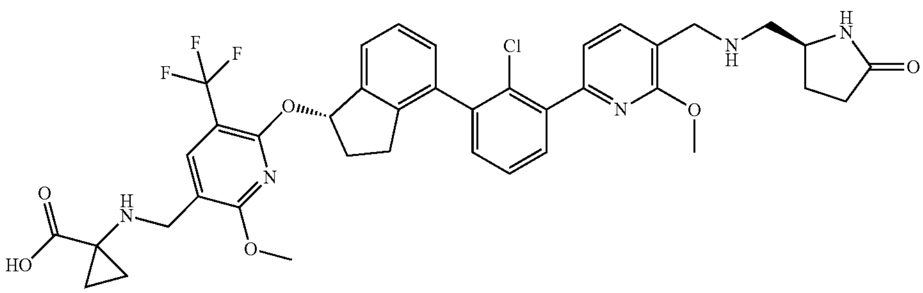 [SMILES: COc1nc(-c2cccc(-c3cccc4c3CC[C@@H]4Oc3nc(OC)c(CNC4(C(=O)O)CC4)cc3C(F)(F)F)c2Cl)ccc1CNC[C@@H]1CCC(=O)N1] | 767.2 |
| B-37 | 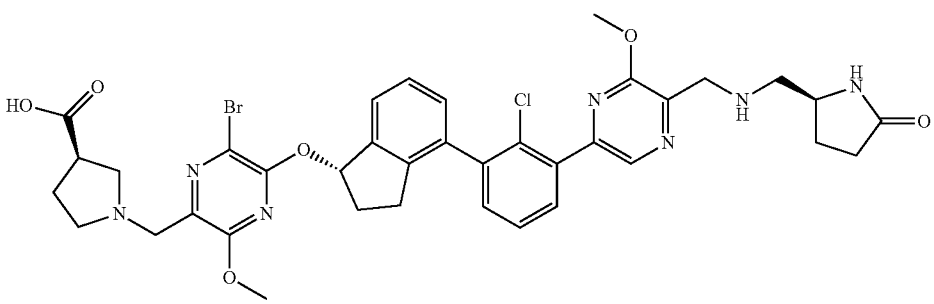 [SMILES: COc1nc(-c2cccc(-c3cccc4c3CC[C@@H]4Oc3nc(OC)c(CN4CC[C@@H](C(=O)O)C4)nc3Br)c2Cl)cnc1CNC[C@@H]1CCC(=O)N1] | 792.1 |
| B-38 | 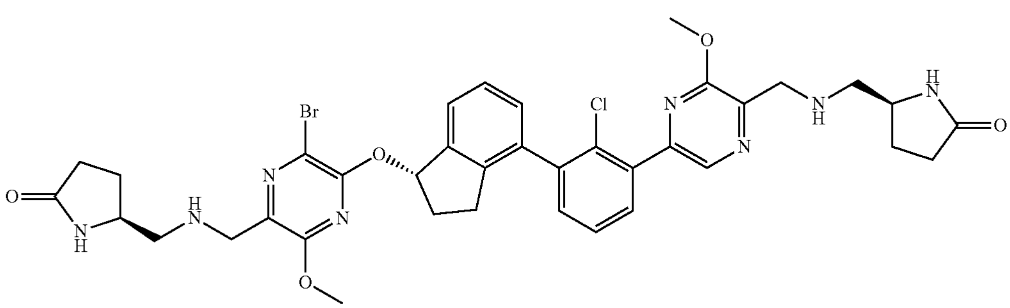 | 791.2 |

TABLE 1B-continued

| No. | Structure | LCMS |
|---|---|---|
| B-39 | 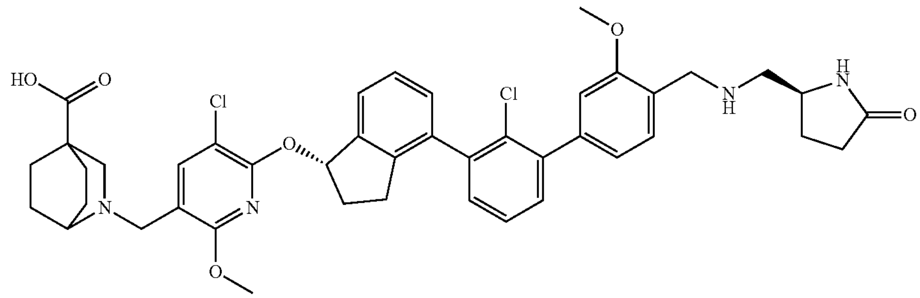 [SMILES: COc1cc(-c2cccc(-c3cccc4c3CC[C@@H]4Oc3nc(OC)c(CN4CC5(C(=O)O)CCC4CC5)cc3Cl)c2Cl)ccc1CNC[C@@H]1CCC(=O)N1] | 785.29 |
| B-40 | 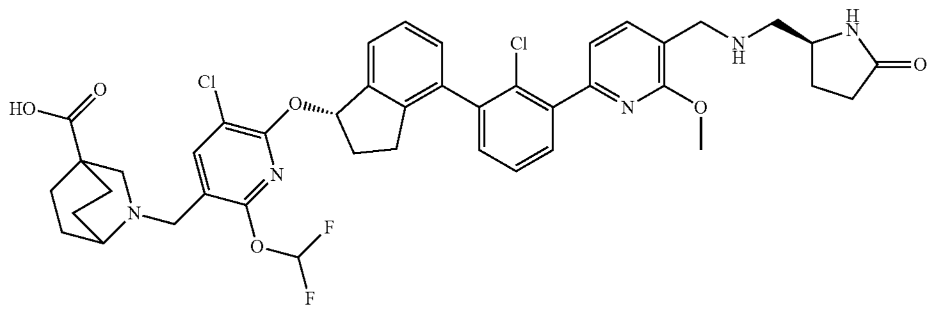 [SMILES: COc1nc(-c2cccc(-c3cccc4c3CC[C@@H]4Oc3nc(OC(F)F)c(CN4CC5(C(=O)O)CCC4CC5)cc3Cl)c2Cl)ccc1CNC[C@@H]1CCC(=O)N1] | 823.7 |
| B-41 | 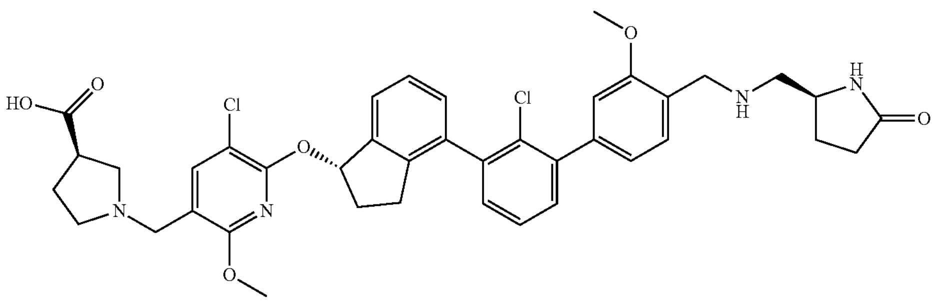 [SMILES: COc1cc(-c2cccc(-c3cccc4c3CC[C@@H]4Oc3nc(OC)c(CN4CC[C@@H](C(=O)O)C4)cc3Cl)c2Cl)ccc1CNC[C@@H]1CCC(=O)N1] | 745.26 |
| B-42 | 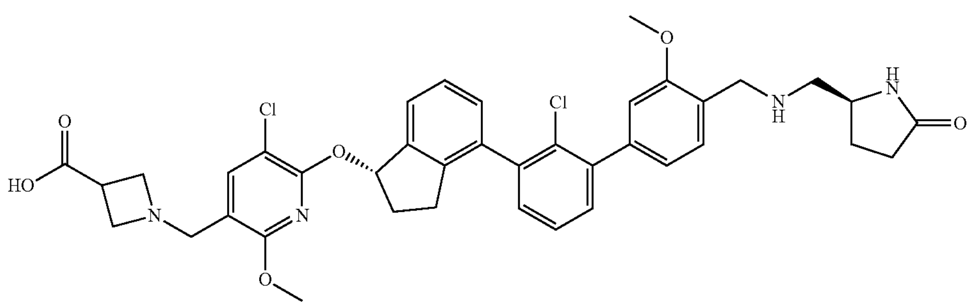 [SMILES: COc1cc(-c2cccc(-c3cccc4c3CC[C@@H]4Oc3nc(OC)c(CN4CC(C(=O)O)C4)cc3Cl)c2Cl)ccc1CNC[C@@H]1CCC(=O)N1] | 731.24 |
| B-43 | 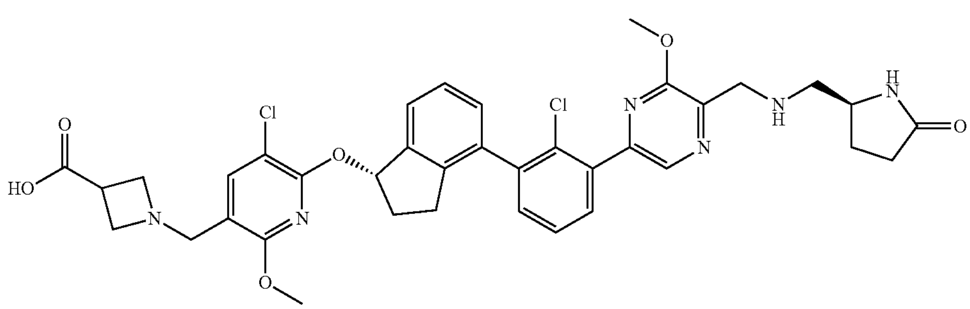 [SMILES: COc1nc(O[C@H]2CCc3c(-c4cccc(-c5cnc(CNC[C@@H]6CCC(=O)N6)c(OC)n5)c4Cl)cccc32)c(Cl)cc1CN1CC(C(=O)O)C1] | 733.23 |

TABLE 1B-continued

| No. | Structure | LCMS |
|---|---|---|
| B-44 | 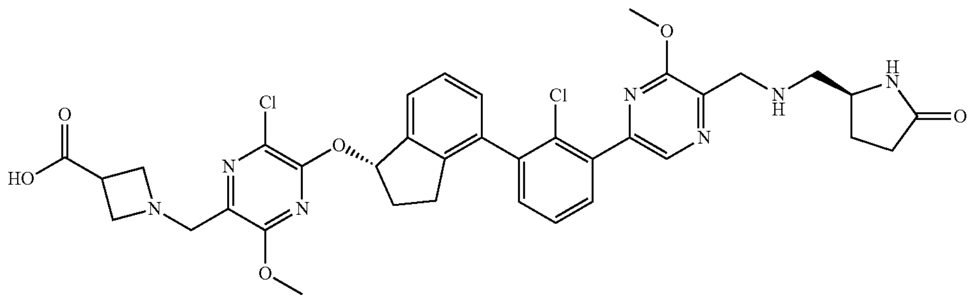 [SMILES: COc1nc(-c2cccc(-c3cccc4c3CC[C@@H]4Oc3nc(OC)c(CN4CC(C(=O)O)C4)nc3Cl)c2Cl)cnc1CNC[C@@H]1CCC(=O)N1] | 734.2 |
| B-45 | 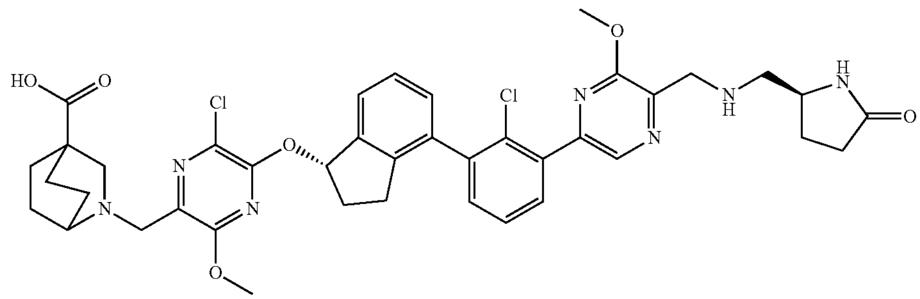 | 788.3 |
| B-46 | 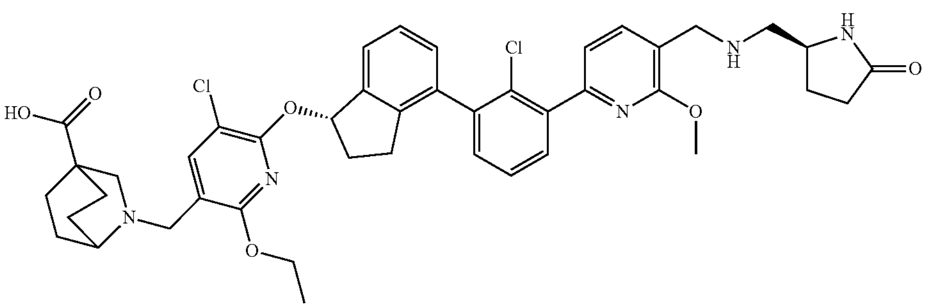 [SMILES: CCOc1nc(O[C@H]2CCc3c(-c4cccc(-c5ccc(CNC[C@@H]6CCC(=O)N6)c(OC)n5)c4Cl)cccc32)c(Cl)cc1CN1CC2(C(=O)O)CCC1CC2] | 801.8 |
| B-47 | 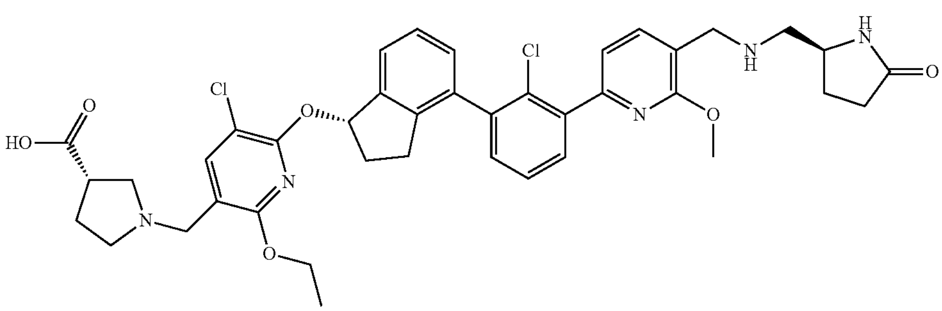 [SMILES: CCOc1nc(O[C@H]2CCc3c(-c4cccc(-c5ccc(CNC[C@@H]6CCC(=O)N6)c(OC)n5)c4Cl)cccc32)c(Cl)cc1CN1CC[C@H](C(=O)O)C1] | 761.7 |
| B-48 | 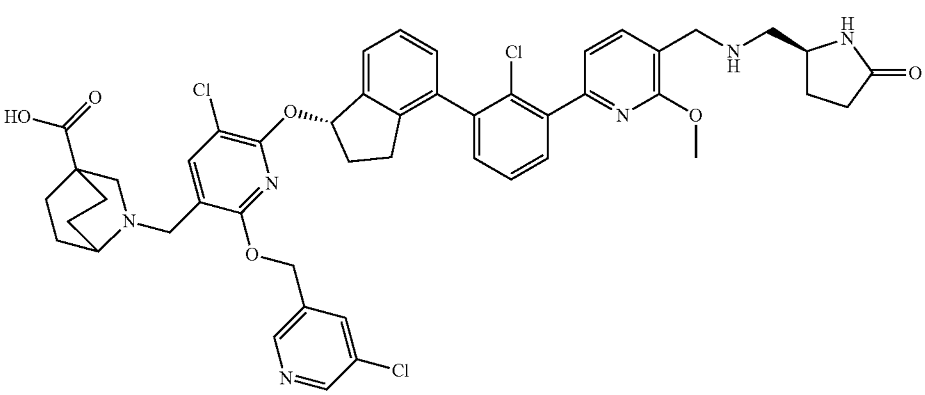 [SMILES: COc1nc(-c2cccc(-c3cccc4c3CC[C@@H]4Oc3nc(OCc4cncc(Cl)c4)c(CN4CC5(C(=O)O)CCC4CC5)cc3Cl)c2Cl)ccc1CNC[C@@H]1CCC(=O)N1] | 899.3 |

TABLE 1B-continued

| No. | Structure | LCMS |
|---|---|---|
| B-49 | 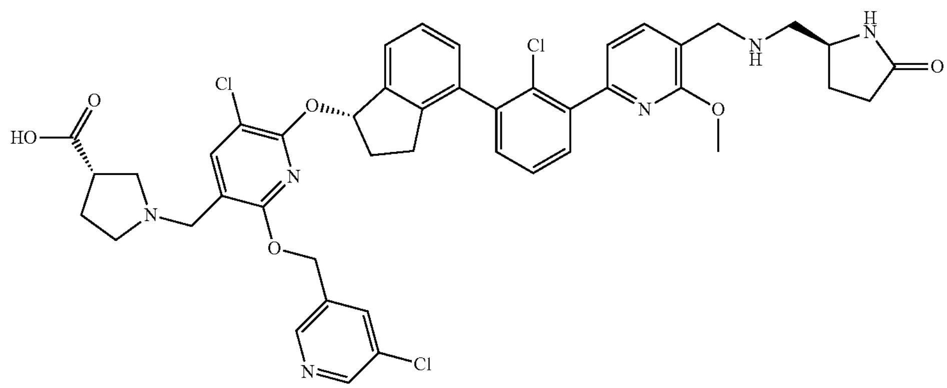 [SMILES: COc1nc(-c2cccc(-c3cccc4c3CC[C@@H]4Oc3nc(OCc4cncc(Cl)c4)c(CN4CC[C@H](C(=O)O)C4)cc3Cl)c2Cl)ccc1CNC[C@@H]1CCC(=O)N1] | 859.2 |
| B-50 | 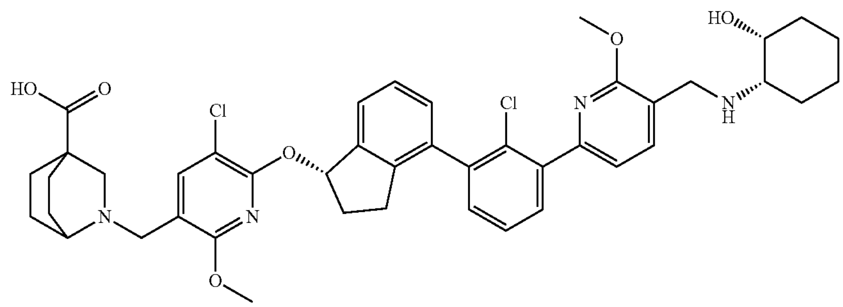 [SMILES: COc1nc(-c2cccc(-c3cccc4c3CC[C@@H]4Oc3nc(OC)c(CN4CC5(C(=O)O)CCC4CC5)cc3Cl)c2Cl)ccc1CN[C@H]1CCCC[C@H]1O] | 787.3 |
| B-51 | 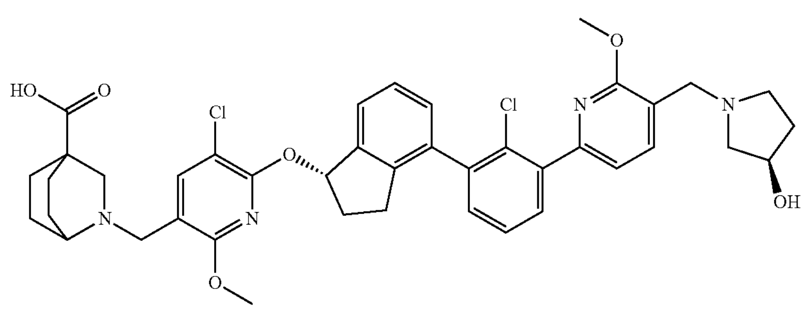 [SMILES: COc1nc(-c2cccc(-c3cccc4c3CC[C@@H]4Oc3nc(OC)c(CN4CC5(C(=O)O)CCC4CC5)cc3Cl)c2Cl)ccc1CN1CC[C@@H](O)C1] | 759.29 |
| B-52 | 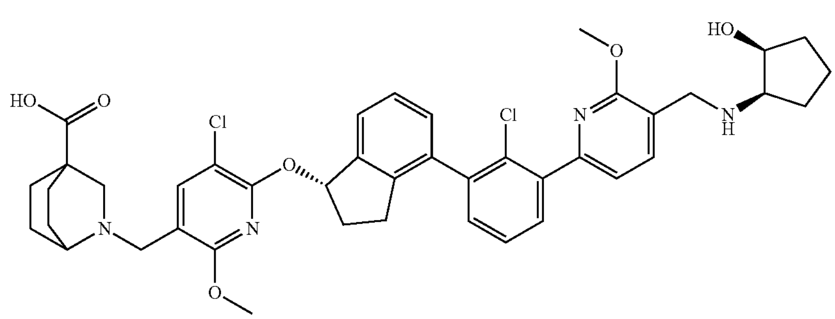 [SMILES: COc1nc(-c2cccc(-c3cccc4c3CC[C@@H]4Oc3nc(OC)c(CN4CC5(C(=O)O)CCC4CC5)cc3Cl)c2Cl)ccc1CN[C@@H]1CCC[C@@H]1O] | 773.29 |

TABLE 1B-continued

| No. | Structure | LCMS |
|---|---|---|
| B-53 | 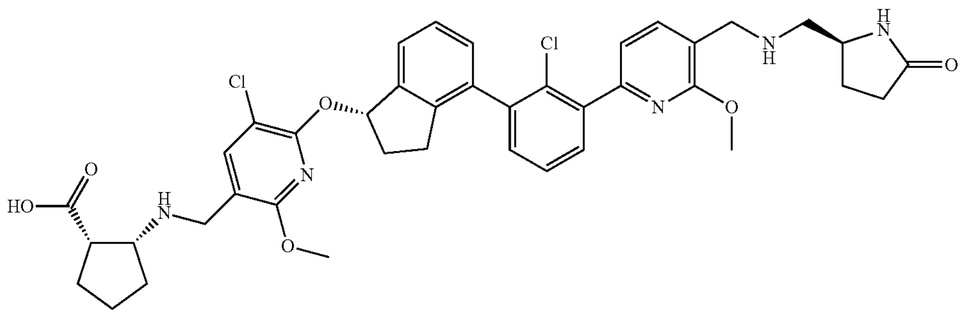 [SMILES: COc1nc(-c2cccc(-c3cccc4c3CC[C@@H]4Oc3nc(OC)c(CN[C@@H]4CCC[C@@H]4C(=O)O)cc3Cl)c2Cl)ccc1CNC[C@@H]1CCC(=O)N1] | 761.7 |
| B-54 | 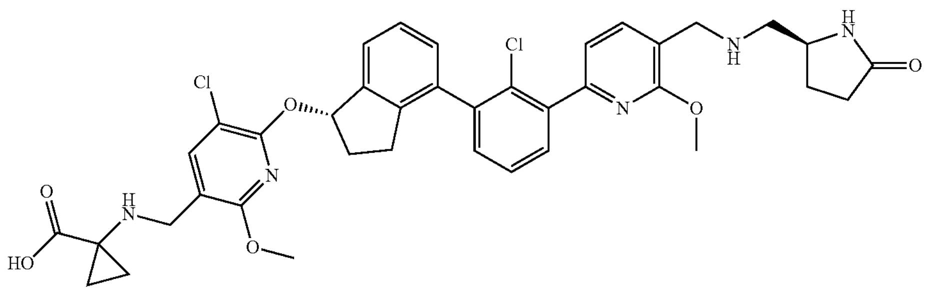 [SMILES: COc1nc(-c2cccc(-c3cccc4c3CC[C@@H]4Oc3nc(OC)c(CNC4(C(=O)O)CC4)cc3Cl)c2Cl)ccc1CNC[C@@H]1CCC(=O)N1] | 733.7 |
| B-55 | 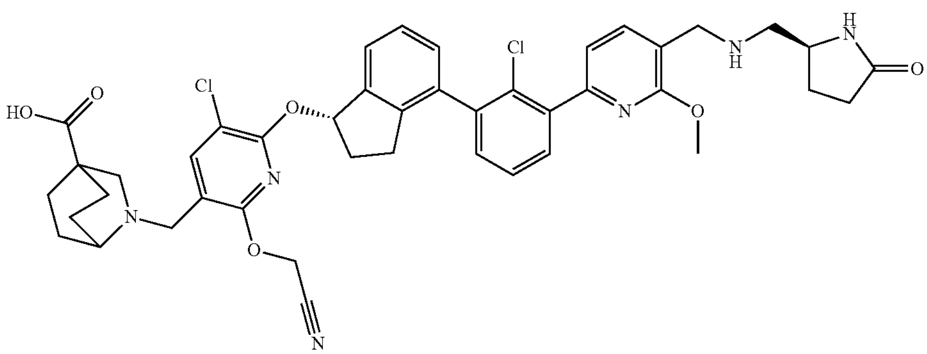 [SMILES: COc1nc(-c2cccc(-c3cccc4c3CC[C@@H]4Oc3nc(OCC#N)c(CN4CC5(C(=O)O)CCC4CC5)cc3Cl)c2Cl)ccc1CNC[C@@H]1CCC(=O)N1] | 812.8 |
| B-56 | 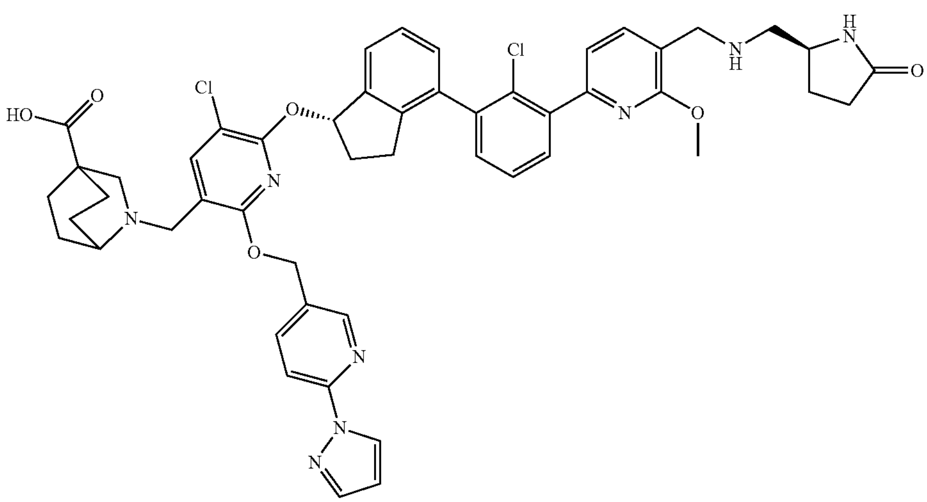 [SMILES: COc1nc(-c2cccc(-c3cccc4c3CC[C@@H]4Oc3nc(OCc4ccc(-n5cccn5)nc4)c(CN4CC5(C(=O)O)CCC4CC5)cc3Cl)c2Cl)ccc1CNC[C@@H]1CCC(=O)N1] | 930.9 |

TABLE 1B-continued

| No. | Structure | LCMS |
|---|---|---|
| B-57 | 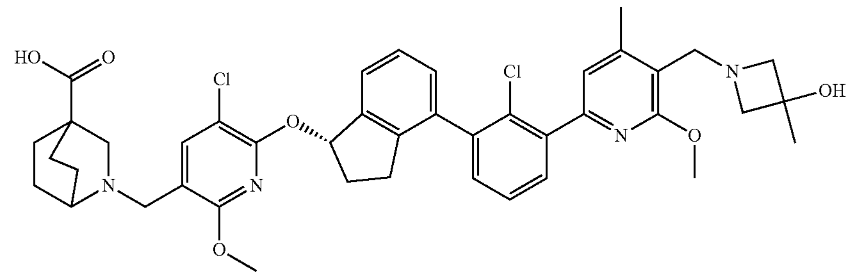 [SMILES: COc1nc(O[C@H]2CCc3c(-c4cccc(-c5cc(C)c(CN6CC(C)(O)C6)c(OC)n5)c4Cl)cccc32)c(Cl)cc1CN1CC2(C(=O)O)CCC1CC2] | 772.942 |
| B-58 | 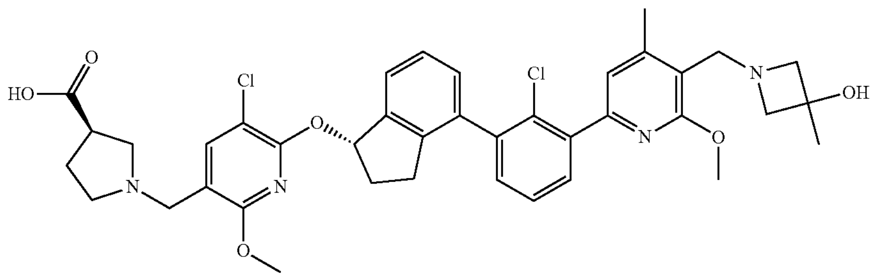 [SMILES: COc1nc(O[C@H]2CCc3c(-c4cccc(-c5cc(C)c(CN6CC(C)(O)C6)c(OC)n5)c4Cl)cccc32)c(Cl)cc1CN1CC[C@@H](C(=O)O)C1] | 732.979 |
| B-59 | 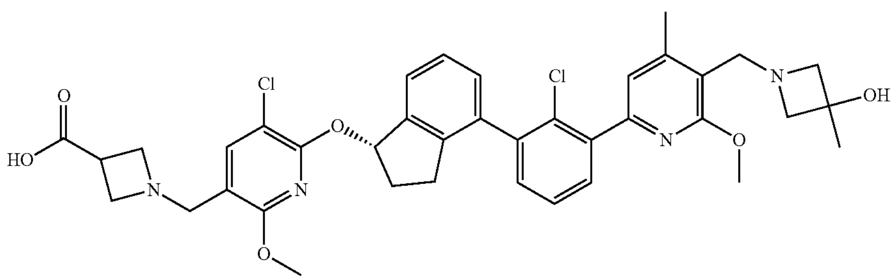 [SMILES: COc1nc(O[C@H]2CCc3c(-c4cccc(-c5cc(C)c(CN6CC(C)(O)C6)c(OC)n5)c4Cl)cccc32)c(Cl)cc1CN1CC(C(=O)O)C1] | 718.984 |
| B-60 | 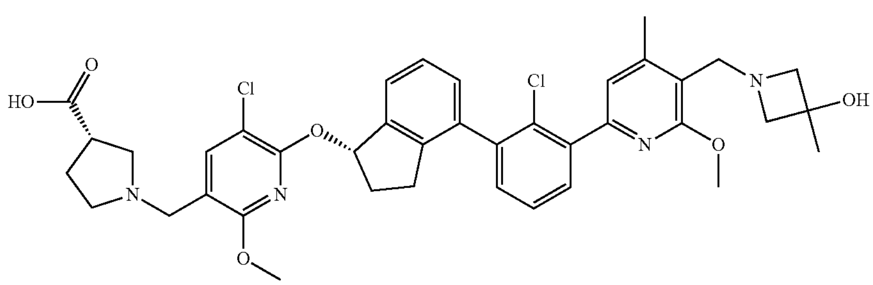 [SMILES: COc1nc(O[C@H]2CCc3c(-c4cccc(-c5cc(C)c(CN6CC(C)(O)C6)c(OC)n5)c4Cl)cccc32)c(Cl)cc1CN1CC[C@H](C(=O)O)C1] | 732.981 |
| B-61 | 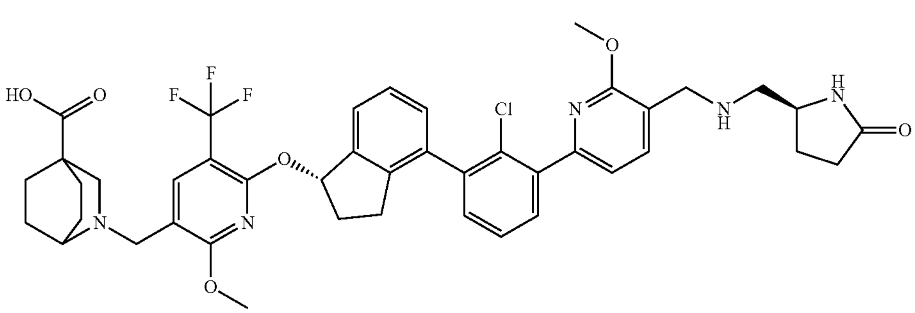 [SMILES: COc1nc(-c2cccc(-c3cccc4c3CC[C@@H]4Oc3nc(OC)c(CN4CC5(C(=O)O)CCC4CC5)cc3C(F)(F)F)c2Cl)ccc1CNC[C@@H]1CCC(=O)N1] | 820.31 |

TABLE 1B-continued
| No. | Structure | LCMS |
|---|---|---|
| B-62 | 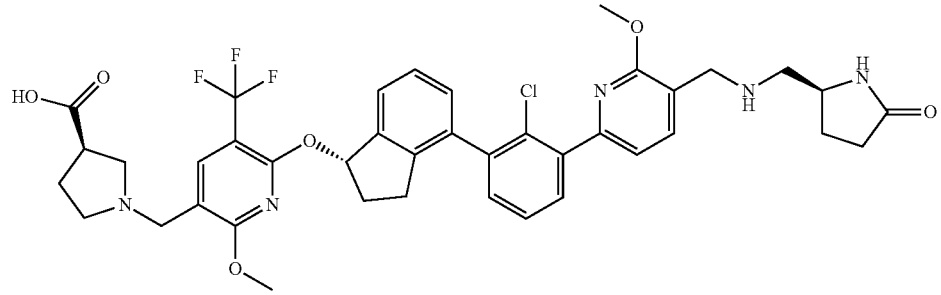 [SMILES: COc1nc(-c2cccc(-c3cccc4c3CC[C@@H]4Oc3nc(OC)c(CN4CC[C@@H](C(=O)O)C4)cc3C(F)(F)F)c2Cl)ccc1CNC[C@@H]1CCC(=O)N1] | 780.28 |
| B-63 | 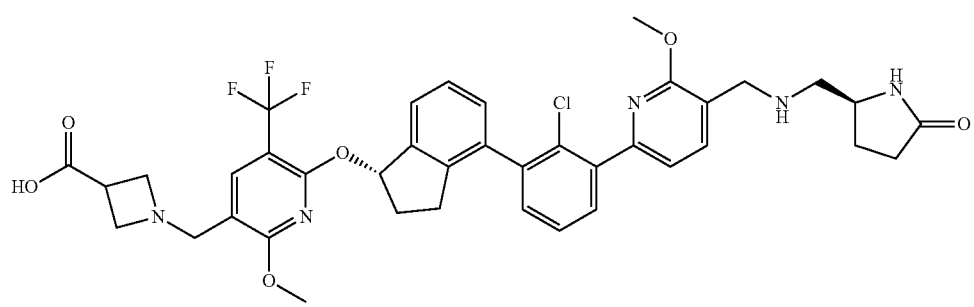 [SMILES: COc1nc(-c2cccc(-c3cccc4c3CC[C@@H]4Oc3nc(OC)c(CN4CC(C(=O)O)C4)cc3C(F)(F)F)c2Cl)ccc1CNC[C@@H]1CCC(=O)N1] | 766.26 |
| B-64 | 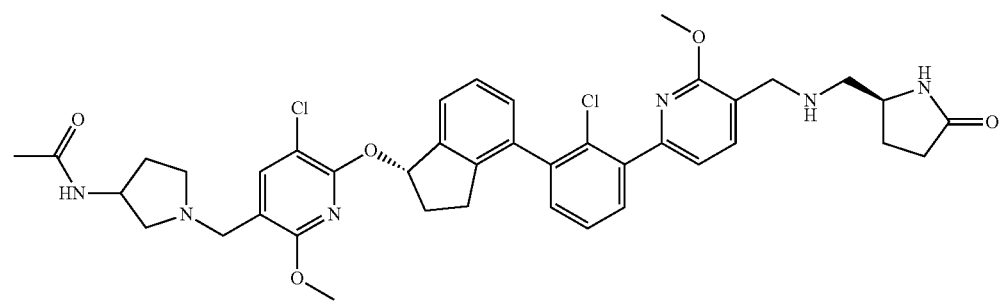 [SMILES: COc1nc(-c2cccc(-c3cccc4c3CC[C@@H]4Oc3nc(OC)c(CN4CCC(NC(C)=O)C4)cc3Cl)c2Cl)ccc1CNC[C@@H]1CCC(=O)N1] | 759 |
| B-65 | 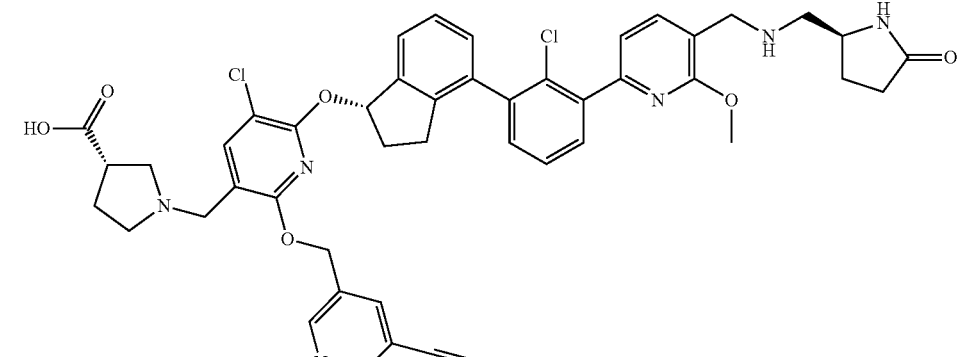 | 849.8 |

TABLE 1B-continued

| No. | Structure | LCMS |
|---|---|---|
| B-66 | 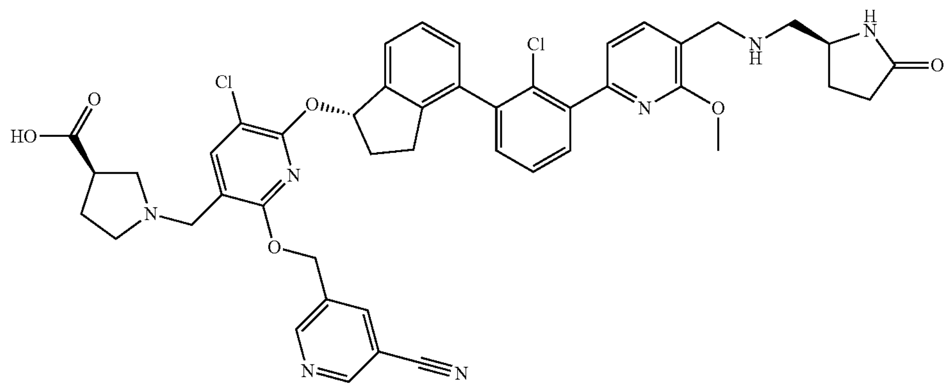 [SMILES: COc1nc(-c2cccc(-c3cccc4c3CC[C@@H]4Oc3nc(OCc4cncc(C#N)c4)c(CN4CC[C@@H](C(=O)O)C4)cc3Cl)c2Cl)ccc1CNC[C@@H]1CCC(=O)N1] | 849.8 |
| B-67 | 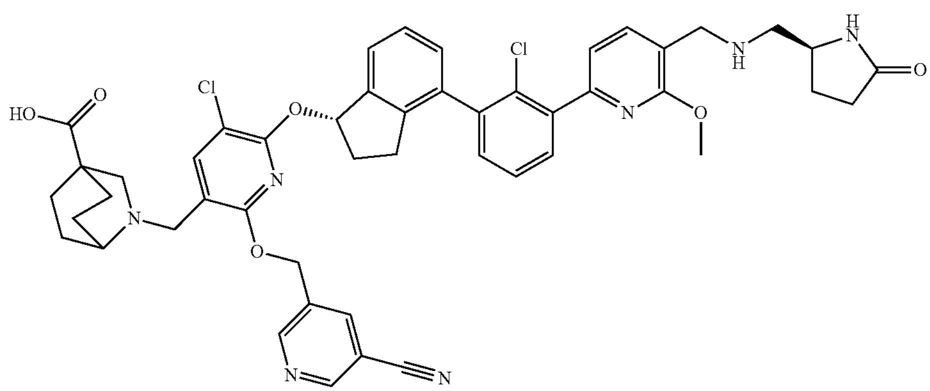 [SMILES: COc1nc(-c2cccc(-c3cccc4c3CC[C@@H]4Oc3nc(OCc4cncc(C#N)c4)c(CN4CC5(C(=O)O)CCC4CC5)cc3Cl)c2Cl)ccc1CNC[C@@H]1CCC(=O)N1] | 889.8 |
| B-68 | 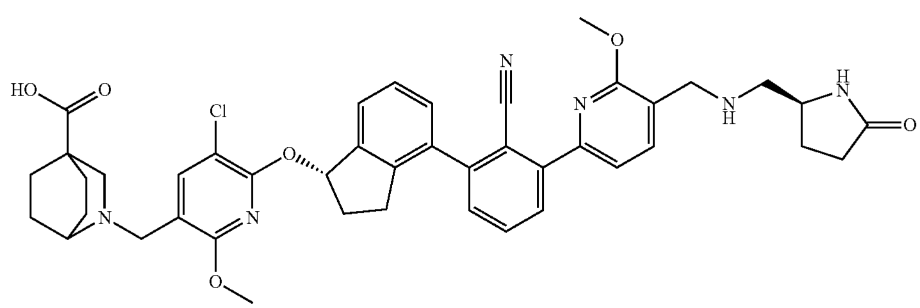 [SMILES: COc1nc(-c2cccc(-c3cccc4c3CC[C@@H]4Oc3nc(OC)c(CN4CC5(C(=O)O)CCC4CC5)cc3Cl)c2C#N)ccc1CNC[C@@H]1CCC(=O)N1] | 777.32 |
| B-69 | 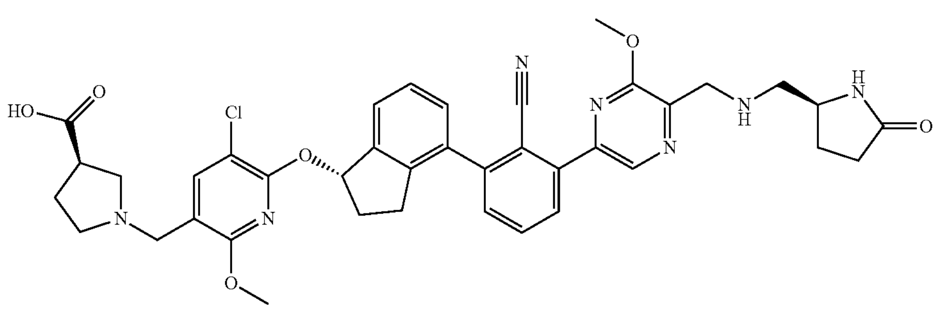 | 738.28 |

TABLE 1B-continued

| No. | Structure | LCMS |
|---|---|---|
| B-70 | 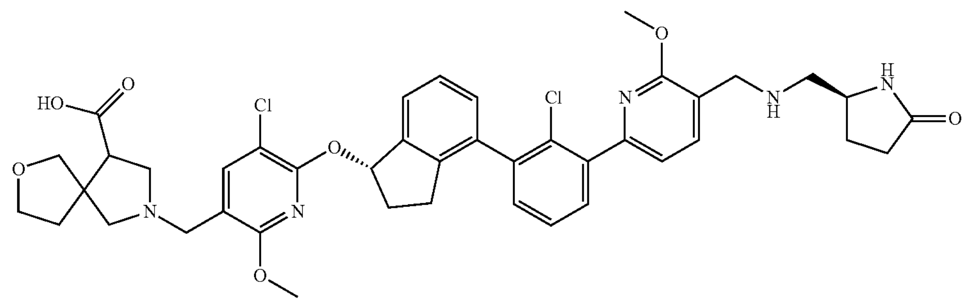 [SMILES: COc1nc(-c2cccc(-c3cccc4c3CC[C@@H]4Oc3nc(OC)c(CN4CC(C(=O)O)C5(CCOC5)C4)cc3Cl)c2Cl)ccc1CNC[C@@H]1CCC(=O)N1] | 801.9 |
| B-71 | 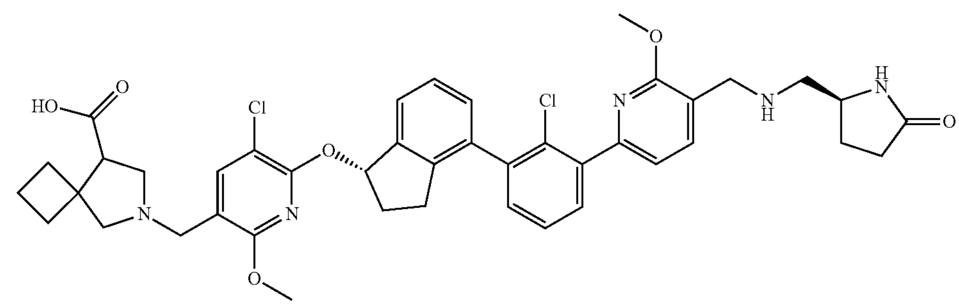 [SMILES: COc1nc(-c2cccc(-c3cccc4c3CC[C@@H]4Oc3nc(OC)c(CN4CC(C(=O)O)C5(CCC5)C4)cc3Cl)c2Cl)ccc1CNC[C@@H]1CCC(=O)N1] | 786 |
| B-72 | 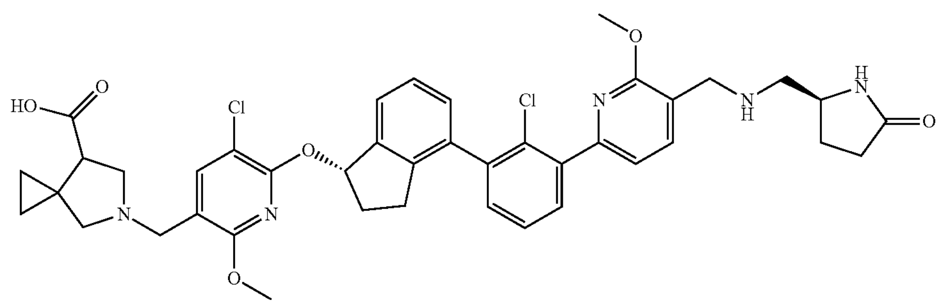 [SMILES: COc1nc(-c2cccc(-c3cccc4c3CC[C@@H]4Oc3nc(OC)c(CN4CC(C(=O)O)C5(CC5)C4)cc3Cl)c2Cl)ccc1CNC[C@@H]1CCC(=O)N1] | 771.9 |
| B-73 | 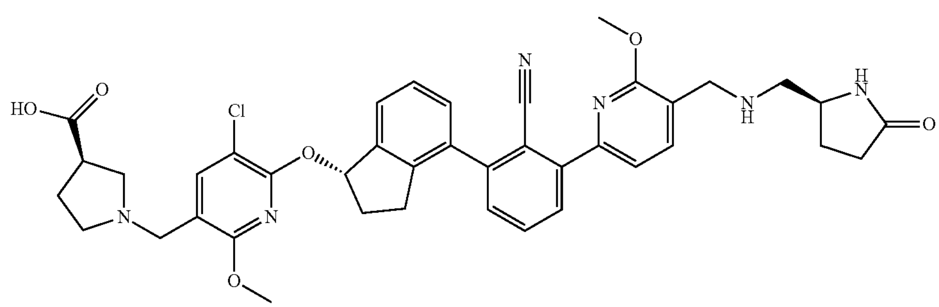 | 737.29 |
| B-74 | 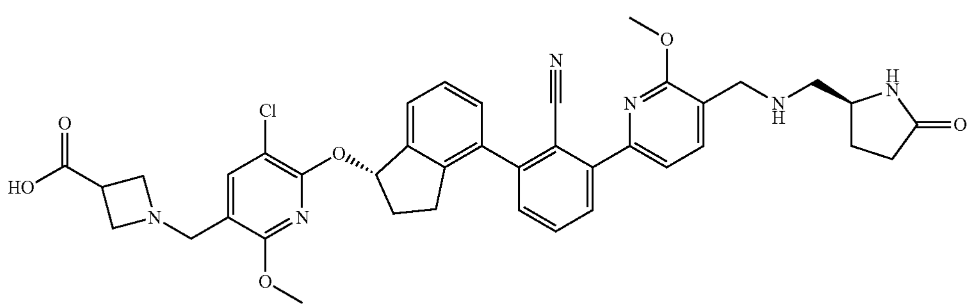 [SMILES: COc1nc(-c2cccc(-c3cccc4c3CC[C@@H]4Oc3nc(OC)c(CN4CC(C(=O)O)C4)cc3Cl)c2C#N)ccc1CNC[C@@H]1CCC(=O)N1] | 723.27 |

TABLE 1B-continued

| No. | Structure | LCMS |
|---|---|---|
| B-75 | 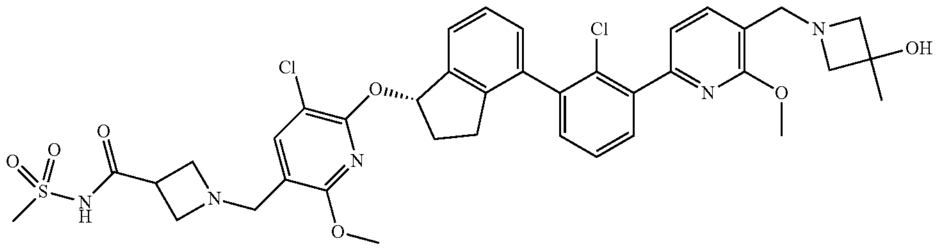 [SMILES: COc1nc(-c2cccc(-c3cccc4c3CC[C@@H]4Oc3nc(OC)c(CN4CC(C(=O)NS(C)(=O)=O)C4)cc3Cl)c2Cl)ccc1CN1CC(C)(O)C1] | 783.7 |
| B-76 | 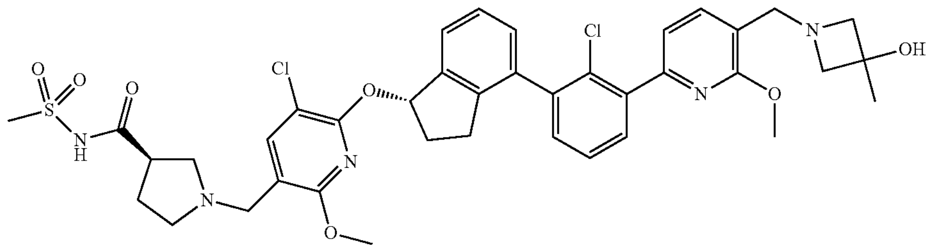 [SMILES: COc1nc(-c2cccc(-c3cccc4c3CC[C@@H]4Oc3nc(OC)c(CN4CC[C@@H](C(=O)NS(C)(=O)=O)C4)cc3Cl)c2Cl)ccc1CN1CC(C)(O)C1] | 797.8 |
| B-77 | 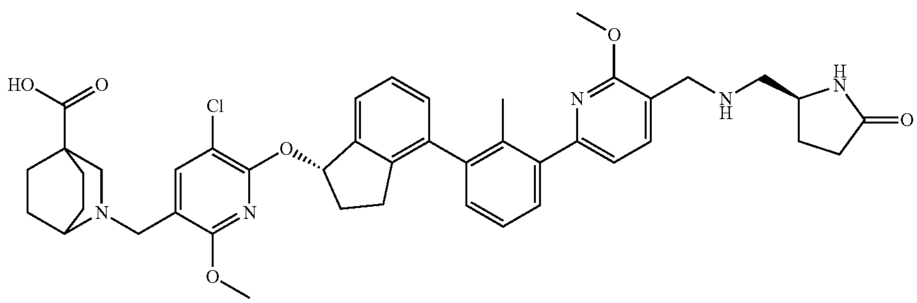 [SMILES: COc1nc(-c2cccc(-c3cccc4c3CC[C@@H]4Oc3nc(OC)c(CN4CC5(C(=O)O)CCC4CC5)cc3Cl)c2C)ccc1CNC[C@@H]1CCC(=O)N1] | 766.34 |
| B-78 | 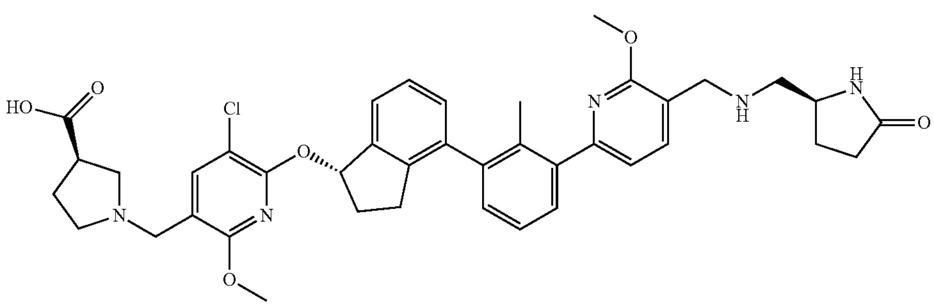 | 726.31 |
| B-79 | 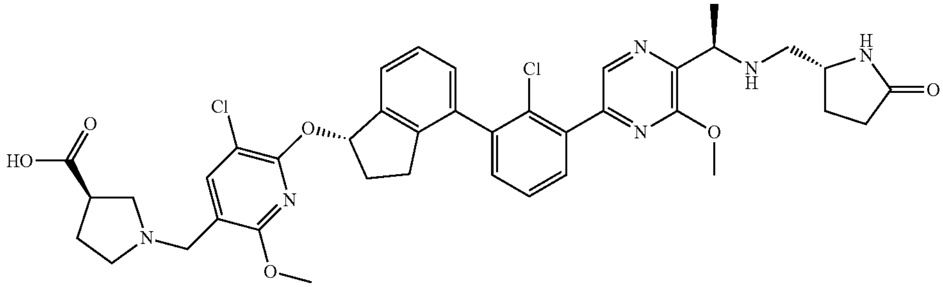 [SMILES: COc1nc(O[C@H]2CCc3c(-c4cccc(-c5cnc([C@@H](C)NC[C@H]6CCC(=O)N6)c(OC)n5)c4Cl)cccc32)c(Cl)cc1CN1CC[C@@H](C(=O)O)C1] | 762.7 |

TABLE 1B-continued
| No. | Structure | LCMS |
|---|---|---|
| B-80 | 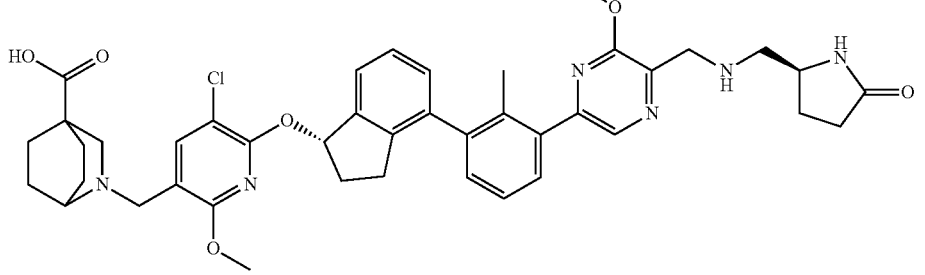 | 767.33 |
| B-81 | 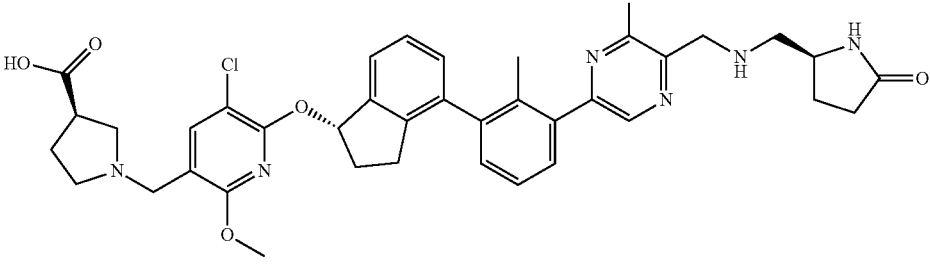 | 727.3 |
| B-82 | 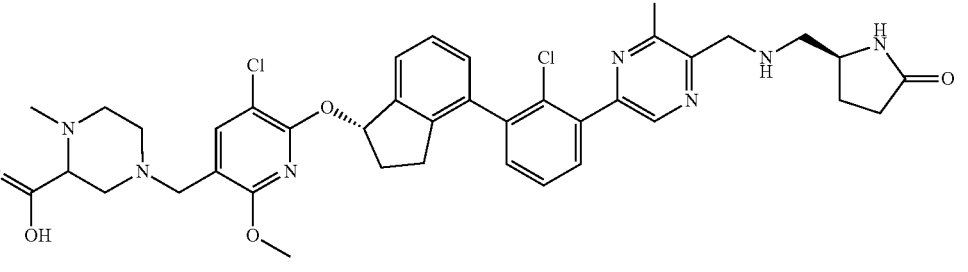 | 775.28 |
| B-83 | 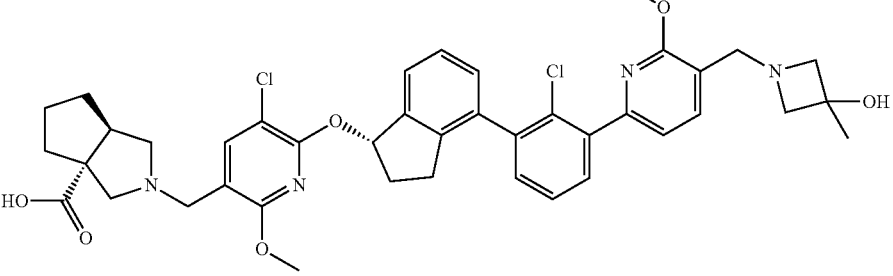 | 758.9 |
| B-84 | 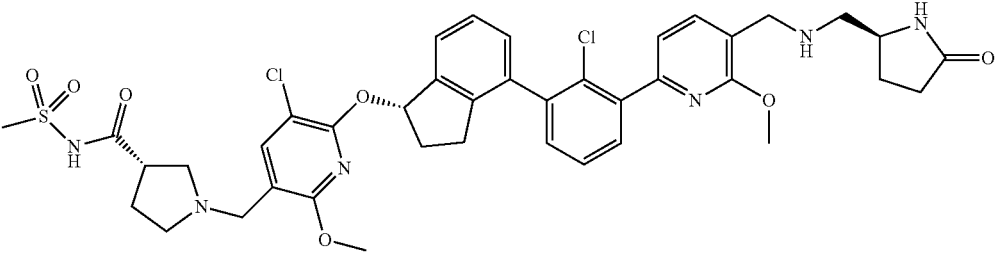 [SMILES: COc1nc(-c2cccc(-c3cccc4c3CC[C@@H]4Oc3nc(OC)c(CN4CC[C@H](C(=O)NS(C)(=O)=O)C4)cc3Cl)c2Cl)ccc1CNC[C@@H]1CCC(=O)N1] | 824.8 |

TABLE 1B-continued

| No. | Structure | LCMS |
|---|---|---|
| B-85 | 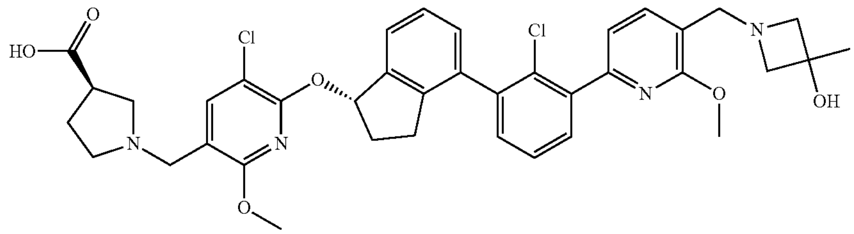 [SMILES: COc1nc(-c2cccc(-c3cccc4c3CC[C@@H]4Oc3nc(OC)c(CN4CC[C@@H](C(=O)O)C4)cc3Cl)c2Cl)ccc1CN1CC(C)(O)C1] | 718.955 |
| B-86 | 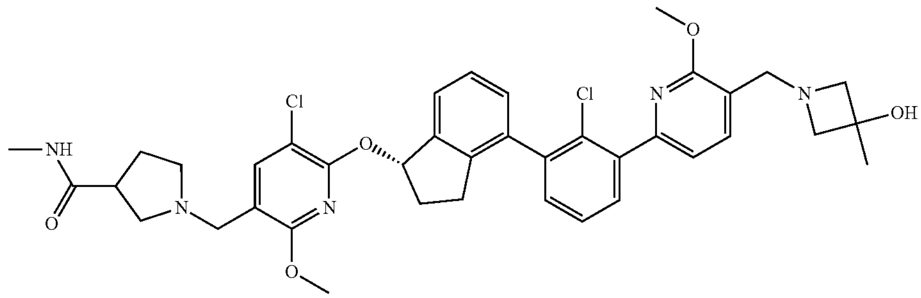 [SMILES: CNC(=O)C1CCN(Cc2cc(Cl)c(O[C@H]3CCc4c(-c5cccc(-c6ccc(CN7CC(C)(O)C7)c(OC)n6)c5Cl)cccc43)nc2OC)C1] | 731.9 |
| B-87 | 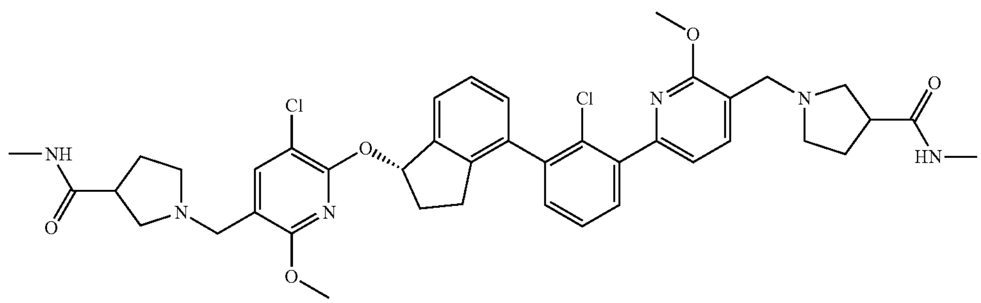 | 772.9 |
| B-88 | 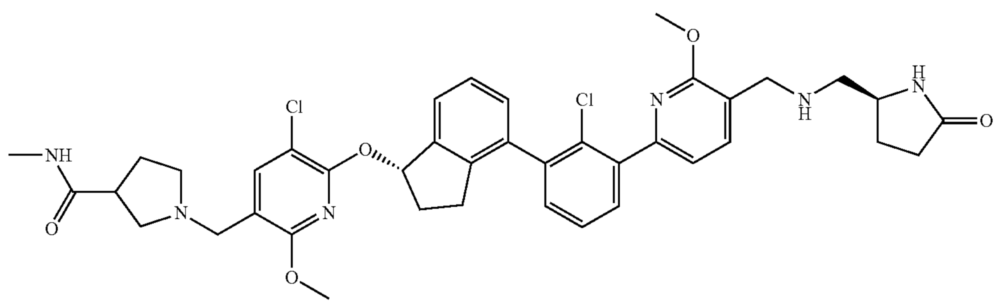 [SMILES: CNC(=O)C1CCN(Cc2cc(Cl)c(O[C@H]3CCc4c(-c5cccc(-c6ccc(CNC[C@@H]7CCC(=O)N7)c(OC)n6)c5Cl)cccc43)nc2OC)C1] | 759 |
| B-89 | 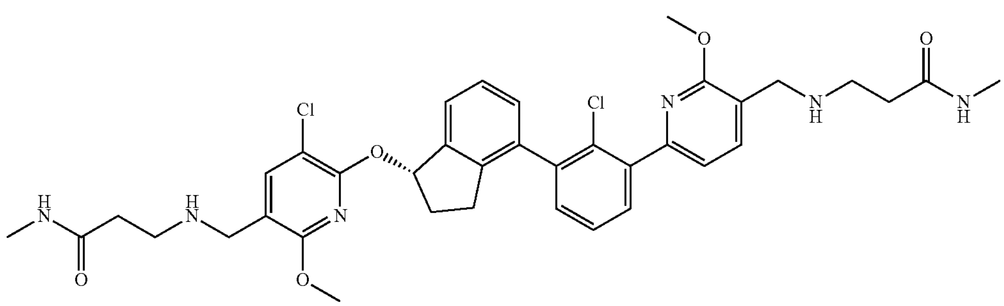 | 720.9 |

TABLE 1B-continued

| No. | Structure | LCMS |
|---|---|---|
| B-90 | 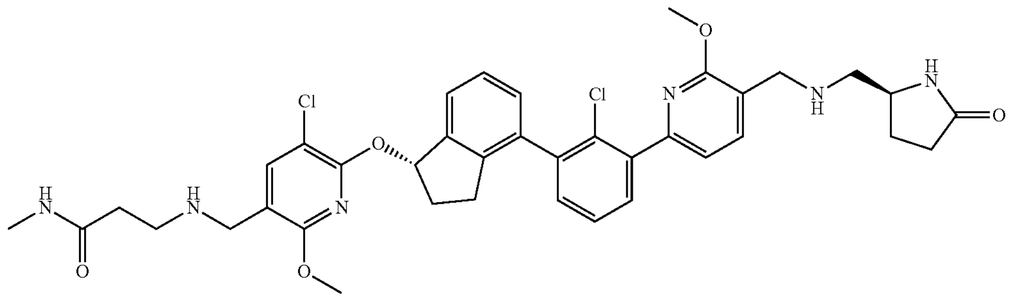 [SMILES: CNC(=O)CCNCc1cc(Cl)c(O[C@H]2CCc3c(-c4cccc(-c5ccc(CNC[C@@H]6CCC(=O)N6)c(OC)n5)c4Cl)cccc32)nc1OC] | 733 |
| B-91 | 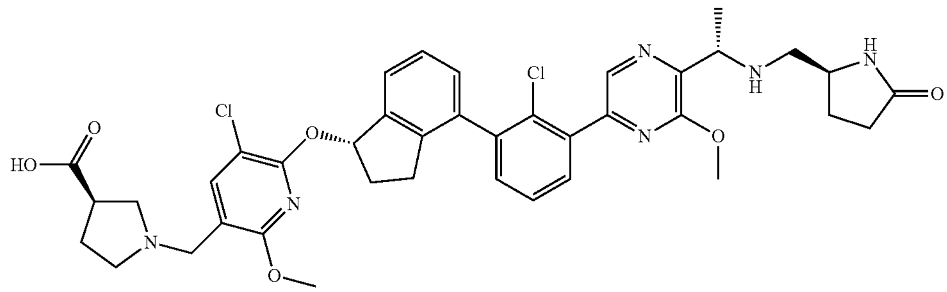 [SMILES: COc1nc(O[C@H]2CCc3c(-c4cccc(-c5cnc([C@H](C)NC[C@@H]6CCC(=O)N6)c(OC)n5)c4Cl)cccc32)c(Cl)cc1CN1CC[C@@H](C(=O)O)C1] | 762.7 |
| B-92 | 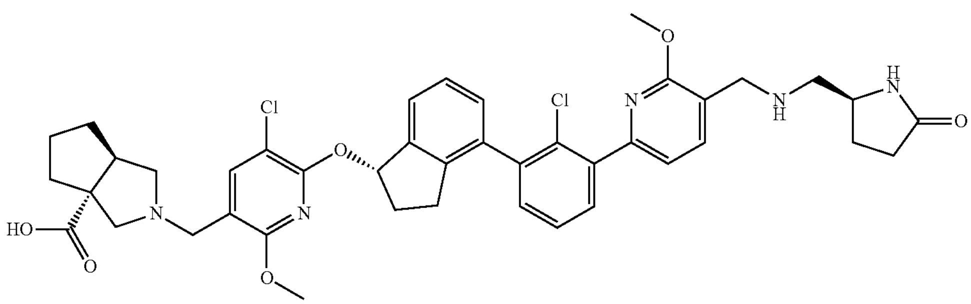 [SMILES: COc1nc(-c2cccc(-c3cccc4c3CC[C@@H]4Oc3nc(OC)c(CN4C[C@@H]5CCC[C@]5(C(=O)O)C4)cc3Cl)c2Cl)ccc1CNC[C@@H]1CCC(=O)N1] | 785.9 |
| B-93 | 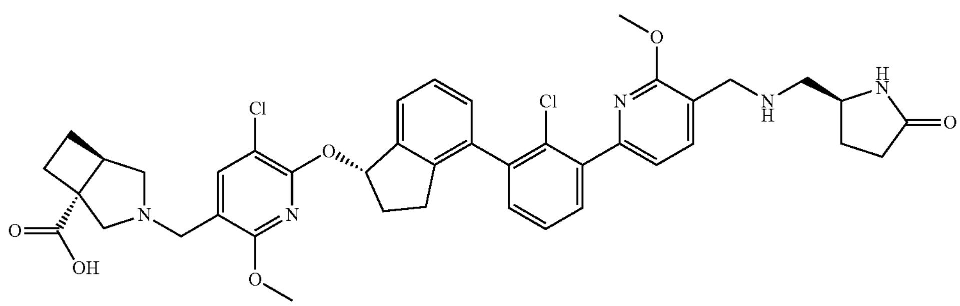 [SMILES: COc1nc(-c2cccc(-c3cccc4c3CC[C@@H]4Oc3nc(OC)c(CN4C[C@@H]5CC[C@]5(C(=O)O)C4)cc3Cl)c2Cl)ccc1CNC[C@@H]1CCC(=O)N1] | 771.9 |
| B-94 | 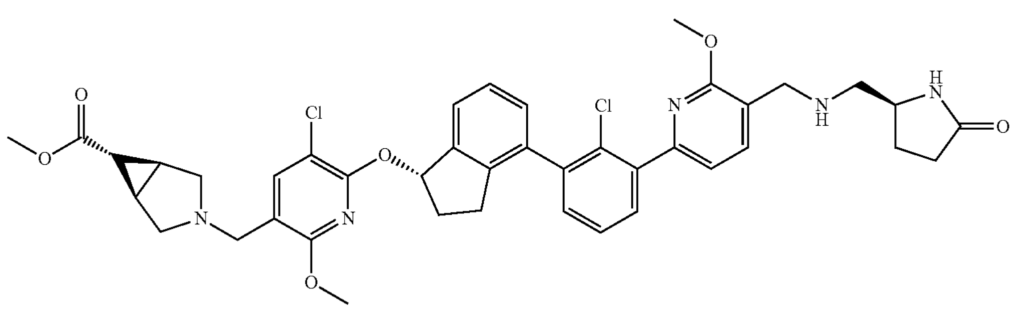 [SMILES: COC(=O)[C@H]1[C@@H]2CN(Cc3cc(Cl)c(O[C@H]4CCc5c(-c6cccc(-c7ccc(CNC[C@@H]8CCC(=O)N8)c(OC)n7)c6Cl)cccc54)nc3OC)C[C@@H]21] | 770.8 |

TABLE 1B-continued
| No. | Structure | LCMS |
|---|---|---|
| B-95 | 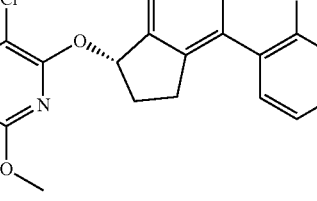 | 757.8 |
| B-96 | 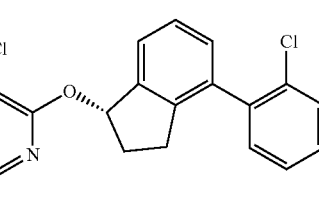 | 703.22 |
| B-97 | 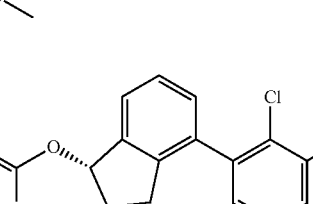 | 717.24 |
| B-98 | 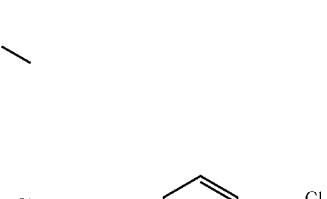 | 786.28 |
| B-99 | 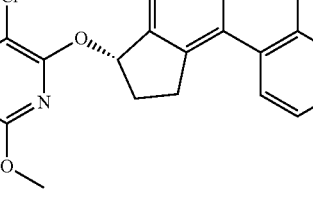 | 758.2 |

TABLE 1B-continued

| No. | Structure | LCMS |
|---|---|---|
| B-100 | 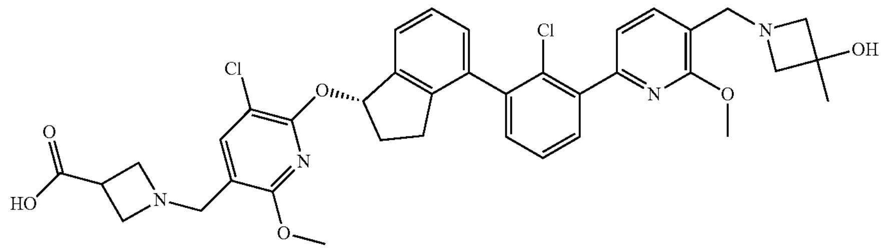 [SMILES: COc1nc(-c2cccc(-c3cccc4c3CC[C@@H]4Oc3nc(OC)c(CN4CC(C(=O)O)C4)cc3Cl)c2Cl)ccc1CN1CC(C)(O)C1] | 706.6 |
| B-101 | 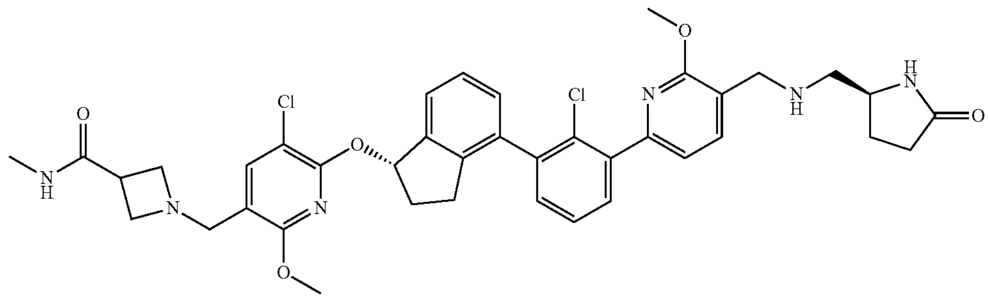 [SMILES: CNC(=O)C1CN(Cc2cc(Cl)c(O[C@H]3CCc4c(-c5cccc(-c6ccc(CNC[C@@H]7CCC(=O)N7)c(OC)n6)c5Cl)cccc43)nc2OC)C1] | 745.2 |
| B-102 | 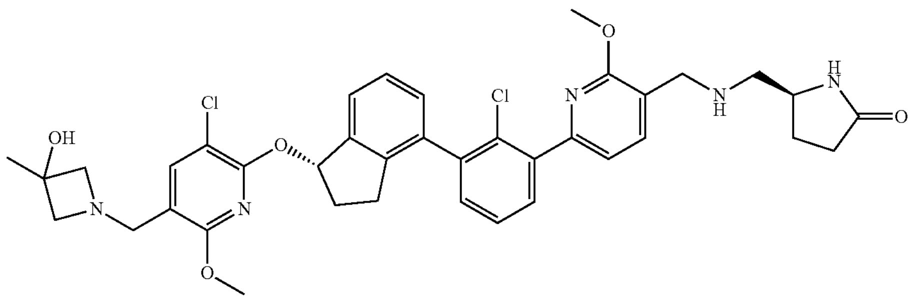 [SMILES: COc1nc(-c2cccc(-c3cccc4c3CC[C@@H]4Oc3nc(OC)c(CN4CC(C)(O)C4)cc3Cl)c2Cl)ccc1CNC[C@@H]1CCC(=O)N1] | 718.3 |
| B-103 | 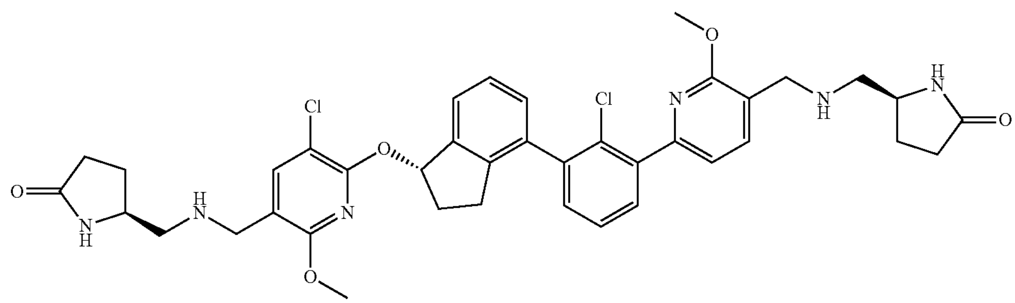 [SMILES: COc1nc(-c2cccc(-c3cccc4c3CC[C@@H]4Oc3nc(OC)c(CNC[C@@H]4CCC(=O)N4)cc3Cl)c2Cl)ccc1CNC[C@@H]1CCC(=O)N1] | 763.2 |
| B-104 | 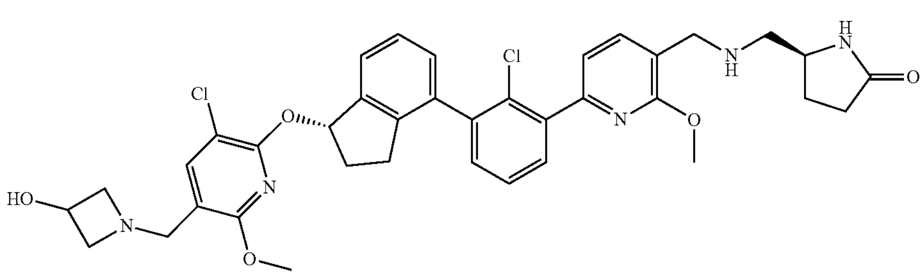 [SMILES: COc1nc(-c2cccc(-c3cccc4c3CC[C@@H]4Oc3nc(OC)c(CN4CC(O)C4)cc3Cl)c2Cl)ccc1CNC[C@@H]1CCC(=O)N1] | 722.6 |

TABLE 1B-continued

| No. | Structure | LCMS |
|---|---|---|
| B-105 | 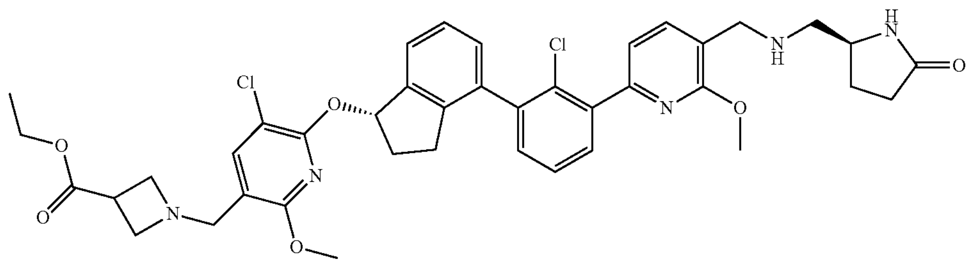 [SMILES: CCOC(=O)C1CN(Cc2cc(Cl)c(O[C@H]3CCc4c(-c5cccc(-c6ccc(CNC[C@@H]7CCC(=O)N7)c(OC)n6)c5Cl)cccc43)nc2OC)C1] | 761.7 |
| B-106 | 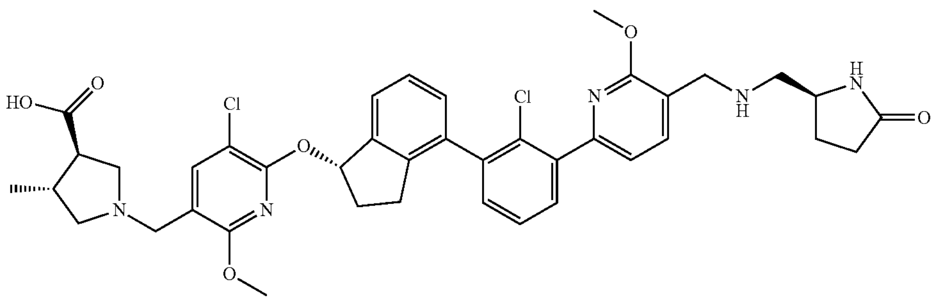 [SMILES: COc1nc(-c2cccc(-c3cccc4c3CC[C@@H]4Oc3nc(OC)c(CN4C[C@H](C(=O)O)[C@@H](C)C4)cc3Cl)c2Cl)ccc1CNC[C@@H]1CCC(=O)N1] | 760.27 |
| B-107 | 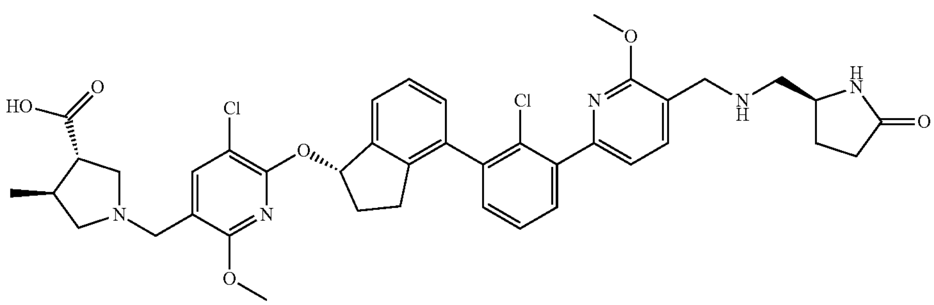 [SMILES: COc1nc(-c2cccc(-c3cccc4c3CC[C@@H]4Oc3nc(OC)c(CN4C[C@@H](C)[C@H](C(=O)O)C4)cc3Cl)c2Cl)ccc1CNC[C@@H]1CCC(=O)N1] | 760.27 |
| B-108 | 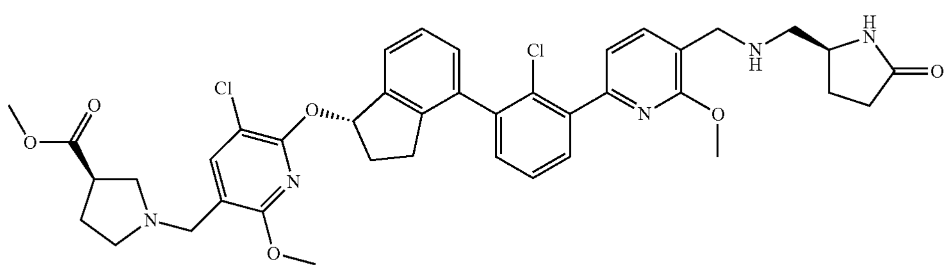 [SMILES: COC(=O)[C@@H]1CCN(Cc2cc(Cl)c(O[C@H]3CCc4c(-c5cccc(-c6ccc(CNC[C@@H]7CCC(=O)N7)c(OC)n6)c5Cl)cccc43)nc2OC)C1] | 761.7 |
| B-109 | 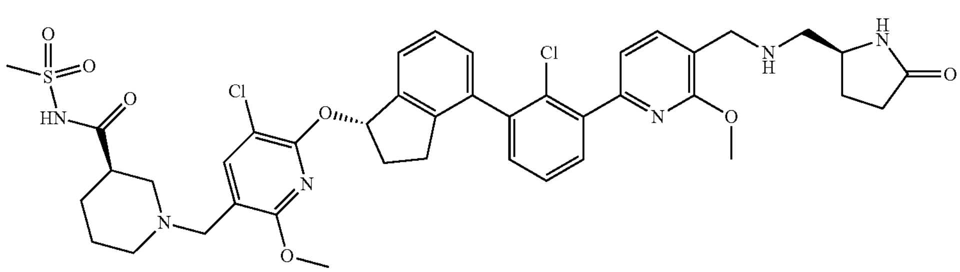 [SMILES: COc1nc(-c2cccc(-c3cccc4c3CC[C@@H]4Oc3nc(OC)c(CN4CCC[C@@H](C(=O)NS(C)(=O)=O)C4)cc3Cl)c2Cl)ccc1CNC[C@@H]1CCC(=O)N1] | 838.8 |

TABLE 1B-continued

| No. | Structure | LCMS |
|---|---|---|
| B-110 | 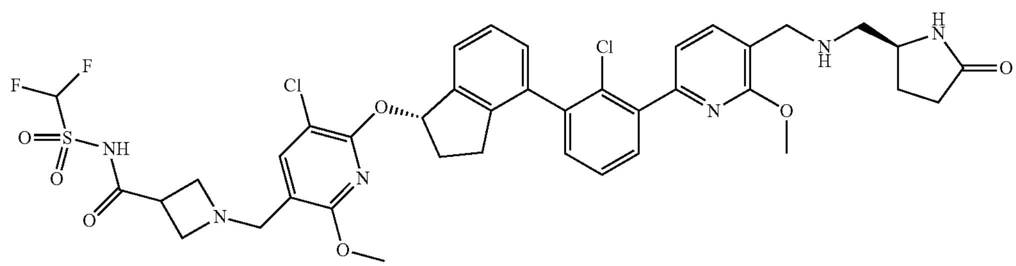 [SMILES: COc1nc(-c2cccc(-c3cccc4c3CC[C@@H]4Oc3nc(OC)c(CN4CC(C(=O)NS(=O)(=O)C(F)F)C4)cc3Cl)c2Cl)ccc1CNC[C@@H]1CCC(=O)N1] | 846.7 |
| B-111 | 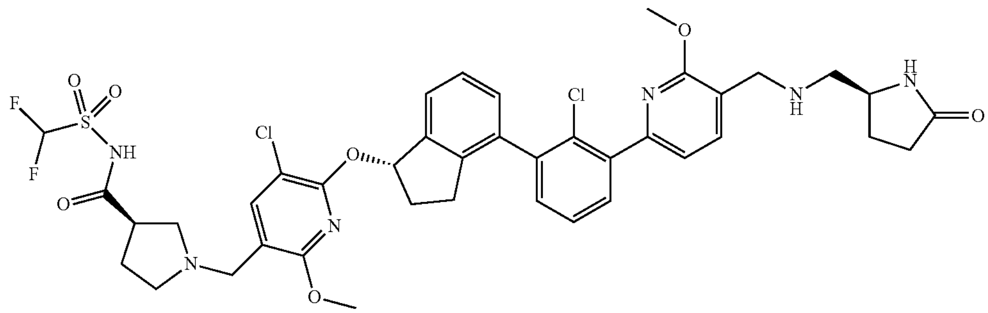 [SMILES: COc1nc(-c2cccc(-c3cccc4c3CC[C@@H]4Oc3nc(OC)c(CN4CC[C@@H](C(=O)NS(=O)(=O)C(F)F)C4)cc3Cl)c2Cl)ccc1CNC[C@@H]1CCC(=O)N1] | 860.8 |
| B-112 | 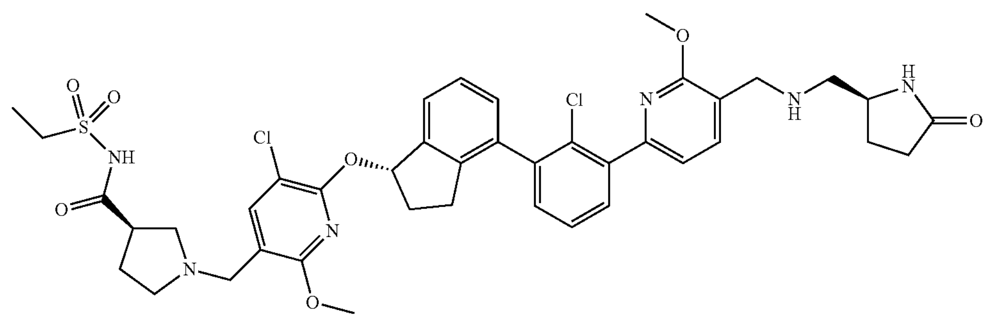 [SMILES: CCS(=O)(=O)NC(=O)[C@@H]1CCN(Cc2cc(Cl)c(O[C@H]3CCc4c(-c5cccc(-c6ccc(CNC[C@@H]7CCC(=O)N7)c(OC)n6)c5Cl)cccc43)nc2OC)C1] | 838.8 |
| B-113 | 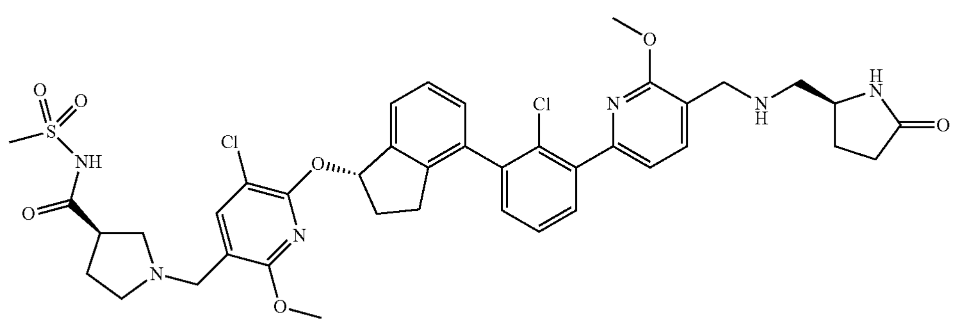 [SMILES: COc1nc(-c2cccc(-c3cccc4c3CC[C@@H]4Oc3nc(OC)c(CN4CC[C@@H](C(=O)NS(C)(=O)=O)C4)cc3Cl)c2Cl)ccc1CNC[C@@H]1CCC(=O)N1] | 824.8 |
| B-114 | 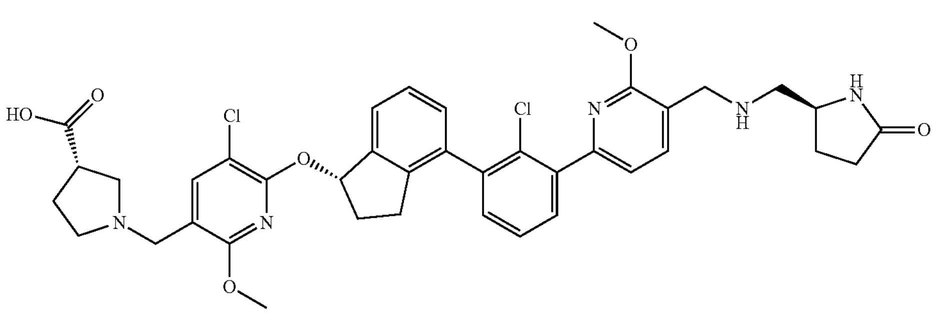 [SMILES: COc1nc(-c2cccc(-c3cccc4c3CC[C@@H]4Oc3nc(OC)c(CN4CC[C@H](C(=O)O)C4)cc3Cl)c2Cl)ccc1CNC[C@@H]1CCC(=O)N1] | 746.25 |

TABLE 1B-continued

| No. | Structure | LCMS |
|---|---|---|
| B-115 | 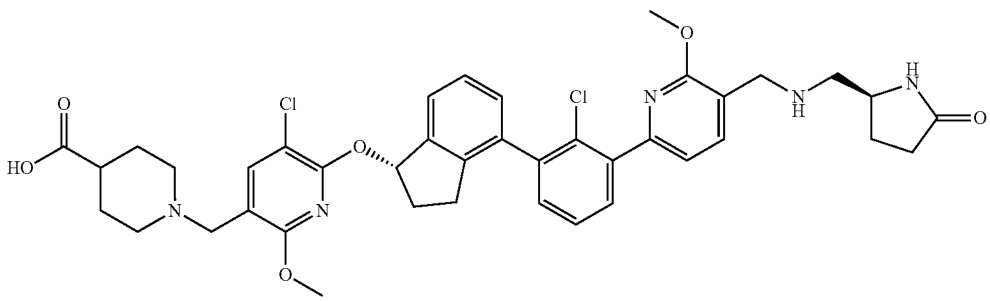 [SMILES: COc1nc(-c2cccc(-c3cccc4c3CC[C@@H]4Oc3nc(OC)c(CN4CCC(C(=O)O)CC4)cc3Cl)c2Cl)ccc1CNC[C@@H]1CCC(=O)N1] | 760.27 |
| B-116 | 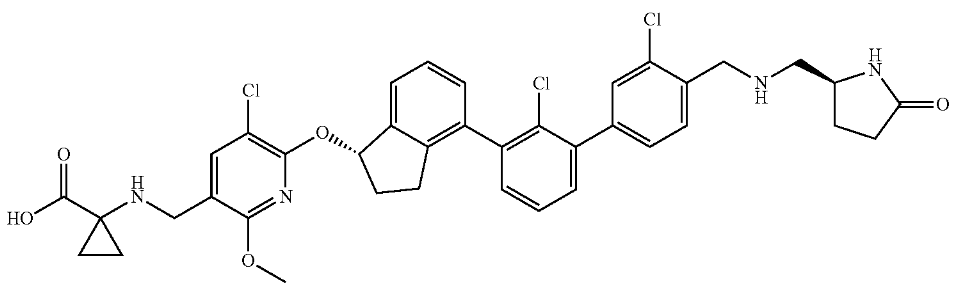 [SMILES: COc1nc(O[C@H]2CCc3c(-c4cccc(-c5ccc(CNC[C@@H]6CCC(=O)N6)c(Cl)c5)c4Cl)cccc32)c(Cl)cc1CNC1(C(=O)O)CC1] | 734.791 |
| B-117 | 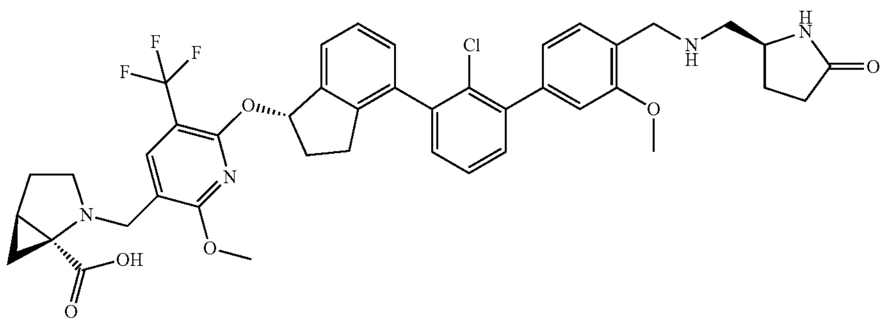 [SMILES: COc1cc(-c2cccc(-c3cccc4c3CC[C@@H]4Oc3nc(OC)c(CN4CC[C@@H]5C[C@@]54C(=O)O)cc3C(F)(F)F)c2Cl)ccc1CNC[C@@H]1CCC(=O)N1] | 792.3 |
| B-118 | 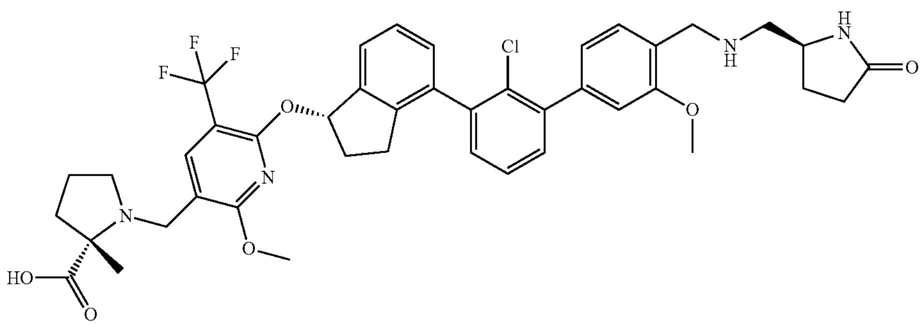 [SMILES: COc1cc(-c2cccc(-c3cccc4c3CC[C@@H]4Oc3nc(OC)c(CN4CCC[C@@]4(C)C(=O)O)cc3C(F)(F)F)c2Cl)ccc1CNC[C@@H]1CCC(=O)N1] | 794.3 |
| B-119 | 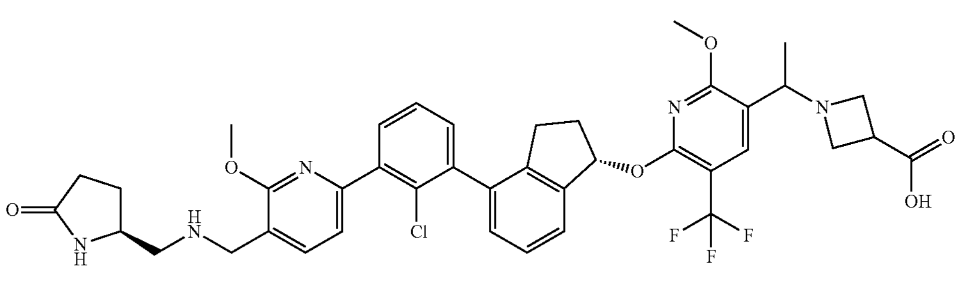 [SMILES: COc1nc(-c2cccc(-c3cccc4c3CC[C@@H]4Oc3nc(OC)c(C(C)N4CC(C(=O)O)C4)cc3C(F)(F)F)c2Cl)ccc1CNC[C@@H]1CCC(=O)N1] | 780.200 |

TABLE 1B-continued

| No. | Structure | LCMS |
|---|---|---|
| B-120 | 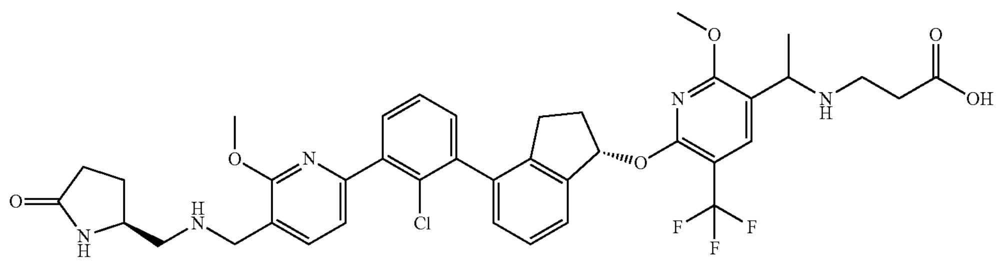 [SMILES: COc1nc(-c2cccc(-c3cccc4c3CC[C@@H]4Oc3nc(OC)c(C(C)NCCC(=O)O)cc3C(F)(F)F)c2Cl)ccc1CNC[C@@H]1CCC(=O)N1] | 768.200 |
| B-121 | 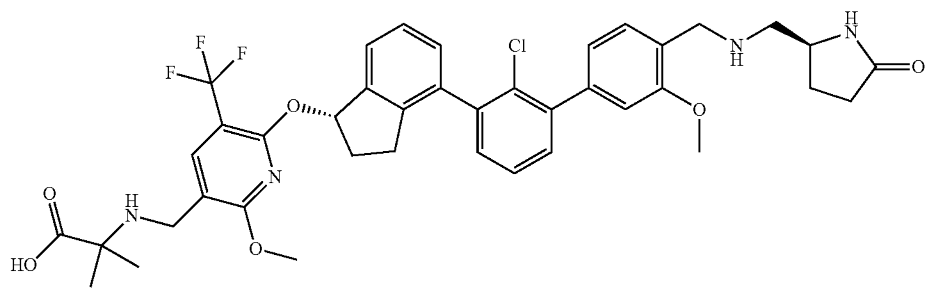 [SMILES: COc1cc(-c2cccc(-c3cccc4c3CC[C@@H]4Oc3nc(OC)c(CNC(C)(C)C(=O)O)cc3C(F)(F)F)c2Cl)ccc1CNC[C@@H]1CCC(=O)N1] | 768.2 |
| B-122 | 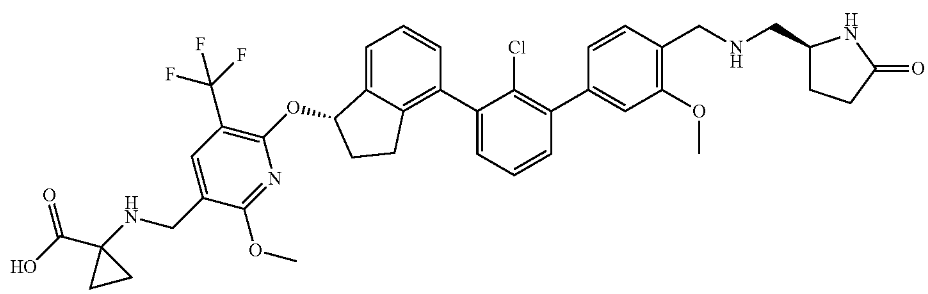 [SMILES: COc1cc(-c2cccc(-c3cccc4c3CC[C@@H]4Oc3nc(OC)c(CNC4(C(=O)O)CC4)cc3C(F)(F)F)c2Cl)ccc1CNC[C@@H]1CCC(=O)N1] | 766.2 |
| B-123 | 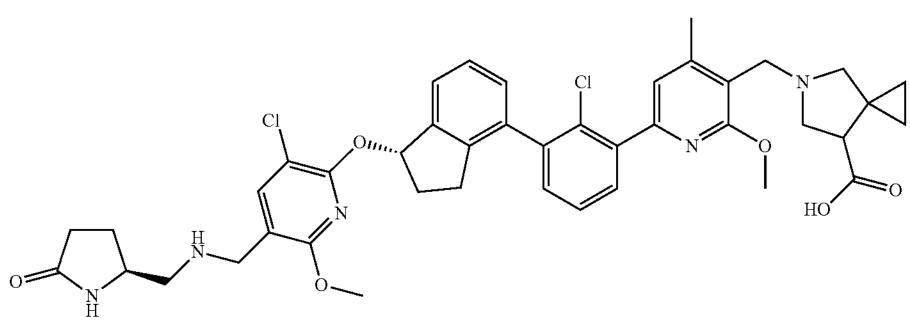 [SMILES: COc1nc(O[C@H]2CCc3c(-c4cccc(-c5cc(C)c(CN6CC(C(=O)O)C7(CC7)C6)c(OC)n5)c4Cl)cccc32)c(Cl)cc1CNC[C@@H]1CCC(=O)N1] | 786.181 |
| B-124 | 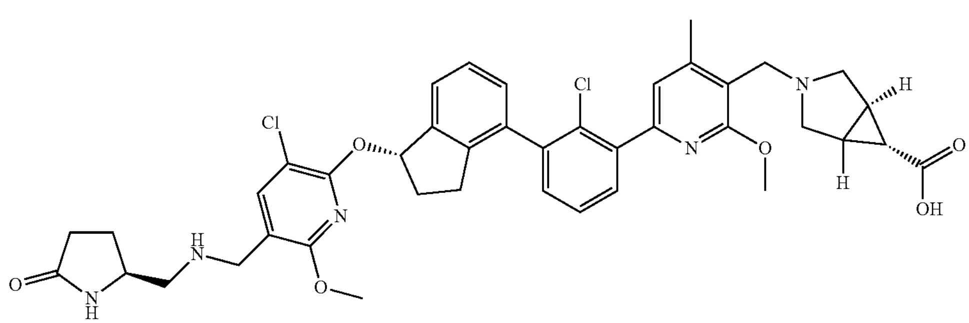 [SMILES: COc1nc(O[C@H]2CCc3c(-c4cccc(-c5cc(C)c(CN6CC7[C@@H](C6)[C@@H]7C(=O)O)c(OC)n5)c4Cl)cccc32)c(Cl)cc1CNC[C@@H]1CCC(=O)N1] | 772.001 |

TABLE 1B-continued

| No. | Structure | LCMS |
|---|---|---|
| B-125 | 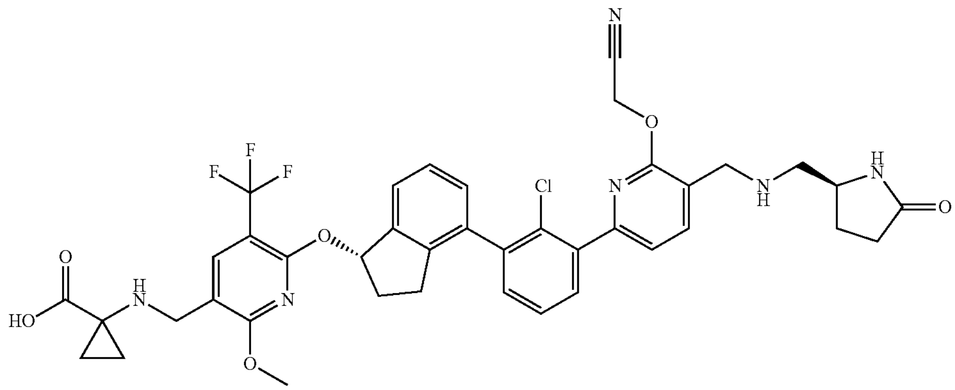 [SMILES: COc1nc(O[C@H]2CCc3c(-c4cccc(-c5ccc(CNC[C@@H]6CCC(=O)N6)c(OCC#N)n5)c4Cl)cccc32)c(C(F)(F)F)cc1CNC1(C(=O)O)CC1] | 791.2 (M + 1) |
| B-126 | 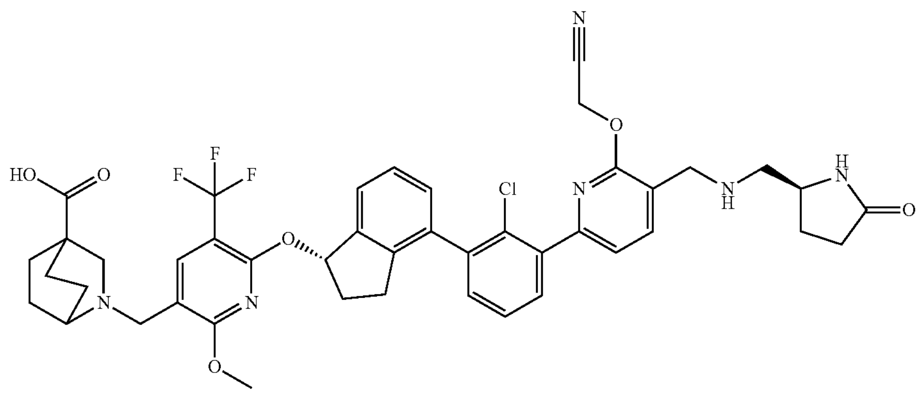 [SMILES: COc1nc(O[C@H]2CCc3c(-c4cccc(-c5ccc(CNC[C@@H]6CCC(=O)N6)c(OCC#N)n5)c4Cl)cccc32)c(C(F)(F)F)cc1CN1CC2(C(=O)O)CCC1CC2] | 845.2 (M + 1) |
| B-127 | 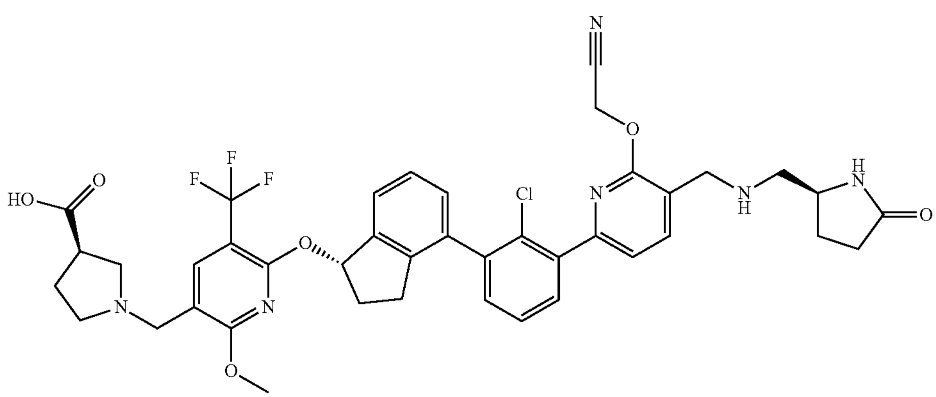 [SMILES: COc1nc(O[C@H]2CCc3c(-c4cccc(-c5ccc(CNC[C@@H]6CCC(=O)N6)c(OCC#N)n5)c4Cl)cccc32)c(C(F)(F)F)cc1CN1CC[C@@H](C(=O)O)C1] | 805.2 (M + 1) |
| B-128 | 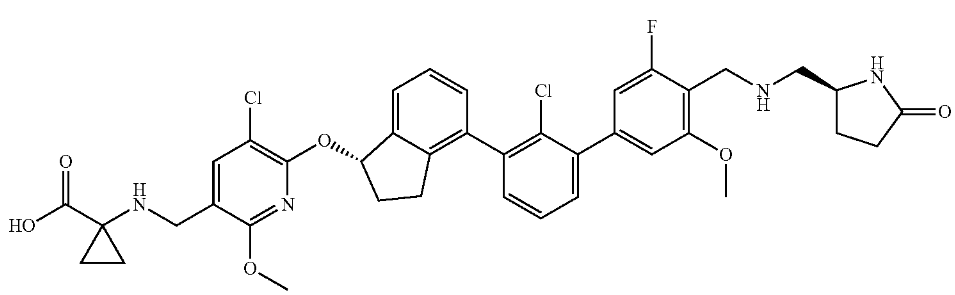 [SMILES: COc1cc(-c2cccc(-c3cccc4c3CC[C@@H]4Oc3nc(OC)c(CNC4(C(=O)O)CC4)cc3Cl)c2Cl)cc(F)c1CNC[C@@H]1CCC(=O)N1] | 748.858 |

TABLE 1B-continued

| No. | Structure | LCMS |
|---|---|---|
| B-129 | 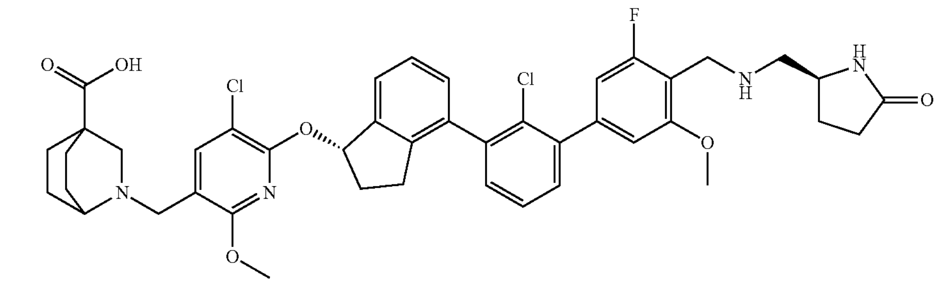 [SMILES: COc1cc(-c2cccc(-c3cccc4c3CC[C@@H]4Oc3nc(OC)c(CN4CC5(C(=O)O)CCC4CC5)cc3Cl)c2Cl)cc(F)c1CNC[C@@H]1CCC(=O)N1] | 803.003 |
| B-130 | 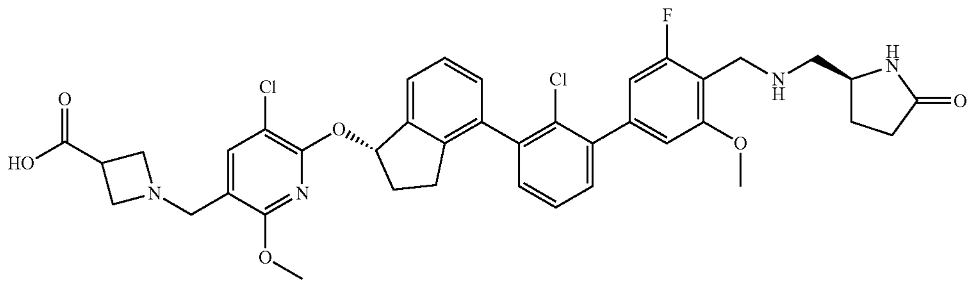 [SMILES: COc1cc(-c2cccc(-c3cccc4c3CC[C@@H]4Oc3nc(OC)c(CN4CC(C(=O)O)C4)cc3Cl)c2Cl)cc(F)c1CNC[C@@H]1CCC(=O)N1] | 748.966 |
| B-131 | 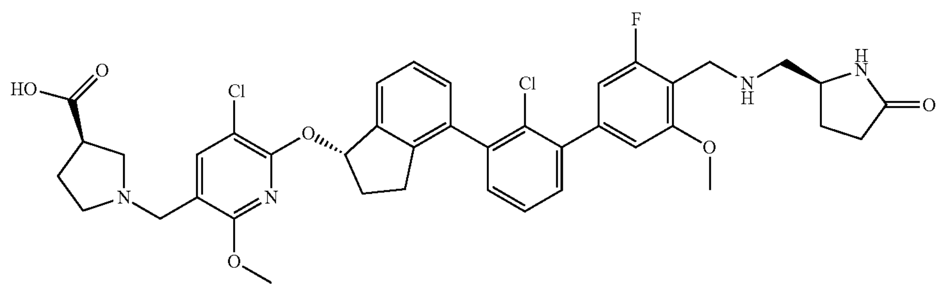 [SMILES: COc1cc(-c2cccc(-c3cccc4c3CC[C@@H]4Oc3nc(OC)c(CN4CC[C@@H](C(=O)O)C4)cc3Cl)c2Cl)cc(F)c1CNC[C@@H]1CCC(=O)N1] | 762.975 |
| B-132 | 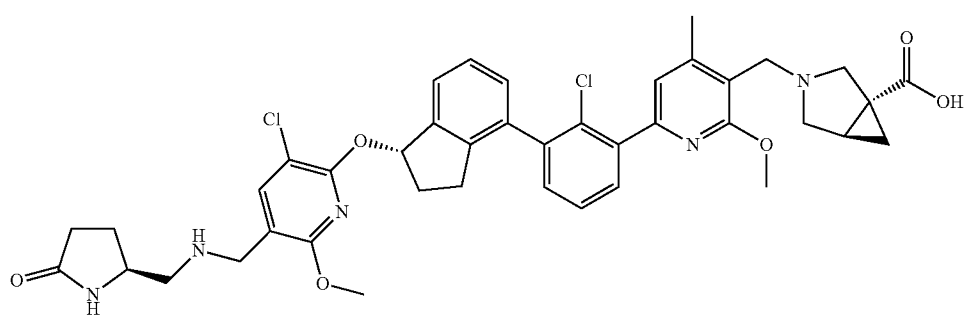 [SMILES: COc1nc(O[C@H]2CCc3c(-c4cccc(-c5cc(C)c(CN6C[C@@H]7C[C@]7(C(=O)O)C6)c(OC)n5)c4Cl)cccc32)c(Cl)cc1CNC[C@@H]1CCC(=O)N1] | 772.053 |
| B-133 | 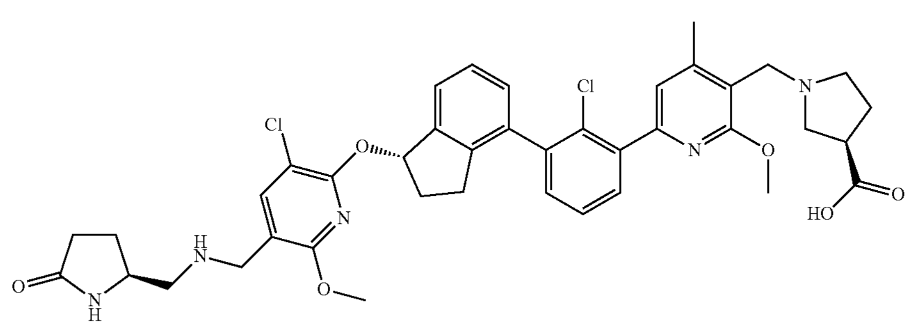 [SMILES: COc1nc(O[C@H]2CCc3c(-c4cccc(-c5cc(C)c(CN6CC[C@@H](C(=O)O)C6)c(OC)n5)c4Cl)cccc32)c(Cl)cc1CNC[C@@H]1CCC(=O)N1] | 760.064 |

TABLE 1B-continued
| No. | Structure | LCMS |
|---|---|---|
| B-134 | 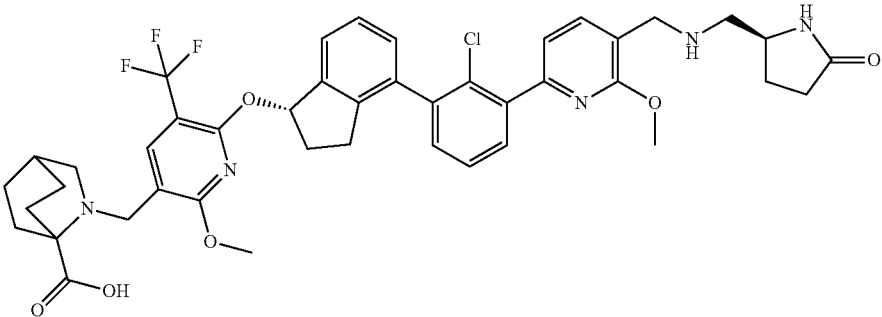 [SMILES: COc1nc(-c2cccc(-c3cccc4c3CC[C@@H]4Oc3nc(OC)c(CN4CC5CCC4(C(=O)O)CC5)cc3C(F)(F)F)c2Cl)ccc1CNC[C@@H]1CCC(=O)N1] | 821.3 |
| B-135 | 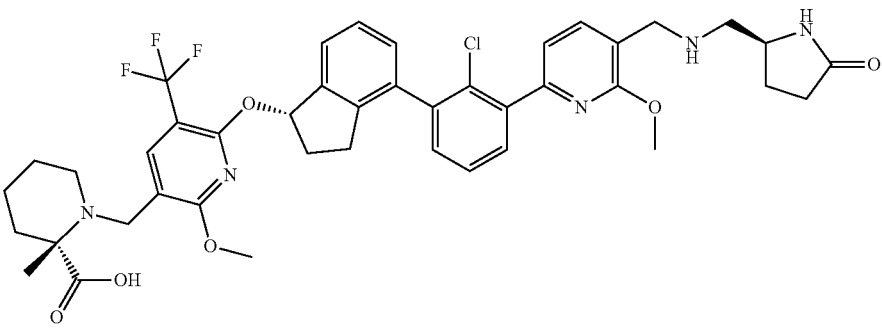 [SMILES: COc1nc(-c2cccc(-c3cccc4c3CC[C@@H]4Oc3nc(OC)c(CN4CCCC[C@@]4(C)C(=O)O)cc3C(F)(F)F)c2Cl)ccc1CNC[C@@H]1CCC(=O)N1] | 809.3 |
| B-136 | 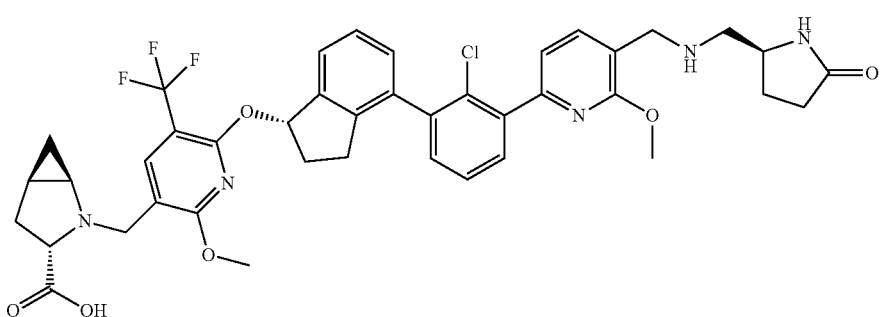 [SMILES: COc1nc(-c2cccc(-c3cccc4c3CC[C@@H]4Oc3nc(OC)c(CN4[C@@H]5C[C@@H]5C[C@H]4C(=O)O)cc3C(F)(F)F)c2Cl)ccc1CNC[C@@H]1CCC(=O)N1] | 793.2 |
| B-137 | 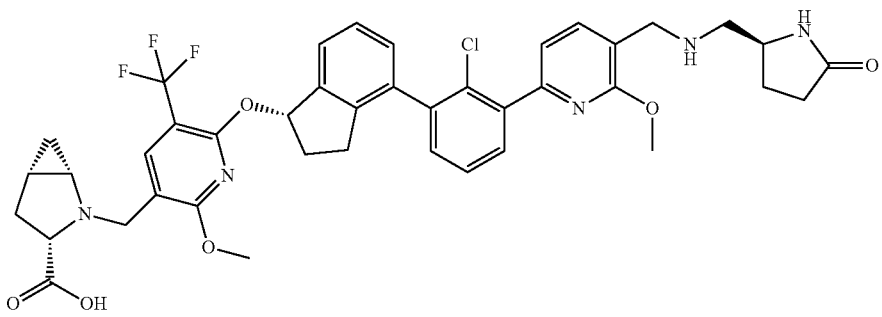 [SMILES: COc1nc(-c2cccc(-c3cccc4c3CC[C@@H]4Oc3nc(OC)c(CN4[C@H](C(=O)O)C[C@@H]5C[C@@H]54)cc3C(F)(F)F)c2Cl)ccc1CNC[C@@H]1CCC(=O)N1] | 793.2 |
| B-138 | 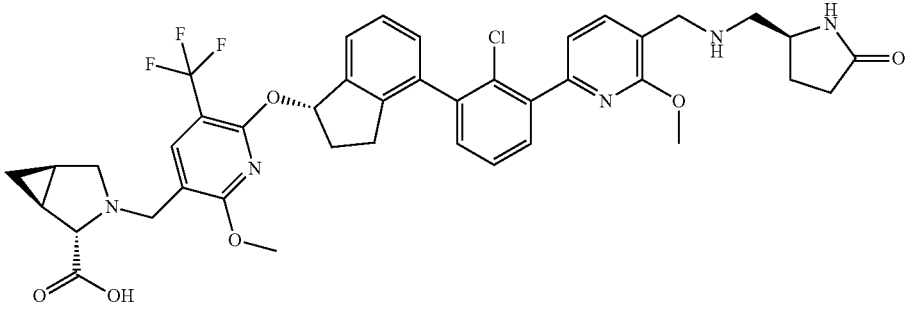 [SMILES: COc1nc(-c2cccc(-c3cccc4c3CC[C@@H]4Oc3nc(OC)c(CN4C[C@@H]5C[C@@H]5[C@H]4C(=O)O)cc3C(F)(F)F)c2Cl)ccc1CNC[C@@H]1CCC(=O)N1] | 793.2 |

TABLE 1B-continued

| No. | Structure | LCMS |
|---|---|---|
| B-139 | 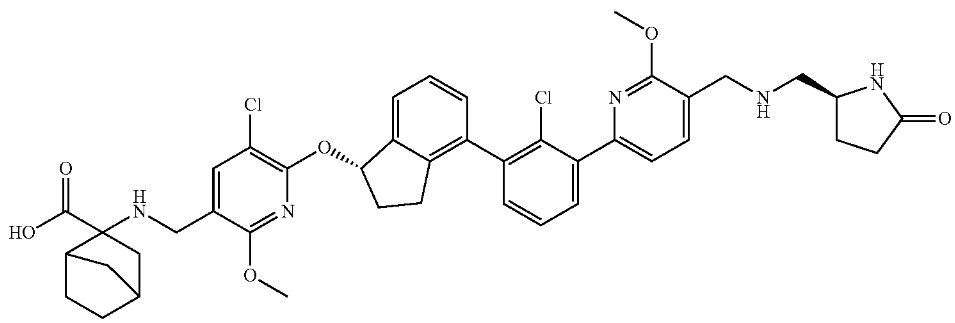 [SMILES: COc1nc(-c2cccc(-c3cccc4c3CC[C@@H]4Oc3nc(OC)c(CNC4(C(=O)O)CC5CCC4C5)cc3Cl)c2Cl)ccc1CNC[C@@H]1CCC(=O)N1] | 786.2 (M + 1) |
| B-140 | 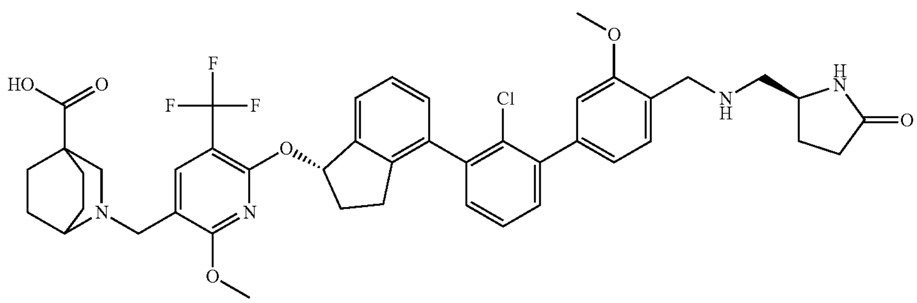 [SMILES: COc1cc(-c2cccc(-c3cccc4c3CC[C@@H]4Oc3nc(OC)c(CN4CC5(C(=O)O)CCC4CC5)cc3C(F)(F)F)c2Cl)ccc1CNC[C@@H]1CCC(=O)N1] | 819.31 |
| B-141 | 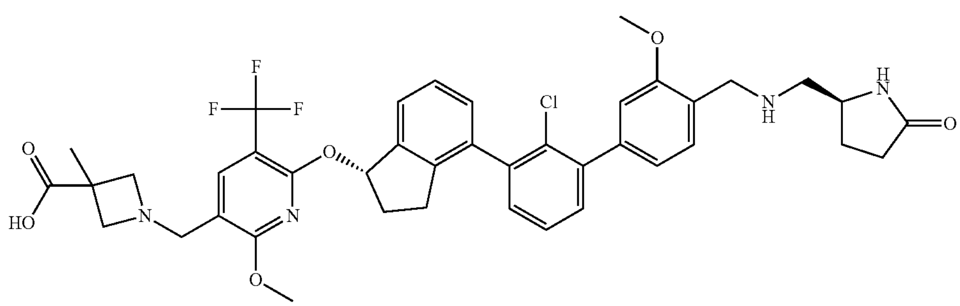 [SMILES: COc1cc(-c2cccc(-c3cccc4c3CC[C@@H]4Oc3nc(OC)c(CN4CC(C)(C(=O)O)C4)cc3C(F)(F)F)c2Cl)ccc1CNC[C@@H]1CCC(=O)N1] | 779.28 |
| B-142 | 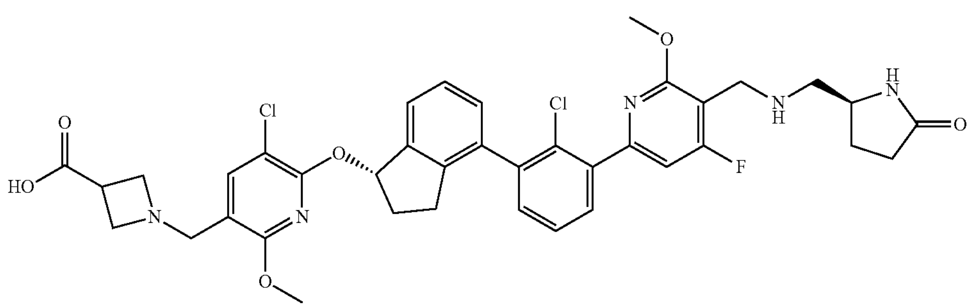 [SMILES: COc1nc(O[C@H]2CCc3c(-c4cccc(-c5cc(F)c(CNC[C@@H]6CCC(=O)N6)c(OC)n5)c4Cl)cccc32)c(Cl)cc1CN1CC(C(=O)O)C1] | 749.9 |
| B-143 | 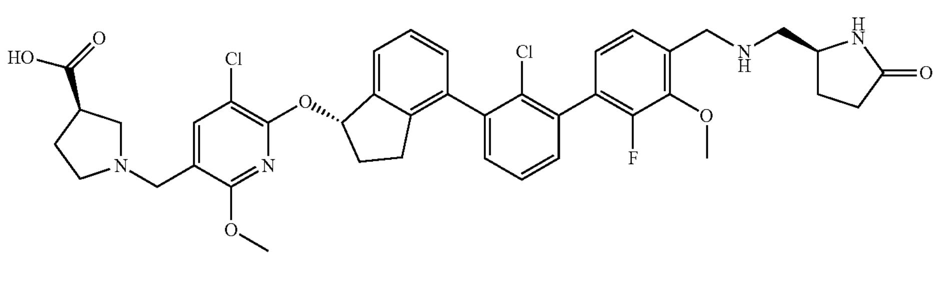 [SMILES: COc1nc(O[C@H]2CCc3c(-c4cccc(-c5ccc(CNC[C@@H]6CCC(=O)N6)c(OC)c5F)c4Cl)cccc32)c(Cl)cc1CN1CC[C@@H](C(=O)O)C1] | 762.941 |

TABLE 1B-continued

| No. | Structure | LCMS |
|---|---|---|
| B-144 | 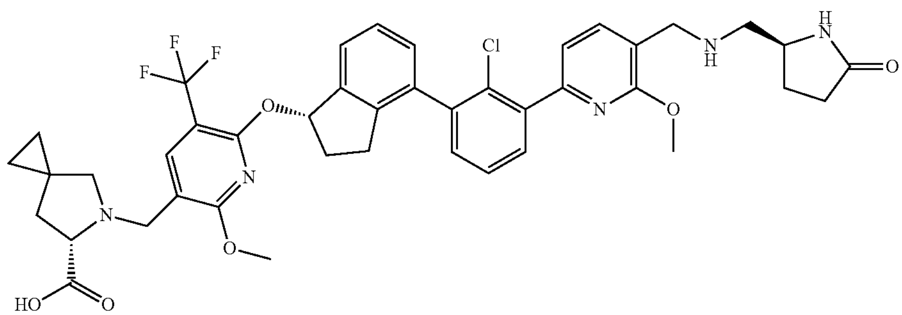 [SMILES: COc1nc(-c2cccc(-c3cccc4c3CC[C@@H]4Oc3nc(OC)c(CN4CC5(CC5)C[C@H]4C(=O)O)cc3C(F)(F)F)c2Cl)ccc1CNC[C@@H]1CCC(=O)N1] | 807.3 |
| B-145 | 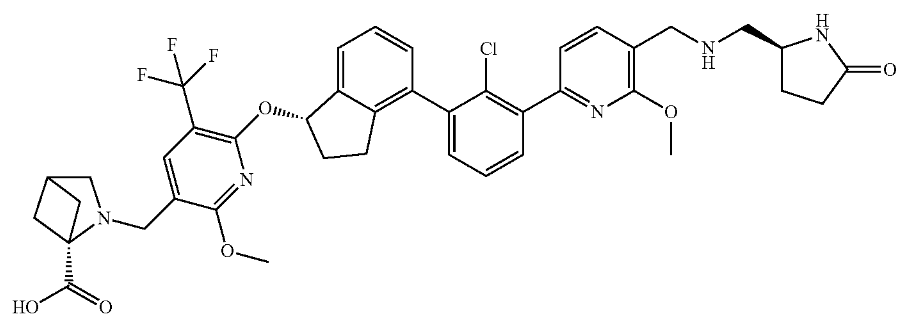 | 793.2 |
| B-146 | 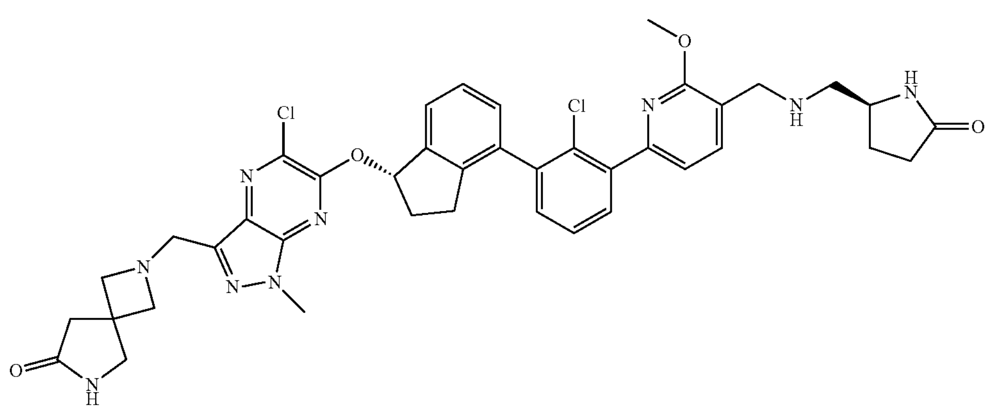 [SMILES: COc1nc(-c2cccc(-c3cccc4c3CC[C@@H]4Oc3nc4c(nc3Cl)c(CN3CC5(CNC(=O)C5)C3)nn4C)c2Cl)ccc1CNC[C@@H]1CCC(=O)N1] | 782.3 |
| B-147 | 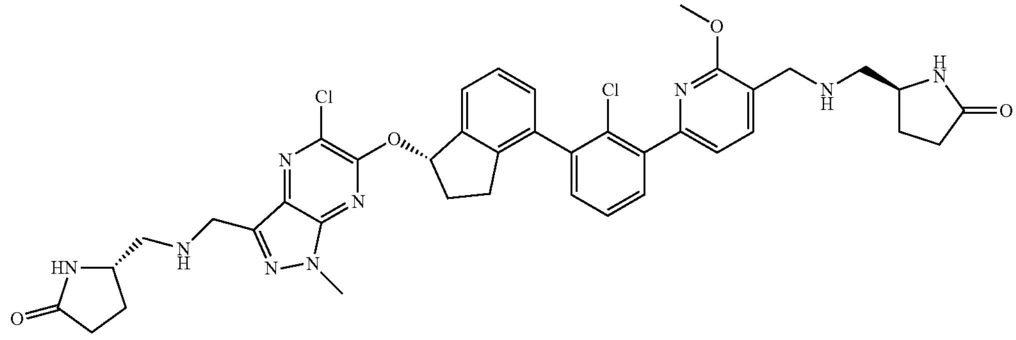 [SMILES: COc1nc(-c2cccc(-c3cccc4c3CC[C@@H]4Oc3nc4c(nc3Cl)c(CNC[C@@H]3CCC(=O)N3)nn4C)c2Cl)ccc1CNC[C@@H]1CCC(=O)N1] | 770.2 |

TABLE 1B-continued

| No. | Structure | LCMS |
|---|---|---|
| B-148 | 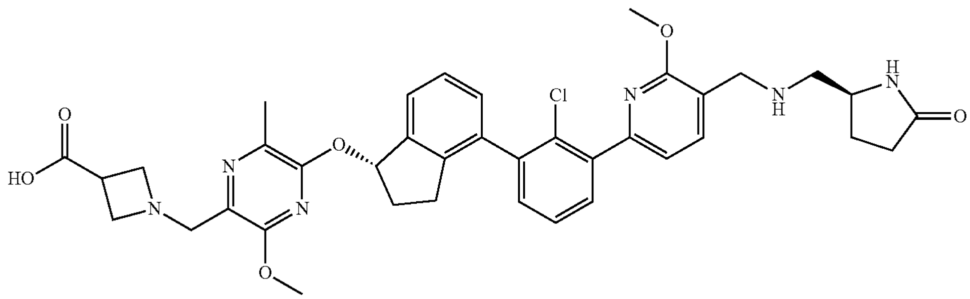 [SMILES: COc1nc(-c2cccc(-c3cccc4c3CC[C@@H]4Oc3nc(OC)c(CN4CC(C(=O)O)C4)nc3C)c2Cl)ccc1CNC[C@@H]1CCC(=O)N1] | 713.2 |
| B-149 | 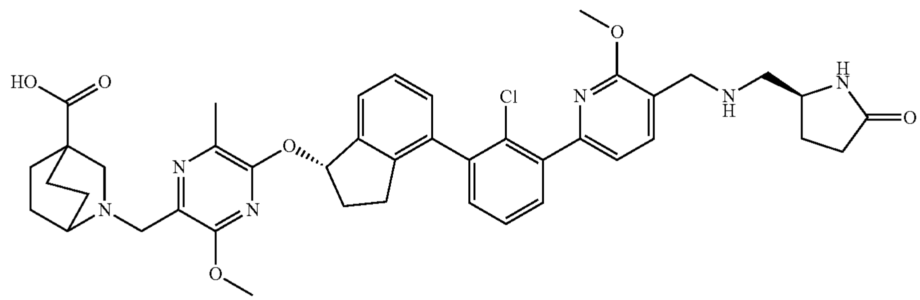 [SMILES: COc1nc(-c2cccc(-c3cccc4c3CC[C@@H]4Oc3nc(OC)c(CN4CC5(C(=O)O)CCC4CC5)nc3C)c2Cl)ccc1CNC[C@@H]1CCC(=O)N1] | 767.3 |
| B-150 | 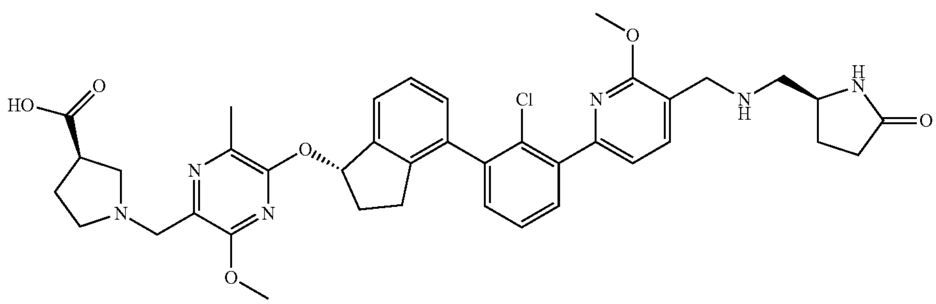 [SMILES: COc1nc(-c2cccc(-c3cccc4c3CC[C@@H]4Oc3nc(OC)c(CN4CC[C@@H](C(=O)O)C4)nc3C)c2Cl)ccc1CNC[C@@H]1CCC(=O)N1] | 727.3 |
| B-151 | 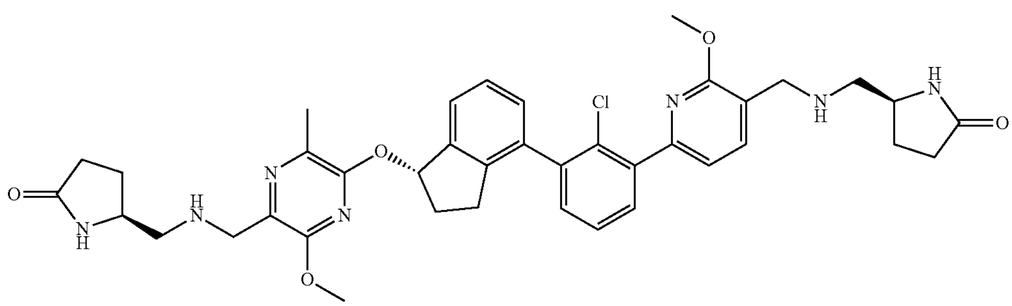 [SMILES: COc1nc(-c2cccc(-c3cccc4c3CC[C@@H]4Oc3nc(OC)c(CNC[C@@H]4CCC(=O)N4)nc3C)c2Cl)ccc1CNC[C@@H]1CCC(=O)N1] | 726.3 |
| B-152 | 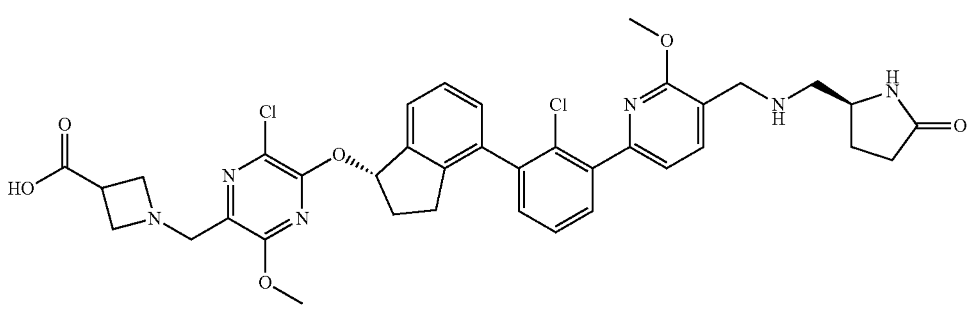 [SMILES: COc1nc(-c2cccc(-c3cccc4c3CC[C@@H]4Oc3nc(OC)c(CN4CC(C(=O)O)C4)nc3Cl)c2Cl)ccc1CNC[C@@H]1CCC(=O)N1] | 733.2 |

TABLE 1B-continued

| No. | Structure | LCMS |
|---|---|---|
| B-153 | 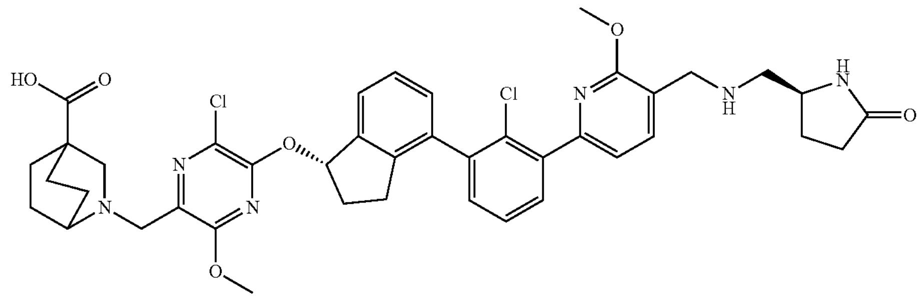 [SMILES: COc1nc(-c2cccc(-c3cccc4c3CC[C@@H]4Oc3nc(OC)c(CN4CC5(C(=O)O)CCC4CC5)nc3Cl)c2Cl)ccc1CNC[C@@H]1CCC(=O)N1] | 787.3 |
| B-154 | 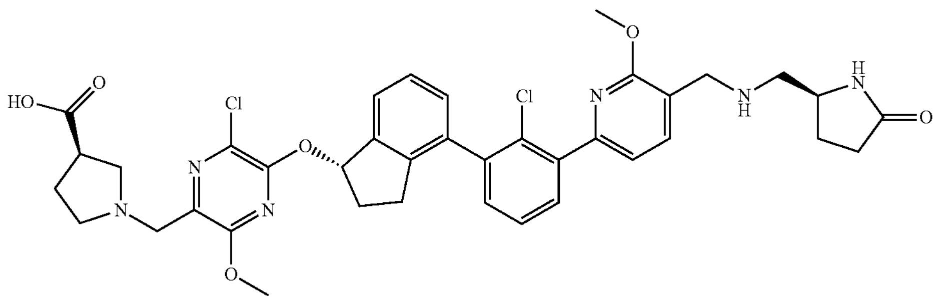 [SMILES: COc1nc(-c2cccc(-c3cccc4c3CC[C@@H]4Oc3nc(OC)c(CN4CC[C@@H](C(=O)O)C4)nc3Cl)c2Cl)ccc1CNC[C@@H]1CCC(=O)N1] | 747.2 |
| B-155 | 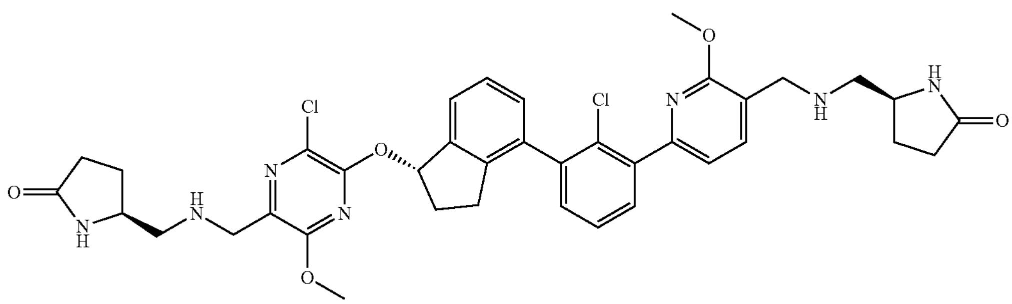 [SMILES: COc1nc(-c2cccc(-c3cccc4c3CC[C@@H]4Oc3nc(OC)c(CNC[C@@H]4CCC(=O)N4)nc3Cl)c2Cl)ccc1CNC[C@@H]1CCC(=O)N1] | 746.2 |
| B-156 | 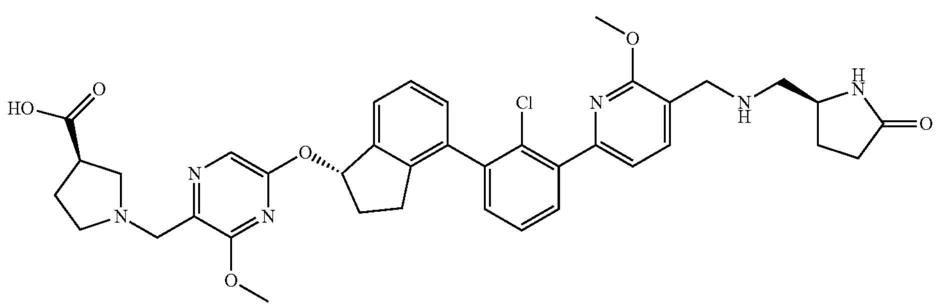 [SMILES: COc1nc(-c2cccc(-c3cccc4c3CC[C@@H]4Oc3cnc(CN4CC[C@@H](C(=O)O)C4)c(OC)n3)c2Cl)ccc1CNC[C@@H]1CCC(=O)N1] | 713.2 |
| B-157 | 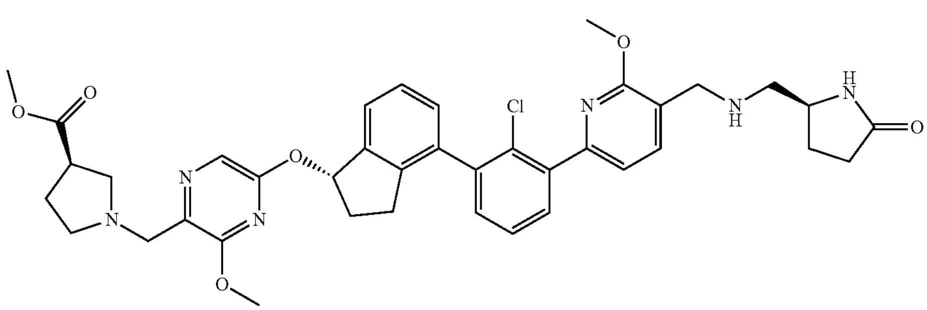 [SMILES: COC(=O)[C@@H]1CCN(Cc2ncc(O[C@H]3CCc4c(-c5cccc(-c6ccc(CNC[C@@H]7CCC(=O)N7)c(OC)n6)c5Cl)cccc43)nc2OC)C1] | 727.3 |

TABLE 1B-continued

| No. | Structure | LCMS |
|---|---|---|
| B-158 | 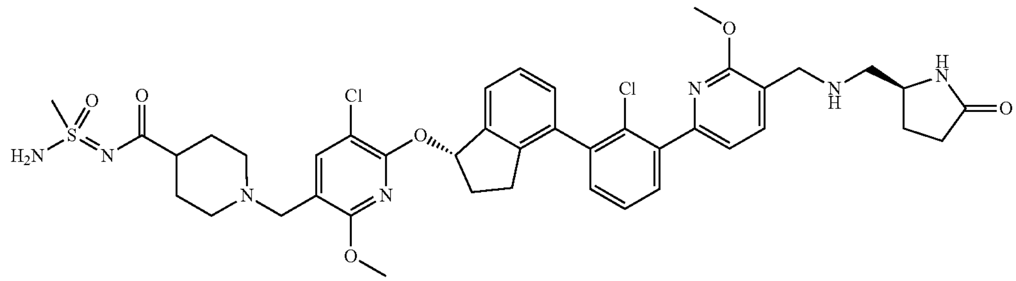 [SMILES: COc1nc(-c2cccc(-c3cccc4c3CC[C@@H]4Oc3nc(OC)c(CN4CCC(C(=O)N=S(C)(N)=O)CC4)cc3Cl)c2Cl)ccc1CNC[C@@H]1CCC(=O)N1] | 836.2 |
| B-159 | 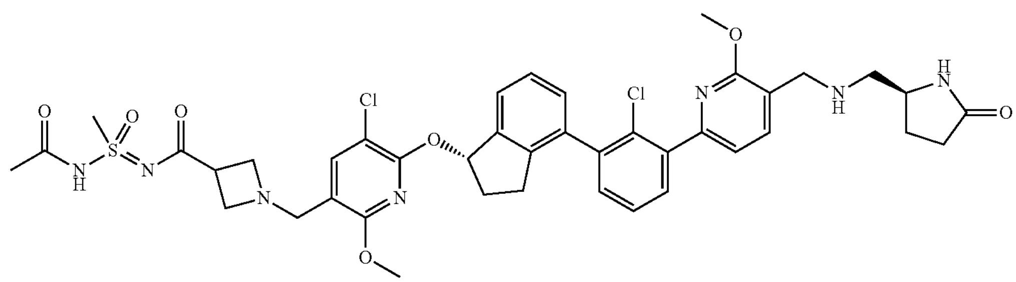 [SMILES: COc1nc(-c2cccc(-c3cccc4c3CC[C@@H]4Oc3nc(OC)c(CN4CC(C(=O)N=S(C)(=O)NC(C)=O)C4)cc3Cl)c2Cl)ccc1CNC[C@@H]1CCC(=O)N1] | 850.2 |
| B-160 | 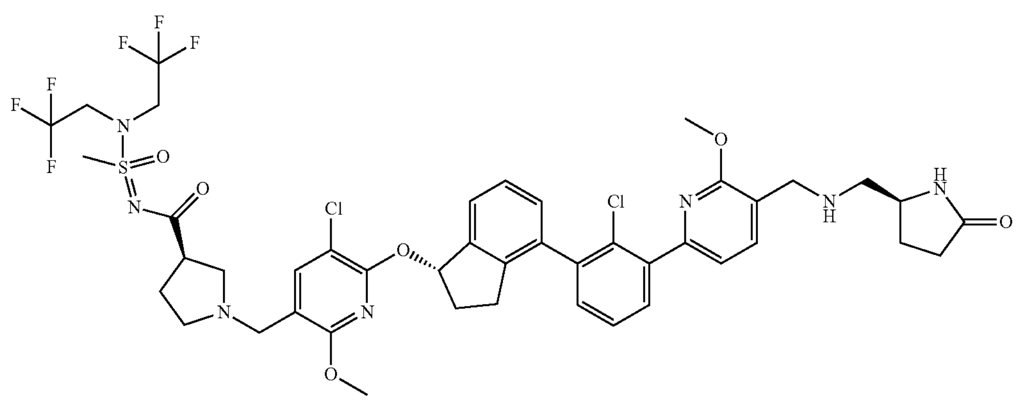 [SMILES: COc1nc(-c2cccc(-c3cccc4c3CC[C@@H]4Oc3nc(OC)c(CN4CC[C@@H](C(=O)N=S(C)(=O)N(CC(F)(F)F)CC(F)(F)F)C4)cc3Cl)c2Cl)ccc1CNC[C@@H]1CCC(=O)N1] | 986.2 |
| B-161 | 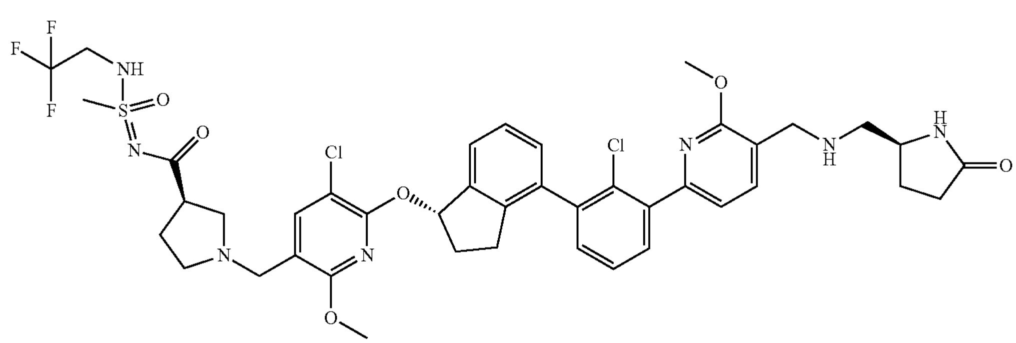 [SMILES: COc1nc(-c2cccc(-c3cccc4c3CC[C@@H]4Oc3nc(OC)c(CN4CC[C@@H](C(=O)N=S(C)(=O)NCC(F)(F)F)C4)cc3Cl)c2Cl)ccc1CNC[C@@H]1CCC(=O)N1] | 904.2 |

| No. | Structure | LCMS |
|---|---|---|
| B-162 | 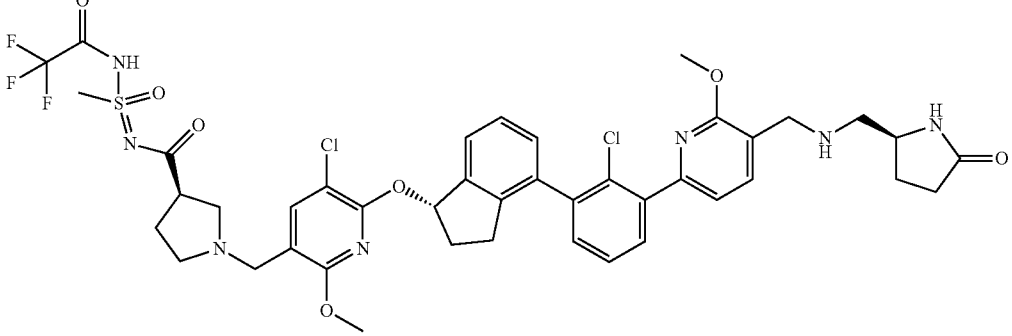 | 918.2 |
| B-163 | 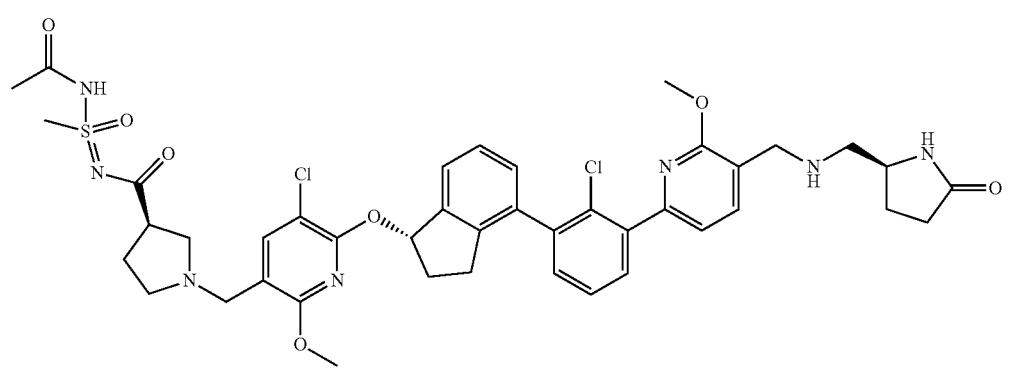 [SMILES: COc1nc(-c2cccc(-c3cccc4c3CC[C@@H]4Oc3nc(OC)c(CN4CC[C@@H](C(=O)N=S(C)(=O)NC(C)=O)C4)cc3Cl)c2Cl)ccc1CNC[C@@H]1CCC(=O)N1] | 864.2 |
| B-164 | 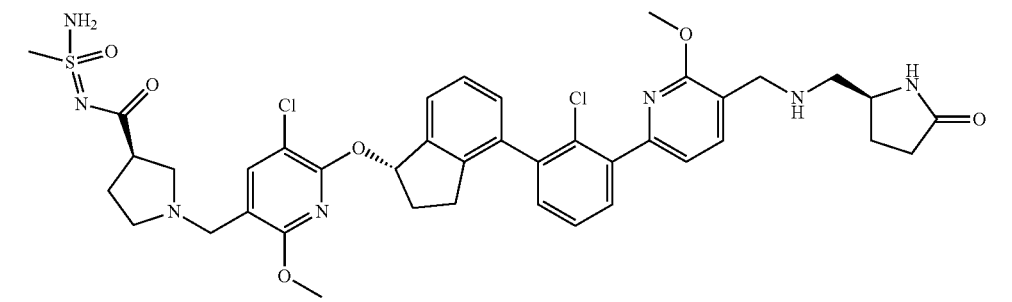 [SMILES: COc1nc(-c2cccc(-c3cccc4c3CC[C@@H]4Oc3nc(OC)c(CN4CC[C@@H](C(=O)N=S(C)(N)=O)C4)cc3Cl)c2Cl)ccc1CNC[C@@H]1CCC(=O)N1] | 822.2 |
| B-165 | 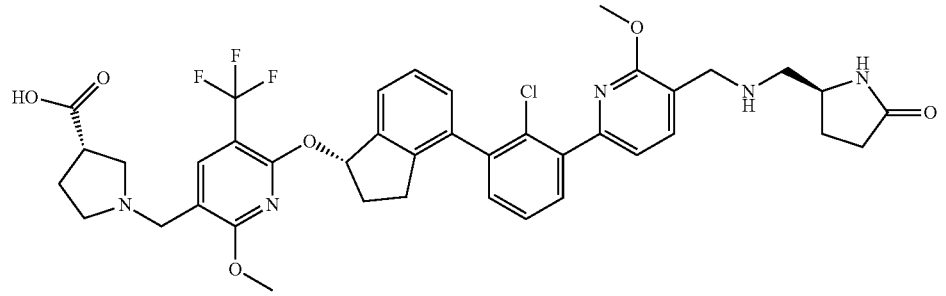 [SMILES: COc1nc(-c2cccc(-c3cccc4c3CC[C@@H]4Oc3nc(OC)c(CN4CC[C@H](C(=O)O)C4)cc3C(F)(F)F)c2Cl)ccc1CNC[C@@H]1CCC(=O)N1] | 779.12 |

TABLE 1B-continued

| No. | Structure | LCMS |
|---|---|---|
| B-166 | 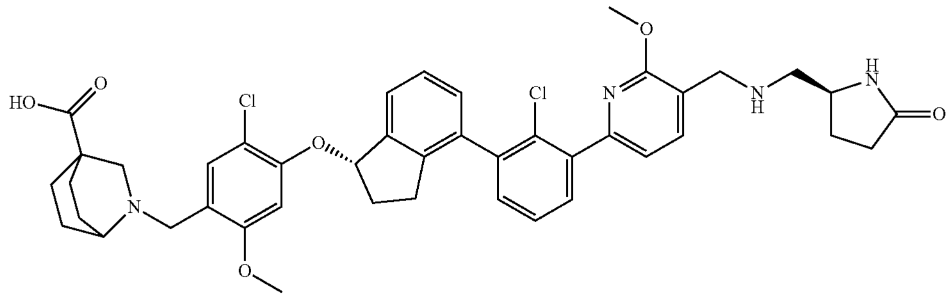 [SMILES: COc1cc(O[C@H]2CCc3c(-c4cccc(-c5ccc(CNC[C@@H]6CCC(=O)N6)c(OC)n5)c4Cl)cccc32)c(Cl)cc1CN1CC2(C(=O)O)CCC1CC2] | 785.12 |
| B-167 | 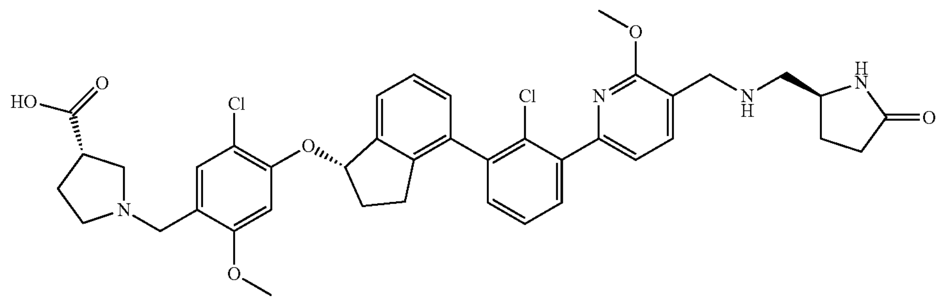 | 745.12 |
| B-168 | 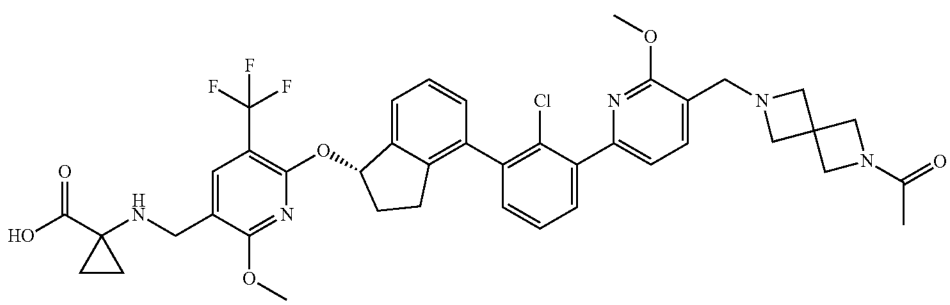 [SMILES: COc1nc(-c2cccc(-c3cccc4c3CC[C@@H]4Oc3nc(OC)c(CNC4(C(=O)O)CC4)cc3C(F)(F)F)c2Cl)ccc1CN1CC2(C1)CN(C(C)=O)C2] | 792.2 |
| B-169 | 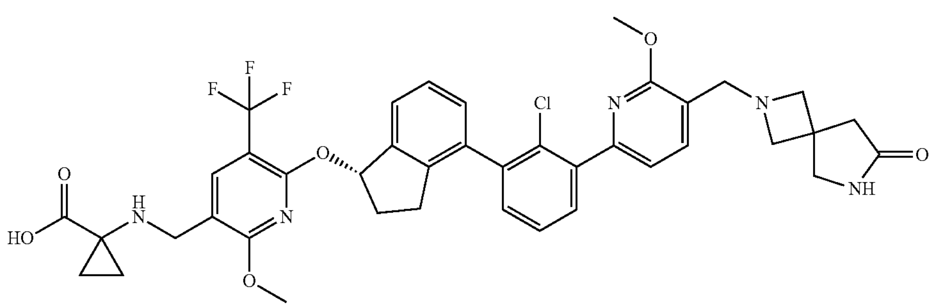 [SMILES: COc1nc(-c2cccc(-c3cccc4c3CC[C@@H]4Oc3nc(OC)c(CNC4(C(=O)O)CC4)cc3C(F)(F)F)c2Cl)ccc1CN1CC2(CNC(=O)C2)C1] | 778.2 |
| B-170 | 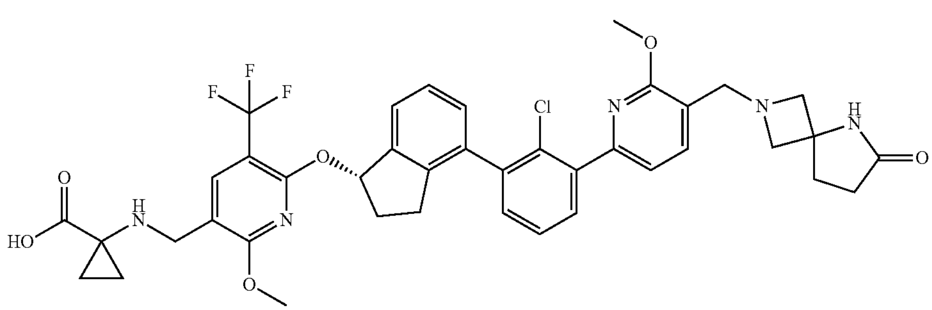 [SMILES: COc1nc(-c2cccc(-c3cccc4c3CC[C@@H]4Oc3nc(OC)c(CNC4(C(=O)O)CC4)cc3C(F)(F)F)c2Cl)ccc1CN1CC2(CCC(=O)N2)C1] | 778.2 |

TABLE 1B-continued

| No. | Structure | LCMS |
|---|---|---|
| B-171 | 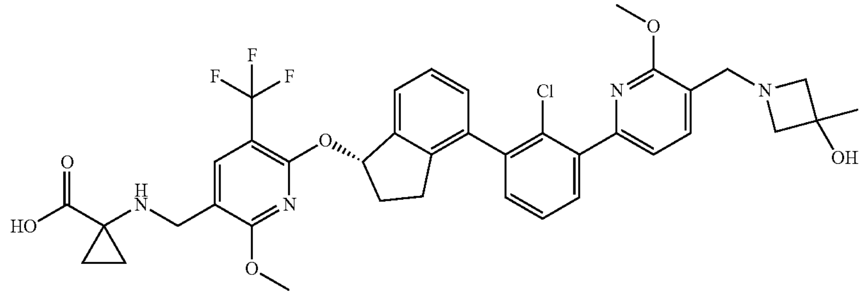 [SMILES: COc1nc(-c2cccc(-c3cccc4c3CC[C@@H]4Oc3nc(OC)c(CNC4(C(=O)O)CC4)cc3C(F)(F)F)c2Cl)ccc1CN1CC(C)(O)C1] | 739.2 |
| B-172 | 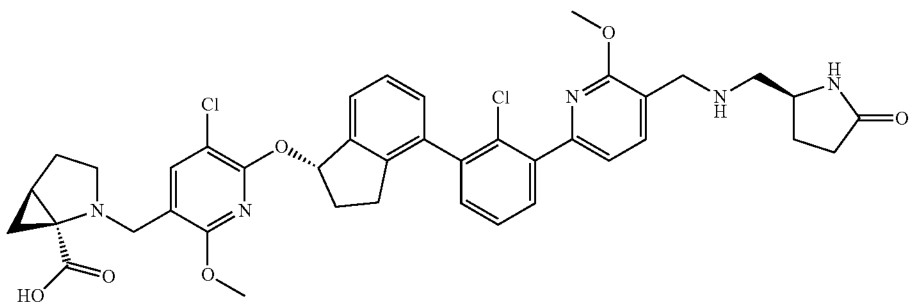 [SMILES: COc1nc(-c2cccc(-c3cccc4c3CC[C@@H]4Oc3nc(OC)c(CN4CC[C@@H]5C[C@@]54C(=O)O)cc3Cl)c2Cl)ccc1CNC[C@@H]1CCC(=O)N1] | 752.8 |
| B-173 | 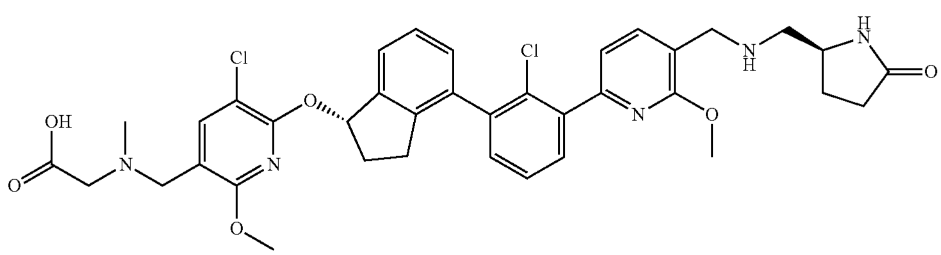 [SMILES: COc1nc(-c2cccc(-c3cccc4c3CC[C@@H]4Oc3nc(OC)c(CN(C)CC(=O)O)cc3Cl)c2Cl)ccc1CNC[C@@H]1CCC(=O)N1] | 719.909 |
| B-174 | 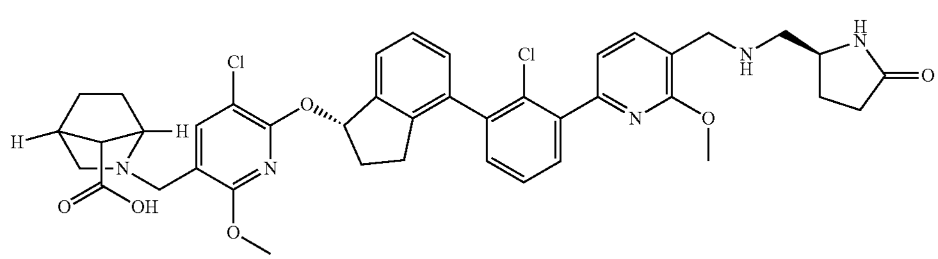 [SMILES: COc1nc(-c2cccc(-c3cccc4c3CC[C@@H]4Oc3nc(OC)c(CN4CC5CCC4C5C(=O)O)cc3Cl)c2Cl)ccc1CNC[C@@H]1CCC(=O)N1] | 771.977 |
| B-175 | 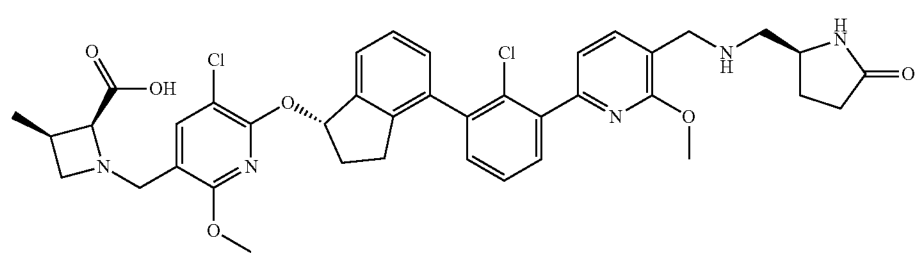 [SMILES: COc1nc(-c2cccc(-c3cccc4c3CC[C@@H]4Oc3nc(OC)c(CN4C[C@@H](C)[C@H]4C(=O)O)cc3Cl)c2Cl)ccc1CNC[C@@H]1CCC(=O)N1] | 745.897 |

TABLE 1B-continued

| No. | Structure | LCMS |
|---|---|---|
| B-176 | 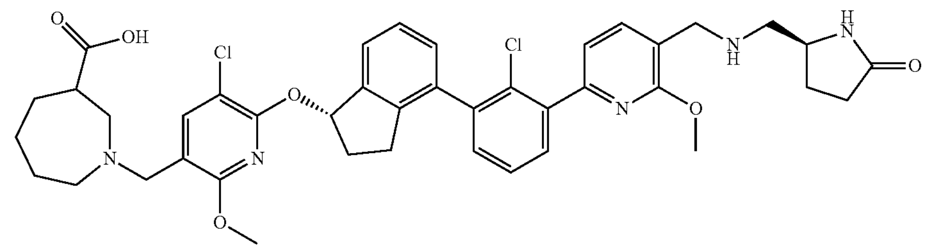 [SMILES: COc1nc(-c2cccc(-c3cccc4c3CC[C@@H]4Oc3nc(OC)c(CN4CCCCC(C(=O)O)C4)cc3Cl)c2Cl)ccc1CNC[C@@H]1CCC(=O)N1] | 774.137 |
| B-177 | 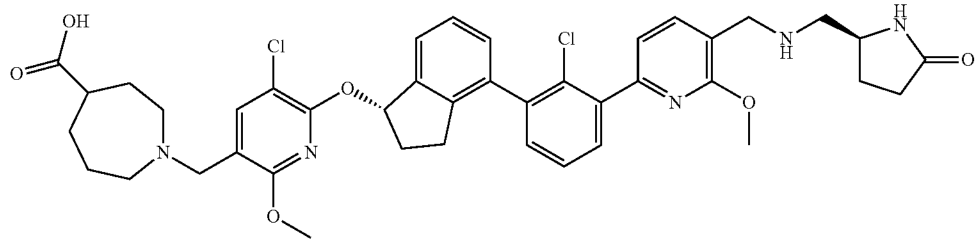 [SMILES: COc1nc(-c2cccc(-c3cccc4c3CC[C@@H]4Oc3nc(OC)c(CN4CCCC(C(=O)O)CC4)cc3Cl)c2Cl)ccc1CNC[C@@H]1CCC(=O)N1] | 774.054 |
| B-178 | 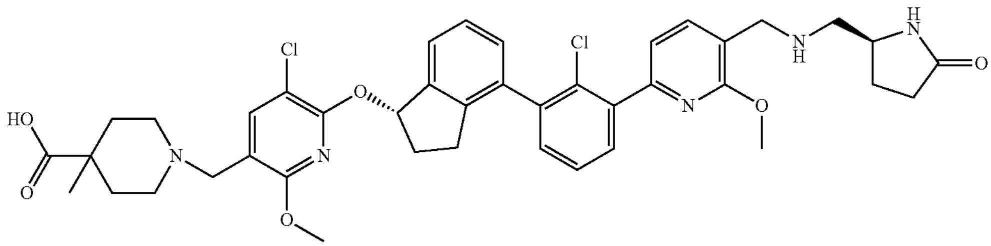 [SMILES: COc1nc(-c2cccc(-c3cccc4c3CC[C@@H]4Oc3nc(OC)c(CN4CCC(C)(C(=O)O)CC4)cc3Cl)c2Cl)ccc1CNC[C@@H]1CCC(=O)N1] | 774.083 |
| B-179 | 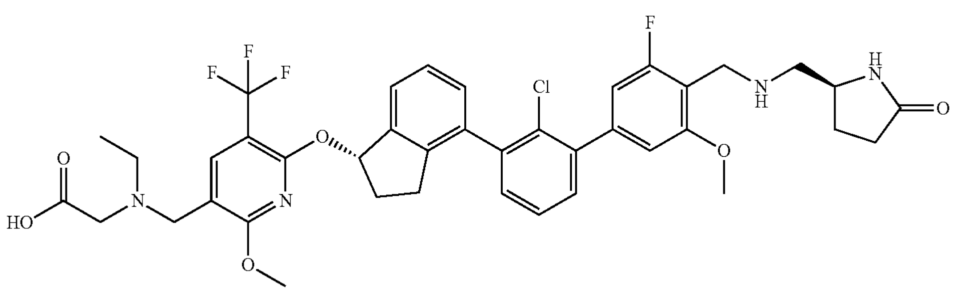 [SMILES: CCN(CC(=O)O)Cc1cc(C(F)(F)F)c(O[C@H]2CCc3c(-c4cccc(-c5cc(F)c(CNC[C@@H]6CCC(=O)N6)c(OC)c5)c4Cl)cccc32)nc1OC] | 784.894 |
| B-180 | 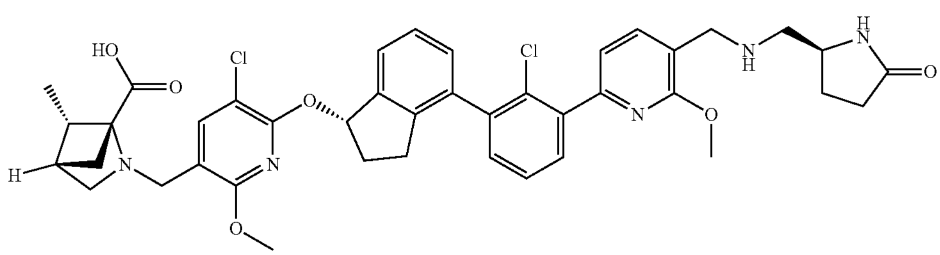 [SMILES: COc1nc(-c2cccc(-c3cccc4c3CC[C@@H]4Oc3nc(OC)c(CN4C[C@H]5C[C@]4(C(=O)O)[C@H]5C)cc3Cl)c2Cl)ccc1CNC[C@@H]1CCC(=O)N1] | 771.937 |
| B-181 | 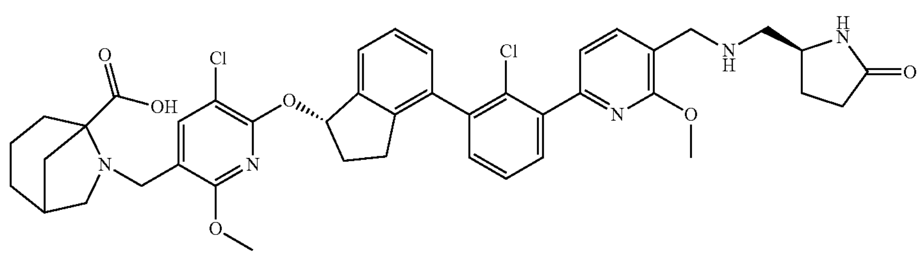 [SMILES: COc1nc(-c2cccc(-c3cccc4c3CC[C@@H]4Oc3nc(OC)c(CN4CC5CCCC4(C(=O)O)C5)cc3Cl)c2Cl)ccc1CNC[C@@H]1CCC(=O)N1] | 785.952 |

TABLE 1B-continued

| No. | Structure | LCMS |
|---|---|---|
| B-182 | 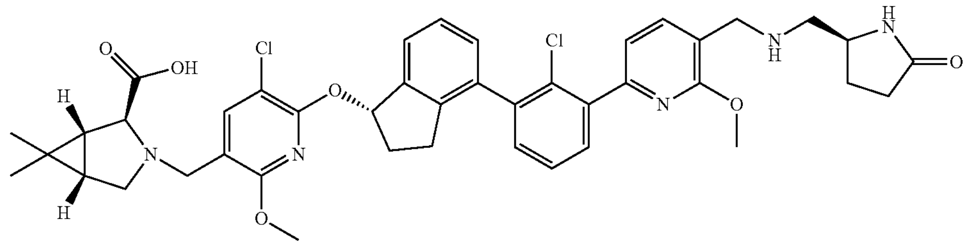 [SMILES: COc1nc(-c2cccc(-c3cccc4c3CC[C@@H]4Oc3nc(OC)c(CN4C[C@H]5[C@@H]([C@H]4C(=O)O)C5(C)C)cc3Cl)c2Cl)ccc1CNC[C@@H]1CCC(=O)N1] | 785.947 |
| B-183 | 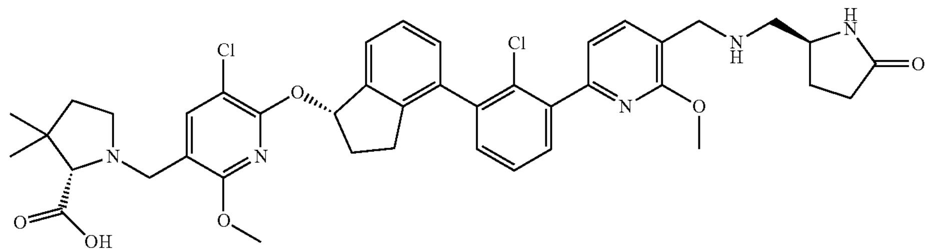 [SMILES: COc1nc(-c2cccc(-c3cccc4c3CC[C@@H]4Oc3nc(OC)c(CN4CCC(C)(C)[C@H]4C(=O)O)cc3Cl)c2Cl)ccc1CNC[C@@H]1CCC(=O)N1] | 773.976 |
| B-184 | 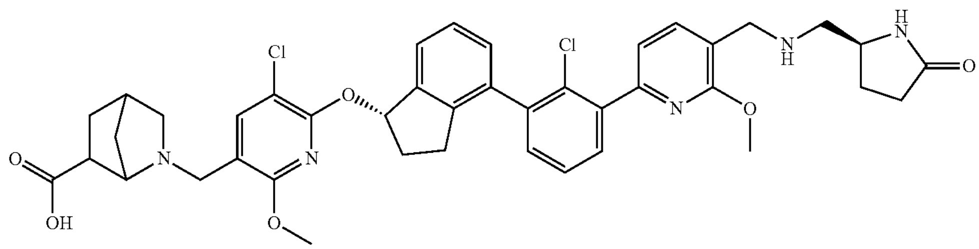 [SMILES: COc1nc(-c2cccc(-c3cccc4c3CC[C@@H]4Oc3nc(OC)c(CN4CC5CC(C(=O)O)C4C5)cc3Cl)c2Cl)ccc1CNC[C@@H]1CCC(=O)N1] | 771.972 |
| B-185 | 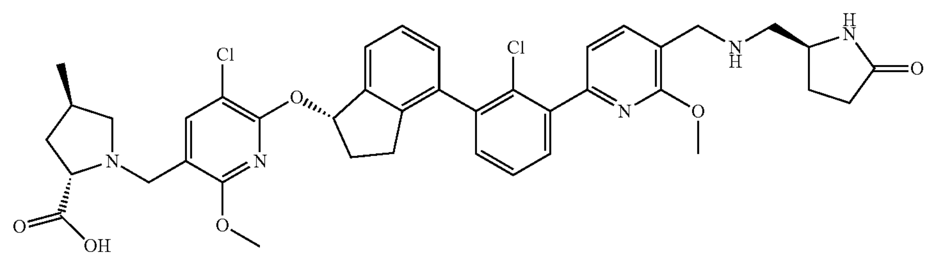 [SMILES: COc1nc(-c2cccc(-c3cccc4c3CC[C@@H]4Oc3nc(OC)c(CN4C[C@H](C)C[C@H]4C(=O)O)cc3Cl)c2Cl)ccc1CNC[C@@H]1CCC(=O)N1] | 759.931 |
| B-186 | 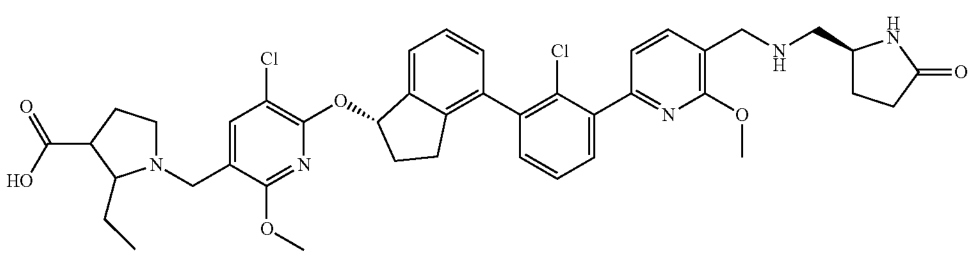 [SMILES: CCC1C(C(=O)O)CCN1Cc1cc(Cl)c(O[C@H]2CCc3c(-c4cccc(-c5ccc(CNC[C@@H]6CCC(=O)N6)c(OC)n5)c4Cl)cccc32)nc1OC] | 774.14 |
| B-187 | 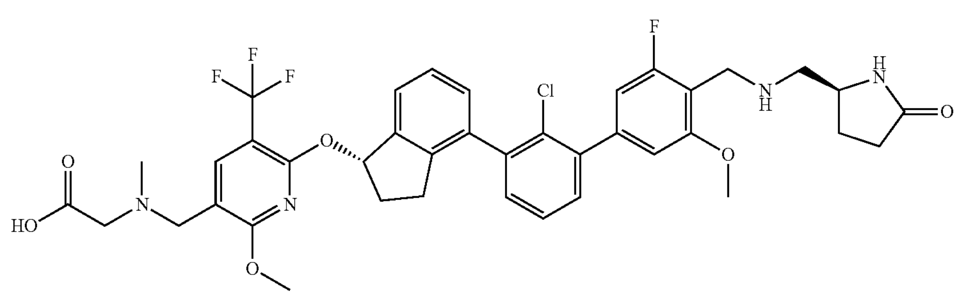 [SMILES: COc1cc(-c2cccc(-c3cccc4c3CC[C@@H]4Oc3nc(OC)c(CN(C)CC(=O)O)cc3C(F)(F)F)c2Cl)cc(F)c1CNC[C@@H]1CCC(=O)N1] | 770.89 |

TABLE 1B-continued

| No. | Structure | LCMS |
|---|---|---|
| B-188 | 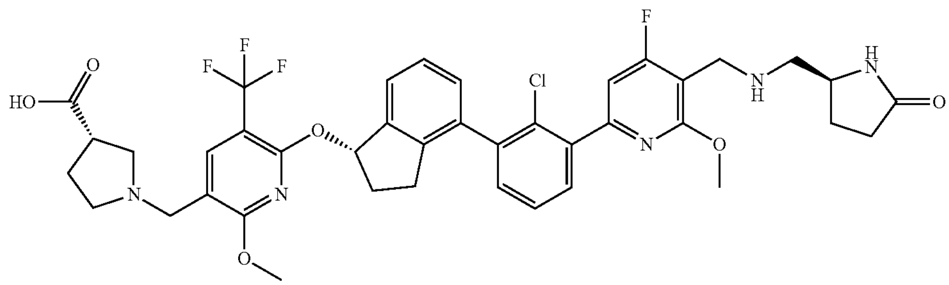 [SMILES: COc1nc(O[C@H]2CCc3c(-c4cccc(-c5cc(F)c(CNC[C@@H]6CCC(=O)N6)c(OC)n5)c4Cl)cccc32)c(C(F)(F)F)cc1CN1CC[C@H](C(=O)O)C1] | 798.005 |
| B-189 | 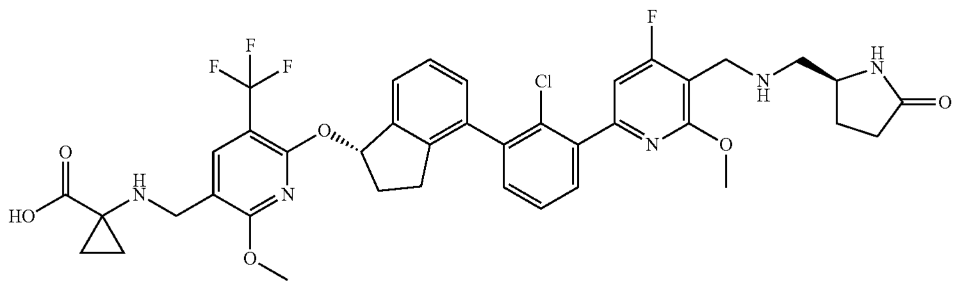 [SMILES: COc1nc(O[C@H]2CCc3c(-c4cccc(-c5cc(F)c(CNC[C@@H]6CCC(=O)N6)c(OC)n5)c4Cl)cccc32)c(C(F)(F)F)cc1CNC1(C(=O)O)CC1] | 783.931 |
| B-190 | 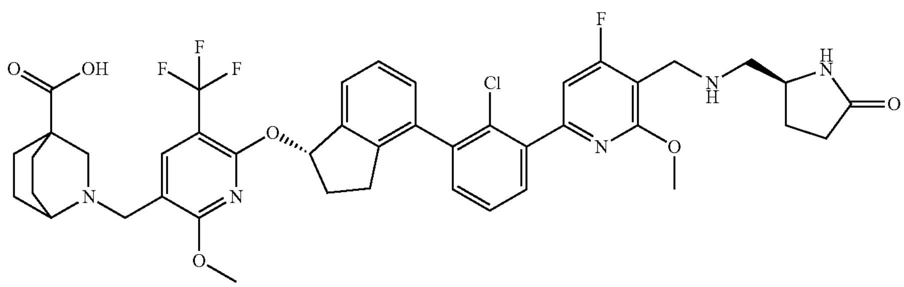 [SMILES: COc1nc(O[C@H]2CCc3c(-c4cccc(-c5cc(F)c(CNC[C@@H]6CCC(=O)N6)c(OC)n5)c4Cl)cccc32)c(C(F)(F)F)cc1CN1CC2(C(=O)O)CCC1CC2] | 838.02 |
| B-191 | 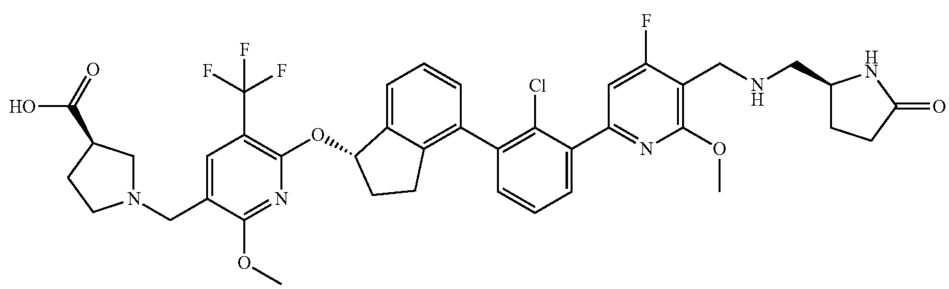 [SMILES: COc1nc(O[C@H]2CCc3c(-c4cccc(-c5cc(F)c(CNC[C@@H]6CCC(=O)N6)c(OC)n5)c4Cl)cccc32)c(C(F)(F)F)cc1CN1CC[C@@H](C(=O)O)C1] | 797.984 |
| B-192 | 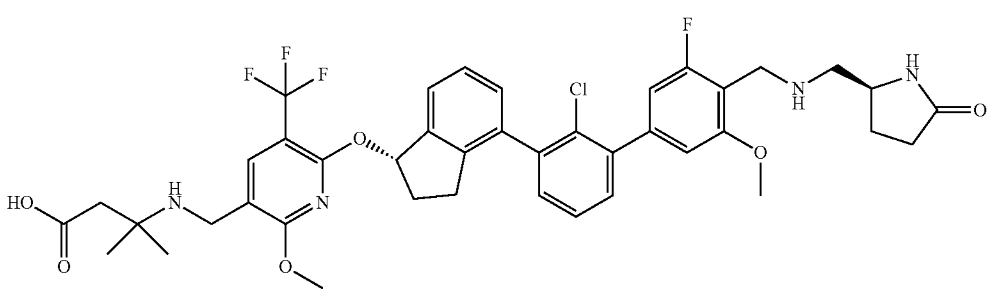 [SMILES: COc1cc(-c2cccc(-c3cccc4c3CC[C@@H]4Oc3nc(OC)c(CNC(C)(C)CC(=O)O)cc3C(F)(F)F)c2Cl)cc(F)c1CNC[C@@H]1CCC(=O)N1] | 799.017 |

TABLE 1B-continued

| No. | Structure | LCMS |
|---|---|---|
| B-193 | 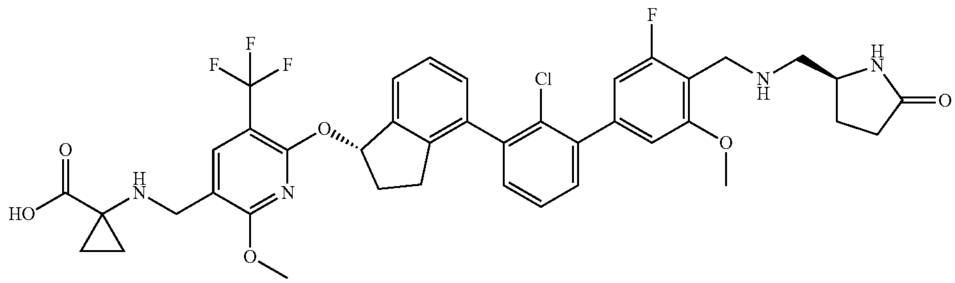 [SMILES: COc1cc(-c2cccc(-c3cccc4c3CC[C@@H]4Oc3nc(OC)c(CNC4(C(=O)O)CC4)cc3C(F)(F)F)c2Cl)cc(F)c1CNC[C@@H]1CCC(=O)N1] | 782.902 |
| B-194 | 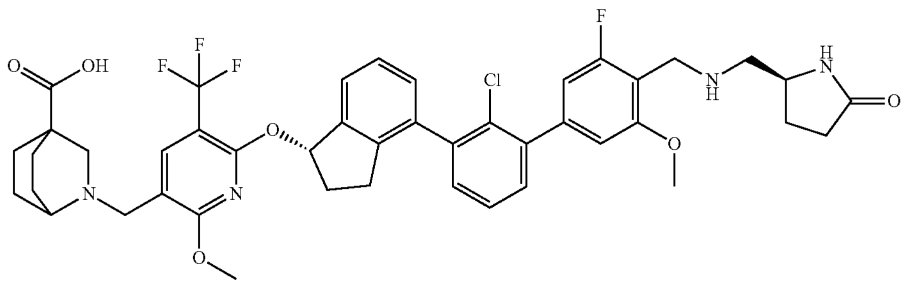 [SMILES: COc1cc(-c2cccc(-c3cccc4c3CC[C@@H]4Oc3nc(OC)c(CN4CC5(C(=O)O)CCC4CC5)cc3C(F)(F)F)c2Cl)cc(F)c1CNC[C@@H]1CCC(=O)N1] | 837.042 |
| B-195 | 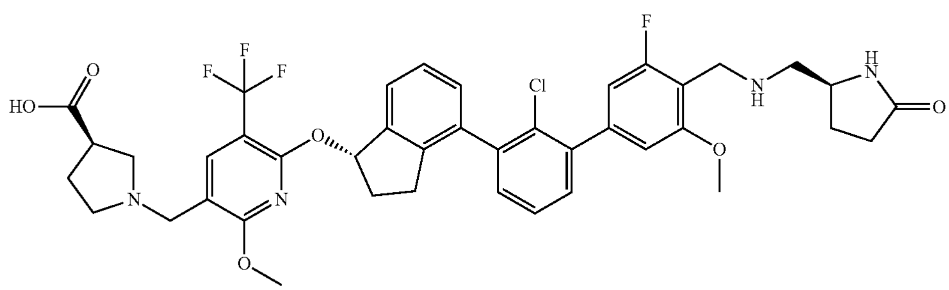 | 797.001 |
| B-196 | 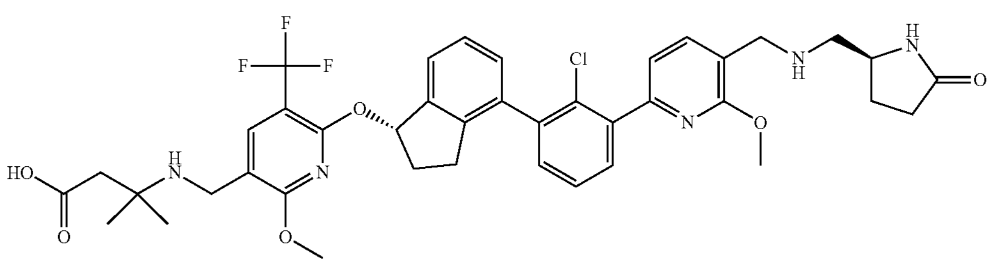 [SMILES: COc1nc(-c2cccc(-c3cccc4c3CC[C@@H]4Oc3nc(OC)c(CNC(C)(C)CC(=O)O)cc3C(F)(F)F)c2Cl)ccc1CNC[C@@H]1CCC(=O)N1] | 781.986 |
| B-197 | 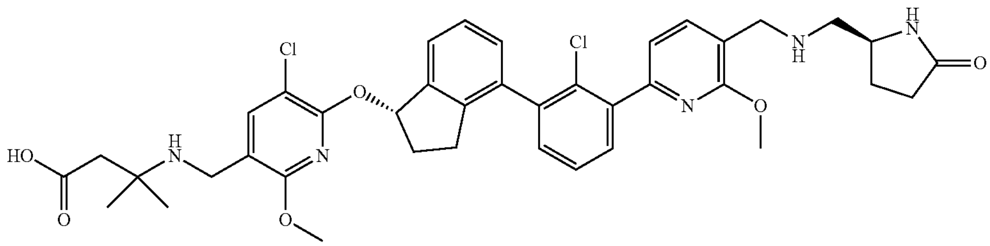 [SMILES: COc1nc(-c2cccc(-c3cccc4c3CC[C@@H]4Oc3nc(OC)c(CNC(C)(C)CC(=O)O)cc3Cl)c2Cl)ccc1CNC[C@@H]1CCC(=O)N1] | 747.985 |

TABLE 1B-continued

| No. | Structure | LCMS |
|---|---|---|
| B-198 | 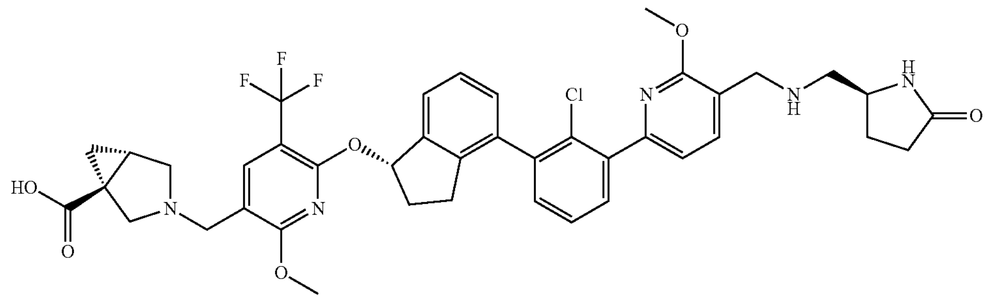 [SMILES: COc1nc(-c2cccc(-c3cccc4c3CC[C@@H]4Oc3nc(OC)c(CN4C[C@H]5C[C@@]5(C(=O)O)C4)cc3C(F)(F)F)c2Cl)ccc1CNC[C@@H]1CCC(=O)N1] | 792.28 |
| B-199 | 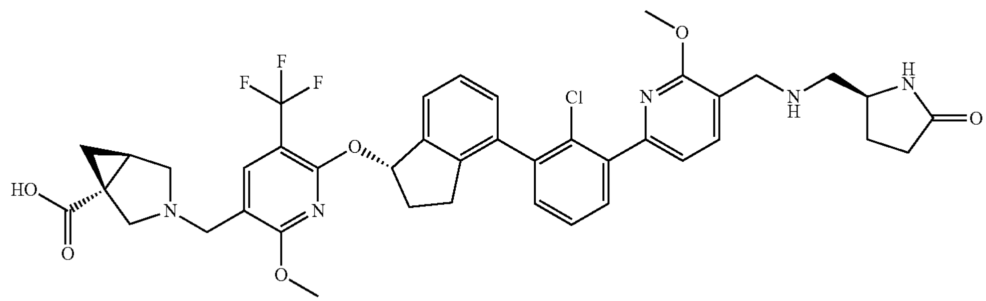 [SMILES: COc1nc(-c2cccc(-c3cccc4c3CC[C@@H]4Oc3nc(OC)c(CN4C[C@@H]5C[C@]5(C(=O)O)C4)cc3C(F)(F)F)c2Cl)ccc1CNC[C@@H]1CCC(=O)N1] | 792.28 |
| B-200 | 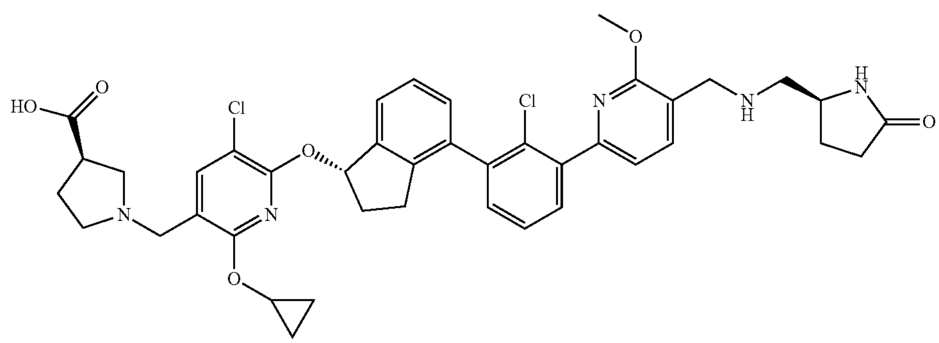 [SMILES: COc1nc(-c2cccc(-c3cccc4c3CC[C@@H]4Oc3nc(OC4CC4)c(CN4CC[C@@H](C(=O)O)C4)cc3Cl)c2Cl)ccc1CNC[C@@H]1CCC(=O)N1] | 772.27 |
| B-201 | 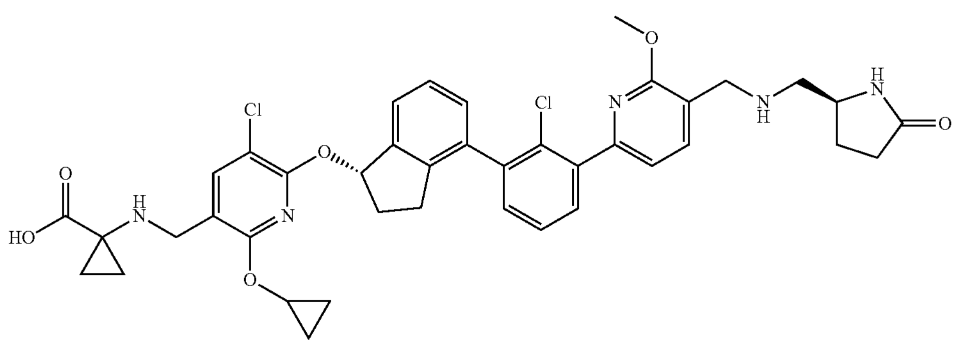 [SMILES: COc1nc(-c2cccc(-c3cccc4c3CC[C@@H]4Oc3nc(OC4CC4)c(CNC4(C(=O)O)CC4)cc3Cl)c2Cl)ccc1CNC[C@@H]1CCC(=O)N1] | 758.25 |
| B-202 | 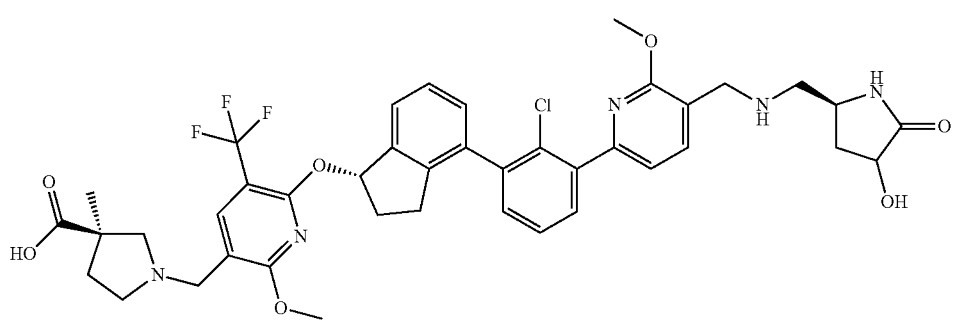 [SMILES: COc1nc(-c2cccc(-c3cccc4c3CC[C@@H]4Oc3nc(OC)c(CN4CC[C@@](C)(C(=O)O)C4)cc3C(F)(F)F)c2Cl)ccc1CNC[C@@H]1CC(O)C(=O)N1] | 810.1 |

TABLE 1B-continued

| No. | Structure | LCMS |
|---|---|---|
| B-203 | 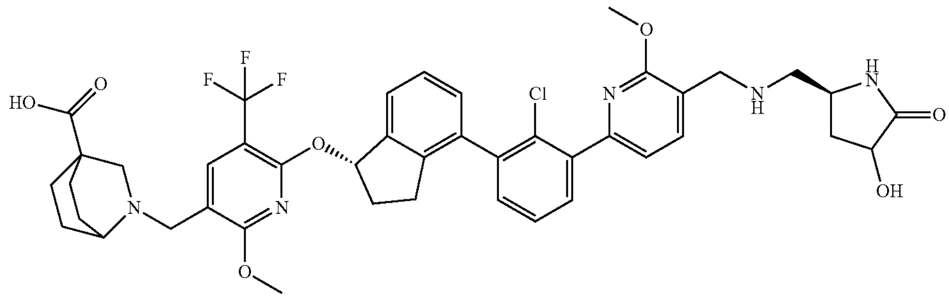 [SMILES: COc1nc(-c2cccc(-c3cccc4c3CC[C@@H]4Oc3nc(OC)c(CN4CC5(C(=O)O)CCC4CC5)cc3C(F)(F)F)c2Cl)ccc1CNC[C@@H]1CC(O)C(=O)N1] | 836.16 |
| B-204 | 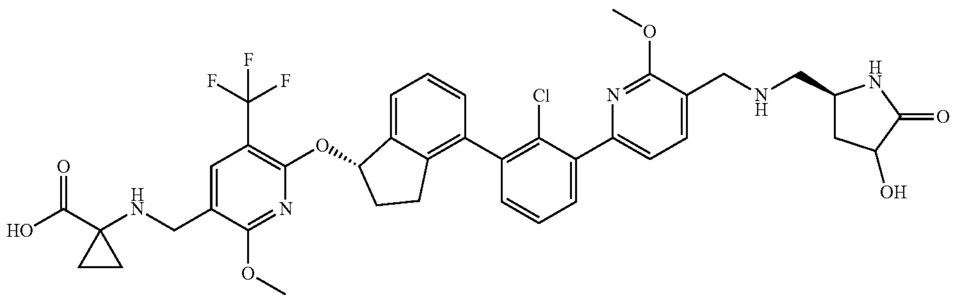 [SMILES: COc1nc(-c2cccc(-c3cccc4c3CC[C@@H]4Oc3nc(OC)c(CNC4(C(=O)O)CC4)cc3C(F)(F)F)c2Cl)ccc1CNC[C@@H]1CC(O)C(=O)N1] | 782.06 |
| B-205 | 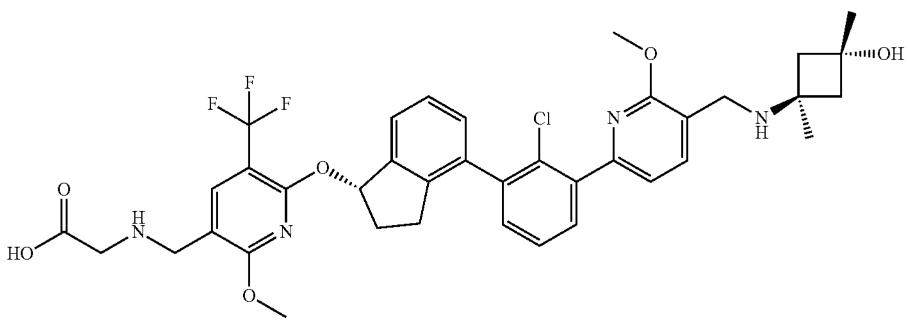 [SMILES: COc1nc(-c2cccc(-c3cccc4c3CC[C@@H]4Oc3nc(OC)c(CNCC(=O)O)cc3C(F)(F)F)c2Cl)ccc1CN[C@]1(C)C[C@@](C)(O)C1] | 741.15 |
| B-206 | 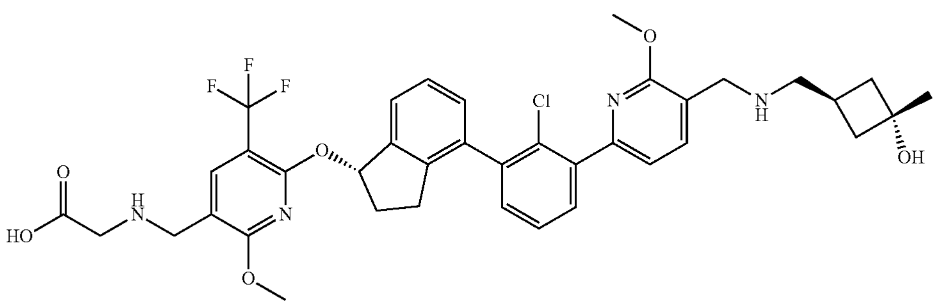 [SMILES: COc1nc(-c2cccc(-c3cccc4c3CC[C@@H]4Oc3nc(OC)c(CNCC(=O)O)cc3C(F)(F)F)c2Cl)ccc1CNC[C@H]1C[C@](C)(O)C1] | 741.07 |
| B-207 | 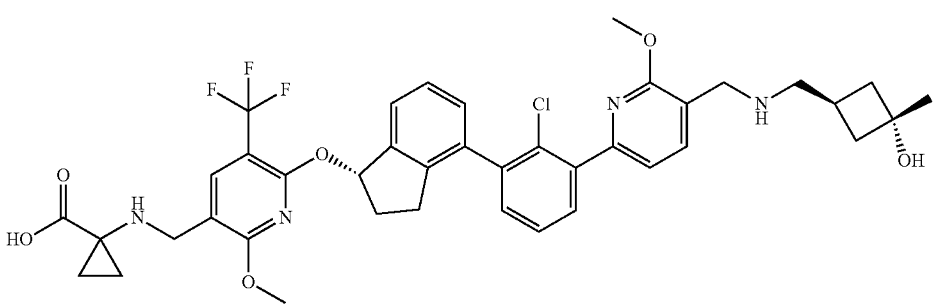 [SMILES: COc1nc(-c2cccc(-c3cccc4c3CC[C@@H]4Oc3nc(OC)c(CNC4(C(=O)O)CC4)cc3C(F)(F)F)c2Cl)ccc1CNC[C@H]1C[C@](C)(O)C1] | 767.12 |

TABLE 1B-continued

| No. | Structure | LCMS |
|---|---|---|
| B-208 | 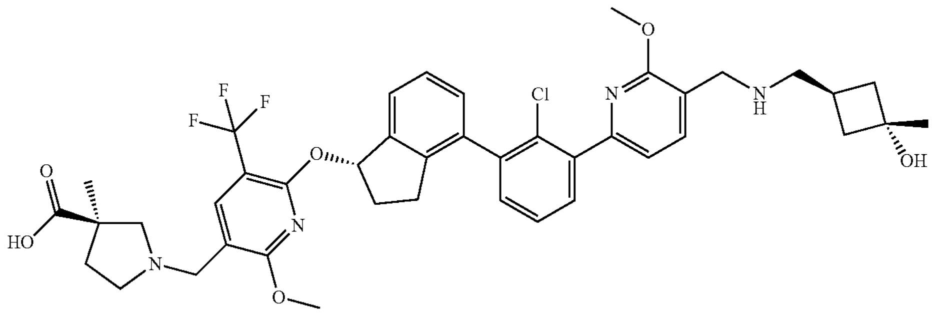 [SMILES: COc1nc(-c2cccc(-c3cccc4c3CC[C@@H]4Oc3nc(OC)c(CN4CC[C@@](C)(C(=O)O)C4)cc3C(F)(F)F)c2Cl)ccc1CNC[C@H]1C[C@](C)(O)C1] | 795.15 |
| B-209 | 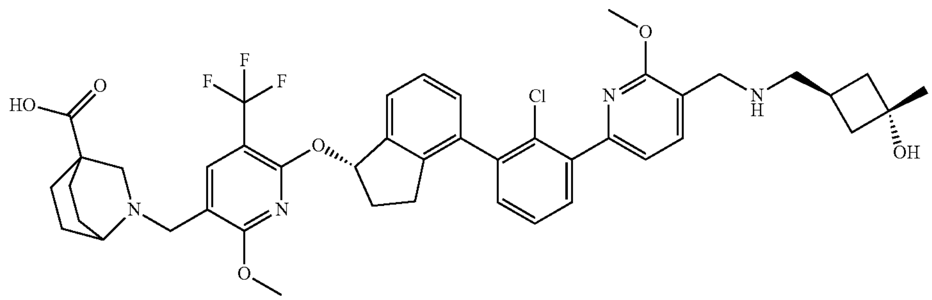 [SMILES: COc1nc(-c2cccc(-c3cccc4c3CC[C@@H]4Oc3nc(OC)c(CN4CC5(C(=O)O)CCC4CC5)cc3C(F)(F)F)c2Cl)ccc1CNC[C@H]1C[C@](C)(O)C1] | 821.09 |
| B-210 | 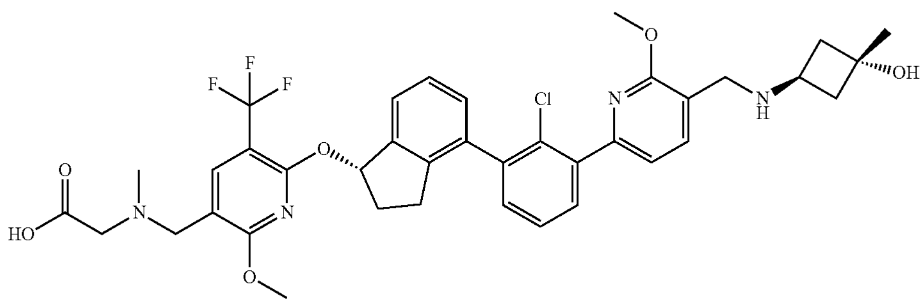 [SMILES: COc1nc(-c2cccc(-c3cccc4c3CC[C@@H]4Oc3nc(OC)c(CN(C)CC(=O)O)cc3C(F)(F)F)c2Cl)ccc1CN[C@H]1C[C@](C)(O)C1] | 741.05 |
| B-211 | 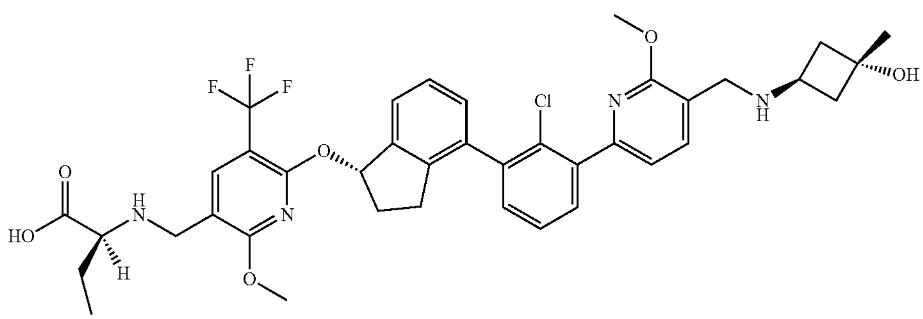 [SMILES: CC[C@H](NCc1cc(C(F)(F)F)c(O[C@H]2CCc3c(-c4cccc(-c5ccc(CN[C@H]6C[C@](C)(O)C6)c(OC)n5)c4Cl)cccc32)nc1OC)C(=O)O] | 755.12 |
| B-212 | 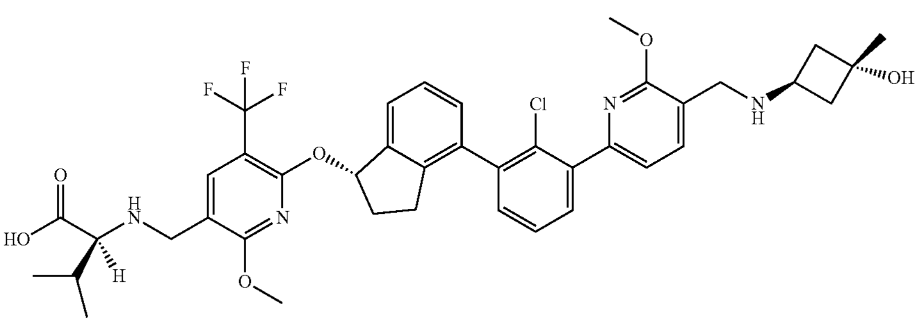 [SMILES: COc1nc(-c2cccc(-c3cccc4c3CC[C@@H]4Oc3nc(OC)c(CN[C@H](C(=O)O)C(C)C)cc3C(F)(F)F)c2Cl)ccc1CN[C@H]1C[C@](C)(O)C1] | 769.07 |

TABLE 1B-continued

| No. | Structure | LCMS |
|---|---|---|
| B-213 | 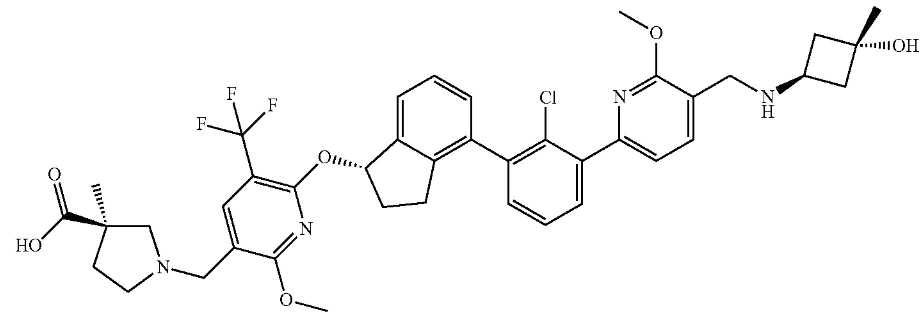 [SMILES: COc1nc(-c2cccc(-c3cccc4c3CC[C@@H]4Oc3nc(OC)c(CN4CC[C@@](C)(C(=O)O)C4)cc3C(F)(F)F)c2Cl)ccc1CN[C@H]1C[C@](C)(O)C1] | 780.29 |
| B-214 | 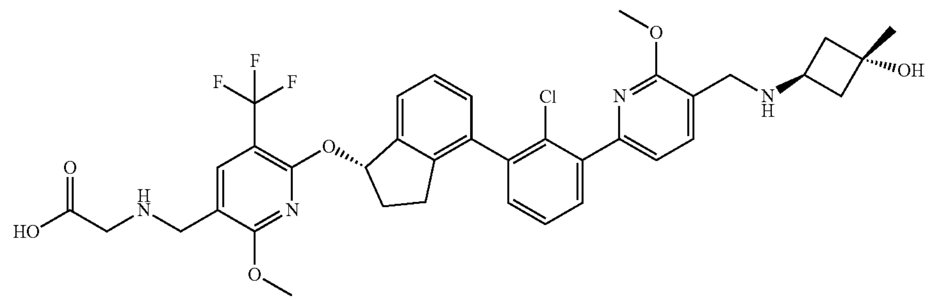 [SMILES: COc1nc(-c2cccc(-c3cccc4c3CC[C@@H]4Oc3nc(OC)c(CNCC(=O)O)cc3C(F)(F)F)c2Cl)ccc1CN[C@H]1C[C@](C)(O)C1] | 724.03 |
| B-215 | 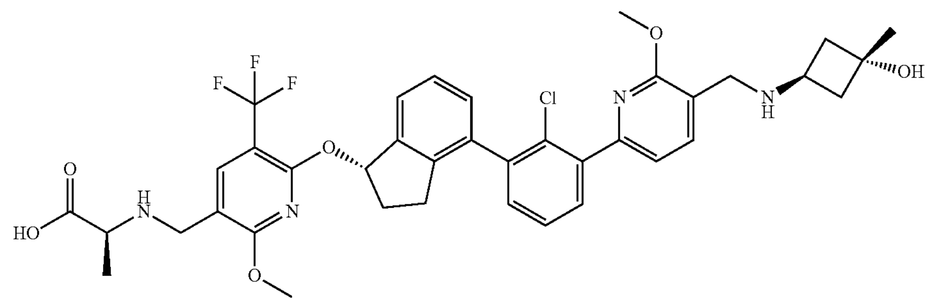 [SMILES: COc1nc(-c2cccc(-c3cccc4c3CC[C@@H]4Oc3nc(OC)c(CN[C@@H](C)C(=O)O)cc3C(F)(F)F)c2Cl)ccc1CN[C@H]1C[C@](C)(O)C1] | 741.07 |
| B-216 | 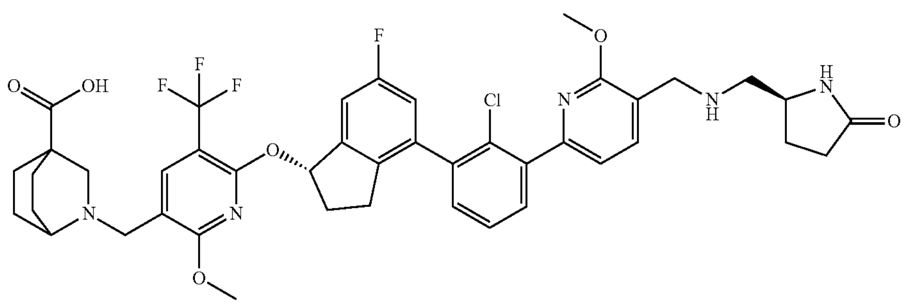 [SMILES: COc1nc(-c2cccc(-c3cc(F)cc4c3CC[C@@H]4Oc3nc(OC)c(CN4CC5(C(=O)O)CCC4CC5)cc3C(F)(F)F)c2Cl)ccc1CNC[C@@H]1CCC(=O)N1] | 838.16 |
| B-217 | 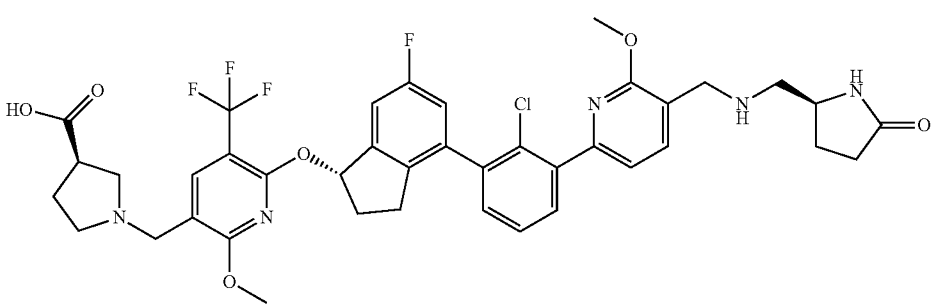 [SMILES: COc1nc(-c2cccc(-c3cc(F)cc4c3CC[C@@H]4Oc3nc(OC)c(CN4CC[C@@H](C(=O)O)C4)cc3C(F)(F)F)c2Cl)ccc1CNC[C@@H]1CCC(=O)N1] | 798.1 |

TABLE 1B-continued

| No. | Structure | LCMS |
|---|---|---|
| B-218 | 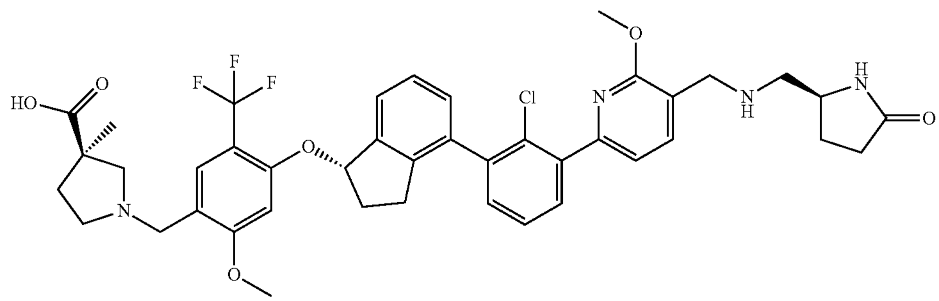 [SMILES: COc1cc(O[C@H]2CCc3c(-c4cccc(-c5ccc(CNC[C@@H]6CCC(=O)N6)c(OC)n5)c4Cl)cccc32)c(C(F)(F)F)cc1CN1CC[C@@](C)(C(=O)O)C1] | 793.16 |
| B-219 | 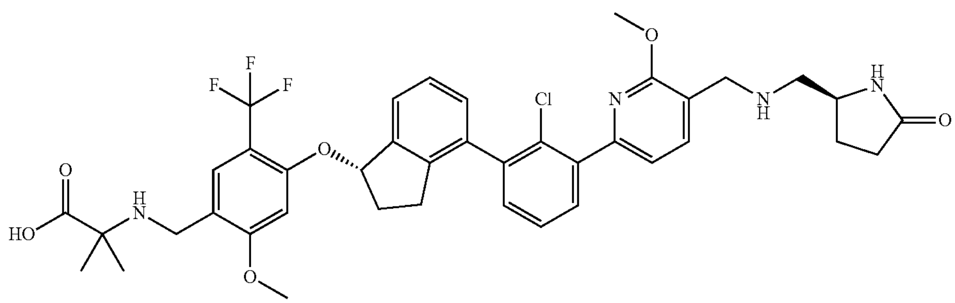 [SMILES: COc1cc(O[C@H]2CCc3c(-c4cccc(-c5ccc(CNC[C@@H]6CCC(=O)N6)c(OC)n5)c4Cl)cccc32)c(C(F)(F)F)cc1CNC(C)(C)C(=O)O] | 767.05 |
| B-220 | 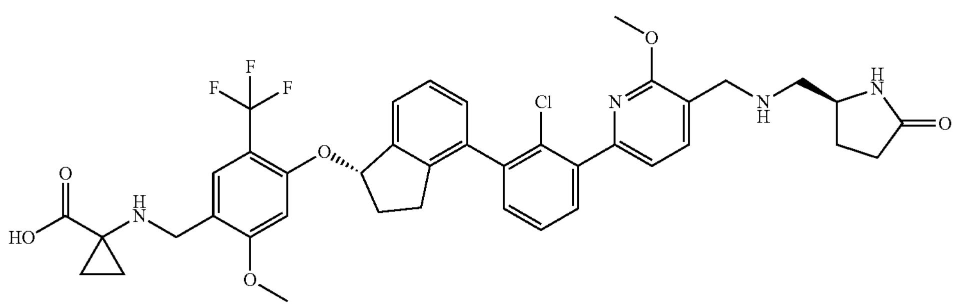 [SMILES: COc1cc(O[C@H]2CCc3c(-c4cccc(-c5ccc(CNC[C@@H]6CCC(=O)N6)c(OC)n5)c4Cl)cccc32)c(C(F)(F)F)cc1CNC1(C(=O)O)CC1] | 765.01 |
| B-221 | 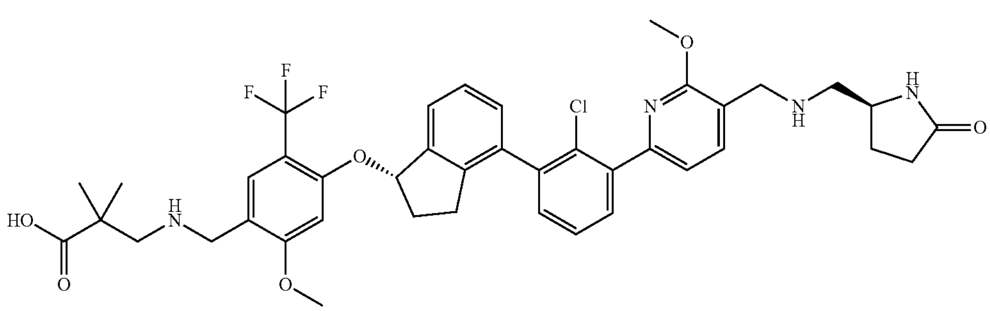 [SMILES: COc1cc(O[C@H]2CCc3c(-c4cccc(-c5ccc(CNC[C@@H]6CCC(=O)N6)c(OC)n5)c4Cl)cccc32)c(C(F)(F)F)cc1CNCC(C)(C)C(=O)O] | 781.12 |
| B-222 | 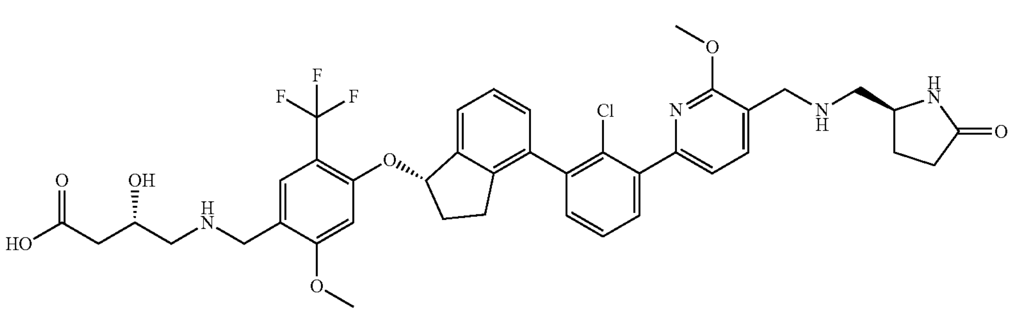 [SMILES: COc1cc(O[C@H]2CCc3c(-c4cccc(-c5ccc(CNC[C@@H]6CCC(=O)N6)c(OC)n5)c4Cl)cccc32)c(C(F)(F)F)cc1CNC[C@@H](O)CC(=O)O] | 783.13 |

TABLE 1B-continued

| No. | Structure | LCMS |
|---|---|---|
| B-223 | 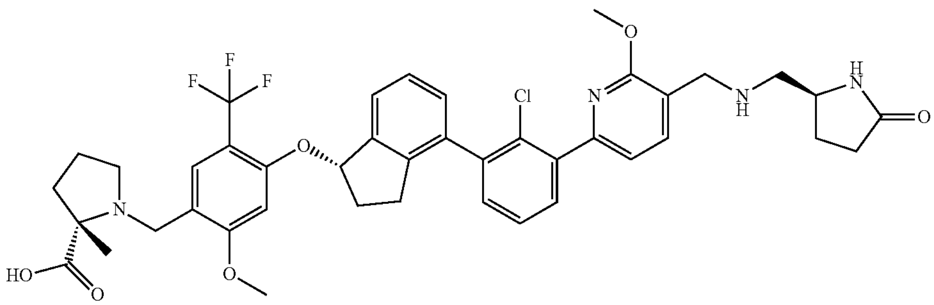 [SMILES: COc1cc(O[C@H]2CCc3c(-c4cccc(-c5ccc(CNC[C@@H]6CCC(=O)N6)c(OC)n5)c4Cl)cccc32)c(C(F)(F)F)cc1CN1CCC[C@@]1(C)C(=O)O] | |
| B-224 | 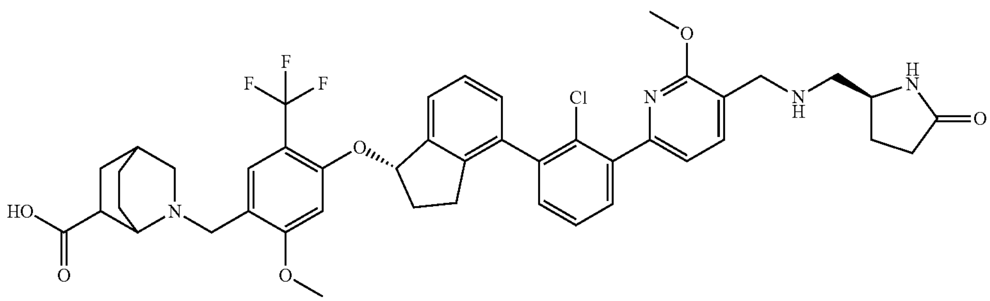 [SMILES: COc1cc(O[C@H]2CCc3c(-c4cccc(-c5ccc(CNC[C@@H]6CCC(=O)N6)c(OC)n5)c4Cl)cccc32)c(C(F)(F)F)cc1CN1CC2CCC1C(C(=O)O)C2] | |
| B-225 | 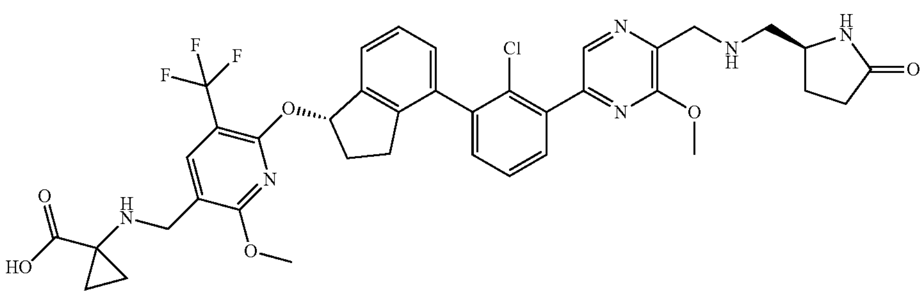 [SMILES: COc1nc(O[C@H]2CCc3c(-c4cccc(-c5cnc(CNC[C@@H]6CCC(=O)N6)c(OC)n5)c4Cl)cccc32)c(C(F)(F)F)cc1CNC1(C(=O)O)CC1] | 767.2 |
| B-226 | 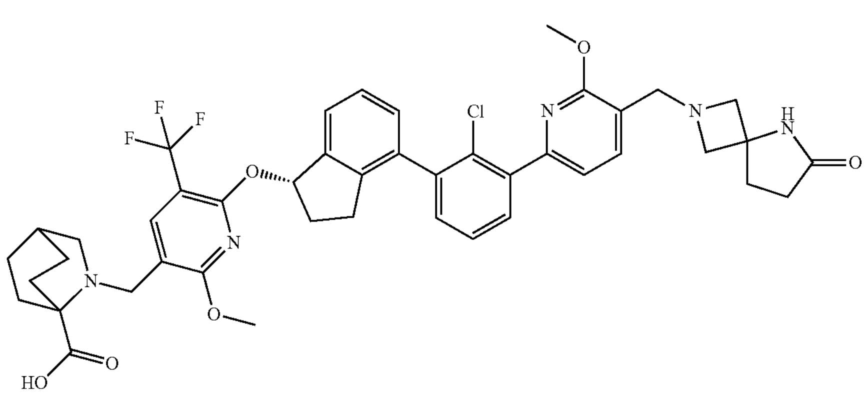 [SMILES: COc1nc(-c2cccc(-c3cccc4c3CC[C@@H]4Oc3nc(OC)c(CN4CC5CCC4(C(=O)O)CC5)cc3C(F)(F)F)c2Cl)ccc1CN1CC2(CCC(=O)N2)C1] | 832.3 |

TABLE 1B-continued

| No. | Structure | LCMS |
|---|---|---|
| B-227 | 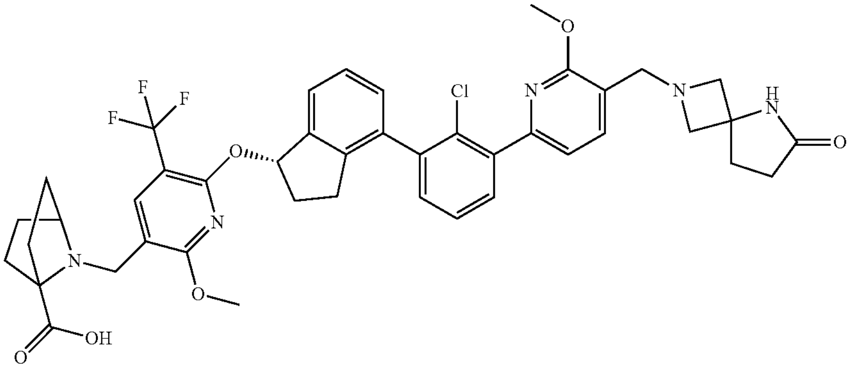 [SMILES: COc1nc(-c2cccc(-c3cccc4c3CC[C@@H]4Oc3nc(OC)c(CN4C5CCC4(C(=O)O)CC5)cc3C(F)(F)F)c2Cl)ccc1CN1CC2(CCC(=O)N2)C1] | 818.3 |
| B-228 | 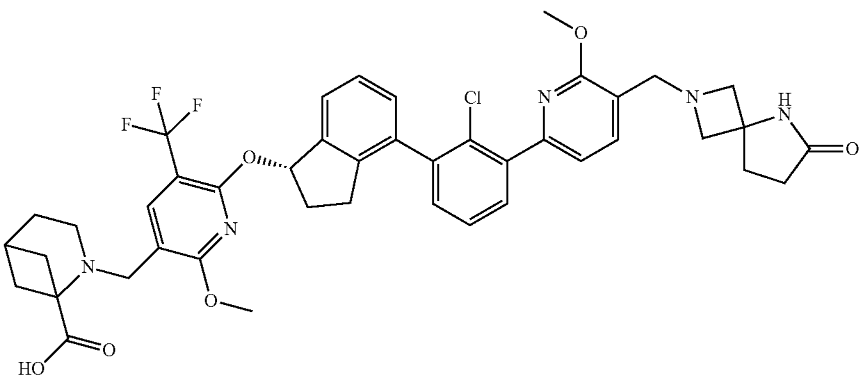 [SMILES: COc1nc(-c2cccc(-c3cccc4c3CC[C@@H]4Oc3nc(OC)c(CN4CCC5CC4(C(=O)O)C5)cc3C(F)(F)F)c2Cl)ccc1CN1CC2(CCC(=O)N2)C1] | 818.2 |
| B-229 | 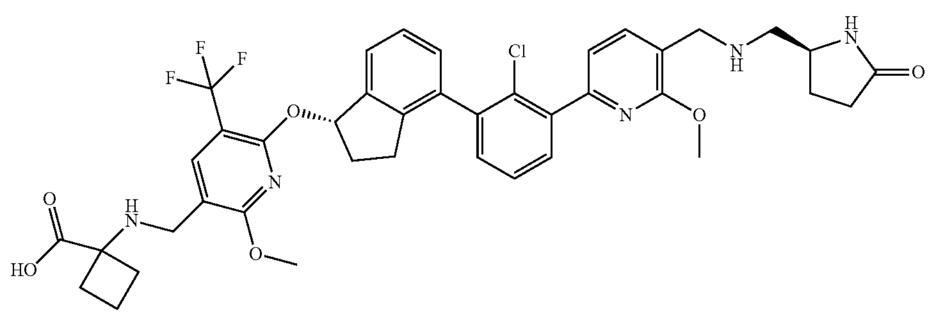 [SMILES: COc1nc(-c2cccc(-c3cccc4c3CC[C@@H]4Oc3nc(OC)c(CNC4(C(=O)O)CCC4)cc3C(F)(F)F)c2Cl)ccc1CNC[C@@H]1CCC(=O)N1] | 780.2 |
| B-230 | 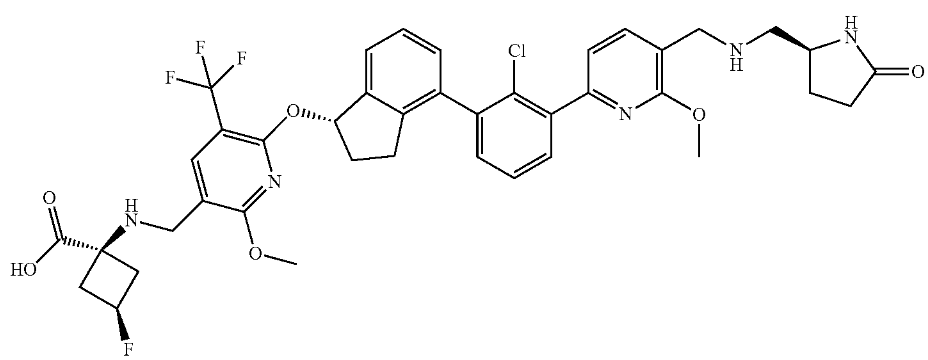 [SMILES: COc1nc(-c2cccc(-c3cccc4c3CC[C@@H]4Oc3nc(OC)c(CN[C@]4(C(=O)O)C[C@H](F)C4)cc3C(F)(F)F)c2Cl)ccc1CNC[C@@H]1CCC(=O)N1] | 798.2 |

TABLE 1B-continued
| No. | Structure | LCMS |
|---|---|---|
| B-231 | 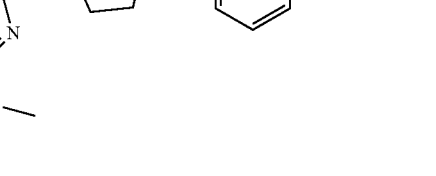 | 786.7 |
| B-232 | 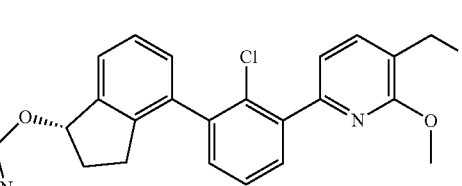 | 806.3 |
| B-233 | 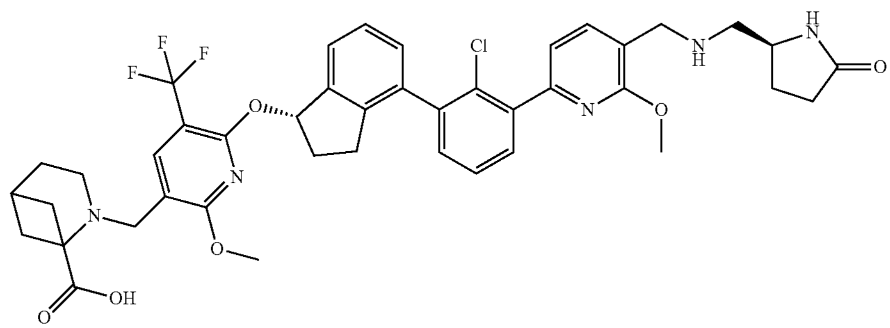 [SMILES: COc1nc(-c2cccc(-c3cccc4c3CC[C@@H]4Oc3nc(OC)c(CN4CCC5CC4(C(=O)O)C5)cc3C(F)(F)F)c2Cl)ccc1CNC[C@@H]1CCC(=O)N1] | 806.3 |
| B-234 | 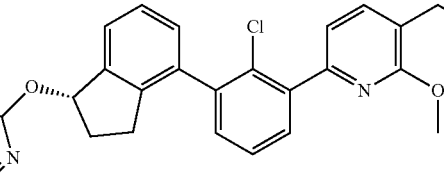 | 792.2 |
| B-235 | 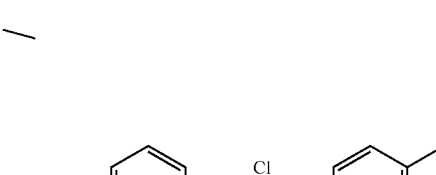 | 782.3 |

TABLE 1B-continued
| No. | Structure | LCMS |
|---|---|---|
| B-236 | 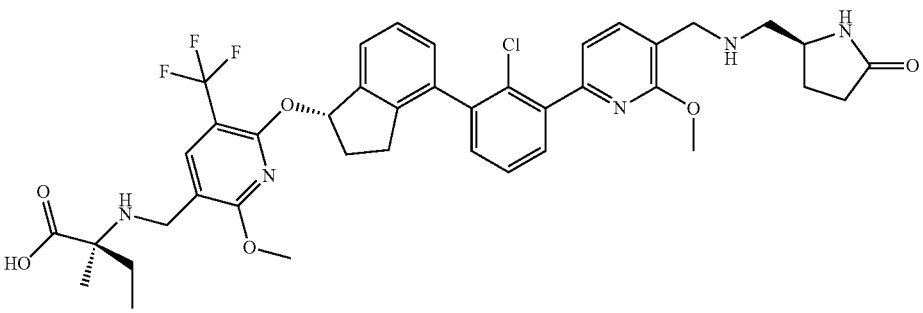 [SMILES: CC[C@](C)(NCc1cc(C(F)(F)F)c(O[C@H]2CCc3c(-c4cccc(-c5ccc(CNC[C@@H]6CCC(=O)N6)c(OC)n5)c4Cl)cccc32)nc1OC)C(=O)O] | 782.3 |
| B-237 | 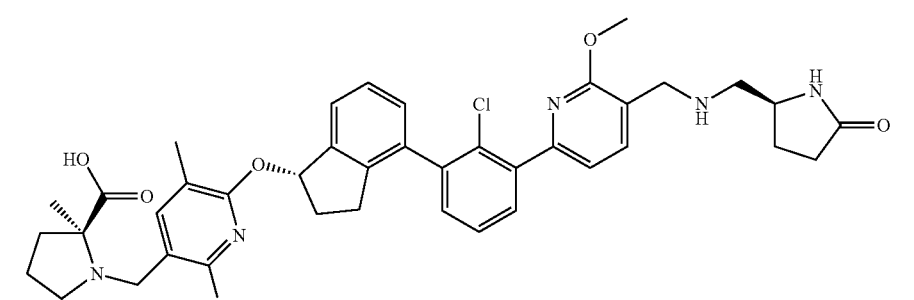 | 740.2 |
| B-238 | 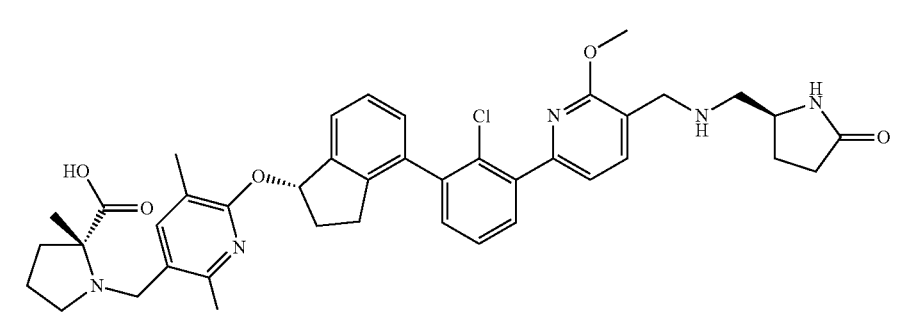 | 740.1 |
| B-239 | 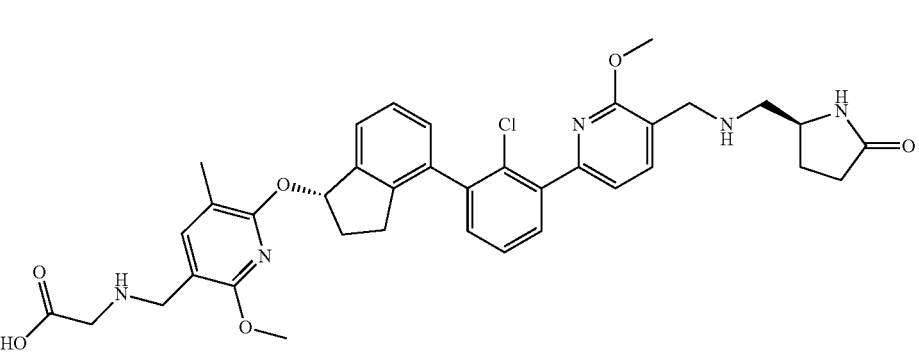 [SMILES: COc1nc(-c2cccc(-c3cccc4c3CC[C@@H]4Oc3nc(OC)c(CNCC(=O)O)cc3C)c2Cl)ccc1CNC[C@@H]1CCC(=O)N1] | 686 |

TABLE 1B-continued
| No. | Structure | LCMS |
|---|---|---|
| B-240 | 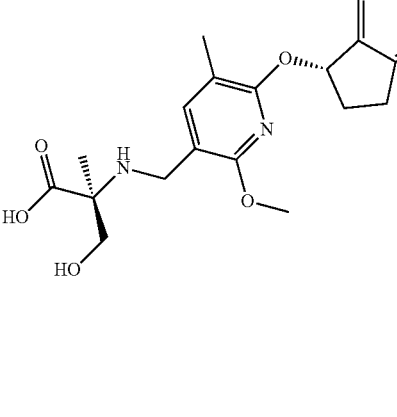 | 730.1 |
| B-241 | 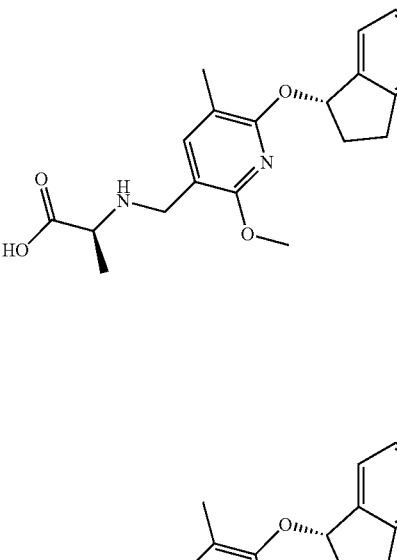 | 700 |
| B-242 | 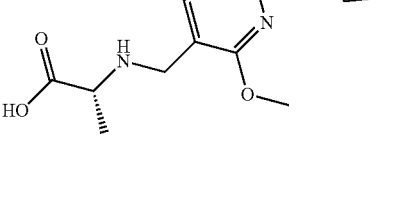 | 700 |
| B-243 | 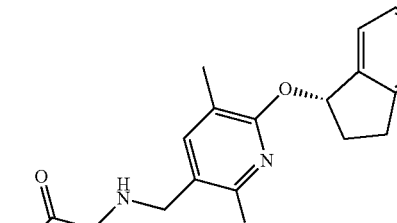 | 728 |

TABLE 1B-continued

| No. | Structure | LCMS |
|---|---|---|
| B-244 | 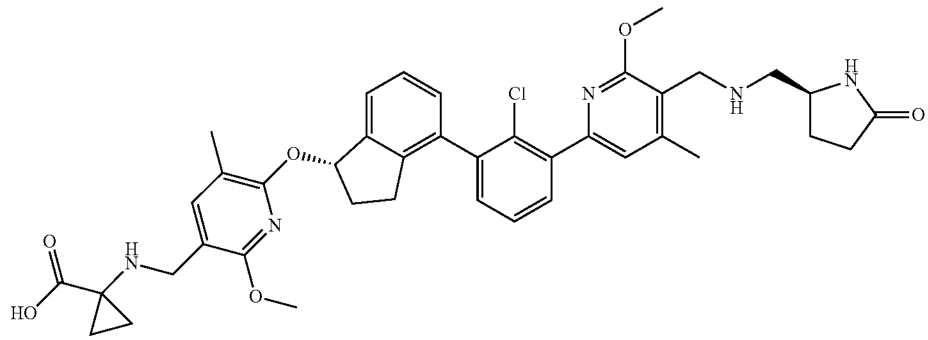 [SMILES: COc1nc(O[C@H]2CCc3c(-c4cccc(-c5cc(C)c(CNC[C@@H]6CCC(=O)N6)c(OC)n5)c4Cl)cccc32)c(C)cc1CNC1(C(=O)O)CC1] | 725.9 |
| B-245 | 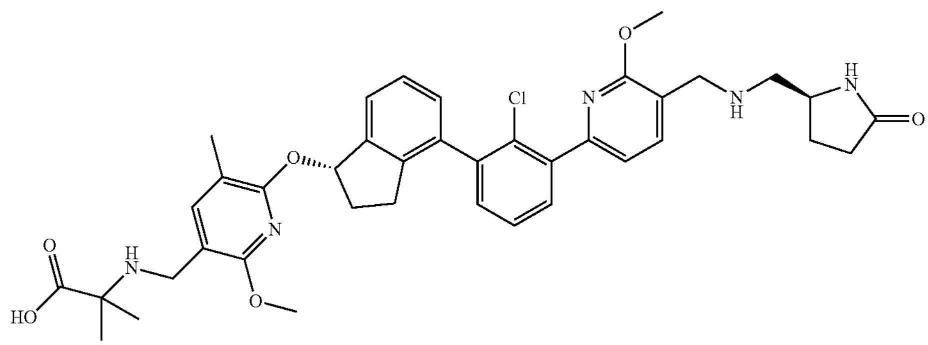 [SMILES: COc1nc(-c2cccc(-c3cccc4c3CC[C@@H]4Oc3nc(OC)c(CNC(C)(C)C(=O)O)cc3C)c2Cl)ccc1CNC[C@@H]1CCC(=O)N1] | 714 |
| B-246 | 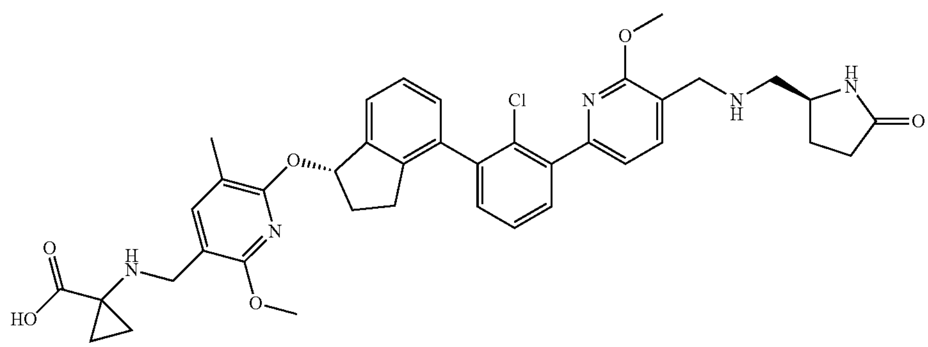 [SMILES: COc1nc(-c2cccc(-c3cccc4c3CC[C@@H]4Oc3nc(OC)c(CNC4(C(=O)O)CC4)cc3C)c2Cl)ccc1CNC[C@@H]1CCC(=O)N1] | 712 |
| B-247 | 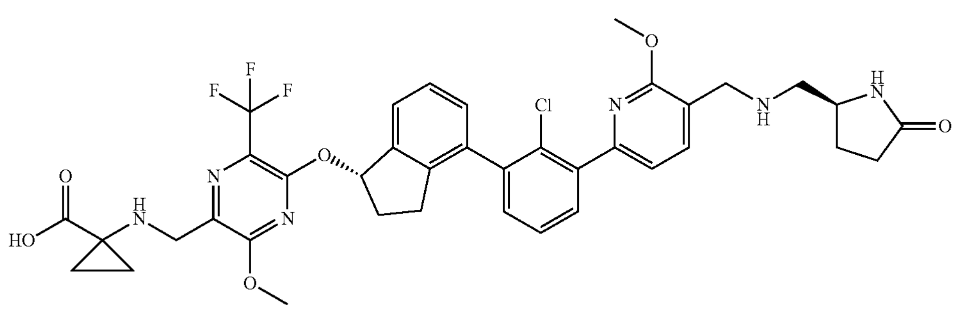 [SMILES: COc1nc(-c2cccc(-c3cccc4c3CC[C@@H]4Oc3nc(OC)c(CNC4(C(=O)O)CC4)nc3C(F)(F)F)c2Cl)ccc1CNC[C@@H]1CCC(=O)N1] | 767.05 |

TABLE 1B-continued

| No. | Structure | LCMS |
|---|---|---|
| B-248 | 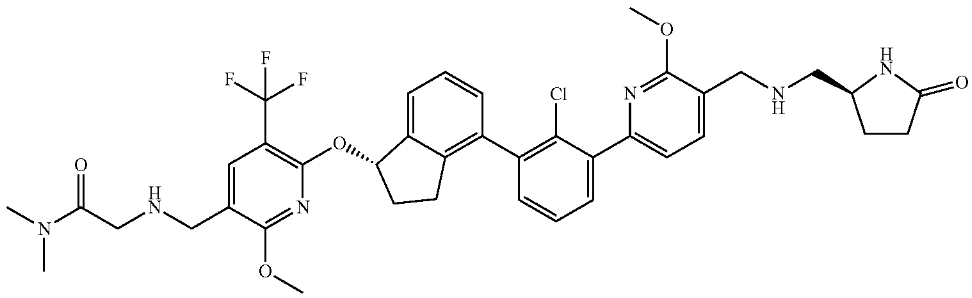 [SMILES: COc1nc(-c2cccc(-c3cccc4c3CC[C@@H]4Oc3nc(OC)c(CNCC(=O)N(C)C)cc3C(F)(F)F)c2Cl)ccc1CNC[C@@H]1CCC(=O)N1] | 766.89 |
| B-249 | 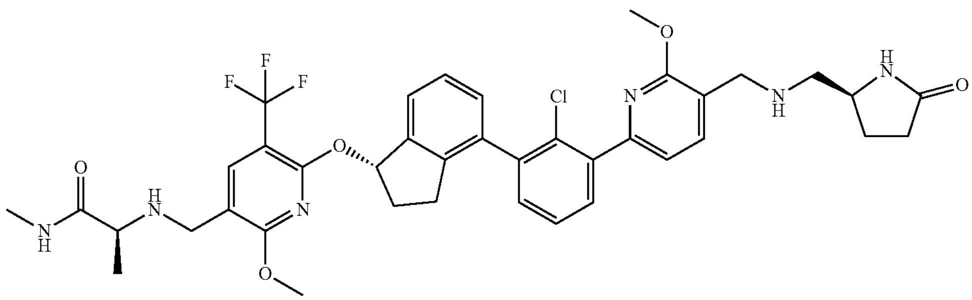 [SMILES: CNC(=O)[C@H](C)NCc1cc(C(F)(F)F)c(O[C@H]2CCc3c(-c4cccc(-c5ccc(CNC[C@@H]6CCC(=O)N6)c(OC)n5)c4Cl)cccc32)nc1OC] | 766.94 |
| B-250 | 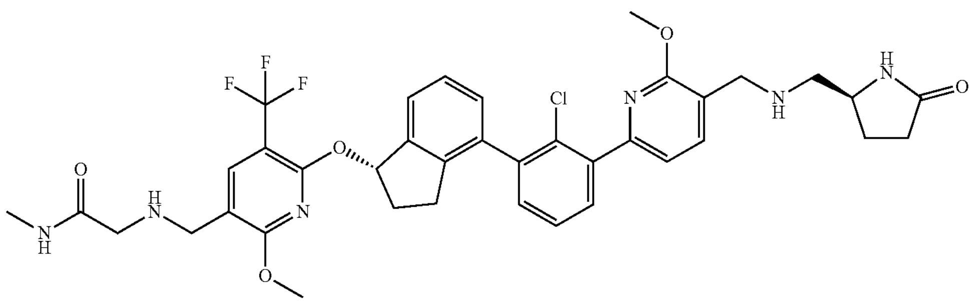 [SMILES: CNC(=O)CNCc1cc(C(F)(F)F)c(O[C@H]2CCc3c(-c4cccc(-c5ccc(CNC[C@@H]6CCC(=O)N6)c(OC)n5)c4Cl)cccc32)nc1OC] | 752.87 |
| B-251 | 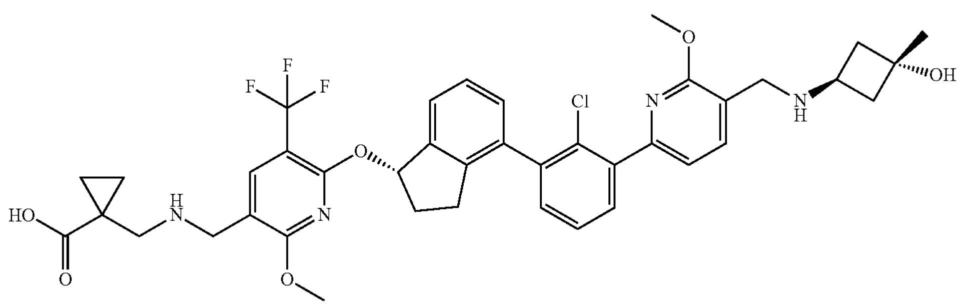 [SMILES: COc1nc(-c2cccc(-c3cccc4c3CC[C@@H]4Oc3nc(OC)c(CNCC4(C(=O)O)CC4)cc3C(F)(F)F)c2Cl)ccc1CN[C@H]1C[C@](C)(O)C1] | 767.04 |
| B-252 | 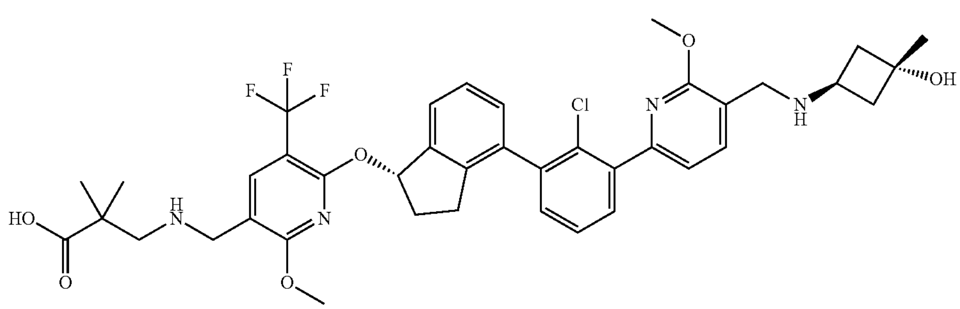 [SMILES: COc1nc(-c2cccc(-c3cccc4c3CC[C@@H]4Oc3nc(OC)c(CNCC(C)(C)C(=O)O)cc3C(F)(F)F)c2Cl)ccc1CN[C@H]1C[C@](C)(O)C1] | 769.01 |

TABLE 1B-continued
| No. | Structure | LCMS |
|---|---|---|
| B-253 | 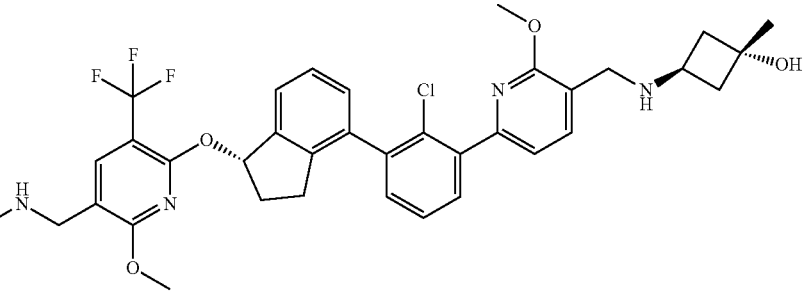 | 754.97 |
| B-254 | 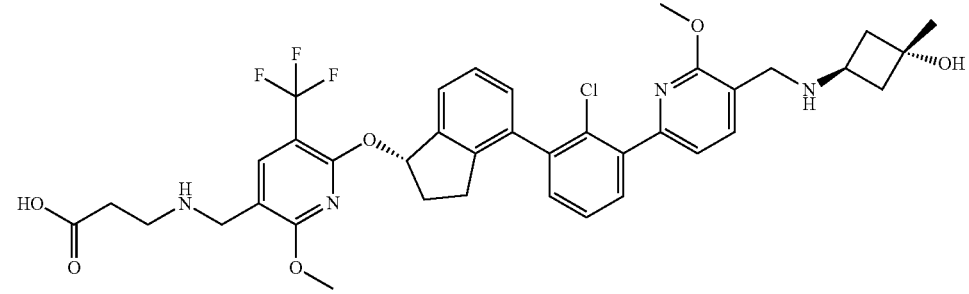 [SMILES: COc1nc(-c2cccc(-c3cccc4c3CC[C@@H]4Oc3nc(OC)c(CNCCC(=O)O)cc3C(F)(F)F)c2Cl)ccc1CN[C@H]1C[C@](C)(O)C1] | 740.96 |
| B-255 | 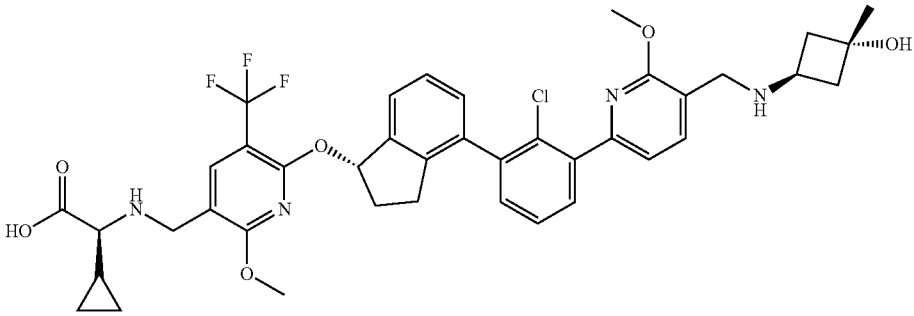 [SMILES: COc1nc(-c2cccc(-c3cccc4c3CC[C@@H]4Oc3nc(OC)c(CN[C@H](C(=O)O)C4CC4)cc3C(F)(F)F)c2Cl)ccc1CN[C@H]1C[C@](C)(O)C1] | 766.93 |
| B-256 | 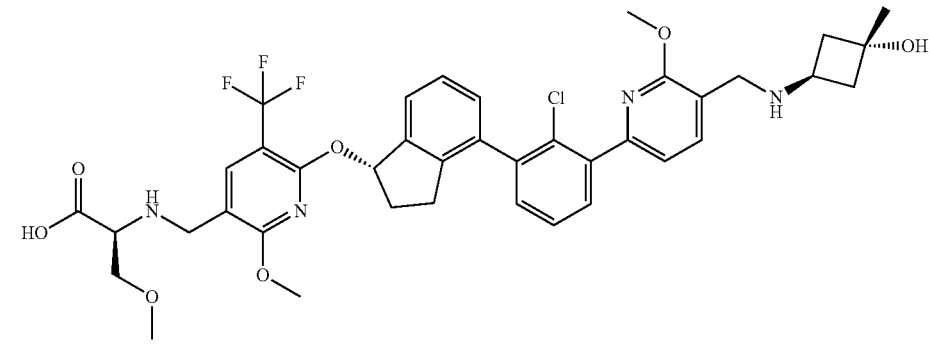 [SMILES: COC[C@H](NCc1cc(C(F)(F)F)c(O[C@H]2CCc3c(-c4cccc(-c5ccc(CN[C@H]6C[C@](C)(O)C6)c(OC)n5)c4Cl)cccc32)nc1OC)C(=O)O] | 770.97 |
| B-257 | 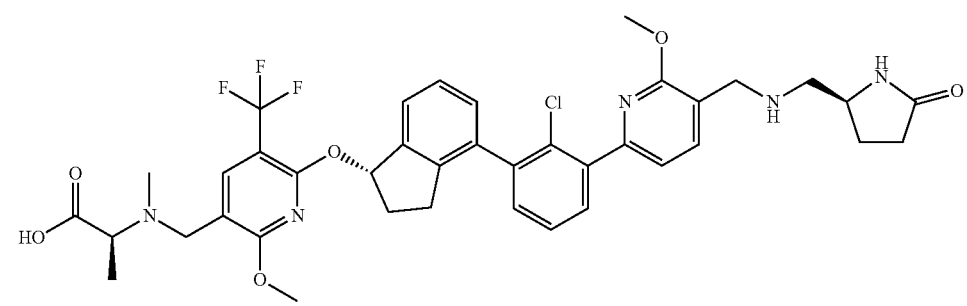 [SMILES: COc1nc(-c2cccc(-c3cccc4c3CC[C@@H]4Oc3nc(OC)c(CN(C)[C@@H](C)C(=O)O)cc3C(F)(F)F)c2Cl)ccc1CNC[C@@H]1CCC(=O)N1] | 767.87 |

TABLE 1B-continued

| No. | Structure | LCMS |
|---|---|---|
| B-258 | 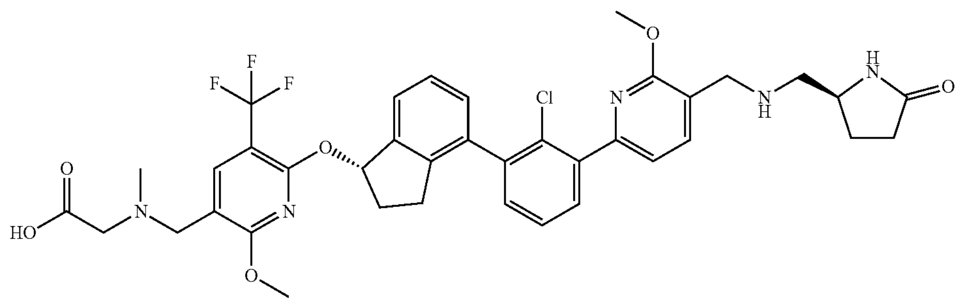 [SMILES: COc1nc(-c2cccc(-c3cccc4c3CC[C@@H]4Oc3nc(OC)c(CN(C)CC(=O)O)cc3C(F)(F)F)c2Cl)ccc1CNC[C@@H]1CCC(=O)N1] | 753.87 |
| B-259 | 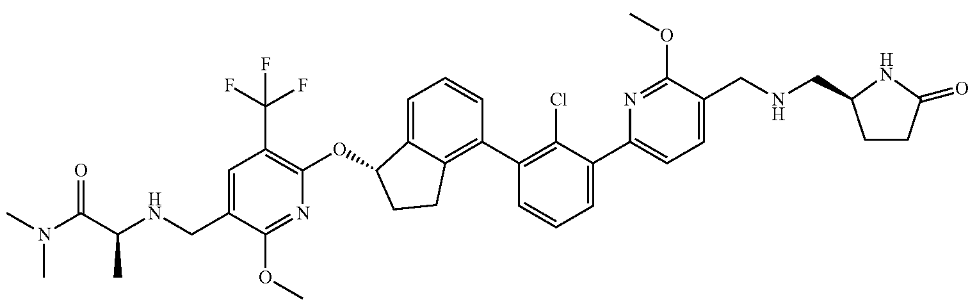 [SMILES: COc1nc(-c2cccc(-c3cccc4c3CC[C@@H]4Oc3nc(OC)c(CN[C@@H](C)C(=O)N(C)C)cc3C(F)(F)F)c2Cl)ccc1CNC[C@@H]1CCC(=O)N1] | 783.91 |
| B-260 | 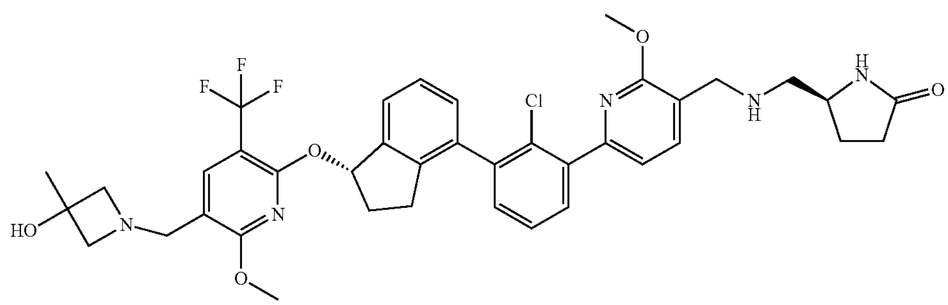 [SMILES: COc1nc(-c2cccc(-c3cccc4c3CC[C@@H]4Oc3nc(OC)c(CN4CC(C)(O)C4)cc3C(F)(F)F)c2Cl)ccc1CNC[C@@H]1CCC(=O)N1] | 751.99 |
| B-261 | 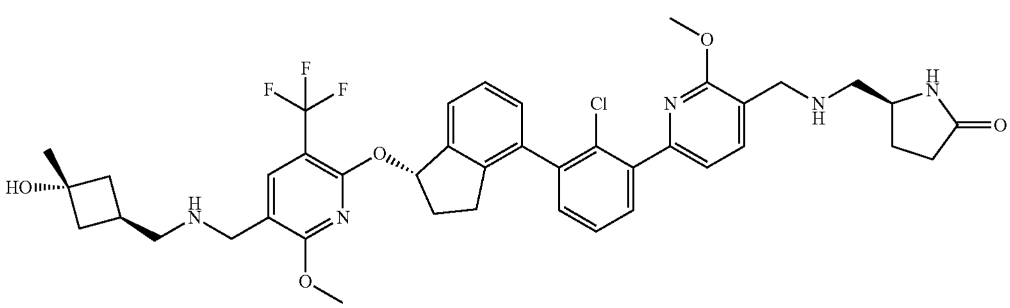 [SMILES: COc1nc(-c2cccc(-c3cccc4c3CC[C@@H]4Oc3nc(OC)c(CNC[C@H]4C[C@](C)(O)C4)cc3C(F)(F)F)c2Cl)ccc1CNC[C@@H]1CCC(=O)N1] | 779.94 |
| B-262 | 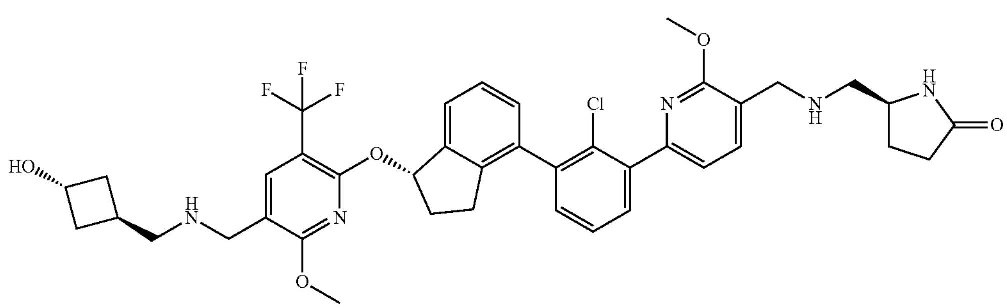 [SMILES: COc1nc(-c2cccc(-c3cccc4c3CC[C@@H]4Oc3nc(OC)c(CNC[C@H]4C[C@H](O)C4)cc3C(F)(F)F)c2Cl)ccc1CNC[C@@H]1CCC(=O)N1] | 765.99 |

TABLE 1B-continued

| No. | Structure | LCMS |
|---|---|---|
| B-263 | 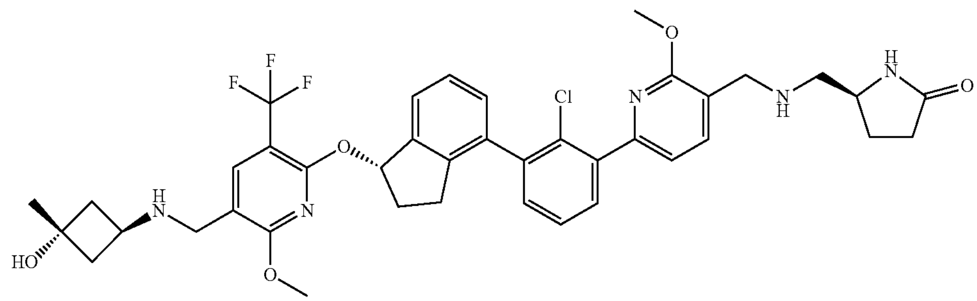 [SMILES: COc1nc(-c2cccc(-c3cccc4c3CC[C@@H]4Oc3nc(OC)c(CN[C@H]4C[C@](C)(O)C4)cc3C(F)(F)F)c2Cl)ccc1CNC[C@@H]1CCC(=O)N1] | 765.95 |
| B-264 | 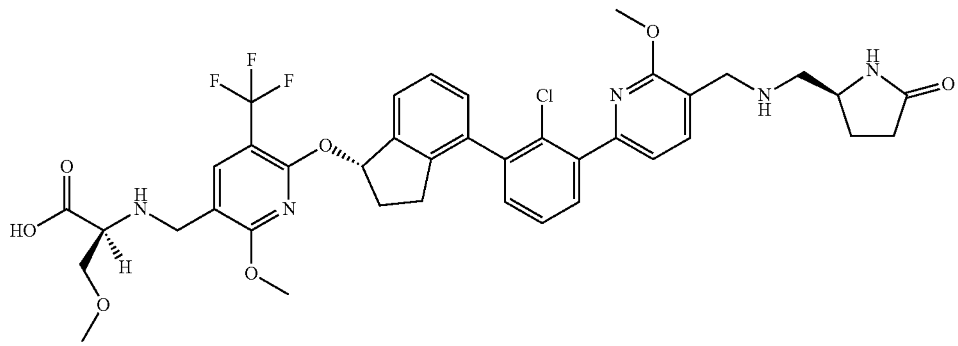 [SMILES: COC[C@H](NCc1cc(C(F)(F)F)c(O[C@H]2CCc3c(-c4cccc(-c5ccc(CNC[C@@H]6CCC(=O)N6)c(OC)n5)c4Cl)cccc32)nc1OC)C(=O)O] | 783.88 |
| B-265 | 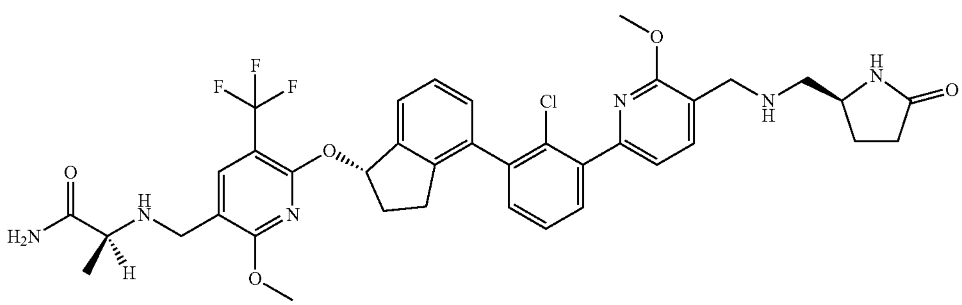 [SMILES: COc1nc(-c2cccc(-c3cccc4c3CC[C@@H]4Oc3nc(OC)c(CN[C@@H](C)C(N)=O)cc3C(F)(F)F)c2Cl)ccc1CNC[C@@H]1CCC(=O)N1] | 752.88 |
| B-266 | 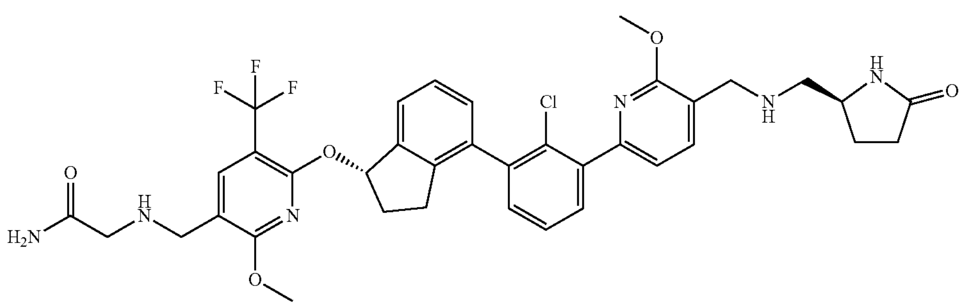 [SMILES: COc1nc(-c2cccc(-c3cccc4c3CC[C@@H]4Oc3nc(OC)c(CNCC(N)=O)cc3C(F)(F)F)c2Cl)ccc1CNC[C@@H]1CCC(=O)N1] | 738.92 |
| B-267 | 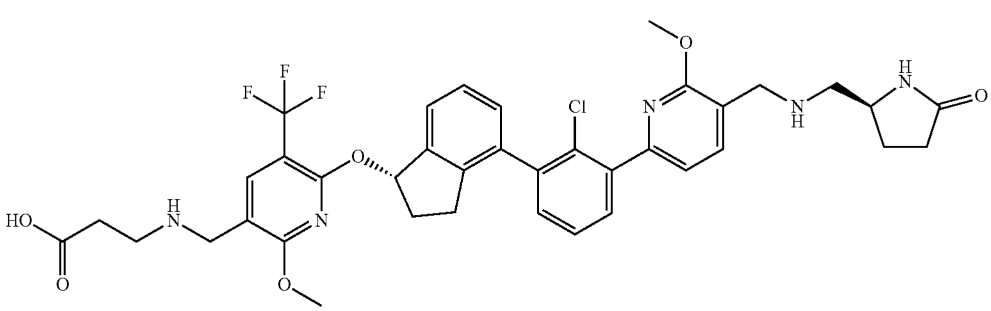 [SMILES: COc1nc(-c2cccc(-c3cccc4c3CC[C@@H]4Oc3nc(OC)c(CNCCC(=O)O)cc3C(F)(F)F)c2Cl)ccc1CNC[C@@H]1CCC(=O)N1] | 753.93 |

TABLE 1B-continued
| No. | Structure | LCMS |
|---|---|---|
| B-268 | 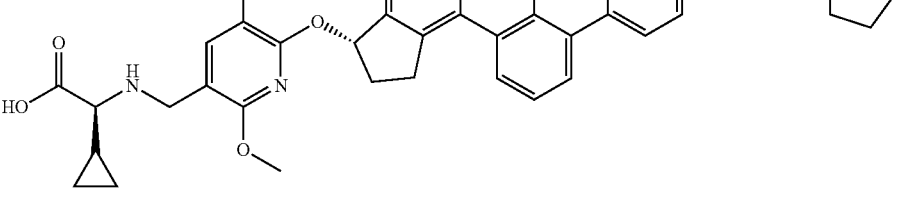 | 779.87 |
| B-269 | 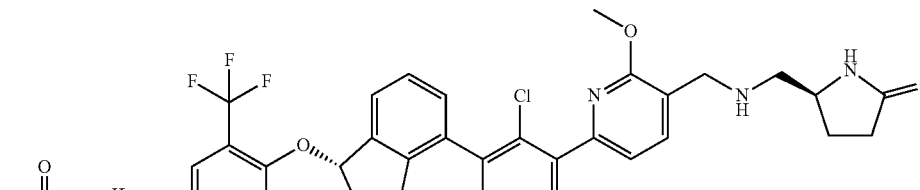 | 767.91 |
| B-270 | 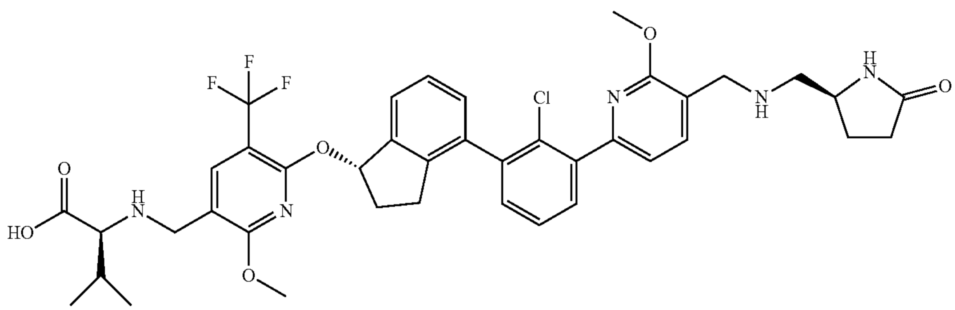 [SMILES: COc1nc(-c2cccc(-c3cccc4c3CC[C@@H]4Oc3nc(OC)c(CN[C@H](C(=O)O)C(C)C)cc3C(F)(F)F)c2Cl)ccc1CNC[C@@H]1CCC(=O)N1] | 781.93 |
| B-271 | 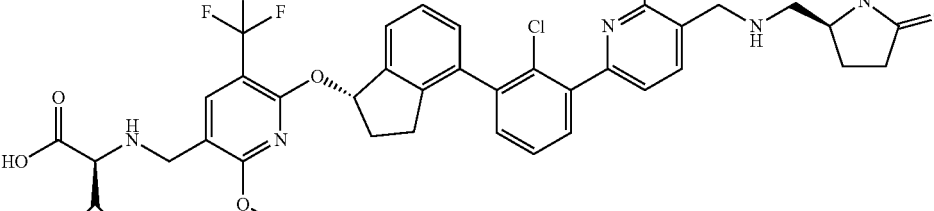 | 753.98 |
| B-272 | 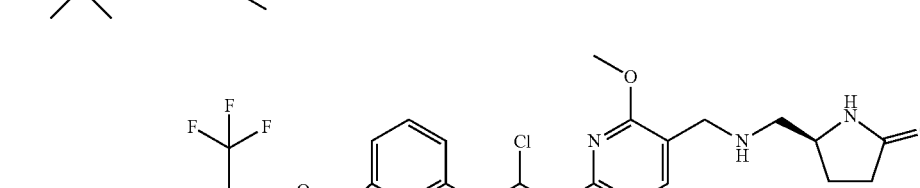 | 739.87 |

NMR data for select compounds is shown below in Table 2A and Table 2B.

TABLE 2A

| No. | NMR |
|---|---|
| A-1 | $^1$H NMR (400 MHz, Methanol-$d_4$) δ 7.99-7.84 (m, 2H), 7.59 (d, J = 7.9 Hz, 1H), 7.48 (t, J = 7.6 Hz, 1H), 7.44-7.23 (m, 4H), 7.23-7.11 (m, 1H), 6.00-5.82 (m, 1H), 4.41-4.24 (m, 4H), 4.13-3.99 (m, 4H), 3.94 (s, 3H), 3.59 (d, J = 12.4 Hz, 1H), 3.46 (s, 1H), 3.28-3.18 (m, 2H), 2.80 (s, 2H), 2.67-2.55 (m, 1H), 2.49-2.30 (m, 4H), 2.20-1.74 (m, 9H). |
| A-2 | $^1$H NMR (400 MHz, Methanol-$d_4$) δ 7.95-7.79 (m, 2H), 7.59 (d, J = 8.1 Hz, 1H), 7.48 (t, J = 7.6 Hz, 1H), 7.41-7.21 (m, 4H), 7.21-7.12 (m, 1H), 5.99-5.80 (m, 1H), 4.41-4.23 (m, 4H), 4.10 (s, 3H), 4.08-3.80 (m, 5H), 3.61 (s, 1H), 3.44-3.33 (m, 1H), 3.28-3.19 (m, 2H), 3.13-2.72 (m, 3H), 2.69-2.25 (m, 5H), 2.25-1.83 (m, 3H), 1.46 (d, J = 15.8 Hz, 3H). |
| A-3 | $^1$H NMR (400 MHz, Methanol-$d_4$) δ 8.02-7.74 (m, 2H), 7.62 (d, J = 8.1 Hz, 1H), 7.51 (t, J = 7.6 Hz, 1H), 7.45-7.25 (m, 4H), 7.23-7.12 (m, 1H), 5.93 (t, J = 8.2 Hz, 1H), 4.47-4.20 (m, 4H), 4.13 (s, 3H), 4.11-4.03 (m, 1H), 3.98 (s, 3H), 3.90-3.67 (m, 1H), 3.67-3.39 (m, 2H), 3.30-3.23 (m, 3H), 2.90-2.70 (m, 2H), 2.67-2.59 (m, 1H), 2.59-2.19 (m, 5H), 2.17-1.87 (m, 2H). |
| A-4 | $^1$H NMR (400 MHz, Methanol-$d_4$) δ 7.94-7.82 (m, 2H), 7.59 (d, J = 7.7 Hz, 1H), 7.48 (t, J = 7.7 Hz, 1H), 7.43-7.22 (m, 4H), 7.22-7.10 (m, 1H), 5.91 (t, J = 8.3 Hz, 1H), 4.45-4.18 (m, 4H), 4.15-4.08 (m, 3H), 4.08-4.01 (m, 1H), 3.96 (s, 3H), 3.89-3.65 (m, 1H), 3.61-3.46 (m, 2H), 3.28-3.19 (m, 3H), 2.81 (d, J = 9.1 Hz, 2H), 2.67-1.82 (m, 8H). |
| A-5 | $^1$H NMR (400 MHz, Methanol-$d_4$) δ 8.01-7.83 (m, 1H), 7.69 (s, 1H), 7.67-7.55 (m, 1H), 7.55-7.46 (m, 1H), 7.46-7.34 (m, 2H), 7.31 (d, J = 4.9 Hz, 1H), 7.18 (s, 1H), 5.84 (t, J = 8.1 Hz, 1H), 4.52-4.22 (m, 4H), 4.17-4.00 (m, 4H), 3.93 (s, 3H), 3.61 (d, J = 12.3 Hz, 1H), 3.52-3.39 (m, 2H), 3.30-3.22 (m, 2H), 2.91-2.74 (m, 2H), 2.72-2.57 (m, 1H), 2.57-2.30 (m, 4H), 2.17-1.80 (m, 9H). |
| A-6 | $^1$H NMR (400 MHz, Methanol-$d_4$) δ 7.91 (d, J = 7.6 Hz, 1H), 7.67-7.56 (m, 2H), 7.51 (t, J = 7.6 Hz, 1H), 7.44-7.34 (m, 2H), 7.34-7.23 (m, 2H), 7.23-7.10 (m, 1H), 5.83 (t, J = 8.1 Hz, 1H), 4.43-4.33 (m, 2H), 4.33-4.21 (m, 2H), 4.17-3.97 (m, 8H), 3.93 (s, 3H), 3.30-3.27 (m, 2H), 2.95-2.74 (m, 2H), 2.71-2.54 (m, 1H), 2.52-2.29 (m, 3H), 2.18-1.82 (m, 2H), 1.54 (s, 3H). |
| A-7 | $^1$H NMR (400 MHz, Methanol-$d_4$) δ 7.91 (d, J = 7.6 Hz, 1H), 7.72-7.54 (m, 2H), 7.51 (t, J = 7.6 Hz, 1H), 7.43-7.33 (m, 2H), 7.33-7.23 (m, 2H), 7.23-7.12 (m, 1H), 5.83 (t, J = 8.1 Hz, 1H), 4.47-4.17 (m, 8H), 4.17-4.00 (m, 4H), 3.93 (s, 3H), 3.30-3.26 (m, 2H), 2.99-2.71 (m, 2H), 2.70-2.30 (m, 8H), 2.25-1.83 (m, 2H). |
| A-8 | $^1$H NMR (400 MHz, Methanol-$d_4$) δ 7.91 (d, J = 7.6 Hz, 1H), 7.70-7.55 (m, 2H), 7.51 (t, J = 7.6 Hz, 1H), 7.44-7.35 (m, 2H), 7.31 (d, J = 5.0 Hz, 2H), 7.25-7.10 (m, 1H), 5.85 (t, J = 8.2 Hz, 1H), 4.43-4.20 (m, 4H), 4.13 (s, 3H), 4.11-4.01 (m, 1H), 3.94 (s, 3H), 3.88-3.67 (m, 1H), 3.64-3.40 (m, 3H), 3.31-3.27 (m, 2H), 2.91-2.73 (m, 2H), 2.69-1.88 (m, 8H). |
| A-9 | $^1$H NMR (400 MHz, Methanol-$d_4$) δ 7.92 (d, J = 7.5 Hz, 1H), 7.68-7.58 (m, 2H), 7.51 (t, J = 7.6 Hz, 1H), 7.45-7.34 (m, 2H), 7.34-7.24 (m, 2H), 7.24-7.10 (m, 1H), 5.84 (t, J = 8.2 Hz, 1H), 4.44-4.28 (m, 2H), 4.20-4.11 (m, 5H), 4.11-3.98 (m, 2H), 3.94 (s, 3H), 3.30-3.25 (m, 3H), 3.19 (dd, J = 6.2, 2.5 Hz, 2H), 2.92-2.70 (m, 2H), 2.70-2.54 (m, 1H), 2.54-2.28 (m, 6H), 2.20-2.00 (m, 1H), 2.00-1.85 (m, 2H). |
| A-10 | $^1$H NMR (400 MHz, Methanol-$d_4$) δ 7.89 (d, J = 7.6 Hz, 1H), 7.60 (dd, J = 7.7, 1.7 Hz, 1H), 7.55 (s, 1H), 7.49 (t, J = 7.6 Hz, 1H), 7.43-7.27 (m, 4H), 7.21 (s, 1H), 6.62 (s, 1H), 5.43-5.21 (m, 1H), 4.42-4.16 (m, 4H), 4.16-3.98 (m, 4H), 3.92 (d, J = 7.8 Hz, 3H), 3.83-3.34 (m, 5H), 3.28-3.19 (m, 3H), 2.92-2.74 (m, 2H), 2.74-2.59 (m, 1H), 2.59-2.15 (m, 5H), 2.08-1.85 (m, 2H). |
| A-11 | $^1$H NMR (400 MHz, Methanol-$d_4$) δ 7.89 (d, J = 7.6 Hz, 1H), 7.65-7.57 (m, 1H), 7.55 (s, 1H), 7.49 (t, J = 7.6 Hz, 1H), 7.40-7.27 (m, 4H), 7.22 (s, 1H), 6.62 (s, 1H), 5.42-5.25 (m, 1H), 4.45-4.26 (m, 4H), 4.17-4.00 (m, 4H), 3.99-3.85 (m, 3H), 3.85-3.37 (m, 4H), 3.28-3.17 (m, 3H), 3.05-2.74 (m, 2H), 2.74-2.62 (m, 1H), 2.60-2.14 (m, 5H), 2.10-1.82 (m, 2H). |
| A-12 | $^1$H NMR (400 MHz, Methanol-$d_4$) δ 7.91 (dd, J = 22.2, 7.6 Hz, 1H), 7.60 (d, J = 7.6 Hz, 2H), 7.49 (t, J = 7.5 Hz, 1H), 7.44-7.26 (m, 4H), 7.22 (s, 1H), 6.61 (s, 1H), 5.35 (s, 1H), 4.56-4.18 (m, 4H), 4.18-3.96 (m, 4H), 3.91 (d, J = 9.0 Hz, 3H), 3.57 (d, J = 12.4 Hz, 1H), 3.41 (s, 1H), 3.28-3.19 (m, 2H), 2.93-2.73 (m, 2H), 2.74-2.56 (m, 1H), 2.51-2.30 (m, 4H), 2.19-1.75 (m, 9H). |
| A-13 | $^1$H NMR (400 MHz, Methanol-$d_4$) δ 8.04-7.82 (m, 1H), 7.70-7.58 (m, 1H), 7.57-7.44 (m, 1H), 7.44-7.27 (m, 5H), 7.20 (s, 1H), 6.57 (d, J = 10.7 Hz, 1H), 5.40-5.23 (m, 1H), 4.57-4.21 (m, 4H), 4.15-4.01 (m, 4H), 3.85 (d, J = 13.7 Hz, 3H), 3.57 (d, J = 12.5 Hz, 1H), 3.41 (s, 2H), 3.28-3.22 (m, 2H), 2.91-2.72 (m, 2H), 2.72-2.53 (m, 1H), 2.52-2.27 (m, 4H), 2.26-1.71 (m, 9H). |
| A-14 | $^1$H NMR (400 MHz, Methanol-$d_4$) δ 7.99-7.84 (m, 1H), 7.72-7.54 (m, 1H), 7.54-7.45 (m, 1H), 7.44-7.28 (m, 5H), 7.20 (s, 1H), 6.65-6.49 (m, 1H), 5.39-5.23 (m, 1H), 4.41-4.22 (m, 4H), 4.15-4.00 (m, 4H), 4.00-3.81 (m, 4H), 3.65-3.51 (m, 1H), 3.44-3.35 (m, 1H), 3.29-3.20 (m, 2H), 3.08-2.95 (m, 1H), 2.92-2.70 (m, 2H), 2.68-2.62 (m, 1H), 2.57-2.22 (m, 4H), 2.20-1.82 (m, 3H), 1.45 (d, J = 14.6 Hz, 3H). |
| A-15 | $^1$H NMR (400 MHz, Methanol-$d_4$) δ 8.00-7.83 (m, 1H), 7.66-7.56 (m, 1H), 7.56-7.44 (m, 1H), 7.44-7.26 (m, 5H), 7.26-7.14 (m, 1H), 6.58 (d, J = 9.2 Hz, 1H), 5.40-5.20 (m, 1H), 4.42-4.18 (m, 4H), 4.15-3.97 (m, 4H), 3.86 (d, J = 12.4 Hz, 3H), 3.81-3.60 (m, 1H), 3.60-3.36 (m, 3H), 3.28-3.19 (m, 3H), 2.92-2.71 (m, 2H), 2.71-2.58 (m, 1H), 2.58-2.12 (m, 5H), 2.08-1.83 (m, 2H). |
| A-16 | $^1$H NMR (400 MHz, Methanol-$d_4$) δ 7.92-7.86 (m, 1H), 7.65-7.56 (m, 1H), 7.49 (t, J = 7.6 Hz, 1H), 7.44-7.26 (m, 5H), 7.25-7.14 (m, 1H), 6.58 (d, J = 9.5 Hz, 1H), 5.38-5.21 (m, 1H), 4.45-4.20 (m, 4H), 4.18-3.97 (m, 4H), 3.86 (d, J = 12.5 Hz, 3H), 3.79-3.36 (m, 4H), 3.28-3.21 (m, 3H), 2.93-2.73 (m, 2H), 2.72-2.59 (m, 1H), 2.58-2.10 (m, 5H), 2.07-1.84 (m, 2H). |
| A-17 | $^1$H NMR (400 MHz, Methanol-$d_4$) δ 7.89 (d, J = 7.5 Hz, 1H), 7.67-7.54 (m, 1H), 7.48 (t, J = 7.5 Hz, 1H), 7.43-7.22 (m, 4H), 7.22-7.09 (m, 1H), 5.93-5.73 (m, 1H), 4.40-4.27 (m, 2H), 4.19-3.99 (m, 6H), 3.96 (s, 3H), 3.28-3.21 (m, 2H), 2.92-2.70 (m, 2H), 2.69-2.51 (m, 1H), 2.51-2.24 (m, 3H), 2.19-2.03 (m, 1H), 1.99-1.81 (m, 1H). |

TABLE 2A-continued

| No. | NMR |
|---|---|
| A-18 | ¹H NMR (400 MHz, Methanol-d₄) δ 8.00-7.87 (m, 1H), 7.70-7.56 (m, 1H), 7.56-7.47 (m, 1H), 7.46-7.26 (m, 4H), 7.24-7.13 (m, 1H), 6.00-5.79 (m, 1H), 4.60-4.29 (m, 4H), 4.16-4.02 (m, 4H), 3.99 (s, 3H), 3.77 (d, J = 12.5 Hz, 1H), 3.61 (m, 1H), 3.30-3.27 (m, 2H), 2.92-2.71 (m, 2H), 2.63 (s, 1H), 2.50-2.35 (m, 4H), 2.24-1.77 (m, 9H). |
| A-19 | ¹H NMR (400 MHz, DMSO-d₆) δ 7.88 (d, J = 7.5 Hz, 1H), 7.59 (d, J = 8.1 Hz, 1H), 7.48 (t, J = 7.6 Hz, 1H), 7.43-7.23 (m, 4H), 7.23-7.11 (m, 1H), 5.93-5.81 (m, 1H), 4.45 (s, 2H), 4.34 (s, 2H), 4.20-3.93 (m, 8H), 3.93-3.50 (m, 2H), 3.46-3.35 (m, 1H), 3.27-3.20 (m, 3H), 2.90-2.70 (m, 2H), 2.66-2.56 (m, 1H), 2.54-2.17 (m, 5H), 2.18-2.05 (m, 1H), 2.02-1.82 (m, 1H). |
| A-20 | ¹H NMR (400 MHz, Methanol-d₄) δ 7.89 (d, J = 7.5 Hz, 1H), 7.59 (d, J = 7.6 Hz, 1H), 7.48 (t, J = 7.8 Hz, 1H), 7.43-7.22 (m, 4H), 7.22-7.12 (m, 1H), 5.96-5.76 (m, 1H), 4.46 (s, 2H), 4.40-4.30 (m, 2H), 4.16-4.02 (m, 4H), 3.96 (s, 3H), 3.84-3.67 (m, 1H), 3.61-3.47 (m, 1H), 3.28-3.14 (m, 2H), 2.95-2.72 (m, 2H), 2.71-2.50 (m, 2H), 2.50-2.28 (m, 3H), 2.24-2.06 (m, 2H), 2.05-1.84 (m, 2H), 1.46 (s, 3H). |
| A-21 | ¹H NMR (400 MHz, Methanol-d₄) δ 7.91 (d, J = 7.6 Hz, 1H), 7.86 (s, 1H), 7.64-7.58 (m, 1H), 7.51 (t, J = 7.6 Hz, 1H), 7.43-7.24 (m, 4H), 7.20 (d, J = 8.7 Hz, 1H), 5.92 (s, 1H), 4.36 (t, J = 5.1 Hz, 4H), 4.12 (s, 4H), 3.97 (s, 3H), 3.67 (d, J = 26.1 Hz, 3H), 3.30-3.23 (m, 2H), 2.93-2.73 (m, 2H), 2.65 (d, J = 18.4 Hz, 2H), 2.50-2.32 (m, 4H), 2.12 (q, J = 10.9, 10.1 Hz, 1H), 2.00-1.86 (m, 1H), 1.70 (s, 1H), 1.34 (d, J = 21.9 Hz, 1H). |
| A-22 | ¹H NMR (400 MHz, Methanol-d₄) δ 7.91 (d, J = 7.6 Hz, 1H), 7.82 (s, 1H), 7.62 (d, J = 7.7 Hz, 1H), 7.51 (t, J = 7.6 Hz, 1H), 7.42-7.34 (m, 2H), 7.34-7.24 (m, 2H), 7.18 (t, J = 8.4 Hz, 1H), 5.91 (t, J = 8.4 Hz, 1H), 4.37 (d, J = 2.7 Hz, 2H), 4.11 (d, J = 13.2 Hz, 6H), 3.97 (s, 3H), 3.28 (dd, J = 6.2, 4.1 Hz, 2H), 2.92-2.74 (m, 2H), 2.72-2.24 (m, 9H), 2.19-2.03 (m, 3H), 2.02-1.86 (m, 1H). |
| A-23 | ¹H NMR (400 MHz, Methanol-d₄) δ 7.84 (s, 1H), 7.48 (t, J = 7.6 Hz, 1H), 7.42 (dd, J = 7.7, 1.8 Hz, 1H), 7.29 (dq, J = 12.9, 7.6, 6.8 Hz, 3H), 7.23-7.11 (m, 3H), 5.90 (t, J = 8.2 Hz, 1H), 4.51 (s, 2H), 4.37 (d, J = 3.0 Hz, 5H), 3.97 (d, J = 16.4 Hz, 6H), 2.82 (d, J = 8.8 Hz, 2H), 2.69-2.58 (m, 1H), 2.57-2.46 (m, 2H), 2.46-2.35 (m, 2H), 2.19-2.00 (m, 2H), 1.61 (t, J = 4.1 Hz, 2H), 1.48-1.40 (m, 2H). |
| A-24 | ¹H NMR (400 MHz, Methanol-d₄) δ 7.90 (d, J = 7.4 Hz, 2H), 7.61 (d, J = 7.7 Hz, 1H), 7.51 (t, J = 7.6 Hz, 1H), 7.46-7.24 (m, 4H), 7.20 (d, J = 8.5 Hz, 1H), 5.92 (s, 1H), 4.59-4.23 (m, 9H), 4.11 (s, 3H), 3.97 (s, 3H), 3.90-3.40 (m, 4H), 2.94-2.02 (m, 10H). |
| A-25 | ¹H NMR (400 MHz, Methanol-d₄) δ 7.90 (d, J = 7.8 Hz, 2H), 7.61 (d, J = 7.6 Hz, 1H), 7.50 (t, J = 7.6 Hz, 1H), 7.43-7.24 (m, 4H), 7.20 (d, J = 8.5 Hz, 1H), 5.92 (d, J = 7.5 Hz, 1H), 4.51 (d, J = 23.8 Hz, 2H), 4.42-4.03 (m, 9H), 3.97 (s, 7H), 2.83 (d, J = 8.4 Hz, 2H), 2.71-2.04 (m, 4H), 1.56 (s, 3H). |
| A-26 | 1H NMR (400 MHz, Methanol-d₄) δ 8.03 (d, J = 7.7 Hz, 1H), 7.69 (d, J = 7.8 Hz, 1H), 7.58 (d, J = 7.7 Hz, 1H), 7.52 (t, J = 7.6 Hz, 1H), 7.38 (t, J = 9.7 Hz, 1H), 7.31 (q, J = 6.0, 4.6 Hz, 2H), 7.19 (d, J = 8.6 Hz, 1H), 5.87 (d, J = 8.6 Hz, 1H), 5.29 (s, 2H), 4.45 (d, J = 7.7 Hz, 2H), 4.40 (d, J = 1.5 Hz, 2H), 4.07 (p, J = 6.5, 6.1 Hz, 1H), 3.97 (d, J = 2.0 Hz, 3H), 3.93-3.72 (m, 1H), 2.84 (t, J = 8.8 Hz, 2H), 2.64 (d, J = 14.3 Hz, 1H), 2.49-2.35 (m, 3H), 2.16 (s, 1H), 2.01-1.89 (m, 1H), 1.47 (s, 3H). |
| A-27 | ¹H NMR (400 MHz, Methanol-d₄) δ 8.03 (d, J = 7.7 Hz, 1H), 7.87 (s, 1H), 7.69 (d, J = 7.7 Hz, 1H), 7.58 (d, J = 7.6 Hz, 1H), 7.52 (t, J = 7.6 Hz, 1H), 7.39 (t, J = 8.1 Hz, 1H), 7.34-7.24 (m, 2H), 7.18 (d, J = 8.4 Hz, 1H), 5.90 (d, J = 7.8 Hz, 1H), 5.29 (s, 2H), 4.48-4.33 (m, 3H), 4.16-4.01 (m, 2H), 3.95 (s, 3H), 3.40 (s, 1H), 2.81 (d, J = 9.2 Hz, 2H), 2.62 (s, 1H), 2.49-2.31 (m, 3H), 2.23 (d, J = 11.4 Hz, 1H), 2.11 (d, J = 9.9 Hz, 1H), 2.02-1.89 (m, 2H), 1.72 (s, 3H), 1.30 (s, 1H). |
| A-28 | ¹H NMR (400 MHz, Methanol-d₄) δ 8.03 (d, J = 7.7 Hz, 1H), 7.87 (s, 1H), 7.69 (d, J = 7.7 Hz, 1H), 7.58 (d, J = 7.6 Hz, 1H), 7.52 (t, J = 7.7 Hz, 1H), 7.40 (d, J = 8.3 Hz, 1H), 7.33-7.24 (m, 2H), 7.18 (d, J = 8.3 Hz, 1H), 5.91 (d, J = 8.3 Hz, 1H), 5.29 (s, 2H), 4.48-4.33 (m, 3H), 4.16-4.01 (m, 2H), 3.96 (s, 3H), 2.81 (d, J = 8.7 Hz, 1H), 2.67-2.56 (m, 1H), 2.49-2.31 (m, 3H), 2.24 (d, J = 11.9 Hz, 1H), 2.04-1.89 (m, 2H), 1.72 (s, 3H). |
| A-29 | 1H NMR (400 MHz, Methanol-d4) δ 8.03 (d, J = 7.6 Hz, 1H), 7.82 (s, 1H), 7.69 (d, J = 7.7 Hz, 1H), 7.57 (d, J = 7.6 Hz, 1H), 7.51 (t, J = 7.6 Hz, 1H), 7.38 (t, J = 8.2 Hz, 1H), 7.28 (dt, J = 13.9, 7.6 Hz, 2H), 7.17 (t, J = 8.1 Hz, 1H), 5.88 (d, J = 8.2 Hz, 1H), 5.28 (s, 2H), 4.40 (d, J = 1.4 Hz, 2H), 4.36 (s, 2H), 4.13-4.02 (m, 2H), 3.93 (s, 3H), 2.92-2.71 (m, 2H), 2.69-2.54 (m, 1H), 2.50-2.30 (m, 3H), 2.06 (d, J = 23.9 Hz, 1H), 2.00-1.85 (m, 1H), 1.68-1.54 (m, 2H), 1.53-1.38 (m, 2H). |
| A-30 | 1H NMR (400 MHz, Methanol-d4) δ 7.55-7.14 (m, 6H), 7.08 (s, 1H), 7.02 (d, J = 10.2 Hz, 1H), 5.96-5.85 (m, 1H), 4.46 (s, 2H), 4.43 (s, 2H), 4.12-3.90 (m, 9H), 3.32-3.24 (m, 2H), 3.00 (s, 3H), 2.92-1.80 (m, 8H). |
| A-31 | 1H NMR (400 MHz, Methanol-d4) δ 7.58-7.12 (m, 6H), 7.08 (s, 1H), 7.02 (dd, J = 9.8, 1.4 Hz, 1H), 5.94-5.83 (m, 1H), 4.57-4.39 (m, 4H), 4.11-4.01 (m, 4H), 3.99 (s, 3H), 3.92-3.44 (m, 5H), 3.32-3.22 (m, 2H), 2.96-1.76 (m, 10H). |
| A-32 | 1H NMR (400 MHz, Methanol-d4) δ 7.57-7.12 (m, 6H), 7.08 (s, 1H), 7.02 (dd, J = 9.8, 1.4 Hz, 1H), 5.92-5.83 (m, 1H), 4.49 (s, 2H), 4.43 (s, 2H), 4.14-4.00 (m, 4H), 3.98 (s, 3H), 3.29 (dd, J = 6.2, 2.2 Hz, 2H), 2.98-1.82 (m, 8H), 1.63 (t, J = 4.1 Hz, 2H), 1.53-1.37 (m, 2H). |
| A-33 | ¹H NMR (400 MHz, Methanol-d4) δ 7.57-7.12 (m, 6H), 7.08 (s, 1H), 7.02 (dd, J = 9.9, 1.4 Hz, 1H), 5.89 (t, J = 8.3 Hz, 1H), 4.58-4.33 (m, 4H), 4.12-4.00 (m, 4H), 3.99 (s, 3H), 3.77 (d, J = 12.6 Hz, 1H), 3.61 (s, 3H), 3.32-3.22 (m, 2H), 2.92-1.75 (m, 17H). |
| A-34 | 1H NMR (400 MHz, Methanol-d4) δ 7.91 (d, J = 7.6 Hz, 1H), 7.62 (d, J = 7.8 Hz, 1H), 7.51 (t, J = 7.6 Hz, 1H), 7.35 (dd, J = 25.8, 7.2 Hz, 4H), 7.20 (s, 1H), 5.90 (s, 1H), 4.46 (s, 2H), 4.37 (d, J = 2.8 Hz, 2H), 4.15-3.91 (m, 9H), 3.31-3.21 (m, 2H), 3.00 (s, 3H), 2.95-1.82 (m, 8H). |
| A-35 | 1H NMR (400 MHz, Methanol-d4) δ 7.95-7.84 (m, 2H), 7.69-7.57 (m, 1H), 7.51 (t, J = 7.6 Hz, 1H), 7.42-7.25 (m, 4H), 7.20 (d, J = 8.3 Hz, 1H), 5.94 (t, J = 8.2 Hz, 1H), 4.40-4.27 (m, 4H), 4.15-3.99 (m, 6H), 3.97 (s, 3H), 3.31-3.23 (m, 2H), 2.92 (s, 3H), 2.90-1.80 (m, 8H). |
| A-36 | ¹H NMR (400 MHz, Methanol-d4) δ 7.87 (s, 1H), 7.58-7.04 (m, 9H), 6.09-5.74 (m, 1H), 4.46-4.19 (m, 4H), 4.10-4.01 (m, 1H), 3.98 (s, 3H), 3.95 (s, 3H), 3.90-3.65 (m, 1H), 3.65-3.37 (m, 3H), 3.27-3.14 (m, 2H), 2.91-2.68 (m, 2H), 2.67-2.57 (m, 1H), |

TABLE 2A-continued

| No. | NMR |
|---|---|
| | 2.57-2.15 (m, 5H), 2.15-1.97 (m, 1H), 1.97-1.82 (m, 1H). |
| A-37 | $^1$H NMR (400 MHz, Methanol-d$_4$) δ 7.98-7.83 (m, 1H), 7.71-7.55 (m, 1H), 7.55-7.45 (m, 1H), 7.44-7.29 (m, 4H), 7.29-7.16 (m, 1H), 6.99 (d, J = 13.3 Hz, 1H), 5.44-5.31 (m, 1H), 4.48 (s, 2H), 4.40-4.20 (m, 2H), 4.16-4.01 (m, 4H), 3.92 (d, J = 14.6 Hz, 3H), 3.29-3.20 (m, 2H), 2.93-2.75 (m, 2H), 2.75-2.56 (m, 1H), 2.53-2.28 (m, 3H), 2.11-1.81 (m, 2H), 1.67-1.56 (m, 2H), 1.51-1.35 (m, 2H). |
| A-38 | $^1$H NMR (400 MHz, Methanol-d$_4$) δ 8.01-7.77 (m, 2H), 7.59 (d, J = 7.9 Hz, 1H), 7.48 (t, J = 7.6 Hz, 1H), 7.44-7.23 (m, 4H), 7.23-7.07 (m, 1H), 6.03-5.69 (m, 1H), 4.55-4.21 (m, 3H), 4.19-4.02 (m, 5H), 3.96 (s, 3H), 3.28-3.22 (m, 2H), 2.91-2.70 (m, 2H), 2.68-2.52 (m, 2H), 2.51-2.28 (m, 4H), 2.26-1.82 (m, 5H), 1.80-1.43 (m, 3H). |
| A-39 | $^1$H NMR (400 MHz, Methanol-d$_4$) δ 7.91-7.82 (m, 2H), 7.59 (d, J = 7.9 Hz, 1H), 7.48 (t, J = 7.6 Hz, 1H), 7.44-7.22 (m, 4H), 7.22-7.11 (m, 1H), 5.97-5.82 (m, 1H), 4.54-4.24 (m, 3H), 4.21-4.00 (m, 5H), 3.95 (s, 3H), 3.28-3.21 (m, 2H), 2.89-2.70 (m, 2H), 2.68-2.54 (m, 2H), 2.51-2.27 (m, 4H), 2.25-2.04 (m, 3H), 2.01-1.84 (m, 2H), 1.81-1.43 (m, 3H). |
| A-40 | $^1$H NMR (400 MHz, Methanol-d$_4$) δ 7.89 (d, J = 7.6 Hz, 1H), 7.82 (s, 1H), 7.59 (d, J = 7.9 Hz, 1H), 7.48 (t, J = 7.6 Hz, 1H), 7.42-7.31 (m, 2H), 7.31-7.21 (m, 2H), 7.21-7.10 (m, 1H), 5.89 (t, J = 8.1 Hz, 1H), 4.43-4.21 (m, 2H), 4.14-4.01 (m, 6H), 3.94 (s, 3H), 3.29-3.20 (m, 2H), 2.90-2.71 (m, 2H), 2.71-2.53 (m, 1H), 2.53-2.25 (m, 3H), 2.19-2.01 (m, 1H), 2.01-1.78 (m, 1H), 1.66 (s, 6H). |
| A-41 | $^1$H NMR (400 MHz, Methanol-d$_4$) δ 7.92 (d, J = 7.6 Hz, 1H), 7.84 (s, 1H), 7.62 (d, J = 7.7 Hz, 1H), 7.51 (t, J = 7.6 Hz, 1H), 7.43-7.23 (m, 4H), 7.19 (t, J = 8.2 Hz, 1H), 6.02-5.79 (m, 1H), 4.46-4.22 (m, 4H), 4.17-4.00 (m, 4H), 3.95 (s, 3H), 3.31-3.22 (m, 2H), 2.94-2.69 (m, 2H), 2.69-2.52 (m, 1H), 2.52-2.18 (m, 3H), 2.18-2.03 (m, 1H), 2.03-1.78 (m, 1H), 1.74-1.55 (m, 2H), 1.54-1.38 (m, 2H). |
| A-42 | $^1$H NMR (400 MHz, Methanol-d$_4$) δ 7.92 (d, J = 7.6 Hz, 1H), 7.69-7.57 (m, 1H), 7.52 (t, J = 7.6 Hz, 1H), 7.47-7.30 (m, 4H), 7.30-7.18 (m, 1H), 7.03 (d, J = 11.9 Hz, 1H), 5.53-5.26 (m, 1H), 4.60-4.45 (m, 2H), 4.45-4.16 (m, 2H), 4.16-4.02 (m, 4H), 4.02-3.71 (m, 4H), 3.65-3.49 (m, 1H), 3.31-3.19 (m, 2H), 3.19-3.07 (m, 1H), 2.95-2.77 (m, 2H), 2.76-2.58 (m, 2H), 2.57-2.30 (m, 3H), 2.25-1.80 (m, 3H), 1.49 (s, 3H). |
| A-43 | $^1$H NMR (400 MHz, Methanol-d$_4$) δ 7.89 (d, J = 7.5 Hz, 1H), 7.66-7.57 (m, 1H), 7.50 (t, J = 7.6 Hz, 1H), 7.44-7.29 (m, 4H), 7.28-7.17 (m, 1H), 7.07-6.87 (m, 1H), 5.46-5.29 (m, 1H), 4.55-4.41 (m, 2H), 4.41-4.27 (m, 2H), 4.15-3.97 (m, 5H), 3.93 (d, J = 12.3 Hz, 4H), 3.80-3.69 (m, 1H), 3.62-3.35 (m, 1H), 3.29-3.19 (m, 2H), 3.01-2.74 (m, 2H), 2.71-2.64 (m, 1H), 2.60-2.14 (m, 6H), 2.11-1.86 (m, 2H). |
| A-44 | $^1$H NMR (400 MHz, Methanol-d$_4$) δ 7.80 (d, J = 7.5 Hz, 1H), 7.59 (dd, J = 7.7, 1.7 Hz, 1H), 7.47 (t, J = 7.6 Hz, 1H), 7.42-7.11 (m, 5H), 6.99 (d, J = 23.2 Hz, 1H), 5.35 (s, 1H), 4.56 (s, 1H), 4.12 (s, 2H), 4.05 (s, 5H), 3.91 (d, J = 20.6 Hz, 4H), 3.06-2.50 (m, 4H), 2.35 (s, 3H), 2.08-1.74 (m, 2H). |
| A-45 | 1H NMR (400 MHz, Methanol-d4) δ 7.91 (dd, 1H), 7.62 (d, 1H), 7.51 (t, 1H), 7.44-7.24 (m, 4H), 7.19 (t, 1H), 5.87 (d-1H), 4.43-4.33 (m, 3H), 4.31 (s, 2H), 4.12 (d, 4H), 3.98 (s, 3H), 3.30-3.19 (m, 1H), 2.85 (d, 2H), 2.68 (s, 3H), 2.44-2.08 (m, 3H), 1.65 (d, 3H). |
| A-46 | 1H NMR (400 MHz, Methanol-d4) δ 7.91 (dd, 1H), 7.62 (d, 1H), 7.51 (t, 1H), 7.44-7.25 (m, 4H), 7.20 (t, 1H), 5.87 (d, 1H), 4.44-4.34 (m, 3H), 4.31 (s, 2H), 4.12 (s, 3H), 3.99 (d, 5H), 3.30-3.14 (m, 2H), 2.85 (d, 2H), 2.68 (s, 2H), 2.45-2.07 (m, 3H). |
| A-47 | 1H NMR (400 MHz, Methanol-d4) δ 7.91 (dd, 1H), 7.62 (d, 1H), 7.51 (t, 1H), 7.43-7.25 (m, 4H), 7.25-7.14 (m, 1H), 5.89 (d, 1H), 4.59-4.35 (m, 4H), 4.34-4.22 (m, 1H), 4.12 (s, 3H), 4.07 (m, 1H), 4.03-3.94 (m, 3H), 3.78 (d, 1H), 3.61 (s, 1H), 3.38 (d, 1H), 3.31-3.19 (m, 2H), 2.85 (d, 2H), 2.68 (m, 3H), 2.50-1.84 (m, 7H). |
| A-48 | 1H NMR (400 MHz, Methanol-d4) δ 7.89 (td-1H), 7.63 (t, 1H), 7.51 (td, 1H), 7.48-7.24 (m, 4H), 7.21 (d, 1H), 5.87 (s, 1H), 4.39 (q, J = 6.6 Hz, 1H), 4.30 (d, 2H), 4.17-4.06 (m, 6H), 3.98 (d, 3H), 3.24 (m, 2H), 2.85 (m, 3H), 2.68 (s, 3H), 2.33-2.11 (m, 2H), 1.65 (d, 2H). |
| A-49 | 1H NMR (400 MHz, Methanol-d4) δ 7.89 (d, 1H), 7.61 (d, 1H), 7.51 (t, 1H), 7.44-7.25 (m, 4H), 7.25-7.14 (m, 1H), 5.87 (d, 1H), 4.44-4.35 (m, 1H), 4.30 (s, 2H), 4.11 (s, 3H), 4.03 (s, 2H), 3.98 (d, 3H), 3.24 (m, 2H), 2.84 (t, 2H), 2.76-2.55 (m, 3H), 2.22 (m, 4H). |
| A-50 | 1H NMR (400 MHz, Methanol-d4) δ 7.89 (d, 1H), 7.61 (d, 1H), 7.50 (t, 1H), 7.43-7.24 (m, 4H), 7.24-7.11 (m, 1H), 5.87 (d, 1H), 4.31 (s, 2H), 4.20 (s, 2H), 4.11 (s, 4H), 3.97 (d, 3H), 2.84 (d, 2H), 2.68 (s, 2H), 2.42 (m-2H), 2.35-2.02 (m, 3H), 1.66 (d, 2H), 1.41 (s, 3H). |
| A-51 | 1H NMR (400 MHz, Methanol-d4) δ 8.02 (s, 1H), 7.90 (s, 1H), 7.62 (d, J = 7.8 Hz, 1H), 7.51 (t, J = 7.7 Hz, 1H), 7.35 (dd, J = 28.9, 7.1 Hz, 4H), 7.18 (s, 1H), 5.94 (m, 1H), 5.51 (s, 4H), 4.52 (d, J = 28.0 Hz, 2H), 4.17 (d, J = 47.4 Hz, 8H), 3.95 (s, 3H), 3.25-3.11 (m, 1H), 2.83 (s, 1H), 2.68 (s, 1H), 2.06 (s, 5H), 1.73 (d, J = 11.8 Hz, 4H), 1.56 (s, 3H). |
| A-52 | 1H NMR (400 MHz, Methanol-d4) δ 8.02 (s, 1H), 7.90 (s, 1H), 7.62 (d, J = 7.9 Hz, 1H), 7.51 (t, J = 7.6 Hz, 1H), 7.45-7.24 (m, 4H), 7.20 (d, J = 9.8 Hz, 1H), 5.92 (s, 1H), 5.51 (s, 2H), 4.52 (d, J = 28.1 Hz, 2H), 4.33-3.99 (m, 8H), 3.94 (s, 2H), 3.25-3.11 (m, 0H), 2.83 (s, 1H), 2.66 (d, J = 16.5 Hz, 1H), 2.10 (d, J = 11.9 Hz, 1H), 2.05-1.66 (m, 4H), 1.56 (s, 3H). |
| A-53 | 1H NMR (400 MHz, Methanol-d4) δ 7.90 (d, J = 7.6 Hz, 1H), 7.84 (s, 1H), 7.60 (d, J = 7.9 Hz, 1H), 7.49 (t, J = 7.6 Hz, 1H), 7.40-7.22 (m, 4H), 7.17 (t, J = 8.4 Hz, 1H), 5.89 (d, J = 7.5 Hz, 1H), 4.45 (d, J = 10.9 Hz, 2H), 4.37-4.22 (m, 3H), 4.16-3.98 (m, 5H), 3.94 (s, 3H), 2.81 (d, J = 8.4 Hz, 2H), 2.68-2.55 (m, 1H), 2.51-2.33 (m, 2H), 2.17-2.00 (m, 1H), 1.98-1.84 (m, 1H), 1.60 (s, 3H). |
| A-54 | 1H NMR (400 MHz, Methanol-d4) δ 7.92-7.80 (m, 2H), 7.60 (d, J = 7.7 Hz, 1H), 7.49 (t, J = 7.6 Hz, 1H), 7.40-7.22 (m, 4H), 7.16 (t, J = 8.5 Hz, 1H), 5.89 (d, J = 8.0 Hz, 1H), 4.50 (s, 2H), 4.31 (d, J = 8.9 Hz, 6H), 4.21 (d, J = 11.1 Hz, 2H), 4.10 (d, J = 13.5 Hz, 5H), 3.94 (s, 3H), 3.63 (p, J = 8.4 Hz, 1H), 2.80 (d, J = 8.6 Hz, 2H), 2.62 (t, J = 13.1 Hz, 1H), 2.08 (t, J = 10.6 Hz, 1H), 1.54 (s, 3H). |
| A-55 | 1H NMR (400 MHz, Methanol-d4) δ 7.89 (d, J = 7.6 Hz, 1H), 7.84 (s, 1H), 7.60 (d, J = 7.8 Hz, 1H), 7.49 (t, J = 7.6 Hz, 1H), 7.41-7.22 (m, 4H), 7.17 (t, J = 8.5 Hz, 1H), 5.89 (d, J = 7.8 Hz, 1H), 4.42-4.20 (m, 7H), 4.10 (s, 4H), 3.94 (s, 3H), 3.63 (p, J = 8.4 Hz, 1H), 3.28-3.19 (m, 2H), 2.82 (t, J = 11.5 Hz, 2H), |

TABLE 2A-continued

| No. | NMR |
|---|---|
| | 2.70-2.54 (m, 1H), 2.51-2.30 (m, 3H), 2.18-2.01 (m, 1H), 2.01-1.84 (m, 1H). |
| A-56 | 1H NMR (400 MHz, Methanol-d4) δ 8.00 (s, 1H), 7.88 (d, J = 7.5 Hz, 1H), 7.60 (d, J = 7.7 Hz, 1H), 7.49 (t, J = 7.6 Hz, 1H), 7.42-7.23 (m, 4H), 7.18 (d, J = 9.0 Hz, 1H), 5.91 (s, 1H), 4.50 (d, J = 20.8 Hz, 3H), 4.32-4.02 (m, 7H), 3.95 (s, 3H), 3.58 (s, 2H), 2.95-2.53 (m, 6H), 2.15 (d, J = 94.3 Hz, 6H), 1.54 (s, 3H). |
| A-57 | 1H NMR (400 MHz, Methanol-d4) δ 7.89-7.82 (m, 2H), 7.59 (d, J = 7.6 Hz, 1H), 7.49 (t, J = 7.6 Hz, 1H), 7.41-7.22 (m, 4H), 7.17 (t, J = 8.5 Hz, 1H), 5.90 (t, J = 8.2 Hz, 1H), 4.35-4.29 (m, 7H), 4.18 (s, 2H), 4.09 (d, J = 3.1 Hz, 3H), 3.95 (s, 4H), 3.69 (dp, J = 16.7, 8.7 Hz, 1H), 2.79 (d, J = 11.1 Hz, 2H), 2.63 (t, J = 12.3 Hz, 1H), 2.41 (ddd, J = 10.7, 8.0, 3.0 Hz, 1H), 2.31-2.16 (m, 2H), 2.15-2.01 (m, 1H), 1.39 (d, J = 2.7 Hz, 3H). |
| A-58 | 1H NMR (400 MHz, Methanol-d4) δ 7.99 (s, 1H), 7.87 (d, J = 7.6 Hz, 1H), 7.59 (d, J = 7.7 Hz, 1H), 7.49 (t, J = 7.6 Hz, 1H), 7.41-7.22 (m, 4H), 7.17 (t, J = 8.6 Hz, 1H), 5.91 (s, 1H), 4.69-3.83 (m, 11H), 3.60 (d, J = 27.6 Hz, 1H), 2.96-2.53 (m, 6H), 2.53-1.89 (m, 9H), 1.39 (s, 3H). |
| A-59 | 1H NMR (400 MHz, Methanol-d4) δ 8.01 (s, 1H), 7.92 (d, J = 7.6 Hz, 1H), 7.62 (d, J = 7.8 Hz, 1H), 7.51 (t, J = 7.6 Hz, 1H), 7.47-6.95 (m, 5H), 5.94 (s, 1H), 4.37 (d, J = 2.8 Hz, 2H), 4.11 (d, J = 16.9 Hz, 4H), 3.98 (s, 3H), 3.78-3.46 (m, 1H), 3.31-3.23 (m, 2H), 2.85 (t, J = 11.6 Hz, 2H), 2.67 (d, J = 28.9 Hz, 2H), 2.52-2.21 (m, 3H), 2.11 (dd, J = 12.3, 8.9 Hz, 1H), 2.04-1.85 (m, 1H), 1.41 (s, 1H). |
| A-60 | 1H NMR (400 MHz, Methanol-d4) δ 7.88 (d, J = 10.8 Hz, 2H), 7.60 (d, J = 7.6 Hz, 1H), 7.49 (t, J = 7.6 Hz, 1H), 7.43-7.10 (m, 4H), 5.91 (s, 1H), 4.60-4.37 (m, 3H), 4.31-4.00 (m, 7H), 3.95 (d, J = 1.3 Hz, 3H), 2.94-2.72 (m, 2H), 2.53 (td, J = 28.6, 27.0, 11.4 Hz, 2H), 2.25 (dt, J = 13.6, 10.0 Hz, 3H), 2.16-1.82 (m, 3H), 1.54 (s, 3H). |
| A-61 | 1H NMR (400 MHz, Methanol-d4) δ 7.94-7.81 (m, 2H), 7.60 (d, J = 7.7 Hz, 1H), 7.49 (t, J = 7.6 Hz, 1H), 7.36 (d, J = 7.5 Hz, 2H), 7.31-7.23 (m, 2H), 7.17 (t, J = 8.6 Hz, 1H), 5.91 (s, 1H), 4.48-4.29 (m, 3H), 4.25-4.01 (m, 6H), 3.95 (d, J = 1.5 Hz, 3H), 3.29-3.19 (m, 2H), 2.83 (t, J = 12.3 Hz, 2H), 2.68-2.17 (m, 9H), 2.16-1.81 (m, 3H). |
| A-62 | 1H NMR (400 MHz, Methanol-d4) δ 7.90 (d, J = 7.6 Hz, 1H), 7.60 (d, J = 7.8 Hz, 1H), 7.49 (t, J = 7.6 Hz, 1H), 7.43-7.07 (m, 5H), 5.86 (d, J = 9.6 Hz, 1H), 4.61-4.23 (m, 4H), 4.03 (d, J = 58.6 Hz, 7H), 3.76 (d, J = 12.4 Hz, 1H), 3.59 (s, 1H), 3.36 (d, J = 12.7 Hz, 1H), 3.29-3.20 (m, 2H), 2.84 (t, J = 8.7 Hz, 2H), 2.61 (d, J = 9.4 Hz, 1H), 2.51-2.29 (m, 3H), 2.23-1.82 (m, 7H). |
| A-63 | 1H NMR (400 MHz, Methanol-d4) δ 7.90 (s, 1H), 7.84 (s, 1H), 7.62 (d, J = 7.8 Hz, 1H), 7.51 (t, J = 7.6 Hz, 1H), 7.34 (dd, J = 29.2, 7.2 Hz, 3H), 7.20 (d, J = 9.0 Hz, 1H), 5.91 (t, J = 8.2 Hz, 1H), 4.52 (d, J = 27.4 Hz, 2H), 4.31-4.06 (m, 9H), 4.07-3.88 (m, 4H), 2.83 (d, J = 9.3 Hz, 2H), 2.66 (d, J = 16.7 Hz, 1H), 2.19-1.99 (m, 1H), 1.67-1.50 (m, 6H). |
| A-64 | 1H NMR (400 MHz, Methanol-d4) δ 7.90 (d, J = 7.5 Hz, 1H), 7.82 (s, 1H), 7.60 (d, J = 7.9 Hz, 1H), 7.49 (t, J = 7.6 Hz, 1H), 7.41-7.22 (m, 3H), 7.17 (s, 1H), 5.90 (t, J = 8.3 Hz, 1H), 4.35 (d, J = 2.8 Hz, 2H), 4.22-3.85 (m, 10H), 3.27 (dd, J = 6.2, 3.9 Hz, 1H), 2.81 (d, J = 9.1 Hz, 2H), 2.64 (d, J = 12.4 Hz, 1H), 2.52-2.33 (m, 3H), 2.03 (s, 2H), 2.00-1.84 (m, 1H), 1.60 (d, J = 7.2 Hz, 3H). |
| A-65 | 1H NMR (400 MHz, Methanol-d4) δ 7.89 (t, J = 8.0 Hz, 1H), 7.82 (s, 1H), 7.60 (d, J = 8.0 Hz, 1H), 7.49 (t, J = 7.6 Hz, 1H), 7.44-7.23 (m, 3H), 7.18 (d, J = 8.7 Hz, 1H), 5.90 (t, J = 8.2 Hz, 1H), 4.40-4.30 (m, 2H), 4.17 (s, 2H), 4.11 (s, 4H), 3.95 (d, J = 2.6 Hz, 3H), 3.87 (s, 2H), 3.30-3.20 (m, 2H), 2.84 (d, J = 21.5 Hz, 1H), 2.68-2.57 (m, 1H), 2.49-2.34 (m, 3H), 2.09 (dt, J = 19.9, 9.2 Hz, 1H), 1.97-1.87 (m, 1H). |
| A-66 | 1H NMR (400 MHz, Methanol-d4) δ 7.87 (d, J = 7.5 Hz, 1H), 7.82 (s, 1H), 7.59 (d, J = 7.7 Hz, 1H), 7.49 (t, J = 7.6 Hz, 1H), 7.41-7.23 (m, 4H), 7.18 (d, J = 9.2 Hz, 1H), 5.90 (t, J = 8.2 Hz, 1H), 4.17 (d, J = 5.6 Hz, 4H), 4.10 (s, 3H), 4.06-3.90 (m, 5H), 2.81 (d, J = 8.8 Hz, 2H), 2.70-2.55 (m, 1H), 2.41 (ddd, J = 10.7, 8.0, 3.0 Hz, 1H), 2.28-2.16 (m, 1H), 2.15-2.01 (m, 2H), 1.60 (d, J = 7.2 Hz, 3H), 1.40 (s, 3H). |
| A-67 | 1H NMR (400 MHz, Methanol-d4) δ 7.87 (d, J = 7.5 Hz, 1H), 7.82 (s, 1H), 7.59 (d, J = 7.7 Hz, 1H), 7.49 (t, J = 7.6 Hz, 1H), 7.41-7.22 (m, 5H), 7.17 (t, J = 8.3 Hz, 1H), 5.90 (t, J = 8.2 Hz, 1H), 4.18 (d, J = 2.8 Hz, 5H), 4.10 (s, 4H), 3.95 (s, 4H), 3.88 (s, 2H), 2.81 (d, J = 9.3 Hz, 2H), 2.67-2.57 (m, 1H), 2.41 (ddd, J = 10.7, 8.0, 3.0 Hz, 2H), 2.23 (ddd, J = 11.0, 8.4, 3.0 Hz, 2H), 2.14-2.01 (m, 1H), 1.40 (s, 3H). |
| A-68 | 1H NMR (400 MHz, Methanol-d4) δ 7.88 (d, J = 7.5 Hz, 1H), 7.60 (d, J = 7.7 Hz, 1H), 7.49 (t, J = 7.6 Hz, 1H), 7.41-7.23 (m, 4H), 7.19 (d, J = 9.1 Hz, 1H), 5.87 (d, J = 7.4 Hz, 1H), 4.50 (d, J = 25.2 Hz, 4H), 4.22 (d, J = 11.1 Hz, 3H), 4.10 (d, J = 13.7 Hz, 5H), 3.97 (s, 3H), 3.93-3.70 (m, 1H), 3.51 (s, 1H), 2.83 (d, J = 9.5 Hz, 2H), 2.69-2.56 (m, 1H), 2.14 (d, J = 10.1 Hz, 1H), 1.54 (s, 3H), 1.47 (s, 3H). |
| A-69 | 1H NMR (400 MHz, Methanol-d4) δ 7.92 (d, J = 7.6 Hz, 1H), 7.62 (d, J = 7.7 Hz, 1H), 7.51 (t, J = 7.6 Hz, 1H), 7.42-7.12 (m, 5H), 5.97-5.82 (m, 1H), 4.81-4.66 (m, 1H), 4.43-4.27 (m, 3H), 4.20 (d, J = 14.0 Hz, 1H), 4.15-4.04 (m, 4H), 4.03-3.92 (m, 3H), 3.31-3.23 (m, 2H), 2.99-1.78 (m, 16H). |
| A-70 | 1H NMR (400 MHz, Methanol-d4) δ 7.92 (d, J = 7.6 Hz, 1H), 7.62 (d, J = 7.7 Hz, 1H), 7.51 (t, J = 7.6 Hz, 1H), 7.45-7.10 (m, 5H), 5.96-5.82 (m, 1H), 4.69-4.29 (m, 4H), 4.16-4.03 (m, 4H), 3.98 (s, 3H), 3.92-3.57 (m, 2H), 3.31-3.23 (m, 2H), 3.04-1.82 (m, 15H). |
| A-71 | 1H NMR (400 MHz, Methanol-d4) δ 7.95 (d, J = 7.6 Hz, 1H), 7.64 (d, J = 7.7 Hz, 1H), 7.51 (t, J = 7.6 Hz, 1H), 7.45-7.12 (m, 5H), 5.92-5.81 (m, 1H), 4.60-4.41 (m, 4H), 4.36-4.02 (m, 7H), 3.98 (s, 3H), 3.87-2.06 (m, 11H), 1.56 (d, J = 13.7 Hz, 3H). |
| A-72 | 1H NMR (400 MHz, Methanol-d4) δ 7.90 (t, J = 8.1 Hz, 1H), 7.62 (d, J = 7.8 Hz, 1H), 7.51 (t, J = 7.6 Hz, 1H), 7.45-7.12 (m, 5H), 5.94-5.83 (m, 1H), 4.60-4.34 (m, 5H), 4.31 (s, 2H), 4.22-3.88 (m, 10H), 2.96-2.74 (m, 2H), 2.70-2.55 (m, 1H), 2.25-2.09 (m, 1H), 1.66 (d, J = 7.2 Hz, 3H). |
| A-73 | 1H NMR (400 MHz, Methanol-d4) δ 7.91 (d, J = 7.5 Hz, 1H), 7.62 (d, J = 7.7 Hz, 1H), 7.51 (t, J = 7.6 Hz, 1H), 7.45-7.07 (m, 5H), 5.95-5.81 (m, 1H), 4.56-4.36 (m, 5H), 4.31 (s, 2H), 4.19-3.87 (m, 10H), 2.95-2.75 (m, 2H), 2.70-2.56 (m, 1H), 2.24-2.07 (m, 1H). |
| A-74 | 1H NMR (400 MHz, Methanol-d4) δ 7.91 (d, J = 7.4 Hz, 1H), 7.62 (d, J = 7.7 Hz, 1H), 7.51 (t, J = 7.6 Hz, 1H), 7.44-7.07 (m, 5H), 5.93-5.80 (broad, 1H), 4.59-4.45 (m, 2H), 4.35-3.83 (m, 13H), 2.93-2.76 (m, 2H), 2.66-2.56 (m, 1H), 2.25-2.08 (m, 1H), 1.64 (d, J = 7.2 Hz, 3H), 1.56 (s, 3H). |

TABLE 2A-continued

| No. | NMR |
|---|---|
| A-75 | 1H NMR (400 MHz, Methanol-d4) δ 7.91 (d, J = 7.5 Hz, 1H), 7.62 (d, J = 7.8 Hz, 1H), 7.51 (t, J = 7.6 Hz, 1H), 7.45-7.10 (m, 5H), 5.88 (broad, 1H), 4.51 (d, J = 31.4 Hz, 2H), 4.31 (s, 2H), 4.28-4.07 (m, 7H), 4.04-3.95 (m, 5H), 2.93-2.77 (m, 2H), 2.68-2.58 (m, 1H), 2.25-2.09 (m, 2H), 1.56 (s, 3H). |
| A-76 | 1H NMR (400 MHz, Methanol-d4) δ 7.92 (d, J = 7.5 Hz, 1H), 7.62 (d, J = 7.9 Hz, 1H), 7.51 (t, J = 7.6 Hz, 1H), 7.45-7.09 (m, 5H), 5.96-5.83 (m, 1H), 4.57-4.41 (m, 2H), 4.37 (d, J = 2.7 Hz, 2H), 4.17-4.04 (m, 4H), 3.99 (s, 3H), 3.85-3.75 (m, 1H), 3.31-3.25 (m, 2H), 3.09-1.71 (m, 13H), 1.16 (d, J = 6.2 Hz, 3H). |
| A-77 | 1H NMR (400 MHz, Methanol-d4) δ 7.92 (d, J = 7.6 Hz, 1H), 7.62 (d, J = 7.8 Hz, 1H), 7.51 (t, J = 7.6 Hz, 1H), 7.44-7.09 (m, 5H), 5.98-5.83 (m, 1H), 4.53 (dd, J = 14.3, 2.6 Hz, 1H), 4.44-4.26 (m, 3H), 4.16-4.04 (m, 4H), 4.04-3.86 (m, 4H), 3.75-3.56 (m, 2H), 3.46-3.38 (m, 1H), 3.31-3.23 (m, 2H), 3.00-1.69 (m, 12H), 1.18-1.02 (m, 3H). |
| A-78 | 1H NMR (400 MHz, Methanol-d4) δ 7.91 (d, J = 7.6 Hz, 1H), 7.86 (s, 1H), 7.62 (d, J = 7.8 Hz, 1H), 7.51 (t, J = 7.6 Hz, 1H), 7.44-7.11 (m, 5H), 5.91 (s, 1H), 4.40-4.22 (m, 4H), 4.13 (s, 3H), 4.11-4.02 (m, 1H), 3.97 (s, 3H), 3.72-3.64 (m, 1H), 3.31-3.25 (m, 2H), 2.99-1.81 (m, 13H), 1.16 (d, J = 6.1 Hz, 3H). |
| A-79 | 1H NMR (400 MHz, Methanol-d4) δ 7.92 (d, J = 7.2 Hz, 1H), 7.62 (d, J = 7.9 Hz, 1H), 7.51 (t, J = 7.6 Hz, 1H), 7.45-7.11 (m, 5H), 5.93 (d, J = 9.8 Hz, 1H), 4.58-4.29 (m, 4H), 4.27-4.03 (m, 5H), 4.02-3.93 (m, 3H), 3.92-1.66 (m, 15H), 3.31-3.23 (m, 2H), 1.20-1.02 (m, 3H). |
| A-80 | 1H NMR (400 MHz, Methanol-d4) δ 7.92 (d, J = 7.6 Hz, 1H), 7.62 (d, J = 7.7 Hz, 1H), 7.52 (t, J = 7.6 Hz, 1H), 7.43-7.13 (m, 5H), 5.94-5.84 (m, 1H), 4.54-4.22 (m, 4H), 4.16-4.04 (m, 4H), 3.99 (s, 3H), 3.59-1.55 (m, 17H), 3.31-3.25 (m, 2H). |
| A-81 | 1H NMR (400 MHz, Methanol-d4) δ 7.92 (d, J = 7.6 Hz, 1H), 7.62 (d, J = 7.8 Hz, 1H), 7.51 (t, J = 7.6 Hz, 1H), 7.46-7.12 (m, 5H), 5.95-5.85 (m, 1H), 4.54-4.24 (m, 4H), 4.16-4.04 (m, 4H), 3.99 (s, 3H), 3.52-3.43 (m, 1H), 3.31-3.19 (m, 2H), 3.13-1.72 (m, 16H). |
| A-82 | 1H NMR (400 MHz, Methanol-d4) δ 7.92 (d, J = 7.6 Hz, 1H), 7.62 (d, J = 7.7 Hz, 1H), 7.51 (t, J = 7.6 Hz, 1H), 7.46-7.24 (m, 4H), 7.20 (t, J = 8.7 Hz, 1H), 5.88 (q, J = 9.4 Hz, 1H), 4.53 (d, J = 14.5 Hz, 1H), 4.49-4.31 (m, 3H), 4.12 (s, 4H), 3.98 (d, J = 4.8 Hz, 3H), 3.74 (s, 3H), 3.62 (s, 1H), 3.40 (d, J = 12.5 Hz, 4H), 3.32-3.19 (m, 3H), 2.85 (d, J = 8.5 Hz, 2H), 2.62 (s, 1H), 2.51-2.34 (m, 3H), 2.34-1.98 (m, 5H), 1.98-1.79 (m, 3H). |
| A-83 | 1H NMR (400 MHz, Methanol-d4) δ 7.89 (d, 1H), 7.84 (s, 1H), 7.61 (d, 1H), 7.50 (t, 1H), 7.44-7.24 (m, 4H), 7.18 (t, 1H), 5.91 (s, 1H), 4.27 (s, 2H), 4.18 (s, 2H), 4.11 (s, 3H), 3.96 (s, 3H), 3.20 (d, 2H), 2.94-2.76 (m, 3H), 2.68 (s, 1H), 2.38-2.23 (m, 2H), 2.11 (dd, 1H), 1.98-1.84 (m, 2H), 1.61 (dd, 2H), 1.35 (s, 3H). |
| A-84 | 1H NMR (400 MHz, Methanol-d4) δ 7.89 (d, 1H), 7.83 (s, 1H), 7.61 (d, 1H), 7.50 (t, 1H), 7.44-7.24 (m, 4H), 7.20 (d, 1H), 5.92 (t, 1H), 4.27 (s, 2H), 4.19 (s, 2H), 4.11 (s, 3H), 3.97 (s, 3H), 3.89 (s, 2H), 3.20 (d, 2H), 2.91-2.75 (m, 3H), 2.66 (d, 1H), 2.36-2.23 (m, 2H), 2.09 (m, 1H), 1.99-1.87 (m, 2H), 1.62-1.44 (m, 2H), 1.35 (s, 3H). |
| A-85 | 1H NMR (400 MHz, Methanol-d4) δ 7.89 (d, 1H), 7.61 (d, 1H), 7.51 (t, 1H), 7.43-7.24 (m, 4H), 7.19 (t, 1H), 5.87 (d, 1H), 4.50 (s, 2H), 4.27 (s, 2H), 4.11 (s, 3H), 3.97 (d, 3H), 3.21 (d, 2H), 2.96-2.75 (m, 3H), 2.65 (d, 1H), 2.37-2.25 (m, 2H), 2.16 (m, 1H), 2.00-1.86 (m, 2H), 1.70-1.59 (m, 2H), 1.55-1.46 (m, 2H), 1.35 (s, 3H). |
| A-86 | 1H NMR (400 MHz, Methanol-d4) δ 7.89 (d, 1H), 7.61 (d, 1H), 7.51 (t, 1H), 7.44-7.25 (m, 4H), 7.19 (t, 1H), 5.87 (d, J = 8.6 Hz, 1H), 4.31 (s, 2H), 4.20-4.07 (m, 4H), 3.98 (s, 2H), 3.21 (d, 2H), 2.96-2.75 (m, 3H), 2.68 (m, 6H), 2.40-2.25 (m, 2H), 2.15 (d, 1H), 2.00-1.86 (m, 2H), 1.66 (d, 2H), 1.35 (s, 3H). |
| A-87 | 1H NMR (400 MHz, Methanol-d4) δ 7.89 (d, 1H), 7.61 (d, 1H), 7.51 (t, 1H), 7.44-7.25 (m, 4H), 7.19 (t, 1H), 5.87 (d, 1H), 4.31 (s, 2H), 4.20-4.07 (m, 4H), 3.98 (s, 2H), 3.21 (d, 2H), 2.96-2.75 (m, 3H), 2.68 (m, 6H), 2.40-2.25 (m, 2H), 2.15 (d, 1H), 2.00-1.86 (m, 2H), 1.66 (d, 2H), 1.35 (s, 3H). |
| A-88 | 1H NMR (400 MHz, Methanol-d4) δ 7.92 (d, 1H), 7.62 (d, 1H), 7.51 (t, 1H), 7.45-7.24 (m, 4H), 7.24-7.14 (m, 1H), 5.94-5.82 (m, 1H), 4.37 (d, 2H), 4.29 (s, 2H), 4.12 (s, 4H), 3.97 (d, 4H), 3.89 (s, 2H), 3.29 (dd, 1H), 2.82 (s, 4H), 2.68 (s, 2H), 2.50-2.34 (m, 3H), 2.16 (m, 1H), 1.95 (m, 1H). |
| A-89 | 1H NMR (400 MHz, Methanol-d4) δ 7.89 (d, 1H), 7.84 (s, 1H), 7.61 (d, 1H), 7.50 (m, 1H), 7.42-7.24 (m, 4H), 7.19 (t, 1H), 5.91 (t, 1H), 4.20 (s, 2H), 4.16 (s, 2H), 4.11 (d, 3H), 4.03-3.92 (m, 4H), 3.29 (d, 2H), 2.92-2.76 (m, 4H), 2.72-2.56 (m, 1H), 2.42 (m, 2H), 2.36-2.20 (m, 2H), 2.10 (m, 1H), 1.41 (s, 3H). |
| A-90 | 1H NMR (400 MHz, Methanol-d4) δ 7.89 (d, 1H), 7.83 (s, 1H), 7.61 (d, 1H), 7.50 (t, 1H), 7.44-7.25 (m, 4H), 7.18 (t, 1H), 5.90 (d, 1H), 4.30-4.16 (m, 4H), 4.11 (s, 3H), 3.97 (d, 4H), 2.97-2.75 (m, 3H), 2.72-2.57 (m, 1H), 2.42 (m, 2H), 2.28 (m, 2H), 2.12 (t, 1H), 1.41 (s, 3H), 1.32-1.18 (m, 1H), 0.91-0.59 (m, 4H). |
| A-91 | 1H NMR (400 MHz, Methanol-d4) δ 7.89 (d, 1H), 7.84 (s, 1H), 7.61 (d, 1H), 7.50 (m, 1H), 7.43-7.24 (m, 4H), 7.19 (d, 1H), 5.90 (d, 1H), 4.32-4.17 (m, 4H), 4.16-4.08 (m, 4H), 4.04-3.85 (m, 6H), 3.43 (s, 3H), 3.00-2.74 (m, 2H), 2.65 (s, 1H), 2.42 (m, 2H), 2.34-2.22 (m, 2H), 2.18-2.01 (m, 1H), 1.41 (s, 3H). |
| A-92 | 1H NMR (400 MHz, Methanol-d4) δ 7.89 (dd, 1H), 7.85 (s, 1H), 7.61 (d, 1H), 7.50 (m, 1H), 7.43-7.24 (m, 4H), 7.19 (d, 1H), 5.90 (d, 1H), 4.20 (s, 2H), 4.15 (s, 2H), 4.11 (d, 3H), 4.05-3.90 (m, 4H), 2.96-2.74 (m, 3H), 2.71-2.56 (m, 1H), 2.43 (m, 2H), 2.34-2.20 (m, 2H), 2.20-1.99 (m, 1H), 1.68 (s, 5H), 1.41 (s, 3H). |
| A-93 | 1H NMR (400 MHz, Methanol-d4) δ 7.89 (d, 1H), 7.61 (d, 1H), 7.50 (t, 1H), 7.43-7.26 (m, 4H), 7.19 (t, 1H), 5.87 (d, 1H), 4.29 (s, 2H), 4.20 (s, 2H), 4.11 (s, 3H), 4.04-3.92 (m, 4H), 3.40 (t, 2H), 2.84 (t, 4H), 2.65 (d, 2H), 2.42 (m, 2H), 2.35-2.05 (m, 3H), 1.41 (s, 3H). |
| A-94 | 1H NMR (400 MHz, Methanol-d4) δ 7.89 (d, 1H), 7.61 (d, 1H), 7.51 (t, 1H), 7.33 (m, 4H), 7.19 (t, 1H), 5.87 (d, 1H), 4.47-4.28 (m, 2H), 4.20 (s, 2H), 4.11 (s, 3H), 4.02-3.91 (m, 4H), 3.46 (d-1H), 2.96-2.77 (m, 2H), 2.68 (s, 1H), 2.42 (m, 2H), 2.32-2.04 (m, 3H), 1.41 (s, 3H), 1.26 (m, 1H), 0.98-0.68 (m, 4H). |
| A-95 | 1H NMR (400 MHz, Methanol-d4) δ 7.89 (dd, 1H), 7.61 (d, 1H), 7.51 (t, 1H), 7.44-7.24 (m, 4H), 7.19 (t, 1H), 5.98-5.80 (m, 1H), 4.28 (s, 2H), 4.20 (s, 2H), 4.11 (s, 3H), 4.05-3.88 (m, 4H), 2.99-2.74 (m, 2H), 2.65 (d, 1H), 2.43 (m, 2H), 2.32-2.07 (m, 3H), 1.70 (s, 6H), 1.41 (s, 3H). |
| A-96 | 1H NMR (400 MHz, Methanol-d4) δ 7.92 (d, 1H), 7.62 (d, 1H), 7.51 (m, 1H), 7.47-7.25 (m, 3H), 7.20 (m, 1H), 5.91 (t, 1H), 4.56-4.39 (m, 2H), 4.37 (d, 2H), 4.26 (m, 1H), 4.12 |

TABLE 2A-continued

| No. | NMR |
|---|---|
| | (s, 4H), 3.98 (t, 3H), 3.29 (m, 2H), 2.99 (s, 3H), 2.85 (m, 2H), 2.68 (s, 2H), 2.52-2.33 (m, 3H), 2.16 (m, 1H), 2.02-1.88 (m, 1H), 1.69 (d, 3H). |
| A-97 | 1H NMR (400 MHz, Methanol-d4) δ 8.00-7.87 (m, 1H), 7.62 (d, 1H), 7.51 (t, 1H), 7.45-7.24 (m, 4H), 7.19 (t, 1H), 5.95-5.80 (m, 1H), 4.55 (m, 1H), 4.37 (d, 2H), 4.23 (m, 2H), 4.12 (d, 4H), 3.98 (d, 3H), 3.31-3.23 (m, 2H), 3.09 (s, 3H), 2.98 (d, 3H), 2.87 (m, 2H), 2.68 (m, H), 2.54-2.31 (m, 3H), 2.16 (m, 1H), 2.04-1.88 (m, 1H), 1.53 (d, 3H). |
| A-98 | 1H NMR (400 MHz, Methanol-d4) δ 7.92 (d, 1H), 7.82 (s, 1H), 7.62 (d, 1H), 7.51 (t, 1H), 7.45-7.23 (m, 4H), 7.19 (t, 1H), 5.91 (s, 1H), 4.37 (d, 2H), 4.12 (d, 6H), 3.96 (s, 3H), 3.91 (t, 1H), 3.31-3.23 (m, 2H), 2.82 (d, 2H), 2.68 (s, 2H), 2.52-2.32 (m, 3H), 2.20-2.04 (m, 1H), 2.02-1.87 (m, 1H), 1.58 (d, 3H). |
| A-99 | 1H NMR (400 MHz, Methanol-d4) δ 7.92 (d, 1H), 7.62 (d, 1H), 7.51 (t, 1H), 7.45-7.24 (m, 4H), 7.23-7.10 (m, 1H), 5.87 (m, 1H), 4.37 (d, 2H), 4.32 (s, 2H), 4.26 (m, 1H), 4.18-4.06 (m, 4H), 3.97 (d, 3H), 3.88 (s, 3H), 3.31-3.24 (m, 2H), 2.86 (m, 2H), 2.66 (d, 1H), 2.51-2.32 (m, 3H), 2.16 (m, 1H), 2.03-1.86 (m, 1H), 1.66 (d, 3H). |
| A-100 | 1H NMR (400 MHz, Methanol-d4) δ 7.92 (d, 1H), 7.62 (d, 1H), 7.51 (m, 1H), 7.46-7.26 (m, 4H), 7.21 (d, 1H), 5.88 (d, 1H), 4.48-4.19 (m, 5H), 4.13 (s, 4H), 3.98 (s, 3H), 3.58-3.41 (m, 2H), 3.29 (m, 1H), 2.84 (m, 2H), 2.68 (s, 5H), 2.53-2.34 (m, 3H), 2.15 (s, 1H), 2.04-1.87 (m, 1H). |
| A-101 | 1H NMR (400 MHz, Methanol-d4) δ 7.95 (dd, 1H), 7.62 (d, 1H), 7.56-7.47 (m, 1H), 7.47-7.25 (m, 4H), 7.21 (d, 1H), 5.88 (d, 1H), 4.46-4.28 (m, 3H), 4.18-4.04 (m, 4H), 3.98 (s, 3H), 3.53-3.40 (m, 1H), 3.29 (m, 1H), 2.85 (d, 2H), 2.71-2.34 (m, 5H), 2.15 (s, 1H), 2.04-1.86 (m, 1H), 1.36-1.15 (m, 1H), 1.01-0.60 (m, 3H). |
| A-102 | 1H NMR (400 MHz, Methanol-d4) δ 7.92 (d, 1H), 7.62 (d, 1H), 7.51 (m, 1H), 7.33 (m, 4H), 7.20 (m, 1H), 5.87 (d, 1H), 4.37 (d, 2H), 4.25 (s, 2H), 4.18-4.01 (m, 4H), 3.97 (d, 3H), 3.32-3.22 (m, 2H), 2.85 (d, J = 9.3 Hz, 2H), 2.68 (s, 2H), 2.52-2.34 (m, 2H), 2.16 (m, 1H), 2.01-1.88 (m, 1H), 1.62 (d, 3H). |
| A-103 | 1H NMR (400 MHz, Methanol-d4) δ 7.92 (d, 1H), 7.62 (d, 1H), 7.51 (m, 1H), 7.45-7.25 (m, 4H), 7.20 (m, 1H), 5.87 (d, 1H), 4.37 (d, 2H), 4.30 (s, 2H), 4.12 (s, 4H), 3.98 (d, 3H), 3.93 (s, 2H), 3.29 (m, 2H), 2.85 (d, 2H), 2.68 (s, 1H), 2.50-2.34 (m, 3H), 2.15 (d, 1H), 2.03-1.88 (m, 1H). |
| A-104 | 1H NMR (400 MHz, Methanol-d4) δ 7.95 (dd, 1H), 7.63 (m, 1H), 7.52 (m, 1H), 7.46-7.26 (m, 4H), 7.20 (m, 1H), 5.88 (d, 1H), 4.45-4.23 (m, 4H), 4.21-4.02 (m, 4H), 3.97 (s, 3H), 3.43 (d, 1H), 3.32-3.23 (m, 1H), 2.91 (d, 3H), 2.68 (s, 2H), 2.56-2.32 (m, 3H), 2.27-1.84 (m, 2H), 1.10 (d, 3H). |
| A-105 | 1H NMR (400 MHz, Methanol-d4) δ 7.95 (dd, 1H), 7.63 (m, 1H), 7.52 (m, 1H), 7.47-7.24 (m, 4H), 7.20 (m, 1H), 5.88 (d, 1H), 4.37 (d, 1H), 4.31 (s, 2H), 4.13 (d, 3H), 3.98 (d, 4H), 3.42 (d, 1H), 3.29 (m, 1H), 2.91 (m, 4H), 2.70-2.36 (m, 5H), 2.16 (s, 1H), 2.02-1.86 (m, 1H), 1.15 (m, 6H). |
| A-106 | 1H NMR (400 MHz, Methanol-d4) δ 7.92 (d, 1H), 7.62 (d, 1H), 7.51 (m, 1H), 7.44-7.25 (m, 4H), 7.20 (m, 1H), 5.87 (m, 1H), 4.37 (d, 2H), 4.32 (s, 2H), 4.16 (m, 3H), 4.02-3.92 (m, 3H), 3.32-3.21 (m, 2H), 2.97-2.76 (m, 2H), 2.68 (s, 2H), 2.51-2.34 (m, 3H), 2.16 (m, 1H), 2.02-1.87 (m, 1H), 1.66 (d, 3H). |
| A-107 | 1H NMR (400 MHz, Methanol-d4) δ 7.92 (d, 1H), 7.62 (d, 1H), 7.51 (m, 1H), 7.44-7.24 (m, 4H), 7.19 (m, 1H), 5.97-5.78 (m, 1H), 4.37 (d, 2H), 4.32 (s, 2H), 4.12 (s, 4H), 4.03 (s, 2H), 3.97 (d, 3H), 3.32-3.21 (m, 2H), 2.85 (m, 2H), 2.68 (s, 2H), 2.52-2.32 (m, 3H), 2.16 (m, 1H), 2.02-1.87 (m, 1H). |
| A-108 | 1H NMR (400 MHz, Methanol-d4) δ 7.53-7.38 (m, 3H), 7.38-7.23 (m, 3H), 7.24-7.10 (m, 3H), 5.88 (s, 2H), 4.42 (s, 1H), 4.30 (d, J = 1.8 Hz, 2H), 4.21 (s, 3H), 3.99 (d, J = 9.3 Hz, 4H), 3.94 (d, J = 5.0 Hz, 2H), 3.55 (t, J = 8.0 Hz, 2H), 2.85 (d, J = 9.8 Hz, 3H), 2.72-2.58 (m, 4H), 2.43 (s, 2H), 2.38-2.25 (m, 3H), 2.15 (t, J = 10.3 Hz, 2H). |
| A-109 | $^1$H NMR (400 MHz, Methanol-$d_4$) δ 7.89 (d, J = 7.6 Hz, 1H), 7.62 (d, J = 7.7 Hz, 1H), 7.51 (t, J = 7.6 Hz, 1H), 7.44-7.25 (m, 4H), 7.20 (t, J = 8.9 Hz, 1H), 5.88 (d, J = 7.4 Hz, 1H), 4.31 (p, J = 13.3 Hz, 5H), 4.11 (s, 3H), 3.98 (s, 2H), 3.95 (s, 2H), 3.26 (d, J = 7.7 Hz, 2H), 2.85 (m, 3H), 2.63 (d, J = 7.8 Hz, 2H), 2.16 (s, 2H), 2.02-1.79 (m, 4H), 1.80-1.55 (m, 3H), 1.46-1.29 (m, 2H). |

TABLE 2B

| No. | NMR |
|---|---|
| B-1 | 1H NMR (400 MHz, Methanol-d4) δ 8.07 (s, 1H), 7.88 (d, 1H), 7.62 (dd, 1H), 7.57-7.23 (m, 6H), 6.73 (d, 1H), 4.24 (s, 2H), 4.19 (d, 5H), 4.12 (s, 3H), 4.03-3.93 (m, 1H), 2.77-2.68 (m, 3H), 2.42 (m, 2H), 2.24 (m, 3H), 1.70 (s, 6H), 1.41 (s, 3H). |
| B-2 | 1H NMR (400 MHz, Methanol-d4) δ 8.13 (s, 1H), 7.89 (d, 1H), 7.62 (dd1H), 7.57-7.22 (m, 6H), 6.73 (d, 1H), 4.44 (s, 2H), 4.20 (s, 5H), 4.11 (s, 3H), 4.06-3.91 (m, 1H), 3.42 (m, 3H), 3.20-2.71 (m, 3H), 2.42 (m, 2H), 2.33-2.14 (m, 3H), 1.41 (s, 3H). |
| B-3 | 1H NMR (400 MHz, Methanol-d4) δ 8.10 (s, 1H), 7.88 (d, 1H), 7.62 (dd, 1H), 7.57-7.22 (m, 5H), 6.73 (d, 1H), 4.43 (s, 2H), 4.29-4.15 (m, 4H), 4.11 (s, 3H), 4.06-3.91 (m, 1H), 3.90-3.44 (m, 3H), 2.77 (m, 3H), 2.68 (s, 2H), 2.42 (m, 2H), 2.32-2.15 (m, 3H), 1.41 (s, 3H). |
| B-4 | 1H NMR (400 MHz, Methanol-d4) δ 8.18 (s, 1H), 7.89 (d, 1H), 7.62 (dd, 1H), 7.57-7.23 (m, 6H), 6.73 (d, 1H), 4.46 (d, 2H), 4.19 (m, 5H), 4.11 (s, 3H), 4.03-3.91 (m, 2H), 3.67 (d, 1H), 3.51 (d, 1H), 3.20-2.69 (m, 4H), 2.42 (m, 2H), 2.34-2.17 (m, 3H), 1.99 (m, 7H), 1.41 (s, 3H). |
| B-5 | 1H NMR (400 MHz, Methanol-d4) δ 8.10 (s, 1H), 7.82 (d, J = 7.1 Hz, 1H), 7.63-7.58 (m, 1H), 7.51 (d, J = 7.3 Hz, 2H), 7.36 (s, 2H), 7.26 (d, J = 7.7 Hz, 1H), 6.71 (s, 1H), 4.60 (s, 2H), 4.20 (s, 2H), 4.08 (s, 2H), 3.95 (s, 2H), 3.25 (d, J = 17.4 Hz, 2H), 3.01-2.87 (m, 3H), 2.73 (d, J = 17.6 Hz, 2H), 2.30-2.10 (m, 4H), 1.89 (s, 2H), 1.67 (d, J = 22.6 Hz, 3H), 1.50-1.37 (m, 2H), 1.31 (s, 3H). |
| B-6 | $^1$H NMR (400 MHz, Methanol-$d_4$) δ 8.11 (s, 1H), 7.82 (d, J = 7.1 Hz, 1H), 7.63-7.58 (m, 1H), 7.49 (d, J = 7.3 Hz, 2H), 7.36 (s, 2H), 7.26 (d, J = 7.7 Hz, 1H), 6.71 (s, 1H), 4.60 (s, 2H), 4.20 (s, 2H), 4.08 (s, 2H), 3.95 (s, 2H), 3.26 (d, J = 17.4 Hz, 2H), 3.01-2.87 (m, 3H), 2.73 (d, J = 17.6 Hz, 2H), 2.30-2.10 (m, 4H), 1.89 (s, 2H), 1.67 (d, J = 22.6 Hz, 3H), 1.50-1.37 (m, 2H), 1.31 (s, 3H). |
| B-7 | 1H NMR (400 MHz, Methanol-d4) δ 8.11 (s, 1H), 7.82 (d, J = 7.1 Hz, 1H), 7.63-7.58 |

TABLE 2B-continued

| No. | NMR |
|---|---|
| | (m, 1H), 7.49 (d, J = 7.3 Hz, 2H), 7.36 (s, 2H), 7.26 (d, J = 7.7 Hz, 1H), 6.71 (s, 1H), 4.60 (s, 2H), 4.20 (s, 2H), 4.08 (s, 2H), 3.95 (s, 2H), 3.26 (d, J = 17.4 Hz, 2H), 3.01-2.87 (m, 3H), 2.73 (d, J = 17.6 Hz, 2H), 2.55-2.11 (m, 6H), 1.89 (s, 1H), 1.67 (d, J = 22.6 Hz, 3H), 1.50-1.37 (m, 2H), 1.31 (s, 3H). |
| B-8 | 1H NMR (400 MHz, Methanol-d4) δ 8.10 (s, 1H), 7.82 (d, J = 7.1 Hz, 1H), 7.62-7.57 (m, 1H), 7.50 (d, J = 7.2 Hz, 2H), 7.36 (s, 2H), 7.26 (d, J = 7.8 Hz, 1H), 6.67 (s, 1H), 4.61 (s, 2H), 4.20 (s, 2H), 4.12 (s, 2H), 3.97 (s, 2H), 3.26 (d, J = 17.4 Hz, 2H), 3.01-2.88 (m, 3H), 2.73 (d, J = 17.6 Hz, 2H), 2.30-2.10 (m, 3H), 1.89 (s, 1H), 1.69 (s, 3H), 1.67 (d, J = 22.6 Hz, 3H), 1.50-1.37 (m, 2H), 1.31 (s, 3H). |
| B-9 | 1H NMR (400 MHz, Methanol-d4) δ 7.91 (d, J = 8.1 Hz, 2H), 7.63 (dd, J = 7.7, 1.8 Hz, 1H), 7.56-7.43 (m, 3H), 7.42-7.32 (m, 2H), 7.27 (d, J = 7.6 Hz, 1H), 6.67 (s, 1H), 4.73-4.65 (m, 1H), 4.37 (s, 3H), 4.23 (d, J = 9.3 Hz, 2H), 4.13 (d, J = 5.2 Hz, 8H), 3.44 (t, J = 9.1 Hz, 1H), 3.32-3.21 (m, 2H), 3.02 (s, 1H), 2.83 (d, J = 18.1 Hz, 1H), 2.78-2.65 (m, 2H), 2.52-2.35 (m, 3H), 2.23 (s, 1H), 1.94 (dtd, J = 12.6, 6.8, 5.9, 3.4 Hz, 1H), 1.56-1.41 (m, 3H). |
| B-10 | 1H NMR (400 MHz, Methanol-d4) δ 7.91 (d, J = 7.6 Hz, 1H), 7.86 (s, 1H), 7.63 (dd, J = 7.6, 1.8 Hz, 1H), 7.56-7.44 (m, 3H), 7.43-7.32 (m, 2H), 7.27 (d, J = 7.5 Hz, 1H), 6.67 (s, 1H), 4.51 (d, J = 10.9 Hz, 2H), 4.42-4.28 (m, 4H), 4.13 (d, J = 1.5 Hz, 9H), 3.28 (dd, J = 6.2, 3.7 Hz, 2H), 3.06-2.97 (m, 1H), 2.83 (q, J = 5.0 Hz, 1H), 2.79-2.65 (m, 1H), 2.52-2.35 (m, 3H), 2.29-2.15 (m, 1H), 2.00-1.88 (m, 1H), 1.63 (s, 3H). |
| B-11 | 1H NMR (400 MHz, Methanol-d4) δ 7.95-7.88 (m, 2H), 7.63 (dd, J = 7.7, 1.8 Hz, 1H), 7.53 (d, J = 7.5 Hz, 2H), 7.37 (dd, J = 9.8, 7.4 Hz, 3H), 7.27 (d, J = 7.5 Hz, 1H), 6.68 (s, 1H), 4.43-4.31 (m, 4H), 4.12 (d, J = 1.5 Hz, 7H), 3.63 (d, J = 12.4 Hz, 1H), 3.38 (d, J = 9.4 Hz, 2H), 3.28 (dd, J = 6.2, 4.0 Hz, 2H), 3.26-3.13 (m, 1H), 3.13-2.89 (m, 1H), 2.90-2.79 (m, 1H), 2.78-2.70 (m, 1H), 2.65 (d, J = 18.5 Hz, 2H), 2.51-2.34 (m, 3H), 2.26 (dt, J = 13.7, 7.1 Hz, 2H), 2.15-1.91 (m, 3H), 1.96-1.84 (m, 2H). |
| B-12 | ¹H NMR (400 MHz, Methanol-d4) δ 8.08 (s, 1H), 7.86 (d, J = 7.7 Hz, 1H), 7.59 (s, 1H), 7.48 (d, J = 7.6 Hz, 2H), 7.34 (d, J = 8.3 Hz, 2H), 7.23 (d, J = 7.4 Hz, 1H), 6.70 (s, 1H), 4.25 (s, 1H), 4.15 (d, J = 4.4 Hz, 3H), 4.09 (s, 2H), 3.48 (d, J = 1.6 Hz, 1H), 3.26-3.20 (m, 5H), 3.13 (d, J = 1.9 Hz, 1H), 2.39 (d, J = 6.7 Hz, 2H), 1.66 (t, J = 8.2 Hz, 4H), 1.56 (s, 3H), 1.02 (s, 6H). |
| B-13 | ¹H NMR (400 MHz, Methanol-d4) δ 8.09 (s, 1H), 7.86 (d, J = 7.5 Hz, 1H), 7.60 (dd, J = 7.6, 1.8 Hz, 1H), 7.48 (d, J = 7.2 Hz, 2H), 7.34 (d, J = 7.5 Hz, 2H), 7.24 (d, J = 7.5 Hz, 1H), 6.69 (s, 1H), 4.22 (d, J = 24.4 Hz, 4H), 4.09 (s, 4H), 3.48-3.38 (m, 2H), 3.27-3.11 (m, 5H), 2.72 (s, 1H), 2.44-2.32 (m, 3H), 2.06 (s, 2H), 1.93-1.82 (m, 2H), 1.66 (d, J = 13.2 Hz, 5H), 1.28 (s, 3H). |
| B-14 | 1H NMR (400 MHz, Methanol-d4) δ 8.03 (d, J = 7.7 Hz, 1H), 7.83 (s, 1H), 7.71 (dd, J = 7.7, 1.8 Hz, 1H), 7.59 (d, J = 7.7 Hz, 1H), 7.56-7.38 (m, 3H), 7.34 (t, J = 7.6 Hz, 1H), 7.25 (d, J = 7.3 Hz, 1H), 6.65 (s, 1H), 5.29 (s, 2H), 4.40 (s, 4H), 4.10 (s, 3H), 4.07 (t, J = 6.7 Hz, 1H), 2.71 (dd, J = 13.5, 6.6 Hz, 1H), 2.51-2.31 (m, 3H), 2.21 (s, 1H), 2.01-1.88 (m, 1H), 1.66-1.58 (m, 2H), 1.48-1.39 (m, 2H). |
| B-15 | ¹H NMR (400 MHz, Methanol-d₄) δ 7.89 (d, J = 7.6 Hz, 1H), 7.81 (s, 1H), 7.60 (dd, J = 7.7, 1.7 Hz, 1H), 7.48 (d, J = 7.1 Hz, 2H), 7.34 (dd, J = 17.8, 7.7 Hz, 2H), 7.24 (d, J = 7.4 Hz, 1H), 6.63 (s, 1H), 4.34 (d, J = 2.4 Hz, 2H), 3.95 (d, J = 11.4 Hz, 2H), 3.81 (t, J = 11.6 Hz, 2H), 3.28-3.15 (m, 8H), 2.46-2.34 (m, 3H), 2.28 (d, J = 12.6 Hz, 2H), 1.88 (ddd, J = 24.5, 11.6, 5.5 Hz, 3H), 1.65 (q, J = 8.3 Hz, 6H), 1.28 (s, 2H). |
| B-16 | ¹H NMR (400 MHz, Methanol-d₄) δ 7.89 (d, J = 7.5 Hz, 1H), 7.85 (s, 1H), 7.60 (dd, J = 7.7, 1.8 Hz, 2H), 7.49 (d, J = 7.3 Hz, 1H), 7.35 (dd, J = 14.3, 7.3 Hz, 2H), 7.24 (d, J = 7.5 Hz, 1H), 6.63 (s, 1H), 4.35 (d, J = 6.1 Hz, 2H), 4.10 (s, 3H), 4.07 (s, 1H), 3.69-3.61 (m, 1H), 3.27-3.18 (m, 7H), 2.21-2.10 (m, 2H), 1.96 (s, 1H), 1.65 (q, J = 8.2 Hz, 6H), 1.28 (s, 6H). |
| B-17 | ¹H NMR (400 MHz, Methanol-d₄) δ 7.86 (d, J = 6.9 Hz, 2H), 7.60 (dd, J = 7.5, 1.8 Hz, 1H), 7.50 (d, J = 7.5 Hz, 2H), 7.34 (t, J = 7.8 Hz, 2H), 7.24 (d, J = 7.5 Hz, 1H), 6.63 (s, 1H), 4.37 (d, J = 12.9 Hz, 4H), 4.27 (s, 1H), 4.11 (d, J = 10.2 Hz, 4H), 4.05-3.98 (m, 2H), 3.49-3.40 (m, 2H), 3.26-3.13 (m, 6H), 2.44-2.36 (m, 3H), 2.05 (s, 1H), 1.90 (s, 1H), 1.65 (q, J = 8.6 Hz, 6H), 1.30 (d, J = 9.5 Hz, 4H). |
| B-18 | 1H NMR (400 MHz, Methanol-d4) δ 7.90 (d, J = 7.5 Hz, 1H), 7.85 (s, 1H), 7.58 (dd, J = 7.7, 1.8 Hz, 2H), 7.49 (d, J = 7.3 Hz, 1H), 7.34 (dd, J = 14.3, 7.3 Hz, 2H), 7.24 (d, J = 7.5 Hz, 1H), 6.63 (s, 1H), 4.34 (d, J = 6.1 Hz, 2H), 4.10 (s, 3H), 4.07 (s, 1H), 3.69-3.61 (m, 1H), 3.27-3.18 (m, 7H), 2.21-2.10 (m, 2H), 1.96 (s, 1H), 1.65 (q, J = 8.2 Hz, 6H), 1.28 (s, 6H). |
| B-19 | 1H NMR (400 MHz, Methanol-d4) δ 8.03 (d, J = 7.7 Hz, 2H), 7.88 (s, 1H), 7.71 (dd, J = 7.7, 1.8 Hz, 1H), 7.59 (d, J = 7.5 Hz, 1H), 7.52 (dd, J = 11.8, 7.3 Hz, 2H), 7.36 (t, J = 7.7 Hz, 1H), 7.26 (d, J = 7.4 Hz, 1H), 6.66 (s, 1H), 5.29 (s, 2H), 4.38 (d, J = 12.0 Hz, 4H), 4.12 (s, 3H), 4.06 (q, J = 6.7 Hz, 1H), 2.78-2.63 (m, 1H), 2.51-2.31 (m, 3H), 2.22 (s, 1H), 1.98-1.86 (m, 1H). |
| B-20 | ¹H NMR (400 MHz, DMSO-d₆) δ 8.83 (s, 1H), 8.61 (s, 1H), 7.99-7.90 (m, 2H), 7.61 (d, J = 8.0 Hz, 1H), 7.55 (d, J = 7.5 Hz, 2H), 7.46 (s, 4H), 7.37 (dd, J = 15.9, 7.7 Hz, 2H), 7.28 (d, J = 7.4 Hz, 1H), 6.60 (s, 1H), 4.21 (s, 2H), 3.98 (dd, J = 10.0, 1.8 Hz, 6H), 3.88 (s, 1H), 3.21-2.60 (m, 4H) 2.55-2.49 (m, 7H), 2.23 (s, 6H), 2.16 (d, J = 19.1 Hz, 2H), 1.78 (s, 1H). |
| B-21 | ¹H NMR (400 MHz, DMSO-d₆) δ 10.37 (s, 1H), 9.91 (s, 1H), 9.81 (s, 1H), 8.99 (s, 1H), 8.05-7.91 (m, 2H), 7.59 (d, J = 7.2 Hz, 1H), 7.58-7.39 (m, 3H), 7.37 (t, J = 7.5 Hz, 1H), 7.28 (d, J = 7.5 Hz, 1H), 7.02-6.90 (m, 1H), 6.61 (d, J = 7.1 Hz, 1H), 4.51 (dd, J = 17.9, 5.2 Hz, 2H), 4.27 (dd, J = 17.1, 10.8 Hz, 3H), 4.26-4.13 (m, 1H), 4.00 (s, 4H), 3.65 (s, 3H), 3.18 (s, 1H), 2.87 (d, J = 4.0 Hz, 3H), 2.79-2.66 (m, 2H), 2.10 (s, 4H), 2.11-2.02 (m, 1H), 1.85 (s, 1H), 1.50-1.37 (m, 3H). |
| B-22 | ¹H NMR (400 MHz, Methanol-d₄) δ 7.93 (d, J = 7.5 Hz, 1H), 7.87 (s, 1H), 7.59 (d, J = 7.7, 1.8 Hz, 2H), 7.49 (d, J = 7.3 Hz, 1H), 7.34 (dd, J = 14.3, 7.3 Hz, 2H), 7.24 (d, J = 7.5 Hz, 1H), 6.63 (s, 1H), 4.56 (s, 2H), 4.02 (s, 2H), 3.25-3.21 (m, 6H), 1.95 (s, 3H), 1.66 (dt, J = 16.1, 8.0 Hz, 8H), 1.29-1.26 (m, 4H). |
| B-23 | 1H NMR (400 MHz, Methanol-d4) δ 7.93 (d, J = 6.1 Hz, 2H), 7.62 (dd, J = 7.7, 1.8 Hz, 1H), 7.56-7.42 (m, 3H), 7.39 (s, 2H), 7.36 (d, J = 7.8 Hz, 1H), 7.27 (d, J = 7.6 Hz, 1H), |

TABLE 2B-continued

| No. | NMR |
|---|---|
| | 6.68 (s, 1H), 4.73 (d, J = 3.6 Hz, 1H), 4.67 (d, J = 5.1 Hz, 1H), 4.51-4.31 (m, 5H), 4.13 (s, 6H), 3.93-3.82 (m, 1H), 3.72 (dd, J = 10.5, 5.2 Hz, 1H), 3.64 (d, J = 12.5 Hz, 1H), 3.51 (s, 1H), 3.04-2.97 (m, 1H), 2.92-2.83 (m, 1H), 2.83-2.70 (m, 1H), 2.47 (d, J = 14.8 Hz, 3H), 2.30-2.19 (m, 2H), 2.14-1.98 (m, 5H), 2.00-1.85 (m, 2H), 1.81-1.67 (m, 1H), 1.65 (td, J = 11.0, 10.6, 4.0 Hz, 1H), 1.58-1.41 (m, 1H). |
| B-26 | 1H NMR (400 MHz, DMSO-d6) δ 8.83 (s, 1H), 8.61 (s, 1H), 7.99-7.90 (m, 2H), 7.61 (d, J = 8.0 Hz, 1H), 7.55 (d, J = 7.5 Hz, 2H), 7.46 (s, 4H), 7.37 (dd, J = 15.9, 7.7 Hz, 2H), 7.28 (d, J = 7.4 Hz, 1H), 6.60 (s, 1H), 4.21 (s, 2H), 3.98 (dd, J = 10.0, 1.8 Hz, 6H), 3.88 (s, 1H), 3.21-2.60 (m, 4H) 2.55-2.49 (m, 7H), 2.23 (s, 6H), 2.16 (d, J = 19.1 Hz, 2H), 1.78 (s, 1H). |
| B-28 | $^1$H NMR (400 MHz, Methanol-d$_4$) δ 8.52 (d, J = 4.1 Hz, 1H), 7.88 (s, 2H), 7.73-7.30 (m, 4H), 7.25 (d, J = 7.5 Hz, 1H), 6.65 (s, 1H), 4.65-4.46 (m, 3H), 4.39 (s, 4H), 4.12 (q, J = 7.2, 4.4 Hz, 9H), 3.85-3.44 (m, 3H), 3.43-3.33 (m, 3H), 3.26-2.87 (m, 1H), 2.75 (d, J = 4.0 Hz, 5H), 2.58-2.07 (m, 4H), 2.03-1.83 (m, 1H). |
| B-29 | $^1$H NMR (400 MHz, Methanol-d$_4$) δ 8.71 (d, J = 1.8 Hz, 1H), 8.54 (d, J = 2.3 Hz, 1H), 8.17-8.08 (m, 2H), 7.91 (d, J = 7.6 Hz, 1H), 7.62 (dd, J = 7.6, 1.8 Hz, 1H), 7.51 (t, J = 7.6 Hz, 1H), 7.40 (dd, J = 17.0, 9.4 Hz, 2H), 7.26 (t, J = 11.7 Hz, 2H), 6.61 (s, 1H), 5.69 (s, 2H), 4.45 (s, 2H), 4.37 (d, J = 2.5 Hz, 2H), 4.12 (s, 3H), 3.30-3.23 (m, 4H), 2.57 (s, 1H), 2.49-2.34 (m, 2H), 2.10 (s, 4H), 1.98-1.90 (m, 1H), 1.68 (p, J = 7.9 Hz, 3H), 1.57-1.49 (m, 2H), 1.36-1.33 (m, 1H). |
| B-30 | 1H NMR (400 MHz, Methanol-d4) δ 8.03 (s, 1H), 7.89-7.79 (m, 3H), 7.73 (s, 1H), 7.61 (dd, J = 7.7, 1.8 Hz, 1H), 7.47 (d, J = 7.6 Hz, 1H), 7.38 (d, J = 7.6 Hz, 1H), 7.31-7.22 (m, 3H), 6.53 (s, 1H), 5.57 (s, 2H), 4.41 (s, 2H), 4.05 (s, 4H), 3.42 (s, 1H), 3.27-3.20 (m, 3H), 2.94 (t, J = 6.2 Hz, 2H), 2.39-2.31 (m, 3H), 1.87 (d, J = 15.2 Hz, 4H), 1.65 (q, J = 8.4 Hz, 4H), 1.30-1.26 (m, 7H). |
| B-31 | $^1$H NMR (400 MHz, Methanol-d$_4$) δ 7.97 (s, 1H), 7.88-7.78 (m, 3H), 7.73 (s, 1H), 7.59 (dd, J = 7.7, 1.8 Hz, 1H), 7.46 (d, J = 7.6 Hz, 1H), 7.38 (d, J = 7.6 Hz, 1H), 7.30-7.22 (m, 3H), 6.53 (s, 1H), 5.56 (s, 2H), 4.41 (s, 2H), 4.05 (s, 4H), 3.42 (s, 1H), 3.27-3.20 (m, 3H), 2.94 (t, J = 6.2 Hz, 2H), 2.39-2.31 (m, 3H), 1.87 (d, J = 15.2 Hz, 4H), 1.65 (q, J = 8.4 Hz, 4H), 1.30-1.26 (m, 7H). |
| B-32 | $^1$H NMR (400 MHz, Methanol-d$_4$) δ 8.67 (s, 1H), 8.51 (d, J = 2.3 Hz, 1H), 8.10 (s, 1H), 7.90 (d, J = 7.6 Hz, 2H), 7.62 (dd, J = 7.6, 1.7 Hz, 1H), 7.51 (t, J = 7.6 Hz, 1H), 7.37 (d, J = 7.5 Hz, 2H), 7.27 (d, J = 17.2 Hz, 2H), 6.49 (s, 1H), 5.60 (s, 2H), 4.33 (s, 2H), 4.12 (s, 3H), 3.27-3.23 (m, 4H), 2.44-2.38 (m, 2H), 2.07 (dd, J = 15.3, 6.6 Hz, 1H), 1.96-1.90 (m, 1H), 1.70-1.64 (m, 4H), 1.32 (d, J = 8.6 Hz, 6H). |
| B-33 | $^1$H NMR (400 MHz, Methanol-d$_4$) δ 8.60 (s, 1H), 8.47 (s, 1H), 8.00 (s, 1H), 7.87 (dd, J = 14.4, 8.5 Hz, 2H), 7.66-7.59 (m, 1H), 7.51 (t, J = 7.6 Hz, 1H), 7.37 (d, J = 7.5 Hz, 3H), 7.27 (d, J = 7.0 Hz, 1H), 6.59 (s, 1H), 5.65 (s, 2H), 4.45 (s, 2H), 4.30 (s, 2H), 4.12 (s, 4H), 3.50 (dd, J = 3.3, 1.7 Hz, 2H), 3.28-3.22 (m, 5H), 2.61 (d, J = 20.4 Hz, 2H), 2.43-2.38 (m, 2H), 2.18-2.09 (m, 2H), 2.01 (s, 1H), 1.90 (m, 3H), 1.68 (t, J = 8.3 Hz, 5H). |
| B-34 | $^1$H NMR (400 MHz, Methanol-d$_4$) δ 8.56 (s, 1H), 7.84 (d, J = 2.8 Hz, 1H), 7.68 (dd, J = 7.7, 1.8 Hz, 2H), 7.61-7.48 (m, 3H), 7.41 (dt, J = 27.9, 8.1 Hz, 2H), 7.34-7.23 (m, 1H), 6.67 (s, 1H), 4.55 (d, J = 3.9 Hz, 2H), 4.25-3.97 (m, 1H), 3.70-3.47 (m, 1H), 3.45-3.36 (m, 2H), 3.01 (s, 1H), 2.92-2.56 (m, 2H), 2.54-2.35 (m, 3H), 2.20 (qd, J = 8.8, 2.8 Hz, 2H), 1.96 (d, J = 4.9 Hz, 5H). |
| B-35 | $^1$H NMR (400 MHz, Methanol-d$_4$) δ 7.89 (d, J = 7.6 Hz, 1H), 7.81 (s, 1H), 7.60 (t, J = 7.7, 1.8 Hz, 1H), 7.49 (t, J = 6.9 Hz, 2H), 7.39-7.31 (m, 2H), 7.25-7.21 (m, 1H), 6.63 (s, 1H), 4.34 (d, J = 2.6 Hz, 2H), 4.16-3.98 (m, 8H), 3.27-3.17 (m, 3H), 2.95 (d, J = 26.1 Hz, 1H), 2.69 (dd, J = 13.9, 7.3 Hz, 2H), 2.62-2.53 (m, 2H), 2.45-2.37 (m, 3H), 2.28-2.15 (m, 2H), 2.03 (dq, J = 9.6, 5.3, 4.2 Hz, 1H), 1.94-1.87 (m, 1H), 1.66 (dt, J = 16.1, 7.8 Hz, 2H), 1.28 (s, 1H). |
| B-36 | $^1$H NMR (400 MHz, Methanol-d$_4$) δ 8.03 (s, 1H), 7.88 (d, J = 7.6 Hz, 1H), 7.60 (dd, J = 7.7, 1.8 Hz, 1H), 7.48 (dd, J = 11.8, 7.3 Hz, 2H), 7.34 (dd, J = 17.2, 7.6 Hz, 2H), 7.23 (d, J = 7.5 Hz, 1H), 6.68 (s, 1H), 4.33 (d, J = 3.1 Hz, 2H), 4.15 (s, 2H), 4.10 (s, 4H), 3.27-3.19 (m, 4H), 2.71 (s, 2H), 2.47-2.36 (m, 3H), 2.19 (s, 1H), 1.94-1.88 (m, 1H), 1.69-1.63 (m, 1H), 1.47-1.39 (m, 3H), 1.28 (s, 1H), 1.26-1.19 (m, 2H). |
| B-37 | 1H NMR (400 MHz, Methanol-d4) δ 8.54 (s, 1H), 7.67 (dd, J = 7.6, 1.8 Hz, 1H), 7.61-7.41 (m, 3H), 7.38 (t, J = 7.5 Hz, 1H), 7.28 (d, J = 7.5 Hz, 1H), 6.63 (s, 1H), 4.61-4.28 (m, 4H), 4.14 (s, 3H), 4.13 (s, 3H), 4.13-4.06 (m, 1H), 4.07-2.32 (m, 15H), 2.34-2.19 (m, 1H), 2.05-1.92 (m, 1H). |
| B-38 | 1H NMR (400 MHz, Methanol-d4) δ 8.54 (s, 1H), 7.67 (dd, J = 7.6, 1.8 Hz, 1H), 7.61-7.40 (m, 3H), 7.37 (t, J = 7.6 Hz, 1H), 7.28 (d, J = 7.5 Hz, 1H), 6.69-6.56 (m, 1H), 4.60-4.45 (m, 2H), 4.45-4.27 (m, 2H), 4.15 (s, 3H), 4.14-4.01 (m, 2H), 4.12 (s, 3H), 3.42-3.20 (m, 4H), 3.12-2.66 (m, 3H), 2.52-2.31 (m, 6H), 2.32-2.18 (m, 2H), 2.05-1.86 (m, 2H). |
| B-39 | 1H NMR (400 MHz, Methanol-d4) δ 7.94 (s, 1H), 7.55-7.45 (m, 3H), 7.48-7.36 (m, 2H), 7.36 (t, J = 7.5 Hz, 1H), 7.29-7.20 (m, 2H), 7.16 (dd, J = 7.7, 1.5 Hz, 1H), 6.68 (s, 1H), 4.42 (d, J = 7.0 Hz, 2H), 4.37 (d, J = 3.6 Hz, 2H), 4.13 (s, 3H), 4.08 (d, J = 6.6 Hz, 1H), 4.01 (s, 2H), 3.64 (d, J = 12.4 Hz, 1H), 3.51 (s, 1H), 3.39 (d, J = 6.9 Hz, 1H), 3.29-3.18 (m, 2H), 3.08-2.93 (m, 2H), 2.87-2.65 (m, 3H), 2.51-2.34 (m, 4H), 2.29-2.21 (m, 2H), 2.16-2.01 (m, 4H), 2.01-1.80 (m, 2H). |
| B-40 | 1H NMR (400 MHz, Methanol-d4) δ 7.94-7.83 (m, 2H), 7.60 (dd, J = 7.6, 1.8 Hz, 1H), 7.48 (d, J = 8.1 Hz, 2H), 7.35 (d, J = 7.8 Hz, 2H), 7.24 (d, J = 7.6 Hz, 2H), 6.61 (s, 1H), 4.55 (d, J = 7.2 Hz, 2H), 4.34 (d, J = 26.8 Hz, 3H), 4.09 (s, 3H), 3.48 (s, 1H), 3.23 (dd, J = 11.0, 6.3 Hz, 5H), 2.74-2.61 (m, 2H), 2.46-2.35 (m, 3H), 2.20 (d, J = 5.3 Hz, 1H), 2.06-1.90 (m, 4H), 1.66 (t, J = 8.5 Hz, 4H), 1.44-1.26 (m, 3H). |
| B-41 | 1H NMR (400 MHz, Methanol-d4) δ 7.90 (s, 1H), 7.50 (t, J = 9.2 Hz, 3H), 7.46-7.32 (m, 3H), 7.29-7.20 (m, 2H), 7.16 (dd, J = 7.5, 1.5 Hz, 1H), 6.67 (s, 1H), 4.43-4.31 (m, 3H), 4.13 (s, 3H), 4.11-4.04 (m, 1H), 4.01 (s, 3H), 3.92-3.84 (m, 1H), 3.81-3.74 (m, 1H), 3.60 (ddd, J = 22.1, 13.3, 5.1 Hz, 3H), 3.31-3.18 (m, 3H), 3.07-2.92 (m, 2H), 2.91-2.69 (m, 2H), 2.57 (s, 1H), 2.50-2.34 (m, 3H), 2.30-2.21 (m, 2H), 2.01-1.87 (m, 1H). |

TABLE 2B-continued

| No. | NMR |
|---|---|
| B-42 | 1H NMR (400 MHz, Methanol-d4) δ 7.86 (s, 1H), 7.55-7.45 (m, 3H), 7.43 (dd, J = 7.7, 1.9 Hz, 1H), 7.41-7.29 (m, 2H), 7.29-7.20 (m, 2H), 7.16 (dd, J = 7.7, 1.5 Hz, 1H), 6.66 (s, 1H), 4.38 (q, J = 4.9, 3.8 Hz, 7H), 4.12 (s, 3H), 4.13-4.05 (m, 1H), 4.01 (s, 3H), 3.72 (p, J = 8.4 Hz, 1H), 3.30-3.18 (m, 2H), 3.03-2.91 (m, 2H), 2.85-2.77 (m, 2H), 2.77-2.65 (m, 1H), 2.53-2.34 (m, 2H), 2.30-2.18 (m, 1H), 2.01-1.86 (m, 1H). |
| B-43 | 1H NMR (400 MHz, Methanol-d4) δ 8.56 (s, 1H), 7.86 (s, 1H), 7.68 (dd, J = 7.6, 1.8 Hz, 1H), 7.61-7.43 (m, 3H), 7.38 (t, J = 7.6 Hz, 1H), 7.28 (d, J = 7.6 Hz, 1H), 6.67 (s, 1H), 4.62-4.48 (m, 2H), 4.39 (d, J = 5.8 Hz, 4H), 4.14 (d, J = 8.3 Hz, 7H), 3.72 (p, J = 8.4 Hz, 1H), 3.45-3.34 (m, 2H), 3.05-2.93 (m, 2H), 2.85-2.76 (m, 2H), 2.78-2.65 (m, 1H), 2.54-2.34 (m, 2H), 2.31-2.17 (m, 2H), 2.08-1.93 (m, 1H). |
| B-44 | 1H NMR (400 MHz, Methanol-d4) δ 8.54 (s, 1H), 7.66 (dd, J = 7.7, 1.8 Hz, 1H), 7.58-7.40 (m, 3H), 7.37 (t, J = 7.6 Hz, 1H), 7.28 (d, J = 7.5 Hz, 1H), 6.68-6.58 (m, 1H), 4.62-4.18 (m, 8H), 4.14 (s, 3H), 4.13-4.07 (m, 1H), 4.12 (s, 3H), 3.83-3.63 (m, 1H), 3.42-3.27 (m, 2H), 3.11-2.67 (m, 3H), 2.52-2.36 (m, 3H), 2.34-2.19 (m, 1H), 2.06-1.86 (m, 1H). |
| B-45 | 1H NMR (400 MHz, Methanol-d4) δ 8.54 (s, 1H), 7.67 (dd, J = 7.6, 1.8 Hz, 1H), 7.61-7.42 (m, 3H), 7.38 (t, J = 7.6 Hz, 1H), 7.28 (d, J = 7.5 Hz, 1H), 6.70-6.60 (m, 1H), 4.61-4.39 (m, 4H), 4.15 (s, 3H), 4.13 (s, 3H), 4.13-4.07 (m, 1H), 3.81-3.71 (m, 1H), 3.62-1.78 (m, 20H). |
| B-46 | $^1$H NMR (400 MHz, Methanol-$d_4$) δ 7.94-7.83 (m, 2H), 7.60 (dd, J = 7.6, 1.8 Hz, 1H), 7.48 (d, J = 8.1 Hz, 2H), 7.35 (d, J = 7.8 Hz, 2H), 7.24 (d, J = 7.6 Hz, 1H), 6.61 (s, 1H), 4.55 (d, J = 7.2 Hz, 2H), 4.34 (d, J = 26.8 Hz, 3H), 4.09 (s, 3H), 3.48 (s, 1H), 3.23 (dd, J = 11.0, 6.3 Hz, 5H), 2.74-2.61 (m, 2H), 2.46-2.35 (m, 3H), 2.20 (d, J = 5.3 Hz, 1H), 2.06-1.90 (m, 5H), 1.66 (t, J = 8.5 Hz, 4H), 1.44-1.26 (m, 6H). |
| B-47 | 1H NMR (400 MHz, Methanol-d4) δ 7.93-7.83 (m, 2H), 7.60 (dd, J = 7.6, 1.8 Hz, 1H), 7.49 (d, J = 8.1 Hz, 2H), 7.35 (d, J = 7.8 Hz, 2H), 7.24 (d, J = 7.6 Hz, 1H), 6.60 (s, 1H), 4.55 (d, J = 7.2 Hz, 2H), 4.34 (d, J = 26.8 Hz, 3H), 4.09 (s, 3H), 3.48 (s, 1H), 3.23 (dd, J = 11.0, 6.3 Hz, 4H), 2.74-2.61 (m, 2H), 2.46-2.35 (m, 2H), 2.20 (d, J = 5.3 Hz, 1H), 2.06-1.90 (m, 3H), 1.66 (t, J = 8.5 Hz, 4H), 1.44-1.26 (m, 6H). |
| B-48 | 1H NMR (400 MHz, Methanol-d4) δ 8.58 (s, 1H), 8.46 (s, 1H), 8.00 (s, 1H), 7.82 (dd, J = 14.4, 8.5 Hz, 2H), 7.66-7.58 (m, 1H), 7.49 (t, J = 7.6 Hz, 1H), 7.35 (d, J = 7.5 Hz, 3H), 7.27 (d, J = 7.0 Hz, 1H), 6.59 (s, 1H), 5.65 (s, 2H), 4.45 (s, 2H), 4.30 (s, 2H), 4.12 (s, 4H), 3.50 (dd, J = 3.3, 1.7 Hz, 2H), 3.28-3.21 (m, 5H), 2.60 (d, J = 20.4 Hz, 2H), 2.43-2.38 (m, 2H), 2.18-2.09 (m, 2H), 2.01 (s, 1H), 1.90 (s, 3H), 1.68 (t, J = 8.3 Hz, 5H). |
| B-49 | 1H NMR (400 MHz, Methanol-d4) δ 8.58 (s, 1H), 8.46 (s, 1H), 8.00 (s, 1H), 7.82 (dd, J = 14.4, 8.5 Hz, 2H), 7.66-7.58 (m, 1H), 7.49 (t, J = 7.6 Hz, 1H), 7.35 (d, J = 7.5 Hz, 3H), 7.27 (d, J = 7.0 Hz, 1H), 6.59 (s, 1H), 5.65 (s, 2H), 4.45 (s, 2H), 4.30 (s, 2H), 4.12 (s, 4H), 3.50 (dd, J = 3.3, 1.7 Hz, 2H), 3.28-3.21 (m, 3H), 2.60 (d, J = 20.4 Hz, 2H), 2.43-2.38 (m, 1H), 2.18-2.09 (m, 1H), 2.01 (s, 1H), 1.90 (s, 3H), 1.68 (t, J = 8.3 Hz, 5H). |
| B-50 | 1H NMR (400 MHz, Methanol-d4) δ 7.97-7.86 (m, 2H), 7.63 (dd, J = 7.7, 1.8 Hz, 1H), 7.52 (d, J = 7.6 Hz, 2H), 7.49-7.34 (m, 3H), 7.27 (d, J = 7.3 Hz, 1H), 6.68 (s, 1H), 4.44 (d, J = 13.5 Hz, 1H), 4.43-4.31 (m, 2H), 4.26 (d, J = 13.2 Hz, 2H), 4.12 (d, J = 8.6 Hz, 6H), 3.64 (d, J = 12.3 Hz, 1H), 3.24 (d, J = 9.5 Hz, 3H), 3.04-2.93 (m, 2H), 2.89-2.79 (m, 2H), 2.75 (d, J = 9.1 Hz, 1H), 2.46-2.40 (m, 2H), 2.25 (dd, J = 16.2, 6.2 Hz, 2H), 2.17-2.02 (m, 4H), 1.95 (dd, J = 11.0, 5.9 Hz, 2H), 1.92-1.80 (m, 2H), 1.72-1.36 (m, 4H). |
| B-51 | 1H NMR (400 MHz, Methanol-d4) δ 7.94 (t, J = 3.8 Hz, 2H), 7.65 (dd, J = 7.7, 1.8 Hz, 1H), 7.53 (d, J = 7.3 Hz, 2H), 7.49-7.33 (m, 3H), 7.28 (d, J = 7.5 Hz, 1H), 6.68 (s, 1H), 4.59 (d, J = 18.2 Hz, 2H), 4.45 (dd, J = 23.7, 6.0 Hz, 2H), 4.12 (d, J = 5.0 Hz, 6H), 3.74-3.60 (m, 3H), 3.51 (s, 1H), 3.38 (s, 1H), 2.99 (d, J = 16.9 Hz, 1H), 2.81-2.70 (m, 1H), 2.49-2.39 (m, 2H), 2.28-2.08 (m, 3H), 2.14-1.98 (m, 5H), 2.00-1.93 (m, 3H), 1.93-1.82 (m, 2H). |
| B-52 | 1H NMR (400 MHz, Methanol-d4) δ 7.97-7.86 (m, 2H), 7.63 (dd, J = 7.7, 1.8 Hz, 1H), 7.57-7.40 (m, 3H), 7.36 (d, J = 7.0 Hz, 2H), 7.27 (d, J = 7.6 Hz, 1H), 6.68 (s, 1H), 4.48-4.34 (m, 3H), 4.36-4.24 (m, 2H), 4.12 (d, J = 8.9 Hz, 6H), 3.64 (d, J = 12.6 Hz, 1H), 3.50 (p, J = 4.6 Hz, 2H), 3.46-3.33 (m, 2H), 3.07-2.96 (m, 2H), 2.90-2.81 (m, 2H), 2.83-2.65 (m, 2H), 2.52-2.35 (m, 2H), 2.28-2.18 (m, 2H), 2.21-1.98 (m, 3H), 2.00-1.78 (m, 3H), 1.79-1.66 (m, 1H), 1.37-1.28 (m, 1H). |
| B-53 | $^1$H NMR (400 MHz, Methanol-$d_4$) δ 7.89 (d, J = 7.6 Hz, 1H), 7.82 (s, 1H), 7.60 (dd, J = 7.6, 1.8 Hz, 1H), 7.49 (d, J = 6.0 Hz, 2H), 7.34 (dd, J = 14.2, 7.4 Hz, 2H), 7.24 (d, J = 7.5 Hz, 1H), 6.63 (s, 1H), 4.33 (d, J = 2.4 Hz, 2H), 4.10 (d, J = 4.0 Hz, 6H), 3.64 (q, J = 6.9 Hz, 1H), 3.27-3.20 (m, 5H), 3.06-3.00 (m, 1H), 2.86-2.62 (m, 3H), 2.45-2.37 (m, 2H), 2.19 (d, J = 9.4 Hz, 2H), 2.09-1.97 (m, 2H), 1.92 (q, J = 5.8 Hz, 2H), 1.66 (p, J = 7.8 Hz, 4H). |
| B-54 | $^1$H NMR (400 MHz, Methanol-$d_4$) δ 7.89 (d, J = 7.6 Hz, 1H), 7.81 (s, 1H), 7.60 (dd, J = 7.6, 1.8 Hz, 1H), 7.48 (d, J = 7.5 Hz, 2H), 7.34 (dd, J = 17.8, 7.6 Hz, 2H), 7.24 (d, J = 7.5 Hz, 1H), 6.63 (s, 1H), 4.36-4.27 (m, 3H), 4.09 (d, J = 6.8 Hz, 5H), 3.28-3.18 (m, 4H), 2.95 (d, J = 21.7 Hz, 1H), 2.69 (dd, J = 13.5, 6.8 Hz, 1H), 2.49-2.34 (m, 3H), 2.24-2.15 (m, 1H), 1.95-1.87 (m, 1H), 1.70-1.61 (m, 3H), 1.44-1.46 (m, 2H), 1.33-1.26 (m, 2H). |
| B-55 | $^1$H NMR (400 MHz, Methanol-$d_4$) δ 8.03 (s, 1H), 7.88 (d, J = 7.5 Hz, 1H), 7.60 (dd, J = 7.6, 1.8 Hz, 1H), 7.50 (t, J = 7.9 Hz, 2H), 7.37 (t, J = 6.8 Hz, 2H), 7.29-7.24 (m, 1H), 6.69 (s, 1H), 5.35-5.24 (m, 1H), 4.42 (s, 2H), 4.32 (d, J = 2.6 Hz, 2H), 4.10 (s, 4H), 3.50-3.42 (m, 2H), 3.25-3.21 (m, 5H), 2.79 (s, 2H), 2.42-2.37 (m, 2H), 2.22 (s, 1H), 2.05 (d, J = 12.7 Hz, 2H), 1.97-1.90 (m, 4H), 1.69-1.63 (m, 4H). |
| B-56 | $^1$H NMR (400 MHz, Methanol-$d_4$) δ 8.59 (d, J = 6.9 Hz, 2H), 8.14-8.06 (m, 1H), 7.88 (d, J = 7.5 Hz, 1H), 7.77 (s, 1H), 7.60 (dd, J = 7.7, 1.8 Hz, 1H), 7.49 (t, J = 7.6 Hz, 1H), 7.43-7.19 (m, 4H), 6.64 (s, 1H), 6.54 (s, 1H), 5.62 (s, 2H), 4.42 (s, 2H), 4.30 (d, J = 2.8 Hz, 2H), 4.09 (s, 3H), 3.53-3.42 (m, 2H), 3.27-3.11 (m, 3H), 2.65 (d, J = 7.7 Hz, 4H), 2.46-2.30 (m, 3H), 2.20-1.77 (m, 8H), 1.66 (dt, J = 16.1, 7.9 Hz, 2H), 1.30 (d, J = 11.3 Hz, 3H). |

TABLE 2B-continued

| No. | NMR |
|---|---|
| B-57 | 1H NMR (400 MHz, Methanol-d4) δ 7.94 (s, 1H), 7.66-7.19 (m, 7H), 6.68 (s, 1H), 4.71-3.44 (m, 16H), 3.15-1.75 (m, 16H), 1.57 (d, J = 14.9 Hz, 3H). |
| B-58 | 1H NMR (400 MHz, Methanol-d4) δ 7.90 (s, 1H), 7.60 (dd, J = 7.7, 1.8 Hz, 1H), 7.56-7.19 (m, 6H), 6.68 (s, 1H), 4.68-3.41 (m, 16H), 3.12-2.11 (m, 12H), 1.57 (d, J = 14.9 Hz, 3H). |
| B-59 | 1H NMR (400 MHz, Methanol-d4) δ 7.86 (s, 1H), 7.60 (dd, J = 7.6, 1.8 Hz, 1H), 7.43 (dt, J = 57.1, 7.5 Hz, 4H), 7.26 (d, J = 6.9 Hz, 2H), 6.66 (s, 1H), 4.70-3.55 (m, 21H), 3.11-2.12 (m, 5H), 1.57 (d, J = 14.6 Hz, 3H). |
| B-60 | 1H NMR (400 MHz, Methanol-d4) δ 7.90 (s, 1H), 7.60 (dd, J = 7.7, 1.8 Hz, 1H), 7.44 (dt, J = 56.4, 7.8 Hz, 4H), 7.27 (d, J = 6.9 Hz, 2H), 6.68 (s, 1H), 4.71-4.01 (m, 14H), 3.99-2.12 (m, 14H), 1.57 (d, J = 14.8 Hz, 3H). |
| B-61 | 1H NMR (400 MHz, Methanol-d4) δ 8.18 (s, 1H), 7.91 (d, J = 7.6 Hz, 1H), 7.63 (dd, J = 7.7, 1.8 Hz, 1H), 7.51 (d, J = 7.5 Hz, 2H), 7.49-7.33 (m, 3H), 7.27 (d, J = 7.4 Hz, 1H), 6.74 (s, 1H), 4.54-4.40 (m, 2H), 4.37 (d, J = 2.7 Hz, 2H), 4.20 (s, 3H), 4.13 (s, 3H), 4.07 (q, J = 6.7 Hz, 1H), 3.65 (d, J = 12.3 Hz, 1H), 3.52 (s, 1H), 3.39 (s, 1H), 3.32-3.21 (m, 2H), 3.03 (s, 1H), 2.95 (d, J = 13.8 Hz, 1H), 2.93-2.83 (m, 1H), 2.76 (s, 3H), 2.52-2.35 (m, 4H), 2.28-2.16 (m, 1H), 2.08 (dd, J = 16.0, 8.4 Hz, 3H), 2.00-1.89 (m, 2H), 1.87 (s, 1H). |
| B-62 | 1H NMR (400 MHz, Methanol-d4) δ 8.13 (s, 1H), 7.91 (d, J = 7.6 Hz, 1H), 7.63 (dd, J = 7.6, 1.8 Hz, 1H), 7.51 (d, J = 7.5 Hz, 2H), 7.49-7.32 (m, 3H), 7.27 (d, J = 7.4 Hz, 1H), 6.73 (s, 1H), 4.46-4.31 (m, 4H), 4.21 (s, 4H), 4.13 (s, 3H), 4.07 (q, J = 6.6 Hz, 1H), 3.89 (s, 1H), 3.78 (s, 1H), 3.62 (s, 2H), 3.32-3.21 (m, 2H), 3.07-3.00 (m, 1H), 3.01-2.82 (m, 1H), 2.76 (s, 2H), 2.63-2.51 (m, 1H), 2.52-2.35 (m, 3H), 2.28-2.16 (m, 1H), 2.02-1.88 (m, 1H). |
| B-63 | 1H NMR (400 MHz, Methanol-d4) δ 8.09 (s, 1H), 7.91 (d, J = 7.6 Hz, 1H), 7.63 (dd, J = 7.6, 1.8 Hz, 1H), 7.52 (dd, J = 11.4, 7.4 Hz, 2H), 7.48-7.32 (m, 3H), 7.27 (d, J = 7.5 Hz, 1H), 6.72 (s, 1H), 4.46-4.28 (m, 7H), 4.20 (s, 3H), 4.13 (s, 3H), 4.12-4.02 (m, 1H), 3.72 (p, J = 8.4 Hz, 1H), 3.28 (dd, J = 6.2, 3.8 Hz, 2H), 3.02 (s, 1H), 2.86 (s, 1H), 2.75 (s, 2H), 2.52-2.35 (m, 3H), 2.27-2.15 (m, 1H), 1.94 (tdd, J = 9.3, 6.7, 3.2 Hz, 1H). |
| B-64 | 1H NMR (400 MHz, Methanol-d4) δ 7.93-7.79 (m, 2H), 7.60 (dd, J = 7.6, 1.8 Hz, 1H), 7.49 (s, 2H), 7.44-7.30 (m, 4H), 7.25 (d, J = 7.5 Hz, 1H), 6.65 (s, 1H), 4.47-4.24 (m, 5H), 4.11 (d, J = 5.2 Hz, 8H), 3.47 (s, 2H), 3.27-3.21 (m, 2H), 3.08-2.51 (m, 3H), 2.49-2.30 (dd, J = 46.8 Hz, 2H), 2.15 (d, J = 19.4 Hz, 5H), 1.93 (d, J = 19.4 Hz, 5H). |
| B-65 | ¹H NMR (400 MHz, Methanol-d₄) δ 8.99 (s, 1H), 8.87 (s, 1H), 8.39 (s, 1H), 7.97 (s, 1H), 7.91 (d, J = 7.5 Hz, 1H), 7.63 (dd, J = 7.6, 1.8 Hz, 1H), 7.52 (t, J = 7.6 Hz, 1H), 7.41 (dd, J = 19.8, 7.5 Hz, 2H), 7.35-7.23 (m, 2H), 6.56 (s, 1H), 5.68 (s, 2H), 4.46 (s, 2H), 4.36 (d, J = 2.6 Hz, 2H), 4.12 (s, 3H), 3.74-3.43 (m, 4H), 3.25 (dd, J = 8.0, 4.1 Hz, 5H), 2.58 (s, 1H), 2.45-2.39 (m, 2H), 2.16-2.07 (m, 1H), 1.94 (q, J = 6.9, 6.4 Hz, 1H), 1.69 (dd, J = 10.4, 6.2 Hz, 5H). |
| B-66 | ¹H NMR (400 MHz, Methanol-d₄) δ 8.99 (s, 1H), 8.87 (s, 1H), 8.39 (s, 1H), 7.97 (s, 1H), 7.91 (d, J = 7.5 Hz, 1H), 7.63 (dd, J = 7.6, 1.8 Hz, 1H), 7.52 (t, J = 7.6 Hz, 1H), 7.41 (dd, J = 19.8, 7.5 Hz, 2H), 7.35-7.23 (m, 2H), 6.56 (s, 1H), 5.68 (s, 2H), 4.46 (s, 2H), 4.36 (d, J = 2.6 Hz, 2H), 4.12 (s, 3H), 3.73-3.43 (m, 4H), 3.24 (dd, J = 8.0, 4.1 Hz, 5H), 2.58 (s, 1H), 2.45-2.39 (m, 2H), 2.16-2.07 (m, 1H), 1.94 (q, J = 6.7, 6.4 Hz, 1H), 1.71 (dd, J = 10.4, 6.2 Hz, 5H). |
| B-67 | 1H NMR (400 MHz, Methanol-d4) δ 8.56 (s, 1H), 8.47 (s, 1H), 8.00 (s, 1H), 7.82 (dd, J = 14.2, 8.5 Hz, 2H), 7.63-7.57 (m, 1H), 7.49 (t, J = 7.6 Hz, 1H), 7.35 (d, J = 7.5 Hz, 3H), 7.27 (d, J = 7.0 Hz, 1H), 6.59 (s, 1H), 5.64 (s, 2H), 4.45 (s, 2H), 4.30 (s, 2H), 4.12 (s, 4H), 3.50 (dd, J = 3.3, 1.7 Hz, 2H), 3.28-3.21 (m, 5H), 2.60 (d, J = 20.4 Hz, 2H), 2.43-2.38 (m, 2H), 2.18-2.09 (m, 2H), 2.01 (s, 1H), 1.90 (s, 3H), 1.68 (t, J = 8.3 Hz, 5H). |
| B-68 | 1H NMR (400 MHz, Methanol-d4) δ 8.00 (d, J = 7.6 Hz, 1H), 7.97-7.81 (m, 3H), 7.67-7.55 (m, 3H), 7.48-7.36 (m, 2H), 6.70 (t, J = 5.9 Hz, 1H), 4.49-4.33 (m, 4H), 4.21 (s, 3H), 4.13 (s, 4H), 3.64 (d, J = 12.4 Hz, 1H), 3.51 (s, 1H), 3.43-3.36 (m, 1H), 3.34-3.22 (m, 3H), 3.08 (ddd, J = 14.0, 8.5, 5.1 Hz, 1H), 3.00-2.87 (m, 1H), 2.78 (dq, J = 13.6, 7.4 Hz, 1H), 2.55-2.33 (m, 4H), 2.34-2.19 (m, 1H), 2.06 (ddt, J = 12.3, 8.5, 3.6 Hz, 4H), 2.00-1.82 (m, 2H). |
| B-69 | 1H NMR (400 MHz, Methanol-d4) δ 8.74 (s, 1H), 8.00 (dd, J = 7.9, 1.2 Hz, 1H), 7.97-7.85 (m, 3H), 7.74-7.64 (m, 2H), 7.61 (dd, J = 6.8, 1.8 Hz, 1H), 7.49-7.38 (m, 2H), 6.71 (dd, J = 6.8, 4.8 Hz, 1H), 4.58 (d, J = 3.7 Hz, 2H), 4.39 (s, 2H), 4.22 (s, 4H), 4.14 (s, 4H), 3.82-3.72 (m, 1H), 3.65-3.57 (m, 2H), 3.45-3.34 (m, 4H), 3.09 (ddd, J = 14.1, 8.5, 5.1 Hz, 1H), 2.94 (dt, J = 15.7, 7.3 Hz, 1H), 2.78 (dq, J = 13.5, 7.4 Hz, 1H), 2.55-2.34 (m, 4H), 2.34-2.21 (m, 2H), 2.06-1.93 (m, 1H). |
| B-70 | ¹H NMR (400 MHz, Methanol-d₄) δ 7.89 (d, J = 7.1 Hz, 2H), 7.60 (dd, J = 7.6, 1.8 Hz, 1H), 7.55-7.30 (m, 4H), 7.25 (d, J = 7.5 Hz, 1H), 6.65 (s, 1H), 4.44 (s, 2H), 4.34 (d, J = 2.6 Hz, 2H), 4.11 (dd, J = 4.4, 1.5 Hz, 7H), 3.99-3.57 (m, 4H), 3.26 (dd, J = 6.0, 3.7 Hz, 4H), 3.13-2.62 (m, 4H), 2.56-2.29 (m, 4H), 2.29-1.82 (m, 4H). |
| B-71 | ¹H NMR (400 MHz, Methanol-d₄) δ 8.01-7.79 (m, 3H), 7.60 (dd, J = 7.6, 1.8 Hz, 1H), 7.50 (d, J = 7.0 Hz, 2H), 7.35 (dd, J = 11.9, 7.4 Hz, 2H), 7.25 (d, J = 7.5 Hz, 1H), 6.66 (s, 1H), 4.55-4.25 (m, 4H), 4.10 (d, J = 3.0 Hz, 7H), 3.74 (s, 1H), 3.28-3.10 (m, 2H), 2.69 (d, J = 31.8 Hz, 2H), 2.55-2.30 (m, 3H), 2.20 (s, 4H), 2.13-1.82 (m, 8H). |
| B-72 | ¹H NMR (400 MHz, Methanol-d₄) δ 8.02-7.80 (m, 2H), 7.60 (dd, J = 7.6, 1.8 Hz, 1H), 7.56-7.30 (m, 7H), 7.24 (d, J = 7.6 Hz, 1H), 6.65 (s, 1H), 4.64-4.25 (m, 4H), 4.10 (s, 7H), 4.10-3.43 (m, 2H), 3.26 (dd, J = 6.2, 3.9 Hz, 2H), 2.65 (s, 4H), 2.55-2.30 (m, 4H), 2.21 (s, 1H), 2.04-1.83 (m, 1H), 0.95 (d, J = 64.2 Hz, 6H). |
| B-73 | 1H NMR (400 MHz, Methanol-d4) δ 8.00 (d, J = 7.6 Hz, 1H), 7.97-7.83 (m, 3H), 7.69-7.55 (m, 3H), 7.48-7.36 (m, 2H), 6.74-6.66 (m, 1H), 4.39 (d, J = 1.9 Hz, 3H), 4.21 (s, 4H), 4.14 (s, 4H), 4.07 (q, J = 6.6 Hz, 1H), 3.77 (s, 1H), 3.65-3.55 (m, 3H), 3.29 (dd, J = 6.2, 3.6 Hz, 2H), 3.08 (ddd, J = 14.2, 8.5, 5.0 Hz, 1H), 3.00-2.87 (m, 1H), 2.78 (dq, J = 13.6, 7.2 Hz, 1H), 2.58 (s, 1H), 2.51-2.34 (m, 3H), 2.33-2.22 (m, 3H), 2.02-1.85 (m, 1H). |
| B-74 | 1H NMR (400 MHz, Methanol-d4) δ 8.00 (d, J = 7.6 Hz, 1H), 7.97-7.83 (m, 3H), 7.61 (ddd, J = 21.9, 7.5, 2.2 Hz, 3H), 7.48-7.36 (m, 2H), |

TABLE 2B-continued

| No. | NMR |
|---|---|
|  | 6.69 (dd, J = 6.9, 4.8 Hz, 1H), 4.39 (t, J = 4.0 Hz, 8H), 4.21 (s, 3H), 4.13 (s, 4H), 3.72 (p, J = 8.4 Hz, 1H), 3.32-3.22 (m, 2H), 3.08 (ddd, J = 14.1, 8.5, 5.1 Hz, 1H), 2.99-2.86 (m, 1H), 2.77 (dq, J = 13.4, 7.3 Hz, 1H), 2.51-2.32 (m, 3H), 2.26 (ddt, J = 13.6, 8.6, 5.6 Hz, 1H), 2.05 (s, 1H), 2.02-1.85 (m, 1H). |
| B-75 | 1H NMR (400 MHz, Methanol-d4) δ 7.92-7.82 (m, 2H), 7.63-7.57 (m, 1H), 7.50 (d, J = 7.7 Hz, 2H), 7.35 (t, J = 8.5 Hz, 2H), 7.24 (d, J = 7.6 Hz, 1H), 6.65 (s, 1H), 4.47 (s, 3H), 4.36 (d, J = 18.2 Hz, 2H), 4.19 (d, J = 11.1 Hz, 2H), 4.13-4.02 (m, 4H), 3.50-3.42 (m, 3H), 3.20-3.01 (m, 4H), 2.92 (s, 3H), 2.67 (s, 2H), 2.21 (s, 2H), 1.55-1.52 (s, 5H). |
| B-76 | $^1$H NMR (400 MHz, Methanol-d$_4$) δ 7.93-7.82 (m, 2H), 7.63-7.57 (m, 1H), 7.50 (d, J = 7.7 Hz, 2H), 7.35 (t, J = 8.5 Hz, 2H), 7.24 (d, J = 7.6 Hz, 1H), 6.65 (s, 1H), 4.48 (s, 3H), 4.36 (d, J = 18.2 Hz, 2H), 4.19 (d, J = 11.1 Hz, 2H), 4.13-4.02 (m, 4H), 3.50-3.42 (m, 3H), 3.20-3.01 (m, 5H), 2.92 (s, 3H), 2.67 (s, 2H), 2.21 (s, 2H), 1.55-1.52 (s, 5H). |
| B-77 | 1H NMR (400 MHz, Methanol-d4) δ 7.97-7.87 (m, 2H), 7.54-7.19 (m, 7H), 6.69 (t, J = 5.7 Hz, 1H), 4.42 (d, J = 7.3 Hz, 2H), 4.36 (d, J = 2.6 Hz, 2H), 4.12 (d, J = 11.7 Hz, 7H), 3.64 (d, J = 12.4 Hz, 1H), 3.43-3.36 (m, 1H), 3.32-3.22 (m, 3H), 3.03-2.94 (m, 1H), 2.88-2.78 (m, 1H), 2.77-2.61 (m, 2H), 2.51-2.35 (m, 4H), 2.28-2.15 (m, 3H), 2.15-1.98 (m, 4H), 2.00-1.82 (m, 3H). |
| B-78 | 1H NMR (400 MHz, Methanol-d4) δ 7.94-7.87 (m, 2H), 7.53-7.27 (m, 5H), 7.27-7.19 (m, 2H), 6.68 (t, J = 5.6 Hz, 1H), 4.42-4.30 (m, 2H), 4.12 (d, J = 14.6 Hz, 7H), 3.88 (s, 1H), 3.77 (s, 1H), 3.61 (s, 3H), 3.39-3.34 (m, 1H), 3.29 (dt, J = 6.8, 4.4 Hz, 4H), 3.04-2.92 (m, 1H), 2.91-2.65 (m, 3H), 2.49-2.35 (m, 3H), 2.26-2.20 (m, 1H), 2.15 (d, J = 18.8 Hz, 1H), 2.02-1.88 (m, 1H). |
| B-79 | $^1$H NMR (400 MHz, Methanol-d$_4$) δ 8.57 (s, 1H), 7.88 (s, 1H), 7.68 (dd, J = 7.6, 1.8 Hz, 1H), 7.59-7.46 (m, 3H), 7.35 (t, J = 7.6 Hz, 1H), 7.28-7.23 (m, 1H), 6.66 (s, 1H), 4.35 (s, 2H), 4.12 (d, J = 7.5 Hz, 6H), 4.04 (t, J = 6.8 Hz, 1H), 3.72-3.38 (m, 6H), 3.27-3.08 (m, 3H), 3.02-2.93 (m, 1H), 2.72 (dd, J = 13.8, 6.7 Hz, 1H), 2.49-2.31 (m, 5H), 2.23 (d, J = 7.5 Hz, 1H), 1.94 (dd, J = 8.5, 4.6 Hz, 1H), 1.67 (d, J = 6.8 Hz, 3H). |
| B-80 | 1H NMR (400 MHz, Methanol-d4) δ 8.41 (s, 1H), 7.94 (s, 1H), 7.50 (dd, J = 7.6, 1.5 Hz, 2H), 7.47-7.26 (m, 3H), 7.23 (d, J = 7.6 Hz, 1H), 6.69 (t, J = 5.7 Hz, 1H), 4.54 (d, J = 3.7 Hz, 2H), 4.49-4.35 (m, 2H), 4.13 (d, J = 4.6 Hz, 9H), 3.64 (d, J = 12.4 Hz, 1H), 3.51 (s, 1H), 3.45-3.34 (m, 4H), 2.99 (d, J = 11.4 Hz, 1H), 2.89-2.65 (m, 3H), 2.55-2.36 (m, 3H), 2.19 (dd, J = 19.4, 6.6 Hz, 4H), 2.17-2.04 (m, 3H), 2.03-1.83 (m, 2H). |
| B-81 | 1H NMR (400 MHz, Methanol-d4) δ 8.41 (s, 1H), 7.90 (s, 1H), 7.55-7.46 (m, 2H), 7.46-7.34 (m, 2H), 7.37-7.26 (m, 1H), 7.23 (d, J = 7.5 Hz, 1H), 6.69 (t, J = 5.7 Hz, 1H), 4.54 (d, J = 3.7 Hz, 2H), 4.39 (d, J = 9.8 Hz, 2H), 4.13 (d, J = 7.3 Hz, 7H), 3.82-3.73 (m, 1H), 3.62 (s, 2H), 3.45-3.31 (m, 5H), 3.05-2.93 (m, 1H), 2.89-2.70 (m, 1H), 2.69 (d, J = 9.3 Hz, 2H), 2.55-2.34 (m, 3H), 2.28-2.10 (m, 4H), 2.06-1.93 (m, 1H). |
| B-82 | 1H NMR (400 MHz, Methanol-d4) δ 7.91 (d, J = 7.6 Hz, 1H), 7.75 (s, 1H), 7.62 (dd, J = 7.6, 1.8 Hz, 1H), 7.51 (d, J = 7.7 Hz, 2H), |
|  | 7.46-7.31 (m, 3H), 7.26 (d, J = 7.3 Hz, 1H), 6.63 (s, 1H), 4.37 (d, J = 2.6 Hz, 2H), 4.09 (d, J = 33.8 Hz, 6H), 3.97 (s, 3H), 3.75 (s, 2H), 3.37 (s, 1H), 3.29 (dd, J = 6.2, 3.7 Hz, 2H), 3.24-3.14 (m, 1H), 3.06 (d, J = 13.0 Hz, 1H), 2.92 (s, 4H), 2.80 (s, 1H), 2.74 (s, 3H), 2.52-2.35 (m, 3H), 2.20 (dd, J = 13.6, 9.0 Hz, 2H), 2.00-1.88 (m, 1H). |
| B-84 | HPLC retention time = 4.85 min. |
| B-85 | 1H NMR (400 MHz, Methanol-d4) δ 7.91 (s, 1H), 7.63 (dd, J = 7.6, 1.8 Hz, 1H), 7.58-7.32 (m, 6H), 7.28 (d, J = 7.4 Hz, 1H), 6.69 (s, 1H), 4.60-4.16 (m, 7H), 4.13 (d, J = 12.5 Hz, 7H), 4.01-2.10 (m, 11H), 1.56 (s, 3H). |
| B-86 | $^1$H NMR (400 MHz, Methanol-d$_4$) δ 7.93-7.79 (m, 2H), 7.60 (dd, J = 7.6, 1.8 Hz, 1H), 7.49 (s, 2H), 7.44-7.30 (m, 4H), 7.25 (d, J = 7.5 Hz, 1H), 6.65 (s, 1H), 4.47-4.24 (m, 5H), 4.11 (d, J = 5.2 Hz, 8H), 3.47 (s, 2H), 3.27-3.21 (m, 2H), 3.08-2.51 (m, 3H), 2.49-2.30 (m, 3H), 2.15 (d, J = 46.8 Hz, 2H), 1.93 (d, J = 19.4 Hz, 5H). |
| B-87 | $^1$H NMR (400 MHz, DMSO-d$_6$) δ 9.89 (d, J = 55.9 Hz, 2H), 8.09 (s, 1H), 8.00 (s, 1H), 7.90 (dd, J = 12.4, 7.2 Hz, 1H), 7.62 (d, J = 7.4 Hz, 1H), 7.57-7.43 (m, 3H), 7.37 (t, J = 7.6 Hz, 2H), 7.28 (d, J = 7.7 Hz, 1H), 6.61 (s, 1H), 4.43 (d, J = 5.3 Hz, 2H), 4.28 (d, J = 23.4 Hz, 2H), 4.09 (d, J = 24.2 Hz, 3H), 3.98 (d, J = 12.5 Hz, 6H), 3.04 (s, 2H), 2.96-2.67 (m, 2H), 2.64-2.51 (m, 8H), 2.38-1.83 (m, 4H), 1.42 (d, J = 9.7 Hz, 3H). |
| B-88 | $^1$H NMR (400 MHz, DMSO-d$_6$) δ 9.84 (s, 2H), 8.09 (s, 2H), 8.00 (d, J = 9.3 Hz, 2H), 7.64 (d, J = 7.5 Hz, 1H), 7.59-7.33 (m, 5H), 7.28 (d, J = 7.4 Hz, 1H), 6.61 (s, 1H), 4.51-4.35 (m, 2H), 4.28 (d, J = 24.4 Hz, 2H), 3.99 (d, J = 10.6 Hz, 6H), 3.60 (s, 4H), 3.29-2.96 (m, 4H), 2.95-2.63 (m, 3H), 2.60 (t, J = 5.0 Hz, 7H), 2.31 (s, 1H), 2.12 (s, 4H), 1.91 (s, 1H). |
| B-89 | $^1$H NMR (400 MHz, DMSO-d$_6$) δ 8.76 (s, 2H), 8.64 (s, 3H), 8.06 (s, 2H), 7.96 (s, 1H), 7.95-7.88 (m, 1H), 7.62 (dd, J = 7.6, 1.8 Hz, 1H), 7.53 (t, J = 7.6 Hz, 1H), 7.46 (s, 2H), 7.36 (t, J = 7.2 Hz, 2H), 7.28 (d, J = 7.5 Hz, 1H), 6.61 (s, 1H), 4.18 (d, J = 6.2 Hz, 2H), 4.07 (s, 2H), 4.03-3.89 (m, 6H), 3.15 (d, J = 29.7 Hz, 4H), 2.98-2.63 (m, 2H), 2.64-2.51 (m, 7H), 2.30-1.93 (m, 1H). |
| B-90 | $^1$H NMR (400 MHz, DMSO-d$_6$) δ 8.86 (s, 1H), 8.63 (s, 4H), 8.18-7.84 (m, 3H), 7.70-7.34 (m, 7H), 7.28 (d, J = 7.4 Hz, 1H), 6.61 (s, 1H), 4.21 (s, 3H), 4.07 (s, 4H), 3.98 (d, J = 9.6 Hz, 6H), 3.89 (s, 1H), 3.12 (s, 4H), 2.95-2.57 (m, 6H), 2.35-2.00 (m, 4H), 1.78 (s, 1H). |
| B-91 | $^1$H NMR (400 MHz, Methanol-d$_4$) δ 8.57 (s, 1H), 7.88 (s, 1H), 7.68 (dd, J = 7.6, 1.8 Hz, 1H), 7.59-7.46 (m, 3H), 7.35 (t, J = 7.6 Hz, 1H), 7.28-7.23 (m, 1H), 6.66 (s, 1H), 4.35 (s, 2H), 4.12 (d, J = 7.5 Hz, 6H), 4.04 (t, J = 6.8 Hz, 1H), 3.72-3.38 (m, 6H), 3.27-3.08 (m, 3H), 3.02-2.93 (m, 1H), 2.72 (dd, J = 13.8, 6.7 Hz, 1H), 2.49-2.31 (m, 5H), 2.23 (d, J = 7.5 Hz, 1H), 1.94 (dd, J = 8.5, 4.6 Hz, 1H), 1.67 (d, J = 6.8 Hz, 3H). |
| B-92 | $^1$H NMR (400 MHz, DMSO-d$_6$) δ 9.72 (s, 1H), 8.87 (s, 1H), 8.64 (s, 1H), 8.06-7.85 (m, 2H), 7.67-7.33 (m, 8H), 7.28 (d, J = 7.5 Hz, 1H), 6.61 (s, 1H), 4.38-4.13 (m, 4H), 3.99 (d, J = 14.1 Hz, 7H), 3.88 (d, J = 6.3 Hz, 1H), 3.65 (s, 1H), 3.22-2.91 (m, 2H), 2.95-2.60 (m, 3H), 2.37-1.98 (m, 5H), 2.01-1.45 (m, 8H). |
| B-93 | $^1$H NMR (400 MHz, DMSO-d$_6$) δ 10.41 (s, 1H), 8.86 (s, 1H), 8.64 (s, 1H), 8.10-7.85 (m, 2H), 7.68-7.32 (m, 8H), 7.28 (d, |

TABLE 2B-continued

| No. | NMR |
|---|---|
|  | J = 7.5 Hz, 1H), 6.62 (s, 1H), 4.37 (s, 2H), 4.21 (s, 2H), 3.98 (d, J = 9.6 Hz, 6H), 3.88 (d, J = 6.9 Hz, 1H), 3.62 (d, J = 48.6 Hz, 1H), 3.25-2.96 (m, 4H), 2.97-2.58 (m, 3H), 2.47 (s, 3H), 2.32-2.00 (m, 6H), 1.96-1.62 (m, 3H). |
| B-95 | $^1$H NMR (400 MHz, DMSO-d$_6$) δ 9.70-9.58 (m, 1H), 8.83 (s, 1H), 8.62 (s, 1H), 7.94 (d, J = 7.6 Hz, 2H), 7.70-7.15 (m, 9H), 6.61 (s, 1H), 4.32 (s, 2H), 4.21 (s, 2H), 3.98 (d, J = 9.4 Hz, 6H), 3.88-3.50 (m, 4H), 3.14 (s, 4H), 2.95-2.60 (m, 3H), 2.33-2.02 (m, 6H), 1.75 (d, J = 15.6 Hz, 1H), 1.40 (d, J = 25.9 Hz, 2H). |
| B-96 | 1H NMR (400 MHz, Methanol-d4) δ 9.07 (s, 1H), 8.87 (d, J = 1.5 Hz, 1H), 7.86 (s, 1H), 7.67 (dd, J = 7.6, 1.9 Hz, 1H), 7.59 (dd, J = 15.1, 7.5 Hz, 2H), 7.53 (d, J = 8.0 Hz, 1H), 7.38 (t, J = 7.5 Hz, 1H), 7.29 (d, J = 7.6 Hz, 1H), 6.67 (s, 1H), 4.71-4.58 (m, 2H), 4.39 (s, 7H), 4.13 (s, 3H), 3.72 (q, J = 8.3 Hz, 1H), 3.37 (d, J = 5.3 Hz, 1H), 3.01 (s, 1H), 2.83-2.75 (m, 1H), 2.54-2.36 (m, 3H), 2.23 (s, 1H), 2.08-1.93 (m, 1H). |
| B-97 | 1H NMR (400 MHz, Methanol-d4) δ 9.06 (s, 1H), 8.87 (d, J = 1.5 Hz, 1H), 7.90 (s, 1H), 7.67 (dd, J = 7.6, 1.9 Hz, 1H), 7.66-7.56 (m, 1H), 7.59-7.45 (m, 2H), 7.38 (t, J = 7.6 Hz, 1H), 7.38-7.26 (m, 1H), 6.68 (s, 1H), 4.71-4.58 (m, 2H), 4.39 (s, 2H), 4.14 (s, 4H), 4.02-3.97 (m, 1H), 3.93-3.83 (m, 1H), 3.78 (s, 1H), 3.61 (s, 2H), 3.43-3.34 (m, 2H), 3.09-2.94 (m, 1H), 2.79-2.71 (m, 1H), 2.72-2.65 (m, 1H), 2.57 (s, 1H), 2.54-2.33 (m, 3H), 2.24 (s, 2H), 2.04-1.92 (m, 1H). |
| B-98 | 1H NMR (400 MHz, Methanol-d4) δ 7.96-7.87 (m, 2H), 7.63 (dd, J = 7.7, 1.8 Hz, 1H), 7.56-7.41 (m, 3H), 7.37 (t, J = 7.7 Hz, 2H), 7.31-7.23 (m, 1H), 6.67 (s, 1H), 4.46 (d, J = 13.4 Hz, 1H), 4.43-4.28 (m, 1H), 4.17-4.04 (m, 7H), 3.63 (dd, J = 24.1, 9.3 Hz, 2H), 3.34-3.21 (m, 3H), 3.17-3.09 (m, 1H), 3.06-2.92 (m, 2H), 2.88-2.68 (m, 2H), 2.51-2.34 (m, 4H), 2.33-2.19 (m, 2H), 2.14 (s, 1H), 2.02-1.81 (m, 3H), 1.79-1.69 (m, 1H). |
| B-99 | 1H NMR (400 MHz, Methanol-d4) δ 7.90 (d, J = 7.6 Hz, 1H), 7.85 (s, 1H), 7.61 (dd, J = 7.6, 1.8 Hz, 1H), 7.50 (d, J = 6.9 Hz, 2H), 7.46-7.31 (m, 3H), 7.26 (d, J = 7.4 Hz, 1H), 6.66 (s, 1H), 4.35 (d, J = 2.7 Hz, 4H), 4.11 (d, J = 1.2 Hz, 6H), 4.09-4.01 (m, 1H), 3.27 (dd, J = 6.2, 3.9 Hz, 2H), 3.07-2.65 (m, 2H), 2.49-2.31 (m, 4H), 2.21 (s, 1H), 2.01-1.83 (m, 1H). |
| B-100 | $^1$H NMR (400 MHz, Methanol-d$_4$) δ 7.93-7.81 (m, 2H), 7.67-7.58 (m, 1H), 7.51 (d, J = 7.3 Hz, 2H), 7.38 (q, J = 10.1, 7.8 Hz, 2H), 7.27 (d, J = 7.5 Hz, 1H), 6.66 (s, 1H), 4.46 (d, J = 43.4 Hz, 2H), 4.37-4.27 (m, 4H), 4.22 (d, J = 11.1 Hz, 1H), 4.14-4.07 (m, 5H), 3.64-3.44 (m, 2H), 3.18-2.58 (m, 7H), 2.22 (s, 1H), 1.56 (s, 2H). |
| B-101 | 1H NMR (400 MHz, Methanol-d4) δ 7.90 (d, J = 7.6 Hz, 1H), 7.86 (s, 1H), 7.61 (dd, J = 7.6, 1.8 Hz, 1H), 7.49 (d, J = 7.5 Hz, 2H), 7.46-7.30 (m, 3H), 7.25 (d, J = 7.3 Hz, 1H), 6.64 (s, 1H), 4.42-4.19 (m, 8H), 4.10 (d, J = 1.8 Hz, 6H), 4.06 (q, J = 6.8 Hz, 1H), 3.58 (p, J = 8.1 Hz, 1H), 2.98 (dd, J = 29.6, 12.1 Hz, 1H), 2.88-2.64 (m, 5H), 2.49-2.31 (m, 3H), 2.20 (s, 1H), 2.00-1.84 (m, 1H). |
| B-102 | 1H NMR (400 MHz, Methanol-d4) δ 7.90 (d, J = 7.6 Hz, 1H), 7.84 (s, 1H), 7.61 (dd, J = 7.7, 1.8 Hz, 1H), 7.49 (d, J = 7.6 Hz, 2H), 7.46-7.29 (m, 3H), 7.28-7.21 (m, 1H), 6.64 (s, 1H), 4.42-4.27 (m, 4H), 4.21-3.98 (m, 11H), 3.06-2.64 (m, 3H), 2.50-2.31 (m, 3H), 2.20 (s, 1H), 2.00-1.82 (m, 1H), 1.53 (s, 3H). |
| B-103 | 1H NMR (400 MHz, Methanol-d4) δ 7.72 (d, J = 7.6 Hz, 1H), 7.70 (s, 1H), 7.65-7.56 (m, 1H), 7.53-7.31 (m, 3H), 7.32-7.17 (m, 3H), 6.78 (t, J = 6.0 Hz, 1H), 4.03 (s, 3H), 4.02 (s, 3H), 3.93-3.77 (m, 5H), 3.76-3.65 (m, 2H), 3.45 (d, J = 13.9 Hz, 1H), 2.77-2.57 (m, 4H), 2.43-2.19 (m, 6H), 1.93-1.72 (m, 2H). |
| B-104 | $^1$H NMR (400 MHz, Methanol-d$_4$) δ 7.93-7.81 (m, 2H), 7.63 (dd, J = 7.6, 1.8 Hz, 1H), 7.51 (d, J = 7.3 Hz, 2H), 7.36 (t, J = 7.2 Hz, 2H), 7.27 (d, J = 7.4 Hz, 1H), 6.66 (s, 1H), 4.65 (s, 2H), 4.41-4.24 (m, 4H), 4.15-3.94 (m, 6H), 3.56-3.46 (m, 1H), 3.25-3.12 (m, 2H), 3.09-2.64 (m, 5H), 2.53-2.31 (m, 3H), 2.22 (s, 1H), 2.07-1.89 (m, 2H). |
| B-105 | 1H NMR (400 MHz, Methanol-d4) δ 7.92-7.83 (m, 2H), 7.65 (dd, J = 7.6, 1.8 Hz, 1H), 7.54 (d, J = 7.3 Hz, 2H), 7.37 (t, J = 7.2 Hz, 2H), 7.27 (d, J = 7.4 Hz, 1H), 6.66 (s, 1H), 4.65 (s, 2H), 4.41-4.24 (m, 4H), 4.15-3.94 (m, 6H), 3.56-3.46 (m, 1H), 3.25-3.12 (m, 2H), 3.09-2.64 (m, 5H), 2.53-2.31 (m, 4H), 2.22 (s, 1H), 2.17-1.04 (m, 7H). |
| B-106 | 1H NMR (400 MHz, Methanol-d4) δ 7.95-7.87 (m, 2H), 7.63 (dd, J = 7.6, 1.8 Hz, 1H), 7.52 (d, J = 7.3 Hz, 2H), 7.37 (dd, J = 10.2, 7.5 Hz, 3H), 7.27 (dd, J = 7.6, 1.2 Hz, 1H), 6.68 (d, J = 5.8 Hz, 1H), 4.44-4.29 (m, 4H), 4.13 (d, J = 3.3 Hz, 7H), 3.68 (s, 1H), 3.60 (s, 1H), 3.32-3.21 (m, 2H), 3.01 (s, 3H), 2.86-2.64 (m, 3H), 2.57 (s, 1H), 2.51-2.34 (m, 3H), 2.23 (s, 1H), 2.02-1.88 (m, 1H), 1.31 (d, J = 6.3 Hz, 3H). |
| B-107 | 1H NMR (400 MHz, Methanol-d4) δ 7.95-7.86 (m, 2H), 7.63 (dd, J = 7.6, 1.8 Hz, 1H), 7.52 (s, 2H), 7.43-7.33 (m, 3H), 7.28 (d, J = 8.0 Hz, 1H), 6.68 (s, 1H), 4.43-4.29 (m, 4H), 4.13 (d, J = 3.0 Hz, 7H), 3.69 (s, 1H), 3.61 (d, J = 11.3 Hz, 1H), 3.29 (dd, J = 6.2, 3.8 Hz, 2H), 3.05-2.94 (m, 3H), 2.84 (s, 2H), 2.74 (d, J = 12.7 Hz, 1H), 2.56 (s, 1H), 2.51-2.35 (m, 3H), 2.23 (s, 2H), 1.99-1.89 (m, 1H), 1.32 (d, J = 6.8 Hz, 2H). |
| B-108 | $^1$H NMR (400 MHz, Methanol-d$_4$) δ 7.96-7.87 (m, 2H), 7.63 (dd, J = 7.7, 1.8 Hz, 1H), 7.52 (d, J = 7.4 Hz, 2H), 7.37 (t, J = 8.0 Hz, 2H), 7.27 (d, J = 7.5 Hz, 1H), 6.67 (s, 1H), 4.43-4.28 (m, 4H), 4.13 (d, J = 3.1 Hz, 6H), 3.78 (s, 2H), 3.31-3.25 (m, 8H), 2.73 (dd, J = 13.7, 6.7 Hz, 1H), 2.45-2.34 (m, 3H), 2.23 (s, 1H), 1.99-1.87 (m, 1H), 1.68 (s, 8H). |
| B-109 | HPLC retention time = 4.87 min. |
| B-110 | HPLC retention time = 5.00 min. |
| B-111 | 1H NMR (400 MHz, Methanol-d4) δ 7.95-7.87 (m, 2H), 7.63 (dd, J = 7.7, 1.8 Hz, 1H), 7.53 (d, J = 7.5 Hz, 2H), 7.37 (dd, J = 10.2, 7.5 Hz, 2H), 7.27 (d, J = 7.4 Hz, 1H), 6.68 (s, 1H), 4.43-4.34 (m, 3H), 4.13 (d, J = 4.5 Hz, 5H), 4.06 (t, 1H) 3.26 (q, J = 2.6 Hz, 8H), 2.77-2.69 (m, 1H), 2.48-2.34 (m, 3H), 2.24 (s, 1H), 1.98-1.90 (m, 1H), 1.75-1.60 (m, 7H). |
| B-112 | 1H NMR (400 MHz, Methanol-d4) δ 7.94-7.87 (m, 2H), 7.63 (dd, J = 7.5, 1.8 Hz, 1H), 7.53 (d, J = 7.5 Hz, 2H), 7.39 (dd, J = 10.2, 7.5 Hz, 2H), 7.27 (d, J = 7.4 Hz, 1H), 6.69 (s, 1H), 4.43-4.34 (m, 3H), 4.13 (d, J = 4.5 Hz, 5H), 3.26 (q, J = 2.6 Hz, 8H), 2.77-2.68 (m, 1H), 2.48-2.34 (m, 3H), 2.24 (s, 1H), 1.98-1.90 (m, 1H), 1.69 (dq, J = 11.9, 8.2, 7.8 Hz, 9H), 1.44 (3H, t). |
| B-113 | $^1$H NMR (400 MHz, Methanol-d$_4$) δ 7.95-7.87 (m, 2H), 7.63 (dd, J = 7.7, 1.8 Hz, 1H), 7.53 (d, J = 7.5 Hz, 2H), 7.37 (dd, J = 10.2, |

TABLE 2B-continued

| No. | NMR |
|---|---|
| | 7.5 Hz, 2H), 7.27 (d, J = 7.4 Hz, 1H), 6.68 (s, 1H), 4.43-4.34 (m, 3H), 4.13 (d, J = 4.5 Hz, 5H), 3.26 (q, J = 2.6 Hz, 8H), 2.77-2.69 (m, 1H), 2.48-2.34 (m, 3H), 2.24 (s, 1H), 1.98-1.90 (m, 1H), 1.69 (dq, J = 11.9, 8.2, 7.8 Hz, 10H). |
| B-114 | 1H NMR (400 MHz, Methanol-d4) δ 7.92 (d, J = 8.0 Hz, 2H), 7.63 (dd, J = 7.7, 1.8 Hz, 1H), 7.53 (d, J = 7.6 Hz, 2H), 7.49-7.33 (m, 3H), 7.27 (d, J = 7.5 Hz, 1H), 6.68 (s, 1H), 4.43-4.31 (m, 4H), 4.13 (d, J = 3.7 Hz, 7H), 3.88 (s, 1H), 3.81-3.74 (m, 1H), 3.62 (s, 2H), 3.32-3.21 (m, 2H), 3.01 (s, 1H), 3.01-2.91 (m, 1H), 2.89-2.79 (m, 1H), 2.72 (d, J = 33.0 Hz, 2H), 2.58 (s, 1H), 2.52-2.35 (m, 3H), 2.24 (s, 2H), 2.02-1.88 (m, 1H). |
| B-115 | 1H NMR (400 MHz, Methanol-d4) δ 7.95-7.86 (m, 2H), 7.63 (dd, J = 7.6, 1.8 Hz, 1H), 7.52 (d, J = 7.3 Hz, 2H), 7.37 (dd, J = 12.5, 7.3 Hz, 3H), 7.27 (d, J = 7.3 Hz, 1H), 6.68 (s, 1H), 4.37 (d, J = 2.7 Hz, 2H), 4.28 (d, J = 7.6 Hz, 2H), 4.13 (d, J = 1.2 Hz, 7H), 3.60 (d, J = 12.8 Hz, 2H), 3.45 (d, J = 12.7 Hz, 1H), 3.32-3.21 (m, 2H), 3.10 (d, J = 12.9 Hz, 1H), 2.99 (d, J = 18.4 Hz, 1H), 2.87-2.80 (m, 1H), 2.78-2.60 (m, 2H), 2.52-2.35 (m, 3H), 2.27 (d, J = 15.9 Hz, 3H), 2.02-1.89 (m, 1H), 1.92-1.81 (m, 2H). |
| B-116 | 1H NMR (400 MHz, Methanol-d4) δ 7.85 (s, 1H), 7.76-7.67 (m, 2H), 7.64-7.30 (m, 6H), 7.26 (d, J = 7.5 Hz, 1H), 6.67 (s, 1H), 4.53 (d, J = 2.4 Hz, 2H), 4.41 (s, 2H), 4.16-4.04 (m, 4H), 3.41-3.32 (m, 2H), 3.09-1.82 (m, 8H), 1.68-1.53 (m, 2H), 1.49-1.37 (m, 2H). |
| B-117 | $^1$H NMR (400 MHz, Methanol-d$_4$) δ 8.11 (s, 1H), 7.48 (d, J = 9.4 Hz, 2H), 7.43-7.32 (m, 3H), 7.25-7.19 (m, 2H), 7.15-7.11 (m, 1H), 6.70 (s, 1H), 4.33 (s, 2H), 4.19-4.11 (m, 3H), 3.98 (s, 2H), 3.47 (d, J = 1.7 Hz, 2H), 3.24-3.17 (m, 2H), 3.13 (s, 2H), 2.45-2.34 (m, 4H), 2.25-2.16 (m, 3H), 2.09 (d, J = 8.1 Hz, 2H), 1.94-1.83 (m, 3H), 1.64-1.58 (m, 2H), 1.55-1.46 (m, 2H), 1.27 (s, 1H). |
| B-118 | $^1$H NMR (400 MHz, Methanol-d$_4$) δ 8.09 (s, 1H), 7.47-7.32 (m, 4H), 7.25-7.07 (m, 4H), 6.70 (d, J = 8.1 Hz, 1H), 4.56 (s, 2H), 4.19 (s, 2H), 3.96 (s, 2H), 3.48 (d, J = 1.7 Hz, 2H), 3.12 (d, J = 2.1 Hz, 2H), 2.43-2.31 (m, 3H), 2.24-1.82 (m, 10H), 1.65 (s, 2H), 1.40-1.25 (m, 4H), 0.90 (s, 2H). |
| B-119 | 1H NMR (400 MHz, Methanol-d4) δ 8.03 (s, 1H), 7.91 (d, J = 7.6 Hz, 1H), 7.63 (dd, J = 7.6, 1.8 Hz, 1H), 7.56-7.47 (m, 2H), 7.47-7.31 (m, 3H), 7.27 (d, J = 7.5 Hz, 1H), 6.80-6.64 (m, 1H), 4.83-4.71 (m, 1H), 4.62-3.95 (m, 13H), 3.79-3.53 (m, 1H), 3.31-3.20 (m, 2H), 3.12-2.67 (m, 3H), 2.53-2.29 (m, 3H), 2.29-2.12 (m, 1H), 2.02-1.86 (m, 1H), 1.59 (d, J = 6.8 Hz, 3H). |
| B-120 | $^1$H NMR (400 MHz, Methanol-d$_4$) δ 8.04 (s, 1H), 7.91 (d, J = 7.6 Hz, 1H), 7.63 (dd, J = 7.6, 1.8 Hz, 1H), 7.56-7.48 (m, 2H), 7.48-7.31 (m, 3H), 7.27 (d, J = 7.5 Hz, 1H), 6.79-6.66 (m, 1H), 4.71-4.49 (m, 1H), 4.43-4.30 (m, 2H), 4.21 (s, 3H), 4.13 (s, 3H), 4.11-4.04 (m, 1H), 3.30-3.17 (m, 6H), 2.87-2.69 (m, 3H), 2.53-2.34 (m, 3H), 2.33-2.12 (m, 1H), 2.05-1.87 (m, 1H), 1.72 (s, J = 6.9 Hz, 3H). |
| B-121 | $^1$H NMR (400 MHz, Methanol-d$_4$) δ 8.08 (d, J = 5.4 Hz, 1H), 7.45-7.22 (m, 6H), 7.09-7.00 (m, 2H), 6.69 (d, J = 5.5 Hz, 1H), 4.56 (s, 2H), 4.15 (d, J = 4.8 Hz, 2H), 3.91 (s, 3H), 3.48-3.45 (m, 1H), 3.12 (d, J = 1.8 Hz, 1H), 2.75 (s, 3H), 2.39-2.11 (m, 7H), 1.81 (d, J = 13.0 Hz, 2H), 1.55 (s, 3H), 1.29 (s, 3H), 0.90 (s, 1H). |
| B-122 | $^1$H NMR (400 MHz, Methanol-d$_4$) δ 8.03 (s, 1H), 7.47-7.33 (m, 4H), 7.24-7.07 (m, 4H), 6.69 (d, J = 8.9 Hz, 1H), 4.56 (s, 2H), 4.30 (s, 2H), 4.17 (d, J = 16.4 Hz, 3H), 3.95 (s, 3H), 3.48 (s, 1H), 3.13 (s, 1H), 3.04 (d, J = 16.0 Hz, 2H), 2.93 (s, 2H), 2.37 (d, J = 10.4 Hz, 3H), 1.87 (d, J = 8.7 Hz, 1H), 1.37 (d, J = 7.1 Hz, 2H), 1.28 (d, J = 3.9 Hz, 2H), 1.18-1.12 (m, 2H). |
| B-123 | 1H NMR (400 MHz, Methanol-d4) δ 7.87 (s, 1H), 7.62 (dd, J = 7.9, 1.6 Hz, 1H), 7.52 (d, J = 7.4 Hz, 2H), 7.36 (t, J = 7.5 Hz, 1H), 7.27 (d, J = 7.5 Hz, 2H), 6.68 (s, 1H), 4.76-4.53 (m, 3H), 4.25 (d, J = 2.6 Hz, 2H), 4.15 (s, 3H), 4.12 (s, 3H), 4.05 (t, J = 6.2 Hz, 1H), 3.61 (s, 1H), 3.23 (dd, J = 6.2, 3.5 Hz, 2H), 2.96 (s, 1H), 2.90-2.66 (m, 1H), 2.58 (s, 3H), 2.51-2.32 (m, 3H), 2.23 (s, 1H), 2.05-1.83 (m, 2H), 1.31 (s, 1H), 1.10 (s, 1H), 0.91 (s, 5H). |
| B-124 | 1H NMR (400 MHz, Methanol-d4) δ 7.87 (s, 1H), 7.62 (d, J = 1.8 Hz, 1H), 7.60 (d, J = 1.8 Hz, 1H), 7.52 (d, J = 7.4 Hz, 2H), 7.36 (t, J = 7.5 Hz, 1H), 7.27 (d, J = 5.7 Hz, 2H), 6.68 (s, 1H), 4.59 (s, 2H), 4.25 (d, J = 2.6 Hz, 2H), 4.15 (s, 3H), 4.10 (s, 3H), 4.05 (t, J = 6.4 Hz, 1H), 3.82 (q, J = 11.9 Hz, 4H), 3.23 (dd, J = 6.2, 3.5 Hz, 2H), 2.91-2.66 (m, 2H), 2.54 (s, 3H), 2.49-2.36 (m, 5H), 2.23 (s, 1H), 2.08 (s, 1H), 2.03-1.89 (m, 1H), 1.31 (s, 1H). |
| B-125 | 1H NMR (400 MHz, Methanol-d4) δ 8.08-7.99 (m, 2H), 7.71 (d, J = 8.0 Hz, 1H), 7.59 (s, 1H), 7.56-7.31 (m, 3H), 7.25 (d, J = 7.4 Hz, 1H), 6.71 (s, 1H), 5.29 (s, 2H), 4.44 (s, 2H), 4.40 (d, J = 1.5 Hz, 2H), 4.17 (s, 3H), 4.06 (q, J = 6.6 Hz, 1H), 2.73 (s, 1H), 2.49-2.34 (m, 3H), 2.18 (dd, J = 13.7, 5.6 Hz, 1H), 2.00-1.89 (m, 1H), 1.64-1.57 (m, 2H), 1.46-1.38 (m, 2H). |
| B-126 | 1H NMR (400 MHz, Methanol-d4) δ 8.16 (s, 1H), 8.03 (d, J = 7.6 Hz, 1H), 7.71 (d, J = 7.6 Hz, 1H), 7.59 (s, 1H), 7.51 (p, J = 7.8 Hz, 3H), 7.36 (t, J = 7.7 Hz, 1H), 7.26 (d, J = 7.5 Hz, 1H), 6.73 (s, 1H), 5.49 (s, 1H), 5.29 (s, 2H), 4.45 (d, J = 8.3 Hz, 2H), 4.40 (s, 2H), 4.18 (s, 3H), 4.06 (q, J = 6.8 Hz, 1H), 3.62 (d, J = 12.3 Hz, 1H), 2.74 (s, 5H), 2.49-2.31 (m, 5H), 2.28-1.79 (m, 11H). |
| B-127 | 1H NMR (400 MHz, Methanol-d4) δ 8.11 (s, 1H), 8.03 (d, J = 7.6 Hz, 1H), 7.71 (d, J = 7.1 Hz, 1H), 7.59 (s, 1H), 7.56-7.32 (m, 3H), 7.26 (d, J = 7.4 Hz, 1H), 6.72 (s, 1H), 5.29 (s, 2H), 4.47-4.34 (m, 4H), 4.19 (s, 3H), 4.07 (p, J = 6.0 Hz, 1H), 2.74 (s, 1H), 2.49-2.31 (m, 3H), 2.20 (dt, J = 13.4, 6.7 Hz, 1H), 2.00-1.86 (m, 1H). |
| B-128 | 1H NMR (400 MHz, Methanol-d4) δ 7.85 (s, 1H), 7.60-7.29 (m, 5H), 7.25 (d, J = 7.5 Hz, 1H), 7.08 (s, 1H), 7.02 (d, J = 9.9 Hz, 1H), 6.67 (s, 1H), 4.43 (d, J = 5.7 Hz, 4H), 4.12 (s, 3H), 4.09-3.97 (m, 4H), 3.31-3.18 (m, 2H), 3.14-2.33 (m, 6H), 2.22 (s, 1H), 2.01-1.86 (m, 1H), 1.68-1.58 (m, 2H), 1.53-1.40 (m, 2H). |
| B-129 | 1H NMR (400 MHz, Methanol-d4) δ 7.94 (s, 1H), 7.58-7.18 (m, 6H), 7.08 (s, 1H), 7.02 (d, J = 9.9 Hz, 1H), 6.68 (s, 1H), 4.50-4.35 (m, 4H), 4.13 (s, 3H), 4.11-3.98 (m, 4H), 3.63 (d, J = 12.4 Hz, 1H), 3.50 (dd, J = 3.3, 1.7 Hz, 1H), 3.30-3.22 (m, 2H), 3.10-1.69 (m, 17H). |
| B-130 | 1H NMR (400 MHz, Methanol-d4) δ 7.86 (s, 1H), 7.57-7.19 (m, 6H), 7.11-6.96 (m, |

TABLE 2B-continued

| No. | NMR |
|---|---|
| | 2H), 6.66 (s, 1H), 4.50-4.29 (m, 8H), 4.13 (s, 3H), 4.11-3.98 (m, 4H), 3.71 (t, J = 8.4 Hz, 1H), 3.30-3.19 (m, 2H), 3.08-1.80 (m, 8H). |
| B-131 | 1H NMR (400 MHz, Methanol-d4) δ 7.90 (s, 1H), 7.59-7.19 (m, 6H), 7.08 (s, 1H), 7.02 (d, J = 10.0 Hz, 1H), 6.68 (s, 1H), 4.47-4.28 (m, 4H), 4.14 (s, 3H), 4.10-3.99 (m, 4H), 3.97-1.81 (m, 17H). |
| B-132 | 1H NMR (400 MHz, DMSO-d6) δ 12.98 (s, 1H), 9.30 (s, 1H), 8.79 (s, 1H), 8.59 (s, 1H), 8.01 (s, 1H), 7.66-7.60 (m, 1H), 7.56 (d, J = 6.6 Hz, 2H), 7.54 (s, 1H), 7.49 (s, 2H), 7.40 (t, J = 7.5 Hz, 1H), 7.32 (s, 1H), 7.31-7.26 (m, 1H), 6.64 (s, 1H), 4.52 (s, 1H), 4.36 (d, J = 6.1 Hz, 1H), 4.13 (d, J = 5.2 Hz, 2H), 4.03 (s, 3H), 3.98 (d, J = 4.5 Hz, 3H), 3.16-2.97 (m, 2H), 2.97-2.86 (m, 1H), 2.84-2.66 (m, 2H), 2.48 (m, 2H), 2.31-2.11 (m, 3H), 2.08 (s, 1H), 1.90 (d, J = 10.0 Hz, 1H), 1.86-1.73 (m, 2H), 1.47 (d, J = 16.1 Hz, 2H). |
| B-133 | 1H NMR (400 MHz, DMSO-d6) δ 12.93 (s, 1H), 9.55 (s, 1H), 8.77 (s, 1H), 8.57 (s, 1H), 8.01 (s, 1H), 7.63 (dt, J = 7.7, 2.0 Hz, 1H), 7.57 (t, J = 3.8 Hz, 2H), 7.49 (d, J = 7.8 Hz, 2H), 7.40 (t, J = 7.6 Hz, 1H), 7.32 (d, J = 1.2 Hz, 1H), 7.29 (d, J = 3.7 Hz, 2H), 6.64 (s, 1H), 4.47 (d, J = 15.1 Hz, 1H), 4.12 (d, J = 5.1 Hz, 2H), 4.03 (s, 3H), 3.98 (s, 3H), 3.86 (d, J = 6.4 Hz, 1H), 3.76 (s, 1H), 3.6 (m, 2H), 3.2 (m, 2H), 3.14-2.98 (m, 2H), 2.96-2.85 (m, 1H), 2.84-2.77 (m, 1H), 2.77-2.66 (m, 2H), 2.31-2.04 (m, 3H), 1.87-1.70 (m, 1H), 1.24 (s, 1H). |
| B-134 | $^1$H NMR (400 MHz, Methanol-d$_4$) δ 8.26 (s, 1H), 7.86 (d, J = 7.5 Hz, 1H), 7.60 (dd, J = 7.6, 1.7 Hz, 1H), 7.52-7.45 (m, 2H), 7.35 (d, J = 6.6 Hz, 2H), 7.24 (d, J = 7.5 Hz, 1H), 6.70 (s, 1H), 4.35 (s, 2H), 4.24 (s, 1H), 4.16 (s, 2H), 4.09 (s, 2H), 4.01 (s, 1H), 3.50-3.46 (m, 1H), 3.25-3.11 (m, 3H), 2.71 (d, J = 13.9 Hz, 1H), 2.45-2.34 (m, 3H), 2.29-2.12 (m, 4H), 2.03 (d, J = 2.3 Hz, 1H), 1.94-1.78 (m, 4H), 1.72-1.63 (m, 2H), 1.57-1.50 (m, 1H), 1.47-1.37 (m, 2H), 1.28 (s, 1H), 1.02 (t, J = 7.3 Hz, 2H). |
| B-135 | HPLC retention time = 5.11 min. |
| B-136 | $^1$H NMR (400 MHz, Methanol-d$_4$) δ 8.17 (s, 1H), 7.84 (d, J = 7.6 Hz, 1H), 7.60 (dd, J = 7.7, 1.7 Hz, 1H), 7.47 (d, J = 8.0 Hz, 2H), 7.33 (d, J = 7.4 Hz, 2H), 7.23 (d, J = 7.6 Hz, 1H), 6.69 (s, 1H), 4.51 (s, 1H), 4.41 (d, J = 13.4 Hz, 1H), 4.22 (d, J = 15.7 Hz, 3H), 4.10-3.97 (m, 4H), 3.47 (d, J = 2.1 Hz, 1H), 3.24-3.12 (m, 4H), 2.73 (s, 1H), 2.59-2.45 (m, 2H), 2.40-2.33 (m, 2H), 2.22 (d, J = 11.2 Hz, 1H), 1.94 (d, J = 1.6 Hz, 2H), 1.70-1.62 (m, 2H), 1.41 (q, J = 7.3 Hz, 2H), 1.31 (d, J = 2.0 Hz, 1H), 0.98-0.91 (m, 1H), 0.81 (s, 1H). |
| B-137 | $^1$H NMR (400 MHz, Methanol-d$_4$) δ 8.17 (s, 1H), 7.85 (d, J = 7.6 Hz, 1H), 7.60 (dd, J = 7.7, 1.7 Hz, 1H), 7.47 (d, J = 8.0 Hz, 2H), 7.33 (d, J = 7.4 Hz, 2H), 7.23 (d, J = 7.6 Hz, 1H), 6.69-6.65 (m, 1H), 4.51 (s, 1H), 4.41 (d, J = 13.4 Hz, 1H), 4.22 (d, J = 15.7 Hz, 3H), 4.10-3.98 (m, 4H), 3.47 (d, J = 2.1 Hz, 1H), 3.24-3.11 (m, 4H), 2.73 (s, 1H), 2.59-2.48 (m, 2H), 2.40-2.34 (m, 2H), 2.22 (d, J = 11.2 Hz, 1H), 1.94 (d, J = 1.6 Hz, 2H), 1.70-1.62 (m, 2H), 1.41 (q, J = 7.4 Hz, 2H), 1.29 (d, J = 2.0 Hz, 1H), 0.98-0.91 (m, 1H), 0.81 (s, 1H). |
| B-138 | $^1$H NMR (400 MHz, Methanol-d$_4$) δ 8.01 (s, 1H), 7.86 (d, J = 7.7 Hz, 1H), 7.60 (dd, J = 7.7, 1.8 Hz, 1H), 7.48 (d, J = 7.2 Hz, 2H), 7.38-7.31 (m, 2H), 7.23 (d, J = 7.5 Hz, 1H), 6.68 (s, 1H), 4.26 (s, 2H), 4.11 (d, J = 17.4 Hz, 4H), 3.52-3.45 (m, 2H), 3.26-3.20 (m, 4H), 2.72 (s, 1H), 2.42-2.36 (m, 2H), 2.17 (d, J = 26.5 Hz, 3H), 1.91 (d, J = 15.6 Hz, 1H), 1.79 (d, J = 11.4 Hz, 1H), 1.66 (dt, J = 16.0, 7.8 Hz, 5H), 1.29 (d, J = 3.9 Hz, 1H), 0.81-0.70 (m, 3H). |
| B-139 | 1H NMR (400 MHz, Methanol-d4) δ 7.89 (d, J = 7.6 Hz, 1H), 7.82 (d, J = 10.9 Hz, 1H), 7.61 (dd, J = 7.7, 1.8 Hz, 1H), 7.49 (d, J = 7.0 Hz, 2H), 7.35 (dd, J = 18.9, 7.5 Hz, 2H), 7.25 (d, J = 7.5 Hz, 1H), 6.65 (s, 1H), 4.35 (d, J = 2.6 Hz, 2H), 4.15-4.02 (m, 9H), 2.86 (s, 1H), 2.75-2.65 (m, 1H), 2.52-2.30 (m, 5H), 2.24-1.39 (m, 4H). |
| B-140 | 1H NMR (400 MHz, Methanol-d4) δ 8.18 (s, 1H), 7.55-7.32 (m, 6H), 7.29-7.20 (m, 2H), 7.19-7.12 (m, 1H), 6.74 (s, 1H), 4.44 (dd, J = 21.2, 7.8 Hz, 2H), 4.37 (d, J = 3.6 Hz, 2H), 4.20 (s, 4H), 4.14-4.00 (m, 4H), 4.01 (s, 3H), 3.70-3.60 (m, 1H), 3.52 (s, 1H), 3.45-3.35 (m, 1H), 3.29-3.18 (m, 2H), 3.00 (s, 1H), 2.83-2.69 (m, 3H), 2.68 (s, 1H), 2.50-2.34 (m, 3H), 2.29-2.16 (m, 3H), 2.16-2.01 (m, 4H), 2.01-1.83 (m, 2H). |
| B-141 | 1H NMR (400 MHz, Methanol-d4) δ 8.09 (s, 1H), 7.55-7.42 (m, 3H), 7.49-7.35 (m, 2H), 7.35 (d, J = 7.5 Hz, 1H), 7.29-7.20 (m, 2H), 7.16 (dd, J = 7.6, 1.5 Hz, 1H), 6.72 (s, 1H), 4.52 (d, J = 10.9 Hz, 2H), 4.45 (s, 2H), 4.43-4.31 (m, 2H), 4.19 (s, 3H), 4.15-4.00 (m, 4H), 4.01 (s, 3H), 3.29-3.18 (m, 2H), 3.01 (s, 1H), 3.01-2.89 (m, 1H), 2.91-2.80 (m, 1H), 2.75 (s, 2H), 2.51-2.34 (m, 3H), 2.21 (ddd, J = 13.6, 9.1, 4.8 Hz, 1H), 2.01-1.87 (m, 1H), 1.63 (s, 3H). |
| B-142 | $^1$H NMR (400 MHz, DMSO-d$_6$) δ 10.08 (d, J = 19.9 Hz, 1H), 8.91 (s, 1H), 8.69 (s, 1H), 7.95 (s, 1H), 7.70-7.60 (m, 1H), 7.60-7.32 (m, 6H), 7.28 (d, J = 7.5 Hz, 1H), 6.64 (d, J = 33.3 Hz, 1H), 4.25 (d, J = 21.9 Hz, 7H), 4.00 (dd, J = 5.2, 1.4 Hz, 6H), 3.93-3.63 (m, 3H), 3.14 (d, J = 20.6 Hz, 1H), 2.99-2.61 (m, 3H), 2.33-1.98 (m, 5H), 1.79 (d, J = 5.0 Hz, 1H). |
| B-143 | 1H NMR (400 MHz, Methanol-d4) δ 7.90 (s, 1H), 7.60-7.10 (m, 8H), 6.68 (s, 1H), 4.45-4.31 (m, 4H), 4.17-3.98 (m, 7H), 3.95-1.82 (m, 17H). |
| B-144 | $^1$H NMR (400 MHz, Methanol-d$_4$) δ 8.09 (s, 1H), 7.72 (d, J = 7.5 Hz, 1H), 7.58 (dd, J = 7.7, 1.8 Hz, 1H), 7.49-7.41 (m, 2H), 7.38-7.29 (m, 2H), 7.23 (d, J = 7.2 Hz, 1H), 6.67 (s, 1H), 4.16 (s, 2H), 4.01 (s, 2H), 3.82 (d, J = 3.5 Hz, 2H), 3.48 (dt, J = 3.3, 1.7 Hz, 1H), 3.13 (dt, J = 3.3, 1.6 Hz, 3H), 2.75-2.63 (m, 3H), 2.39-2.27 (m, 3H), 2.17 (s, 1H), 2.00 (d, J = 14.2 Hz, 1H), 1.82 (d, J = 21.4 Hz, 2H), 1.65 (d, J = 22.7 Hz, 2H), 1.41 (d, J = 7.3 Hz, 1H), 1.31 (d, J = 18.7 Hz, 4H), 0.87 (d, J = 10.6 Hz, 1H), 0.77-0.64 (m, 3H). |
| B-145 | $^1$H NMR (400 MHz, Methanol-d$_4$) δ 8.18 (s, 1H), 7.80 (d, J = 7.6 Hz, 1H), 7.62-7.56 (m, 1H), 7.51-7.43 (m, 2H), 7.34-7.22 (m, 3H), 6.73-6.67 (m, 3H), 4.18 (s, 2H), 4.07 (d, J = 10.2 Hz, 4H), 3.49 (d, J = 8.7 Hz, 2H), 3.27-3.20 (m, 3H), 3.13 (s, 1H), 2.95 (s, 1H), 2.87 (s, 1H), 2.78-2.69 (m, 2H), 2.44-2.32 (m, 4H), 2.21 (s, 1H), 1.69-1.61 (m, 3H), 1.41 (q, J = 7.4 Hz, 3H), 1.28 (s, 2H). |
| B-146 | 1H NMR (400 MHz, Methanol-d4) δ 7.89 (d, J = 7.3 Hz, 1H), 7.66-7.25 (m, 7H), 6.76 (s, 1H), 4.79 (s, 2H), 4.53-4.23 (m, 6H), 4.13 (s, 3H), 4.10 (s, 3H), 4.11-4.00 (m, 1H), 3.77-3.59 (m, 2H), 3.45-3.22 (m, 2H), 3.24-2.52 (m, 5H), 2.52-2.22 (m, 4H), 2.03-1.83 (m, 1H). |

TABLE 2B-continued

| No. | NMR |
|---|---|
| B-147 | 1H NMR (400 MHz, Methanol-d4) δ 7.89 (d, J = 7.2 Hz, 1H), 7.69-7.25 (m, 7H), 6.80-6.74 (m, 1H), 4.63 (s, 2H), 4.41-4.31 (m, 2H), 4.14 (s, 3H), 4.10 (s, 3H), 4.10-4.01 (m, 2H), 3.43-3.19 (m, 4H), 3.21-2.69 (m, 3H), 2.55-2.23 (m, 7H), 2.02-1.80 (m, 2H). |
| B-148 | 1H NMR (400 MHz, Methanol-d4) δ 7.89 (d, J = 7.5 Hz, 1H), 7.60 (dd, J = 7.7, 1.7 Hz, 1H), 7.54-7.31 (m, 5H), 7.24 (d, J = 7.5 Hz, 1H), 6.63-6.53 (m, 1H), 4.61-4.24 (m, 8H), 4.10 (s, 3H), 4.09 (s, 3H), 4.09-4.00 (m, 1H), 3.72 (p, J = 8.2 Hz, 1H), 3.41-3.18 (m, 2H), 3.09-2.67 (m, 3H), 2.46-2.33 (m, 3H), 2.35 (s, 3H), 2.28-2.10 (m, 1H), 2.02-1.85 (m, 1H). |
| B-149 | 1H NMR (400 MHz, Methanol-d4) δ 7.89 (d, J = 7.5 Hz, 1H), 7.60 (d, J = 7.7 Hz, 1H), 7.57-7.30 (m, 5H), 7.25 (d, J = 7.5 Hz, 1H), 6.67-6.55 (m, 1H), 4.55 (d, J = 14.9 Hz, 1H), 4.45 (d, J = 14.2 Hz, 1H), 4.42-4.27 (m, 2H), 4.10 (s, 3H), 4.10 (s, 3H), 4.11-3.97 (m, 1H), 3.74 (d, J = 12.4 Hz, 1H), 3.68-2.52 (m, 7H), 2.52-2.34 (m, 3H), 2.38 (s, 3H), 2.32-1.80 (m, 9H). |
| B-150 | 1H NMR (400 MHz, Methanol-d4) δ 7.89 (d, J = 7.6 Hz, 1H), 7.64-7.58 (m, 1H), 7.55-7.31 (m, 5H), 7.25 (d, J = 7.5 Hz, 1H), 6.67-6.53 (m, 1H), 4.59-4.43 (m, 2H), 4.40-4.29 (m, 2H), 4.10 (s, 3H), 4.10 (s, 3H), 4.11-3.98 (m, 1H), 3.97-2.30 (m, 15H), 2.28-2.14 (m, 1H), 2.03-1.84 (m, 1H). |
| B-151 | 1H NMR (400 MHz, Methanol-d4) δ 7.89 (d, J = 7.6 Hz, 1H), 7.64-7.56 (m, 1H), 7.56-7.29 (m, 5H), 7.25 (d, J = 7.5 Hz, 1H), 6.66-6.54 (m, 1H), 4.38-4.28 (m, 4H), 4.10 (s, 3H), 4.10 (s, 3H), 4.10-3.97 (m, 2H), 3.35-3.18 (m, 4H), 3.15-2.59 (m, 3H), 2.49-2.29 (m, 6H), 2.38 (s, 3H), 2.31-2.10 (m, 1H), 2.03-1.81 (m, 2H). |
| B-152 | 1H NMR (400 MHz, Methanol-d4) δ 7.89 (d, J = 7.5 Hz, 1H), 7.60 (dd, J = 7.6, 1.9 Hz, 1H), 7.56-7.32 (m, 5H), 7.27 (d, J = 7.5 Hz, 1H), 6.68-6.56 (m, 1H), 4.64-4.23 (m, 8H), 4.14 (s, 3H), 4.10 (s, 3H), 4.10-3.95 (m, 1H), 3.73 (p, J = 8.3 Hz, 1H), 3.33-3.19 (m, 2H), 3.10-2.66 (m, 3H), 2.50-2.31 (m, 3H), 2.34-2.17 (m, 1H), 2.01-1.84 (m, 1H). |
| B-153 | 1H NMR (400 MHz, Methanol-d4) δ 7.89 (d, J = 7.7 Hz, 1H), 7.61 (dd, J = 7.6, 1.8 Hz, 1H), 7.58-7.32 (m, 5H), 7.27 (d, J = 7.6 Hz, 1H), 6.72-6.59 (m, 1H), 4.57 (d, J = 14.9 Hz, 1H), 4.47 (d, J = 14.7 Hz, 1H), 4.40-4.30 (m, 2H), 4.15 (s, 3H), 4.10 (s, 3H), 4.09-4.02 (m, 1H), 3.75 (d, J = 12.4 Hz, 1H), 3.59-3.51 (m, 1H), 3.39-3.22 (m, 3H), 3.11-2.67 (m, 3H), 2.49-2.30 (m, 3H), 2.32-2.19 (m, 1H), 2.20-1.84 (m, 8H). |
| B-154 | 1H NMR (400 MHz, Methanol-d4) δ 7.89 (d, J = 7.4 Hz, 1H), 7.60 (dd, J = 7.6, 1.8 Hz, 1H), 7.57-7.32 (m, 5H), 7.27 (d, J = 7.5 Hz, 1H), 6.70-6.58 (m, 1H), 4.60-4.43 (m, 2H), 4.40-4.28 (m, 2H), 4.15 (s, 3H), 4.10 (s, 3H), 4.09-4.00 (m, 1H), 4.00-2.48 (m, 12H), 2.47-2.33 (m, 3H), 2.33-2.17 (m, 1H), 1.97-1.85 (m, 1H). |
| B-155 | 1H NMR (400 MHz, Methanol-d4) δ 7.89 (d, J = 7.5 Hz, 1H), 7.63-7.57 (m, 1H), 7.57-7.32 (m, 5H), 7.27 (d, J = 7.6 Hz, 1H), 6.71-6.58 (m, 1H), 4.42-4.25 (m, 4H), 4.15 (s, 3H), 4.10 (s, 3H), 4.11-4.01 (m, 1H), 3.34-3.18 (m, 4H), 3.09-2.65 (m, 3H), 2.49-2.30 (m, 6H), 2.32-2.17 (m, 1H), 2.01-1.86 (m, 2H). |
| B-156 | 1H NMR (400 MHz, Methanol-d4) δ 7.89 (d, J = 7.6 Hz, 1H), 7.85 (s, 1H), 7.60 (dd, J = 7.6, 1.9 Hz, 1H), 7.54-7.44 (m, 2H), 7.45-7.30 (m, 3H), 7.25 (d, J = 7.6 Hz, 1H), 6.66-6.56 (m, 1H), 4.63-4.47 (m, 2H), 4.40-4.28 (m, 2H), 4.13 (s, 3H), 4.10 (s, 3H), 4.10-4.01 (m, 1H), 4.00-2.47 (m, 12H), 2.47-2.33 (m, 3H), 2.29-2.15 (m, 1H), 1.99-1.82 (m, 1H). |
| B-157 | 1H NMR (400 MHz, Methanol-d4) δ 7.89 (d, J = 7.5 Hz, 1H), 7.85 (s, 1H), 7.66-7.57 (m, 1H), 7.54-7.44 (m, 2H), 7.45-7.30 (m, 3H), 7.25 (d, J = 7.5 Hz, 1H), 6.65-6.56 (m, 1H), 4.64-4.48 (m, 2H), 4.41-4.28 (m, 2H), 4.13 (s, 3H), 4.10 (s, 3H), 4.10-4.01 (m, 1H), 3.96-2.47 (m, 12H), 3.76 (s, 3H), 2.47-2.31 (m, 3H), 2.29-2.12 (m, 1H), 2.02-1.81 (m, 1H). |
| B-158 | $^1$H NMR (400 MHz, Methanol-$d_4$) δ 7.93-7.82 (m, 2H), 7.61 (dd, J = 7.6, 1.8 Hz, 1H), 7.51 (d, J = 7.5 Hz, 2H), 7.46-7.30 (m, 3H), 7.26 (d, J = 7.3 Hz, 1H), 6.66 (s, 1H), 4.35 (d, J = 2.6 Hz, 2H), 4.25 (d, J = 5.8 Hz, 2H), 4.11 (d, J = 2.1 Hz, 6H), 4.06 (q, J = 6.7 Hz, 1H), 3.57 (d, J = 12.5 Hz, 1H), 3.27 (dd, J = 6.2, 3.8 Hz, 2H), 3.07 (t, J = 12.2 Hz, 1H), 2.71 (dd, J = 13.7, 6.3 Hz, 1H), 2.57-2.31 (m, 4H), 2.21 (d, J = 13.5 Hz, 2H), 2.02-1.76 (m, 3H). |
| B-159 | $^1$H NMR (400 MHz, Methanol-$d_4$) δ 7.93-7.81 (m, 2H), 7.61 (dd, J = 7.6, 1.8 Hz, 1H), 7.50 (d, J = 6.8 Hz, 2H), 7.41-7.30 (m, 2H), 7.25 (d, J = 7.6 Hz, 1H), 6.65 (s, 1H), 4.42-4.22 (m, 7H), 4.11 (d, J = 6 Hz, 6H), 4.05 (q, J = 6.7 Hz, 1H), 3.45 (s, 2H), 2.89 (s, 1H), 2.72 (d, J = 14.1 Hz, 1H), 2.50-2.29 (m, 3H), 2.07 (s, 2H), 1.98-1.85 (m, 1H). |
| B-160 | 1H NMR (400 MHz, Methanol-d4) δ 7.90 (d, J = 7.7 Hz, 2H), 7.61 (dd, J = 7.6, 1.8 Hz, 1H), 7.50 (d, J = 6.3 Hz, 2H), 7.47-7.30 (m, 3H), 7.26 (d, J = 7.3 Hz, 1H), 6.66 (s, 1H), 4.42-4.15 (m, 8H), 4.11 (d, J = 3.1 Hz, 6H), 4.06 (q, J = 6.6 Hz, 1H), 3.90-3.52 (m, 3H), 3.44-3.34 (m, 4H), 3.27 (dd, J = 6.2, 3.9 Hz, 3H), 2.62-2.14 (m, 6H), 2.01-1.83 (m, 1H). |
| B-161 | 1H NMR (400 MHz, Methanol-d4) δ 7.90 (d, J = 7.6 Hz, 2H), 7.61 (dd, J = 7.6, 1.8 Hz, 1H), 7.50 (s, 2H), 7.47-7.31 (m, 3H), 7.26 (d, J = 7.4 Hz, 1H), 6.66 (s, 1H), 4.37 (dd, J = 12.9, 3.1 Hz, 4H), 4.11 (d, J = 3.8 Hz, 6H), 4.06 (q, J = 6.6 Hz, 1H), 3.89 (dd, J = 29.5, 8.1 Hz, 3H), 3.64 (dd, J = 36.6, 9.4 Hz, 2H), 3.36 (d, J = 6.4 Hz, 4H), 3.27 (dd, J = 6.2, 3.9 Hz, 3H), 3.07-2.65 (m, 3H), 2.62-2.15 (m, 6H), 2.02-1.84 (m, 1H). |
| B-162 | 1H NMR (400 MHz, Methanol-d4) δ 7.91 (dd, J = 14.5, 7.0 Hz, 2H), 7.61 (dd, J = 7.6, 1.8 Hz, 1H), 7.51 (d, J = 7.6 Hz, 2H), 7.47-7.31 (m, 3H), 7.25 (d, J = 7.5 Hz, 1H), 6.65 (d, J = 5.9 Hz, 1H), 4.43-4.28 (m, 4H), 4.11 (d, J = 1.3 Hz, 6H), 4.05 (q, J = 6.7 Hz, 1H), 3.88-3.49 (m, 2H), 3.36 (s, 4H), 3.27 (dd, J = 6.2, 3.5 Hz, 3H), 3.20 (d, J = 15.9 Hz, 1H), 3.08-2.65 (m, 2H), 2.55-2.13 (m, 5H), 2.00-1.85 (m, 1H). |
| B-163 | 1H NMR (400 MHz, Methanol-d4) δ 7.90 (d, J = 7.6 Hz, 2H), 7.61 (dd, J = 7.7, 1.8 Hz, 1H), 7.51 (d, J = 7.4 Hz, 2H), 7.47-7.31 (m, 3H), 7.26 (d, J = 7.3 Hz, 1H), 6.65 (s, 1H), 4.43-4.28 (m, 4H), 4.11 (d, J = 4.6 Hz, 6H), 4.09-4.02 (m, 1H), 3.49 (s, 3H), 3.27 (dd, J = 6.2, 3.9 Hz, 3H), 3.07-2.89 (m, 1H), 2.89-2.65 (m, 2H), 2.55-2.16 (m, 5H), 2.10 (d, J = 8.0 Hz, 3H), 2.01-1.85 (m, 1H). |
| B-164 | $^1$H NMR (400 MHz, Methanol-$d_4$) δ 7.89 (dd, J = 7.8, 3.5 Hz, 2H), 7.61 (dd, J = 7.6, 1.8 Hz, 1H), 7.51 (d, J = 7.4 Hz, 2H), 7.47-7.31 (m, 3H), 7.26 (d, J = 7.4 Hz, 1H), 6.66 (d, J = 5.9 Hz, 1H), 4.43-4.28 (m, 4H), 4.11 (d, J = 5.1 Hz, 6H), 4.06 (q, J = 6.8 Hz, 1H), |

TABLE 2B-continued

| No. | NMR |
|---|---|
| | 3.73-3.52 (m, 2H), 3.36 (d, J = 10.5 Hz, 4H), 3.27 (dd, J = 6.2, 4.0 Hz, 2H), 3.10-2.66 (m, 2H), 2.57-2.31 (m, 3H), 2.23 (d, J = 12.8 Hz, 1H), 2.00-1.85 (m, 1H). |
| B-165 | 1H NMR (400 MHz, Methanol-d4) δ 7.89 (d, J = 7.6 Hz, 2H), 7.70 (s, 2H), 7.60 (dd, J = 7.7, 1.8 Hz, 2H), 7.46 (tt, J = 15.1, 8.0 Hz, 6H), 7.35 (t, J = 7.3 Hz, 5H), 7.25 (dd, J = 7.6, 1.1 Hz, 2H), 7.12 (s, 2H), 6.17 (s, 2H), 4.42 (s, 3H), 4.40-4.28 (m, 6H), 4.08 (d, J = 11.7 Hz, 13H), 3.81 (s, 1H), 3.71 (s, 1H), 3.56 (s, 2H), 3.33 (s, 5H), 3.30-3.19 (m, 7H), 3.02 (s, 1H), 2.93 (d, J = 10.4 Hz, 2H), 2.86 (s, 1H), 2.71 (s, 2H), 2.65 (s, 1H), 2.54 (s, 1H), 2.49-2.32 (m, 2H), 2.24-2.14 (m, 3H), 2.00-1.86 (m, 3H), 1.39 (s, 1H), 1.25 (d, J = 6.3 Hz, 2H. 19F NMR (376 MHz, Methanol-d4) δ −63.10 (d, J = 14.5 Hz), −77. |
| B-166 | $^1$H NMR (400 MHz, Methanol-d$_4$) δ 7.98-7.80 (m, 1H), 7.60 (dd, J = 7.6, 1.8 Hz, 1H), 7.55-7.40 (m, 2H), 7.36 (d, J = 7.6 Hz, 1H), 7.31-7.19 (m, 1H), 7.10-6.93 (m, 1H), 6.07 (s, 1H), 4.53-4.27 (m, 2H), 4.21-4.01 (m, 2H), 3.99 (s, 1H), 3.59 (d, J = 12.6 Hz, 1H), 3.29-3.15 (m, 1H), 3.10-2.54 (m, 3H), 2.54-2.28 (m, 2H), 2.19 (ddt, J = 13.3, 8.9, 5.0 Hz, 1H), 2.09-1.75 (m, 4H). $^{19}$F NMR (376 MHz, Methanol-d$_4$) δ −77.60. |
| B-167 | $^1$H NMR (400 MHz, Methanol-d$_4$) δ 7.89 (d, J = 7.5 Hz, 1H), 7.60 (dd, J = 7.7, 1.8 Hz, 1H), 7.46 (d, J = 21.8 Hz, 2H), 7.40-7.20 (m, 3H), 7.07-6.92 (m, 1H), 6.06 (s, 1H), 4.44-4.27 (m, 3H), 4.10 (s, 3H), 4.05-3.87 (m, 3H), 3.80-3.49 (m, 3H), 3.45 (s, 1H), 3.28-3.13 (m, 2H), 3.04-2.51 (m, 4H), 2.51-2.32 (m, 3H), 2.31-2.11 (m, 2H), 1.98 (s, 2H), 1.94-1.75 (m, 1H). $^{19}$F NMR (376 MHz, Methanol-d$_4$) δ-77.56. |
| B-168 | 1H NMR (400 MHz, Methanol-d4) δ 8.05 (s, 1H), 7.87 (d, J = 7.6 Hz, 1H), 7.60 (dd, J = 7.7, 1.8 Hz, 1H), 7.49 (dd, J = 11.2, 7.5 Hz, 2H), 7.45-7.30 (m, 3H), 7.25 (d, J = 7.4 Hz, 1H), 6.71 (d, J = 6.0 Hz, 1H), 4.43 (d, J = 17.3 Hz, 10H), 4.17 (s, 5H), 4.09 (s, 3H), 3.07-2.64 (m, 3H), 2.26-2.11 (m, 1H), 1.85 (s, 3H), 1.71-1.57 (m, 2H), 1.55-1.41 (m, 2H). |
| B-169 | $^1$H NMR (400 MHz, Methanol-d$_4$) δ 8.05 (s, 1H), 7.89 (d, J = 7.6 Hz, 1H), 7.60 (dd, J = 7.7, 1.8 Hz, 1H), 7.49 (dd, J = 11.2, 7.4 Hz, 2H), 7.45-7.29 (m, 3H), 7.25 (d, J = 7.5 Hz, 1H), 6.70 (s, 1H), 4.48 (d, J = 15.4 Hz, 4H), 4.32 (d, J = 9.7 Hz, 4H), 4.17 (s, 3H), 4.09 (s, 3H), 3.70 (s, 2H), 2.75 (s, 3H), 2.28-2.10 (m, 1H), 1.64 (t, J = 4.1 Hz, 2H), 1.56-1.40 (m, 2H). |
| B-170 | $^1$H NMR (400 MHz, Methanol-d$_4$) δ 8.05 (s, 1H), 7.88 (d, J = 7.6 Hz, 1H), 7.61 (dd, J = 7.7, 1.8 Hz, 1H), 7.50 (dd, J = 11.9, 7.4 Hz, 2H), 7.46-7.29 (m, 3H), 7.25 (d, J = 7.4 Hz, 1H), 6.71 (d, J = 6.0 Hz, 1H), 4.50 (s, 2H), 4.47-4.29 (m, 6H), 4.17 (s, 3H), 4.10 (s, 3H), 2.81 (d, J = 67.5 Hz, 2H), 2.50 (d, J = 7.5 Hz, 2H), 2.46-2.35 (m, 2H), 2.19 (ddd, J = 13.6, 9.1, 4.5 Hz, 1H), 1.64 (t, J = 4.1 Hz, 2H), 1.56-1.41 (m, 2H). |
| B-171 | 1H NMR (400 MHz, Methanol-d4) δ 8.05 (s, 1H), 7.88 (d, J = 7.5 Hz, 1H), 7.61 (dd, J = 7.7, 1.8 Hz, 1H), 7.49 (dd, J = 11.1, 7.4 Hz, 2H), 7.46-7.29 (m, 3H), 7.25 (d, J = 7.4 Hz, 1H), 6.71 (d, J = 6.0 Hz, 1H), 4.49 (d, J = 28.7 Hz, 4H), 4.19 (d, J = 14.5 Hz, 5H), 4.10 (d, J = 13.3 Hz, 5H), 3.07-2.63 (m, 2H), 2.26-2.12 (m, 1H), 1.68-1.60 (m, 2H), 1.54 (s, 3H), 1.51-1.44 (m, 2H). |
| B-172 | 1H NMR (400 MHz, Methanol-d4) δ 7.93-7.84 (m, 2H), 7.61 (dd, J = 7.7, 1.8 Hz, 1H), 7.50 (d, J = 6.1 Hz, 2H), 7.47-7.31 (m, 3H), 7.29-7.21 (m, 1H), 6.65 (s, 1H), 4.65 (d, J = 13.1 Hz, 1H), 4.35 (d, J = 2.6 Hz, 2H), 4.28 (d, J = 13.1 Hz, 1H), 4.11 (d, J = 3.5 Hz, 6H), 4.09-4.03 (m, 1H), 3.48 (d, J = 20.2 Hz, 1H), 3.27 (dd, J = 6.2, 3.7 Hz, 2H), 3.12-3.04 (m, 1H), 2.71 (dd, J = 13.6, 6.8 Hz, 1H), 2.49-2.31 (m, 4H), 2.31-2.12 (m, 1H), 2.01-1.85 (m, 1H), 1.84-1.70 (m, 2H). |
| B-173 | 1H NMR (400 MHz, Methanol-d4) δ 7.94-7.87 (m, 2H), 7.63 (dd, J = 7.7, 1.8 Hz, 1H), 7.57-7.30 (m, 5H), 7.27 (d, J = 7.5 Hz, 1H), 6.68 (s, 1H), 4.43-4.28 (m, 4H), 4.22-4.02 (m, 7H), 3.97 (s, 2H), 3.30-3.13 (m, 2H), 3.10-2.63 (m, 4H), 2.52-1.88 (m, 7H). |
| B-174 | 1H NMR (400 MHz, Methanol-d4) δ 7.91 (d, J = 7.1 Hz, 2H), 7.63 (d, J = 7.6, 1.8 Hz, 1H), 7.58-7.32 (m, 5H), 7.27 (d, J = 7.5 Hz, 1H), 6.68 (s, 1H), 4.46-4.30 (m, 3H), 4.30-4.20 (m, 1H), 4.19-3.98 (m, 7H), 3.60 (s, 1H), 3.39 (s, 2H), 3.28-3.18 (m, 2H), 3.16-2.68 (m, 2H), 2.50-1.81 (m, 11H), 1.62 (s, 1H). |
| B-175 | 1H NMR (400 MHz, Methanol-d4) δ 7.91 (d, J = 7.5 Hz, 1H), 7.83 (s, 1H), 7.63 (dd, J = 7.6, 1.8 Hz, 1H), 7.58-7.33 (m, 5H), 7.30-7.24 (m, 1H), 6.65 (s, 1H), 5.11 (d, J = 9.4 Hz, 1H), 4.45-4.18 (m, 5H), 4.17-4.03 (m, 7H), 3.68 (dd, J = 10.2, 3.9 Hz, 1H), 3.31-3.18 (m, 2H), 3.18-1.83 (m, 12H). |
| B-176 | 1H NMR (400 MHz, Methanol-d4) δ 7.94-7.88 (m, 2H), 7.63 (dd, J = 7.7, 1.8 Hz, 1H), 7.55-7.33 (m, 5H), 7.27 (d, J = 7.5 Hz, 1H), 6.68 (s, 1H), 4.43-4.28 (m, 3H), 4.13 (m, J = 0.8 Hz, 7H), 3.50 (dt, J = 3.3, 1.6 Hz, 1H), 3.29-3.12 (m, 2H), 3.08-1.73 (m, 19H). |
| B-177 | 1H NMR (400 MHz, Methanol-d4) δ 7.92 (d, J = 7.3 Hz, 2H), 7.62 (dd, J = 7.7, 1.8 Hz, 1H), 7.57-7.32 (m, 5H), 7.32-7.23 (d, 1H), 6.68 (s, 1H), 4.45-4.27 (m, 4H), 4.19-4.01 (m, 6H), 3.53-3.42 (m, 1H), 3.29-3.14 (m, 2H), 3.07-1.81 (m, 19H). |
| B-178 | 1H NMR (400 MHz, Methanol-d4) δ 7.95-7.85 (m, 2H), 7.63 (dd, J = 7.6, 1.8 Hz, 1H), 7.58-7.32 (m, 5H), 7.28 (d, J = 7.6 Hz, 1H), 6.69 (s, 1H), 4.44-4.30 (m, 2H), 4.26 (s, 2H), 4.18-4.04 (m, 8H), 3.55-3.44 (m, 2H), 3.32-3.17 (m, 2H), 3.17-1.83 (m, 12H), 1.69 (t, J = 14.1 Hz, 1H), 1.31 (s, 3H). |
| B-179 | 1H NMR (400 MHz, Methanol-d4) δ 8.13 (s, 1H), 7.60-7.30 (m, 5H), 7.30-7.20 (m, 1H), 7.08 (s, 1H), 7.02 (dd, J = 9.9, 1.4 Hz, 1H), 6.74 (s, 1H), 4.47 (s, 2H), 4.43 (s, 2H), 4.19 (s, 3H), 4.12-3.98 (m, 6H), 3.39-3.34 (m, 2H), 3.31-3.24 (m, 2H), 3.12-1.85 (m, 8H), 1.44 (t, J = 7.2 Hz, 3H). |
| B-180 | 1H NMR (400 MHz, Methanol-d4) δ 7.98-7.83 (m, 2H), 7.63 (dd, J = 7.6, 1.8 Hz, 1H), 7.58-7.31 (m, 5H), 7.27 (d, J = 7.4 Hz, 1H), 6.68 (s, 1H), 4.62 (s, J = 13.1 Hz, 1H), 4.46-4.30 (m, 3H), 4.21-4.01 (m, 7H), 3.76 (d, J = 10.5 Hz, 1H), 3.69-3.56 (m, 1H), 3.30-3.24 (m, 2H), 3.14-1.81 (m, 12H), 1.05 (d, J = 6.6 Hz, 3H). |
| B-181 | 1H NMR (400 MHz, Methanol-d4) δ 8.02-7.82 (m, 2H), 7.63 (dd, J = 7.7, 1.8 Hz, 1H), 7.57-7.29 (m, 5H), 7.28 (d, J = 7.4 Hz, 1H), 6.68 (s, 1H), 4.60-4.42 (m, 2H), 4.37 (d, J = 2.6 Hz, 2H), 4.20-4.00 (m, 7H), 3.72-3.62 (m, 1H), 3.52-3.40 (m, 1H), 3.30-3.22 (m, 2H), 3.19-1.66 (m, 17H). |
| B-182 | 1H NMR (400 MHz, Methanol-d4) δ 7.97-7.80 (m, 2H), 7.63 (dd, J = 7.6, 1.8 Hz, 1H), 7.58-7.30 (m, 5H), 7.27 (d, J = 7.4 Hz, 1H), 6.66 (s, 1H), 4.42-4.21 (m, 4H), 4.17-4.02 (m, 7H), 3.98 (d, J = 3.7 Hz, 1H), 3.87 (dd, J = 12.6, 6.9 Hz, 1H), 3.33-3.22 (m, |

TABLE 2B-continued

| No. | NMR |
|---|---|
| | 2H), 3.19-1.77 (m, 11H), 1.27 (s, 3H), 1.16 (s, 3H). |
| B-183 | 1H NMR (400 MHz, Methanol-d4) δ 7.98-7.81 (m, 2H), 7.63 (dd, J = 7.6, 1.8 Hz, 1H), 7.59-7.31 (m, 5H), 7.27 (d, J = 7.1 Hz, 1H), 6.66 (s, 1H), 4.49-4.25 (m, 4H), 4.16-4.03 (m, 7H), 3.76-3.65 (m, 1H), 3.55-3.39 (m, 1H), 3.31-3.21 (m, 2H), 3.11-1.81 (m, 11H), 1.40 (s, 3H), 1.11 (s, 3H). |
| B-184 | 1H NMR (400 MHz, Methanol-d4) δ 7.99-7.86 (m, 2H), 7.63 (dd, J = 7.7, 1.8 Hz, 1H), 7.56-7.31 (m, 5H), 7.27 (d, J = 7.4 Hz, 1H), 6.68 (s, 1H), 4.62-3.92 (m, 11H), 3.65-3.44 (m, 1H), 3.31-3.20 (m, 2H), 3.11-1.75 (m, 16H). |
| B-185 | 1H NMR (400 MHz, Methanol-d4) δ 7.91 (d, J = 7.6 Hz, 1H), 7.87 (s, 1H), 7.63 (dd, J = 7.6, 1.8 Hz, 1H), 7.57-7.32 (m, 5H), 7.27 (d, J = 7.6 Hz, 1H), 6.66 (s, 1H), 4.47-4.29 (m, 4H), 4.13 (d, J = 2.0 Hz, 7H), 3.71 (dd, J = 10.8, 6.4 Hz, 1H), 3.32-3.23 (m, 2H), 3.13-1.80 (m, 13H), 1.17 (d, J = 6.2 Hz, 3H). |
| B-186 | 1H NMR (400 MHz, Methanol-d4) δ 7.98-7.85 (m, 2H), 7.63 (dd, J = 7.7, 1.8 Hz, 1H), 7.60-7.32 (m, 5H), 7.28 (d, J = 7.3 Hz, 1H), 6.69 (s, 1H), 4.55 (dd, J = 23.5, 13.4 Hz, 1H), 4.37 (d, J = 2.7 Hz, 2H), 4.26 (d, J = 13.5 Hz, 1H), 4.19-4.00 (m, 7H), 3.97-1.73 (m, 16H), 3.29 (dd, J = 6.2, 3.8 Hz, 2H), 1.20-0.99 (m, 3H). |
| B-187 | 1H NMR (400 MHz, Methanol-d4) δ 8.12 (s, 1H), 7.57-7.31 (m, 5H), 7.26 (d, J = 7.5 Hz, 1H), 7.08 (s, 1H), 7.02 (dd, J = 9.9, 1.4 Hz, 1H), 6.74 (s, 1H), 4.44 (d, J = 8.1 Hz, 4H), 4.23-4.01 (m, 10H), 3.32-3.26 (m, 2H), 3.11-1.89 (m, 10H). |
| B-188 | 1H NMR (400 MHz, Methanol-d4) δ 8.13 (s, 1H), 7.66 (dd, J = 7.7, 1.8 Hz, 1H), 7.58-7.19 (m, 6H), 6.74 (s, 1H), 4.43 (d, J = 8.0 Hz, 4H), 4.21 (s, 3H), 4.15 (s, 3H), 4.13-4.01 (m, 1H), 3.95-1.82 (m, 17H). |
| B-189 | 1H NMR (400 MHz, Methanol-d4) δ 8.07 (s, 1H), 7.66 (dd, J = 7.7, 1.8 Hz, 1H), 7.60-7.18 (m, 6H), 6.72 (s, 1H), 4.45 (s, 2H), 4.42 (s, 2H), 4.19 (s, 3H), 4.15 (s, 3H), 4.12-4.02 (m, 1H), 3.31-3.25 (m, 2H), 3.11-1.84 (m, 8H), 1.66-1.55 (m, 2H), 1.52-1.40 (m, 2H). |
| B-190 | 1H NMR (400 MHz, Methanol-d4) δ 8.18 (s, 1H), 7.66 (dd, J = 7.6, 1.8 Hz, 1H), 7.60-7.19 (m, 6H), 6.74 (s, 1H), 4.55-4.33 (m, 4H), 4.20 (s, 3H), 4.16 (s, 3H), 4.11-3.99 (m, 1H), 3.65 (d, J = 12.1 Hz, 1H), 3.54-3.48 (m, 1H), 3.30-3.26 (m, 2H), 3.15-1.72 (m, 17H). |
| B-191 | 1H NMR (400 MHz, Methanol-d4) δ 8.13 (s, 1H), 7.66 (dd, J = 7.6, 1.8 Hz, 1H), 7.60-7.16 (m, 6H), 6.73 (s, 1H), 4.49-4.36 (m, 4H), 4.20 (s, 3H), 4.15 (s, 3H), 4.12-3.99 (m, 1H), 4.02-1.85 (m, 17H). |
| B-192 | 1H NMR (400 MHz, Methanol-d4) δ 8.08 (s, 1H), 7.59-7.30 (m, 5H), 7.26 (d, J = 7.5 Hz, 1H), 7.17-6.95 (m, 2H), 6.73 (s, 1H), 4.43 (s, 2H), 4.25 (s, 2H), 4.20 (s, 3H), 4.15-3.94 (m, 4H), 3.32-3.24 (m, 2H), 3.11-1.81 (m, 10H), 1.55 (s, 6H). |
| B-193 | 1H NMR (400 MHz, Methanol-d4) δ 8.07 (s, 1H), 7.57-7.30 (m, 4H), 7.25 (d, J = 7.5 Hz, 1H), 7.08 (s, 1H), 7.02 (dd, J = 9.9, 1.4 Hz, 1H), 6.73 (s, 1H), 4.47 (s, 2H), 4.43 (s, 2H), 4.19 (s, 3H), 414-3.96 (m, 4H), 3.31-3.23 (m, 2H), 3.15-1.78 (m, 8H), 1.71-1.59 (m, 2H), 1.55-1.39 (m, 2H). |
| B-194 | 1H NMR (400 MHz, Methanol-d4) δ 8.18 (s, 1H), 7.58-7.32 (m, 5H), 7.26 (d, J = 7.5 Hz, 1H), 7.08 (s, 1H), 7.02 (d, J = 9.9 Hz, 1H), 6.74 (s, 1H), 4.55-4.38 (m, 4H), 4.20 (s, 3H), 4.14-3.99 (m, 4H), 3.65 (d, J = 12.5 Hz, 1H), 3.57-3.45 (m, 1H), 3.30-3.22 (m, 2H), 3.18-1.72 (m, 17H). |
| B-195 | 1H NMR (400 MHz, Methanol-d4) δ 8.13 (s, 1H), 7.58-7.31 (m, 4H), 7.26 (d, J = 7.5 Hz, 1H), 7.08 (s, 1H), 7.02 (dd, J = 9.9, 1.4 Hz, 1H), 6.74 (s, 1H), 4.50-4.39 (m, 4H), 4.21 (s, 3H), 4.17-3.97 (m, 4H), 3.97-1.83 (m, 17H). |
| B-196 | 1H NMR (400 MHz, Methanol-d4) δ 8.08 (s, 1H), 7.92 (d, J = 7.6 Hz, 1H), 7.63 (dd, J = 7.6, 1.8 Hz, 1H), 7.60-7.31 (m, 5H), 7.27 (d, J = 7.5 Hz, 1H), 6.73 (s, 1H), 4.37 (d, J = 2.7 Hz, 2H), 4.25 (s, 2H), 4.20 (s, 3H), 4.17-4.05 (m, 4H), 3.31-3.25 (m, 2H), 3.13-1.83 (m, 10H), 1.56 (s, 6H). |
| B-197 | 1H NMR (400 MHz, Methanol-d4) δ 7.92 (d, J = 7.6 Hz, 1H), 7.86 (s, 1H), 7.63 (dd, J = 7.7, 1.8 Hz, 1H), 7.58-7.32 (m, 5H), 7.27 (d, J = 7.5 Hz, 1H), 6.67 (s, 1H), 4.37 (d, J = 2.7 Hz, 2H), 4.19 (s, 2H), 4.17-3.99 (m, 7H), 3.31-3.25 (m, 2H), 3.13-1.83 (m, 10H), 1.55 (s, 6H). |
| B-198 | 1H NMR (400 MHz, Methanol-d4) δ 8.10 (s, 1H), 7.92 (d, J = 7.6 Hz, 1H), 7.63 (dd, J = 7.6, 1.8 Hz, 1H), 7.57-7.33 (m, 5H), 7.27 (d, J = 7.5 Hz, 1H), 6.74 (s, 1H), 4.46-4.31 (m, 4H), 4.20 (s, 3H), 4.13 (s, 4H), 3.76 (s, 2H), 3.32-3.22 (m, 2H), 3.03 (s, 1H), 2.98-2.85 (m, 1H), 2.76 (s, 2H), 2.68 (s, 1H), 2.51-2.32 (m, 4H), 2.21 (dt, J = 13.7, 4.7 Hz, 1H), 2.04-1.89 (m, 1H), 1.73 (s, 1H), 1.38 (s, 1H). |
| B-199 | 1H NMR (400 MHz, Methanol-d4) δ 8.10 (s, 1H), 7.91 (d, J = 7.5 Hz, 1H), 7.63 (dd, J = 7.6, 1.8 Hz, 1H), 7.51 (d, J = 7.7 Hz, 2H), 7.48-7.32 (m, 3H), 7.27 (d, J = 7.4 Hz, 1H), 6.73 (s, 1H), 4.46-4.28 (m, 4H), 4.20 (s, 3H), 4.13 (s, 3H), 4.12-3.97 (m, 1H), 3.76 (dd, J = 14.5, 7.8 Hz, 2H), 3.32-3.21 (m, 2H), 3.03 (s, 1H), 2.94 (s, 1H), 2.91-2.83 (m, 1H), 2.76 (s, 2H), 2.68 (s, 1H), 2.52-2.32 (m, 3H), 2.22 (dq, J = 13.7, 5.5, 4.6 Hz, 1H), 2.00-1.88 (m, 1H), 1.75-1.70 (m, 1H) 1.44-1.30 (m, 1H). |
| B-200 | 1H NMR (400 MHz, Methanol-d4) δ 7.95-7.87 (m, 2H), 7.66-7.55 (m, 2H), 7.56-7.44 (m, 1H), 7.37 (dd, J = 12.5, 5.7 Hz, 3H), 7.27 (d, J = 7.6 Hz, 1H), 6.70 (s, 1H), 4.49 (dq, J = 9.2, 4.2 Hz, 1H), 4.43-4.30 (m, 4H), 4.13 (s, 4H), 3.86 (s, 1H), 3.74 (s, 1H), 3.60 (s, 2H), 3.46 (s, 2H), 3.32-3.21 (m, 2H), 3.05-2.94 (m, 1H), 2.72 (d, J = 38.1 Hz, 2H), 2.51-2.34 (m, 3H), 2.25 (s, 2H), 2.02-1.88 (m, 1H), 0.95-0.87 (m, 4H). |
| B-201 | 1H NMR (400 MHz, Methanol-d4) δ 7.91 (d, J = 7.6 Hz, 1H), 7.84 (s, 1H), 7.66-7.55 (m, 2H), 7.52 (t, J = 7.5 Hz, 1H), 7.49-7.31 (m, 3H), 7.27 (d, J = 7.4 Hz, 1H), 6.69 (s, 1H), 4.47 (tt, J = 6.1, 3.2 Hz, 1H), 4.43-4.27 (m, 4H), 4.13 (s, 3H), 4.08 (q, J = 6.8 Hz, 1H), 3.32-3.21 (m, 2H), 3.03 (s, 1H), 2.84 (s, 1H), 2.75 (s, 2H), 2.54-2.32 (m, 3H), 2.25 (s, 1H), 2.02-1.88 (m, 1H), 1.69-1.56 (m, 2H), 1.46 (t, J = 4.0 Hz, 2H), 0.99-0.84 (m, 3H). |
| B-202 | 1H NMR (400 MHz, Methanol-d4) δ 8.13 (s, 1H), 7.91 (d, 1H), 7.63 (dd, 1H), 7.57-7.32 (m, 5H), 7.27 (d, 1H), 6.73 (s, 1H), 4.52-4.34 (m, 5H), 4.34-4.23 (m, 1H), 4.21 (s, 3H), 4.13 (s, 3H), 4.11-4.01 (m, 2H), 3.97-3.40 (m, 3H), 3.29-3.12 (m, 2H), 3.10-2.70 (m, 2H), 2.43-2.13 (m, 3H), 1.50 (m, 4H). |
| B-203 | 1H NMR (400 MHz, Methanol-d4) δ 8.18 (s, 1H), 7.91 (d, 1H), 7.63 (dd, 1H), 7.58-7.32 (m, 5H), 7.27 (d, 1H), 6.74 (d, 1H), 4.57-4.29 (m, 5H), 4.19 (s, 3H), 4.12 (s, 3H), 4.10-3.97 (m, 1H), 3.66 (d, 1H), 3.51 |

TABLE 2B-continued

| No. | NMR |
|---|---|
| | (d, 1H), 3.38 (s, 1H), 3.32-3.14 (m, 2H), 3.15-2.65 (m, 4H), 2.57-2.16 (m, 3H), 2.17-1.75 (m, 7H). |
| B-204 | 1H NMR (400 MHz, Methanol-d4) δ 8.07 (s, 1H), 7.91 (d, 1H), 7.62 (dd, 1H), 7.58-7.30 (m, 5H), 7.26 (d, 1H), 6.72 (d, 1H), 4.47 (s, 2H), 4.43-4.30 (m, 3H), 4.19 (s, 3H), 4.12 (s, 3H), 4.10-3.93 (m, 1H), 3.31-3.15 (m, 2H), 2.72 (d, 2H), 2.68 (s, 3H), 2.42-2.10 (m, 3H), 1.70-1.61 (m, 2H), 1.56-1.43 (m, 2H). |
| B-205 | 1H NMR (400 MHz, Methanol-d4) δ 8.07 (s, 1H), 7.91 (d, 1H), 7.61 (dd, 1H), 7.44 (dt, 5H), 7.31-7.22 (m, 1H), 6.73 (d, 1H), 4.30 (s, 2H), 4.18 (d, 5H), 4.12 (s, 3H), 3.96 (s, 2H), 3.19-2.70 (m, 2H), 2.54-2.42 (m, 2H), 2.30-2.17 (m, 3H), 1.81 (s, 3H), 1.44 (s, 3H). |
| B-206 | 1H NMR (400 MHz, Methanol-d4) δ 8.06 (s, 1H), 7.89 (d, 1H), 7.62 (dd, 1H), 7.56-7.31 (m, 5H), 7.26 (d, 1H), 6.73 (d, 1H), 4.28 (d, 4H), 4.19 (s, 4H), 4.11 (s, 3H), 3.92 (s, 2H), 3.20 (d, 2H), 3.10-2.70 (m, 2H), 2.37-2.15 (m, 3H), 1.99-1.86 (m, 2H), 1.40 (d, 1H), 1.35 (s, 3H). |
| B-207 | 1H NMR (400 MHz, Methanol-d4) δ 8.07 (s, 1H), 7.89 (d, 1H), 7.62 (dd-1H), 7.56-7.31 (m, 5H), 7.26 (d, 1H), 6.72 (d, 1H), 4.47 (s, 2H), 4.27 (s, 2H), 4.19 (s, 3H), 4.11 (s, 3H), 3.20 (d, 2H), 3.11-2.71 (m, 3H), 2.38-2.14 (m, 3H), 2.05 (s, 1H), 1.99-1.87 (m, 2H), 1.69-1.61 (m, 2H), 1.50 (q, 2H), 1.35 (s, 3H). |
| B-208 | 1H NMR (400 MHz, Methanol-d4) δ 8.13 (s, 1H), 7.89 (d, 1H), 7.62 (dd, 1H), 7.57-7.33 (m, 5H), 7.27 (d, 1H), 6.73 (d, 1H), 4.45 (s, 2H), 4.27 (s, 2H), 4.20 (s, 4H), 4.11 (s, 3H), 3.21 (d, 2H), 3.08-2.62 (m, 4H), 2.37-2.14 (m, 4H), 2.00-1.85 (m, 2H), 1.50 (s, 4H), 1.35 (s, 3H). |
| B-209 | 1H NMR (400 MHz, Methanol-d4) δ 8.18 (s, 1H), 7.89 (d, 1H), 7.62 (dd, 1H), 7.57-7.32 (m, 5H), 7.27 (d, 1H), 6.74 (s, 1H), 4.54-4.40 (m, 2H), 4.27 (s, 3H), 4.25-4.16 (m, 4H), 4.11 (s, 4H), 3.66 (d, 1H), 3.51 (dd, 1H), 3.26-3.13 (m, 3H), 3.12-2.65 (m, 3H), 2.45 (s, 1H), 2.37-1.78 (m, 10H), 1.35 (s, 3H). |
| B-210 | 1H NMR (400 MHz, Methanol-d4) δ 8.12 (s, 1H), 7.89 (d, 1H), 7.62 (dd, 1H), 7.58-7.32 (m, 5H), 7.27 (d, 1H), 6.74 (s, 1H), 4.46 (s, 2H), 4.19 (m, 6H), 4.12 (s, 3H), 4.09 (s, 2H), 3.98 (m, 1H), 2.96 (m, 4H), 2.68 (s, 2H), 2.43 (m, 2H), 2.34-2.16 (m, 3H), 1.42 (s, 3H). |
| B-211 | 1H NMR (400 MHz, Methanol-d4) δ 8.06 (s, 1H), 7.89 (d, 1H), 7.62 (dd, 1H), 7.57-7.31 (m, 5H), 7.27 (d, 1H), 6.72 (d, 1H), 4.34-4.23 (m, 4H), 4.19 (d, 5H), 4.11 (s, 3H), 4.04-3.93 (m, 2H), 2.68 (s, 4H), 2.49-2.36 (m, 2H), 2.33-1.94 (m, 4H), 1.41 (s, 3H), 1.09 (t, 3H |
| B-212 | 1H NMR (400 MHz, Methanol-d4) δ 8.07 (s, 1H), 7.89 (d, 1H), 7.62 (dd, 1H), 7.44 (m, , 5H), 7.27 (d, 1H), 6.72 (d, 1H), 4.38-4.24 (m, 2H), 4.19 (d, 5H), 4.12 (s, 3H), 3.98 (m, 1H), 3.88 (d, 1H), 2.68 (s, 4H), 2.48-2.15 (m, 5H), 1.41 (s, 3H), 1.19 (d, 3H), 1.08 (d, 3H). |
| B-213 | 1H NMR (400 MHz, Methanol-d4) δ 8.13 (s, 1H), 7.89 (d, 1H), 7.62 (dd, 1H), 7.44 (m, 5H), 7.27 (d, 1H), 6.73 (d, 1H), 4.44 (s, 2H), 4.19 (d, 6H), 4.11 (s, 3H), 3.98 (m, 2H), 3.50 (m, 2H), 3.22-2.50 (m, 4H), 2.42 (m, 4H), 2.24 (m, 3H), 1.49 (s, 3H), 1.41 (s, 3H). |
| B-214 | 1H NMR (400 MHz, Methanol-d4) δ 8.06 (s, 1H), 7.88 (d, 1H), 7.62 (dd, 1H), 7.58-7.32 (m, 5H), 7.27 (d, 1H), 6.72 (d, 1H), 4.29 (s, 2H), 4.19 (d, 5H), 4.11 (s, 3H), 3.96 (d, 3H), 3.15-2.65 (m, 3H), 2.42 (m-2H), 2.33-2.15 (m, 3H), 1.41 (s, 3H). |
| B-215 | 1H NMR (400 MHz, Methanol-d4) δ 8.06 (s, 1H), 7.91 (dd, 1H), 7.68-7.31 (m, 6H), 7.27 (d, 1H), 6.72 (d, 1H), 4.29 (s, 2H), 4.19 (d, 5H), 4.16-3.93 (m, 6H), 2.77 (d, 2H), 2.43 (m, 2H), 2.34-2.15 (m, 2H), 1.65 (d, 3H), 1.42 (d, 3H). |
| B-216 | No NMR, poor resolution |
| B-217 | 1H NMR (400 MHz, Methanol-d4) δ 8.12 (s, 2H), 7.90 (d, J = 7.6 Hz, 2H), 7.63 (dd, J = 7.6, 1.7 Hz, 2H), 7.51 (t, J = 7.6 Hz, 2H), 7.38 (t, J = 11.1 Hz, 3H), 7.22-7.15 (m, 2H), 7.03 (dd, J = 9.5, 2.5 Hz, 2H), 6.68 (s, 2H), 4.44-4.28 (m, 2H), 4.17 (s, 3H), 4.10 (s, 3H), 3.64-3.58 (m, 1H), 3.34 (s, 2H), 3.30-3.19 (m, 2H), 2.89 (s, 1H), 2.77 (s, 2H), 2.65 (s, 1H), 2.53 (s, 1H), 2.49-2.32 (m, 2H), 2.23 (dt, J = 13.1, 6.0 Hz, 2H), 2.00-1.86 (m, 2H).19F NMR (376 MHz, Methanol-d4) δ −63.89, −77.69, −118.78 |
| B-218 | 1H NMR (400 MHz, Methanol-d4) δ 7.89 (d, J = 7.6 Hz, 1H), 7.70 (s, 1H), 7.60 (dd, J = 7.7, 1.8 Hz, 1H), 7.54-7.30 (m, 4H), 7.25 (d, J = 7.3 Hz, 2H), 7.12 (s, 2H), 6.17 (s, 1H), 4.42 (s, 1H), 4.34 (d, J = 2.7 Hz, 2H), 4.09 (d, J = 11.3 Hz, 5H), 3.98-3.84 (m, 2H), 3.60 (s, 2H), 3.34 (s, 1H), 3.30-3.19 (m, 3H), 3.06 (d, J = 12.5 Hz, 1H), 2.69 (s, 1H), 2.49-2.32 (m, 3H), 2.18 (tt, J = 13.4, 5.9 Hz, 3H), 2.00-1.85 (m, 4H), 1.46 (d, J = 12.2 Hz, 2H).19F NMR (376 MHz, Methanol-d4) δ −63.10 (d, J = 15.1 Hz), −77.54 |
| B-219 | 1H NMR (400 MHz, Methanol-d4) δ 7.89 (d, J = 7.6 Hz, 2H), 7.67 (s, 1H), 7.60 (dd, J = 7.7, 1.8 Hz, 2H), 7.48 (dd, J = 22.4, 7.5 Hz, 3H), 7.35 (dd, J = 15.0, 7.6 Hz, 3H), 7.25 (d, J = 7.4 Hz, 2H), 7.10 (s, 1H), 6.15 (s, 1H), 4.34 (d, J = 2.6 Hz, 3H), 4.20 (s, 2H), 4.08 (d, J = 19.8 Hz, 5H), 3.92 (s, 1H), 3.30-3.19 (m, 5H), 2.99 (s, 1H), 2.86 (d, J = 0.7 Hz, 1H), 2.49-2.32 (m, 4H), 1.97-1.87 (m, 2H), 1.65 (s, 2H). 19F NMR (376 MHz, Methanol-d4) δ −62.93, −62.98, −77.51. |
| B-220 | 1H NMR (400 MHz, Methanol-d4) δ 7.89 (d, J = 7.6 Hz, 1H), 7.68-7.56 (m, 2H), 7.47 (dd, J = 24.6, 7.6 Hz, 2H), 7.40-7.29 (m, 2H), 7.25 (d, J = 7.5 Hz, 1H), 7.10 (s, 1H), 6.16 (s, 1H), 4.45 (s, 2H), 4.34 (d, J = 2.7 Hz, 2H), 4.08 (d, J = 18.5 Hz, 5H), 3.63 (s, 3H), 3.30-3.19 (m, 4H), 2.68 (s, 1H), 2.49-2.32 (m, 3H), 2.18 (dd, J = 8.8, 4.6 Hz, 1H), 2.03 (s, 1H), 1.97-1.87 (m, 1H), 1.65-1.56 (m, 2H), 1.47-1.38 (m, 2H).19F NMR (376 MHz, Methanol-d4) δ −62.98, −63.03, −77.62. |
| B-221 | 1H NMR (400 MHz, Methanol-d4) δ 7.89 (d, J = 7.5 Hz, 1H), 7.66-7.57 (m, 2H), 7.48 (dd, J = 22.0, 7.6 Hz, 2H), 7.39-7.30 (m, 2H), 7.25 (d, J = 7.5 Hz, 1H), 7.12 (s, 1H), 6.15 (s, 1H), 4.34 (d, J = 2.7 Hz, 2H), 4.25 (s, 2H), 4.14-4.00 (m, 5H), 3.30-3.19 (m, 3H), 3.10 (s, 2H), 2.94 (s, 1H), 2.86 (s, 1H), 2.67 (d, J = 13.3 Hz, 1H), 2.49-2.32 (m, 3H), 2.24-2.11 (m, 1H), 1.98-1.85 (m, 1H), 1.32 (s, 4H), 1.25 (d, J = 6.3 Hz, 2H), 0.09 (s, 0H). |
| B-222 | 1H NMR (400 MHz, Methanol-d4) δ 7.98-7.84 (m, 1H), 7.73-7.53 (m, 2H), 7.53-7.31 (m, 3H), 7.25 (dd, J = 7.4, 1.0 Hz, 1H), 7.10 (s, 1H), 6.15 (s, 1H), 4.47-4.21 (m, 3H), 4.14-4.00 (m, 4H), 3.31-3.15 (m, 7H), 3.01 (dd, J = 12.8, 9.8 Hz, 2H), 2.65 (s, 2H), 2.56 (d, J = 6.3 Hz, 1H), 2.51-2.31 (m, 2H), 2.17 (dq, J = 13.6, 6.6 Hz, 1H), 2.02-1.79 (m, 1H), 1.25 (d, J = 6.2 Hz, 1H). |

TABLE 2B-continued

| No. | NMR |
|---|---|
| B-223 | 19F NMR (376 MHz, Methanol-d4) δ −63.01 (d, J = 17.7 Hz), −77.61.19F NMR (376 MHz, Methanol-d4) δ −62.98, −63.03, −77.72. |
| B-225 | 1H NMR (400 MHz, Methanol-d4) δ 8.03 (s, 1H), 7.88 (s, J = 7.6 Hz, 1H), 7.48 (dd, J = 11.8, 7.3 Hz, 2H), 7.34 (dd, J = 17.2, 7.6 Hz, 2H), 7.23 (d, J = 7.5 Hz, 1H), 6.68 (s, 1H), 4.32 (d, J = 3.1 Hz, 2H), 4.17 (s, 2H), 4.10 (s, 4H), 3.27-3.19 (m, 4H), 2.71 (s, 2H), 2.47-2.36 (m, 3H), 2.19 (s, 1H), 1.94-1.88 (m, 1H), 1.69-1.63 (m, 1H), 1.47-1.40 (m, 3H), 1.28 (s, 1H), 1.26-1.19 (m, 2H). |
| B-226 | 1H NMR (400 MHz, Methanol-d4) δ 8.03 (s, 1H), 7.92 (d, J = 7.6 Hz, 1H), 7.63 (dd, J = 7.6, 1.8 Hz, 1H), 7.56-7.46 (m, 2H), 7.38 (dd, J = 15.4, 7.6 Hz, 2H), 7.27 (d, J = 7.5 Hz, 1H), 6.68 (s, 1H), 4.43-4.30 (m, 3H), 4.13 (d, J = 3.5 Hz, 5H), 3.50 (t, J = 1.7 Hz, 1H), 3.31-3.10 (m, 5H), 3.05-2.75 (d, 5H), 2.51-2.32 (m, 4H), 2.28-1.63 (m, 11H). |
| B-227 | 1H NMR (400 MHz, Methanol-d4) δ 8.02 (s, 1H), 7.92 (d, J = 7.6 Hz, 1H), 7.66 (dd, J = 7.6, 1.8 Hz, 1H), 7.56-7.46 (m, 2H), 7.38 (dd, J = 15.4, 7.6 Hz, 2H), 7.27 (d, J = 7.6 Hz, 1H), 6.64 (s, 1H), 4.43-4.30 (m, 3H), 4.16 (d, J = 3.5 Hz, 5H), 3.50 (t, J = 1.7 Hz, 1H), 3.31-3.10 (m, 4H), 3.05-2.75 (d, 4H), 2.51-2.32 (m, 4H), 2.28-1.63 (m, 11H). |
| B-228 | 1H NMR (400 MHz, Methanol-d4) δ 8.03 (s, 1H), 7.94 (d, J = 7.6 Hz, 1H), 7.63 (dd, J = 7.6, 1.7 Hz, 1H), 7.56-7.46 (m, 2H), 7.37 (dd, J = 15.4, 7.6 Hz, 2H), 7.27 (d, J = 7.5 Hz, 1H), 6.68 (s, 1H), 4.42-4.30 (m, 3H), 4.13 (d, J = 3.4 Hz, 5H), 3.50 (t, J = 1.6 Hz, 1H), 3.31-3.10 (m, 4H), 3.05-2.75 (d, 4H), 2.50-2.32 (m, 4H), 2.30-1.60 (m, 11H). |
| B-229 | 1H NMR (400 MHz, Methanol-d4) δ 8.03 (s, 1H), 7.90 (d, J = 7.5 Hz, 1H), 7.59 (dd, J = 7.7, 1.8 Hz, 1H), 7.49 (dd, J = 11.8, 7.3 Hz, 2H), 7.34 (dd, J = 17.2, 7.6 Hz, 2H), 7.23 (d, J = 7.5 Hz, 1H), 6.68 (s, 1H), 4.31 (d, J = 3.1 Hz, 2H), 4.15 (s, 2H), 4.10 (s, 4H), 3.27-3.20 (m, 4H), 2.71 (s, 2H), 2.47-2.36 (m, 3H), 2.19 (s, 1H), 1.95-1.88 (m, 1H), 1.69-1.60 (m, 3H), 1.47-1.39 (m, 4H), 1.28 (s, 1H), 1.26-1.15 (m, 2H). |
| B-230 | 1H NMR (400 MHz, Methanol-d4) δ 8.04 (s, 1H), 7.92 (d, J = 7.5 Hz, 1H), 7.59 (dd, J = 7.7, 1.8 Hz, 1H), 7.49 (dd, J = 11.8, 7.3 Hz, 2H), 7.34 (dd, J = 17.2, 7.6 Hz, 2H), 7.23 (d, J = 7.5 Hz, 1H), 6.68 (s, 1H), 4.31 (d, J = 3.1 Hz, 2H), 4.15 (s, 2H), 4.10 (s, 4H), 3.27-3.20 (m, 4H), 2.71 (s, 2H), 2.48-2.36 (m, 3H), 2.19 (s, 1H), 1.97-1.88 (m, 1H), 1.73-1.70 (m, 1H), 1.47-1.39 (m, 4H), 1.28 (s, 1H), 1.26-1.15 (m, 2H). |
| B-231 | ¹H NMR (400 MHz, Methanol-d₄) δ 8.03 (s, 1H), 7.92 (d, J = 7.6 Hz, 1H), 7.63 (dd, J = 7.6, 1.8 Hz, 1H), 7.56-7.46 (m, 2H), 7.38 (dd, J = 15.4, 7.6 Hz, 2H), 7.27 (d, J = 7.5 Hz, 1H), 6.68 (s, 1H), 4.43-4.30 (m, 3H), 4.13 (d, J = 3.5 Hz, 5H), 3.50 (t, J = 1.7 Hz, 1H), 3.29 (d, J = 2.4 Hz, 3H), 3.18-3.11 (m, 1H), 3.01 (d, J = 14.4 Hz, 2H), 2.78 (d, J = 34.1 Hz, 3H), 2.51-2.32 (m, 4H), 2.28-1.63 (m, 11H). |
| B-232 | 1H NMR (400 MHz, Methanol-d4) δ 8.00 (s, 1H), 7.92 (d, J = 7.4 Hz, 1H), 7.62 (dd, J = 7.4, 1.8 Hz, 1H), 7.56-7.46 (m, 2H), 7.38 (dd, J = 15.4, 7.5 Hz, 2H), 7.28 (d, J = 7.5 Hz, 1H), 6.68 (s, 1H), 4.43-4.30 (m, 3H), 4.13 (d, J = 3.5 Hz, 5H), 3.50 (t, J = 1.7 Hz, 1H), 3.29 (d, J = 2.4 Hz, 2H), 3.18-3.11 (m, 1H), 3.02 (d, J = 14.4 Hz, 2H), 2.78 (d, J = 34.1 Hz, 2H), 2.51-2.32 (m, 4H), 2.29-1.63 (m, 11H). |
| B-233 | 1H NMR (400 MHz, Methanol-d4) δ 8.00 (s, 1H), 7.92 (d, J = 7.4 Hz, 1H), 7.62 (d, J = 7.4, 1.8 Hz, 1H), 7.56-7.46 (m, 2H), 7.38 (dd, J = 15.4, 7.5 Hz, 2H), 7.27 (d, J = 7.5 Hz, 1H), 6.68 (s, 1H), 4.43-4.30 (m, 3H), 4.13 (d, J = 3.5 Hz, 5H), 3.50 (t, J = 1.7 Hz, 1H), 3.29 (d, J = 2.2 Hz, 2H), 3.18-3.11 (m, 1H), 3.02 (d, J = 14.1 Hz, 2H), 2.77 (d, J = 34.1 Hz, 2H), 2.51-2.31 (m, 4H), 2.30-1.61 (m, 11H). |
| B-234 | ¹H NMR (400 MHz, Methanol-d₄) δ 8.02 (s, 1H), 7.89 (d, J = 7.6 Hz, 1H), 7.60 (dd, J = 7.5, 1.7 Hz, 1H), 7.49 (t, J = 8.6 Hz, 2H), 7.35 (dd, J = 13.6, 7.4 Hz, 2H), 7.24 (d, J = 7.5 Hz, 1H), 6.69 (s, 1H), 4.32 (d, J = 13.7 Hz, 4H), 4.12 (d, J = 13.1 Hz, 6H), 3.67-3.56 (m, 2H), 3.26 (dd, J = 6.2, 3.5 Hz, 2H), 2.71 (s, 3H), 2.45-2.29 (m, 3H), 2.26-2.07 (m, 3H), 1.97-1.78 (m, 3H), 0.84-0.72 (m, 2H). |
| B-235 | 1H NMR (400 MHz, Methanol-d4) δ 8.05 (s, 1H), 7.92 (d, J = 7.5 Hz, 1H), 7.59 (dd, J = 7.7, 1.8 Hz, 1H), 7.49 (dd, J = 11.8, 7.3 Hz, 2H), 7.34 (dd, J = 17.2, 7.6 Hz, 2H), 7.23 (d, J = 7.5 Hz, 1H), 6.68 (s, 1H), 4.32 (d, J = 3.1 Hz, 2H), 4.15 (s, 2H), 4.10 (s, 4H), 3.27-3.20 (m, 4H), 2.71 (s, 2H), 2.47-2.36 (m, 3H), 2.19 (s, 1H), 1.95-1.88 (m, 1H), 1.69-1.60 (m, 3H), 1.47-1.39 (m, 5H), 1.28 (s, 1H), 1.26-1.15 (m, 2H). |
| B-236 | 1H NMR (400 MHz, Methanol-d4) δ 8.04 (s, 1H), 7.91 (d, J = 7.5 Hz, 1H), 7.57 (dd, J = 7.7, 1.8 Hz, 1H), 7.49 (dd, J = 11.8, 7.3 Hz, 2H), 7.34 (dd, J = 17.2, 7.6 Hz, 2H), 7.24 (d, J = 7.5 Hz, 1H), 6.68 (s, 1H), 4.32 (d, J = 3.1 Hz, 2H), 4.15 (s, 2H), 4.10 (s, 4H), 3.27-3.20 (m, 4H), 2.71 (s, 2H), 2.49-2.34 (m, 3H), 2.19 (s, 1H), 1.95-1.88 (m, 1H), 1.69-1.60 (m, 3H), 1.47-1.39 (m, 5H), 1.28 (s, 1H), 1.26-1.15 (m, 2H). |
| B-237 | 1H NMR (400 MHz, Methanol-d4) δ 7.89 (d, J = 7.6 Hz, 1H), 7.63-7.56 (m, 2H), 7.49 (dd, J = 12.0, 7.4 Hz, 2H), 7.36 (h, J = 8.4, 7.6 Hz, 3H), 7.22 (dd, J = 7.6, 1.1 Hz, 1H), 6.61 (s, 1H), 4.49-4.37 (m, 1H), 4.34 (d, J = 2.5 Hz, 2H), 4.10 (s, 3H), 4.07 (s, 3H), 3.48 (d, J = 69.8 Hz, 3H), 3.28-3.18 (m, 2H), 3.04-2.67 (m, 4H), 2.48-2.31 (m, 4H), 2.18 (d, J = 15.1 Hz, 3H), 2.11 (s, 3H), 2.02-1.85 (m, 2H), 1.73 (s, 3H). |
| B-238 | 1H NMR (400 MHz, Methanol-d4) δ 7.89 (d, J = 7.6 Hz, 1H), 7.66-7.56 (m, 2H), 7.54-7.44 (m, 2H), 7.34 (dd, J = 20.4, 7.5 Hz, 3H), 7.26-7.17 (m, 1H), 6.62 (s, 1H), 4.48-4.37 (m, 1H), 4.34 (d, J = 2.5 Hz, 2H), 4.10 (s, 3H), 4.07 (s, 3H), 3.57 (s, 2H), 3.28-3.18 (m, 2H), 3.04-2.67 (m, 4H), 2.65 (s, 1H), 2.50-2.29 (m, 3H), 2.17 (d, J = 9.9 Hz, 3H), 2.11 (s, 3H), 2.03-1.84 (m, 3H), 1.72 (s, 3H). |
| B-239 | 1H NMR (400 MHz, Methanol-d4) δ 7.89 (d, J = 7.6 Hz, 1H), 7.68-7.54 (m, 2H), 7.52 (s, 1H), 7.50-7.44 (m, 1H), 7.43-7.27 (m, 3H), 7.22 (d, J = 7.3 Hz, 1H), 6.61 (s, 1H), 4.34 (d, J = 2.5 Hz, 2H), 4.20 (s, 2H), 4.10 (s, 3H), 4.06 (s, 3H), 3.84 (s, 2H), 3.26 (dd, J = 6.2, 3.9 Hz, 1H), 3.00-2.68 (m, 3H), 2.65 (s, 2H), 2.49-2.30 (m, 3H), 2.22-2.12 (m, 1H), 2.12-2.06 (m, 3H), 1.98-1.87 (m, 1H). |
| B-240 | 1H NMR (400 MHz, Methanol-d4) δ 7.89 (d, J = 7.6 Hz, 1H), 7.60 (dd, J = 7.6, 1.8 Hz, 1H), 7.57 (s, 1H), 7.53-7.44 (m, 2H), 7.44-7.27 (m, 3H), 7.22 (dd, J = 7.5, 1.2 Hz, 1H), 6.62 (s, 1H), 4.34 (d, J = 2.5 Hz, 2H), 4.22 (s, 2H), 4.10 (s, 3H), 4.09-4.02 (m, 4H), 3.94-3.85 (m, 1H), 3.26 (dd, J = 6.2, 4.2 Hz, 2H), 3.01-2.65 (m, 4H), 2.49-2.33 (m, 3H), 2.21-2.12 (m, 1H), 2.10 (d, J = 1.5 Hz, 3H), 1.98-1.86 (m, 1H), 1.62 (s, 3H). |

TABLE 2B-continued

| No. | NMR |
|---|---|
| B-241 | 1H NMR (400 MHz, Methanol-d4) δ 7.89 (d, J = 7.5 Hz, 1H), 7.60 (dd, J = 7.6, 1.8 Hz, 1H), 7.53 (s, 1H), 7.52-7.44 (m, 2H), 7.35 (tt, J = 15.1, 8.2 Hz, 3H), 7.25-7.19 (m, 1H), 6.61 (s, 1H), 4.34 (d, J = 2.6 Hz, 2H), 4.19 (d, J = 1.5 Hz, 2H), 4.10 (s, 3H), 4.05 (s, 3H), 4.00 (q, J = 7.2 Hz, 1H), 3.26 (dd, J = 6.2, 4.0 Hz, 2H), 3.01-2.65 (m, 4H), 2.49-2.32 (m, 3H), 2.16 (t, J = 11.0 Hz, 1H), 2.10 (s, 3H), 1.98-1.86 (m, 1H), 1.61 (d, J = 7.2 Hz, 3H). |
| B-242 | 1H NMR (400 MHz, Methanol-d4) δ 7.89 (d, J = 7.6 Hz, 1H), 7.60 (dd, J = 7.7, 1.8 Hz, 1H), 7.53 (s, 1H), 7.48 (q, J = 6.9, 6.3 Hz, 2H), 7.35 (tt, J = 15.1, 8.1 Hz, 3H), 7.24-7.19 (m, 1H), 6.61 (s, 1H), 4.34 (d, J = 2.5 Hz, 2H), 4.20 (s, 2H), 4.10 (s, 3H), 4.05 (s, 3H), 4.01 (q, J = 7.3 Hz, 1H), 3.26 (dd, J = 6.2, 4.0 Hz, 2H), 3.03-2.66 (m, 4H), 2.49-2.31 (m, 3H), 2.17 (d, J = 16.2 Hz, 1H), 2.13-2.07 (m, 3H), 1.98-1.86 (m, 1H), 1.61 (d, J = 7.2 Hz, 3H). |
| B-243 | 1H NMR (400 MHz, Methanol-d4) δ 7.60-7.53 (m, 2H), 7.48 (t, J = 7.9 Hz, 2H), 7.43-7.34 (m, 1H), 7.31 (t, J = 7.6 Hz, 1H), 7.22 (d, J = 9.6 Hz, 2H), 6.62 (s, 1H), 4.39 (s, 2H), 4.15 (s, 2H), 4.09 (s, 3H), 4.06 (s, 3H), 2.89 (d, J = 48.1 Hz, 3H), 2.70 (dd, J = 13.3, 6.0 Hz, 1H), 2.52 (s, 3H), 2.49-2.33 (m, 4H), 2.15 (s, 1H), 2.11 (d, J = 0.8 Hz, 3H), 1.99-1.87 (m, 2H), 1.67 (s, 6H). |
| B-244 | 1H NMR (400 MHz, Methanol-d4) δ 7.57 (dd, J = 7.6, 1.8 Hz, 1H), 7.53 (s, 1H), 7.46 (q, J = 9.3, 8.6 Hz, 2H), 7.42-7.34 (m, 1H), 7.31 (t, J = 7.5 Hz, 1H), 7.24-7.19 (m, 2H), 6.61 (s, 1H), 4.39 (d, J = 2.5 Hz, 4H), 4.08 (s, 3H), 4.05 (s, 3H), 2.87 (dd, J = 38.5, 17.3 Hz, 2H), 2.76-2.62 (m, 2H), 2.51 (s, 3H), 2.48-2.31 (m, 4H), 2.16 (dd, J = 13.6, 6.3 Hz, 1H), 2.09 (d, J = 1.4 Hz, 3H), 1.99-1.85 (m, 2H), 1.66-1.54 (m, 2H), 1.50-1.36 (m, 2H). |
| B-245 | 1H NMR (400 MHz, Methanol-d4) δ 7.89 (d, J = 7.6 Hz, 1H), 7.60 (dd, J = 7.6, 1.7 Hz, 1H), 7.55 (s, 1H), 7.48 (q, J = 6.8, 5.9 Hz, 2H), 7.36 (d, J = 7.5 Hz, 2H), 7.31 (t, J = 7.6 Hz, 1H), 7.22 (dd, J = 7.2, 0.9 Hz, 1H), 6.62 (s, 1H), 4.34 (d, J = 2.7 Hz, 2H), 4.15 (s, 2H), 4.10 (s, 3H), 4.06 (s, 3H), 3.26 (dd, J = 6.2, 3.9 Hz, 2H), 2.70 (dd, J = 13.2, 6.0 Hz, 2H), 2.48-2.35 (m, 4H), 2.15 (s, 1H), 2.11 (s, 3H), 1.97-1.86 (m, 2H), 1.67 (s, 6H). |
| B-246 | 1H NMR (400 MHz, Methanol-d4) δ 7.89 (d, J = 7.6 Hz, 1H), 7.60 (dd, J = 7.6, 1.8 Hz, 1H), 7.53 (s, 1H), 7.48 (q, J = 7.5 Hz, 2H), 7.37 (t, J = 9.4 Hz, 2H), 7.31 (t, J = 7.6 Hz, 1H), 7.22 (dd, J = 7.5, 1.1 Hz, 1H), 6.61 (d, J = 5.3 Hz, 1H), 4.38 (s, 2H), 4.34 (d, J = 2.6 Hz, 2H), 4.10 (s, 3H), 4.05 (s, 3H), 3.26 (dd, J = 6.2, 4.0 Hz, 2H), 2.99-2.66 (m, 4H), 2.48-2.33 (m, 3H), 2.17 (d, J = 14.9 Hz, 2H), 2.10 (s, 3H), 1.98-1.87 (m, 2H), 1.63-1.55 (m, 2H), 1.49-1.37 (m, 2H). |
| B-247 | 1H NMR (400 MHz, DMSO-d6) δ 8.86 (s, 1H), 8.63 (s, 1H), 7.95 (d, J = 7.6 Hz, 1H), 7.66-7.43 (m, 4H), 7.40 (d, J = 7.9 Hz, 2H), 7.33-7.26 (m, 1H), 6.67 (s, 1H), 4.34 (s, 2H), 4.22 (s, 2H), 4.11 (s, 3H), 3.97 (s, 3H), 3.88 (d, J = 7.5 Hz, 1H), 3.15 (s, 1H), 3.08 (s, 1H), 2.88 (s, 1H), 2.76 (d, J = 13.0 Hz, 1H), 2.26-2.10 (m, 1H), 1.84-1.75 (m, 1H), 1.36 (d, J = 13.4 Hz, 4H). |
| B-248 | 1H NMR (400 MHz, Methanol-d4) δ 8.12-8.04 (m, 1H), 7.92 (d, 1H), 7.63 (m, 1H), 7.57-7.31 (m, 5H), 7.26 (d, J1H), 6.79-6.66 (m, 1H), 4.37 (d, 2H), 4.27 (s, 2H), 4.19 (s, 3H), 4.12 (s, 6H), 3.29 (m, 2H), 3.03 (d, J6H), 2.96-2.65 (m, 3H), 2.51-2.34 (m, 3H), 2.21 (m, 1H), 2.00-1.87 (m, 1H). |
| B-249 | 1H NMR (400 MHz, Methanol-d4) δ 8.07-8.00 (m, 1H), 7.92 (d, 1H), 7.63 (dd, 1H), 7.55-7.31 (m, 5H), 7.26 (d, J = 7.5 Hz, 1H), 6.80-6.67 (m, 1H), 4.37 (d, 2H), 4.20 (d, 5H), 4.12 (s, 4H), 3.93 (d, 1H), 3.29 (dd, 2H), 3.15-2.84 (m, 1H), 2.83-2.66 (m, 5H), 2.52-2.32 (m, 3H), 2.21 (dd, 1H), 2.03-1.87 (m, 1H), 1.56 (d, 3H). |
| B-250 | 1H NMR (400 MHz, Methanol-d4) δ 8.06 (d, 1H), 7.92 (d, 1H), 7.63 (m, 1H), 7.57-7.32 (m, 5H), 7.26 (d, 1H), 6.72 (m, 1H), 4.37 (d, 2H), 4.27 (s, 2H), 4.19 (s, 3H), 4.11 (s, 4H), 3.82 (s, 2H), 3.29 (m, 2H), 3.14-2.66 (m, 6H), 2.52-2.34 (m, 3H), 2.21 (m, 1H), 2.01-1.87 (m, 1H). |
| B-251 | 1H NMR (400 MHz, Methanol-d4) δ 8.06 (d, J = 2.6 Hz, 1H), 7.89 (d, 1H), 7.62 (m, 1H), 7.57-7.32 (m, 5H), 7.27 (d, 1H), 6.73 (d, 1H), 4.27 (s, 2H), 4.20 (d, 4H), 4.12 (s, 3H), 3.98 (m, 1H), 3.26 (s, 2H), 3.19-2.66 (m, 2H), 2.42 (m, 2H), 2.32-2.14 (m, 2H), 1.46 (m, 2H), 1.41 (s, 3H), 1.12 (m, 2H). |
| B-252 | 1H NMR (400 MHz, Methanol-d4) δ 8.07 (d, 1H), 7.89 (d, 1H), 7.62 (dd, 1H), 7.57-7.32 (m, 5H), 7.27 (d, 1H), 6.73 (d, 1H), 4.28 (s, 2H), 4.21 (d, 5H), 4.11 (s, 3H), 3.99 (m, 1H), 3.18 (s, 2H), 3.10-2.65 (m, 2H), 2.43 (m, 2H), 2.25 (m, 2H), 1.41 (s, 3H), 1.35 (s, 6H). |
| B-253 | 1H NMR (400 MHz, Methanol-d4) δ 8.09 (s, 1H), 7.89 (d, 1H), 7.62 (dd, 1H), 7.57-7.32 (m, 5H), 7.27 (d, 1H), 6.79-6.66 (m, 1H), 4.39-4.23 (m, 2H), 4.20 (s, 5H), 4.11 (s, 3H), 3.98 (m, 1H), 3.71 (m, 1H), 3.18-2.64 (m, 4H), 2.42 (m, 2H), 2.32-2.14 (m, 3H), 1.49 (m, 2H), 1.41 (s, 3H). |
| B-254 | 1H NMR (400 MHz, Methanol-d4) δ 8.08 (d, 1H), 7.89 (d, 1H), 7.62 (dd, 1H), 7.57-7.32 (m, 5H), 7.27 (d, 1H), 6.73 (d, 1H), 4.27 (s, 2H), 4.20 (s, 5H), 4.12 (s, 3H), 3.98 (t, 1H), 3.19-2.67 (m, 4H), 2.42 (m, 2H), 2.32-2.16 (m, 3H), 1.41 (s, 3H). |
| B-255 | $^1$H NMR (400 MHz, Methanol-$d_4$) δ 8.06 (s, 1H), 7.89 (d, 1H), 7.62 (m, 1H), 7.57-7.31 (m, 5H), 7.27 (d, 1H), 6.72 (d, 1H), 4.40-4.23 (m, 2H), 4.19 (d, 6H), 4.12 (d, 3H), 4.04-3.91 (m, 1H), 3.39 (d, 1H), 3.17-2.67 (m, 3H), 2.42 (m, 2H), 2.32-2.12 (m, 2H), 1.41 (s, 3H), 1.34-1.17 (m, 1H), 0.94-0.81 (m, 2H), 0.76 (m, 1H), 0.70-0.60 (m, 1H). |
| B-256 | 1H NMR (400 MHz, Methanol-d4) δ 8.08 (d, 1H), 7.89 (d, 1H), 7.62 (m, 1H), 7.56-7.34 (m, 5H), 7.27 (d, 1H), 6.73 (d, 1H), 4.33 (s, 2H), 4.19 (s, 5H), 4.12 (s, 3H), 4.03-3.87 (m, 3H), 3.45 (s, 3H), 3.21-2.63 (m, 3H), 2.42 (m, 2H), 2.32-2.13 (m, 3H), 1.41 (s, 3H). |
| B-257 | 1H NMR (400 MHz, Methanol-d4) δ 8.16 (s, 1H), 7.92 (d, 1H), 7.63 (m, 1H), 7.57-7.33 (m, 5H), 7.27 (d, 1H), 6.74 (d, 1H), 4.53-4.31 (m, 4H), 4.19 (s, 4H), 4.12 (d, 4H), 3.31-3.22 (m, 2H), 2.91 (d, 3H), 2.76 (m, 1H), 2.53-2.33 (m, 3H), 2.30-2.16 (m, 1H), 2.03-1.87 (m, 1H), 1.70 (d, 3H). |
| B-258 | 1H NMR (400 MHz, Methanol-d4) δ 8.13 (s, 1H), 7.92 (d, 1H), 7.63 (m, 1H), 7.56-7.32 (m, 5H), 7.30-7.21 (m, 1H), 6.73 (m, 1H), 4.47 (s, 2H), 4.37 (d, 2H), 4.18 (s, 3H), 4.11 (s, 5H), 3.31-3.22 (m, 2H), 2.97 (s, 2H), 2.93-2.69 (m, 2H), 2.53-2.34 (m, 3H), 2.22 (m, 1H), 2.04-1.88 (m, 1H). |
| B-259 | 1H NMR (400 MHz, Methanol-d4) δ 7.92 (d, 1H), 7.62 (d, 1H), 7.51 (t, 1H), 7.46-7.26 (m, 4H), 7.21 (d, 1H), 5.88 (d, J = 7.9 Hz, 1H), 4.48-4.19 (m, 5H), 4.13 (s, 4H), |

TABLE 2B-continued

| No. | NMR |
|---|---|
| | 3.98 (s, 3H), 3.58-3.41 (m, 4H), 3.29 (m, 1H), 2.84 (d, 2H), 2.68 (s, 5H), 2.53-2.34 (m, 3H), 2.15 (s, 1H), 2.04-1.87 (m, 1H). |
| B-260 | 1H NMR (400 MHz, Methanol-d4) δ 8.08 (s, 1H), 7.92 (d, 1H), 7.63 (m, 1H), 7.58-7.31 (m, 5H), 7.27 (d, 1H), 6.72 (d, 1H), 4.54-4.35 (m, 3H), 4.19 (s, 4H), 4.14-4.02 (m, 5H), 3.31-3.22 (m, 2H), 3.13-2.66 (m, 2H), 2.53-2.34 (m, 3H), 2.29-2.14 (m, 1H), 2.03-1.86 (m, 1H), 1.55 (s, 3H). |
| B-261 | $^1$H NMR (400 MHz, Methanol-d$_4$) δ 8.07 (d, 1H), 7.92 (d, 1H), 7.63 (m, 1H), 7.55-7.31 (m, 5H), 7.26 (d, 1H), 6.77-6.64 (m, 1H), 4.37 (d, 2H), 4.19 (d, 5H), 4.12 (s, 4H), 3.37-3.23 (m, 4H), 3.18 (d, 2H), 3.07-2.65 (m, 3H), 2.53-2.14 (m, 6H), 2.01-1.88 (m, 3H), 1.35 (s, 3H). |
| B-262 | 1H NMR (400 MHz, Methanol-d4) δ 8.13-8.03 (m, 1H), 7.92 (d, 1H), 7.63 (m, 1H), 7.56-7.31 (m, 5H), 7.26 (d, 1H), 6.79-6.62 (m, 1H), 4.46-4.32 (m, 3H), 4.20 (d, 5H), 4.12 (s, 4H), 3.29 (m, 2H), 3.21 (m-2H), 3.11-2.60 (m, 4H), 2.51-2.32 (m, 3H), 2.30-2.14 (m, 5H), 2.02-1.87 (m, 1H). |
| B-263 | 1H NMR (400 MHz, Methanol-d4) δ 8.07 (d, 1H), 7.92 (d, 1H), 7.63 (m, 1H), 7.57-7.32 (m, 5H), 7.27 (d, 1H), 6.73 (m, 1H), 4.37 (d, 2H), 4.19 (s, 3H), 4.13 (d, 6H), 3.96 (t, 1H), 3.31-3.23 (m, 2H), 3.11-2.65 (m, 3H), 2.42 (m, 4H), 2.32-2.14 (m, 3H), 2.03-1.85 (m, 1H), 1.41 (s, 3H). |
| B-264 | 1H NMR (400 MHz, Methanol-d4) δ 8.08 (d, 1H), 7.92 (d, 1H), 7.63 (m, 1H), 7.58-7.32 (m, 5H), 7.27 (d, 1H), 6.73 (d, 1H), 4.43-4.26 (m, 4H), 4.23 (t, 1H), 4.18 (s, 3H), 4.12 (s, 4H), 4.01-3.89 (m, 2H), 3.45 (s, 3H), 3.29 (m, 2H), 3.13-2.66 (m, 2H), 2.52-2.33 (m, 3H), 2.22 (m, 1H), 2.02-1.87 (m, 1H). |
| B-265 | 1H NMR (400 MHz, Methanol-d4) δ 8.05 (s, 1H), 7.92 (d, 1H), 7.63 (m, 1H), 7.57-7.31 (m, 5H), 7.27 (d, 1H), 6.72 (d, 1H), 4.37 (d, 2H), 4.20 (d, 5H), 4.12 (s, 4H), 3.98 (q, 1H), 3.31-3.23 (m, 2H), 2.76 (d, 2H), 2.52-2.34 (m, 3H), 2.29-2.13 (m, 1H), 2.03-1.88 (m, 1H), 1.60 (d, 3H). |
| B-266 | 1H NMR (400 MHz, Methanol-d4) δ 8.07 (d, 1H), 7.92 (d, 1H), 7.63 (m, 1H), 7.57-7.32 (m, 5H), 7.27 (d, 1H), 6.72 (s, 1H), 4.42-4.32 (m, 2H), 4.27 (s, 2H), 4.19 (s, 3H), 4.12 (s, 4H), 3.86 (s, 3H), 3.29 (m, 2H), 3.13-2.67 (m, 3H), 2.52-2.32 (m, 3H), 2.21 (m, 1H), 2.02-1.88 (m, 1H). |
| B-267 | 1H NMR (400 MHz, Methanol-d4) δ 8.08 (d, 1H), 7.92 (d, 1H), 7.63 (m, 1H), 7.58-7.32 (m, 5H), 7.27 (d, 1H), 6.73 (d, 1H), 4.37 (m, 2H), 4.27 (m, 2H), 4.20 (s, 4H), 4.12 (s, 3H), 3.31-3.22 (m, 2H), 3.15-2.66 (m, 5H), 2.52-2.34 (m, 2H), 2.29-2.14 (m, 1H), 2.01-1.86 (m, 1H). |
| B-268 | 1H NMR (400 MHz, Methanol-d4) δ 8.06 (s, 1H), 7.92 (d, 1H), 7.63 (m, 1H), 7.58-7.32 (m, 5H), 7.27 (d, 1H), 6.72 (d, 1H), 4.42-4.24 (m, 4H), 4.18 (s, 3H), 4.12 (s, 4H), 3.42 (d, 1H), 3.29 (dd, 2H), 2.71 (d, 1H), 2.52-2.34 (m, 3H), 2.29-2.15 (m, 1H), 2.04-1.87 (m, 1H), 1.34-1.19 (m, 2H), 0.93-0.60 (m, 3H). |
| B-269 | 1H NMR (400 MHz, Methanol-d4) δ 8.07 (d, 1H), 7.92 (d, 1H), 7.63 (m, 1H), 7.58-7.32 (m, 5H), 7.27 (d, 1H), 6.72 (s, 1H), 4.37 (d, 2H), 4.29 (d, 2H), 4.18 (s, 3H), 4.12 (s, 4H), 4.02 (d, 1H), 3.29 (m, 2H), 3.13-2.66 (m, 2H), 2.52-2.35 (m, 4H), 2.31-1.87 (m, 3H), 1.32 (s, 1H), 1.10 (m, 3H). |
| B-270 | $^1$H NMR (400 MHz, Methanol-d$_4$) δ 8.07 (s, 1H), 7.92 (d, 1H), 7.63 (m, 1H), 7.58-7.32 (m, 5H), 7.27 (d, 1H), 6.72 (d, 1H), 4.41-4.22 (m, 4H), 4.18 (m, 4H), 4.12 (s, 4H), 3.91 (d, 1H), 3.30-3.18 (m, 1H), 2.71 (d-3H), 2.53-2.32 (m, 4H), 2.28-2.17 (m, 1H), 2.02-1.90 (m, 1H), 1.32 (s, 1H), 1.19 (d, 3H), 1.08 (d, 3H). |
| B-271 | 1H NMR (400 MHz, Methanol-d4) δ 8.07 (d, 1H), 7.92 (d, 1H), 7.63 (m, 1H), 7.57-7.33 (m, 5H), 7.27 (d, 1H), 6.73 (d, 1H), 4.37 (d, 2H), 4.29 (s, 2H), 4.19 (s, 3H), 4.13 (s, 4H), 3.29 (m, 2H), 3.17-2.70 (m, 3H), 2.68 (s, 1H), 2.53-2.33 (m, 3H), 2.22 (m, 1H), 2.06-1.89 (m, 1H), 1.65 (d, 3H). |
| B-272 | 1H NMR (400 MHz, Methanol-d4) δ 8.07 (d, 1H), 7.92 (d, 1H), 7.63 (m, 1H), 7.58-7.33 (m, 5H), 7.27 (d, 1H), 6.73 (d, 1H), 4.37 (d, 2H), 4.29 (s, 2H), 4.19 (s, 3H), 4.13 (m, 4H), 3.96 (s, 2H), 3.29 (m, 2H), 3.15-2.69 (m, 2H), 2.68 (s, 1H), 2.53-2.35 (m, 3H), 2.30-2.16 (m, 1H), 2.01-1.89 (m, 1H). |

Biological Example 1

PD-1/PD-L1 & CTLA/CD80 Biochemical Protein-Protein Interaction Assay

Compounds were tested in biochemical protein-protein interaction assays to determine if they can specifically block the interaction between the extracellular domains of PD-1/PD-L1 or CTLA/CD80. Binding of the protein pairs is measured using a bead based Amplified Luminescent Proximity Homogeneous Assay (ALPHA) platform. Binding of each protein pair results in proximity of the donor and acceptor beads which leads to an increase in ALPHA signal. Disruption of the protein-protein interaction with a test compound results in a decrease in ALPHA signal. Assays are performed in 25 mM Hepes (pH 7.4), 150 mM NaCl, 3.4 mM EDTA, 0.005% Tween 20, and 0.01% BSA. Final protein concentration in the assays were 0.3 nM (His tagged PD-L1), 2.5 nM (biotinylated Fc-PD-1), 1 nM (His tagged CTLA4) and 1 nM (biotinylated CD80). After an assay reaction time of 60 minutes at 25° C., binding was measured with addition of 20 μg/mL ALPHA assay acceptor beads (anti-His coated) and 20 μg/mL ALPHA assay donor beads (streptavidin coated). $IC_{50}$ values were calculated from the fit of the dose-response curves to a four-parameter equation. Representative data are shown below in Table 3A and Table 3B. All $IC_{50}$ readings of 0.064 nM are equal to or less than 0.064 nM.

TABLE 3A

| No. | $IC_{50}$ PD-L1-PD1 (nM) |
|---|---|
| A-1 | 0.064 |
| A-2 | 0.064 |
| A-3 | 0.064 |
| A-4 | 0.064 |
| A-5 | 0.064 |
| A-6 | 0.67 |
| A-7 | 1.178 |
| A-8 | 0.064 |
| A-9 | 1.659 |
| A-10 | 0.064 |
| A-11 | 0.064 |
| A-12 | 0.064 |
| A-13 | 0.065 |
| A-14 | 0.064 |
| A-15 | 0.064 |
| A-16 | 0.064 |

TABLE 3A-continued

| No. | IC$_{50}$ PD-L1-PD1 (nM) |
|---|---|
| A-17 | 0.077 |
| A-18 | 0.064 |
| A-19 | 0.064 |
| A-20 | 0.064 |
| A-21 | 0.064 |
| A-22 | 0.064 |
| A-23 | 0.064 |
| A-24 | 0.064 |
| A-25 | 0.064 |
| A-26 | 0.064 |
| A-27 | 0.064 |
| A-28 | 0.064 |
| A-29 | 0.064 |
| A-30 | 0.064 |
| A-31 | 0.064 |
| A-32 | 0.064 |
| A-33 | 0.064 |
| A-34 | 0.064 |
| A-35 | 0.064 |
| A-36 | 0.064 |
| A-37 | 0.064 |
| A-38 | 0.064 |
| A-39 | 0.064 |
| A-40 | 0.064 |
| A-41 | 0.064 |
| A-42 | 0.064 |
| A-43 | 0.064 |
| A-44 | 0.064 |
| A-45 | 0.064 |
| A-46 | 0.064 |
| A-47 | 0.064 |
| A-48 | 0.064 |
| A-49 | 0.064 |
| A-50 | 0.064 |
| A-51 | 0.064 |
| A-52 | 0.064 |
| A-53 | 0.064 |
| A-54 | 0.064 |
| A-55 | 0.064 |
| A-56 | 0.064 |
| A-57 | 0.064 |
| A-58 | 0.064 |
| A-59 | 0.064 |
| A-60 | 0.064 |
| A-61 | 0.064 |
| A-62 | 0.064 |
| A-63 | 0.064 |
| A-64 | 0.064 |
| A-65 | 0.064 |
| A-66 | 0.064 |
| A-67 | 0.064 |
| A-68 | 0.064 |
| A-69 | 0.064 |
| A-70 | 0.064 |
| A-71 | 0.064 |
| A-72 | 0.064 |
| A-73 | 0.064 |
| A-74 | 0.064 |
| A-75 | 0.064 |
| A-76 | 0.064 |
| A-77 | 0.064 |
| A-78 | 0.064 |
| A-79 | 0.064 |
| A-80 | 0.064 |
| A-81 | 0.064 |
| A-82 | 0.14 |
| A-83 | 0.064 |
| A-84 | 0.064 |
| A-85 | 0.064 |
| A-86 | 0.064 |
| A-87 | 0.064 |
| A-88 | 0.202 |
| A-89 | 0.072 |
| A-90 | 0.064 |
| A-91 | 0.064 |
| A-92 | 0.064 |
| A-93 | 0.064 |
| A-94 | 0.064 |
| A-95 | 0.064 |
| A-96 | 0.064 |
| A-97 | 0.064 |
| A-98 | 0.064 |
| A-99 | 0.397 |
| A-100 | 0.064 |
| A-101 | 0.064 |
| A-102 | 0.064 |
| A-103 | 0.064 |
| A-104 | 0.064 |
| A-105 | 0.064 |
| A-106 | 0.064 |
| A-107 | 0.064 |
| A-108 | 0.064 |
| A-109 | 0.064 |

TABLE 3B

| No. | IC$_{50}$ PD-L1-PD1 (nM) |
|---|---|
| B-1 | 0.064 |
| B-2 | 0.064 |
| B-3 | 0.066 |
| B-4 | 0.064 |
| B-5 | 0.064 |
| B-6 | 0.064 |
| B-7 | 0.064 |
| B-8 | 0.064 |
| B-9 | 0.064 |
| B-10 | 0.064 |
| B-11 | 0.066 |
| B-12 | 0.064 |
| B-13 | 0.064 |
| B-14 | 0.064 |
| B-15 | 0.064 |
| B-16 | 0.064 |
| B-17 | 0.064 |
| B-18 | 0.064 |
| B-19 | 0.064 |
| B-20 | 0.064 |
| B-21 | 0.064 |
| B-22 | 0.074 |
| B-23 | 0.064 |
| B-24 | 0.064 |
| B-25 | 0.064 |
| B-26 | 0.064 |
| B-27 | 0.064 |
| B-28 | 0.088 |
| B-29 | 0.101 |
| B-30 | 0.158 |
| B-31 | 0.085 |
| B-32 | 0.095 |
| B-33 | 0.064 |
| B-34 | 0.111 |
| B-35 | 0.064 |
| B-36 | 0.064 |
| B-37 | 0.064 |
| B-38 | 0.095 |
| B-39 | 0.064 |
| B-40 | 0.169 |
| B-41 | 0.064 |
| B-42 | 0.064 |
| B-43 | 0.064 |
| B-44 | 0.064 |
| B-45 | 0.064 |
| B-46 | 0.064 |
| B-47 | 0.064 |
| B-48 | 0.064 |
| B-49 | 0.064 |
| B-50 | 0.064 |
| B-51 | 0.064 |
| B-52 | 0.095 |

TABLE 3B-continued

| No. | IC$_{50}$ PD-L1-PD1 (nM) |
|---|---|
| B-53 | 0.064 |
| B-54 | 0.064 |
| B-55 | 0.064 |
| B-56 | 0.189 |
| B-57 | 0.08 |
| B-58 | 0.064 |
| B-59 | 0.113 |
| B-60 | 0.064 |
| B-61 | 0.064 |
| B-62 | 0.064 |
| B-63 | 0.064 |
| B-64 | 0.076 |
| B-65 | 0.064 |
| B-66 | 0.064 |
| B-67 | 0.064 |
| B-68 | 0.064 |
| B-69 | 0.064 |
| B-70 | 0.064 |
| B-71 | 0.064 |
| B-72 | 0.064 |
| B-73 | 0.064 |
| B-74 | 0.064 |
| B-75 | 0.088 |
| B-76 | 0.064 |
| B-77 | 0.064 |
| B-78 | 0.064 |
| B-79 | 0.064 |
| B-80 | 0.064 |
| B-81 | 0.064 |
| B-82 | 0.064 |
| B-83 | 0.064 |
| B-84 | 0.064 |
| B-85 | 0.064 |
| B-86 | 0.235 |
| B-87 | 0.064 |
| B-88 | 0.064 |
| B-89 | 0.387 |
| B-90 | 0.111 |
| B-91 | 0.064 |
| B-92 | 0.064 |
| B-93 | 0.064 |
| B-94 | 0.068 |
| B-95 | 0.064 |
| B-96 | 0.064 |
| B-97 | 0.064 |
| B-98 | 0.111 |
| B-99 | 0.086 |
| B-100 | 0.064 |
| B-101 | 0.201 |
| B-102 | 0.146 |
| B-103 | 0.234 |
| B-104 | 0.308 |
| B-105 | 1.987 |
| B-106 | 0.064 |
| B-107 | 0.064 |
| B-108 | 3.899 |
| B-109 | 0.068 |
| B-110 | 0.199 |
| B-111 | 0.152 |
| B-112 | 0.117 |
| B-113 | 0.064 |
| B-114 | 0.064 |
| B-115 | 0.064 |
| B-116 | 0.064 |
| B-117 | 0.064 |
| B-118 | 0.064 |
| B-119 | 0.064 |
| B-120 | 0.064 |
| B-121 | 0.064 |
| B-122 | 0.064 |
| B-123 | 0.064 |
| B-124 | 0.084 |
| B-125 | 0.064 |
| B-126 | 0.064 |
| B-127 | 0.064 |
| B-128 | 0.064 |
| B-129 | 0.064 |
| B-130 | 0.064 |
| B-131 | 0.064 |
| B-132 | 0.266 |
| B-133 | 0.064 |
| B-134 | 0.064 |
| B-135 | 0.064 |
| B-136 | 0.064 |
| B-137 | 0.064 |
| B-138 | 0.064 |
| B-139 | 0.064 |
| B-140 | 0.064 |
| B-141 | 0.064 |
| B-142 | 0.064 |
| B-143 | 0.064 |
| B-144 | 0.064 |
| B-145 | 0.064 |
| B-146 | 0.41 |
| B-147 | 0.351 |
| B-148 | 0.064 |
| B-149 | 0.064 |
| B-150 | 0.064 |
| B-151 | 0.072 |
| B-152 | 0.064 |
| B-153 | 0.064 |
| B-154 | 0.064 |
| B-155 | 0.22 |
| B-156 | 0.076 |
| B-157 | 0.195 |
| B-158 | 0.064 |
| B-159 | 0.064 |
| B-160 | 0.54 |
| B-161 | 0.073 |
| B-162 | 0.082 |
| B-163 | 0.064 |
| B-164 | 0.27 |
| B-165 | 0.064 |
| B-166 | 0.064 |
| B-167 | 0.064 |
| B-168 | 0.064 |
| B-169 | 0.064 |
| B-170 | 0.064 |
| B-171 | 0.064 |
| B-172 | 0.064 |
| B-173 | 0.064 |
| B-174 | 0.064 |
| B-175 | 0.064 |
| B-176 | 0.064 |
| B-177 | 0.064 |
| B-178 | 0.064 |
| B-179 | 0.064 |
| B-180 | 0.064 |
| B-181 | 0.064 |
| B-182 | 0.064 |
| B-183 | 0.064 |
| B-184 | 0.064 |
| B-185 | 0.064 |
| B-186 | 0.064 |
| B-187 | 0.064 |
| B-188 | 0.064 |
| B-189 | 0.064 |
| B-190 | 0.064 |
| B-191 | 0.064 |
| B-192 | 0.064 |
| B-193 | 0.064 |
| B-194 | 0.064 |
| B-195 | 0.064 |
| B-196 | 0.064 |
| B-197 | 0.064 |
| B-198 | 0.064 |
| B-199 | 0.064 |
| B-200 | 0.064 |
| B-201 | 0.064 |
| B-202 | 0.064 |
| B-203 | 0.064 |
| B-204 | 0.064 |
| B-205 | 0.064 |
| B-206 | 0.064 |

TABLE 3B-continued

| No. | IC$_{50}$ PD-L1-PD1 (nM) |
|---|---|
| B-207 | 0.064 |
| B-208 | 0.064 |
| B-209 | 0.064 |
| B-210 | 0.064 |
| B-211 | 0.064 |
| B-212 | 0.064 |
| B-213 | 0.064 |
| B-214 | 0.064 |
| B-215 | 0.064 |
| B-216 | 0.064 |
| B-217 | 0.065 |
| B-218 | 0.064 |
| B-219 | 0.064 |
| B-220 | 0.064 |
| B-221 | 0.064 |
| B-222 | 0.064 |
| B-223 | 0.064 |
| B-224 | 0.064 |
| B-225 | 0.064 |
| B-226 | 0.064 |
| B-227 | 0.064 |
| B-228 | 0.064 |
| B-229 | 0.064 |
| B-230 | 0.064 |
| B-231 | 0.064 |
| B-232 | 0.064 |
| B-233 | 0.064 |
| B-234 | 0.064 |
| B-235 | 0.064 |
| B-236 | 0.064 |
| B-237 | 0.064 |
| B-238 | 0.064 |
| B-239 | 0.064 |
| B-240 | 0.064 |
| B-241 | 0.064 |
| B-242 | 0.064 |
| B-243 | 0.064 |
| B-244 | 0.064 |
| B-245 | 0.064 |
| B-246 | 0.064 |
| B-247 | 0.064 |
| B-248 | 0.097 |
| B-249 | 0.065 |
| B-250 | 0.237 |
| B-251 | 0.064 |
| B-252 | 0.064 |
| B-253 | 0.064 |
| B-254 | 0.064 |
| B-255 | 0.064 |
| B-256 | 0.064 |
| B-257 | 0.064 |
| B-258 | 0.064 |
| B-259 | 0.064 |
| B-260 | 0.064 |
| B-261 | 0.076 |
| B-262 | 0.064 |
| B-263 | 0.064 |
| B-264 | 0.064 |
| B-265 | 0.079 |
| B-266 | 0.251 |
| B-267 | 0.064 |
| B-268 | 0.064 |
| B-269 | 0.064 |
| B-270 | 0.064 |
| B-271 | 0.064 |
| B-272 | 0.064 |

The above data shows that compounds of the present disclosure are generally effective at blocking the PD-1/PD-L1 interaction.

PD-1/PD-L1 NFAT Reporter Assay:

Compounds were tested in a functional co-culture reporter assay in which TCR-mediated NFAT activity is inhibited by the engagement of PD-1 with PD-L1. Blocking the PD-1/PD-L1 interaction impairs PD-1 mediated blunting of TCR signaling and significantly increases NFAT-mediated transcription of luciferase. CHO cells expressing surface-bound anti-CD3 antibodies and PD-L1 (artificial antigen presenting cells, aAPC-PD-L) were first seeded overnight. Jurkat cells overexpressing PD-1 and expressing a luciferase construct under NFAT control are diluted in RPMI assay medium (RPMI 1640 with 2% FBS), mixed with compounds, and immediately seeded on the monolayer of aAPC-PD-L. The co-culture is then incubated for 6 hrs at 37° C. Luciferase activity is assessed by adding the ONE-Glo reagent and measuring luminescence with a plate reader. EC$_{50}$ values are calculated from the fit of the dose-response curves to a four-parameter equation (Table 4).

PD-L1/PD-L1 Dimerization Biochemical Protein-Protein Interaction Assay:

Compounds were tested in biochemical protein-protein interaction assays to determine if they can specifically dimerize the extracellular domains of PD-L1. Dimerization of the proteins (His-tagged PD-L1 and FLAG-tagged PD-L1) is measured using a bead based Amplified Luminescent Proximity Homogeneous Assay (ALPHA) platform. Compound induced dimerization of PD-L1 results in proximity of the donor and acceptor beads which leads to an increase in ALPHA signal. Assays are performed in 25 mM Hepes (pH 7.4), 150 mM NaCl, 3.4 mM EDTA, 0.005% Tween 20, and 0.01% BSA. Final protein concentration in the assays were 0.5 nM (His tagged PD-L1) and 0.5 nM (FLAG tagged PD-L1). After an assay reaction time of 2 hours at 25° C., 20 µg/mL (final assay concentration) ALPHA assay acceptor beads (anti-His coated) were added and incubated for 60 minutes at 25° C. Binding was measured following a final 60 minute incubation with 40 µg/mL (final assay concentration) ALPHA assay donor beads (anti-FLAG coated). AC$_{50}$ values were calculated from the fit of the dose-response curves to a four-parameter equation (Table 4A and Table 4B).

TABLE 4A

| No. | AC$_{50}$ PDL1 Dimer 1 nM | EC$_{50}$ NFAT Luciferase |
|---|---|---|
| A-1 | 13.25 | 40 |
| A-2 | 13.473 | 11 |
| A-3 | 13.935 | 12 |
| A-4 | 14.333 | 19 |
| A-5 | 113.03 | 38 |
| A-6 | 188.25 | 165 |
| A-7 | 179.65 | 176 |
| A-8 | 79.682 | 66 |
| A-9 | 149.97 | 152 |
| A-10 | 16.711 | 25 |
| A-11 | 34.808 | 57 |
| A-12 | 26.432 | 56 |
| A-13 | 48.819 | 66 |
| A-14 | 30.423 | 24 |
| A-15 | 51.57 | 35 |
| A-16 | 42.079 | 37 |
| A-17 | 13.913 | 20 |
| A-18 | 15.659 | 9 |
| A-19 | 26.091 | 13 |
| A-20 | 29.103 | 20 |
| A-21 | 32.636 | 19 |
| A-22 | 8.168 | 25 |
| A-23 |  | 22 |
| A-24 | 38.849 | 29 |
| A-25 | 28.068 | 21 |
| A-26 | 13.4 | 27 |
| A-27 | 7.771 | 23 |
| A-28 | 18.139 | 26 |
| A-29 | 5.569 | 27 |
| A-30 | 9.895 | 24 |
| A-31 | 6.843 | 11 |

TABLE 4A-continued

| No. | AC$_{50}$ PDL1 Dimer 1 nM | EC$_{50}$ NFAT Luciferase |
|---|---|---|
| A-32 | 12.49 | 26 |
| A-33 | 11.699 | 20 |
| A-34 | 8.257 | 15 |
| A-35 | 13.196 | 6 |
| A-36 | 2.054 | 10 |
| A-37 | 6.256 | 14 |
| A-38 | 16.91 | 8 |
| A-39 | 17.798 | 16 |
| A-40 | 6.812 | 8 |
| A-41 | 7.6 | 10 |
| A-42 | 12.583 | 9 |
| A-43 | 9.89 | 8 |
| A-44 | 10.636 | 18 |
| A-45 | 5.863 | 13 |
| A-46 | 7.18 | 15 |
| A-47 | 22.336 | 23 |
| A-48 | 13.495 | 15 |
| A-49 | 10.674 | 18 |
| A-50 | 17.611 | 22 |
| A-51 | 105.67 | 44 |
| A-52 | 15.256 | 6 |
| A-53 | 16.195 | 13 |
| A-54 | 76.588 | 25 |
| A-55 | 13.168 | 8 |
| A-56 | 11.786 | 16 |
| A-57 | 29.559 | 29 |
| A-58 | 9.377 | 18 |
| A-59 | 7.753 | 20 |
| A-60 | 13.905 | 40 |
| A-61 | 10.587 | 40 |
| A-62 | 45.417 | 29 |
| A-63 | 34.356 | 41 |
| A-64 | 8.036 | 13 |
| A-65 | 14.662 | 22 |
| A-66 | 19.646 | 25 |
| A-67 | 32.882 | 43 |
| A-68 | 83.724 | 43 |
| A-69 | 5.266 | 21 |
| A-70 | 15.604 | 12 |
| A-71 | 52.422 | 35 |
| A-72 | 13.392 | 12 |
| A-73 | 15.739 | 29 |
| A-74 | 9.07 | 6 |
| A-75 | 18.124 | 22 |
| A-76 | 30.241 | 22 |
| A-77 | 26.575 | 12 |
| A-78 | 13.484 | 18 |
| A-79 | 21.362 | 36 |
| A-80 | 19.85 | 21 |
| A-81 | 23.062 | 32 |
| A-82 | 84.897 | 35 |
| A-83 | 23.635 | 46 |
| A-84 | 31.84 | 48 |
| A-85 | 42.459 | 43 |
| A-86 | 29.217 | 37 |
| A-87 | 22.275 | 19 |
| A-88 | 60.444 | 50 |
| A-89 | 81.847 | 46 |
| A-90 | 21.588 | 31 |
| A-91 | 42.691 | 40 |
| A-92 | 15.139 | 20 |
| A-93 | 83.017 | 35 |
| A-94 | 20.657 | 21 |
| A-95 | 21.155 | 42 |
| A-96 | 3.97 | 4 |
| A-97 | 6.279 | 10 |
| A-98 | 40.258 | 33 |
| A-99 | 110.46 | 32 |
| A-100 | 7.109 | 13 |
| A-101 | 3.901 | 9 |
| A-102 | 43.063 | 28 |
| A-103 | 40.246 | 30 |
| A-104 | 16.573 | 29 |
| A-105 | 40.569 | 37 |
| A-106 | 5.04 | 8 |
| A-107 | 8.643 | 15 |
| A-108 | 6.636 | 35 |
| A-109 | 8.976 | 37 |

TABLE 4B

| No. | AC$_{50}$ PDL1 Dimer 1 nM | EC$_{50}$ NFAT Luciferase |
|---|---|---|
| B-1 | 1.114 | 3 |
| B-2 | 17.521 | 15 |
| B-3 | 120.01 | 123 |
| B-4 | 20.941 | 50 |
| B-5 | 2.668 | 6 |
| B-6 | 7.959 | 17 |
| B-7 | 4.038 | 8 |
| B-8 | 13.221 | 14 |
| B-9 | 19.184 | 25 |
| B-10 | 5.398 | 10 |
| B-11 | 71.415 | 53 |
| B-12 | 1.118 | 3 |
| B-13 | 3.916 | 5 |
| B-14 | 15.725 | 22 |
| B-15 | 9.548 | 28 |
| B-16 | 24.504 | 34 |
| B-17 | 4.295 | 4 |
| B-18 | 17.548 | 30 |
| B-19 | 9.333 | 22 |
| B-20 | 33.749 | 49 |
| B-21 | 31.212 | 100 |
| B-22 | 13.366 | 26 |
| B-23 | 62.775 | 72 |
| B-24 | 19.378 | 30 |
| B-25 | 17.8 | 29 |
| B-26 | 18.353 | 17 |
| B-27 | 11.186 | 20 |
| B-28 | 26.935 | 57 |
| B-29 | 4.085 | 7 |
| B-30 | 58.264 | 73 |
| B-31 | 32.28 | 21 |
| B-32 | 12.948 | 22 |
| B-33 | 14.68 | 32 |
| B-34 | 22.287 | 93 |
| B-35 | 9.06 | 19 |
| B-36 | 3.769 | 5 |
| B-37 | 28.041 | 100 |
| B-38 | 46.475 | 42 |
| B-39 | 3.8 | 23 |
| B-40 | 48.571 | 49 |
| B-41 | 3.591 | 7 |
| B-42 | 12.462 | 32 |
| B-43 | 44.269 | 75 |
| B-44 | 17.871 | 43 |
| B-45 | 20.209 | 32 |
| B-46 | 14.723 | 24 |
| B-47 | 27.426 | 25 |
| B-48 | 7.117 | 6 |
| B-49 | 19.12 | 19 |
| B-50 | 26.126 | 31 |
| B-51 | 27.527 | 28 |
| B-52 | 46.384 | 33 |
| B-53 | 31.11 | 55 |
| B-54 | 10.193 | 10 |
| B-55 | 10.652 | 20 |
| B-56 | 41.025 | 59 |
| B-57 | 66.522 | 100 |
| B-58 | 49.735 | 24 |
| B-59 | 106.55 | 59 |
| B-60 | 55.623 | 18 |
| B-61 | 6.22 | 13 |
| B-62 | 9.298 | 6 |
| B-63 | 7.821 | 11 |
| B-64 | 40.473 | 73 |
| B-65 | 15.29 | 24 |

TABLE 4B-continued

| No. | AC$_{50}$ PDL1 Dimer 1 nM | EC$_{50}$ NFAT Luciferase |
|---|---|---|
| B-66 | 38.136 | 44 |
| B-67 | 30.326 | 37 |
| B-68 | 47.954 | 37 |
| B-69 | 155.9 | 57 |
| B-70 | 31.865 | 44 |
| B-71 | 35.688 | 58 |
| B-72 | 25.825 | 38 |
| B-73 | 81.704 | 75 |
| B-74 | 94.116 | 71 |
| B-75 | 93.804 | 124 |
| B-76 | 83.162 | 105 |
| B-77 | 60.397 | 74 |
| B-78 | 57.858 | 61 |
| B-79 | 70.775 | 89 |
| B-80 | 46.943 | 67 |
| B-81 | 117.66 | 58 |
| B-82 | 37.76 | 43 |
| B-83 | 210.51 | 52 |
| B-84 | 37.283 | 41 |
| B-85 | 50.253 | 20 |
| B-86 | 109.12 | 100 |
| B-87 | 90.727 | 59 |
| B-88 | 26.375 | 14 |
| B-89 | 85.008 | 85 |
| B-90 | 18.696 | 24 |
| B-91 | 33.772 | 24 |
| B-92 | 54.461 | 67 |
| B-93 | 55.041 | 56 |
| B-94 | 102.86 | 48 |
| B-95 | 36.23 | 11 |
| B-96 | 48.686 | 68 |
| B-97 | 66.354 | 64 |
| B-98 | 54.295 | 48 |
| B-99 | 67.917 | 22 |
| B-100 | 102.74 | 29 |
| B-101 | 64.757 | 57 |
| B-102 | 80.57 | 69 |
| B-103 | 58.453 | 39 |
| B-104 | 88.536 | 87 |
| B-105 | 783.36 | 60 |
| B-106 | 41.345 | 34 |
| B-107 | 20.078 | 24 |
| B-108 | 696.16 | 40 |
| B-109 | 40.878 | 68 |
| B-110 | 97.135 | 100 |
| B-111 | 138.59 | 166 |
| B-112 | 170.01 | 141 |
| B-113 | 29.894 | 25 |
| B-114 | 20.701 | 23 |
| B-115 | 26.346 | 23 |
| B-116 | 35.475 | 41 |
| B-117 | 0.813 | 3 |
| B-118 | 0.988 | 3 |
| B-119 | 24.507 | 13 |
| B-120 | 18.218 | 22 |
| B-121 | 1.625 | 3 |
| B-122 | 2.654 | 6 |
| B-123 | 132.66 | 40 |
| B-124 | 78.506 | 51 |
| B-125 | 6.788 | 13 |
| B-126 | 3.354 | 12 |
| B-127 | 5.462 | 15 |
| B-128 | 13.522 | 7 |
| B-129 | 16.452 | 15 |
| B-130 | 4.867 | 11 |
| B-131 | 10.486 | 8 |
| B-132 | 301.27 | 57 |
| B-133 | 99.108 | 70 |
| B-134 | 0.727 | 3 |
| B-135 | 2.764 | 3 |
| B-136 | 10.999 | 8 |
| B-137 | 6.191 | 6 |
| B-138 | 11.603 | 16 |
| B-139 | 10.225 | 7 |
| B-140 | 2.28 | 36 |
| B-141 | 5.835 | 19 |
| B-142 | 38.936 | 35 |
| B-143 | 42.087 | 50 |
| B-144 | 8.979 | 19 |
| B-145 | 5.125 | 35 |
| B-146 | 297.49 | 149 |
| B-147 | 178.18 | 87 |
| B-148 | 43.223 | 29 |
| B-149 | 32.424 | 23 |
| B-150 | 65.144 | 50 |
| B-151 | 66.23 | 43 |
| B-152 | 12.674 | 21 |
| B-153 | 18.997 | 23 |
| B-154 | 31.532 | 51 |
| B-155 | 101.51 | 54 |
| B-156 | 323.57 | 113 |
| B-157 | 1424.5 | 92 |
| B-158 | 26.945 | 29 |
| B-159 | 24.903 | 21 |
| B-160 | 308.92 | 161 |
| B-161 | 41.212 | 112 |
| B-162 | 133.77 | 78 |
| B-163 | 39.114 | 40 |
| B-164 | 66.892 | 56 |
| B-165 | 24.642 | 19 |
| B-166 | 43.707 | 51 |
| B-167 | 51.561 | 56 |
| B-168 | 11.831 | 20 |
| B-169 | 11.14 | 15 |
| B-170 | 15.187 | 18 |
| B-171 | 15.215 | 15 |
| B-172 | 7.634 | 5 |
| B-173 | 9.939 | 10 |
| B-174 | 7.967 | 7 |
| B-175 | 14.3 | 28 |
| B-176 | 52.576 | 29 |
| B-177 | 17.873 | 23 |
| B-178 | 21.525 | 26 |
| B-179 | 3.637 | 8 |
| B-180 | 12.528 | 24 |
| B-181 | 18.93 | 21 |
| B-182 | 31.055 | 25 |
| B-183 | 25.108 | 28 |
| B-184 | 19.762 | 24 |
| B-185 | 10.918 | 10 |
| B-186 | 19.669 | 18 |
| B-187 | 2.863 | 4 |
| B-188 | 12.009 | 15 |
| B-189 | 9.848 | 11 |
| B-190 | 8.984 | 14 |
| B-191 | 12.269 | 17 |
| B-192 | 6.796 | 17 |
| B-193 | 3.761 | 6 |
| B-194 | 4.545 | 16 |
| B-195 | 5.792 | 9 |
| B-196 | 6.308 | 18 |
| B-197 | 12.528 | 11 |
| B-198 | 15.298 | 7 |
| B-199 | 17.468 | 6 |
| B-200 | 20.059 | 20 |
| B-201 | 24.387 | 16 |
| B-202 | 3.433 | 3 |
| B-203 | 5.214 | 13 |
| B-204 | 9.704 | 17 |
| B-205 | 7.555 | 19 |
| B-206 | 7.775 | 13 |
| B-207 | 11.873 | 14 |
| B-208 | 23.454 | 26 |
| B-209 | 11.664 | 28 |
| B-210 | 23.743 | 17 |
| B-211 | 9.205 | 25 |
| B-212 | 17.55 | 12 |
| B-213 | 17.022 | 20 |
| B-214 | 3.785 | 8 |
| B-215 | 8.418 | 21 |
| B-216 | 20.068 | 22 |
| B-217 | 28.93 | 18 |

TABLE 4B-continued

| No. | $AC_{50}$ PDL1 Dimer 1 nM | $EC_{50}$ NFAT Luciferase |
|---|---|---|
| B-218 | 17.326 | 26 |
| B-219 | 2.562 | 13 |
| B-220 | 2.04 | 5 |
| B-221 | 17.483 | 29 |
| B-222 | 13.541 | 11 |
| B-223 | 17.968 | 13 |
| B-224 | 10.647 | 21 |
| B-225 | 5.321 | 19 |
| B-226 | 5.332 | 14 |
| B-227 | 3.119 | 13 |
| B-228 | 6.431 | 11 |
| B-229 | 3.142 | 13 |
| B-230 | 27.526 | 28 |
| B-231 | 11.968 | 9 |
| B-232 | 1.794 | 9 |
| B-233 | 0.518 | 3 |
| B-234 | 3.176 | 3 |
| B-235 | 2.417 | 5 |
| B-236 | 3.02 | 4 |
| B-237 | 20.686 | 14 |
| B-238 | 34.934 | 21 |
| B-239 | 21.347 | 28 |
| B-240 | 12.055 | 26 |
| B-241 | 7.579 | 16 |
| B-242 | 18.894 | 25 |
| B-243 | 15.805 | 22 |
| B-244 | 17.953 | 27 |
| B-245 | 5.941 | 8 |
| B-246 | 14.039 | 15 |
| B-247 | 10.357 | 26 |
| B-248 | 15.914 | 16 |
| B-249 | 35.452 | 35 |
| B-250 | 36.375 | 26 |
| B-251 | 17.657 | 32 |
| B-252 | 17.957 | 29 |
| B-253 | 8.728 | 9 |
| B-254 | 11.438 | 10 |
| B-255 | 7.888 | 11 |
| B-256 | 13.105 | 25 |
| B-257 | 8.735 | 5 |
| B-258 | 5.904 | 5 |
| B-259 | 9.804 | 17 |
| B-260 | 18.028 | 28 |
| B-261 | 4.632 | 18 |
| B-262 | 2.196 | 7 |
| B-263 | 4.942 | 25 |
| B-264 | 6.553 | 16 |
| B-265 | 14.242 | 11 |
| B-266 | 28.536 | 31 |
| B-267 | 7.256 | 9 |
| B-268 | 3.763 | 10 |
| B-269 | 6.132 | 15 |
| B-270 | 4.755 | 11 |
| B-271 | 1.905 | 4 |
| B-272 | 2.26 | 6 |

Biological Example 2

GPR4 Assay

Select compounds were tested in a functional GRP40 assay as described in Briscoe, C. P. et al. (*Brit. J. Pharmacol.*, (2006), 148:619-628) to determine agonist/antagonist activity. Activation of GPR40 by fatty acids has been shown to result in an increase in intracellular $Ca^{2+}$ levels, an action mediated via $G\alpha q/11$. Using HEK-293 cell line transiently transduced to express GPR4, the agonist/antagonist activity of select compounds has been assessed.

Methods Summary

| Assay | Source | Stimulus | Incubation | Measured Component | Detection method |
|---|---|---|---|---|---|
| FFA1 (h) (GRP40) (Agonist Effect) | human recombinant (HEK-293 cells) | none (100 µM linoleic acid for control) | Room Temp. | Intracellular $[Ca^{2+}]$ | Fluorimetry |
| FFA1 (h) (GPR40) (Antagonist effect) | human recombinant (HEK-293 cells) | linoleic acid (20000 nM) | Room Temp. | Intracellular $[Ca^{2+}]$ | Fluorimetry |

Results

TABLE 5

Agonist effects

| | Concentration | % of control agonist response | | |
|---|---|---|---|---|
| No. | (µM) | $1^{st}$ | $2^{nd}$ | Mean |
| A-18 | 10 | −0.6 | −1.9 | −1.3 |
| A-41 | 10 | 1.1 | 0.1 | 0.6 |
| B-36 | 10 | −0.4 | −0.5 | −0.4 |
| B-149 | 10 | −2.0 | −0.5 | −1.2 |

TABLE 6

Antagonist effects

| | Concentration | % inhibition of control agonist response | | |
|---|---|---|---|---|
| No. | (µM) | $1^{st}$ | $2^{nd}$ | Mean |
| A-18 | 10 | 8.3 | 17.4 | 12.8 |
| A-41 | 10 | 23.1 | 13.1 | 18.1 |
| B-36 | 10 | 30.5 | 17.0 | 23.7 |
| B-149 | 10 | 8.0 | 15.0 | 11.5 |

CONCLUSION

As shown in the data above, select compounds tested in the functional GRP40 assay as described in Briscoe, C. P. et al. (*Brit. J. Pharmacol.*, (2006), 148: 619-628) showed no agonist activity and very weak antagonist activity (0-43% inhibition at 10 µM).

The invention claimed is:

1. A compound of formula (IIA):

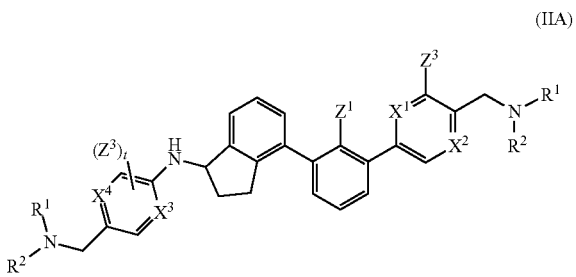

or a pharmaceutically acceptable salt thereof, wherein:
each of $X^1$, $X^2$, $X^3$ and $X^4$ are independently N, CH, or $CZ^3$;
$Z^1$ is halo, —$OR^a$, cyano, or —$C_{1-6}$ alkyl;

each $Z^3$ is independently halo, —$OR^a$, —$N_3$, —$NO_2$, cyano, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{1-6}$ cyanoalkyl, —$C_{1-6}$ haloalkyl, —O—$C_{1-6}$ cyanoalkyl, —O—$C_{1-6}$ haloalkyl, —$C_{3-8}$ cycloalkyl, —$C_{1-6}$ alkyl $C_{3-8}$ cycloalkyl, aryl, heteroaryl, heterocyclyl, and $R^N$; and
  wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$ cyanoalkyl, —$C(O)NR^aR^b$, —$NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$, and —$C_{3-8}$ cycloalkyl;
  $R^N$ is independently —$C_{1-6}$ alkyl$NR^1R^2$, —$OC_{1-6}$ alkyl$NR^1R^2$, —$C_{1-6}$ alkyl$OC_{1-6}$ alkyl$NR^1R^2$, —$NR^a$—$C_{1-6}$ alkyl$NR^1R^2$, —$C_{1-6}$ alkyl$C(O)NR^1R^2$, —O—$C_{1-6}$ alkyl$C(O)NR^1R^2$, —O—$C_{1-6}$ alkyl$C(O)OR^1$, —S—$C_{1-6}$ alkyl$NR^1R^2$, —$C_{1-6}$ alkyl$OR^a$, or

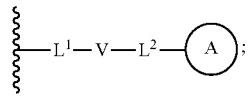

wherein: $L^1$ is independently a bond, —O—, —$NR^a$—, —S—, —S(O)—, or —$S(O)_2$—;
  V is independently selected from a bond, $C_{1-6}$ alkyl, $C_{2-6}$ alkenyl, and $C_{2-6}$ alkynyl;
    wherein each alkyl, alkenyl, or alkynyl is optionally independently substituted with —$OR^a$, halo, cyano, —$NR^aR^b$, or —$C_{3-8}$ cycloalkyl;
  $L^2$ is independently a bond, —O—, —$NR^a$—, —S—, —S(O)—, or —$S(O)_2$—;
  ring A is independently cycloalkyl, aryl, heteroaryl, or heterocyclyl;
    wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$ alkenyl, —$C_{2-6}$ alkynyl, —O—$C_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, —$C_{3-8}$cycloalkyl, heteroaryl, and —$C_{1-6}$alkyl$C_{3-8}$ cycloalkyl; and
      wherein the alkyl, alkenyl, or alkynyl group is optionally independently substituted with —$OR^a$, halo, cyano, —$NR^aR^b$, or —$C_{3-8}$ cycloalkyl;
each t is independently 0, 1, or 2;
each $R^1$ is independently selected from hydrogen, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkyl$C(O)OR^a$, —$C_{2-6}$ alkenyl$C(O)OR^a$, —$S(O)_2R^a$, —$S(O)_2NR^aR^b$, —$C(O)NR^aS(O)_2R^a$, and —$C_{1-6}$ alkyl$C_{3-8}$cycloalkyl;
  wherein each alkyl, alkenyl, cycloalkyl, aryl, heteroaryl, or heterocyclyl is optionally substituted with 1 to 4 groups independently selected from —$OR^a$, cyano, halo, $C_{1-6}$alkyl, —$C_{1-6}$ alkyl$OR^a$, —$C_{1-6}$ cyanoalkyl, —$C_{1-6}$ haloalkyl, $C_{3-8}$ cycloalkyl, —$C_{1-3}$ alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$OC(O)NR^aR^b$, —$NR^aC(O)OR^b$, —$C_{1-6}$ alkyl$NR^aR^b$, —$C(O)NR^aR^b$, —$C_{1-6}$ alkyl$C(O)NR^aR^b$, —$SO_2R^a$, —$C_{1-6}$ alkyl$SO_2R^a$, —$SO_2NR^aR^b$, —$C_{1-6}$ alkyl$SO_2NR^aR^b$, —$C(O)NR^aSO_2R^b$, —$C_{1-6}$ alkyl$C(O)NR^aSO_2R^b$, —$NR^aC(O)R^b$, and —$C_{1-6}$alkyl$NR^aC(O)R^b$;
each $R^2$ is independently selected from hydrogen, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-$OR^a$, —$C_{1-6}$ alkyl$C(O)OR^a$, and —$C_{2-6}$ alkenyl$C(O)OR^a$;
  wherein each alkyl, alkenyl, alkynyl, cycloalkyl, aryl, heteroaryl, or heterocyclyl is optionally substituted with 1 to 4 groups independently selected from —$OR^a$, cyano, halo, $C_{1-6}$ alkyl, —$C_{1-6}$ alkyl$OR^a$, —$C_{1-6}$ cyanoalkyl, —$C_{1-6}$ haloalkyl, —$C_{3-8}$ cycloalkyl, —$C_{1-3}$ alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$C_{1-6}$ alkyl$NR^aR^b$, —$C(O)NR^aR^b$, $C_{1-6}$ alkyl$C(O)NR^aR^b$, —$S(O)_2R^a$, —$C_{1-6}$ alkyl $S(O)_2R^a$, —$S(O)_2NR^aR^b$, —$C_{1-6}$ alkyl $S(O)_2NR^aR^b$, —$C(O)NR^aS(O)_2R^b$, and —$NR^aC(O)R^b$;
or $R^1$ and $R^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$ alkyl$OR^a$, —$C_{1-6}$ haloalkyl, —$C_{1-3}$ alkyl$C_{3-8}$cycloalkyl, —$C(O)R^a$, —$C_{1-6}$ alkyl$C(O)R^a$, —$C_{1-6}$ alkyl$C(O)OR^a$, —$NR^aR^b$, —$C_{1-6}$ alkyl$NR^aR^b$, —$C(O)NR^aR^b$, —$C_{1-6}$ alkyl$C(O)NR^aR^b$, —$S(O)_2R^a$, —$C_{1-6}$ alkyl $S(O)_2R^a$, —$S(O)_2NR^aR^b$, —$C(O)N=S(O)R^aNR^aR^b$, —$C(O)N=S(O)R^aNR^aC(O)R^b$, and —$C_{1-6}$ alkyl $S(O)_2NR^aR^b$;
each $R^a$ is independently selected from hydrogen, —$C_{1-6}$ alkyl, —$C_{1-6}$ cyanoalkyl, —$C_{1-6}$ haloalkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;
each $R^b$ is independently selected from hydrogen, —$C_{1-6}$ alkyl, —$C_{1-6}$ cyanoalkyl, —$C_{1-6}$ haloalkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;
or $R^a$ and $R^b$ may combine together to form a heterocyclyl optionally substituted with 1 to 4 groups independently selected from —$OR^f$, cyano, halo, —$C_{1-6}$ alkyl$OR^f$, —$C_{1-6}$ cyanoalkyl, —$C_{1-6}$ haloalkyl, —$C_{3-8}$ cycloalkyl, —$C_{1-3}$ alkyl$C_{3-8}$cycloalkyl, —$C(O)R^f$, —$C_{1-6}$ alkyl$C(O)R^f$, —$C(O)OR^f$, —$C_{1-6}$ alkyl$C(O)OR^f$, —$NR^fR^g$, —$C_{1-6}$ alkyl$NR^fR^g$, —$C(O)NR^fR^g$, —$C_{1-6}$ alkyl$C(O)NR^fR^g$, —$S(O)_2R^f$, —$C_{1-6}$ alkyl $S(O)_2R^f$, —$S(O)_2NR^fR^g$, —$C_{1-6}$ alkyl $S(O)_2NR^fR^g$, —$C(O)NR^fS(O)_2R^g$, and —$NR^fC(O)R^g$,
each $R^f$ is independently selected from hydrogen, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl, and
each $R^g$ is independently selected from hydrogen, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl.

2. The compound of claim 1, wherein the compound is represented by formula (IIC):

(IIC)

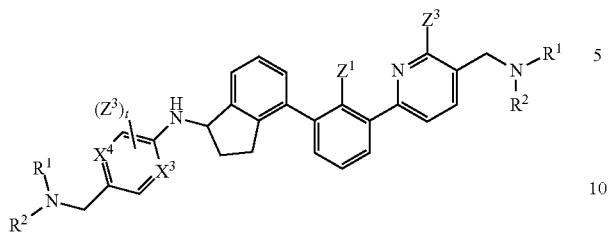

or a pharmaceutically acceptable salt thereof.

3. The compound of claim 1, wherein the compound is represented by formula (VIA):

(VIA)

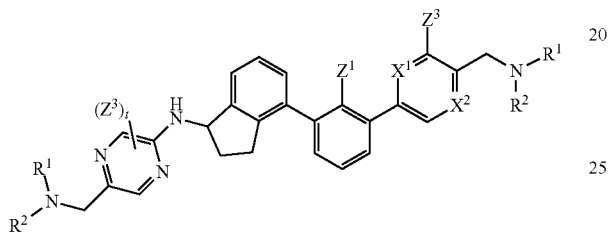

or a pharmaceutically acceptable salt thereof.

4. The compound of claim 1, wherein the compound is represented by formula (VIC):

(VIC)

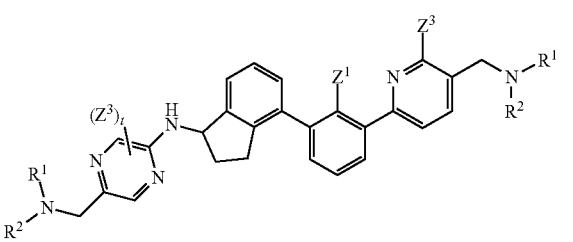

or a pharmaceutically acceptable salt thereof.

5. The compound of claim 1, wherein $Z^1$ is halo.

6. The compound of claim 1, wherein at least one $Z^3$ is halo, —$C_{1-6}$ alkyl, —$C_{1-6}$ haloalkyl, —O-cyanoalkyl, —O—$C_{1-6}$ haloalkyl, or —O—$C_{1-6}$ alkyl.

7. The compound of claim 1, wherein at least one of $R^1$ and $R^2$ is —$C_{1-6}$ alkylheteroaryl or $C_{1-6}$ alkylheterocyclyl.

8. A compound, or a pharmaceutically acceptable salt thereof, selected from:

A-1

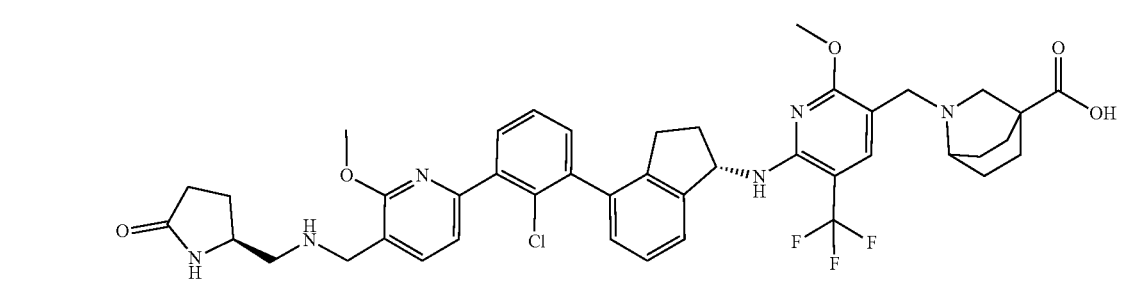

A-2

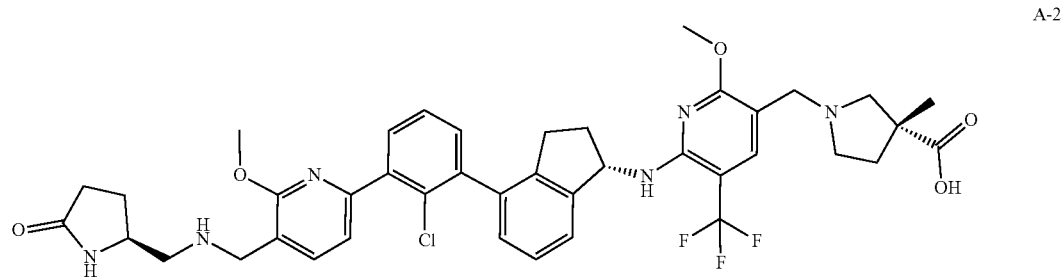

A-3

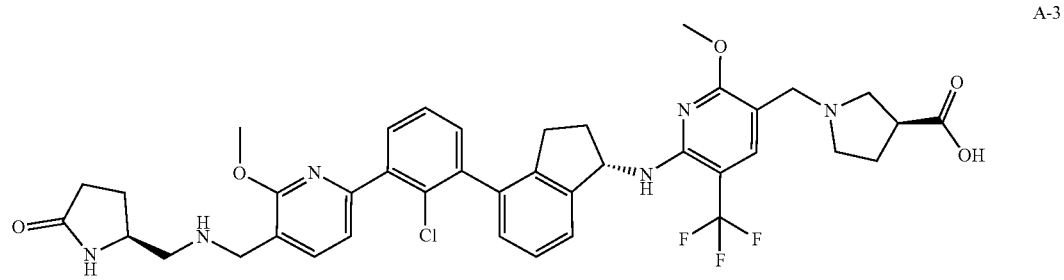

-continued
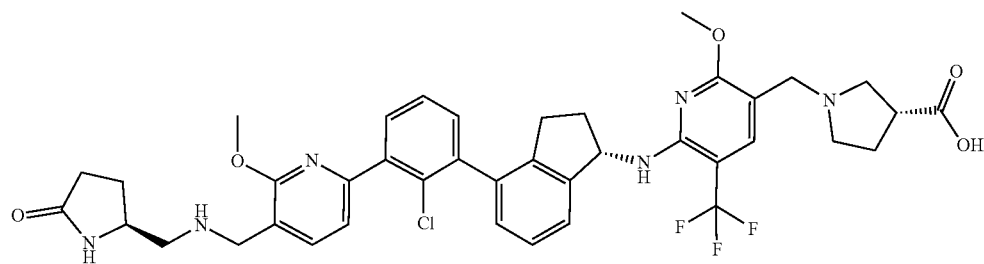
A-4
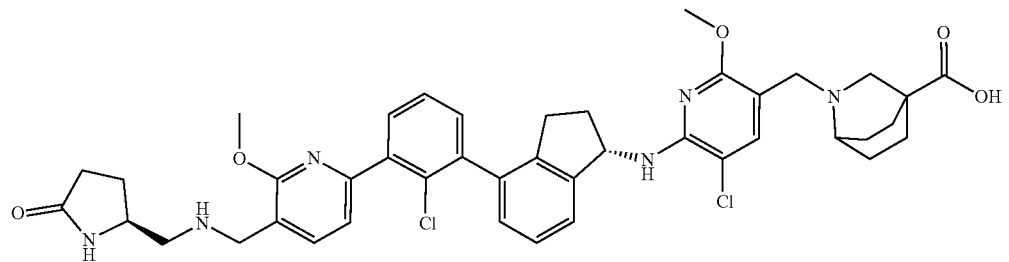
A-5
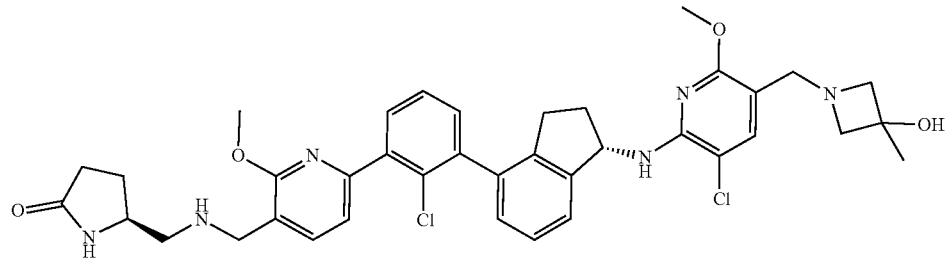
A-6
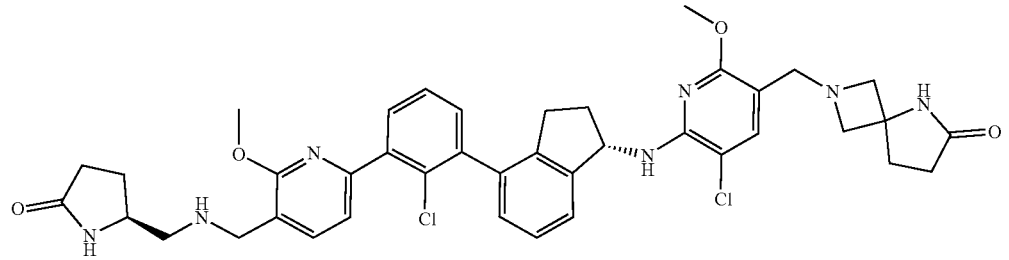
A-7
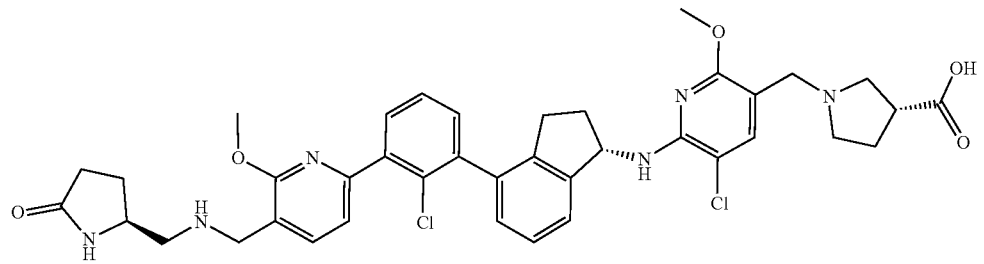
A-8
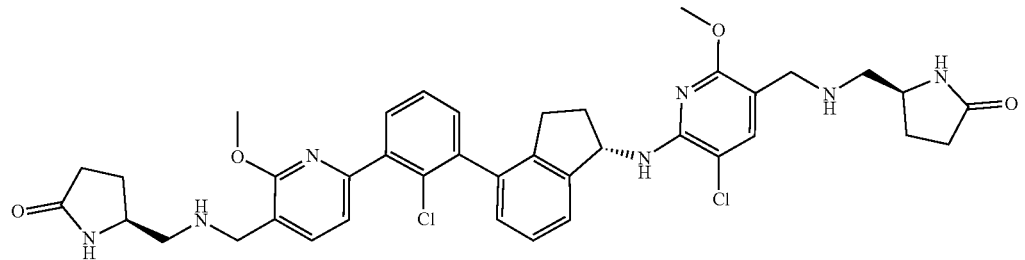
A-9

-continued
A-10
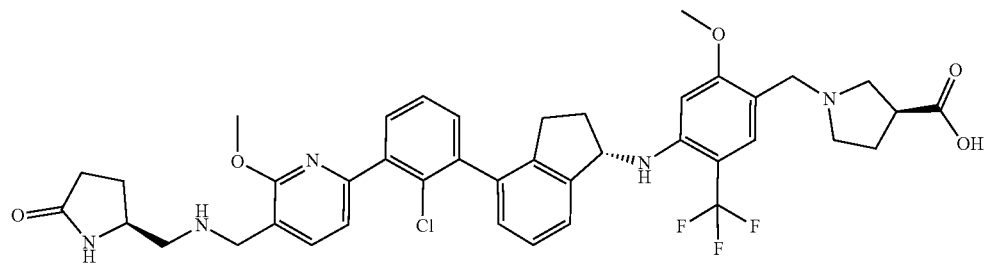
A-11
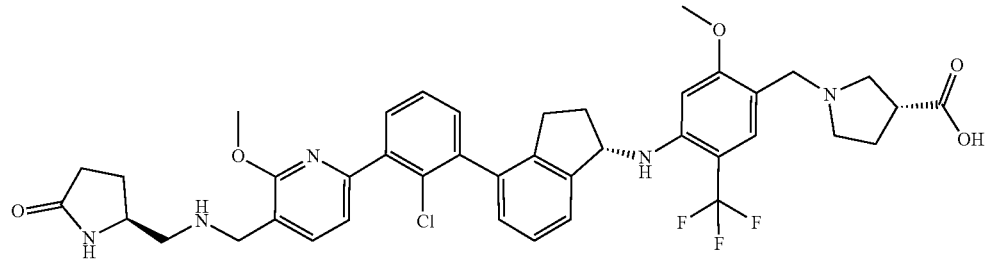
A-12
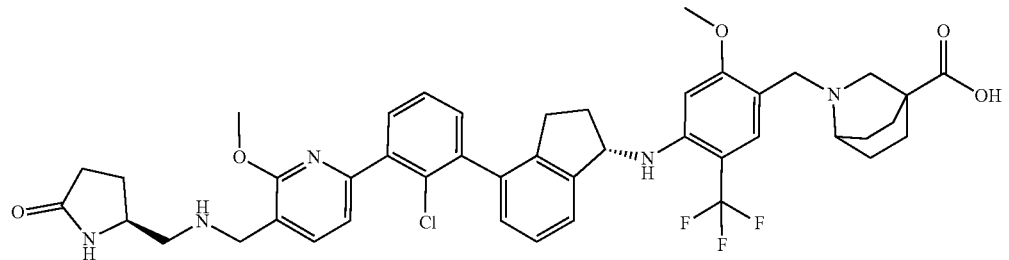
A-13
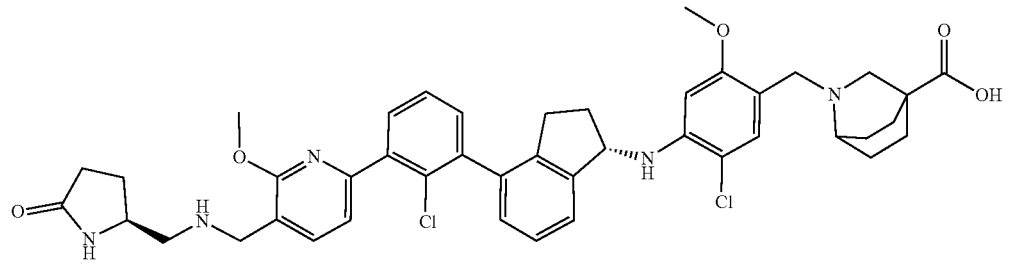
A-14
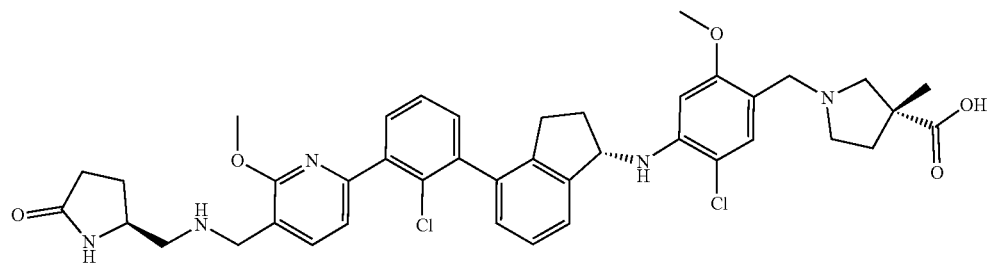
A-15
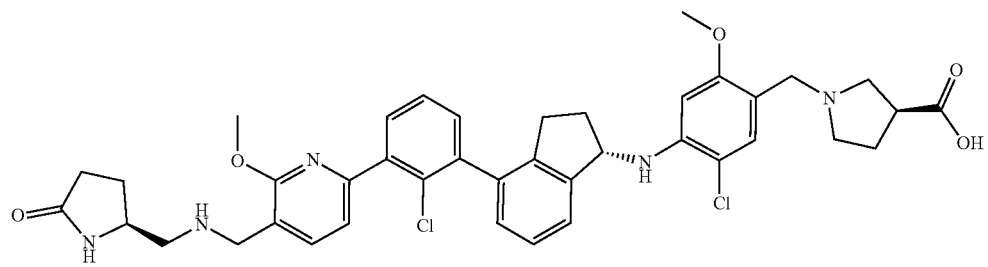

-continued
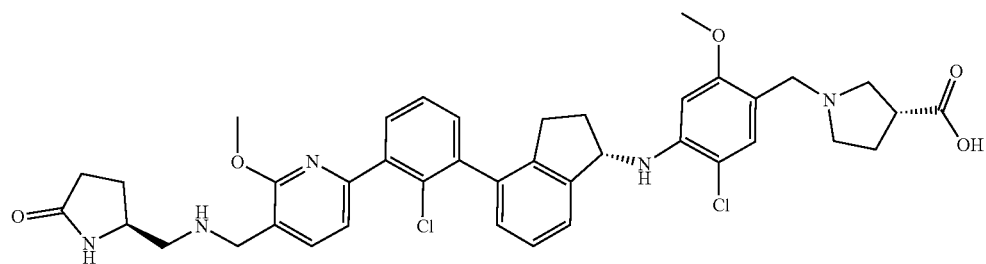
A-16
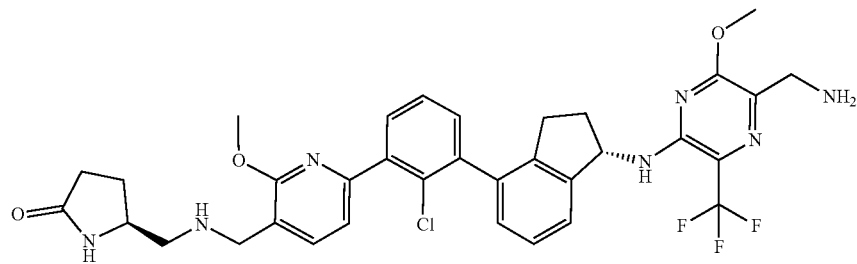
A-17
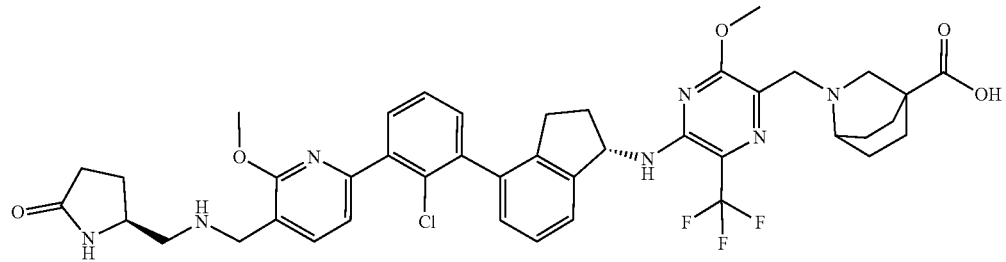
A-18
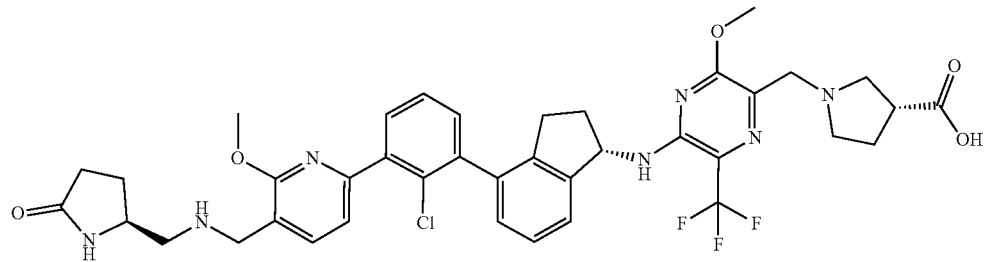
A-19
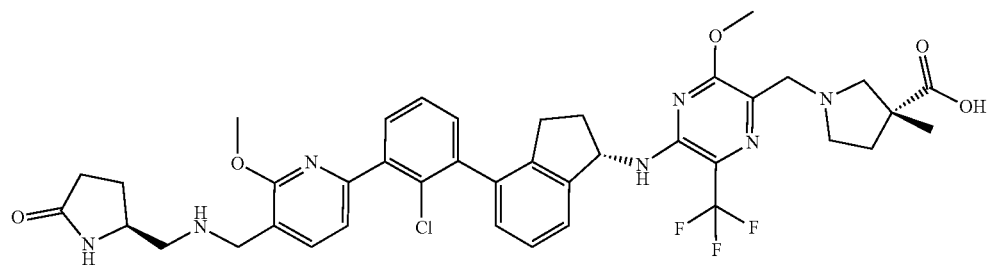
A-20
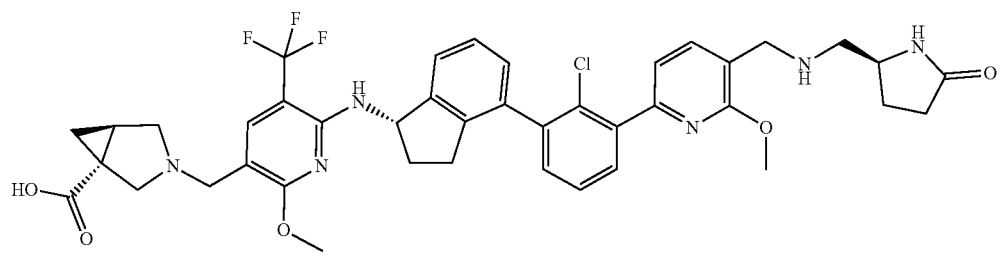
A-21

A-22
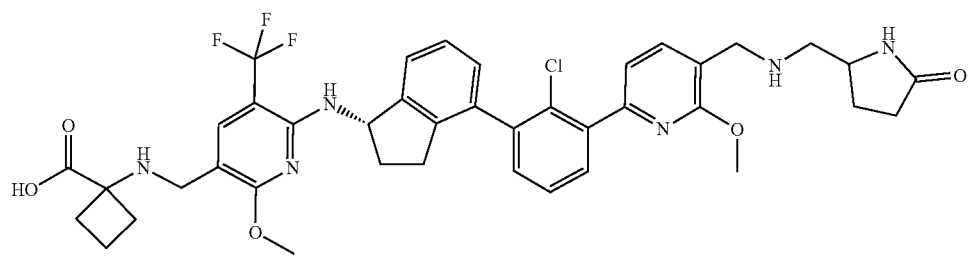
A-23
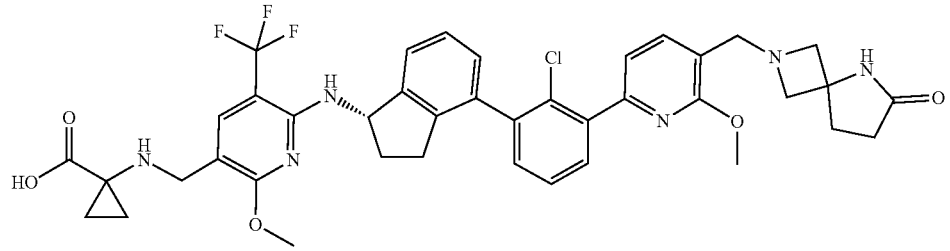
A-24
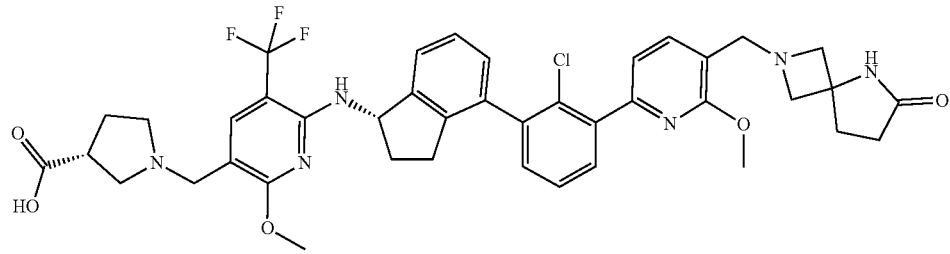
A-25
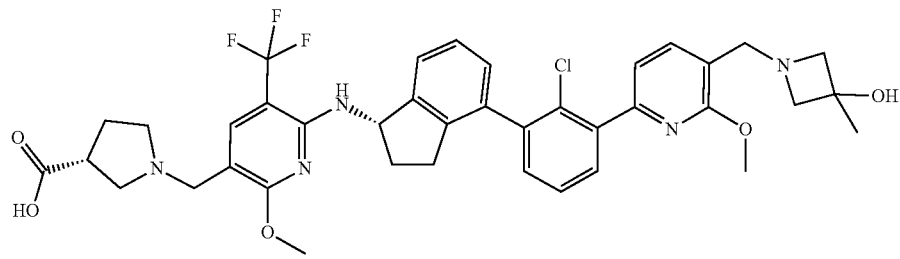
A-26
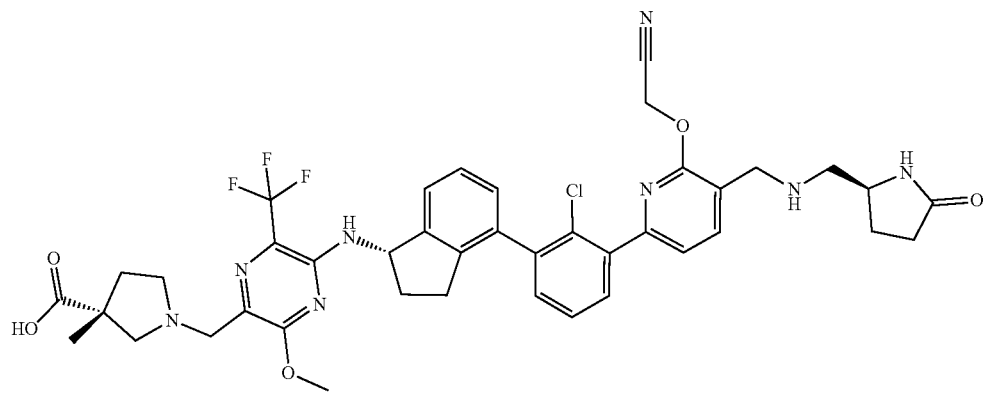

-continued
A-27
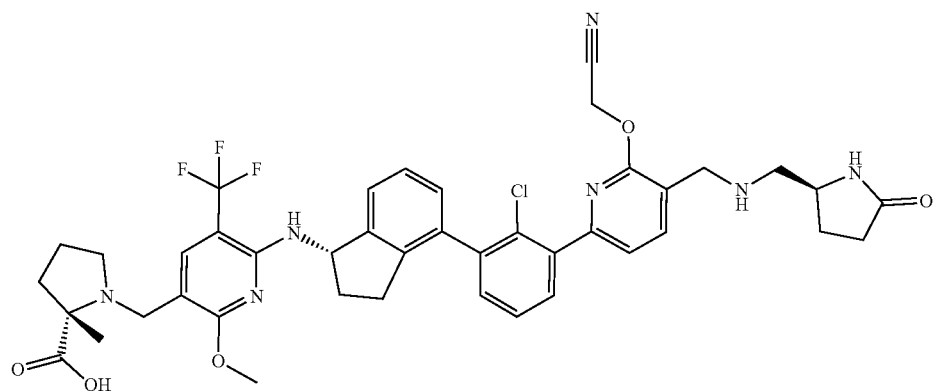
A-28
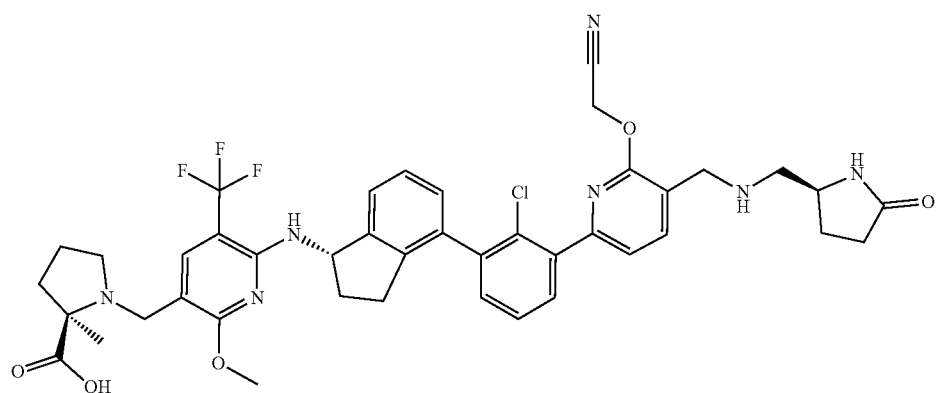
A-29
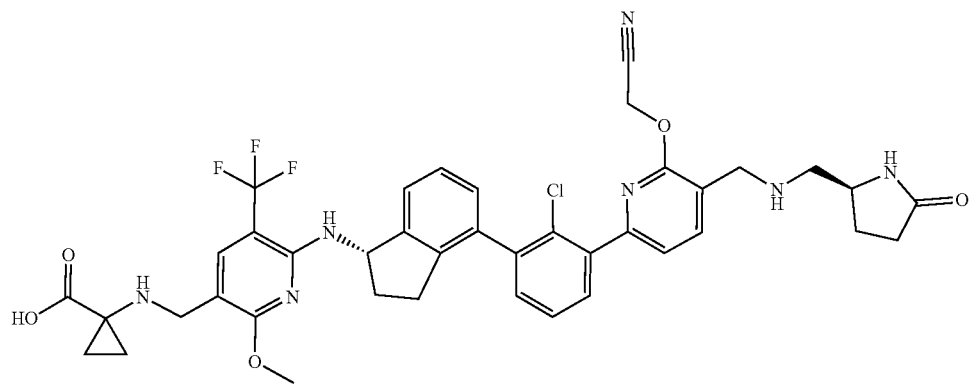
A-30
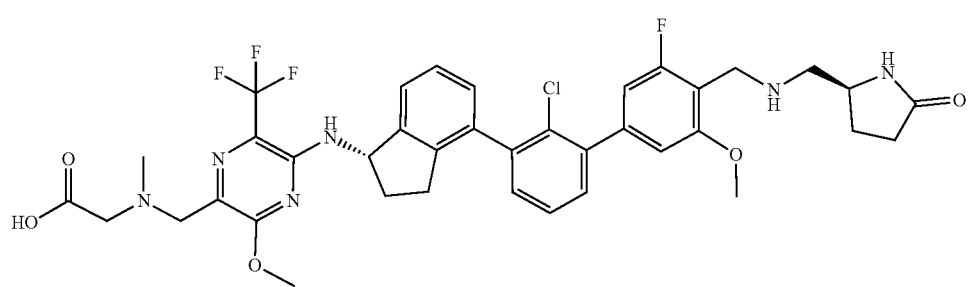

-continued
A-31
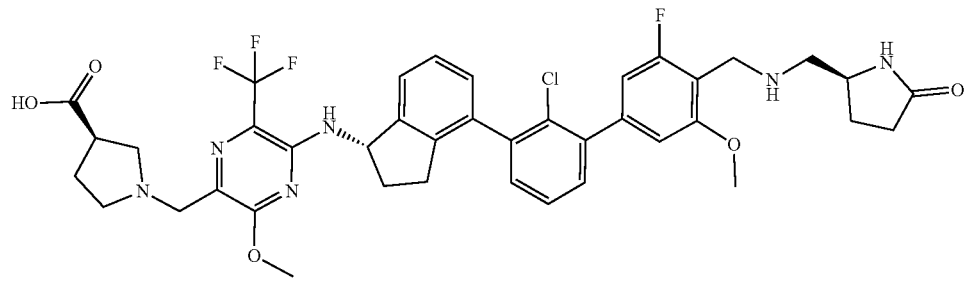
A-32
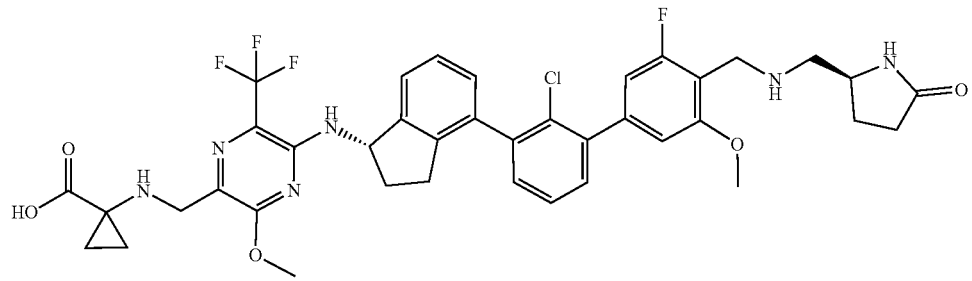
A-33
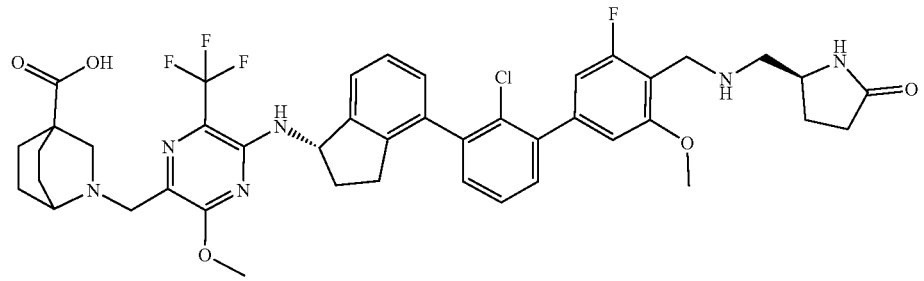
A-34
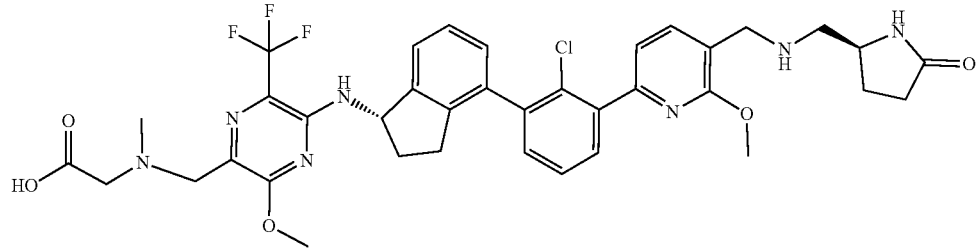
A-35
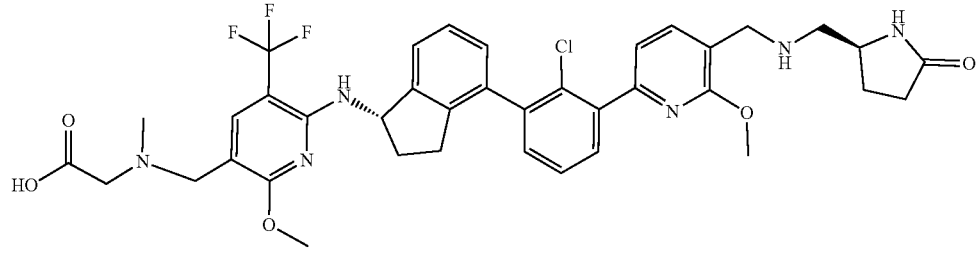
A-36
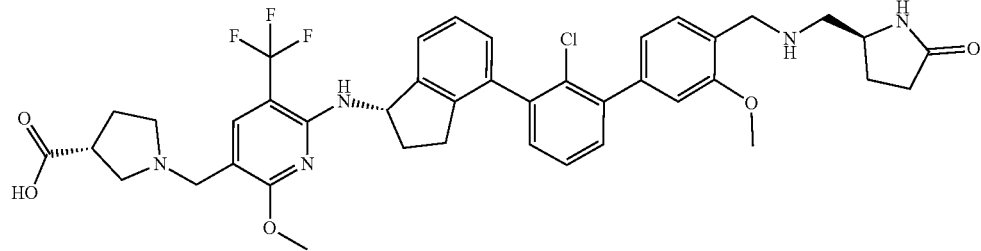

-continued
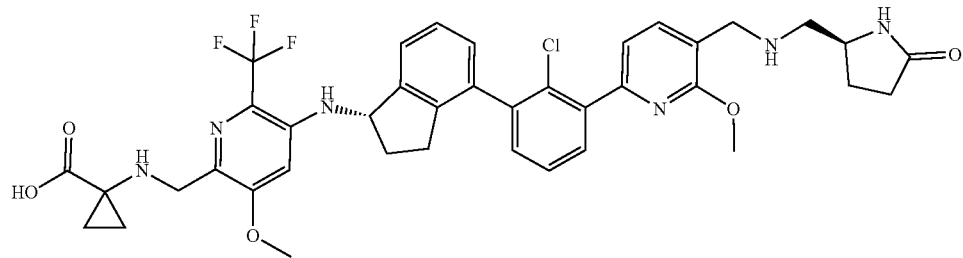
A-37
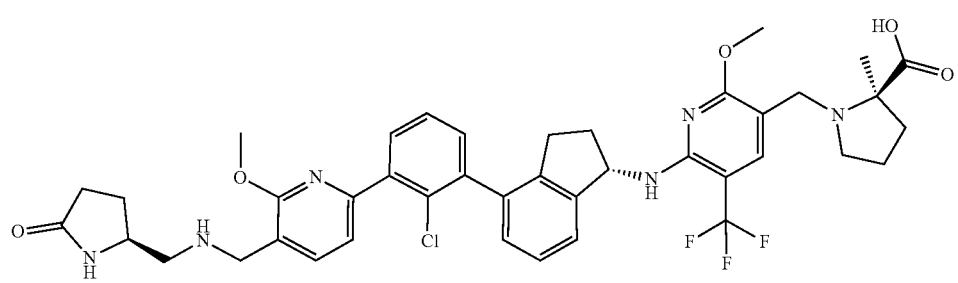
A-38
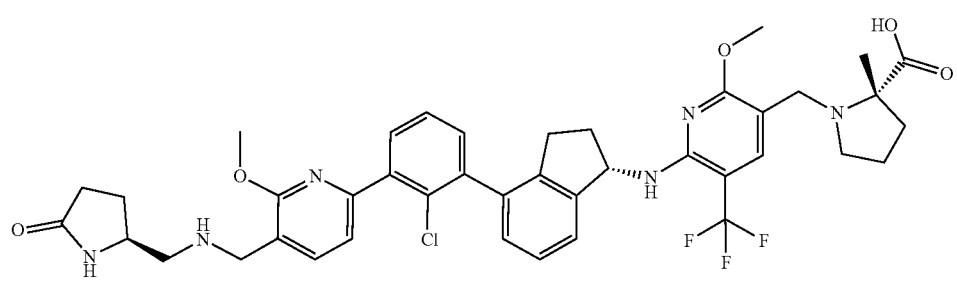
A-39
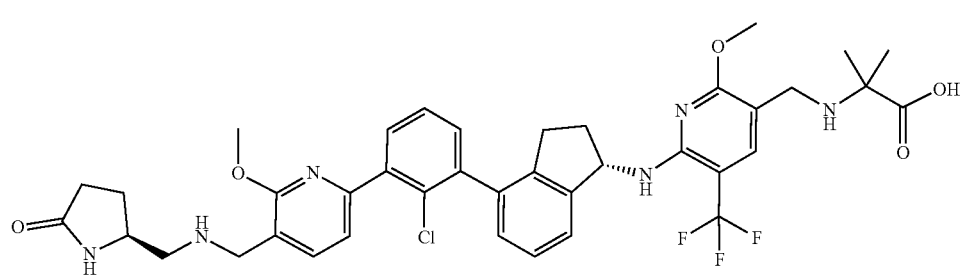
A-40
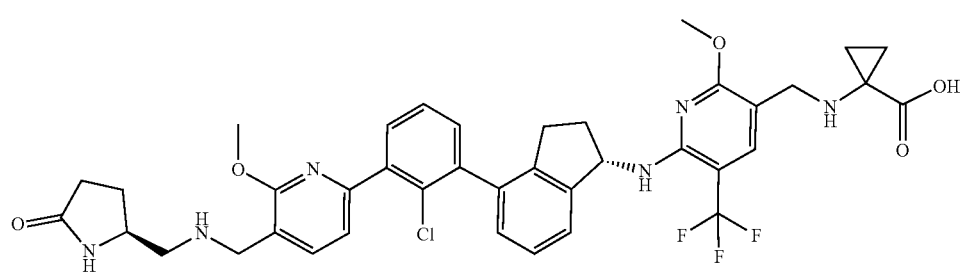
A-41
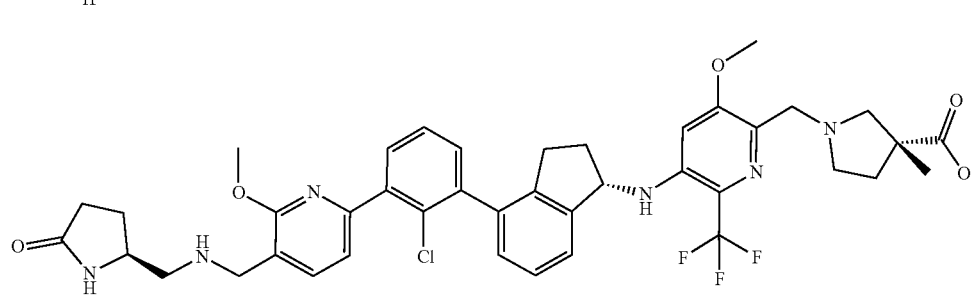
A-42

-continued
A-43
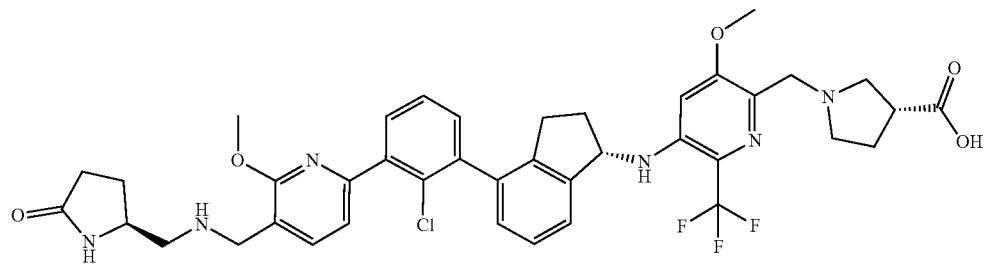
A-44
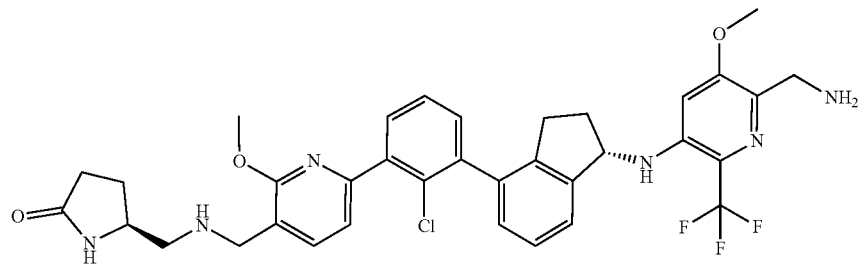
A-45
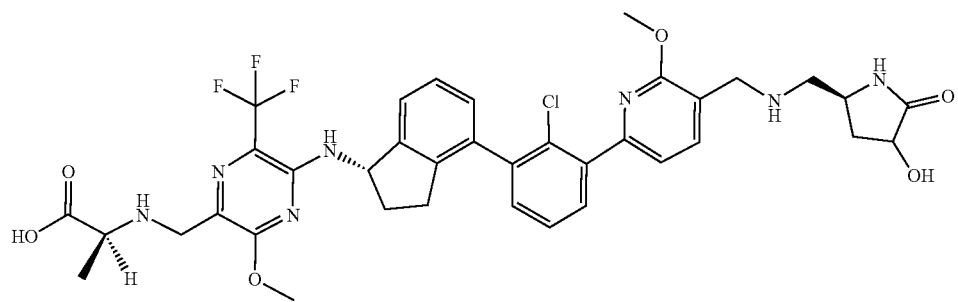
A-46
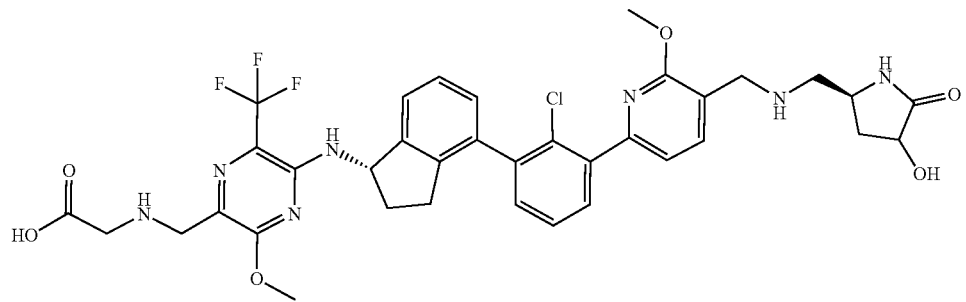
A-47
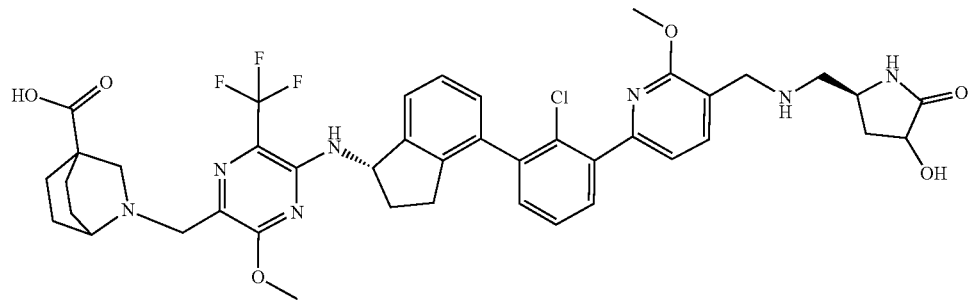

A-48
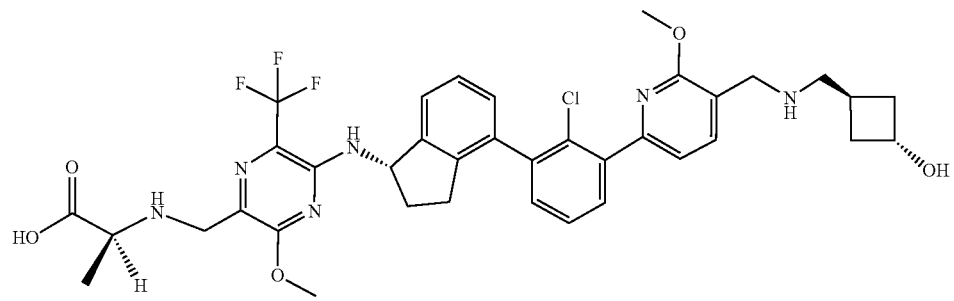
A-49
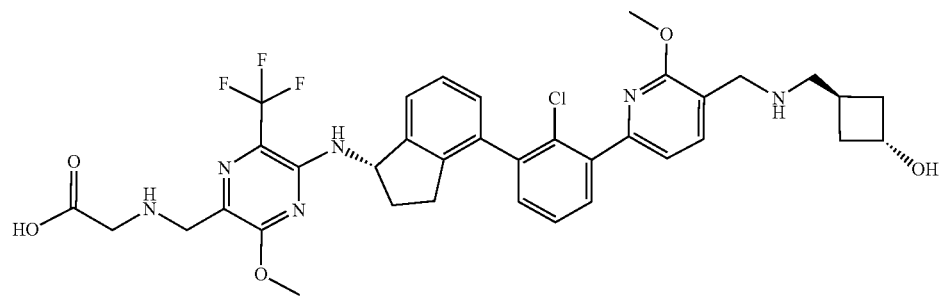
A-50
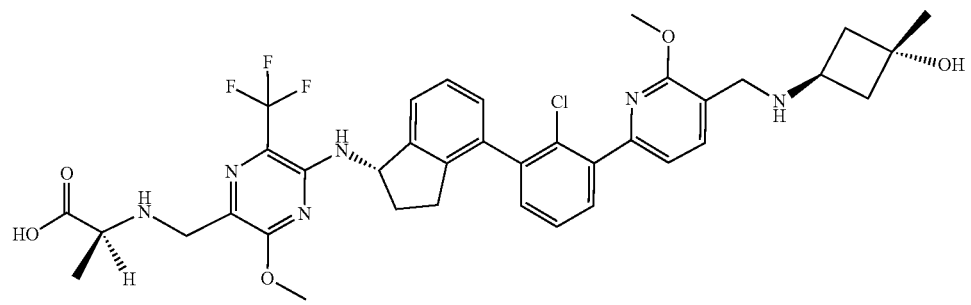
A-51
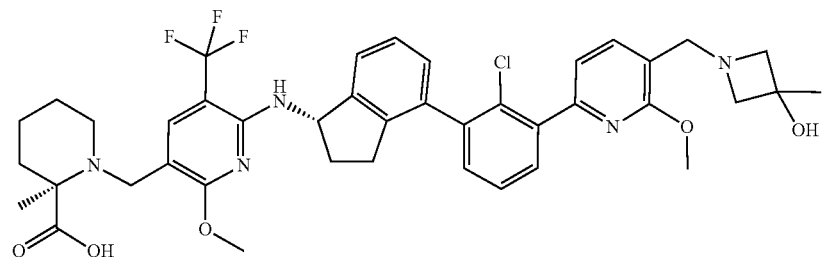
A-52
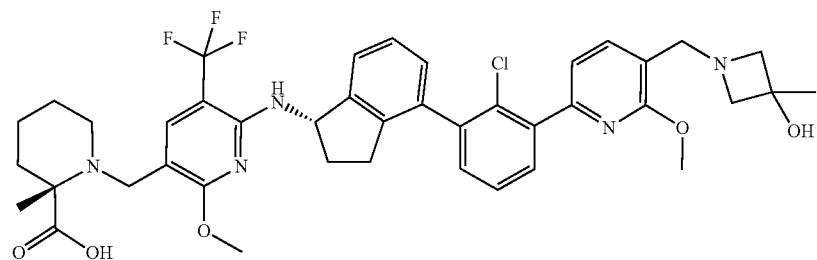

-continued
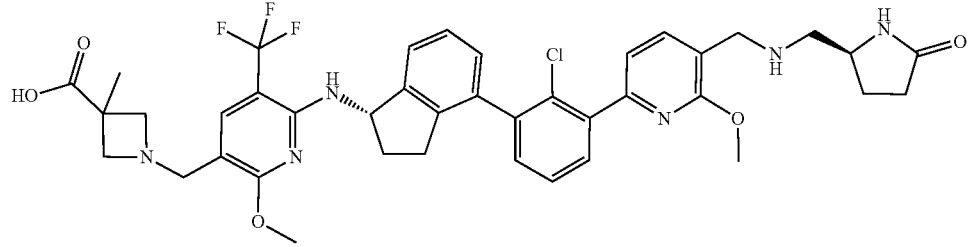
A-53
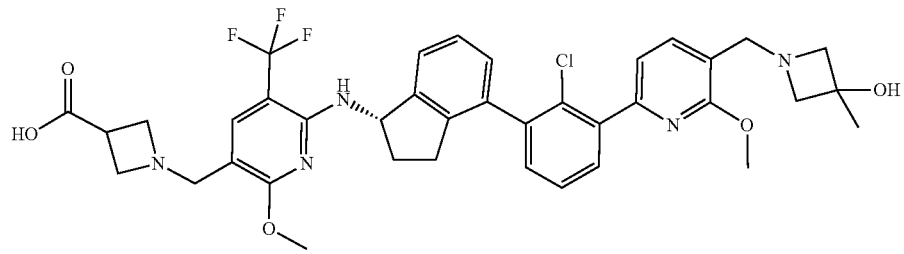
A-54
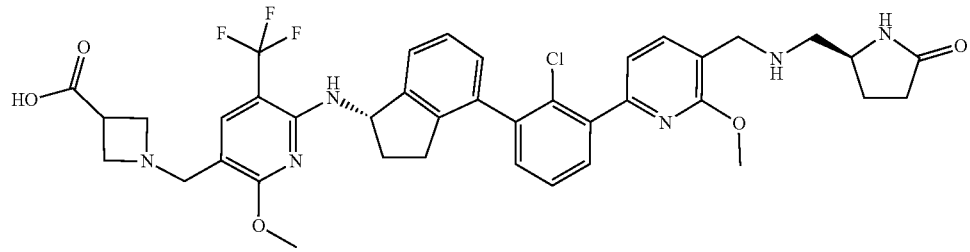
A-55
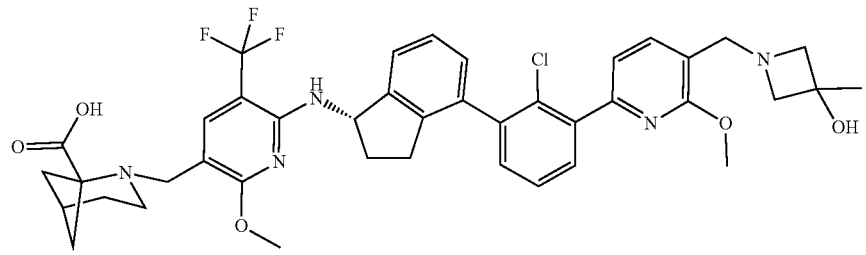
A-56
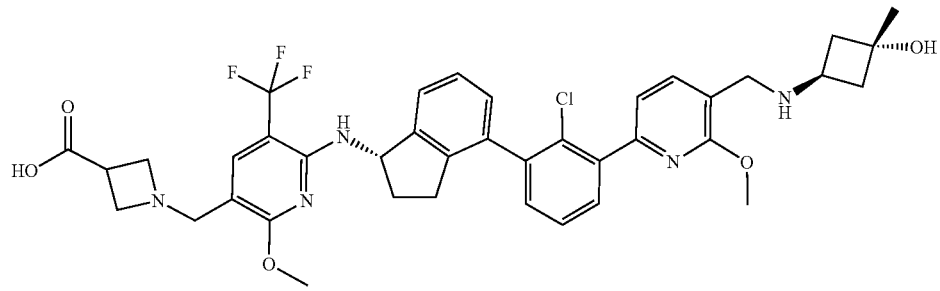
A-57
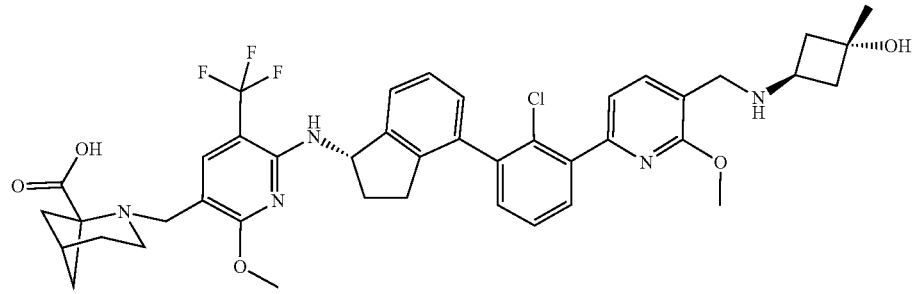
A-58

-continued
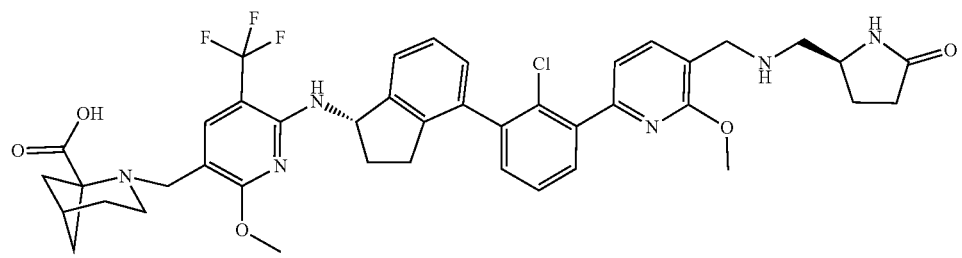
A-59
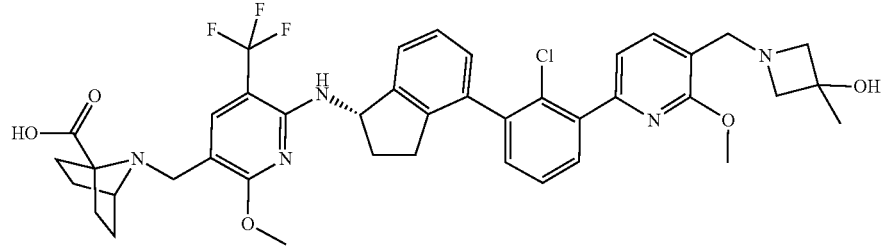
A-60
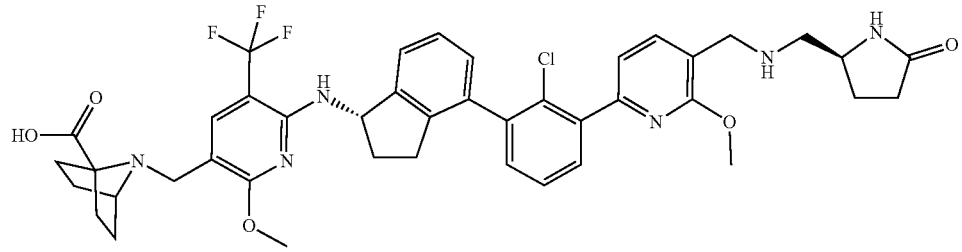
A-61
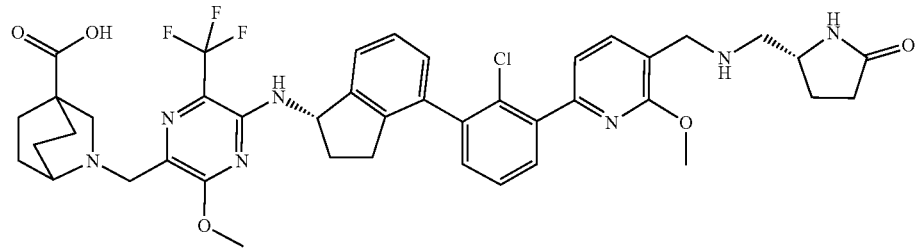
A-62
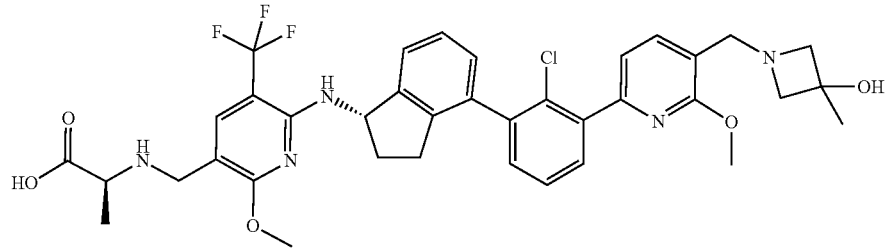
A-63
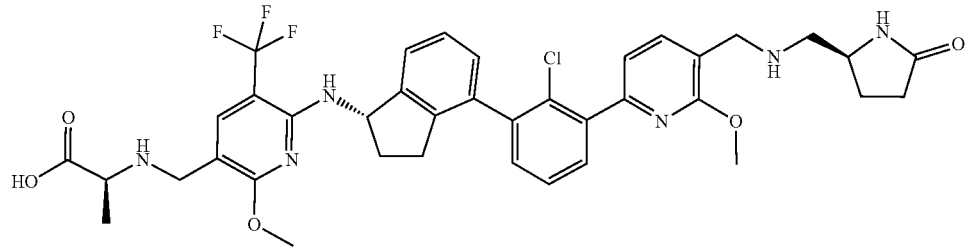
A-64

-continued
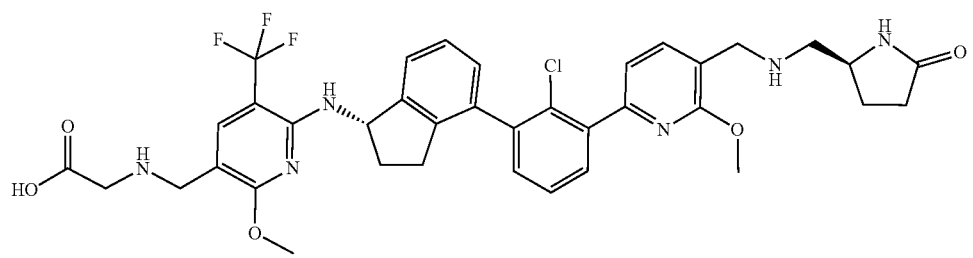
A-65
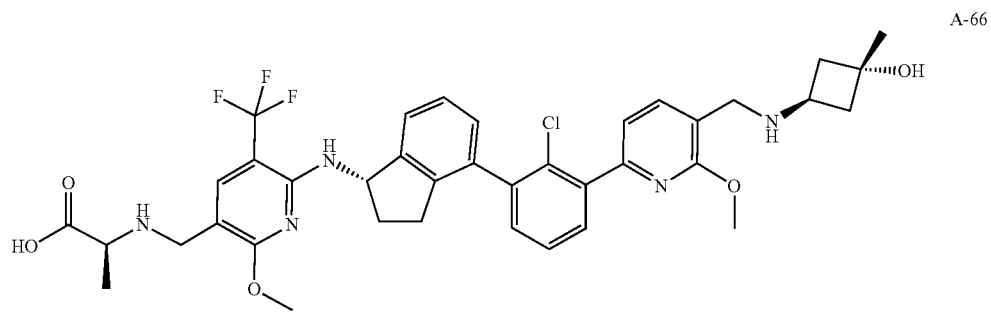
A-66
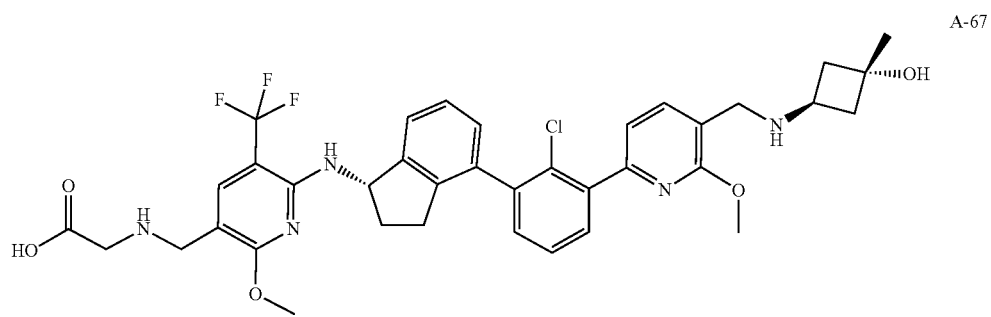
A-67
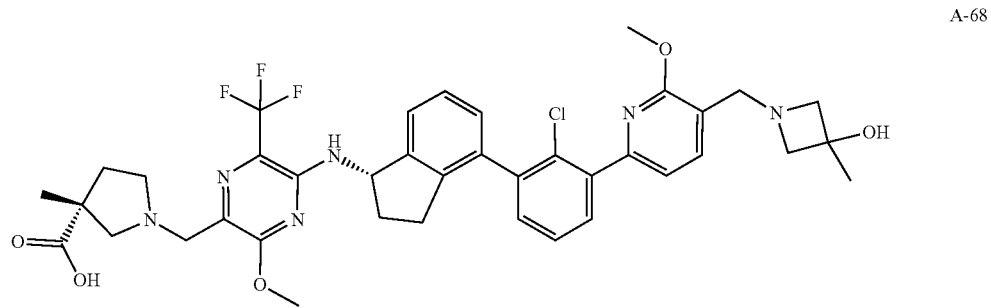
A-68
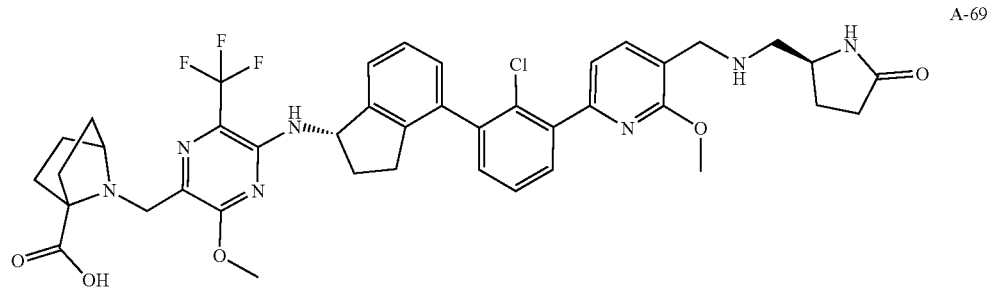
A-69

-continued
A-70
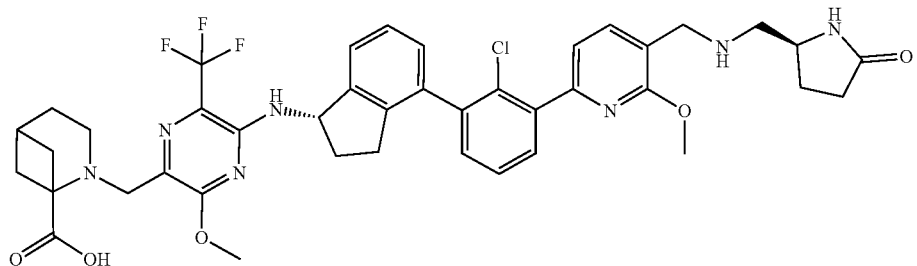
A-71
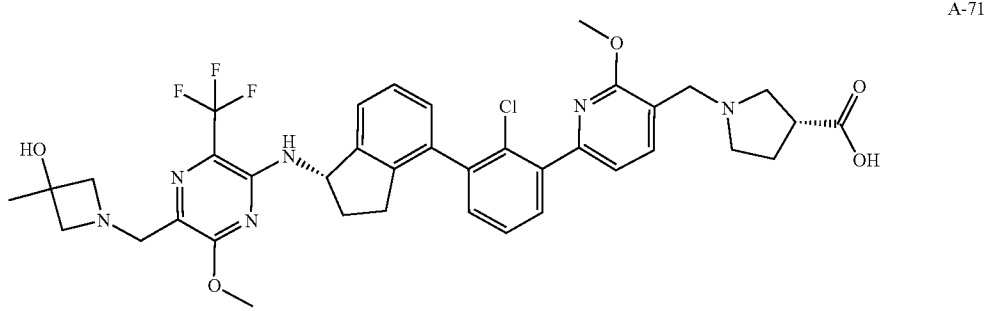
A-72
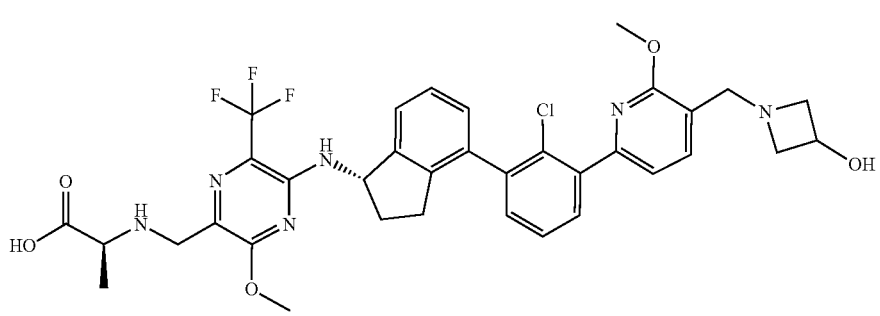
A-73
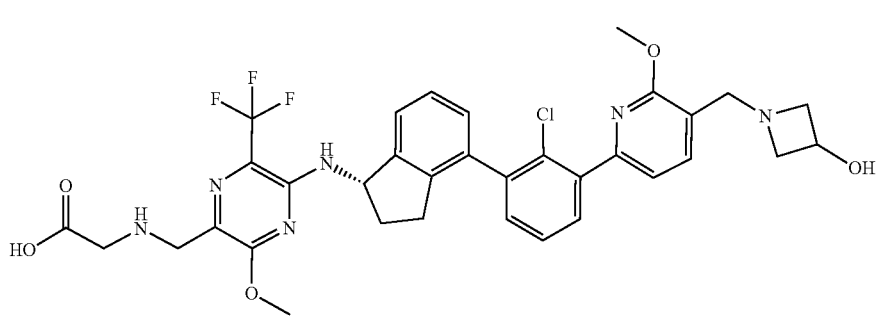
A-74
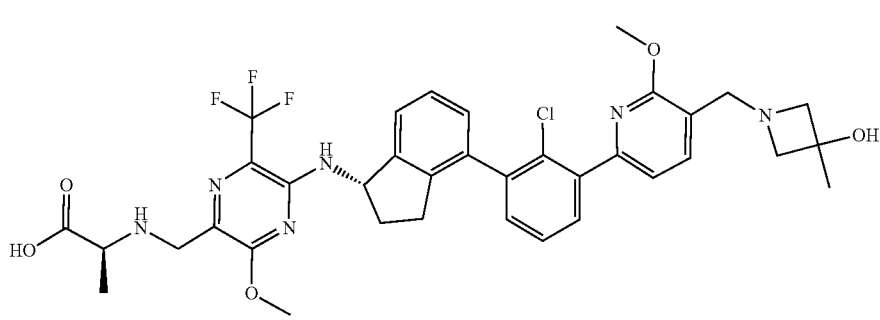

-continued
A-75
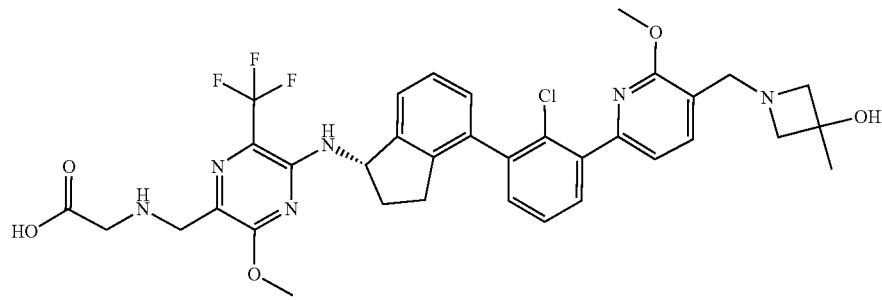
A-76
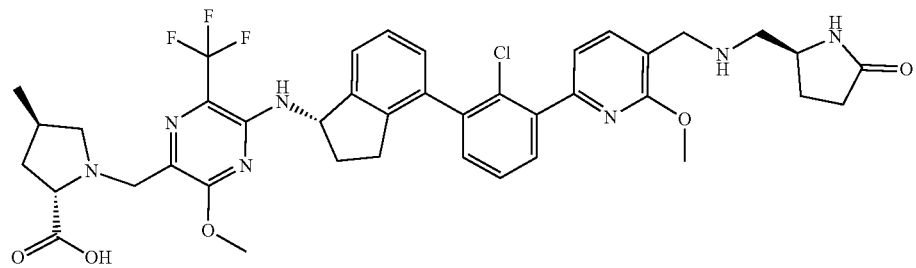
A-77
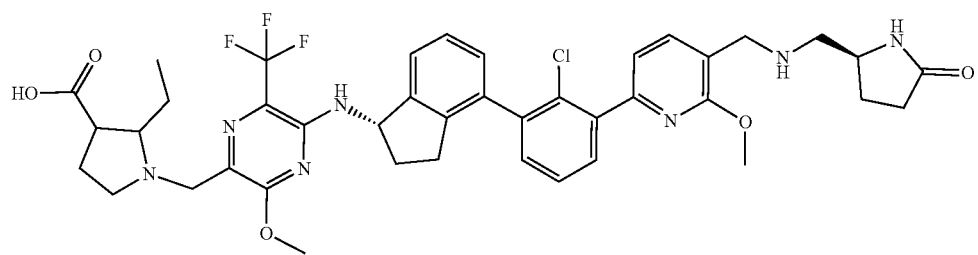
A-78
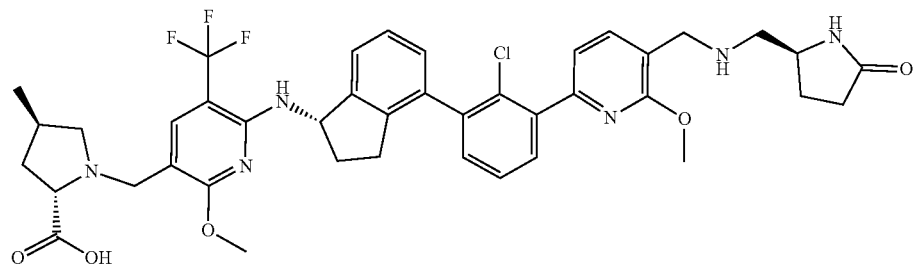
A-79
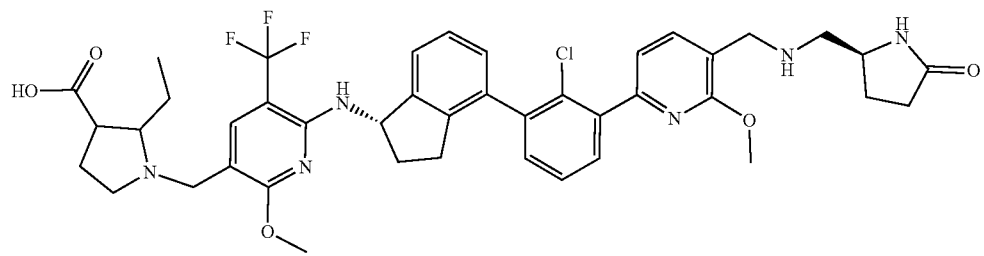
A-80
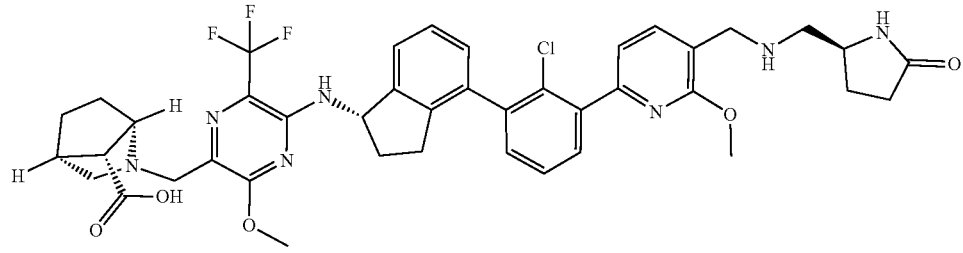

A-81
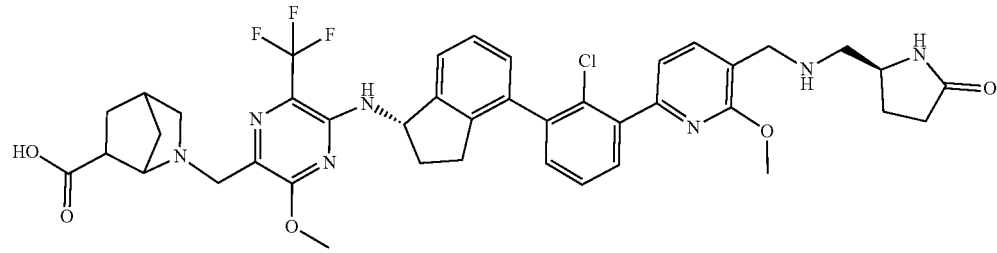
A-82
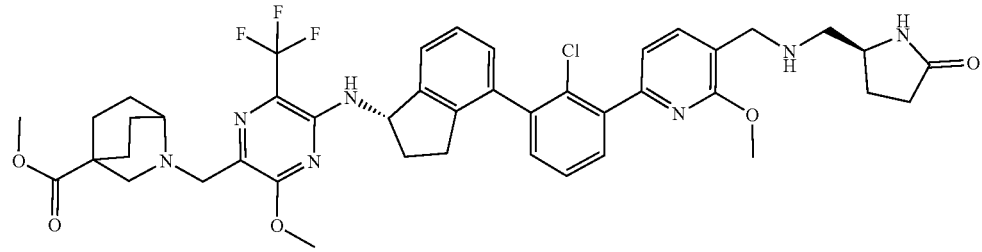
A-83
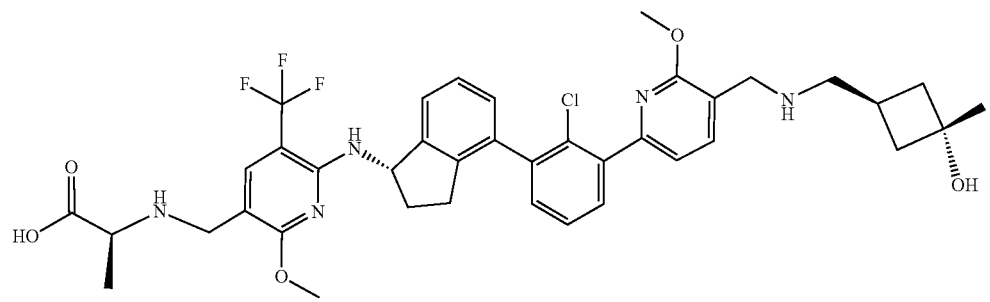
A-84
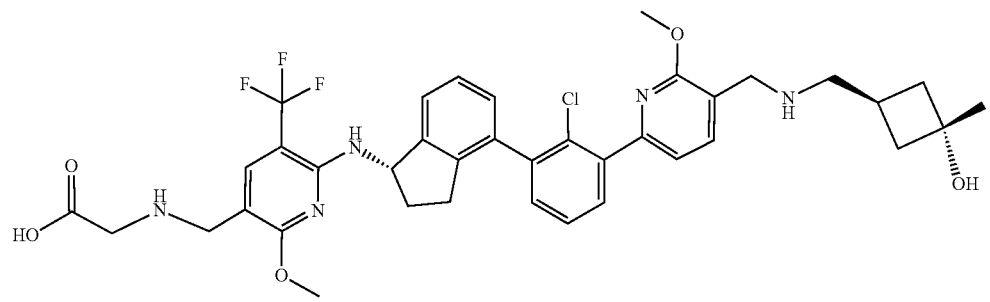
A-85
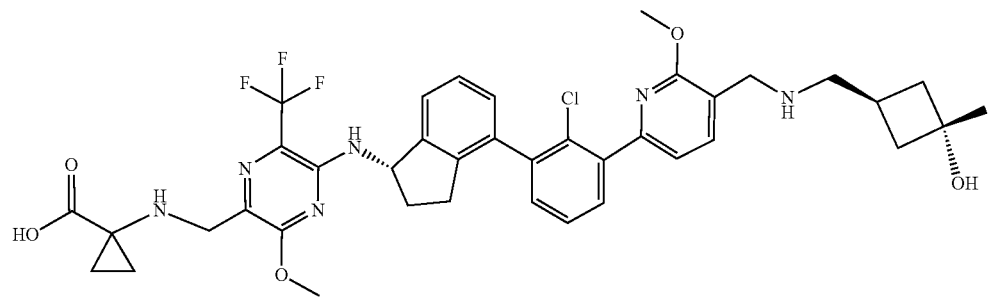

-continued
A-86
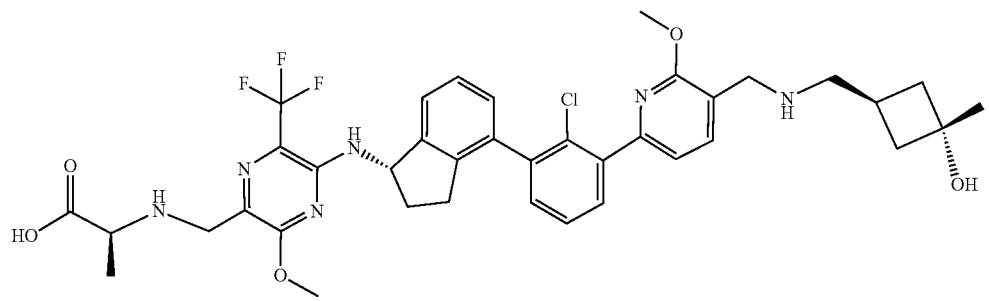
A-87
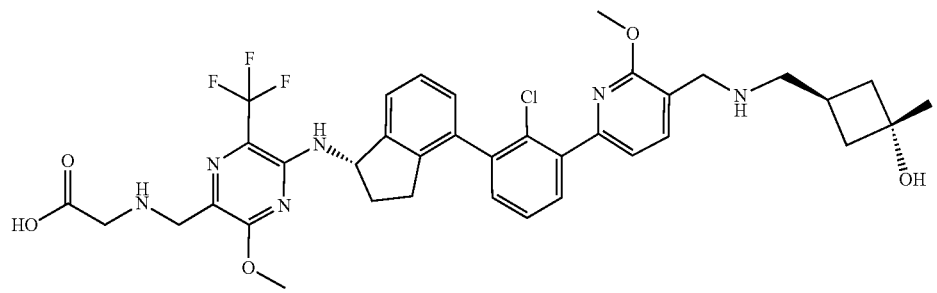
A-88
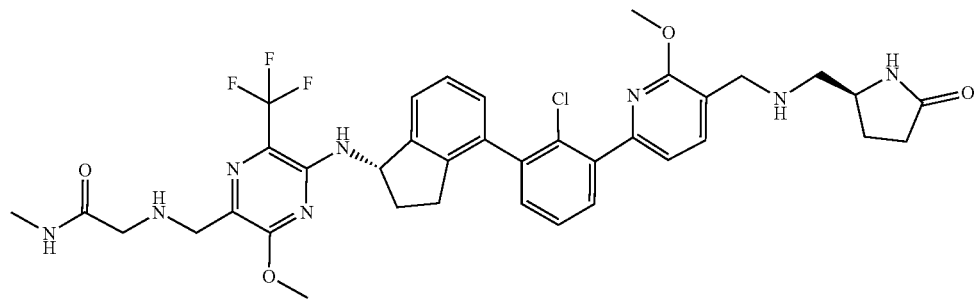
A-89
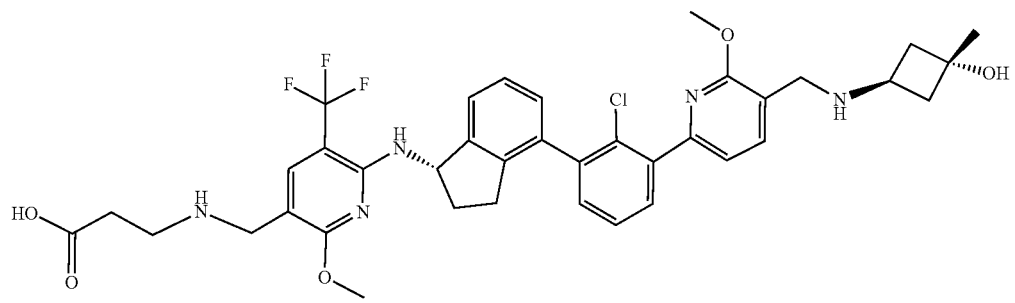
A-90
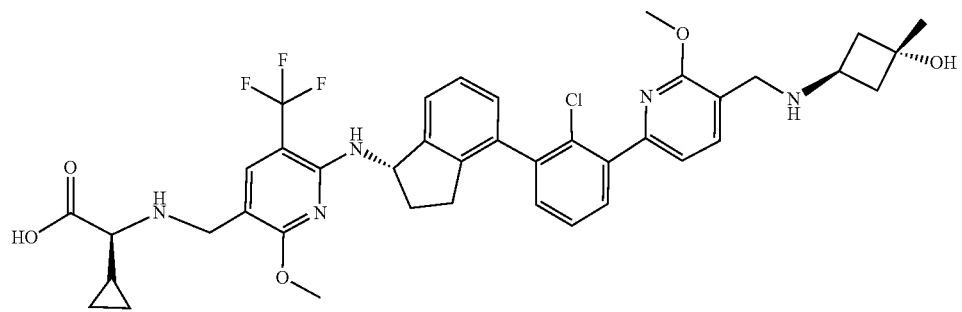

-continued
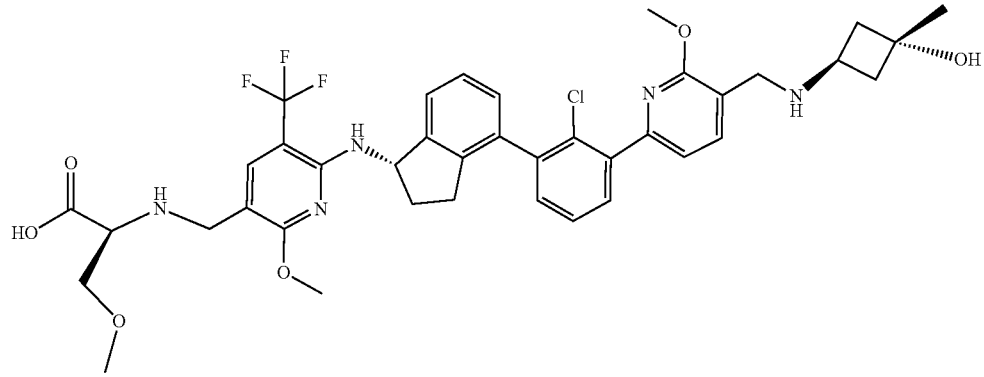
A-91
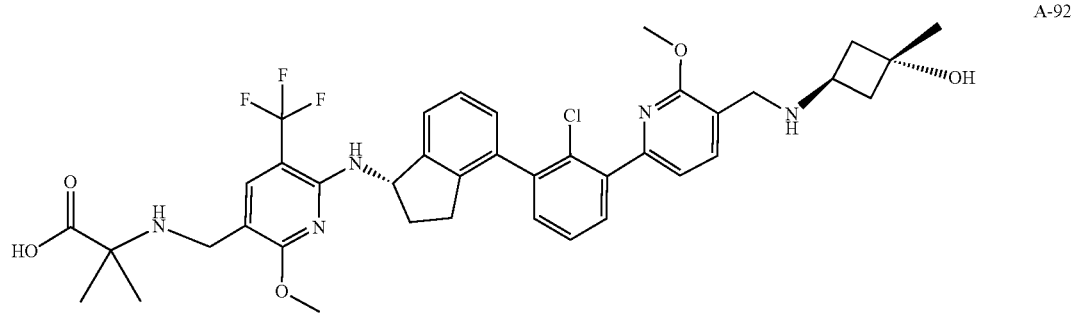
A-92
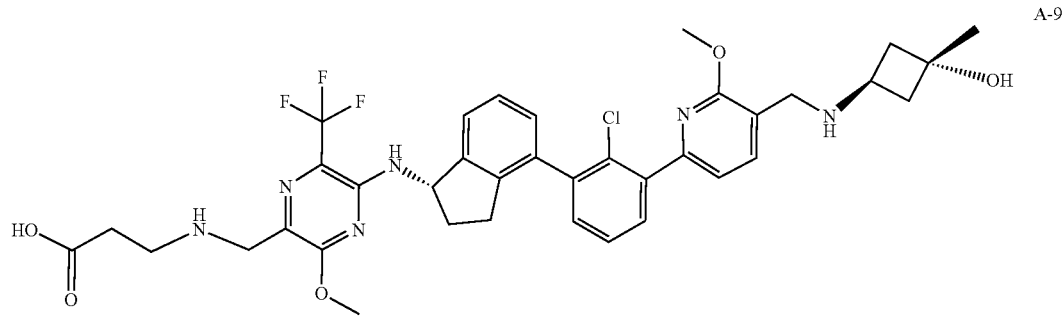
A-93
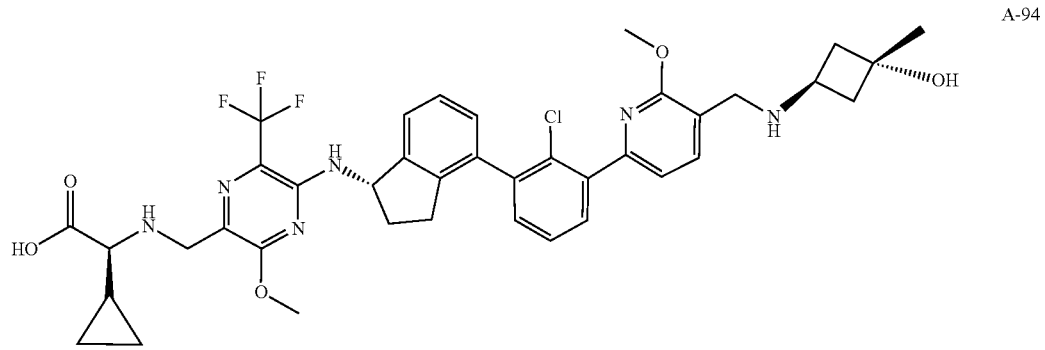
A-94
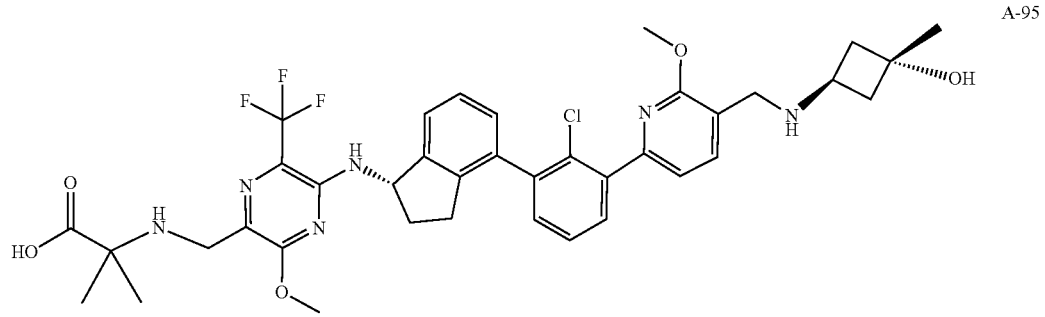
A-95

-continued
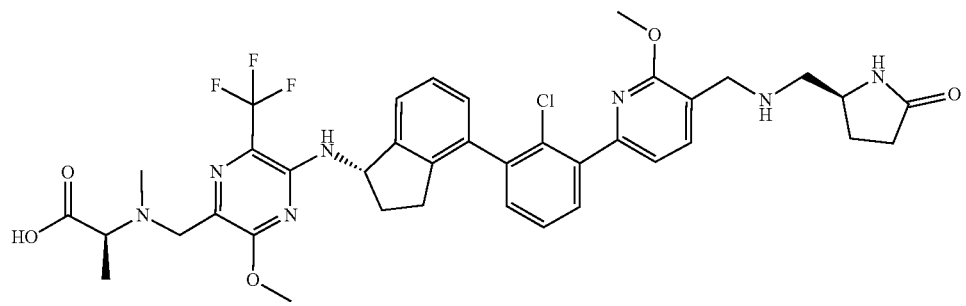
A-96
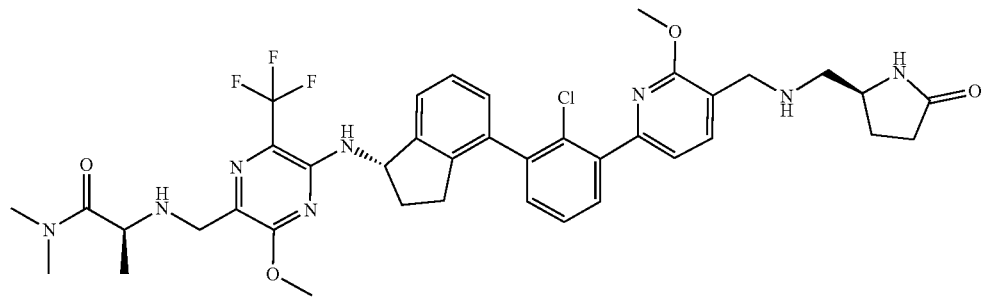
A-97
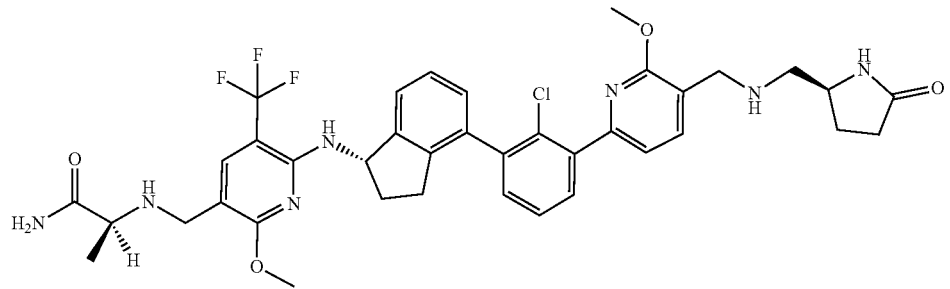
A-98
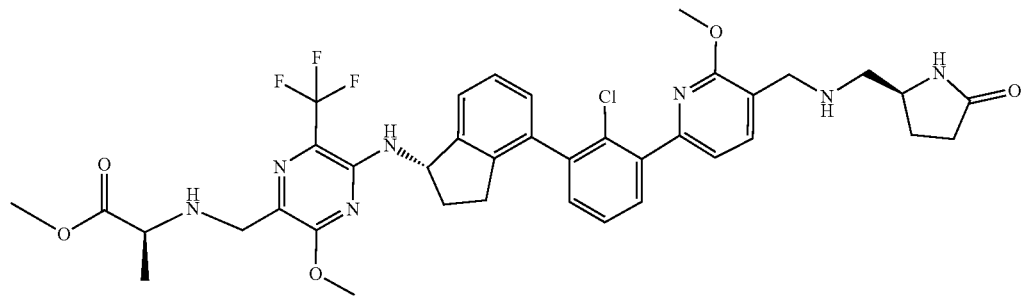
A-99
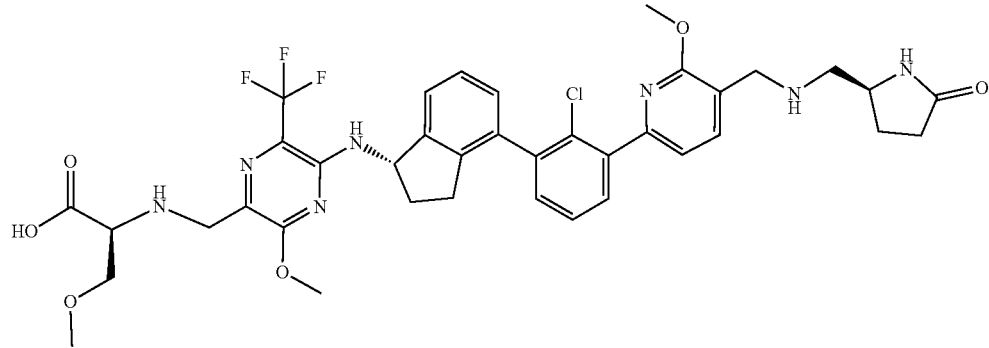
A-100

-continued
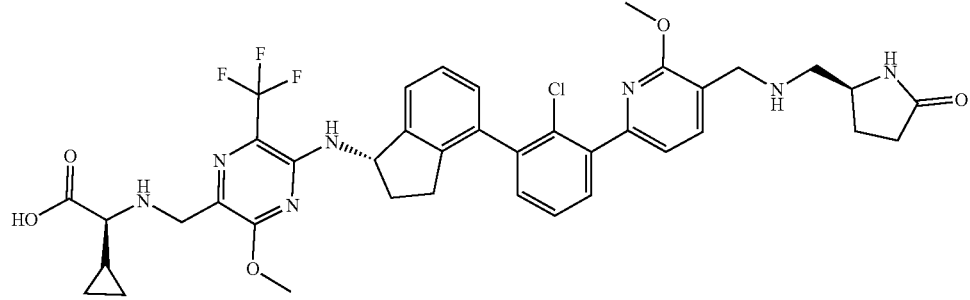
A-101
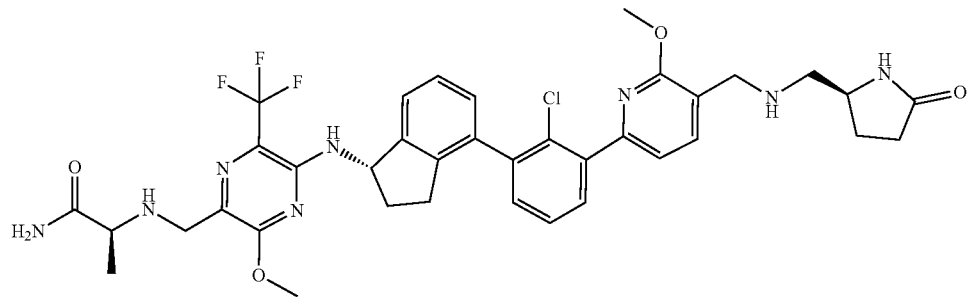
A-102
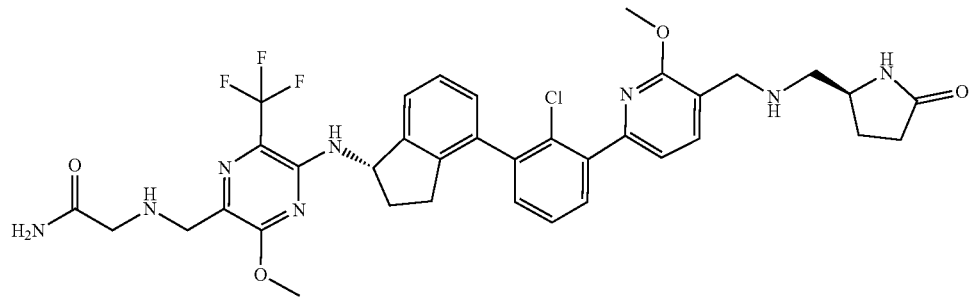
A-103
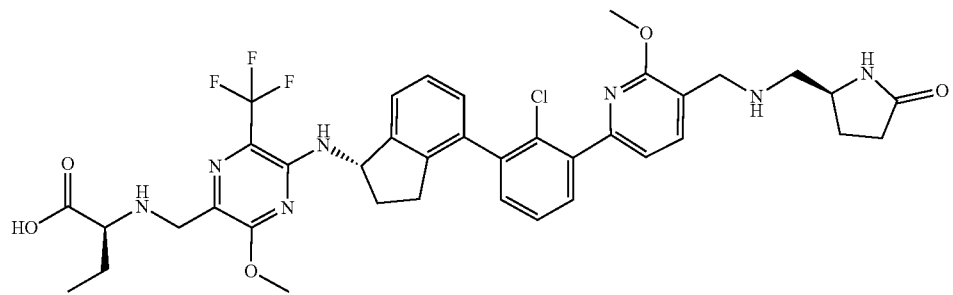
A-104
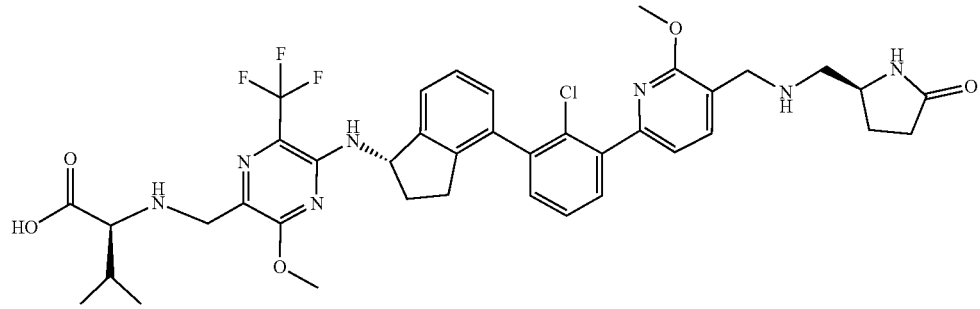
A-105

-continued

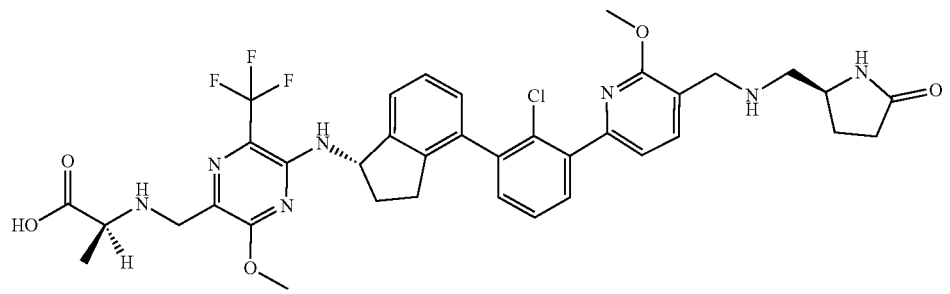

A-106

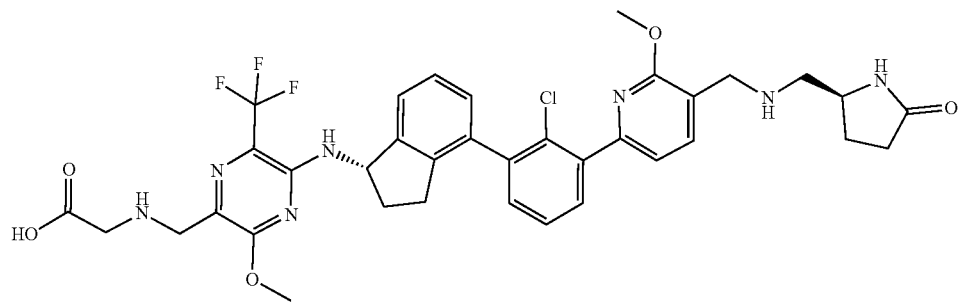

A-107

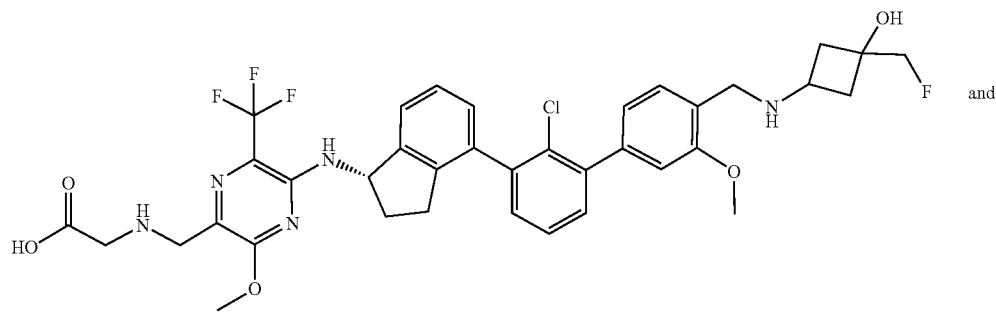

A-108 and

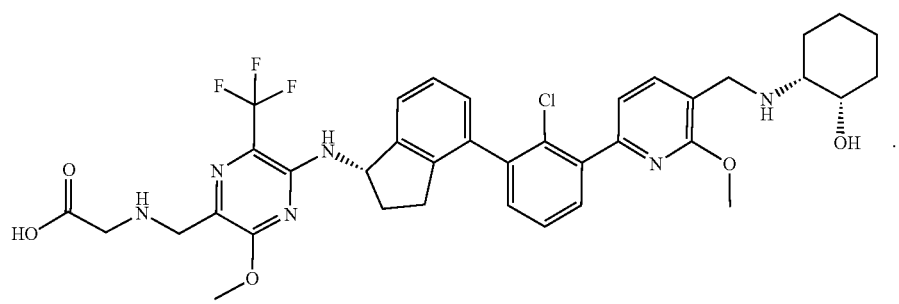

A-109

9. A pharmaceutical composition comprising a compound according to claim 1 or a pharmaceutically acceptable salt thereof, and at least one pharmaceutically acceptable excipient.

10. The pharmaceutical composition according to claim 9, further comprising at least one additional anticancer agent or therapy selected from rituxan, doxorubicin, gemcitabine, nivolumab, pembrolizumab, and ipilimumab, and at least one pharmaceutically acceptable excipient.

11. A method for inhibiting Programmed death-1 (PD-1), Programmed death-ligand 1 (PD-L1) and/or the PD-1/PD-L1 interaction comprising administering a compound according to claim 1 or a pharmaceutically acceptable salt thereof, to a patient in need thereof.

* * * * *